(12) United States Patent
Yano et al.

(10) Patent No.: US 11,299,675 B2
(45) Date of Patent: Apr. 12, 2022

(54) POLYMERIZABLE POLAR COMPOUND, LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Tomohiro Yano, Chiba (JP); Fumitaka Kondo, Chiba (JP); Hiroki Sago, Chiba (JP)

(73) Assignees: JNC CORPORATION, Tokyo (JP); JNC PETROCHEMICAL CORPORATION, Tokyo (JP)

(*) Notice: Subject to any disclaimer, the term of this patent is extended or adjusted under 35 U.S.C. 154(b) by 100 days.

(21) Appl. No.: 16/650,852

(22) PCT Filed: Jul. 13, 2018

(86) PCT No.: PCT/JP2018/026448
§ 371 (c)(1),
(2) Date: Mar. 25, 2020

(87) PCT Pub. No.: WO2019/064827
PCT Pub. Date: Apr. 4, 2019

(65) Prior Publication Data
US 2020/0263089 A1    Aug. 20, 2020

(30) Foreign Application Priority Data
Sep. 26, 2017   (JP) .............................. JP2017-184658

(51) Int. Cl.
*G02F 1/1333*   (2006.01)
*C09K 19/34*   (2006.01)
(Continued)

(52) U.S. Cl.
CPC .......... *C09K 19/3402* (2013.01); *C09K 19/12* (2013.01); *C09K 19/2007* (2013.01);
(Continued)

(58) Field of Classification Search
CPC .............. C09K 19/3402; C09K 19/12; C09K 19/2007; C09K 19/3477; C09K 19/56;
(Continued)

(56) References Cited
U.S. PATENT DOCUMENTS 8,867,002 B2 * 10/2014 Tanabe .................... C08L 33/16
349/123
2017/0090251 A1   3/2017 Mizusaki et al.
(Continued)

FOREIGN PATENT DOCUMENTS

JP   2016085413   5/2016
WO   2015146369   10/2015
(Continued)

OTHER PUBLICATIONS

"International Search Report (Form PCT/ISA/210) of PCT/JP2018/026448," dated Sep. 18, 2018, with English translation thereof, pp. 1-6.

Primary Examiner — Geraldina Visconti
(74) Attorney, Agent, or Firm — JCIPRNET

(57) ABSTRACT

A polar compound having high chemical stability, high capability of aligning liquid crystal molecules, high solubility in a liquid crystal composition, and a large voltage holding ratio when the compound is used in a liquid crystal display device; and a composition containing the compound. The compound is represented by formula (1). In formula (1), for example, $P^1$ is a group represented by any one of formulas (1b) to (1i), $P^2$ is a group represented by formula (1d), $Sp^1$ and $Sp^2$ are a single bond, $Z^1$, $Z^2$, $Z^3$, $Z^4$ and $Z^5$ are —COO—, and ring $A^1$, ring $A^2$, ring $A^3$ and ring $A^4$ are 1,4-phenylene:

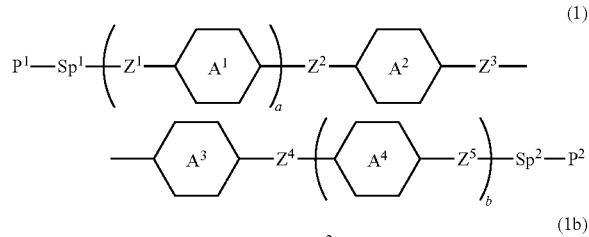

(1)

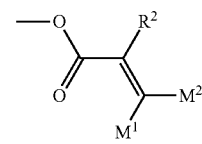

(1b)

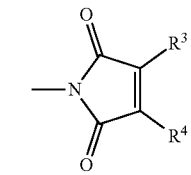

(1c)

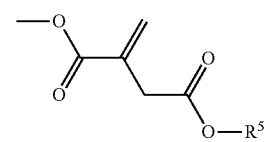

(1d)

(1e)

(Continued)

-continued

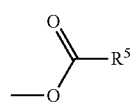 (1f)

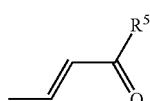

(1g)

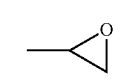

(1h)

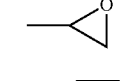

(1i)

17 Claims, No Drawings

(51) Int. Cl.
*C09K 19/12* (2006.01)
*C09K 19/20* (2006.01)
*C09K 19/56* (2006.01)
*G02F 1/139* (2006.01)

(52) U.S. Cl.
CPC .......... C09K 19/3477 (2013.01); C09K 19/56 (2013.01); G02F 1/139 (2013.01); C09K 2019/2035 (2013.01); C09K 2019/3413 (2013.01)

(58) Field of Classification Search
CPC .... C09K 2019/2035; C09K 2019/3413; G02F 1/139; G02F 1/1333
See application file for complete search history.

(56) References Cited

U.S. PATENT DOCUMENTS

| | | |
|---|---|---|
| 2017/0369418 A1 | 12/2017 | Tanaka et al. |
| 2018/0179443 A1 | 6/2018 | Yano et al. |
| 2018/0321560 A1 | 11/2018 | Nakanishi et al. |
| 2020/0190016 A1* | 6/2020 | Yano ..................... C07C 69/732 |
| 2020/0263089 A1* | 8/2020 | Yano ..................... C09K 19/56 |

FOREIGN PATENT DOCUMENTS

| | | |
|---|---|---|
| WO | 2016129490 | 8/2016 |
| WO | 2017047177 | 3/2017 |
| WO | 2017057162 | 4/2017 |

* cited by examiner

POLYMERIZABLE POLAR COMPOUND, LIQUID CRYSTAL COMPOSITION AND LIQUID CRYSTAL DISPLAY DEVICE

CROSS-REFERENCE TO RELATED APPLICATION

This application is a 371 application of the international PCT application serial no. PCT/JP2018/026448, filed on Jul. 13, 2018, which claims the priority benefit of Japan application no. 2017-184658, filed on Sep. 26, 2017. The entirety of each of the above-mentioned patent applications is hereby incorporated by reference herein and made a part of this specification.

TECHNICAL FIELD

The invention relates to a polymerizable polar compound, a liquid crystal composition and a liquid crystal display device. More specifically, the invention relates to a polymerizable polar compound having an itaconate group, a liquid crystal composition that contains the compound and has positive or negative dielectric anisotropy, and a liquid crystal display device including the composition.

BACKGROUND ART

In a liquid crystal display device, a classification based on an operating mode for liquid crystal molecules includes a phase change (PC) mode, a twisted nematic (TN) mode, a super twisted nematic (STN) mode, an electrically controlled birefringence (ECB) mode, an optically compensated bend (OCB) mode, an in-plane switching (IPS) mode, a vertical alignment (VA) mode, a fringe field switching (FFS) mode and a field-induced photo-reactive alignment (FPA) mode. A classification based on a driving mode in the device includes a passive matrix (PM) and an active matrix (AM). The PM is classified into static, multiplex and so forth, and the AM is classified into a thin film transistor (TFT), a metal insulator metal (MIM) and so forth. The TFT is further classified into amorphous silicon and polycrystal silicon. The latter is classified into a high temperature type and a low temperature type based on a production process. A classification based on a light source includes a reflective type utilizing natural light, a transmissive type utilizing backlight and a transflective type utilizing both the natural light and the backlight.

The liquid crystal display device includes a liquid crystal composition having a nematic phase. The composition has suitable characteristics. An AM device having good characteristics can be obtained by improving characteristics of the composition. Table 1 below summarizes a relationship of the characteristics between two aspects. The characteristics of the composition will be further described based on a commercially available AM device. A temperature range of the nematic phase relates to a temperature range in which the device can be used. A preferred maximum temperature of the nematic phase is about 70° C. or higher, and a preferred minimum temperature of the nematic phase is about −10° C. or lower. Viscosity of the composition relates to a response time in the device. A short response time is preferred for displaying moving images on the device. A shorter response time even by one millisecond is desirable. Accordingly, small viscosity of the composition is preferred. The small viscosity at a low temperature is further preferred.

TABLE 1

Characteristics of composition and AM device

| No. | Characteristics of composition | Characteristics of AM device |
|---|---|---|
| 1 | Wide temperature range of a nematic phase | Wide usable temperature range |
| 2 | Small viscosity[1] | Short response time |
| 3 | Suitable optical anisotropy | Large contrast ratio |
| 4 | Large positive or negative dielectric anisotropy | Low threshold voltage and small electric power consumption Large contrast ratio |
| 5 | Large specific resistance | Large voltage holding ratio and large contrast ratio |
| 6 | High stability to ultraviolet light and heat | Long service life |
| 7 | Large elastic constant | Large contrast ratio and short response time |

[1] A liquid crystal composition can be injected into a liquid crystal display device in a short time.

Optical anisotropy of the composition relates to a contrast ratio in the device. According to a mode of the device, large optical anisotropy or small optical anisotropy, more specifically, suitable optical anisotropy is required. A product (Δn× d) of the optical anisotropy (Δn) of the composition and a cell gap (d) in the device is designed so as to maximize the contrast ratio. A suitable value of the product depends on a type of the operating mode. In a device having a mode such as TN, the value is about 0.45 micrometer. The suitable value is in the range of about 0.30 micrometer to about 0.40 micrometer in a device having the VA mode, and is in the range of about 0.20 micrometer to about 0.30 micrometer in a device having the IPS mode or the FFS mode. In the above case, a composition having large optical anisotropy is preferred for a device having a small cell gap. Large dielectric anisotropy in the composition contributes to a low threshold voltage, small electric power consumption and a large contrast ratio in the device. Accordingly, large positive or negative dielectric anisotropy is preferred. Large specific resistance in the composition contributes to a large voltage holding ratio and the large contrast ratio in the device. Accordingly, a composition having large specific resistance at room temperature and also at a temperature close to the maximum temperature of the nematic phase in an initial stage is preferred. The composition having large specific resistance at room temperature and also at a temperature close to the maximum temperature of the nematic phase even after the device has been used for a long period of time is preferred. Stability of the composition to ultraviolet light and heat relates to a service life of the device. In the case where the stability is high, the device has a long service life. Such characteristics are preferred for an AM device used in a liquid crystal projector, a liquid crystal television and so forth.

A composition having positive dielectric anisotropy is used in an AM device having the TN mode. A composition having negative dielectric anisotropy is used in an AM device having the VA mode. In an AM device having the IPS mode or the FFS mode, a composition having positive or negative dielectric anisotropy is used.

In an AM device having a polymer sustained alignment (PSA) mode, a composition having positive or negative dielectric anisotropy is used. In a liquid crystal display device having a polymer sustained alignment (PSA) mode, a liquid crystal composition containing a polymer is used. First, a composition to which a small amount of a polymerizable compound is added is injected into the device. Next, the composition is irradiated with ultraviolet light while voltage is applied between substrates of the device. The polymerizable compound is polymerized to form a network structure of the polymer in the composition. In the composition, alignment of liquid crystal molecules can be controlled by the polymer, and therefore the response time of the device is shortened and also image persistence is improved. Such an effect of the polymer can be expected for a device having the mode such as the TN mode, the ECB mode, the OCB mode, the IPS mode, the VA mode, the FFS mode and the FPA mode.

A report has been made on a method of controlling alignment of liquid crystals by using a low molecular weight compound having a cinnamate group, polyvinyl cinnamate, a low molecular weight compound having a chalcone structure, a low molecular weight compound having an azobenzene structure and dendrimers in place of an alignment film such as polyimide (Patent literature No. 1 or No. 2). In the method of Patent literature No. 1 or No. 2, first, the low molecular weight compound or polymer is dissolved in a liquid crystal composition as an additive. Next, the additive is subjected to phase-separation to form a thin film composed of the low molecular weight compound or polymer on the substrate. Finally, the substrate is irradiated with linearly polarized light at a temperature higher than the maximum temperature of the liquid crystal composition. When the low molecular weight compound or polymer is dimerized or isomerized by this linearly polarized light, the molecules are aligned in a fixed direction. In this method, a horizontal alignment mode device such as IPS and FFS and a vertical alignment mode device such as VA can be produced by selecting a kind of low molecular weight compounds or polymers. In this method, easily caused phase-separation of the compound from the liquid crystal composition is important when the low molecular weight compound or polymer is easily dissolved at a temperature higher than the maximum temperature of the liquid crystal composition and then the temperature of the resulting material is returned to room temperature. However, maintenance of a compatibility between the low molecular weight compound or polymer and the liquid crystal composition is difficult.

In the liquid crystal display device having no alignment film, a compound (Formula 2) having a methacrylate group at a terminal has been so far described in Patent literature No. 2 as a compound in which liquid crystal molecules can be horizontally aligned. However, in the compounds, capability of horizontally aligning liquid crystal molecules is not sufficient.

Formula 2

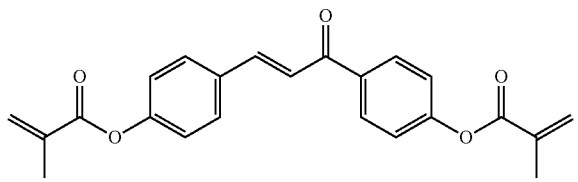

CITATION LIST

Patent Literature

Patent literature No. 1: WO 2015/146369 A.
Patent literature No. 2: WO 2017/057162 A.

SUMMARY OF INVENTION

Technical Problem

The invention provides a polar compound having high chemical stability, high capability of horizontally aligning liquid crystal molecules, high solubility in a liquid crystal composition, and a large voltage holding ratio when the compound is used in a liquid crystal display device. The invention further provides a liquid crystal composition that contains the compound, and satisfies at least one of characteristics such as high maximum temperature of a nematic phase, low minimum temperature of the nematic phase, small viscosity, suitable optical anisotropy, large positive or negative dielectric anisotropy, large specific resistance, high stability to ultraviolet light, high stability to heat and a large elastic constant. The invention still further provides a liquid crystal display device that includes the composition, and has characteristics such as a wide temperature range in which the device can be used, a short response time, a high voltage holding ratio, low threshold voltage, a large contrast ratio and a long service life.

Solution to Problem

The invention concerns a compound represented by formula (1), a composition using the compound, and a liquid crystal display device:

(1)

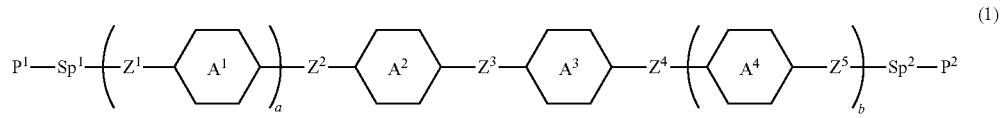

wherein, in formula (1), a and b are 0, 1 or 2, and expressions: 0≤a+b≤3 hold, ring $A^1$, ring $A^2$, ring $A^3$ and ring $A^4$ are independently 1,4-cyclohexylene, 1,4-cyclohexenylene, 1,4-phenylene, naphthalene-2,6-diyl, decahydronaphthalene-2,6-diyl, 1,2,3, 4-tetrahydronaphthalene-2,6-diyl, tetrahydropyran-2,5-diyl, 1,3-dioxane-2,5-diyl, pyrimidine-2,5-diyl, pyridine-2,5-diyl, fluorene-2,7-diyl, phenanthrene-2,7-diyl, anthracene-2, 6-diyl, perhydrocyclopenta[a]phenanthrene-3,17-diyl or 2,3, 4,7,8,9,10,11,12,13,14,15,16,17-tetradecahydrocyclopenta [a]phe nanthrene-3,17-diyl, and in the rings, at least one hydrogen may be replaced by fluorine, chlorine, alkyl having 1 to 12 carbons, alkenyl having 2 to 12 carbons, alkoxy having 1 to 11 carbons or alkenyloxy having 2 to 11 carbons, and in the groups, at least one hydrogen may be replaced by fluorine or chlorine, and when a orb is 2, two of arbitrary ring $A^1$ or ring $A^4$ may be different;

$Z^1$, $Z^2$, $Z^3$, $Z^4$ and $Z^5$ are independently a single bond or alkylene having 1 to 10 carbons, and in the alkylene, at least one —$CH_2$— may be replaced by —O—, —CO—, —COO—, —OCO— or —OCOO—, and at least one —$(CH_2)_2$— may be replaced by —CH=CH— or —C≡C—, and in the groups, at least one hydrogen may be replaced by halogen, in which at least one in $Z^2$, $Z^3$ or $Z^4$ is any one of —COO—, —OCO—, —CH=CHCOO—, —OCOCH=CH—, —CH=CH—, —CH=CHCO— or —COCH=CH—, and when a or b is 2, two arbitrary $Z^1$s or $Z^5$s may be different;

$Sp^1$ and $Sp^2$ are a single bond or alkylene having 1 to 10 carbons, and in the alkylene, at least one —$CH_2$— may be replaced by —O—, —CO—, —COO—, —OCO— or —OCOO—, and at least one —$(CH_2)_2$— may be replaced by —CH=CH— or —C≡C—, and in the groups, at least one hydrogen may be replaced by halogen;

$P^1$ is a group represented by any one of formulas (1b) to (1i); and $P^2$ is a group represented by formula (1d);

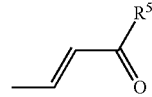

(1b)

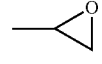

(1c)

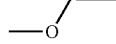

(1d)

(1e)

(1f)

(1g)

(1h)

(1i)

wherein, in formulas (1b) to (1i), $M^1$ and $M^2$ are independently hydrogen, halogen, alkyl having 1 to 5 carbons, or alkyl having 1 to 5 carbons in which at least one hydrogen is replaced by halogen;

$R^2$ is hydrogen, halogen or alkyl having 1 to 5 carbons, and in the alkyl, at least one hydrogen may be replaced by halogen, and at least one —$CH_2$— may be replaced by —O—; and $R^3$, $R^4$ and $R^5$ are independently hydrogen, chain alkyl having 1 to 15 carbons or cyclic alkyl having 1 to 15 carbons, and in the alkyl, at least one —$CH_2$— may be replaced by —O— or —S—, and at least one —$(CH_2)_2$— may be replaced by —CH=CH— or —C≡C—, and in the groups, at least one hydrogen may be replaced by halogen.

Advantageous Effects of Invention

A first advantage of the invention is to provide a polar compound having high chemical stability, high capability of horizontally aligning liquid crystal molecules, high solubility in a liquid crystal composition, and a large voltage holding ratio when the compound is used in a liquid crystal display device. A second advantage is to provide a liquid crystal composition that contains the compound, and satisfies at least one of characteristics such as high maximum temperature of a nematic phase, low minimum temperature of the nematic phase, small viscosity, suitable optical anisotropy, large positive or negative dielectric anisotropy, large specific resistance, high stability to ultraviolet light, high stability to heat and a large elastic constant. A third advantage is to provide a liquid crystal display device that includes the composition, and has characteristics such as a wide temperature range in which the device can be used, a short response time, a high voltage holding ratio, low threshold voltage, a large contrast ratio and a long service life. A formation step of an alignment film becomes unnecessary by utilizing the liquid crystal composition containing the compound of the invention, and therefore a liquid crystal display device in which production cost is reduced can be obtained.

DESCRIPTION OF EMBODIMENTS

Usage of terms herein is as described below. Terms "liquid crystal composition" and "liquid crystal display device" may be occasionally abbreviated as "composition" and "device," respectively. "Liquid crystal display device" is a generic term for a liquid crystal display panel and a liquid crystal display module. "Liquid crystal compound" is a generic term for a compound having a liquid crystal phase such as a nematic phase and a smectic phase, and a compound having no liquid crystal phase but to be mixed with the composition for the purpose of adjusting characteristics such as a temperature range of a nematic phase, viscosity and dielectric anisotropy. The compound has a six-membered ring such as 1,4-cyclohexylene and 1,4-phenylene, and rod like molecular structure. "Polymerizable compound" is a compound to be added for the purpose of forming a polymer in the composition. "Polar compound" assists alignment of liquid crystal molecules by interaction of a polar group with a substrate surface.

The liquid crystal composition is prepared by mixing a plurality of liquid crystal compounds. A proportion (content) of the liquid crystal compounds is expressed in terms of weight percent (% by weight) based on the weight of the liquid crystal composition. An additive such as an optically active compound, an antioxidant, an ultraviolet light absorber, a dye, an antifoaming agent, the polymerizable compound, a polymerization initiator, a polymerization inhibitor and a polar compound is added to the liquid crystal composition when necessary. A proportion (amount of addition) of the additive is expressed in terms of weight percent (% by weight) based on the weight of the liquid crystal composition in a manner similar to the proportion of the liquid crystal compound. Weight parts per million (ppm) may be occasionally used. A proportion of the polymerization initiator and the polymerization inhibitor is exceptionally expressed based on the weight of the polymerizable compound.

A compound represented by formula (1) may be occasionally abbreviated as "compound (1)." Compound (1) means one compound, a mixture of two compounds or a mixture of three or more compounds represented by formula (1). A same rule applies also to at least one compound selected from the group of compounds represented by formula (2), or the like. Symbol $B^1$, $C^1$, F or the like surrounded by a hexagonal shape corresponds to ring $B^1$, ring $C^1$ and ring F, respectively. The hexagonal shape represents a six-membered ring such as a cyclohexane ring and a benzene ring, or a condensed ring such as a naphthalene ring. An oblique line crossing the hexagonal shape represents that arbitrary hydrogen on the ring may be replaced by a group such as -$Sp^1$-$P^1$. A subscript such as e represents the number of groups subjected to replacement. When the subscript is 0, no such replacement exists.

A symbol of terminal group $R^{11}$ is used in a plurality of component compounds. In the compounds, two groups represented by two arbitrary $R^{11}$s may be identical or different. For example, in one case, $R^{11}$ of compound (2) is ethyl and $R^{11}$ of compound (3) is ethyl. In another case, $R^{11}$ of compound (2) is ethyl and $R^{11}$ of compound (3) is propyl. A same rule applies also to a symbol of any other terminal group, ring, bonding group or the like. In formula (8), when i is 2, two of ring $D^1$ exist. In the compound, two groups represented by two of ring $D^1$ may be identical or different. A same rule applies also to two of arbitrary ring $D^1$ when i is larger than 2. A same rule applies also to a symbol of any other ring, bonding group or the like.

An expression "at least one 'A'" means that the number of 'A' is arbitrary. An expression "at least one 'A' may be replaced by 'B'" means that, when the number of 'A' is 1, a position of 'A' is arbitrary, and also when the number of 'A' is 2 or more, positions thereof can be selected without restriction. A same rule applies also to an expression "at least one 'A' is replaced by 'B'." An expression "at least one 'A' may be replaced by 'B', 'C' or 'D'" includes a case where at least one 'A' is replaced by 'B', a case where at least one 'A' is replaced by 'C', and a case where at least one 'A' is replaced by 'D', and also a case where a plurality of 'As' are replaced by at least two 'Bs', 'Cs' and 'Ds'. For example, "alkyl in which at least one —$CH_2$-(or —$CH_2CH_2$—) may be replaced by —O— (or —CH=CH—)" includes alkyl, alkenyl, alkoxy, alkoxyalkyl, alkoxyalkenyl and alkenyloxy-alkyl. In addition, a case where two consecutive —$CH_2$-s are replaced by —O-s to form —O—O— is not preferred. In alkyl or the like, a case where —$CH_2$— of a methyl part (—$CH_2$—H) is replaced by —O— to form —O—H is not preferred, either.

Halogen means fluorine, chlorine, bromine or iodine. Preferred halogen is fluorine or chlorine. Further preferred halogen is fluorine. Alkyl is straight-chain alkyl or branched-chain alkyl, but includes no cyclic alkyl. In general, straight-chain alkyl is preferred to branched-chain alkyl. A same rule applies also to a terminal group such as alkoxy and alkenyl. With regard to a configuration of 1,4-cyclohexylene, trans is preferred to cis for increasing the maximum temperature of the nematic phase. Then, 2-fluoro-1,4-phenylene means two divalent groups described below. In a chemical formula, fluorine may be leftward (L) or rightward (R). A same rule applies also to an asymmetrical divalent group formed by eliminating two hydrogens from a ring, such as tetrahydropyran-2,5-diyl.

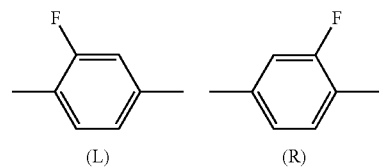

(L)　　　　　(R)

The invention includes items described below.

Item 1. A compound, represented by formula (1):

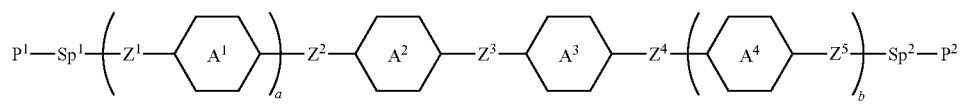

(1)

wherein, in formula (1), a and b are independently 0, 1 or 2, and expressions: 0≤a+b≤3 hold, ring $A^1$, ring $A^2$, ring $A^3$ and ring $A^4$ are independently 1,4-cyclohexylene, 1,4-cyclohexenylene, 1,4-phenylene, naphthalene-2,6-diyl, decahydronaphthalene-2,6-diyl, 1,2,3,4-tetrahydronaphthalene-2,6-diyl, tetrahydropyran-2,5-diyl, 1,3-dioxane-2,5-diyl, pyrimidine-2,5-diyl, pyridine-2,5-diyl, fluorene-2,7-diyl, phenanthrene-2,7-diyl, anthracene-2,6-diyl, perhydrocyclopenta[a]phenanthrene-3,17-diyl or 2,3,4,7,8,9,10,11,12,13,14,15,16,17-tetradecahydrocyclopenta[a]phe nanthrene-3,17-diyl, and in the rings, at least one hydrogen may be replaced by fluorine, chlorine, alkyl having 1 to 12 carbons, alkenyl having 2 to 12 carbons, alkoxy having 1 to 11 carbons or alkenyloxy having 2 to 11 carbons, and in the groups, at least one hydrogen may be replaced by fluorine or chlorine, and when a is 2, two of ring $A^1$ may be different, and when b is 2, two of ring $A^4$ may be different;

$Z^1$, $Z^2$, $Z^3$, $Z^4$ and $Z^5$ are independently a single bond or alkylene having 1 to 10 carbons, and in the alkylene, at least one —CH$_2$— may be replaced by —O—, —CO—, —COO—, —OCO— or —OCOO—, and at least one —(CH$_2$)$_2$— may be replaced by —CH═CH— or —C≡C—, and in the groups, at least one hydrogen may be replaced by halogen, in which at least one in $Z^2$, $Z^3$ or $Z^4$ is —COO—, —OCO—, —CH═CHCOO—, —OCOCH═CH—, —CH═CH—, —CH═CHCO— or —COCH═CH—, and when a is 2, two $Z^1$s may be different, and two $Z^5$s may be different;

Sp$^1$ and Sp$^2$ are independently a single bond or alkylene having 1 to 10 carbons, and in the alkylene, at least one —CH$_2$— may be replaced by —O—, —CO—, —COO—, —OCO— or —OCOO—, and at least one —(CH$_2$)$_2$— may be replaced by —CH═CH— or —C≡C—, and in the groups, at least one hydrogen may be replaced by halogen;

P$^1$ is a group represented by any one of formulas (1b) to (1i); and

P$^2$ is a group represented by formula (1d);

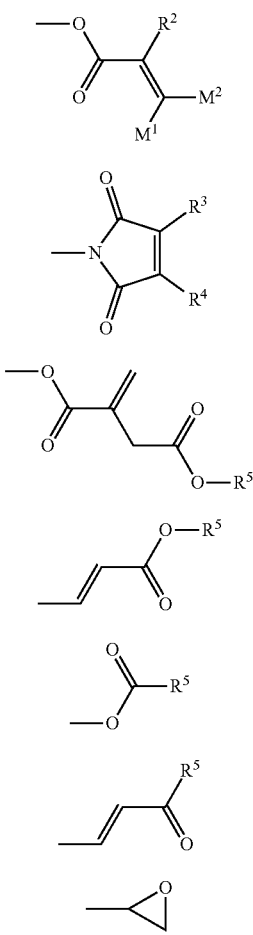

(1b)
(1c)
(1d)
(1e)
(1f)
(1g)
(1h)

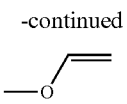

(1i)

wherein, in formulas (1b) to (1i),

M$^1$ and M$^2$ are independently hydrogen, halogen, alkyl having 1 to 5 carbons, or alkyl having 1 to 5 carbons in which at least one hydrogen is replaced by halogen;

R$^2$ is hydrogen, halogen or alkyl having 1 to 5 carbons, and in the alkyl, at least one hydrogen may be replaced by halogen, and at least one —CH$_2$— may be replaced by —O—; and R$^3$, R$^4$ and R$^5$ are independently hydrogen or alkyl having 1 to 15 carbons, and in the alkyl, at least one —CH$_2$— may be replaced by —O— or —S—, and at least one —(CH$_2$)$_2$— may be replaced by —CH═CH— or —C≡C—, and in the groups, at least one hydrogen may be replaced by halogen.

Item 2. The compound according to item 1, represented by formula (1):

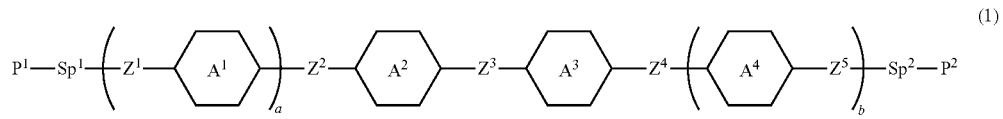

(1)

wherein, in formula (1), a and b are independently 0, 1 or 2, and expressions: 0≤a+b≤2 hold;

ring A$^1$, ring A$^2$, ring A$^3$ and ring A$^4$ are independently 1,4-cyclohexylene, 1,4-cyclohexenylene, 1,4-phenylene, naphthalene-2,6-diyl, decahydronaphthalene-2,6-diyl, 1,2,3,4-tetrahydronaphthalene-2,6-diyl, tetrahydropyran-2,5-diyl, 1,3-dioxane-2,5-diyl, pyrimidine-2,5-diyl, pyridine-2,5-diyl, fluorene-2,7-diyl, phenanthrene-2,7-diyl, anthracene-2,6-diyl, perhydrocyclopenta[a]phenanthrene-3,17-diyl or 2,3,4,7,8,9,10,11,12,13,14,15,16,17-tetradecahydrocyclopenta[a]phenanthrene-3,17-diyl, and in the rings, at least one hydrogen may be replaced by fluorine, chlorine, alkyl having 1 to 12 carbons, alkenyl having 2 to 12 carbons, alkoxy having 1 to 11 carbons or alkenyloxy having 2 to 11 carbons, and in the groups, at least one hydrogen may be replaced by fluorine or chlorine, and when a is 2, two of ring A$^1$ may be different, and when b is 2, two of ring A$^4$ may be different;

$Z^1$, $Z^2$, $Z^3$, $Z^4$ and $Z^5$ are independently a single bond, —(CH$_2$)$_2$—, —C≡C—, —COO—, —OCO—, —CF$_2$O—, —OCF$_2$—, —CH$_2$O—, —OCH$_2$—, —CF═CF—, —CH═CHCOO—, —OCOCH═CH—, —CH═CH—, —CH═CHCO— or —COCH═CH—, in which at least one in $Z^2$, $Z^3$ or $Z^4$ is —COO—, —OCO—, —CH═CHCOO—, —OCOCH═CH—, —CH═CH—, —CH═CHCO— or —COCH═CH—, and when a is 2, two pieces of $Z^1$ may be different, and two pieces of $Z^5$ may be different;

Sp$^1$ and Sp$^2$ are independently a single bond or alkylene having 1 to 10 carbons, and in the alkylene, at least one piece of —CH$_2$— may be replaced by —O—, —COO— or —OCO—, and at least one piece of —(CH$_2$)$_2$— may be replaced by —CH═CH—, and in the groups, at least one hydrogen may be replaced by fluorine or chlorine; and P$^1$ is a group represented by any one of formulas (1b) to (1i), and P$^2$ is a group represented by formula (1d);

(1b) 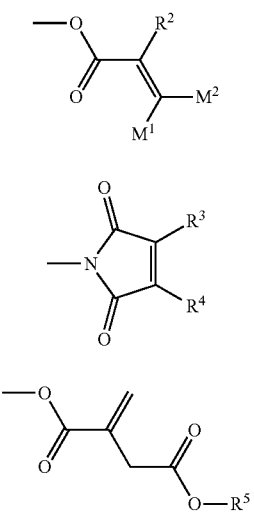
(1c)
(1d)

(1i) 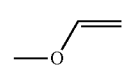

wherein, in formulas (1b) to (1i), $M^1$ and $M^2$ are independently hydrogen, halogen, alkyl having 1 to 5 carbons, or alkyl having 1 to 5 carbons in which at least one hydrogen is replaced by halogen;

$R^2$ is hydrogen, halogen or alkyl having 1 to 5 carbons, and in the alkyl, at least one hydrogen may be replaced by halogen, and at least one piece of —CH$_2$— may be replaced by —O—; and $R^3$, $R^4$ and $R^5$ are independently hydrogen or alkyl having 1 to 15 carbons, and in the alkyl, at least one piece of —CH$_2$— may be replaced by —O— or —S—, and at least one piece of —(CH$_2$)$_2$— may be replaced by —CH=CH— or —C≡C—, and in the groups, at least one hydrogen may be replaced by halogen.

Item 3. The compound according to item 1 or 2, represented by any one of formulas (1-1) to (1-3):

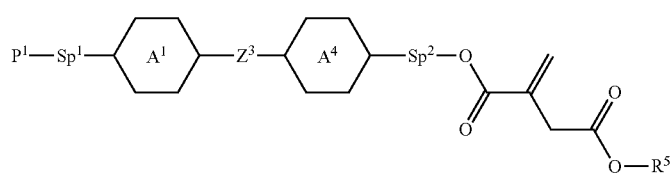
(1-1)

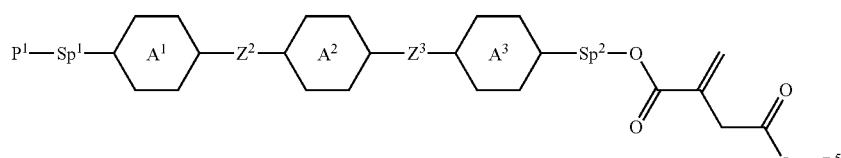
(1-2)

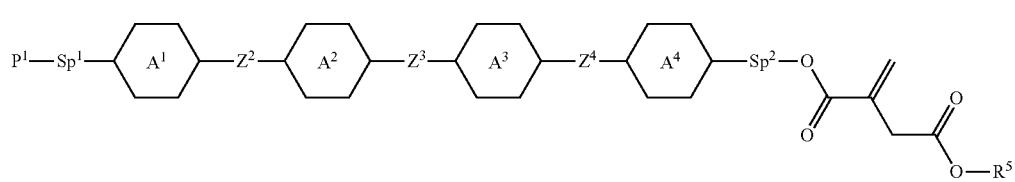
(1-3)

-continued
(1e)
(1f)
(1g)
(1h) 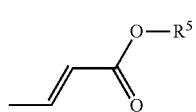

wherein, in formulas (1-1) to (1-3), $R^5$ is hydrogen or alkyl having 1 to 15 carbons, and in the alkyl, at least one piece of —CH$_2$— may be replaced by —O— or —S—, and at least one piece of —(CH$_2$)$_2$— may be replaced by —CH=CH— or —C≡C—, and in the groups, at least one hydrogen may be replaced by halogen;

ring $A^1$, ring $A^2$, ring $A^3$ and ring $A^4$ are independently 1,4-cyclohexylene, 1,4-phenylene, naphthalene-2,6-diyl, pyrimidine-2,5-diyl, pyridine-2,5-diyl, fluorene-2,7-diyl, phenanthrene-2,7-diyl or anthracene-2,6-diyl, and in the rings, at least one hydrogen may be replaced by fluorine, chlorine, alkyl having 1 to 12 carbons, alkenyl having 2 to 12 carbons, alkoxy having 1 to 11 carbons or alkenyloxy having 2 to 11 carbons, and in the groups, at least one hydrogen may be replaced by fluorine or chlorine;

$Z^2$, $Z^3$ and $Z^4$ are independently a single bond, —(CH$_2$)$_2$—, —C≡C—, —COO—, —OCO—, —CF$_2$O—, —OCF$_2$—, —CH$_2$O—, —OCH$_2$—, —CF=CF—, —CH=CHCOO—, —OCOCH=CH—, —CH=CH—, —CH=CHCO— or —COCH=CH—, in which at least one in $Z^2$, $Z^3$ and $Z^4$ is —COO—, —OCO—, —CH=CHCOO—, —OCOCH=CH—, —CH=CH—, —CH=CHCO— or —COCH=CH—;

Sp$^1$ and Sp$^2$ are independently a single bond or alkylene having 1 to 10 carbons, and in the alkylene, at least one piece of —CH$_2$— may be replaced by —O—, —COO—, —OCOO— or —OCO—, and at least one piece of —(CH$_2$)$_2$— may be replaced by —CH=CH—, and in the groups, at least one hydrogen may be replaced by fluorine or chlorine; and P$^1$ is a group represented by any one of formulas (1b) to (1i);

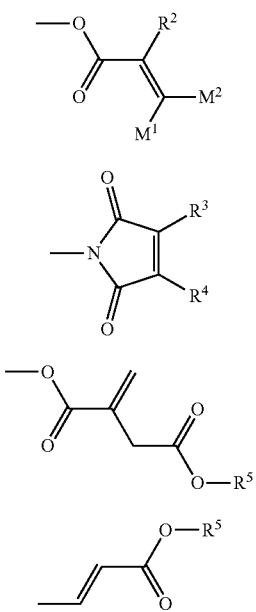

(1b)
(1c)
(1d)
(1e)

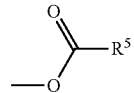

(1f)

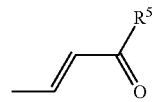

(1g)

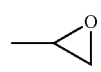

(1h)

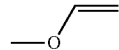

(1i)

wherein

M$^1$ and M$^2$ are independently hydrogen, halogen, alkyl having 1 to 5 carbons, or alkyl having 1 to 5 carbons in which at least one hydrogen is replaced by halogen;

R$^2$ is hydrogen, halogen or alkyl having 1 to 5 carbons, and in the alkyl, at least one hydrogen may be replaced by halogen, and at least one piece of —CH$_2$— may be replaced by —O—; and R$^3$, R$^4$ and R$^5$ are independently hydrogen or straight-chain, branched-chain or cyclic alkyl having 1 to 15 carbons, and in the alkyl, at least one piece of —CH$_2$— may be replaced by —O— or —S—, and at least one piece of —(CH$_2$)$_2$— may be replaced by —CH=CH— or —C≡C—, and in the groups, at least one hydrogen may be replaced by halogen.

Item 4. The compound according to any one of items 1 to 3, represented by any one of formulas (1-1-1), (1-2-1) and (1-3-1):

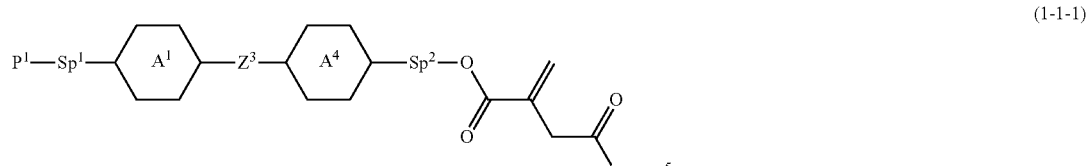

(1-1-1)

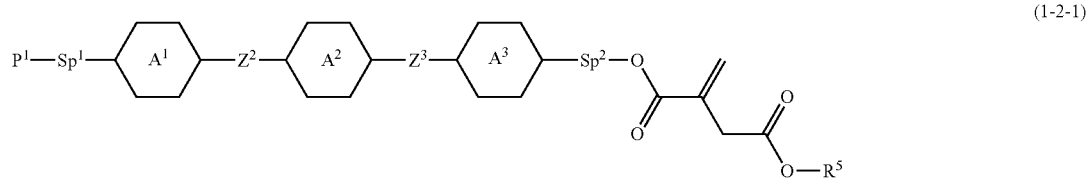

(1-2-1)

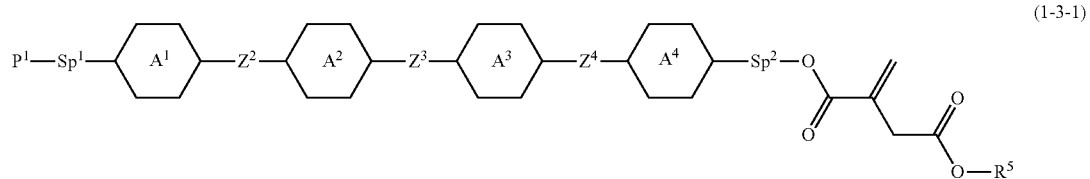

(1-3-1)

wherein, in formulas (1-1-1), (1-2-1) and (1-3-1), $R^5$ is hydrogen or alkyl having 1 to 15 carbons, and in the alkyl, at least one —$CH_2$— may be replaced by —O— or —S—, and at least one —$(CH_2)_2$— may be replaced by —CH=CH— or —C≡C—, and in the groups, at least one hydrogen may be replaced by halogen;

ring $A^1$, ring $A^2$, ring $A^3$ and ring $A^4$ are independently 1,4-cyclohexylene, 1,4-phenylene or fluorene-2,7-diyl, and in the rings, at least one hydrogen may be replaced by fluorine, chlorine, alkyl having 1 to 12 carbons, alkenyl having 2 to 12 carbons, alkoxy having 1 to 11 carbons or alkenyloxy having 2 to 11 carbons;

$Z^2$, $Z^3$ and $Z^4$ are independently a single bond, —COO—, —OCO—, —CH=CHCOO—, —OCOCH=CH—, —CH=CH—, —CH=CHCO— or —COCH=CH—, in which at least one in $Z^2$, $Z^3$ and $Z^4$ is —COO—, —OCO—, —CH=CHCOO—, —OCOCH=CH—, —CH=CH—, —CH=CHCO— or —COCH=CH—;

$Sp^1$ and $Sp^2$ are independently a single bond or alkylene having 1 to 10 carbons, and in the alkylene, at least one —$CH_2$— may be replaced by —O—, —COO—, —OCOO— or —OCO—, and at least one —$(CH_2)_2$— may be replaced by —CH=CH—; and $P^1$ is a group represented by any one of formula (1b), (1c) or (1d);

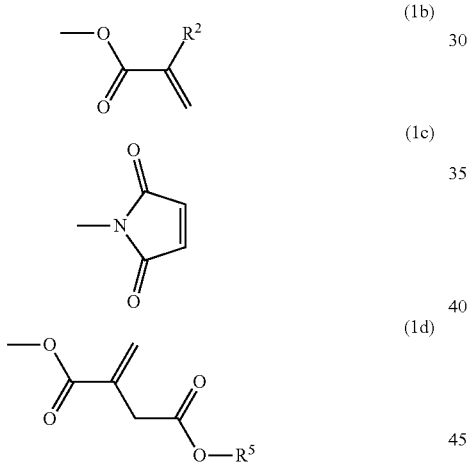

wherein, in formulas (1b) to (1d), $R^2$ is hydrogen, halogen or alkyl having 1 to 5 carbons, and in the alkyl, at least one hydrogen may be replaced by halogen, and at least one —$CH_2$— may be replaced by —O—; and $R^5$ is hydrogen or alkyl having 1 to 15 carbons, and in the alkyl, at least one —$CH_2$— may be replaced by —O— or —S—, and at least one —$(CH_2)_2$— may be replaced by —CH=CH— or —C≡C—, and in the groups, at least one hydrogen may be replaced by halogen.

Item 5. The compound according to item 4, represented by any one of formula (1-1-1), (1-2-1) or (1-3-1), wherein any one of $Z^2$, $Z^3$ or $Z^4$ is —COO— or —OCO—.

Item 6. The compound according to item 4, represented by any one of formula (1-1-1), (1-2-1) or (1-3-1), wherein any one of $Z^2$, $Z^3$ or $Z^4$ is —CH=CHCOO—, —OCOCH=CH—, —CH=CH—, —CH=CHCO— or —COCH=CH—.

Item 7. The compound according to any one of items 1 to 4, represented by formula (1-A):

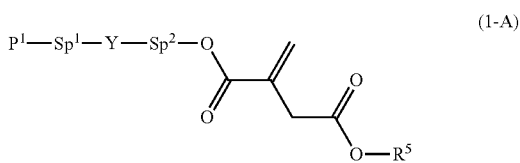

wherein $P^1$ is a group represented by formula (1b), (1c) or (1d);

$Sp^1$ and $Sp^2$ are independently a single bond or alkylene having 1 to 10 carbons, and in the alkylene, at least one —$CH_2$— may be replaced by —O—, —COO—, —OCOO— or —OCO—, and at least one —$(CH_2)_2$— may be replaced by —CH=CH—; and $R^5$ is hydrogen or alkyl having 1 to 15 carbons, and in the alkyl, at least one —$CH_2$— may be replaced by —O— or —S—, and at least one —$(CH_2)_2$— may be replaced by —CH=CH— or —C≡C—, and in the groups, at least one hydrogen may be replaced by halogen;

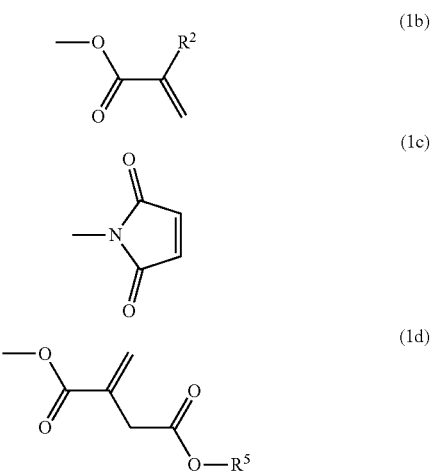

wherein, in formula (1b), $R^2$ is hydrogen, halogen or alkyl having 1 to 5 carbons, and in the alkyl, at least one hydrogen may be replaced by halogen, and at least one —$CH_2$— may be replaced by —O—;

in formula (1d), $R^5$ is hydrogen or alkyl having 1 to 15 carbons, and in the alkyl, at least one —$CH_2$— may be replaced by —O— or —S—, and at least one —$(CH_2)_2$— may be replaced by —CH=CH— or —C≡C—, and in the groups, at least one hydrogen may be replaced by halogen; and Y is a group represented by any one of formulas (MES-1-01) to (MES-1-10);

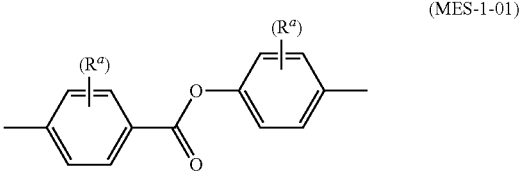

(MES-1-02)
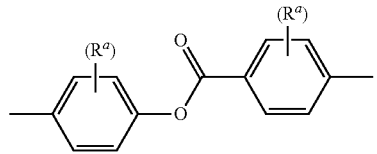

(MES-1-03)
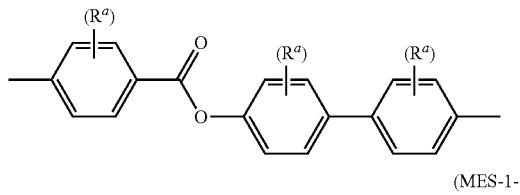

(MES-1-04)
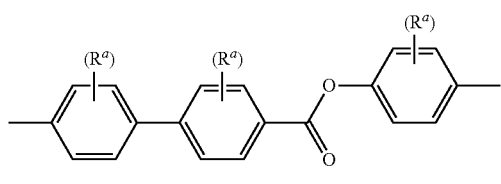

(MES-1-05)
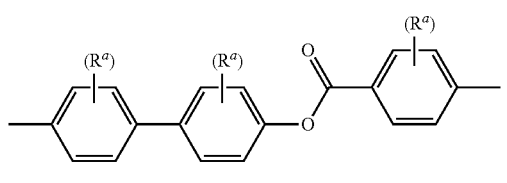

(MES-1-06)
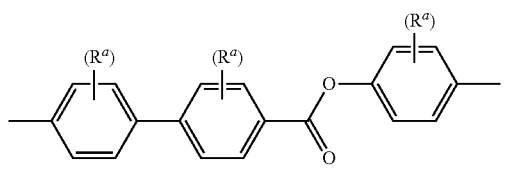

(MES-1-07)
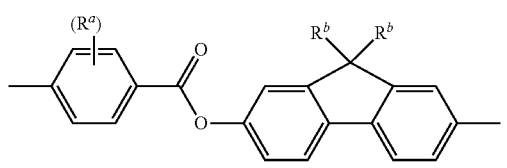

(MES-1-08)
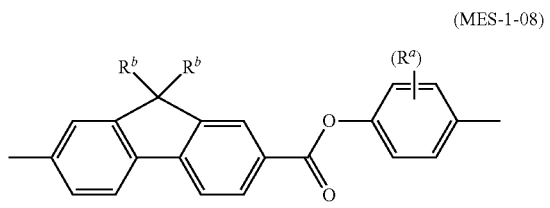

(MES1-09)
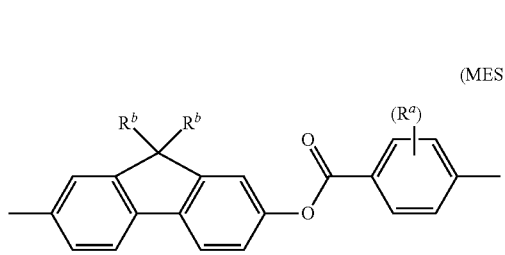

(MES-1-10)
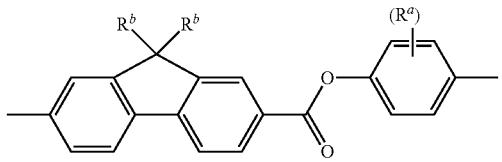

wherein
$R^a$ is independently fluorine, chlorine, methyl or ethyl;
$R^b$ is independently hydrogen, fluorine, methyl or ethyl; and
a representation of connecting 1,4-phenylene with ($R^a$) by a straight line as shown below in the formulas indicates 1,4-phenylene in which one or two hydrogens may be replaced by $R^a$.

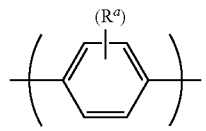

Item 8. The compound according to any one of items 1 to 4, represented by formula (1-A):

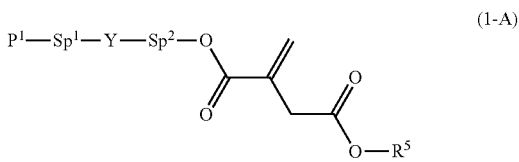
(1-A)

wherein
$P^1$ is a group represented by formula (1b), (1c) or (1d);

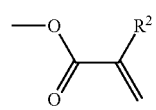
(1b)

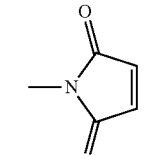
(1c)

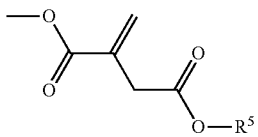
(1d)

wherein
$Sp^1$ and $Sp^2$ are independently a single bond or alkylene having 1 to 10 carbons, and in the alkylene, at least one —$CH_2$— may be replaced by —O—, —COO—, —OCOO— or —OCO—, and at least one —$(CH_2)_2$— may be replaced by —CH=CH—;

$R^2$ is hydrogen, halogen or alkyl having 1 to 5 carbons, and in the alkyl, at least one hydrogen may be replaced by halogen, and at least one —$CH_2$— may be replaced by —O—;

$R^5$ is independently hydrogen or alkyl having 1 to 15 carbons, and in the alkyl, at least one —$CH_2$— may be replaced by —O— or —S—, and at least one —$(CH_2)_2$— may be replaced by —CH=CH— or —C≡C—, and in the groups, at least one hydrogen may be replaced by halogen; and Y is a group represented by any one of (MES-2-01) to (MES-2-16);

(MES-2-01)
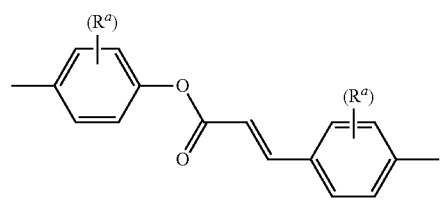

(MES-2-02)
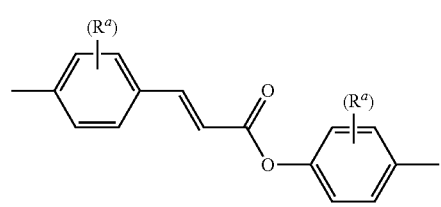

(MES-2-04)
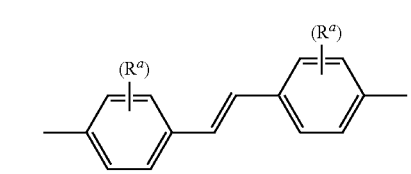

(MES-2-05)
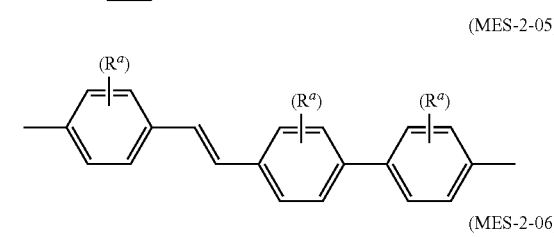

(MES-2-06)
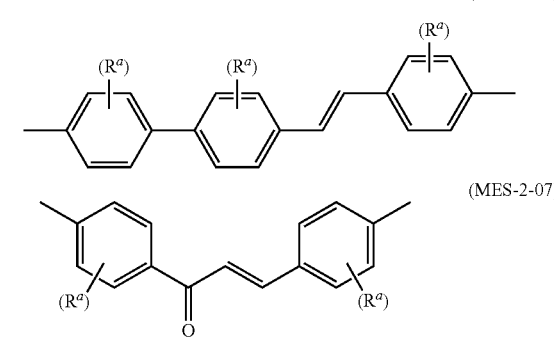

(MES-2-07)
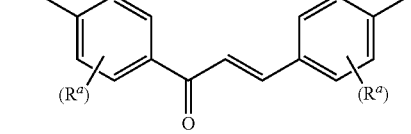

(MES-2-08)
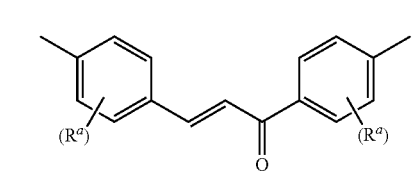

-continued (MES-2-09)
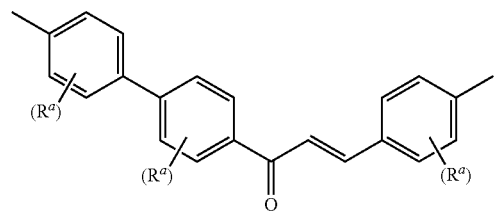

(MES-2-10)
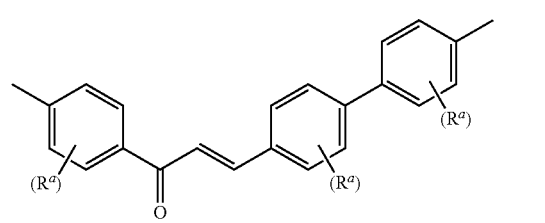

(MES-2-11)
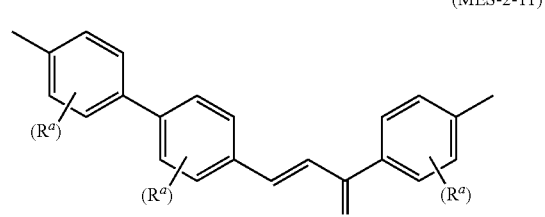

(MES-2-12)
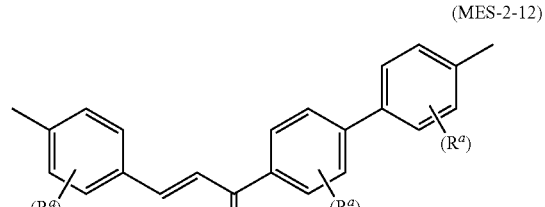

(MES-2-13)
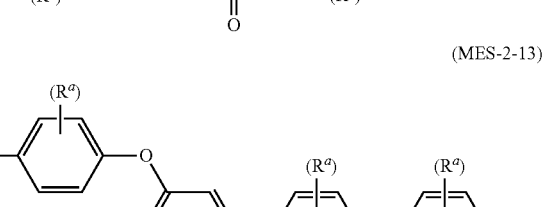

(MES-2-14)
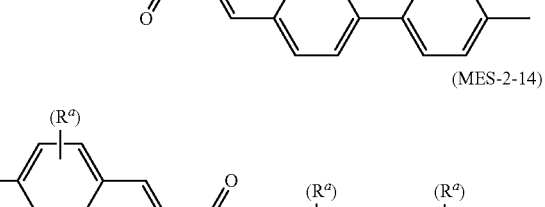

(MES-2-15)
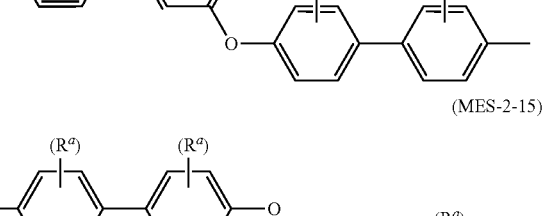

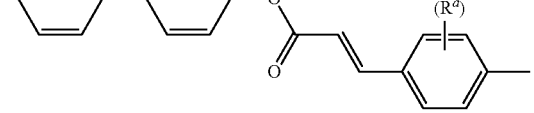

-continued (MES-2-16)
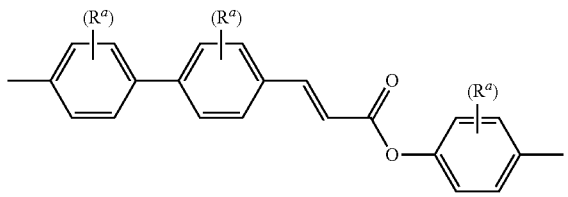

wherein $R^a$ is independently fluorine, chlorine, methyl or ethyl; and a representation of connecting 1,4-phenylene with ($R^a$) by a straight line as shown below in the formulas indicates 1,4-phenylene in which one or two hydrogens may be replaced by $R^a$.

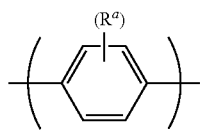

Item 9. A liquid crystal composition, containing at least one compound according to any one of items 1 to 8.

Item 10. The liquid crystal composition according to item 9, further containing at least one compound selected from the group of compounds represented by formulas (2) to (4):

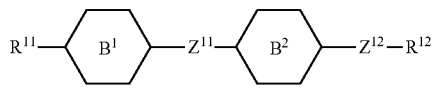
(2)

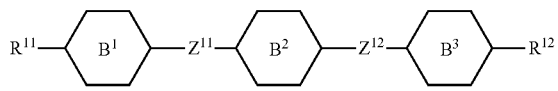
(3)

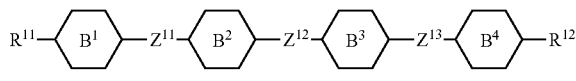
(4)

wherein, in formulas (2) to (4), $R^{11}$ and $R^{12}$ are independently alkyl having 1 to 10 carbons or alkenyl having 2 to 10 carbons, and in the alkyl and the alkenyl, at least one —$CH_2$— may be replaced by —O—, and at least one hydrogen may be replaced by fluorine;

ring $B^1$, ring $B^2$, ring $B^3$ and ring $B^4$ are independently 1,4-cyclohexylene, 1,4-phenylene, 2-fluoro-1,4-phenylene, 2,5-difluoro-1,4-phenylene or pyrimidine-2,5-diyl; and $Z^{11}$, $Z^{12}$ and $Z^{13}$ are independently a single bond, —$CH_2CH_2$—, —CH=CH—, —C≡C— or —COO—.

Item 11. The liquid crystal composition according to item 9 or 10, further containing at least one compound selected from the group of compounds represented by formulas (5) to (7):

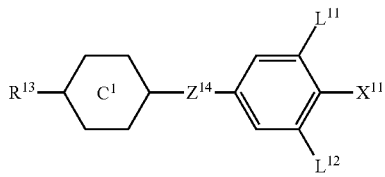
(5)

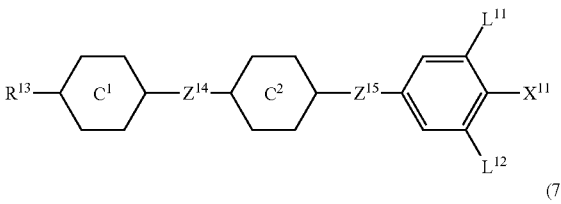
(6)

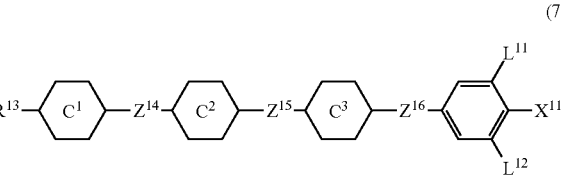
(7)

wherein, in formulas (5) to (7), $R^{13}$ is alkyl having 1 to 10 carbons or alkenyl having 2 to 10 carbons, and in the alkyl and the alkenyl, at least one —$CH_2$— may be replaced by —O—, and at least one hydrogen may be replaced by fluorine;

$X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;

ring $C^1$, ring $C^2$ and ring $C^3$ are independently 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;

$Z^{14}$, $Z^{15}$ and $Z^{16}$ are independently a single bond, —$CH_2CH_2$—, —CH=CH—, —C≡C—, —COO—, —$CF_2O$—, —$OCF_2$—, —$CH_2O$—, —CF=CF—, —CH=CF— or —($CH_2$) 4-; and $L^{11}$ and $L^{12}$ are independently hydrogen or fluorine.

Item 12. The liquid crystal composition according to any one of items 9 to 11, further containing at least one compound selected from the group of compounds represented by formula (8):

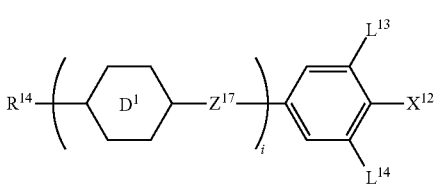
(8)

wherein, in formula (8), $R^{14}$ is alkyl having 1 to 10 carbons or alkenyl having 2 to 10 carbons, and in the alkyl and the alkenyl, at least one —$CH_2$— may be replaced by —O—, and at least one hydrogen may be replaced by fluorine;

$X^{12}$ is —C≡N or —C≡C—C≡N;

ring $D^1$ is 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;

$Z^{17}$ is a single bond, —$CH_2CH_2$—, —C≡C—, —COO—, —$CF_2O$—, —$OCF_2$— or —$CH_2O$—;

$L^{13}$ and $L^{14}$ are independently hydrogen or fluorine; and
i is 1, 2, 3 or 4.

Item 13. The liquid crystal composition according to any one of items 9 to 12, further containing at least one compound selected from the group of compounds represented by formulas (9) to (15):

$L^{15}$ and $L^{16}$ are independently fluorine or chlorine;
$S^{11}$ is hydrogen or methyl;
X is —CHF— or —CF$_2$—; and
j, k, m, n, p, q, r and s are independently 0 or 1, a sum of k, m, n and p is 1 or 2, a sum of q, r and s is 0, 1, 2 or 3, and t is 1, 2 or 3.

(9)
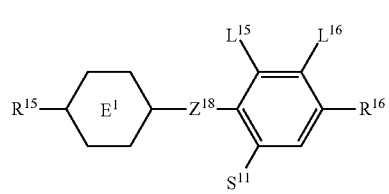

(10)
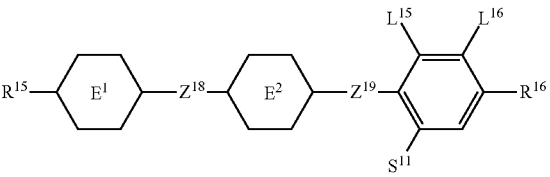

(11)
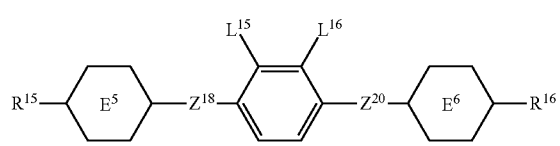

(12)
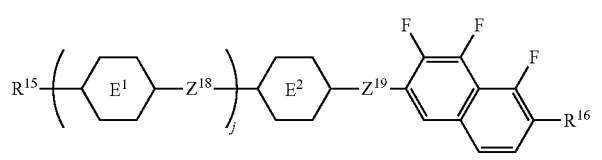

(13)
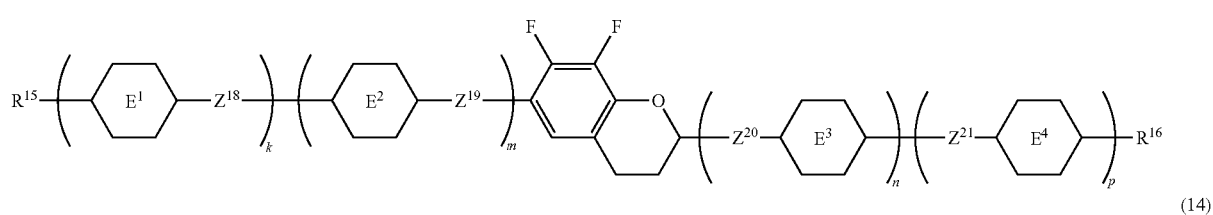

(14)
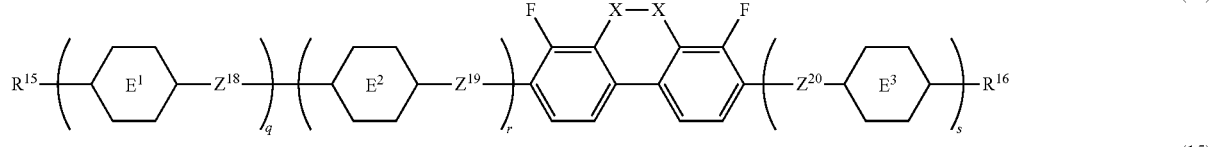

(15)
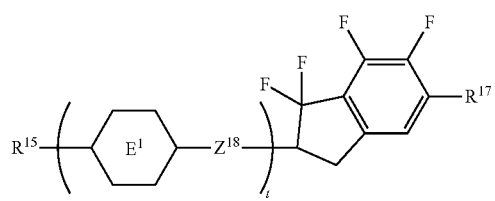

wherein, in formulas (9) to (15), $R^{15}$ and $R^{16}$ are independently alkyl having 1 to 10 carbons or alkenyl having 2 to 10 carbons, and in the alkyl and the alkenyl, at least one —CH$_2$— may be replaced by —O—, and at least one hydrogen may be replaced by fluorine;

$R^{17}$ is hydrogen, fluorine, alkyl having 1 to 10 carbons or alkenyl having 2 to 10 carbons, and in the alkyl and the alkenyl, at least one —CH$_2$— may be replaced by —O—, and at least one hydrogen may be replaced by fluorine;

ring $E^1$, ring $E^2$, ring $E^3$ and ring $E^4$ are independently 1,4-cyclohexylene, 1,4-cyclohexenylene, 1,4-phenylene in which at least one hydrogen may be replaced by fluorine, tetrahydropyran-2,5-diyl or decahydronaphthalene-2,6-diyl;

ring $E^5$ and ring $E^6$ are independently 1,4-cyclohexylene, 1,4-cyclohexenylene, 1,4-phenylene, tetrahydropyran-2,5-diyl or decahydronaphthalene-2,6-diyl;

$Z^{18}$, $Z^{19}$, $Z^{20}$ and $Z^{21}$ are independently a single bond, —CH$_2$CH$_2$—, —COO—, —CH$_2$O—, —OCF$_2$— or —OCF$_2$CH$_2$CH$_2$—;

Item 14. The liquid crystal composition according to any one of items 9 to 13, further containing at least one polymerizable compound selected from the group of compounds represented by formula (16):

(16)
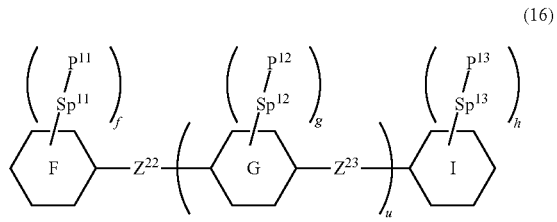

wherein, in formula (16), ring F and ring I are independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in the rings, at least one hydrogen may be replaced by halogen, alkyl having 1 to 12 carbons, or alkyl having 1 to 12 carbons in which at least one hydrogen is replaced by halogen;

ring G is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one hydrogen may be replaced by halogen, alkyl having 1 to 12 carbons, alkoxy having 1 to 12 carbons, or alkyl having 1 to 12 carbons in which at least one hydrogen is replaced by halogen;

$Z^{22}$ and $Z^{23}$ are independently a single bond or alkylene having 1 to 10 carbons, and in the alkylene, at least one —$CH_2$— may be replaced by —O—, —CO—, —COO— or —OCO—, and at least one —$CH_2CH_2$— may be replaced by —CH=CH—, —C(CH$_3$)=CH—, —CH=C(CH$_3$)— or —C(CH$_3$)=C(CH$_3$)—, and in the groups, at least one hydrogen may be replaced by fluorine or chlorine; and $P^{11}$, $P^{12}$ and $P^{13}$ are independently a polymerizable group selected from the group of groups represented by formulas (P-1) to (P-5);

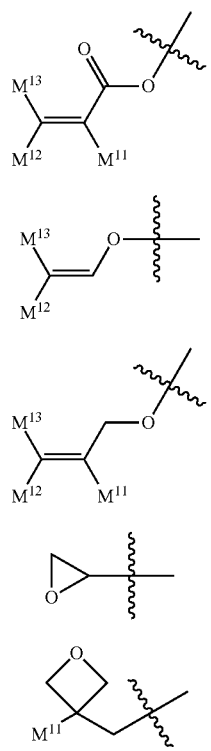

wherein $M^1 M^{12}$ and $M^{13}$ are independently hydrogen, fluorine, alkyl having 1 to 5 carbons, or alkyl having 1 to 5 carbons in which at least one hydrogen is replaced by fluorine or chlorine;

$Sp^{11}$, $Sp^{12}$ and $Sp^{13}$ are independently a single bond or alkylene having 1 to 10 carbons, and in the alkylene, at least one —$CH_2$— may be replaced by —O—, —COO—, —OCO— or —OCOO—, and at least one —$CH_2CH_2$— may be replaced by —CH=CH— or —C≡C—, and in the groups, at least one hydrogen may be replaced by fluorine or chlorine;

u is 0, 1 or 2; and f, g and h are independently 0, 1, 2, 3 or 4, and a sum of f, g and h is 2 or more.

Item 15. The liquid crystal composition according to any one of items 9 to 14, further containing at least one polymerizable compound selected from the group of compounds represented by formulas (16-1) to (16-27):

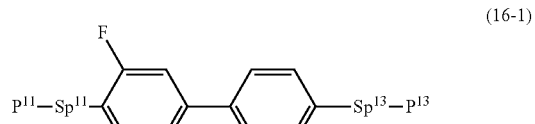

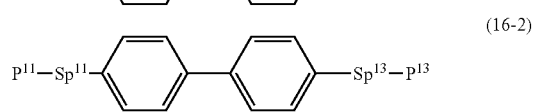

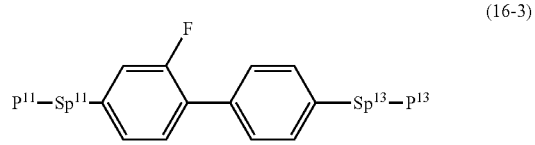

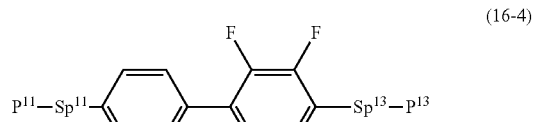

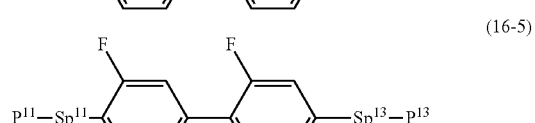

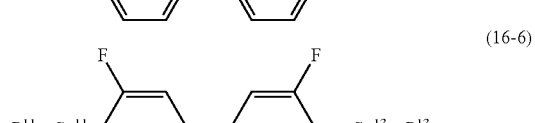

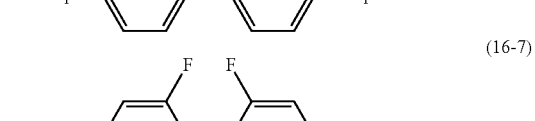

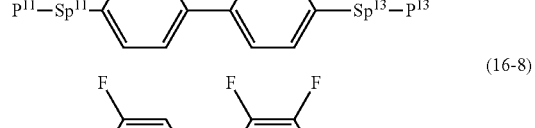

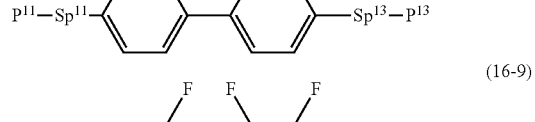

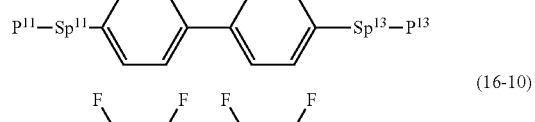

-continued
(16-11)
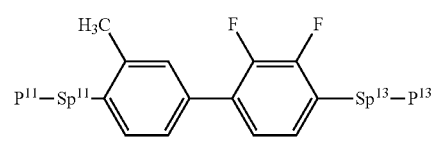
(16-12)
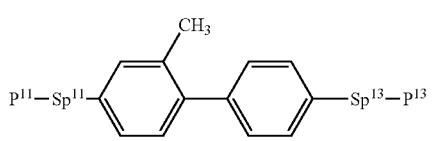
(16-13)
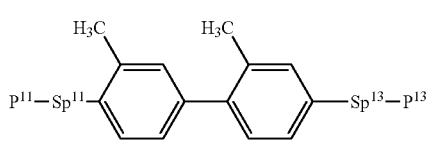
(16-14)
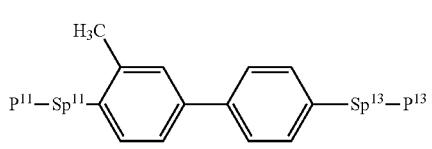
(16-15)
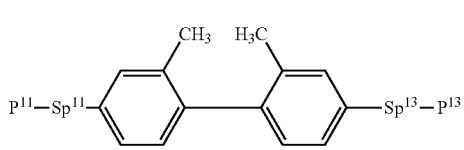
(16-16)
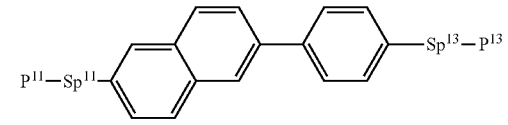
(16-17)
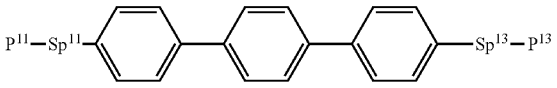
(16-18)
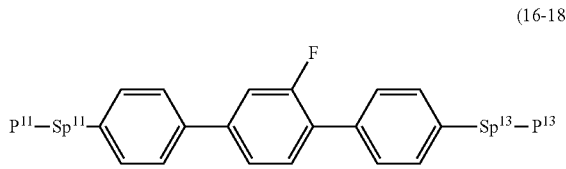
(16-19)

(16-20)
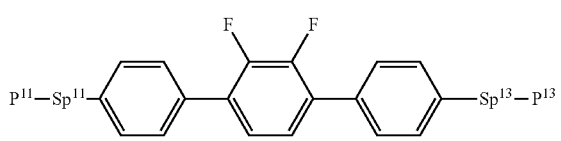
(16-21)
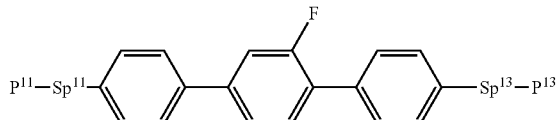
(16-22)
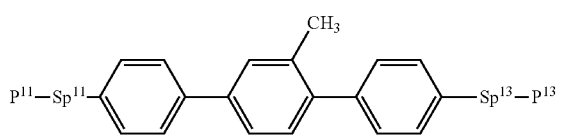
(16-23)
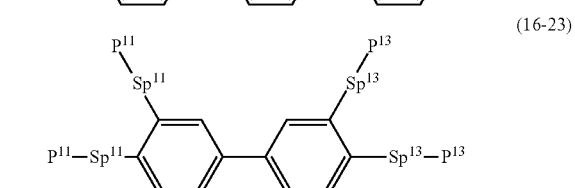
(16-24)
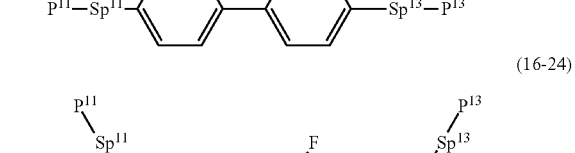
(16-25)
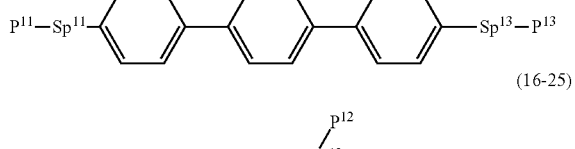
(16-26)
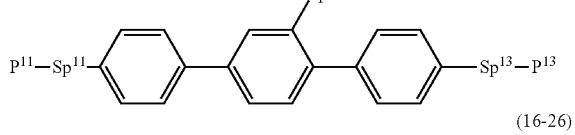
(16-27)
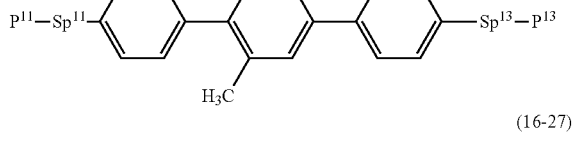
wherein, in formulas (16-1) to (16-27),
$P^{11}$, $P^{12}$ and $P^{13}$ are independently a polymerizable group selected from the group of groups represented by formulas (P-1) to (P-3), in which $M^{11}$, $M^{12}$ and $M^{13}$ are independently hydrogen, fluorine, alkyl having 1 to 5 carbons, or alkyl having 1 to 5 carbons in which at least one hydrogen is replaced by halogen;

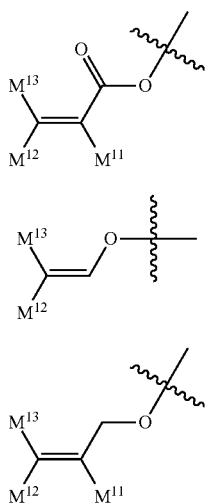

wherein
$Sp^{11}$, $Sp^{12}$ and $Sp^{13}$ are independently a single bond or alkylene having 1 to 10 carbons, and in the alkylene, at least one —$CH_2$— may be replaced by —O—, —COO—, —OCO— or —OCOO—, and at least one —$CH_2CH_2$— may be replaced by —CH=CH— or —C≡C—, and in the groups, at least one hydrogen may be replaced by fluorine or chlorine.

Item 16. The liquid crystal composition according to any one of items 9 to 15, further containing at least one of a polymerizable compound other than formulas (1) and (16), a polymerization initiator, a polymerization inhibitor, an optically active compound, an antioxidant, an ultraviolet light absorber, a light stabilizer, a heat stabilizer and an antifoaming agent.

Item 17. A liquid crystal display device, including at least one liquid crystal composition according to any one of items 9 to 16.

The invention further includes the following items: (a) the liquid crystal composition, further containing at least two of additives such as a polymerizable compound, a polymerization initiator, a polymerization inhibitor, an optically active compound, an antioxidant, an ultraviolet light absorber, a light stabilizer, a heat stabilizer and an antifoaming agent; (b) a polymerizable composition, prepared by adding a polymerizable compound different from compound (1) or compound (16) to the liquid crystal composition; (c) the polymerizable composition prepared by adding compound (1) and compound (16) to the liquid crystal composition; (d) a liquid crystal composite prepared by polymerizing the polymerizable composition; (e) a polymer sustained alignment mode device containing the liquid crystal composite; and (f) a polymer sustained alignment mode device, prepared by using a polymerizable composition prepared by adding compound (1), compound (16), and a polymerizable compound different from compound (1) or compound (16) to the liquid crystal composition.

An aspect of compound (1), synthesis of compound (1), the liquid crystal composition and the liquid crystal display device will be described in the following order.

1. Aspect of Compound (1)

Compound (1) of the invention has a mesogen moiety formed of at least one ring and an itaconate group. The itaconate group noncovalently interacts with a substrate surface of glass (or metal oxide), and therefore compound (1) tends to be unevenly distributed in a vicinity of the substrate surface in comparison with a compound having no itaconate group, and is useful. Thereby, an addition amount thereof becomes small. One of applications is as an additive for the liquid crystal composition used in the liquid crystal display device. Compound (1) is added for the purpose of horizontally controlling alignment of liquid crystal molecules. Such an additive preferably has chemical stability under conditions in which the additive is sealed in the device, high solubility in the liquid crystal composition, and a large voltage holding ratio when the compound is used in the liquid crystal display device. Compound (1) satisfies such characteristics to a significant extent.

Preferred examples of compound (1) will be described. Preferred examples of $R^1$, $Z^1$ to $Z^5$, $A^1$ to $A^5$, $Sp^1$, $Sp^2$, $P^2$ and a in compound (1) apply also to a subordinate formula of formula (1) for compound (1). In compound (1), characteristics can be arbitrarily adjusted by suitably combining kinds of the groups. Compound (1) may contain a larger amount of isotope such as $^2H$ (deuterium) and $^{13}C$ than an amount of natural abundance because no significant difference exists in the characteristics of the compound.

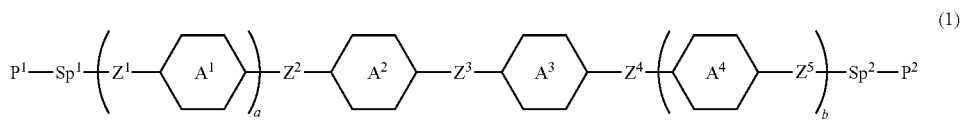

Rings $A^1$, $A^2$, $A^3$ and $A^4$ are independently 1,4-cyclohexylene, 1,4-cyclohexenylene, 1,4-phenylene, naphthalene-2,6-diyl, decahydronaphthalene-2,6-diyl, 1,2,3,4-tetrahydronaphthalene-2,6-diyl, tetrahydropyran-2,5-diyl, 1,3-dioxane-2,5-diyl, pyrimidine-2,5-diyl, pyridine-2,5-diyl, fluorene-2,7-diyl, phenanthrene-2,7-diyl, anthracene-2,6-diyl, perhydrocyclopenta[a]phenanthrene-3,17-diyl or 2,3,4,7,8,9,10,11,12,13,14,15,16,17-tetradecahydrocyclopenta[a]phenanthrene-3,17-diyl, and in the rings, at least one hydrogen may be replaced by fluorine, chlorine, alkyl having 1 to 12 carbons, alkenyl having 2 to 12 carbons, alkoxy having 1 to 11 carbons or alkenyloxy having 2 to 11 carbons, and in the groups, at least one hydrogen may be replaced by fluorine or chlorine, and when a is 2, two of ring $A^1$ may be different, and when b is 2, two of ring $A^4$ may be different.

Preferred rings $A^1$, $A^2$, $A^3$ and $A^4$ are 1,4-cyclohexylene, 1,4-cyclohexenylene, 1,4-phenylene, naphthalene-2,6-diyl, decahydronaphthalene-2,6-diyl, 1,2,3,4-tetrahydronaphthalene-2,6-diyl, tetrahydropyran-2,5-diyl, 1,3-dioxane-2,5-diyl, pyrimidine-2,5-diyl, pyridine-2,5-diyl, perhydrocyclopenta[a]phenanthrene-3,17-diyl or 2,3,4,7,8,9,10,11,12,13,14,15,16,17-tetradecahydrocyclopenta[a]phenanthrene-3,17-diyl, and in the rings, at least one hydrogen may be replaced by fluorine, chlorine, alkyl having 1 to 12 carbons, alkenyl having 2 to 12 carbons, alkoxy having 1 to 11 carbons or alkenyloxy having 2 to 11 carbons, and in the groups, at least one hydrogen may be replaced by fluorine or chlorine. Further preferred rings $A^1$, $A^2$, $A^3$ and $A^4$ are 1,4-cyclohexylene, 1,4-phenylene, perhydrocyclopenta[a]phenanthrene-3,17-diyl or 2,3,4,7,8,9,10,11,12,13,14,15,16,17-tetradecahydrocyclopenta[a]phenanthrene-3,17-diyl, and in the rings, at least one hydrogen may be replaced by fluorine or alkyl having 1 to 5 carbons. Particularly preferred rings $A^1$, $A^2$, $A^3$ and $A^4$ are 1,4-cyclohexylene, 1,4-phenylene or perhydrocyclopenta[a]phenanthrene-3,17-diyl, and in the rings, at least one hydrogen may be replaced by fluorine, methyl or ethyl.

$Z^1$, $Z^2$, $Z^3$, $Z^4$ and $Z^5$ are independently a single bond or alkylene having 1 to 10 carbons, and in the alkylene, at least one —$CH_2$— may be replaced by —O—, —CO—, —COO—, —OCO— or —OCOO—, and at least one —$(CH_2)_2$— may be replaced by —CH=CH— or —C≡C—, and in the groups, at least one hydrogen may be replaced by halogen, in which at least one in $Z^2$, $Z^3$ or $Z^4$ is any one of —COO—, —OCO—, —CH=CHCOO—, —OCOCH=CH—, —CH=CH—, —CH=CHCO— and —COCH=CH—, and when a is 2, two $Z^1$s may be different, and two $Z^5$s may be different.

Preferred $Z^1$, $Z^2$, $Z^3$, $Z^4$ and $Z^5$ are a single bond, —$(CH_2)_2$—, —CH=CH—, —C≡C—, —COO—, —OCO—, —$CF_2$O—, —$OCF_2$—, —$CH_2$O—, —$OCH_2$— or —CF=CF—. Further preferred $Z^1$, $Z^2$, $Z^3$, $Z^4$ and $Z^5$ are a single bond, —$(CH_2)_2$— or —CH=CH—. Particularly preferred $Z^1$, $Z^2$, $Z^3$, $Z^4$ and $Z^5$ are a single bond.

$Sp^1$ and $Sp^2$ are a single bond or alkylene having 1 to 10 carbons, and in the alkylene, at least one —$CH_2$— may be replaced by —O—, —CO—, —COO—, —OCO— or —OCOO—, and at least one —$(CH_2)_2$— may be replaced by —CH=CH— or —C≡C—, and in the groups, at least one hydrogen may be replaced by halogen.

Preferred $Sp^1$ and $Sp^2$ are a single bond, alkylene having 1 to 6 carbons, alkylene having 1 to 6 carbons in which one —$CH_2$— is replaced by —O—, or —OCOO—. Further preferred $Sp^1$ and $Sp^2$ are alkylene having 1 to 6 carbons or —OCOO—.

$P^1$ is a group represented by any one of formulas (1b) to (1i).

Preferred $P^1$ is represented by formulas (1b), (1c) and (1d).

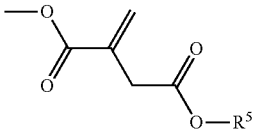

(1b)

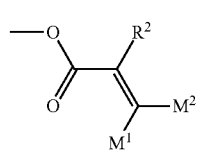

(1c)

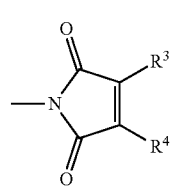

(1d)

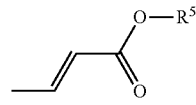

(1e)

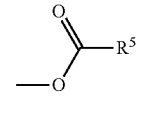

(1f)

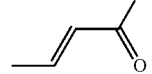

(1g)

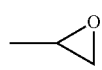

(1h)

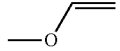

(1i)

In formulas (1b) to (1i), $M^1$ and $M^2$ are independently hydrogen, halogen, alkyl having 1 to 5 carbons, or alkyl having 1 to 5 carbons in which at least one hydrogen is replaced by halogen.

Preferred $M^1$ or $M^2$ is hydrogen, fluorine, methyl, ethyl or trifluoromethyl. Further preferred $M^1$ or $M^2$ is hydrogen.

$R^2$ is hydrogen, halogen or alkyl having 1 to 5 carbons, and in the alkyl, at least one hydrogen may be replaced by halogen, and at least one —$CH_2$— may be replaced by —O—.

Preferred $R^2$ is hydrogen, fluorine, methyl, ethyl, methoxymethyl or trifluoromethyl. Further preferred $R^2$ is hydrogen.

$R^3$, $R^4$ and $R^5$ are independently hydrogen or straight-chain, branched-chain or cyclic alkyl having 1 to 15 carbons, and in the alkyl, at least one —$CH_2$— may be replaced by —O— or —S—, and at least one —$(CH_2)_2$— may be replaced by —CH=CH— or —C≡C—, and in the groups, at least one hydrogen may be replaced by halogen.

Preferred $R^3$, $R^4$ and $R^5$ are hydrogen, straight-chain alkyl having 1 to 10 carbons, straight-chain alkenyl having 2 to 10 carbons, straight-chain alkoxy having 1 to 10 carbons or cyclic alkyl having 3 to 6 carbons. Further preferred $R^3$, $R^4$ and $R^5$ are hydrogen, straight-chain alkyl having 2 to 6 carbons, straight-chain alkenyl having 2 to 6 carbons, straight-chain alkoxy having 1 to 5 carbons or cyclic alkyl having 4 to 6 carbons.

Then, expressions: $0 \leq a+b \leq 2$ preferably hold.

Preferred examples of compound (1) include formulas (1-1) to (1-3).

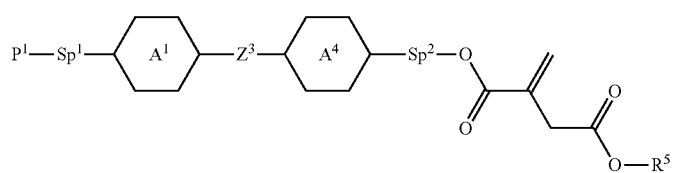
(1-1)

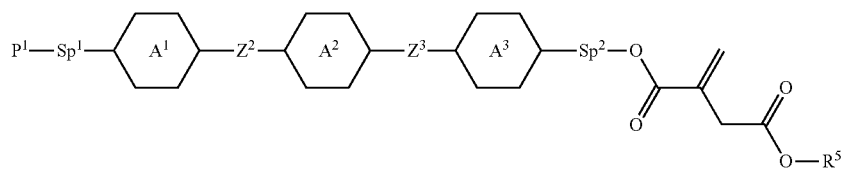
(1-2)

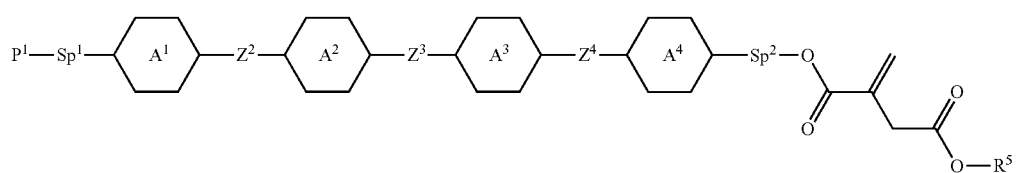
(1-3)

$R^5$ is hydrogen or alkyl having 1 to 15 carbons, and in the alkyl, at least one —CH$_2$— may be replaced by —O— or —S—, and at least one —(CH$_2$)$_2$— may be replaced by —CH=CH— or —C≡C—, and in the groups, at least one hydrogen may be replaced by halogen.

Definition of other symbols in formulas (1-1) to (1-3) and preferred examples are identical to compound (1). Moreover, specific examples of compound (1) will be described in Examples described later.

In formulas (2) to (15), component compounds of the liquid crystal composition are shown. Compounds (2) to (4) have small dielectric anisotropy. Compounds (5) to (7) have large positive dielectric anisotropy. Compound (8) has a cyano group, and therefore has larger positive dielectric anisotropy. Compounds (9) to (15) have large negative dielectric anisotropy. Specific examples of the compounds will be described later.

In compound (16), $P^{11}$, $P^{12}$ and $P^{13}$ are independently a polymerizable group.

Preferred $P^{11}$, $P^{12}$ and $P^{13}$ are a polymerizable group selected from the group of groups represented by formulas (P-1) to (P-5). Further preferred $P^{11}$, $P^{12}$ and $P^{13}$ are group (P-1), group (P-2) or group (P-3). Particularly preferred group (P-1) is —OCO—CH=CH$_2$ or —OCO—C(CH$_3$)=CH$_2$. A wavy line in group (P-1) to group (P-5) represents a site to form a bonding.

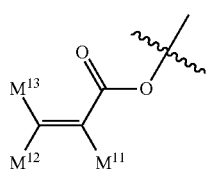
(P-1)

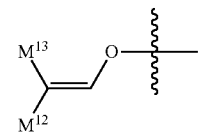
(P-2)

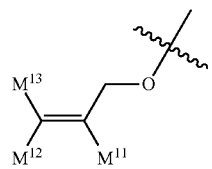
(P-3)

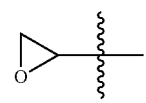
(P-4)

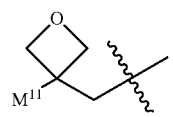
(P-5)

In the groups (P-1) to (P-5), $M^{11}$, $M^{12}$ and $M^{13}$ are independently hydrogen, fluorine, alkyl having 1 to 5 carbons, or alkyl having 1 to 5 carbons in which at least one hydrogen is replaced by halogen.

Preferred $M^{11}$, $M^{12}$ and $M^{13}$ are hydrogen or methyl for increasing reactivity. Further preferred $M^{11}$ is methyl, and further preferred $M^{12}$ and $M^{13}$ are hydrogen.

$Sp^{11}$, $Sp^{12}$ and $Sp^{13}$ are independently a single bond or alkylene having 1 to 10 carbons, and in the alkylene, at least one —CH$_2$— may be replaced by —O—, —COO—, —OCO— or —OCOO—, and at least one —CH$_2$CH$_2$— may be replaced by —CH=CH— or —C≡C—, and in the groups, at least one hydrogen may be replaced by fluorine or chlorine.

Preferred $Sp^{11}$, $Sp^{12}$ and $Sp^{13}$ are a single bond.

Ring F and ring I are independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in the rings, at least one hydrogen may be replaced by halogen, alkyl having 1 to 12 carbons, alkoxy having 1 to 12 carbons, or alkyl having 1 to 12 carbons in which at least one hydrogen is replaced by halogen.

Preferred ring F and ring I are phenyl. Ring G is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one hydrogen may be replaced by halogen, alkyl having 1 to 12 carbons, alkoxy having 1 to 12 carbons, or alkyl having 1 to 12 carbons in which at least one hydrogen is replaced by halogen. Particularly preferred ring G is 1,4-phenylene or 2-fluoro-1,4-phenylene.

$Z^{22}$ and $Z^{23}$ are independently a single bond or alkylene having 1 to 10 carbons, and in the alkylene, at least one —$CH_2$— may be replaced by —O—, —CO—, —COO— or —OCO—, and at least one —$CH_2CH_2$— may be replaced by —CH=CH—, —C(CH$_3$)=CH—, —CH=C(CH$_3$)— or —C(CH$_3$)=C(CH$_3$)—, and in the groups, at least one hydrogen may be replaced by fluorine or chlorine.

Preferred $Z^{22}$ and $Z^{23}$ are a single bond, —$CH_2CH_2$—, —$CH_2O$—, —$OCH_2$—, —COO— or —OCO—. Further preferred $Z^{22}$ and $Z^{23}$ are a single bond.

Then, u is 0, 1 or 2.

Preferred u is 0 or 1. Then, f, g and h are independently 0, 1, 2, 3 or 4, and a sum of f, g and h is 1 or more. Preferred f, g or h is 1 or 2.

2. Synthesis of Compound (1)

A synthesis method of compound (1) will be described. Compound (1) can be prepared by suitably combining methods in synthetic organic chemistry. Any compounds whose synthetic methods are not described above are prepared according to methods described in books such as "Organic Syntheses" (John Wiley & Sons, Inc.), "Organic Reactions" (John Wiley & Sons, Inc.), "Comprehensive Organic Synthesis" (Pergamon Press) and "New Experimental Chemistry Course (Shin Jikken Kagaku Koza in Japanese)" (Maruzen Co., Ltd.).

2-1. Formation of Bonding Groups $Z^1$, $Z^2$, $Z^3$, $Z^4$ and $Z^5$

An example of a method for forming a bonding group in compound (1) is as described in a scheme below. In the scheme, $MSG^1$ (or $MSG^2$) is a monovalent organic group having at least one ring. Monovalent organic groups represented by a plurality of $MSG^1$ (or $MSG^2$) may be identical or different. Compounds (1A) to (1G) correspond to compound (1) or an intermediate of compound (1).

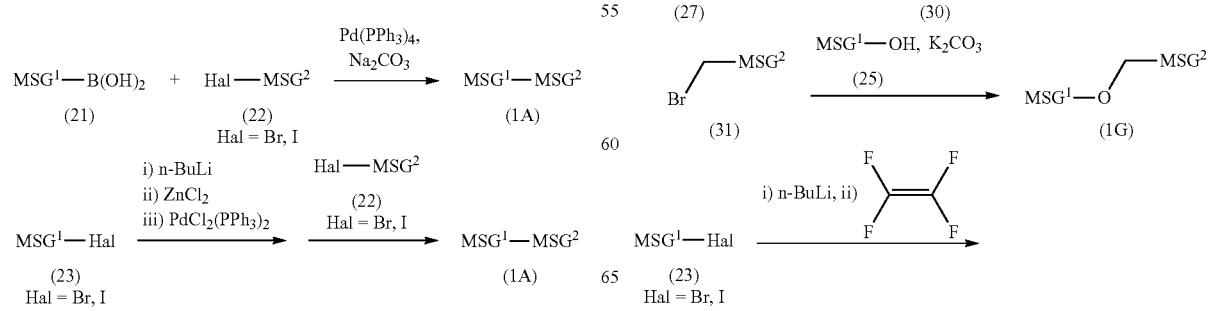

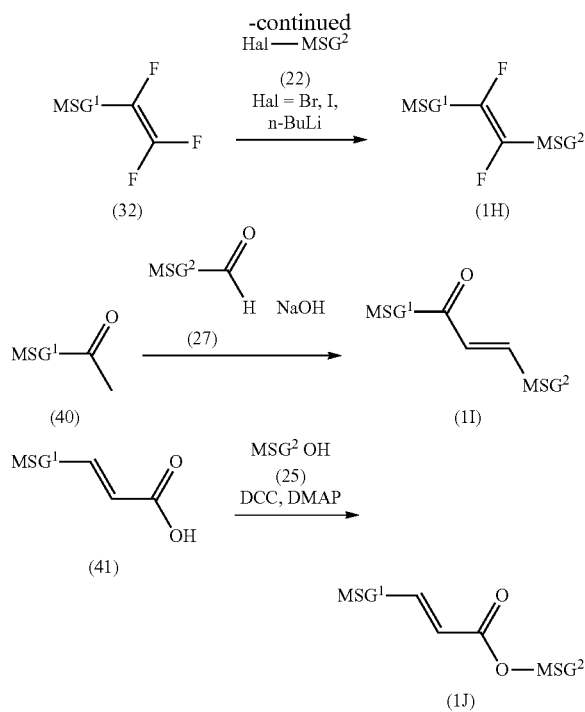

(I) Formation of a Single Bond

Compound (1A) is prepared by allowing aryl boronic acid (21) to react with compound (22) in the presence of carbonate and a tetrakis(triphenylphosphine)palladium catalyst. Compound (1A) is also prepared by allowing compound (23) to react with n-butyllithium and subsequently with zinc chloride, and further with compound (22) in the presence of a dichlorobis(triphenylphosphine)palladium catalyst.

(II) Formation of —COO— and —OCO—

Carboxylic acid (24) is obtained by allowing compound (23) to react with n-butyllithium and subsequently with carbon dioxide. Compound (1B) having —COO— is prepared by dehydration of carboxylic acid (24) and phenol (25) derived from compound (21) in the presence of 1,3-dicyclohexylcarbodiimide (DCC) and 4-dimethylaminopyridine (DMAP). A compound having —OCO— is also prepared according to the method.

(III) Formation of —CF$_2$O— and —OCF$_2$—

Compound (26) is obtained by sulfurizing compound (1B) with Lawesson's reagent. Compound (1C) having —CF$_2$O— is prepared by fluorinating compound (26) with a hydrogen fluoride-pyridine complex and N-bromosuccinimide (NBS). Refer to M. Kuroboshi et al., Chem. Lett., 1992, 827. Compound (1C) is also prepared by fluorinating compound (26) with (diethylamino) sulfur trifluoride (DAST). Refer to W. H. Bunnelle et al., J. Org. Chem. 1990, 55, 768. A compound having —OCF$_2$— is also prepared according to the method.

(IV) Formation of —CH=CH—

Aldehyde (27) is obtained by allowing compound (22) to react with n-butyllithium and subsequently with N,N-dimethylformamide (DMF). Compound (1D) is prepared by allowing phosphorus ylide generated by allowing phosphonium salt (28) to react with potassium t-butoxide to react with aldehyde (27). A cis isomer may be formed depending on reaction conditions, and therefore the cis isomer is isomerized into a trans isomer according to a publicly-known method when necessary.

(V) Formation of —CH$_2$CH$_2$—

Compound (1E) is prepared by hydrogenating compound (1D) in the presence of a palladium on carbon catalyst.

(VI) Formation of —C≡C—

Compound (29) is obtained by allowing compound (23) to react with 2-methyl-3-butyn-2-ol in the presence of a catalyst of dichloropalladium and copper iodide, and then performing deprotection under basic conditions. Compound (1F) is prepared by allowing compound (29) to react with compound (22) in the presence of a catalyst of dichlorobis(triphenylphosphine)palladium and copper halide.

(VII) Formation of —CH$_2$O— and —OCH$_2$—

Compound (30) is obtained by reducing compound (27) with sodium borohydride. Compound (31) is obtained by brominating the obtained compound with hydrobromic acid. Compound (1G) is prepared by allowing compound (25) to react with compound (31) in the presence of potassium carbonate. A compound having —OCH$_2$— is also prepared according to the method.

(VIII) Formation of —CF=CF—

Compound (32) is obtained by treating compound (23) with n-butyllithium, and then allowing the treated material to react with tetrafluoroethylene. Compound (1H) is prepared by treating compound (22) with n-butyllithium, and then allowing the treated material to react with compound (32).

(VIV) Formation of —CH=CHCO— and —COCH=CH—

Compound (1I) is prepared by allowing compound (40) to be subjected to aldol condensation reaction with compound (27) in the presence of NaOH.

(X) Formation of —CH=CHCOO— and —OCOCH=CH—

Compound (1J) is prepared by dehydration of cinnamic acid (41) and compound (25) in the presence of 1,3-dicyclohexylcarbodiimide (DCC) and 4-dimethylaminopyridine (DMAP).

2-2. Formation of Rings A$^1$, A$^2$, A$^3$ and A$^4$

A starting material is commercially available or a synthetic method is well known with regard to a ring such as 1,4-cyclohexylene, 1,4-cyclohexenylene, 1,4-phenylene, 2-fluoro-1,4-phenylene, 2-methyl-1,4-phenylene, 2-ethyl-1,4-phenylene, naphthalene-2,6-diyl, decahydronaphthalene-2,6-diyl, 1,2,3,4-tetrahydronaphthalene-2,6-diyl, tetrahydropyran-2,5-diyl, 1,3-dioxane-2,5-diyl, pyrimidine-2,5-diyl, pyridine-2,5-diyl, perhydrocyclopenta[a]phenanthrene-3,17-diyl and 2,3,4,7,8,9,10,11,12,13,14,15,16,17-tetradecahydrocyclopenta[a]phe nanthrene-3,17-diyl.

2-3. Formation of Linking Group Sp$^1$ or Sp$^2$ and Polymerizable Group P$^1$ or P$^2$ Preferred examples of polymerizable group P$^1$ or P$^2$ include acryloyloxy (1b), maleimide (1c), an itaconic acid ester (1d), oxiranyl (1h) or vinyloxy (1i).

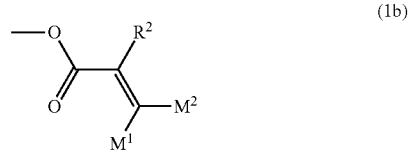

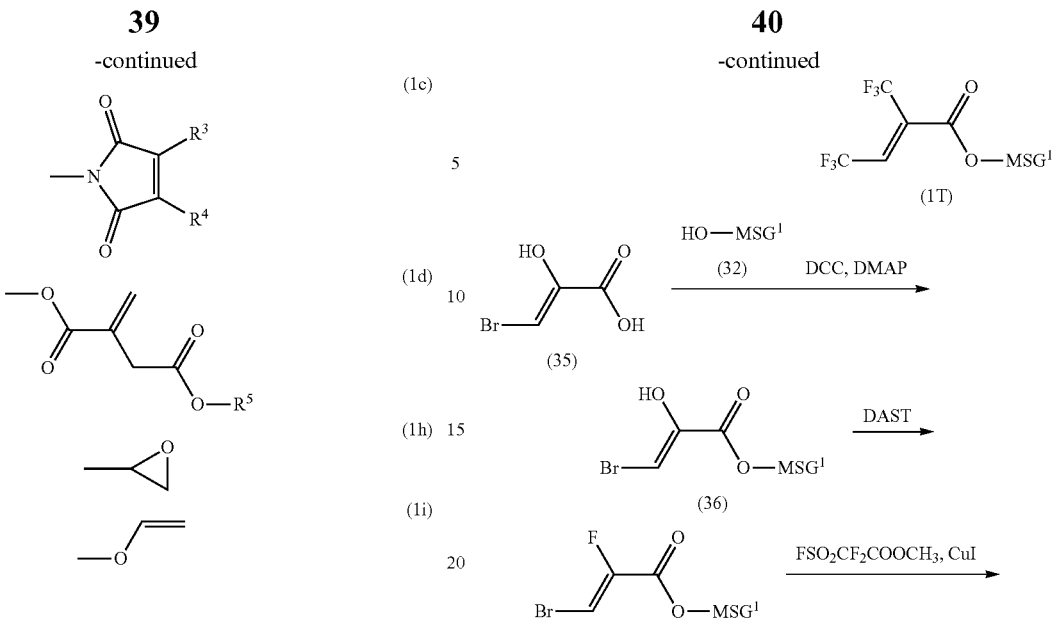

An example of a method for preparing a compound in which the polymerizable group is bonded to a ring through linking group $Sp^1$ or $Sp^2$ is as described below. First, an example in which linking group $Sp^1$ or $Sp^2$ is a single bond will be described.

(1) Synthesis of a Compound Having a Single Bond

A method of preparing a compound having a single bond is as described in a scheme below. In the scheme, $MSG^1$ is a monovalent organic group having at least one ring. Compounds (1S) to (1Z) correspond to compound (1). When the polymerizable group is an acrylate derivative, the acrylate derivative is prepared by performing esterification between the corresponding acrylic acid and HO-$MSG^1$. Allyl ether is prepared by performing etherification between HO-$MSG^1$ and vinyl bromide. An epoxy group is prepared by oxidation of a terminal double bond. A maleimide group is prepared by reaction between an amino group and maleic anhydride. An itaconic acid ester is prepared by performing esterification between the corresponding itaconic acid and HO-$MSG^1$.

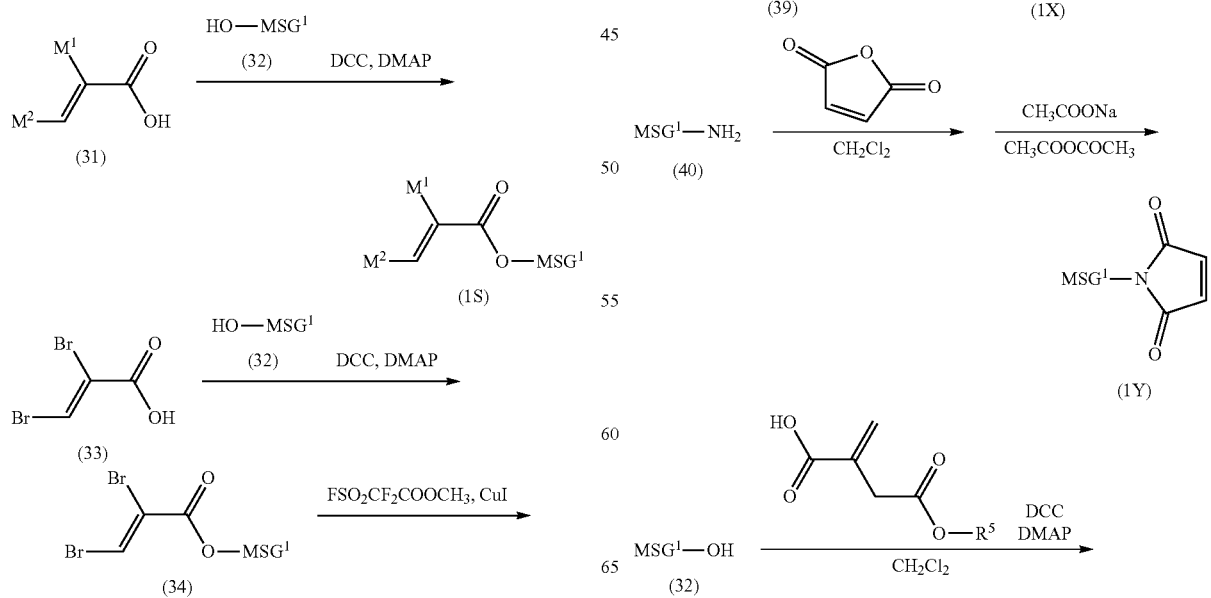

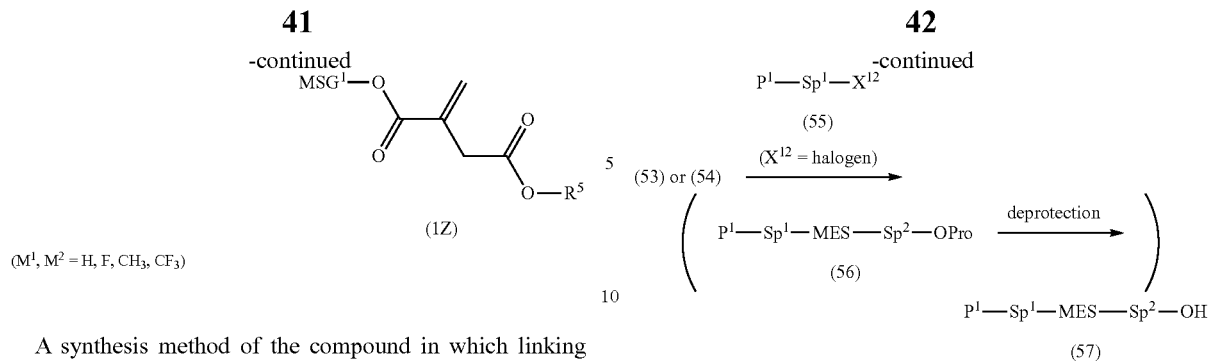

(1Z)

($M^1$, $M^2$ = H, F, $CH_3$, $CF_3$)

A synthesis method of the compound in which linking group $Sp^1$ or $Sp^2$ is a single bond is described above. As for a method of producing other linking groups, other linking groups can be prepared according to the synthesis method of bonding groups $Z^1$, $Z^2$, $Z^3$, $Z^4$ and $Z^5$.

2-4. Synthesis Example

An example of a method for preparing compound (1) is as described below. In the compounds, MES is a mesogen group having at least one ring. Definitions of $P^1$, $M^1$, $M^2$, $Sp^1$ and $Sp^2$ are identical to the definitions described above.

Compound (51A) or compound (51B) is commercially available, or can be prepared according to a common organic synthesis method by using a mesogen (MES) having a suitable ring structure as a starting material. When a compound in which MES and $Sp^1$ is linked through an ether bond is prepared, compound (53) can be obtained by allowing compound (51A) as a starting material to be subjected to etherification by using compound (52) and a base such as potassium hydroxide. Moreover, when a compound in which MES and $Sp^1$ is linked with a single bond is prepared, compound (53) can be obtained by allowing compound (51B) as a starting material to be subjected to cross-coupling reaction by using compound (52), a metal catalyst such as palladium and a base. Compound (53) may be derived to compound (54) in which a protective group such as TMS and THP is allowing to act therewith, when necessary.

Then, compound (56) can be obtained by allowing compound (53) or compound (54) to be subjected to etherification again in the presence of a base such as compound (55) and potassium hydroxide. On this occasion, when the protective group is allowed to act in a previous stage, the protective group is removed by a deprotection reaction.

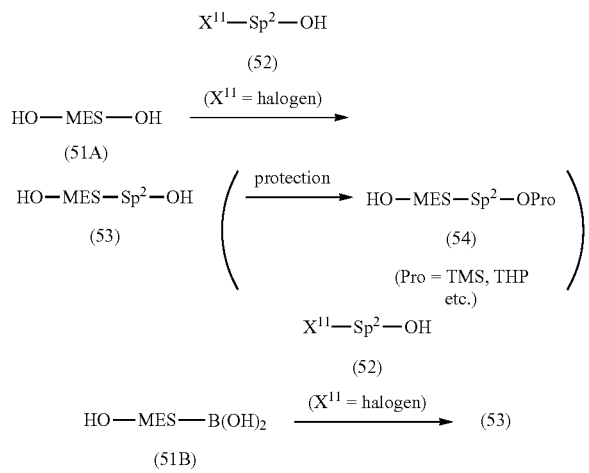

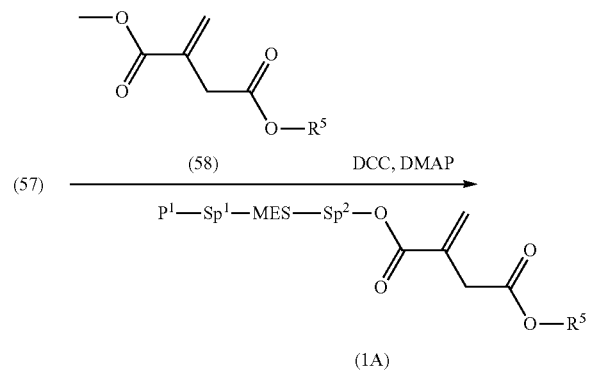

Compound (1A) in which $P^2$ is a group represented by formula (1d) can be prepared with compound (57) according to a method described below. Compound (1A) can be derived by allowing compound (57) to be subjected to an esterification reaction in the presence of compound (58), DCC and DMAP.

3. Liquid Crystal Composition

A liquid crystal composition of the invention contains compound (1) as component A. Compound (1) can control the alignment of liquid crystal molecules by non-covalent interaction with a substrate of the device. The composition contains compound (1) as component A, and preferably further contains a liquid crystal compound selected from components B, C, D and E described below. Component B includes compounds (2) to (4). Component C includes compounds (5) to (7) Component D includes compound (8). Component E includes compounds (9) to (15). The composition may contain any other liquid crystal compound different from compounds (2) to (15). When the composition is prepared, components B, C, D and E are preferably selected by taking into account largeness of positive or negative dielectric anisotropy, or the like. The composition in which the components are suitably selected has high maximum temperature, low minimum temperature, small viscosity, suitable optical anisotropy (more specifically, large optical anisotropy or small optical anisotropy), large positive or negative dielectric anisotropy, large specific resistance, high stability to heat and ultraviolet light and a suitable elastic constant (more specifically, a large elastic constant or a small elastic constant).

A preferred proportion of compound (1) is about 0.01% by weight or more for maintaining high stability to ultraviolet light, and about 5% by weight or less for dissolution in the liquid crystal composition. A further preferred proportion is in the range of about 0.05% by weight to about 2% by weight. A most preferred proportion is in the range of about 0.05% by weight to about 1% by weight.

Component B includes a compound in which two terminal groups are alkyl or the like. Preferred examples of component B include compounds (2-1) to (2-11), compounds (3-1) to (3-19) and compounds (4-1) to (4-7). In the compounds of component B, $R^{11}$ and $R^{12}$ are independently alkyl having 1 to 10 carbons or alkenyl having 2 to 10 carbons, and in the alkyl or the alkenyl, at least one —$CH_2$— may be replaced by —O—, and at least one hydrogen may be replaced by fluorine.

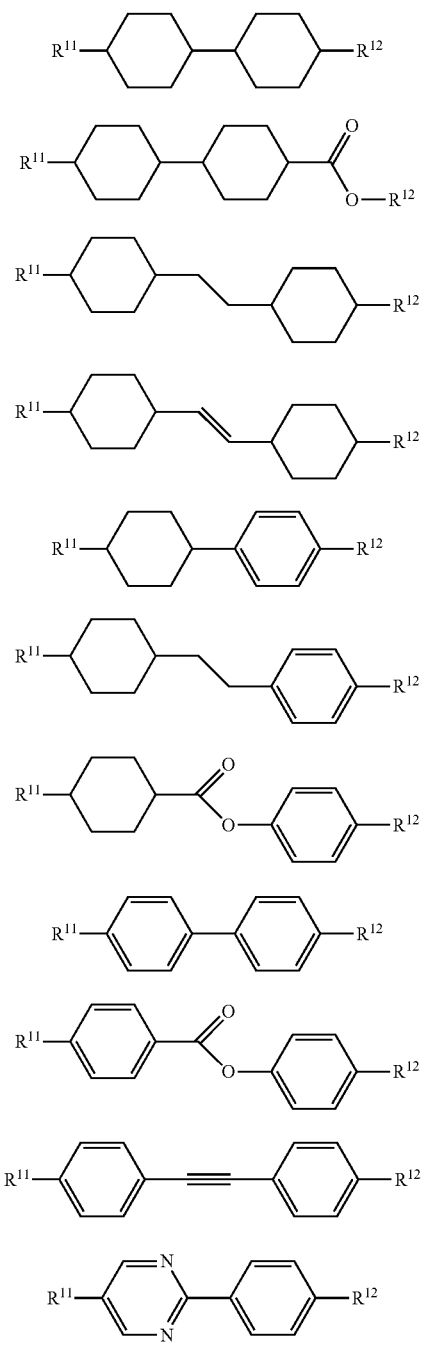

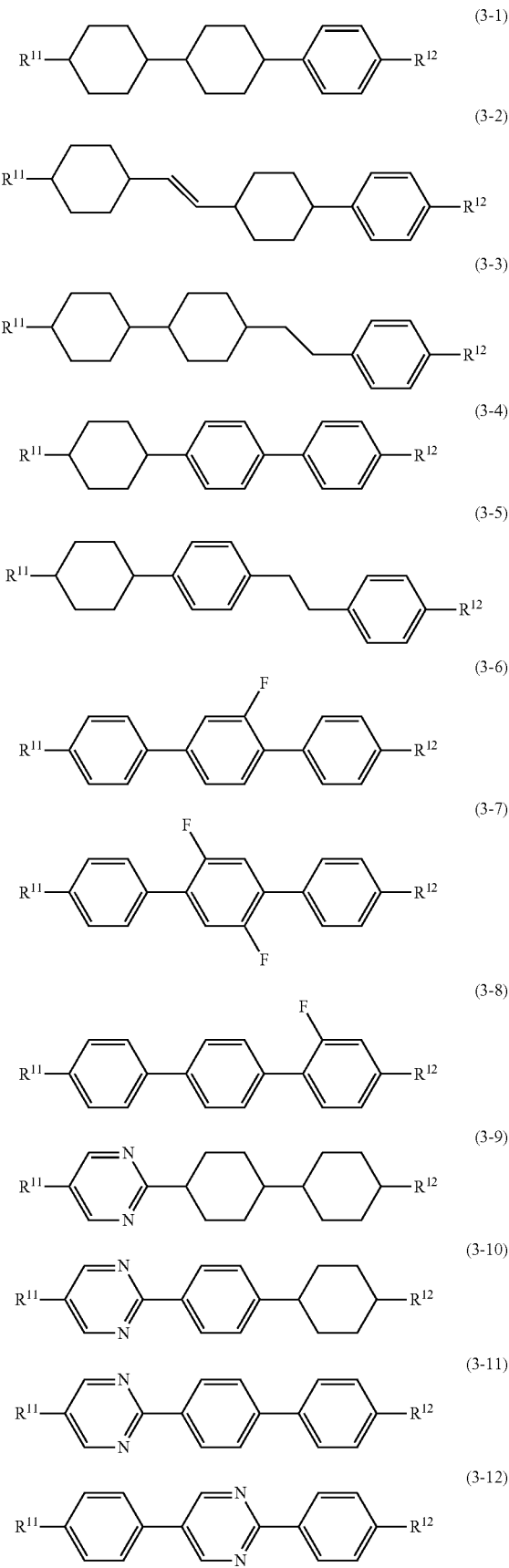

(3-13)
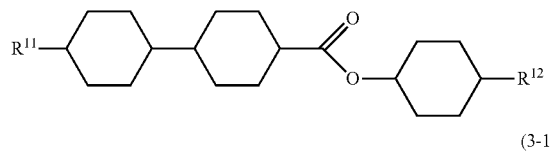

(3-14)
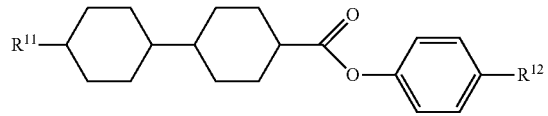

(3-15)
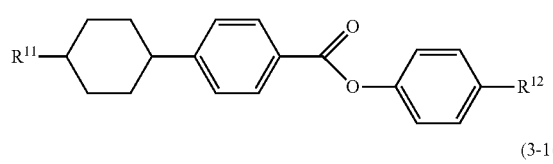

(3-16)
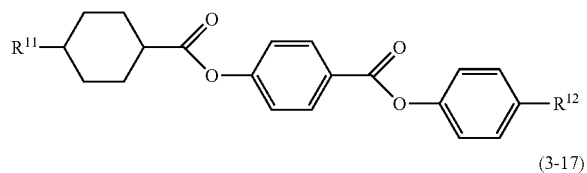

(3-17)
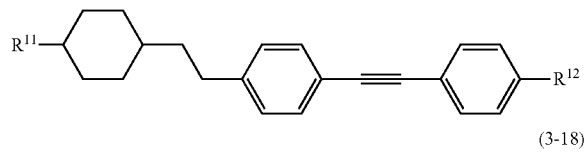

(3-18)
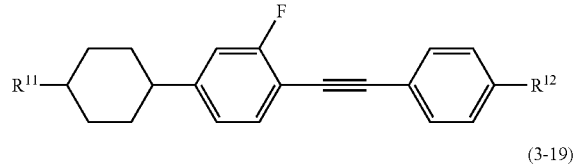

(3-19)
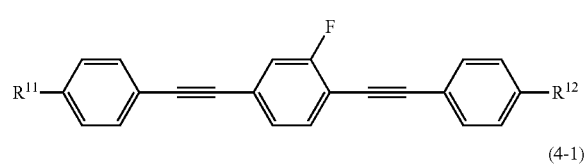

(4-1)
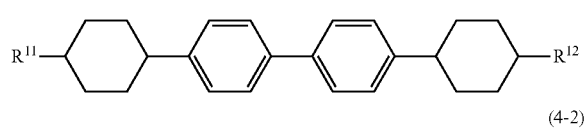

(4-2)
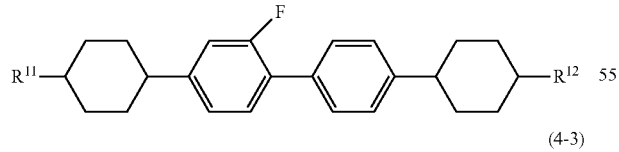

(4-3)
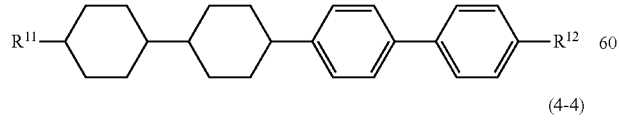

(4-5)
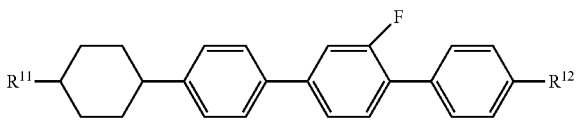

(4-6)
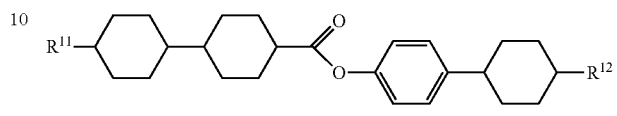

(4-7)
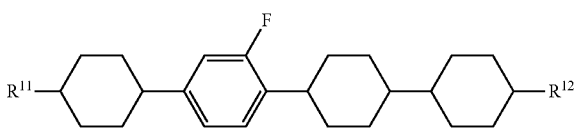

Component B has a small absolute value of dielectric anisotropy, and therefore is a compound close to neutrality. Compound (2) is mainly effective in decreasing the viscosity or adjusting the optical anisotropy. Compounds (3) and (4) are effective in extending a temperature range of a nematic phase by increasing the maximum temperature, or in adjusting the optical anisotropy.

As a content of component B increases, the dielectric anisotropy of the composition decreases, but the viscosity decreases. Thus, as long as a desired value of threshold voltage of a device is met, the content is preferably as large as possible. When a composition for the IPS mode, the VA mode or the like is prepared, the content of component B is preferably 30% by weight or more, and further preferably 40% by weight or more, based on the weight of the liquid crystal composition.

Component C is a compound having a halogen-containing group or a fluorine-containing group at a right terminal. Preferred examples of component C include compounds (5-1) to (5-16), compounds (6-1) to (6-120) and compounds (7-1) to (7-62). In the compounds of component C, $R^{13}$ is alkyl having 1 to 10 carbons or alkenyl having 2 to 10 carbons, and in the alkyl and the alkenyl, at least one —CH$_2$— may be replaced by —O—, and at least one hydrogen may be replaced by fluorine; and $X^{11}$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$.

(5-1)
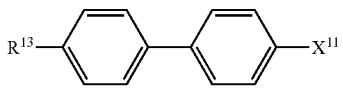

(5-2)
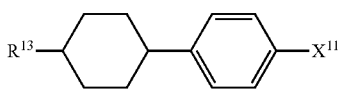

(5-3)
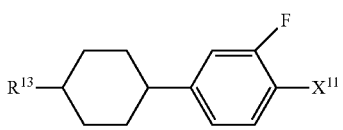

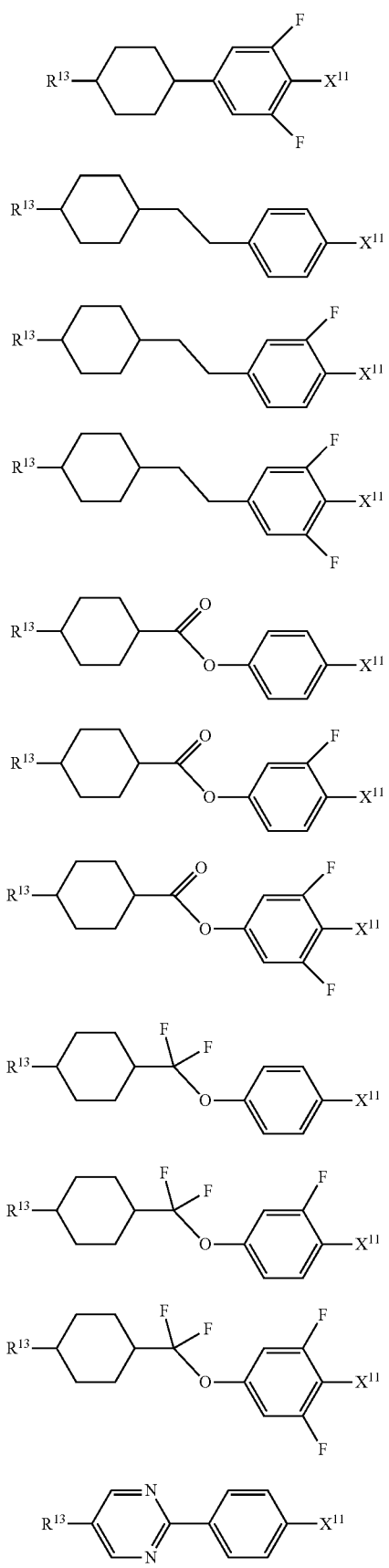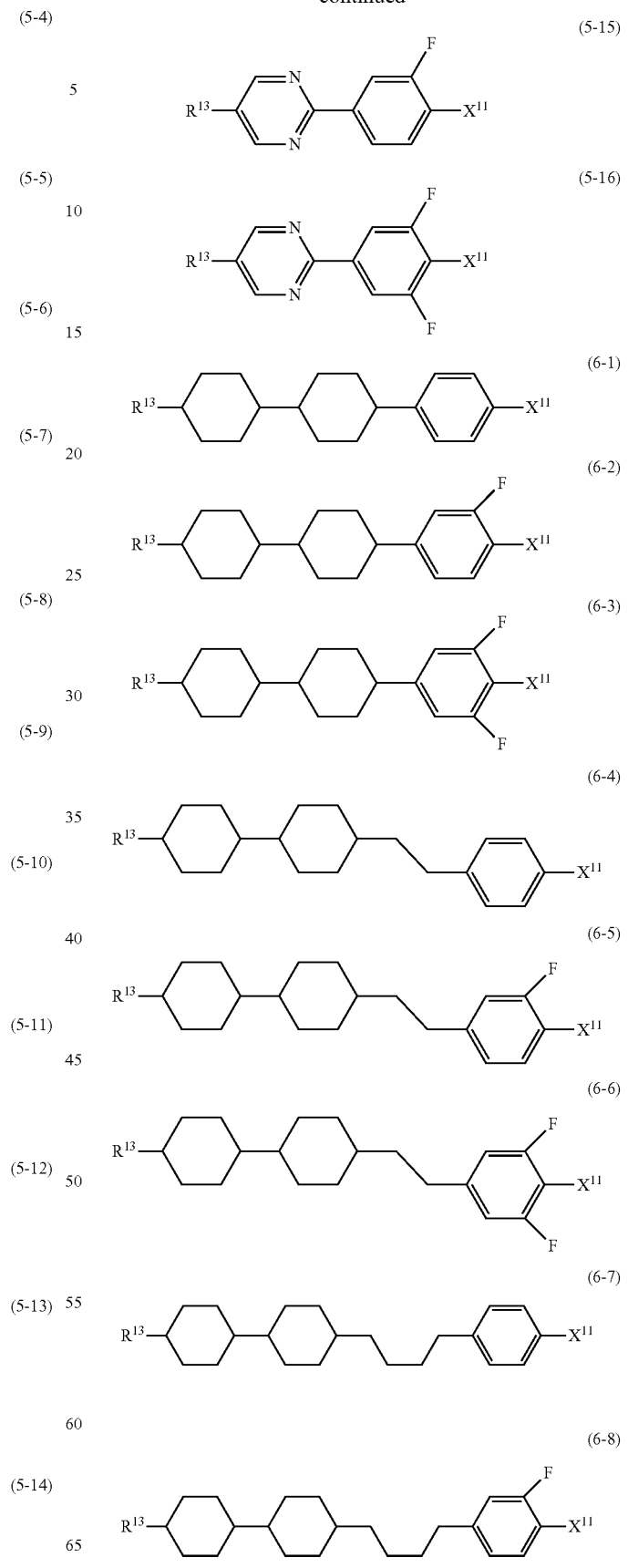

(6-9) 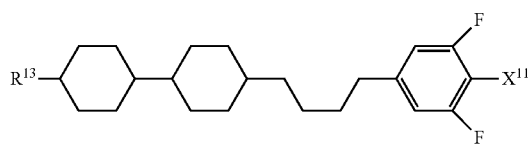
(6-10) 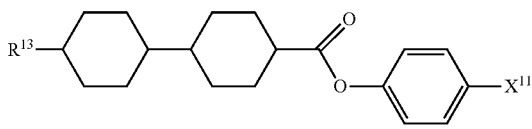
(6-11) 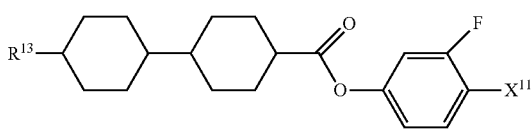
(6-12) 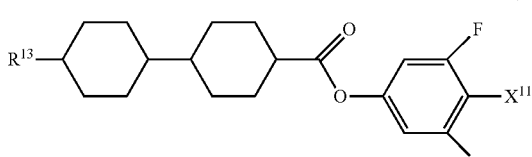
(6-13) 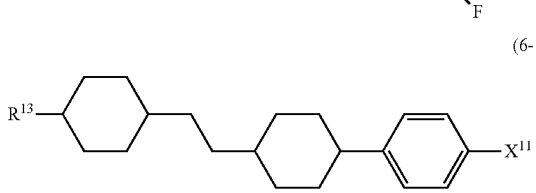
(6-14) 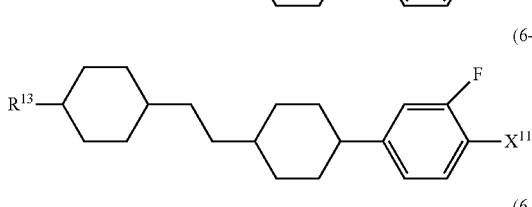
(6-15) 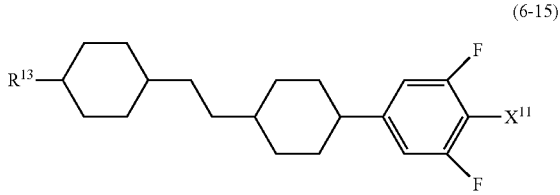
(6-16) 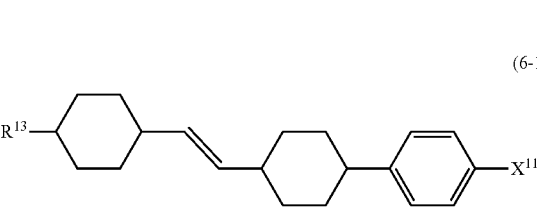
(6-17) 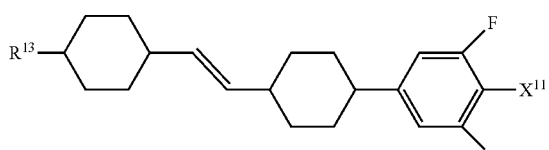
(6-18) 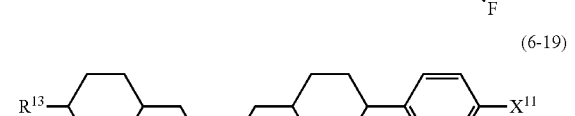
(6-19) 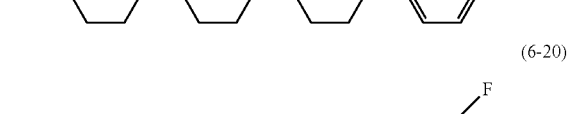
(6-20) 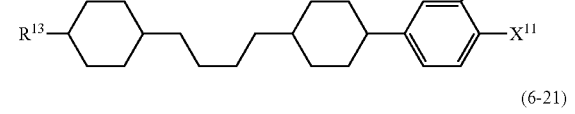
(6-21) 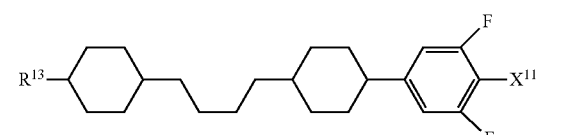
(6-22) 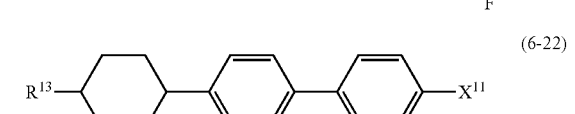
(6-23) 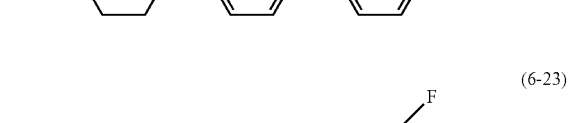
(6-24) 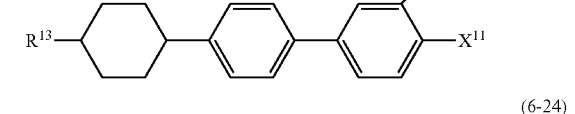
(6-25) 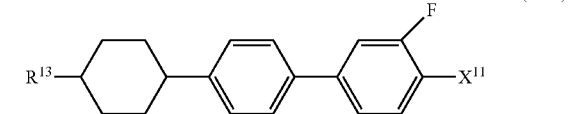
(6-26) 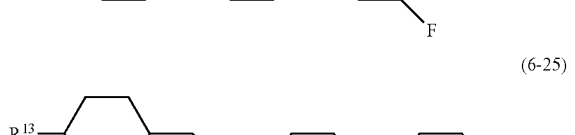
(6-27) 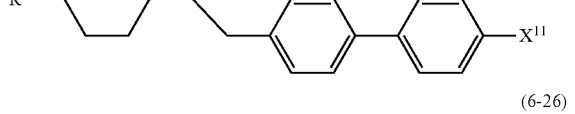

(6-28) 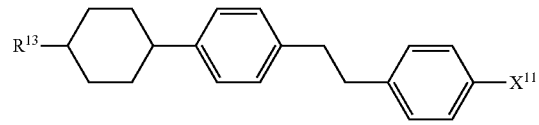
(6-29) 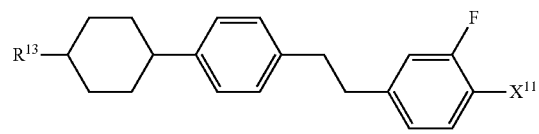
(6-30) 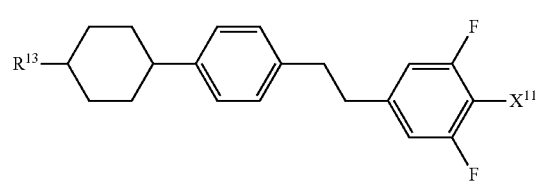
(6-31) 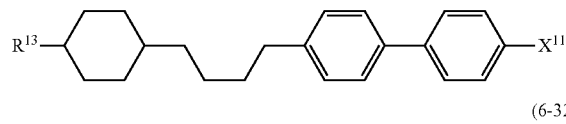
(6-32) 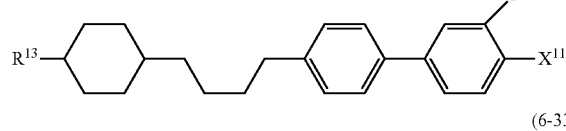
(6-33) 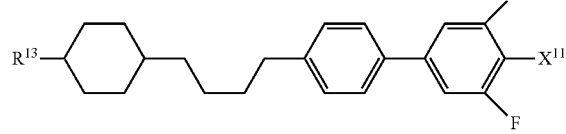
(6-34) 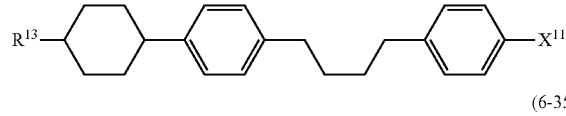
(6-35) 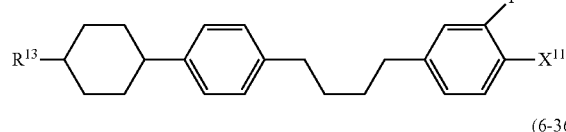
(6-36) 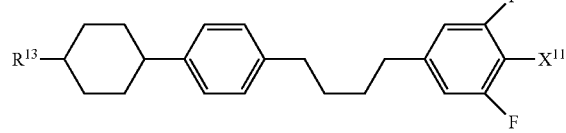
(6-37) 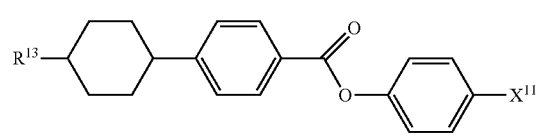
(6-38) 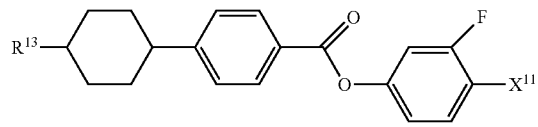
(6-39) 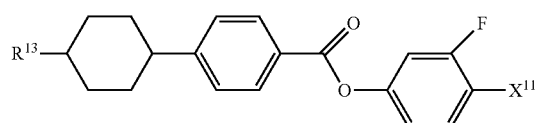
(6-40) 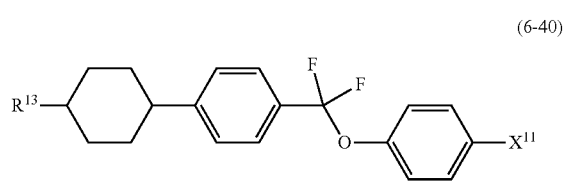
(6-41) 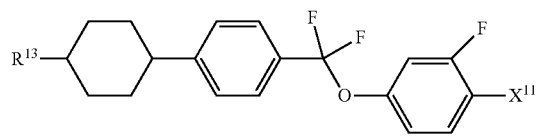
(6-42) 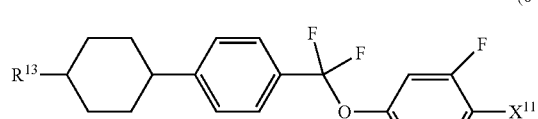
(6-43) 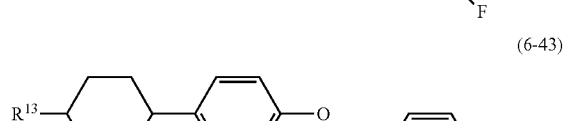
(6-44) 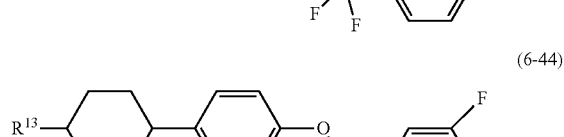
(6-45) 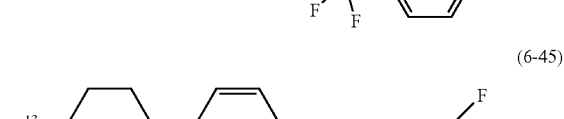
(6-46) 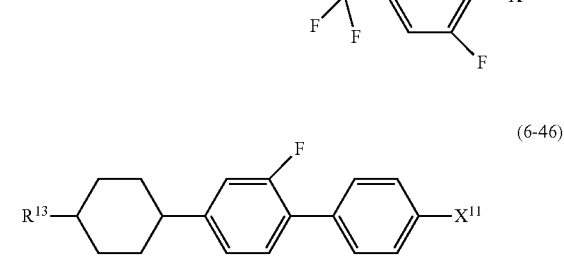

(6-47) 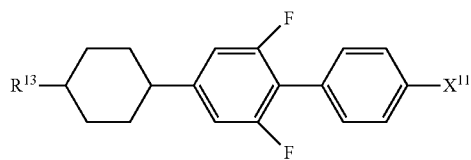
(6-48) 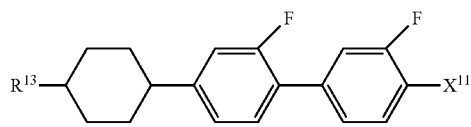
(6-49) 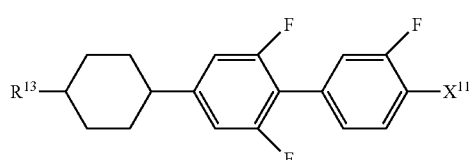
(6-50) 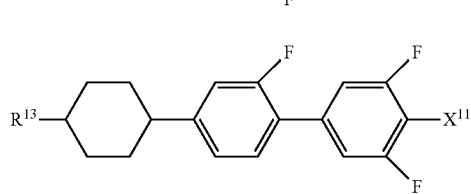
(6-51) 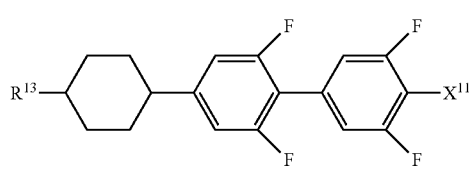
(6-52) 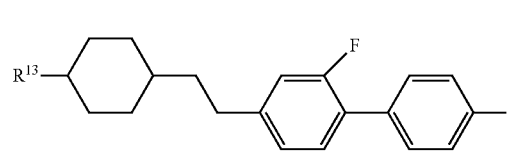
(6-53) 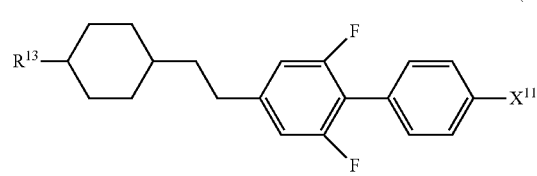
(6-54) 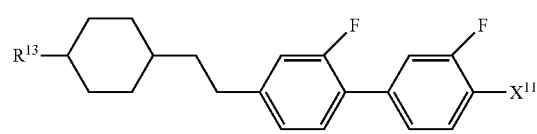
(6-55) 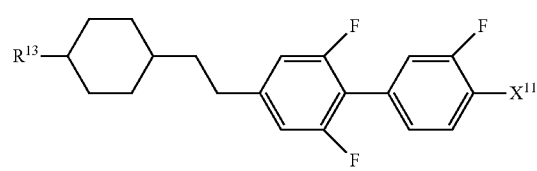
(6-56) 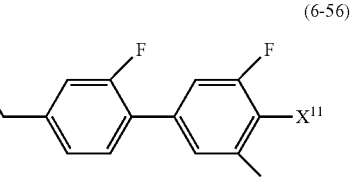
(6-57) 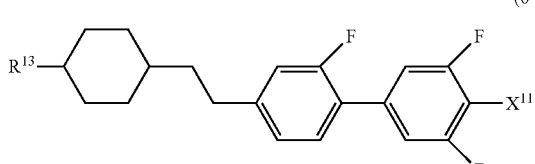
(6-58) 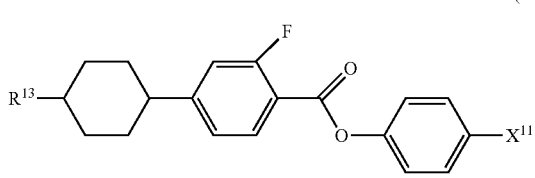
(6-59) 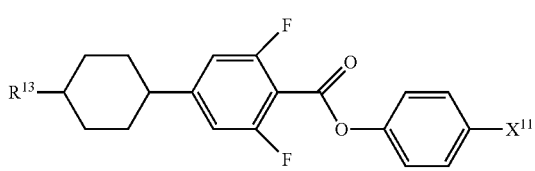
(6-60) 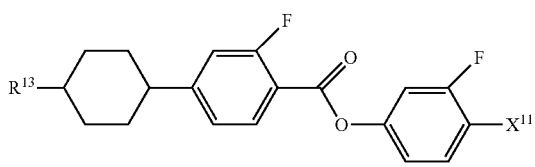
(6-61) 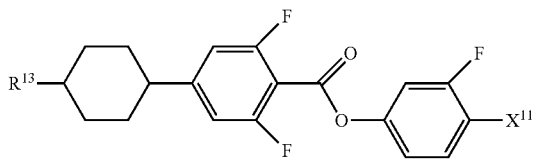
(6-62) 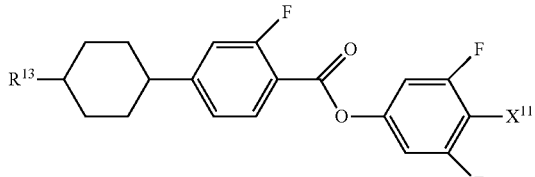
(6-63) 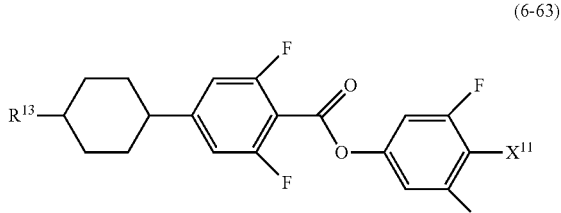

(6-64) 
(6-65) 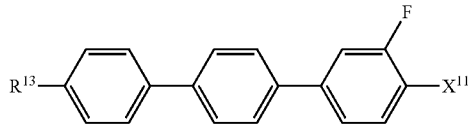
(6-66) 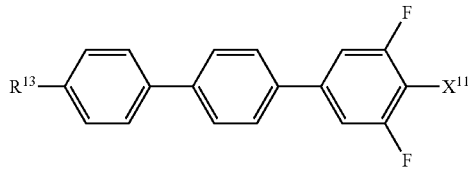
(6-67) 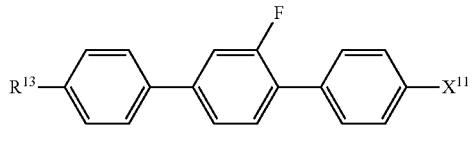
(6-68) 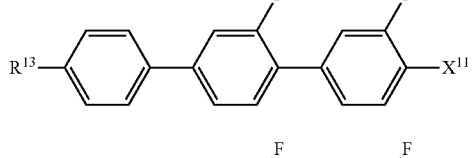
(6-69) 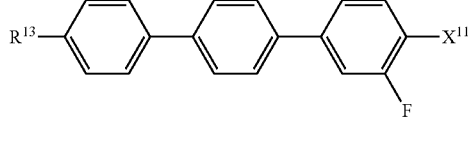
(6-70) 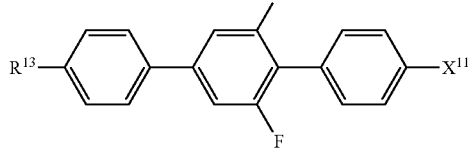
(6-71) 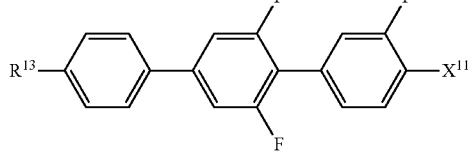
(6-72) 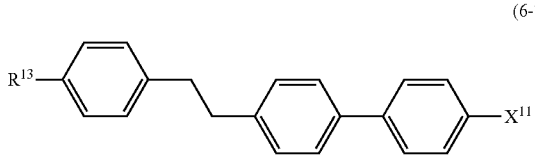
(6-73) 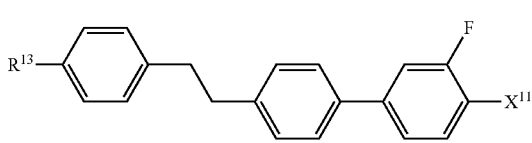
(6-74) 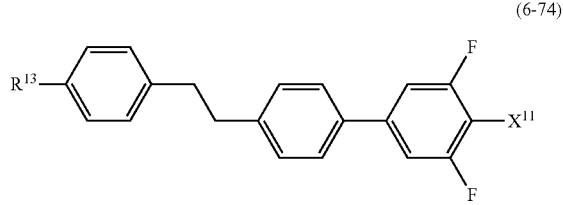
(6-75) 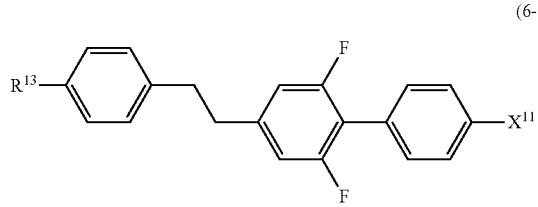
(6-76) 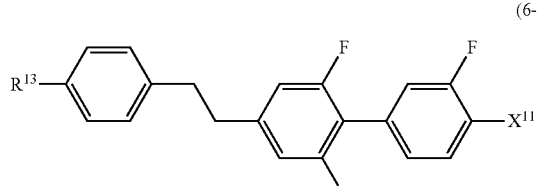
(6-77) 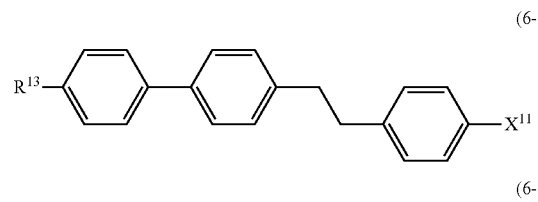
(6-78) 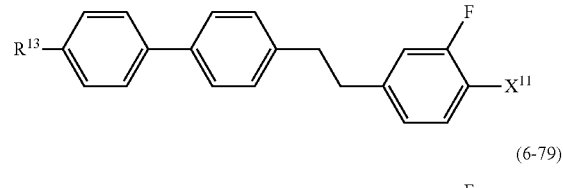
(6-79) 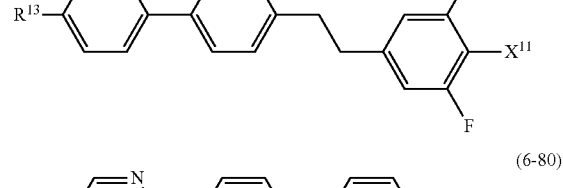
(6-80) 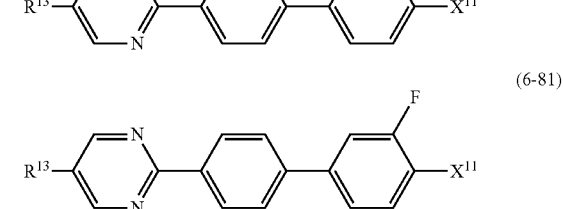
(6-81) 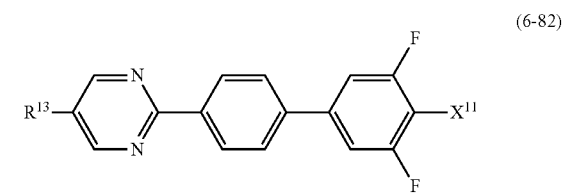
(6-82)

-continued
(6-83)
(6-84)
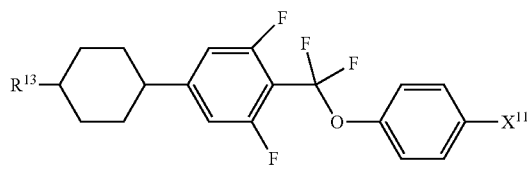
(6-85)
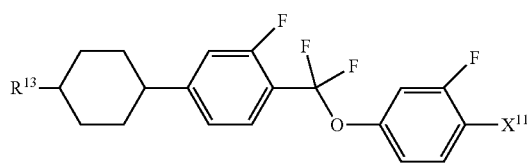
(6-86)
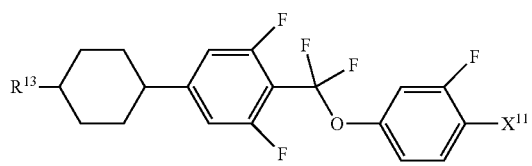
(6-87)
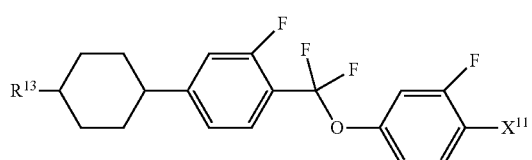
(6-88)
(6-89)
(6-90)
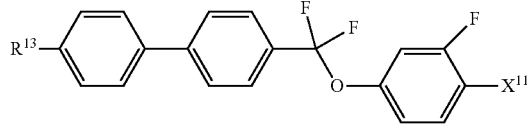
-continued
(6-91)
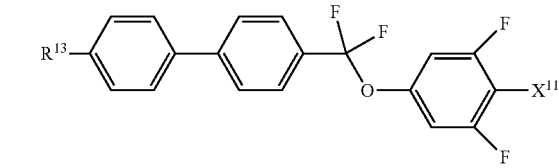
(6-92)
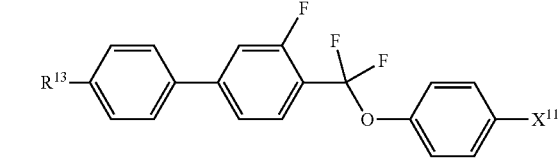
(6-93)
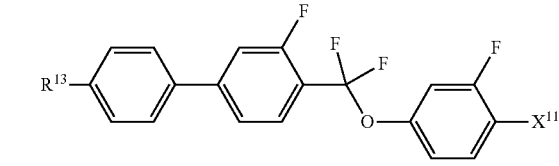
(6-94)
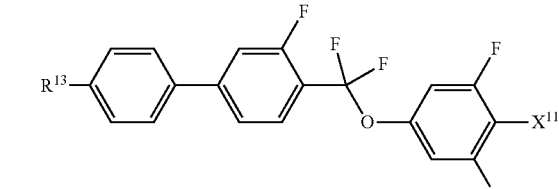
(6-95)
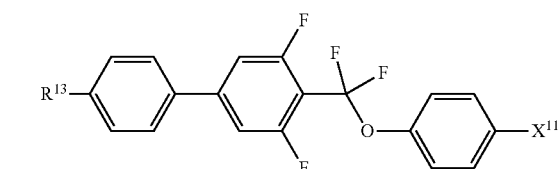
(6-96)
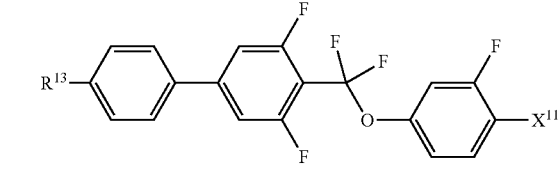
(6-97)
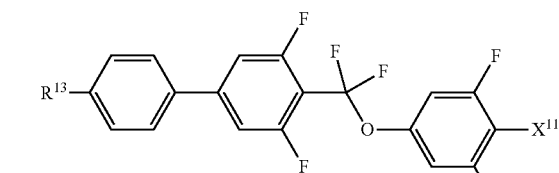
(6-98)
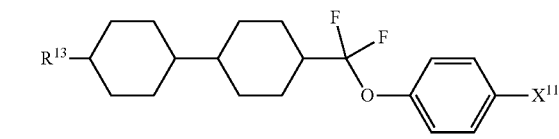

(6-99) 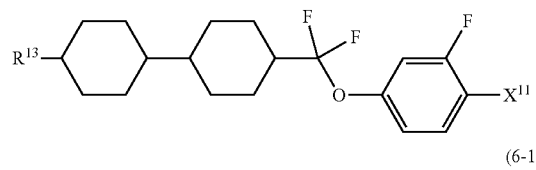
(6-100) 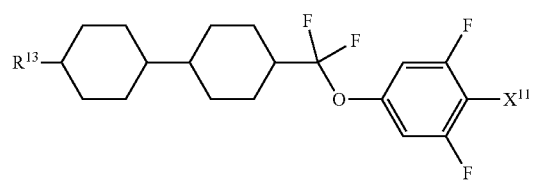
(6-101) 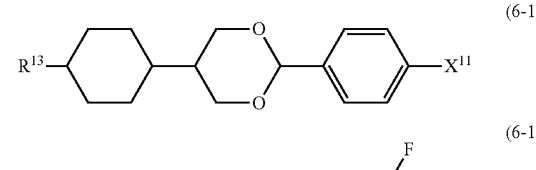
(6-102) 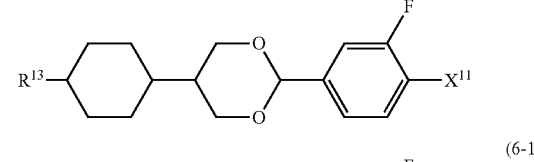
(6-103) 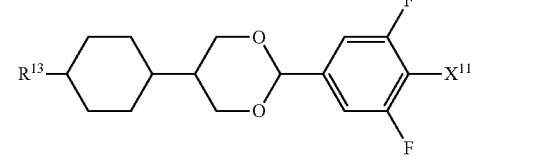
(6-104) 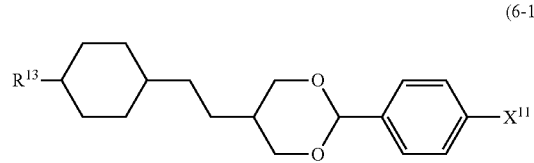
(6-105) 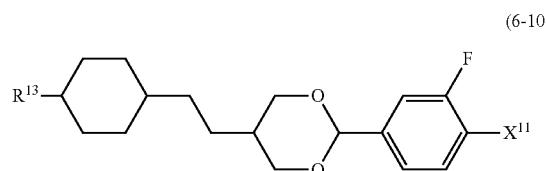
(6-106) 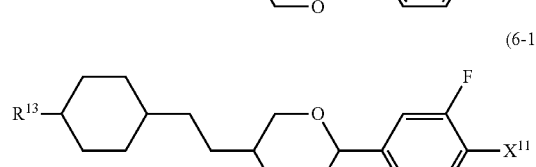
(6-107) 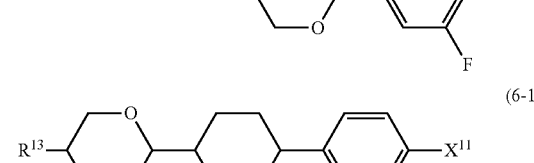
(6-108) 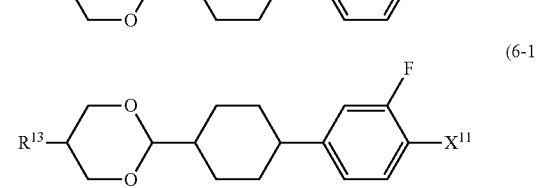
(6-109) 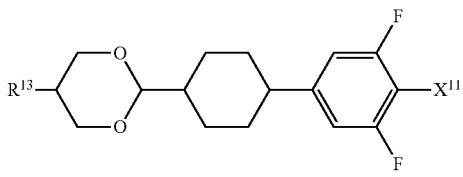
(6-110) 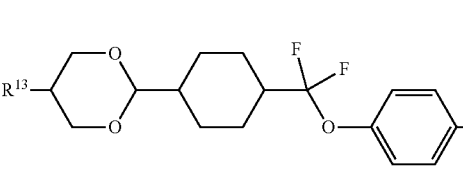
(6-111) 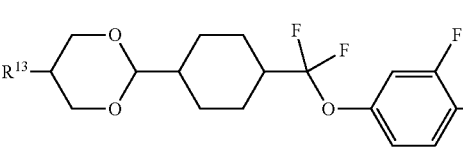
(6-112) 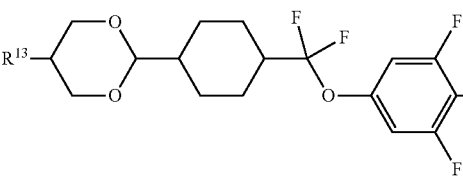
(6-113) 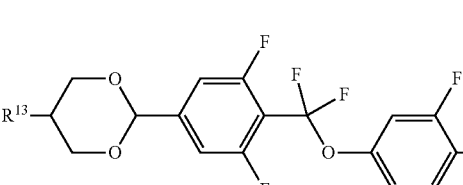
(6-114) 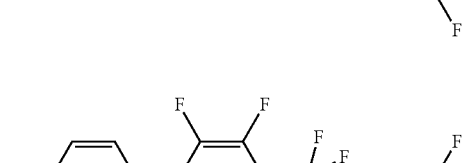
(6-115) 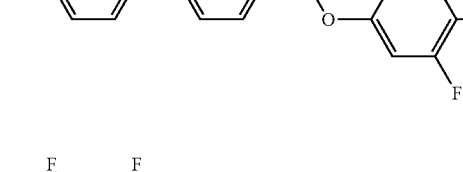
(6-116) 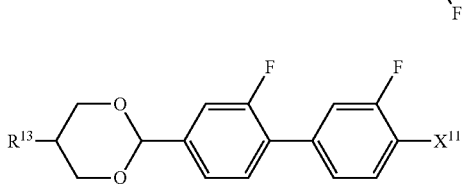

(6-117)
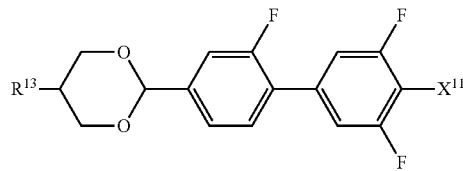
(6-119)
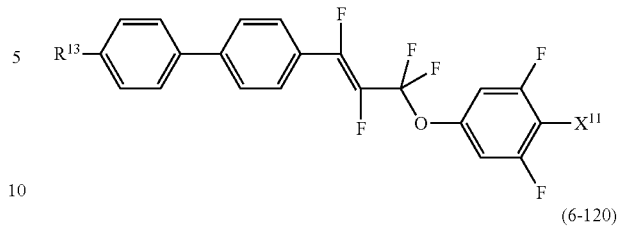
(6-118)
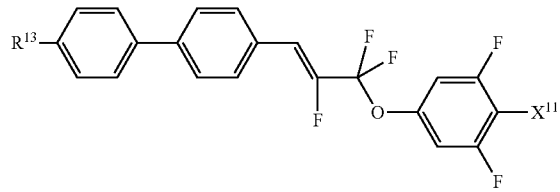
(6-120)
(7-1)
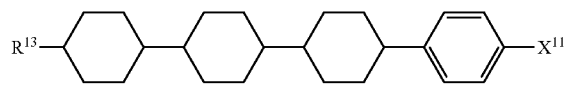
(7-2)
(7-3)
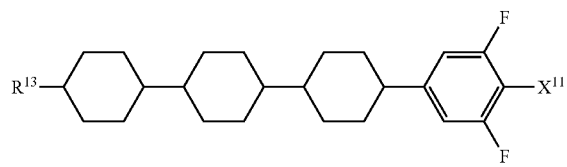
(7-4)
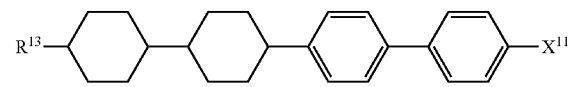
(7-5)
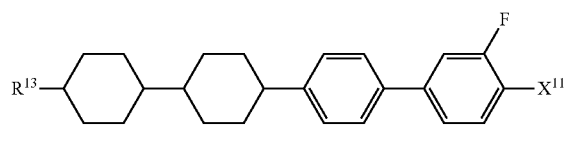
(7-6)
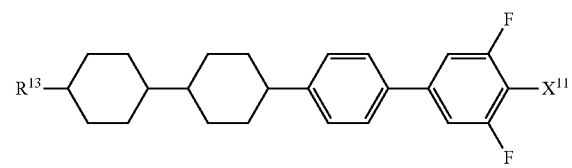
(7-7)
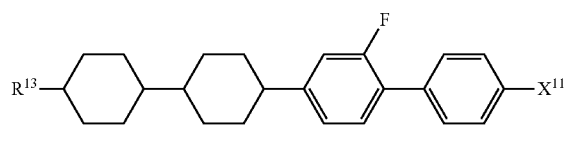
(7-8)
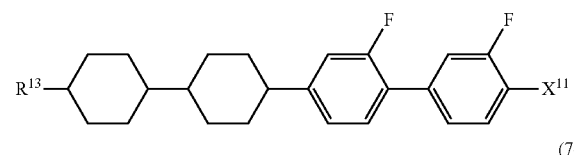
(7-9)
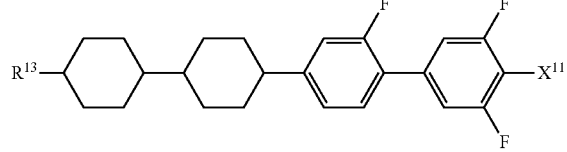
(7-10)
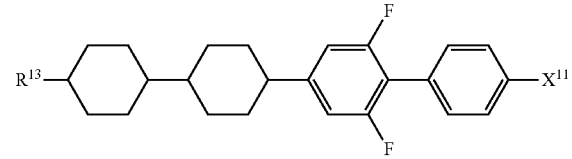
(7-11)
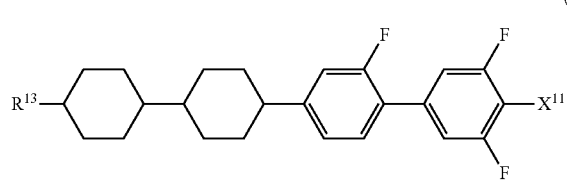
(7-12)
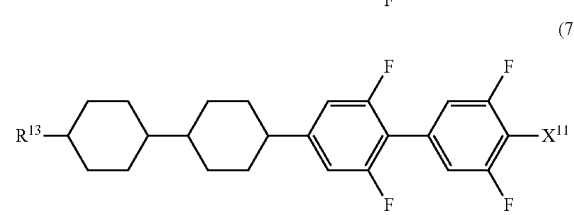

-continued
(7-13) 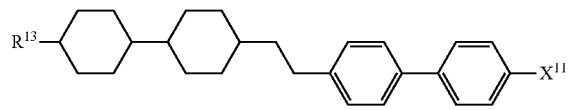
(7-14) 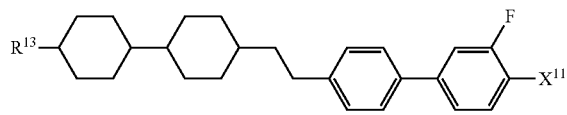
(7-15) 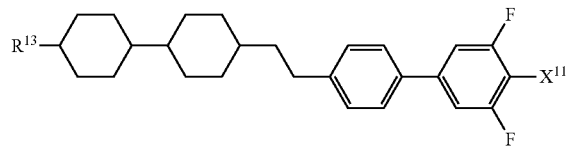
(7-16) 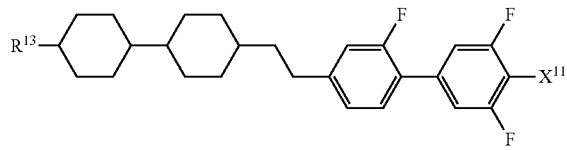
(7-17) 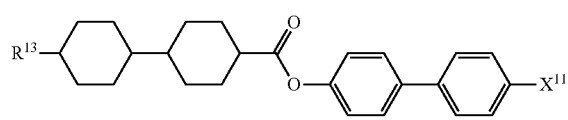
(7-18) 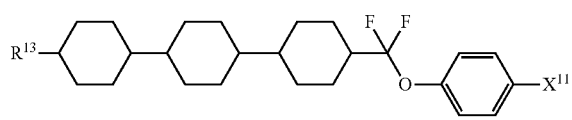
(7-19) 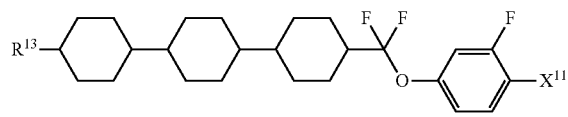
(7-20) 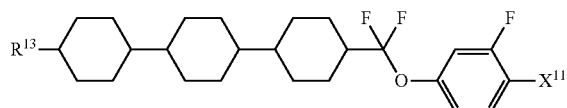
(7-21) 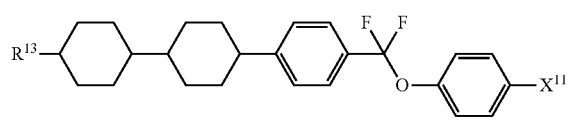
(7-22) 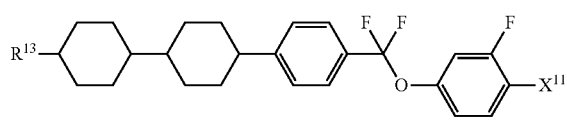
(7-23) 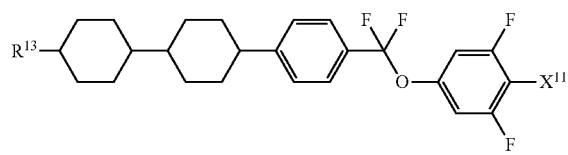
(7-24) 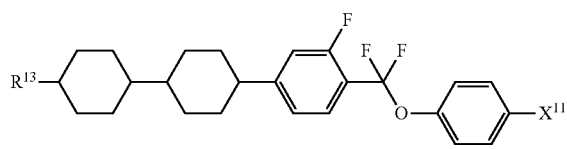
(7-25) 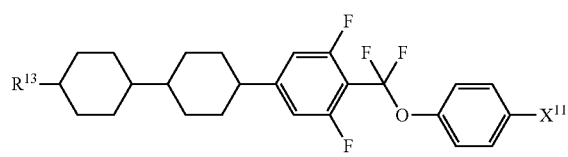
(7-26) 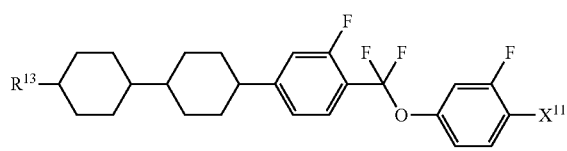
(7-27) 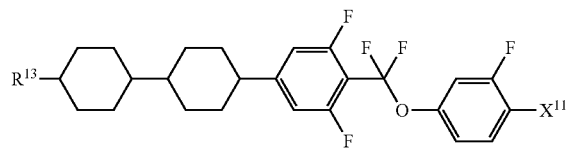
(7-28) 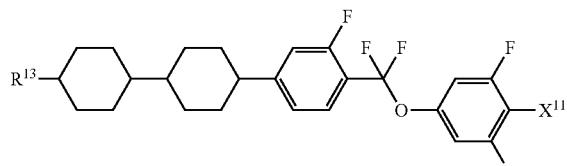
(7-29) 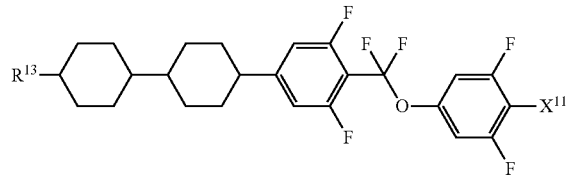
(7-30) 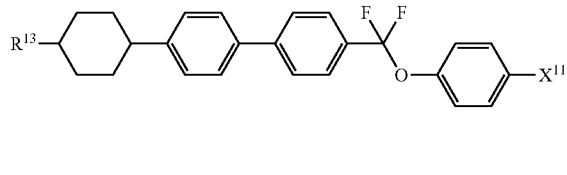

-continued
(7-31)
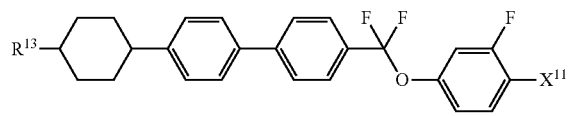
(7-32)
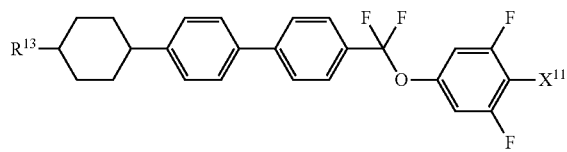
(7-33)
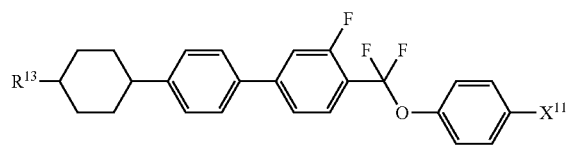
(7-34)
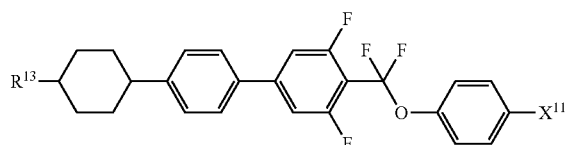
(7-35)
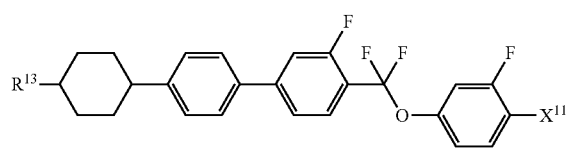
(7-36)
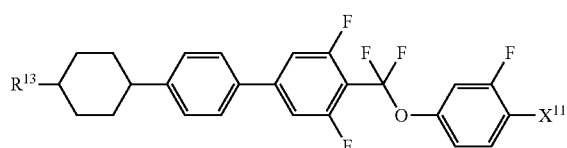
(7-37)
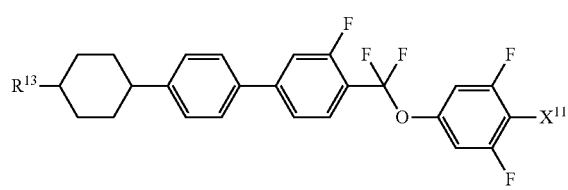
(7-38)
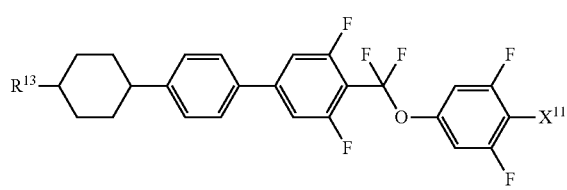
(7-39)
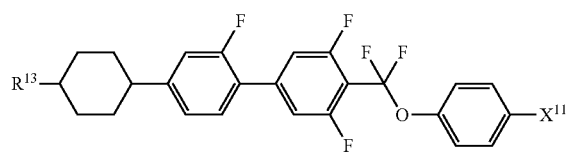
(7-40)
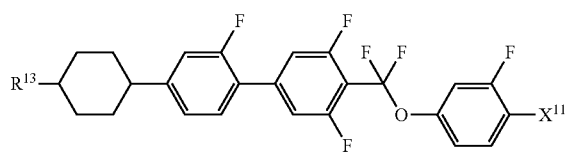
(7-41)
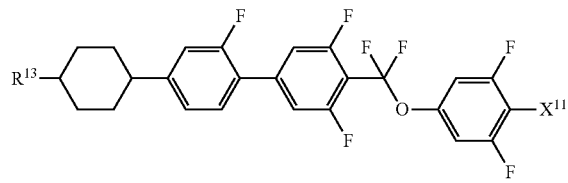
(7-42)
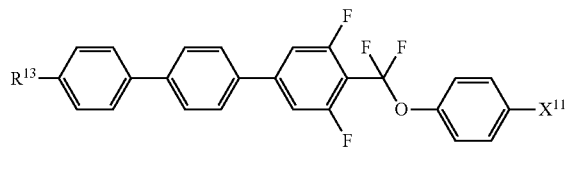
(7-43)
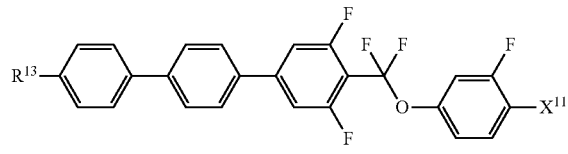
(7-44)
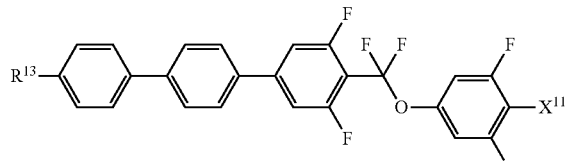
(7-45)
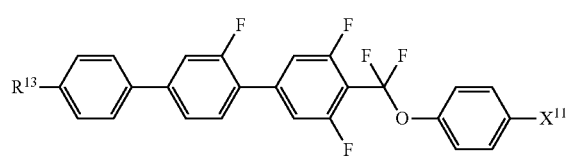
(7-46)
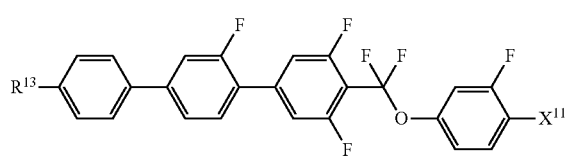

-continued
(7-47)
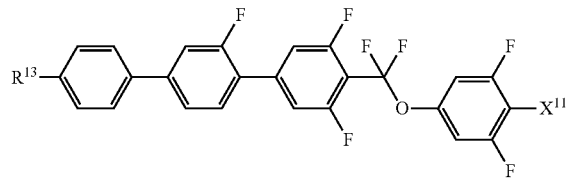
(7-48)
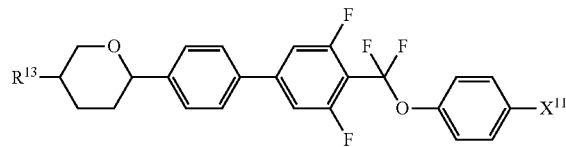
(7-49)
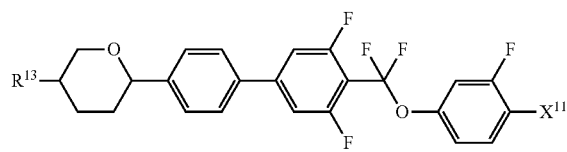
(7-50)
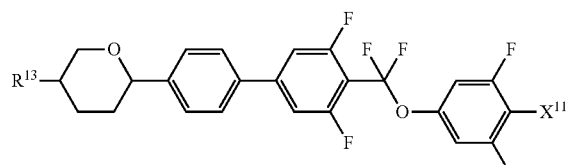
(7-51)
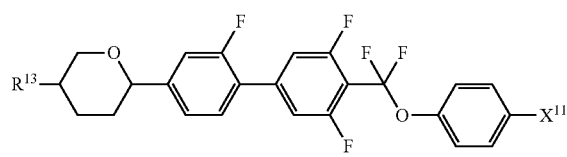
(7-52)
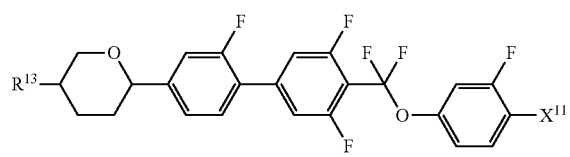
(7-53)
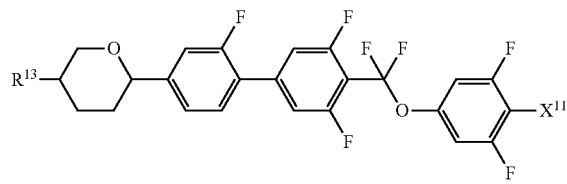
(7-54)
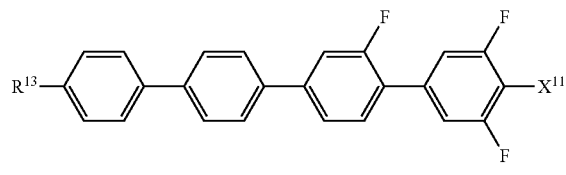
(7-55)
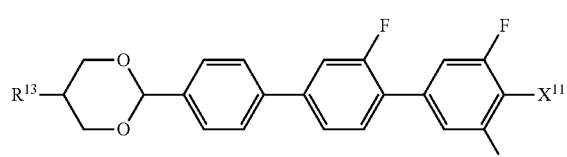
(7-56)
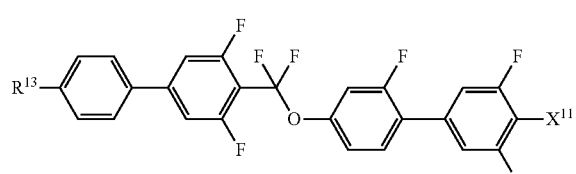
(7-57)
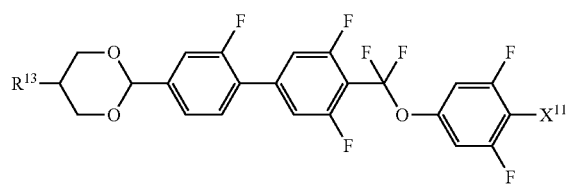
(7-58)
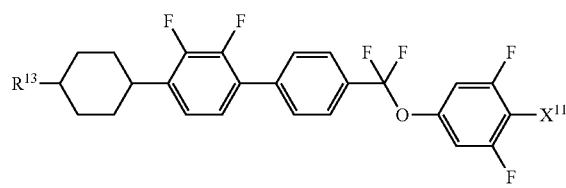
(7-59)
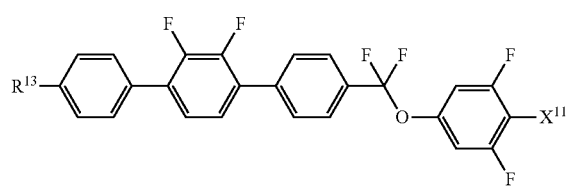
(7-60)
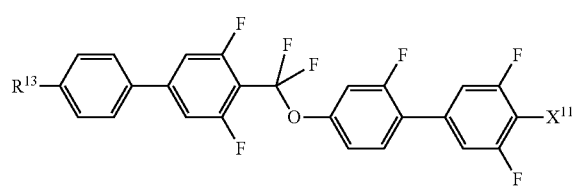
(7-61)
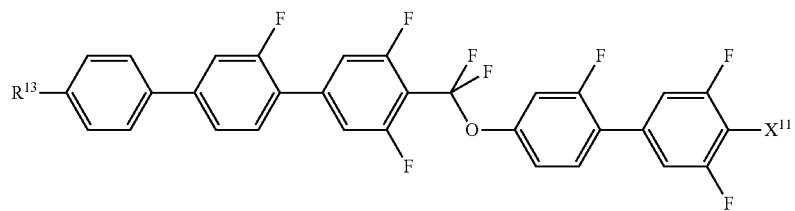

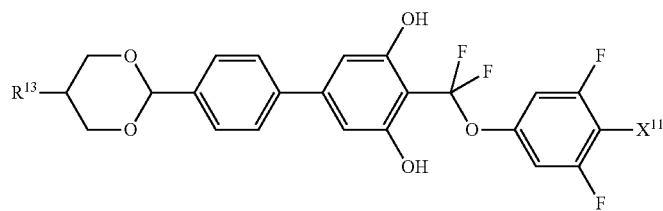
(7-62)

Component C has positive dielectric anisotropy, and superb stability to heat, light and so forth, and therefore is used when a composition for the IPS mode, the FFS mode, the OCB mode or the like is prepared. A content of component C is suitably in the range of 1% by weight to 99% by weight, preferably in the range of 10% by weight to 97% by weight, and further preferably in the range of 40% by weight to 95% by weight, based on the weight of the liquid crystal composition. When component C is added to a composition having negative dielectric anisotropy, the content of component C is preferably 30% by weight or less based on the weight of the liquid crystal composition. Addition of component C allows adjustment of the elastic constant of the composition and adjustment of a voltage-transmittance curve of the device.

Component D is compound (8) in which a right-terminal group is —C≡N or —C≡C—C≡N. Preferred examples of component D include compounds (8-1) to (8-64). In the compounds of component D, $R^{14}$ is alkyl having 1 to 10 carbons or alkenyl having 2 to 10 carbons, and in the alkyl and the alkenyl, at least one —CH$_2$— may be replaced by —O—, and at least one hydrogen may be replaced by fluorine; and —$X^{12}$ is —C≡N or —C≡C—C≡N.

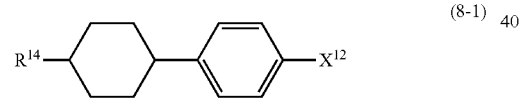
(8-1)

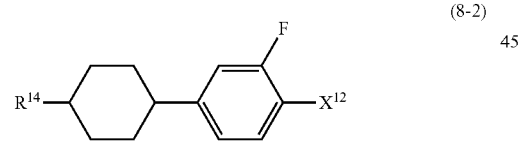
(8-2)

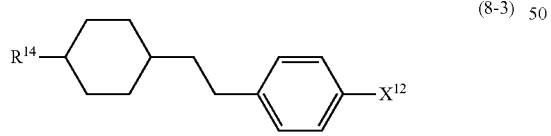
(8-3)

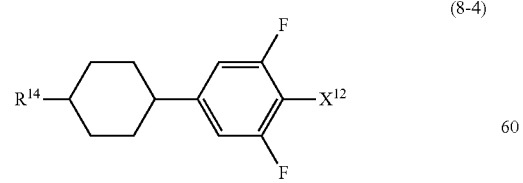
(8-4)

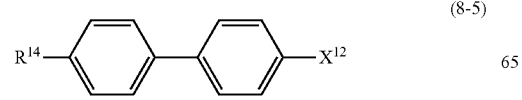
(8-5)

-continued

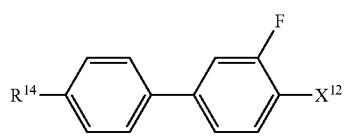
(8-6)

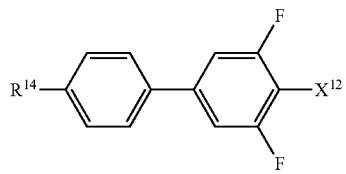
(8-7)

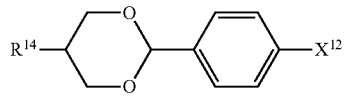
(8-8)

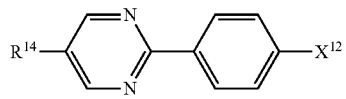
(8-9)

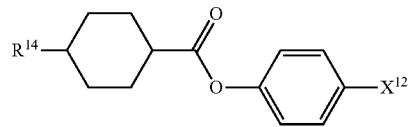
(8-10)

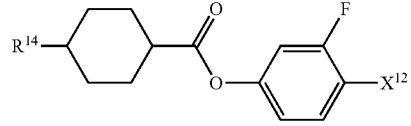
(8-11)

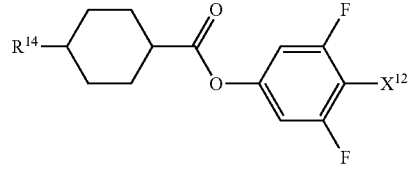
(8-12)

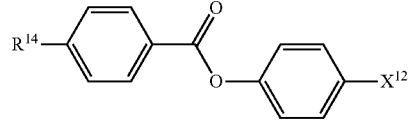
(8-13)

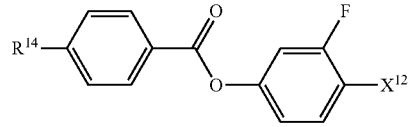
(8-14)

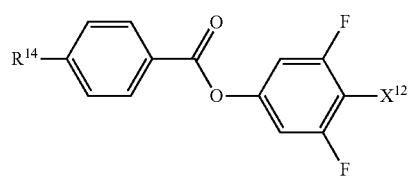 (8-15)
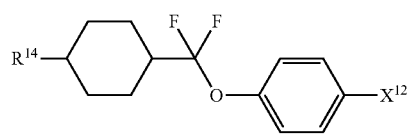 (8-16)
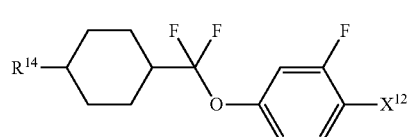 (8-17)
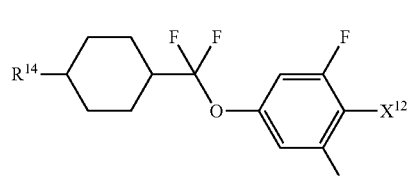 (8-18)
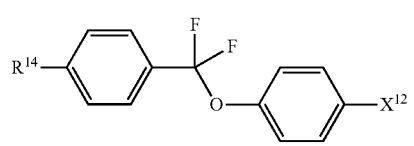 (8-19)
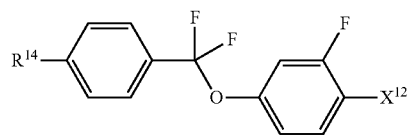 (8-20)
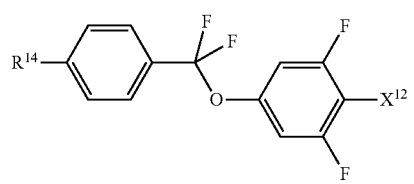 (8-21)
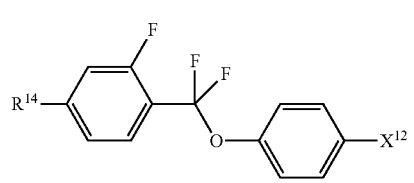 (8-22)
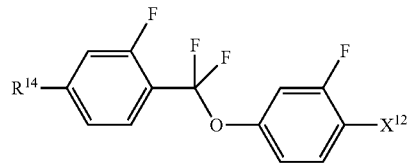 (8-23)
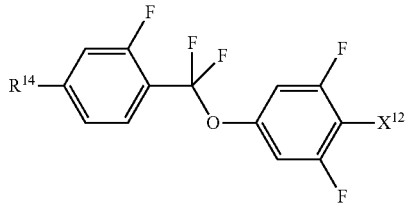 (8-24)
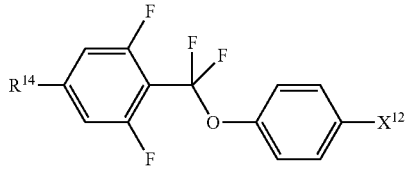 (8-25)
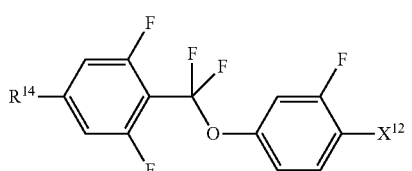 (8-26)
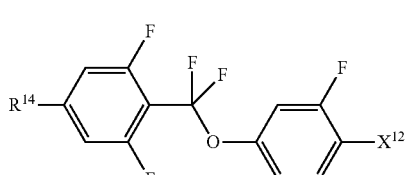 (8-27)
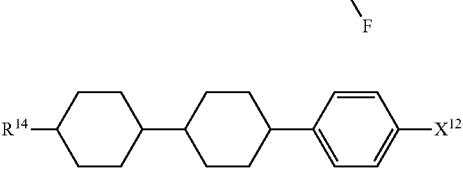 (8-28)
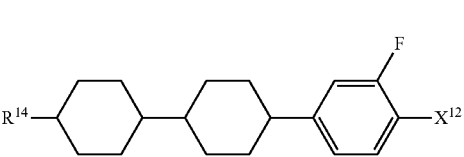 (8-29)
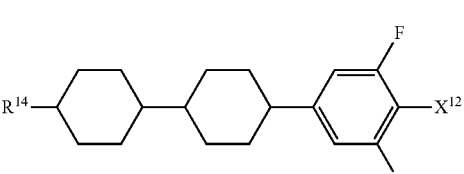 (8-30)
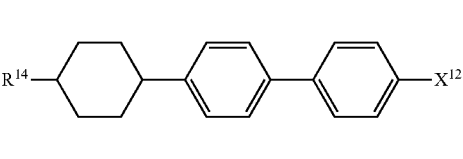 (8-31)
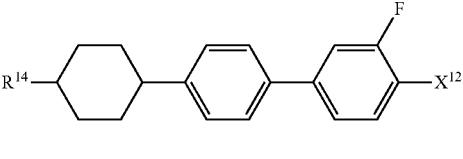 (8-32)

(8-33) 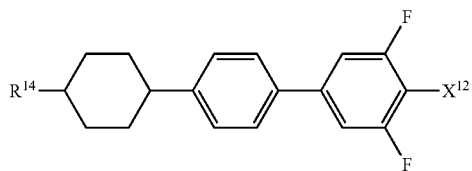
(8-34) 
(8-35) 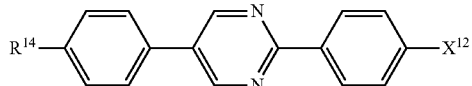
(8-36) 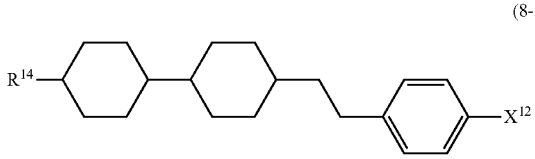
(8-37) 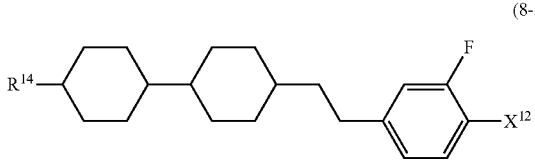
(8-38) 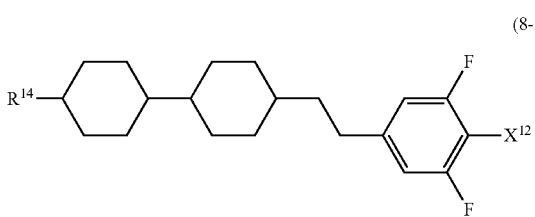
(8-39) 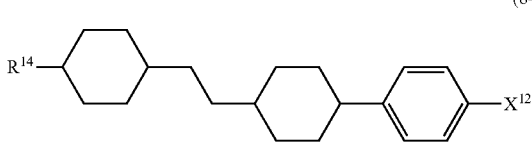
(8-40) 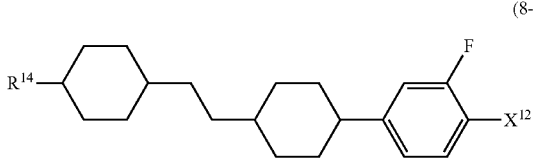
(8-41) 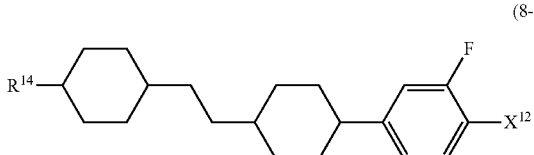
(8-42) 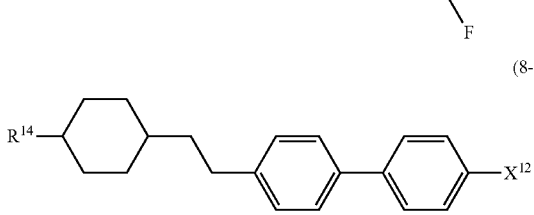
(8-43) 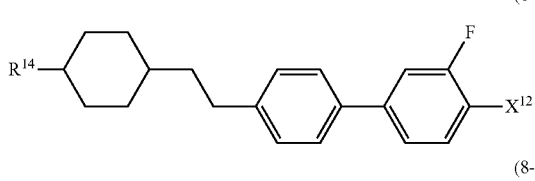
(8-44) 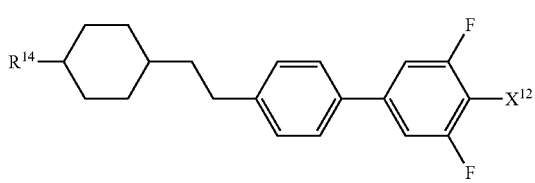
(8-45) 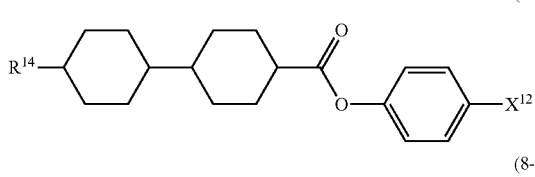
(8-46) 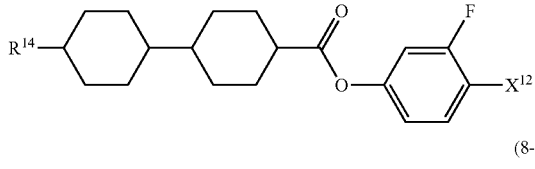
(8-47) 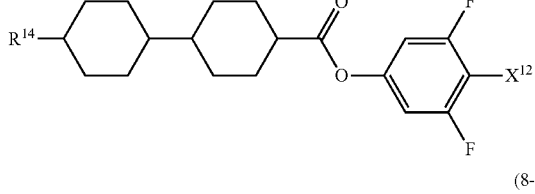
(8-48) 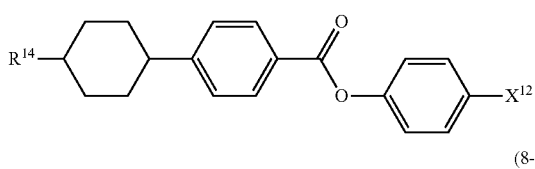
(8-49) 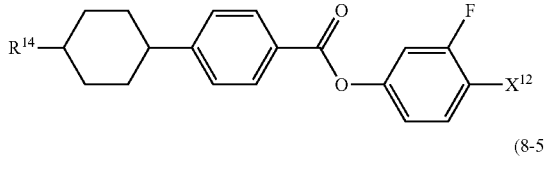
(8-50) 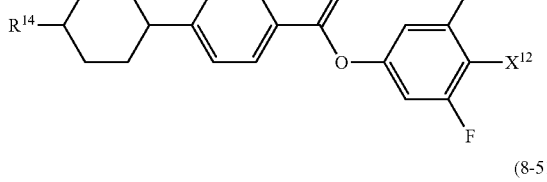
(8-51) 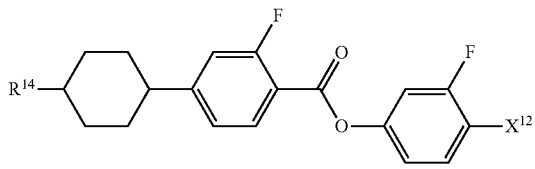

(8-52)
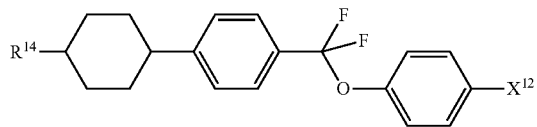

(8-53)
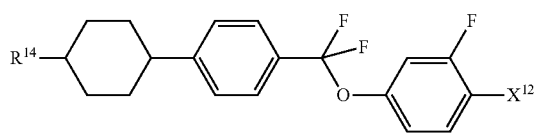

(8-54)
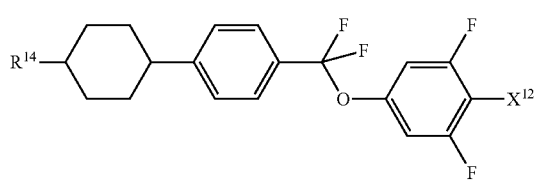

(8-55)
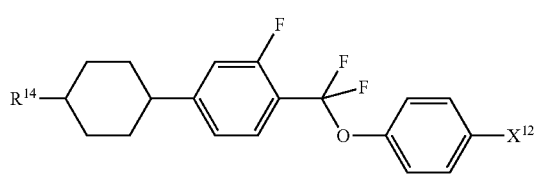

(8-56)
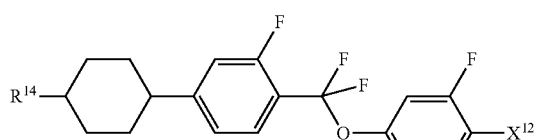

(8-57)
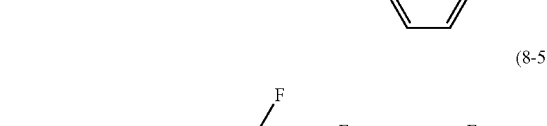

(8-58)

(8-59)

(8-60)
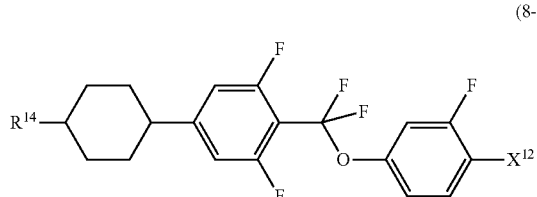

(8-61)
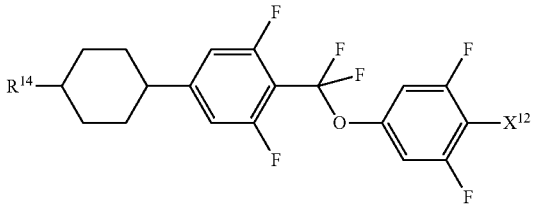

(8-62)
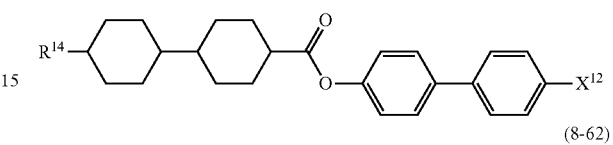

(8-63)
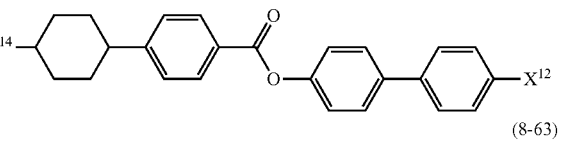

(8-64)

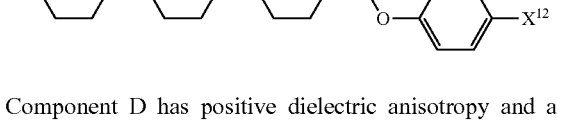

Component D has positive dielectric anisotropy and a value thereof is large, and therefore is mainly used when a composition for the TN mode or the like is prepared. Addition of component D can increase the dielectric anisotropy of the composition. Component D is effective in extending a temperature range of a liquid crystal phase, adjusting the viscosity or adjusting the optical anisotropy. Component D is also useful for adjustment of the voltage-transmittance curve of the device.

When the composition for the TN mode or the like is prepared, a content of component D is suitably in the range of 1% by weight to 99% by weight, preferably in the range of 10% by weight to 97% by weight, and further preferably in the range of 40% by weight to 95% by weight, based on the weight of the liquid crystal composition. When component D is added to a composition having negative dielectric anisotropy, the content of component D is preferably 30% by weight or less based on the weight of the liquid crystal composition. Addition of component D allows adjustment of the elastic constant of the composition and adjustment of the voltage-transmittance curve of the device.

Component E includes compounds (9) to (16). The compounds have phenylene in which hydrogen in lateral positions are replaced by two halogens, such as 2,3-difluoro-1,4-phenylene.

Preferred examples of component E include compounds (9-1) to (9-8), compounds (10-1) to (10-17), compound (11-1), compounds (12-1) to (12-3), compounds (13-1) to (13-11), compounds (14-1) to (14-3), compounds (15-1) to (15-3) and compounds (16-1) to (16-3). In the compounds of component E, $R^{15}$ and $R^{16}$ are independently alkyl having 1 to 10 carbons or alkenyl having 2 to 10 carbons, and in the alkyl and the alkenyl, at least one —CH$_2$— may be replaced by —O—, and at least one hydrogen may be replaced by fluorine; and $R^{17}$ is hydrogen, fluorine, alkyl having 1 to 10 carbons or alkenyl having 2 to 10 carbons, and in the alkyl and the alkenyl, at least one —CH$_2$— may be replaced by —O—, and at least one hydrogen may be replaced by fluorine.
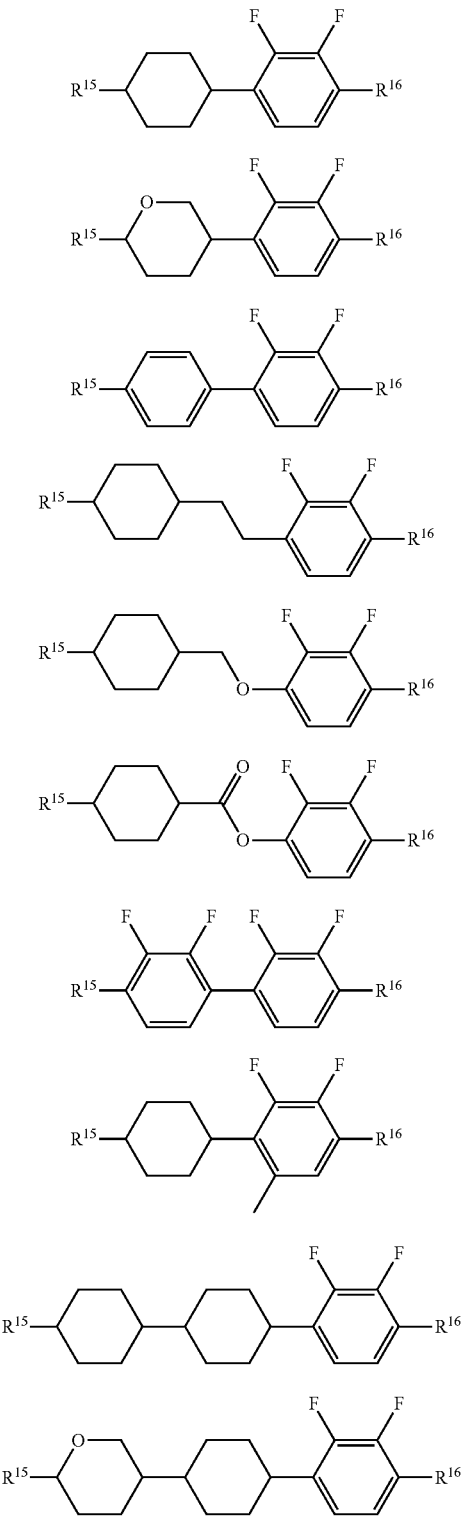
-continued
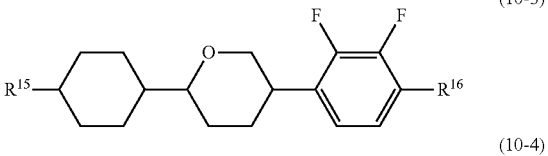
(10-3)
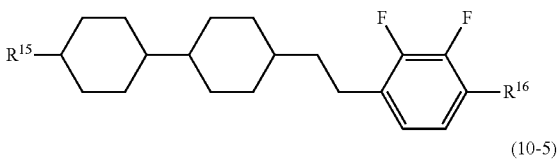
(10-4)
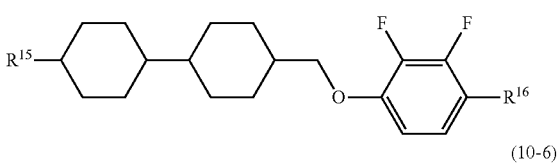
(10-5)
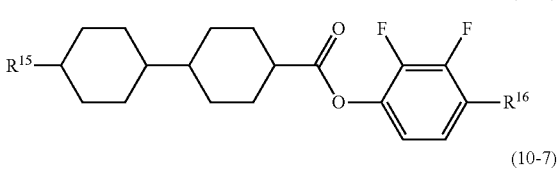
(10-6)
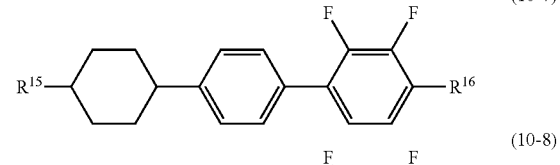
(10-7)
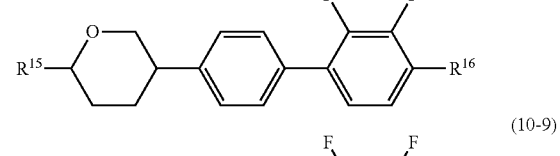
(10-8)
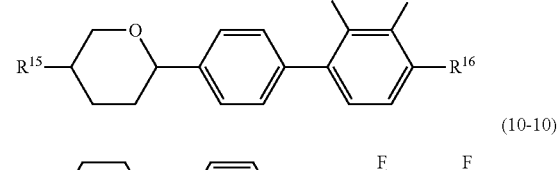
(10-9)
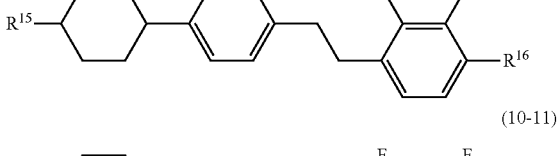
(10-10)
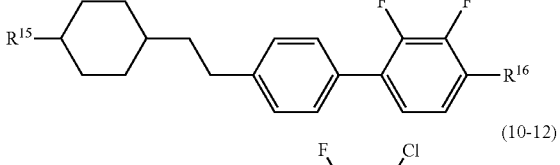
(10-11)
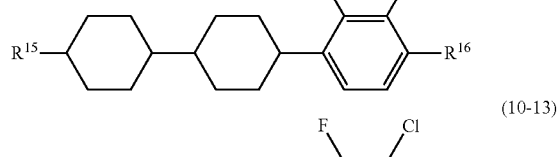
(10-12)
(10-13)

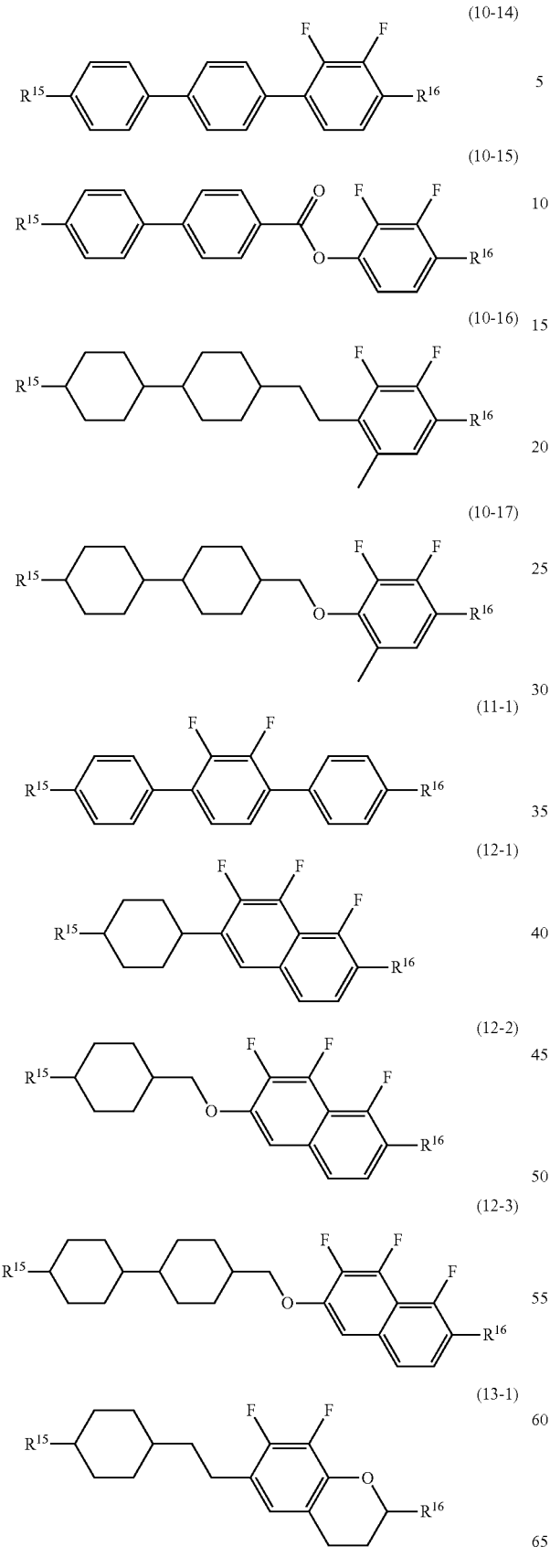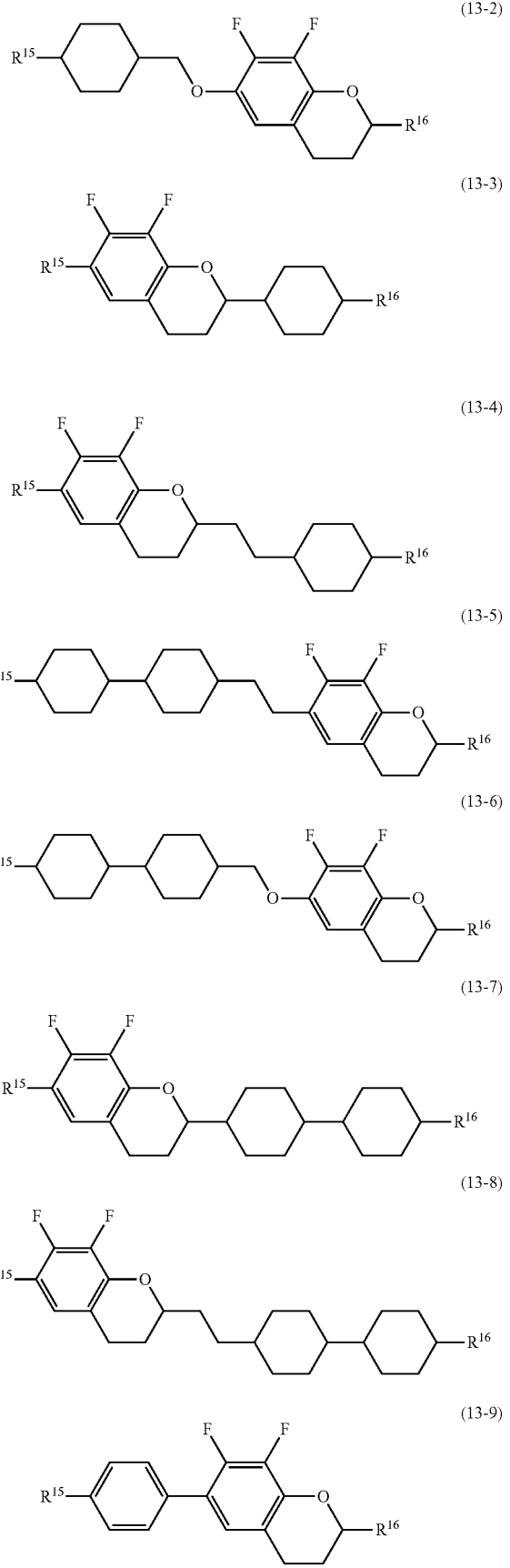

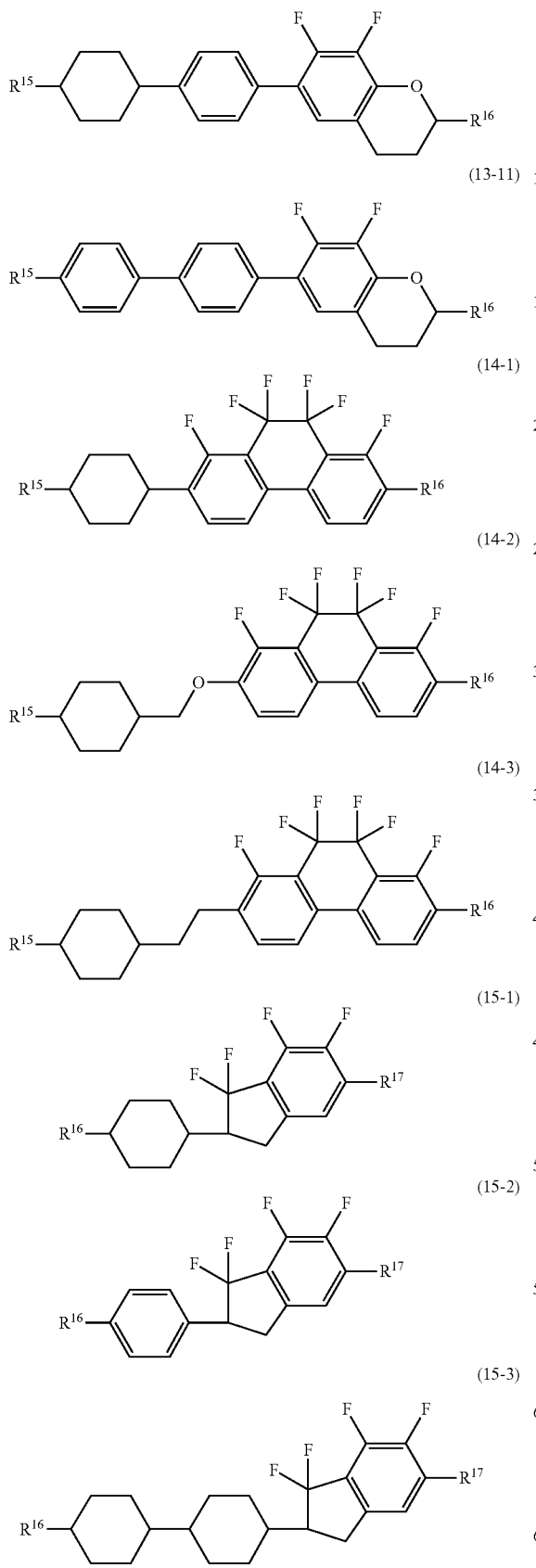
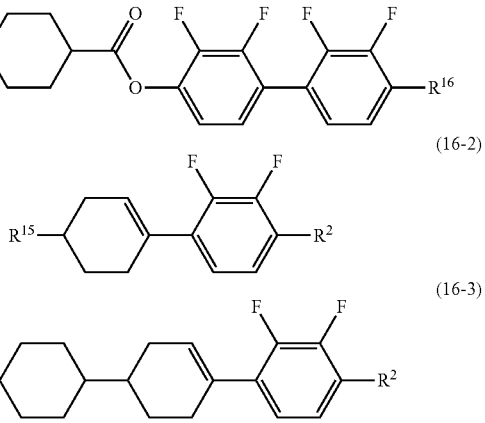

Component E has large negative dielectric anisotropy. Component E is used when a composition for the IPS mode, the VA mode, the PSA mode or the like is prepared. As a content of component E increases, the dielectric anisotropy of the composition negatively increases, but the viscosity increases. Thus, as long as a desired value of threshold voltage of the device is met, the content is preferably as small as possible. When the dielectric anisotropy at a degree of −5 is taken into account, the content is preferably 40% by weight or more in order to allow a sufficient voltage driving.

Among types of component E, compound (9) is a bicyclic compound, and therefore is mainly effective in decreasing the viscosity, adjusting the optical anisotropy or increasing the dielectric anisotropy. Compounds (10) and (11) are a tricyclic compound, and therefore are effective in increasing the maximum temperature, the optical anisotropy or the dielectric anisotropy. Compounds (12) to (15) are effective in increasing the dielectric anisotropy.

When a composition for the IPS mode, the VA mode, the PSA mode or the like is prepared, the content of component E is preferably 40% by weight or more, and further preferably in the range of 50% by weight to 95% by weight, based on the weight of the liquid crystal composition. When component E is added to a composition having positive dielectric anisotropy, the content of component E is preferably 30% by weight or less based on the weight of the liquid crystal composition. Addition of component E allows adjustment of the elastic constant of the composition and adjustment of the voltage-transmittance curve of the device.

The liquid crystal composition satisfying at least one of characteristics such as the high maximum temperature, the low minimum temperature, the small viscosity, the suitable optical anisotropy, the large positive or negative dielectric anisotropy, the large specific resistance, the high stability to ultraviolet light, the high stability to heat and the large elastic constant can be prepared by suitably combining components B, C, D and E described above. A liquid crystal compound different from components B, C, D and E may be added when necessary.

A liquid crystal composition is prepared according to a publicly-known method. For example, the component compounds are mixed and dissolved in each other by heating. According to an application, an additive may be added to the composition. Specific examples of the additives include a polymerizable compound other than formula (1) and formula (16), a polymerization initiator, a polymerization inhibitor, an optically active compound, an antioxidant, an ultraviolet light absorber, a light stabilizer, a heat stabilizer and an antifoaming agent. Such additives are well known to those skilled in the art, and described in literature.

The polymerizable compound is added for the purpose of forming a polymer in the liquid crystal composition. The polymerizable compound and compound (1) are copolymerized by irradiation with ultraviolet light while voltage is applied between electrodes, whereby the polymer is formed in the liquid crystal composition. On the occasion, compound (1) is immobilized in a state in which the polar group noncovalently interacts with the substrate surface of glass (or metal oxide). Thus, capability of controlling the alignment of liquid crystal molecules is further improved, and simultaneously the polar compound no longer leaks into the liquid crystal composition. Moreover, suitable pretilt angle can be obtained even in the substrate surface of glass (or metal oxide), and therefore a liquid crystal display device in which a response time is shortened and the voltage holding ratio is large can be obtained.

Preferred examples of the polymerizable compound include acrylate, methacrylate, a vinyl compound, a vinyloxy compound, propenyl ether, an epoxy compound (oxirane, oxetane) and vinyl ketone. Further preferred examples include a compound having at least one acryloyloxy, and a compound having at least one methacryloyloxy. Still further preferred examples also include a compound having both acryloyloxy and methacryloyloxy.

Still further preferred examples include compounds (M-1) to (M-17) In compounds (M-1) to (M-17), $R^{25}$ to $R^{31}$ are independently hydrogen or methyl; s, v and x are independently 0 or 1; t and u are independently an integer from 1 to 10; and $L^{21}$ to $L^{26}$ are independently hydrogen or fluorine, and $L^{27}$ and $L^{28}$ are independently hydrogen, fluorine or methyl.

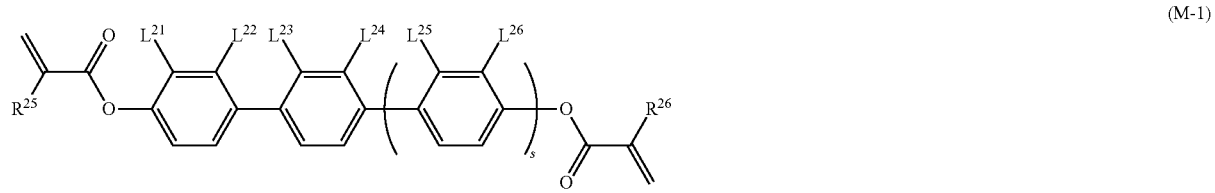

(M-1)

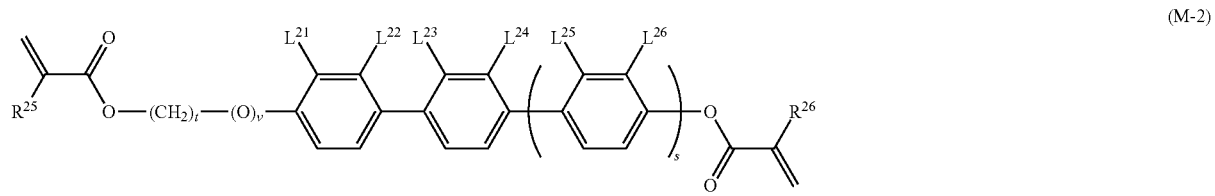

(M-2)

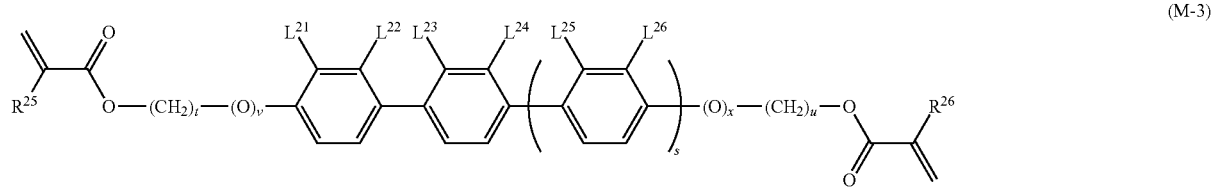

(M-3)

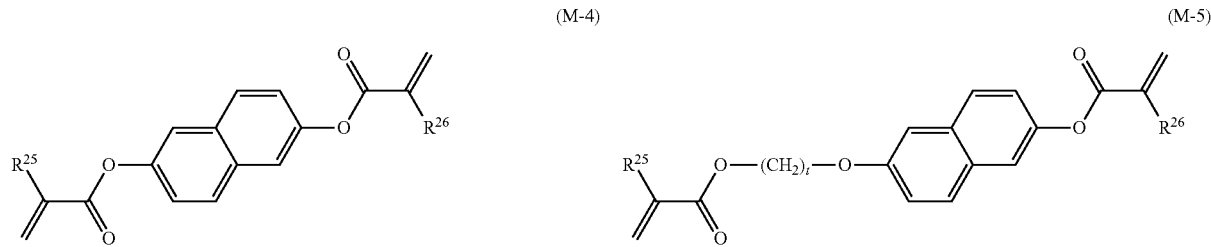

(M-4)     (M-5)

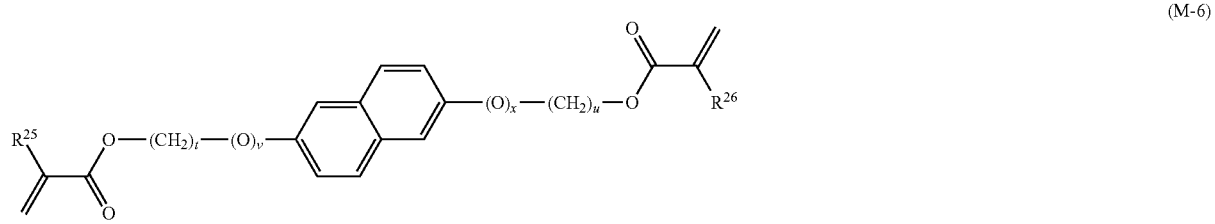

(M-6)

(M-7)
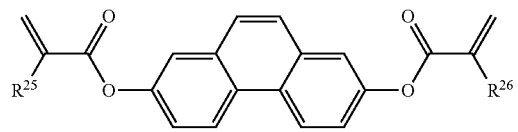
(M-8)
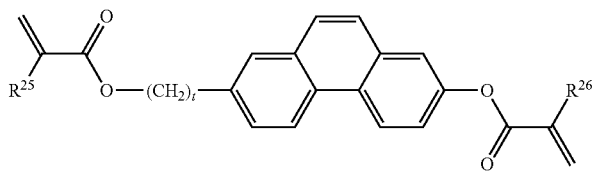
(M-9)
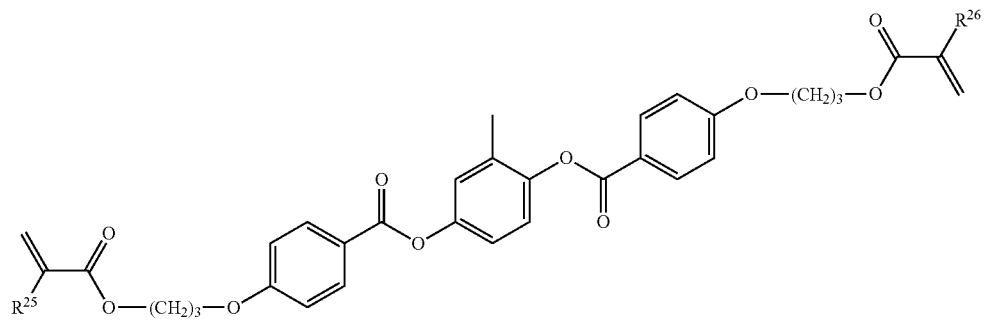
(M-10)
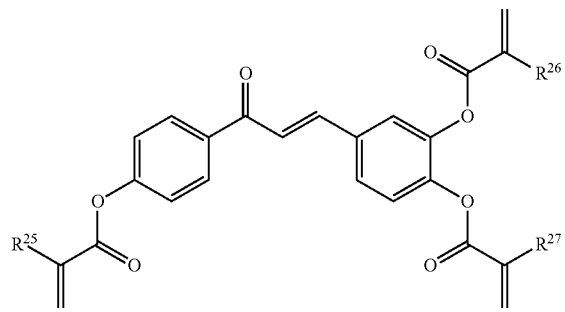
(M-11)
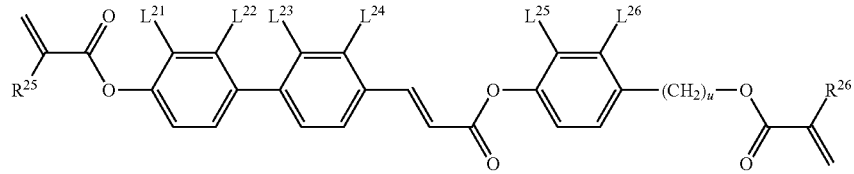
(M-12)
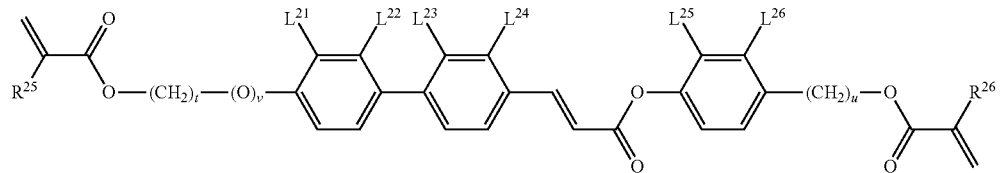
(M-13)
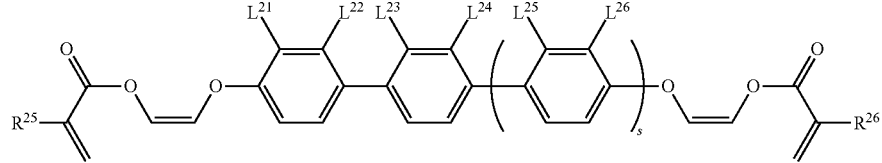
(M-14)
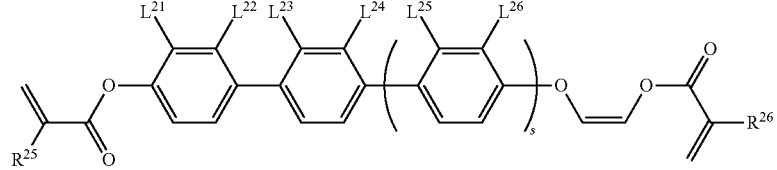

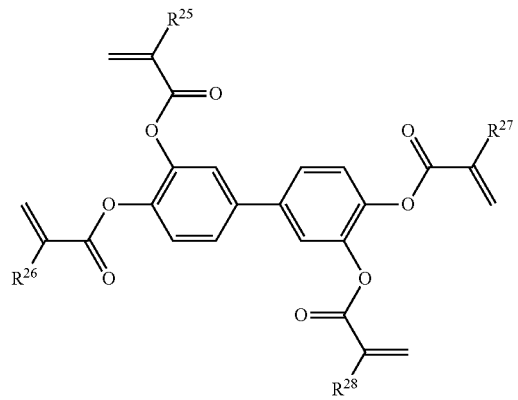
(M-15)

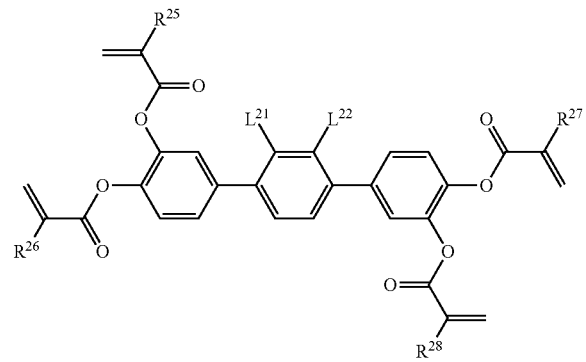
(M-16)

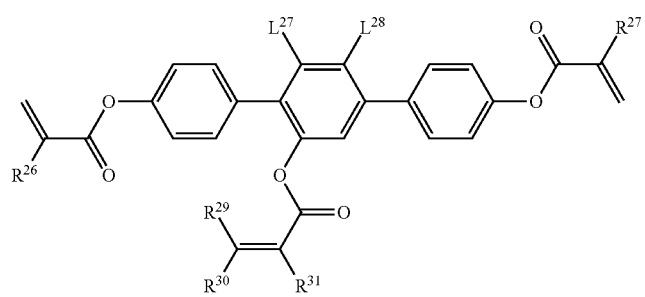
(M-17)

The polymerizable compound can be rapidly polymerized by adding the polymerization initiator. An amount of a remaining polymerizable compound can be decreased by optimizing a reaction temperature. Examples of a photoradical polymerization initiator include TPO, 1173 and 4265 from Darocur series of BASF SE, and 184, 369, 500, 651, 784, 819, 907, 1300, 1700, 1800, 1850 and 2959 from Irgacure series thereof.

Additional examples of the photoradical polymerization initiator include 4-methoxyphenyl-2,4-bis(trichloromethyl) triazine, 2-(4-butoxystyryl)-5-trichloromethyl-1,3,4-oxadiazole, 9-phenylacridine, 9,10-benzphenazine, a benzophenone-Michler's ketone mixture, a hexaarylbiimidazole-mercaptobenzimidazole mixture, 1-(4-isopropylphenyl)-2-hydroxy-2-methylpropane-1-one, benzyl dimethyl ketal, 2-methyl-1-[4-(methylthio)phenyl]-2-morpholinopropane-1-one, a mixture of 2,4-diethylxanthone and methyl p-dimethylaminobenzoate, and a mixture of benzophenone and methyltriethanolamine.

After the photoradical polymerization initiator is added to the liquid crystal composition, polymerization can be performed by irradiation with ultraviolet light in a state in which an electric field is applied thereto. However, an unreacted polymerization initiator or a decomposition product of the polymerization initiator may cause poor display such as image persistence in the device. In order to prevent such an event, photopolymerization may be performed with no addition of the polymerization initiator. A preferred wavelength of light used for irradiation is in the range of 150 nanometers to 500 nanometers. A further preferred wavelength is in the range of 250 nanometers to 450 nanometers, and a most preferred wavelength is in the range of 300 nanometers to 400 nanometers.

Upon mixing compound (1) having an ester-bonding group, a cinnamic acid ester-bond, a chalcone skeleton or a stilbene skeleton in the composition, a main effect of the component compound on the characteristics of the composition is as described below. When Fries rearrangement, photo-dimerization or cis-trans isomerization of a double bond is caused by polarized light, the compound (1) is aligned in a fixed direction at a molecular level. Accordingly, a thin film prepared from the polar compound aligns the liquid crystal molecules in the same manner as an alignment film of polyimide or the like.

In a compound having an aromatic ester and a polymerizable group, photolysis in an aromatic ester moiety is caused by irradiation with ultraviolet light to form a radical, and photo-Fries rearrangement is caused. In the photo-Fries rearrangement, the photolysis of the aromatic ester moiety is caused when a polarization direction of polarized ultraviolet light and a major axis direction of the aromatic ester moiety are identical. Recombination of the compound is caused after photolysis to generate a hydroxyl group in the molecule by tautomerization. Interaction in a substrate interface is caused by the hydroxyl group, and the polar compound is considered to be easily adsorbed with anisotropy on a side of the substrate interface. Moreover, the compound has the polymerizable group, and therefore is immobilized by polymerization. The property is utilized, whereby the thin film capable of aligning the liquid crystal molecule can be prepared. Linearly polarized light is suitable as ultraviolet light used for irradiation in order to prepare the thin film. First, the polar compound is added to the liquid crystal composition in the range of 0.1% by weight to 10% by weight, and the resulting composition is warmed in order to dissolve the polar compound thereinto. The composition is injected into the device having no alignment film. Next, the devise is irradiated with the linearly polarized light while warming the device to cause the photo-Fries rearrangement of the polar compound to polymerize the compound.

The polar compound in which the photo-Fries rearrangement is caused is aligned in a fixed direction, and the thin film formed after polymerization has a function as a liquid crystal alignment film.

Upon storing the polymerizable compound, the polymerization inhibitor may be added thereto for preventing polymerization. The polymerizable compound is ordinarily added to the composition without removing the polymerization inhibitor. Specific examples of the polymerization inhibitor include hydroquinone, a hydroquinone derivative such as methylhydroquinone, 4-t-butylcatechol, 4-methoxyphenol and phenothiazine.

The optically active compound is effective in inducing helical structure in the liquid crystal molecules to give a required twist angle, thereby preventing a reverse twist. A helical pitch can be adjusted by adding the optically active compound thereto. Two or more optically active compounds may be added for the purpose of adjusting temperature dependence of the helical pitch. Specific examples of a preferred optically active compound include compounds (Op-1) to (Op-18) described below. In compound (Op-18), ring J is 1,4-cyclohexylene or 1,4-phenylene, and $R^{28}$ is alkyl having 1 to 10 carbons.

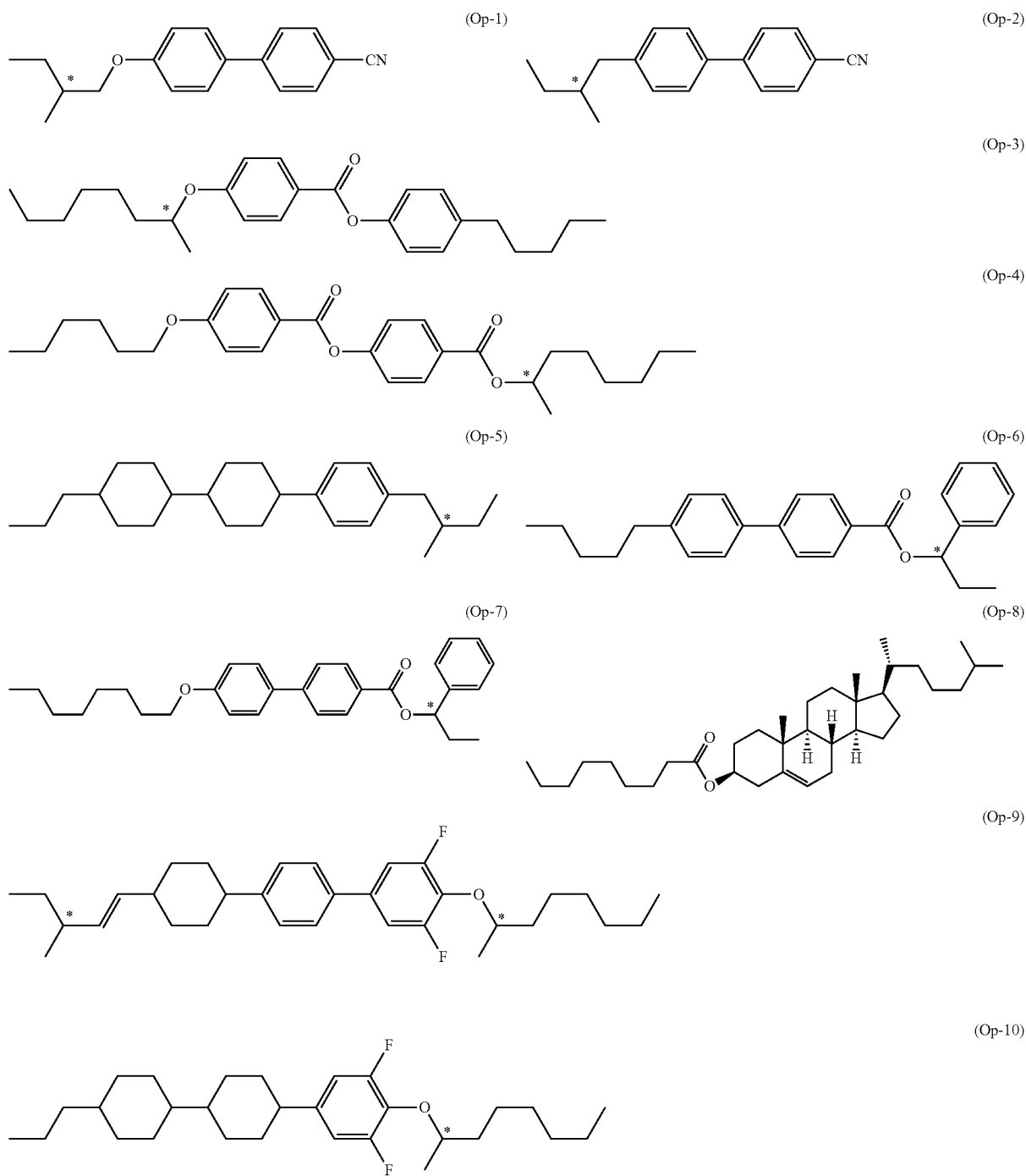

(Op-11)
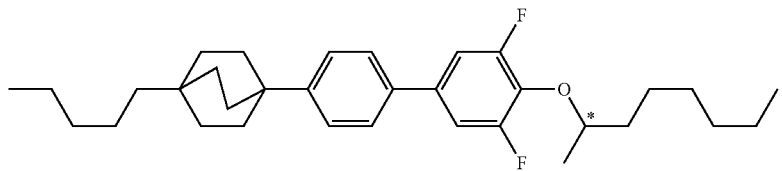

(Op-12)
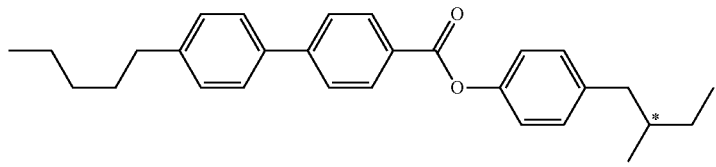

(Op-13)
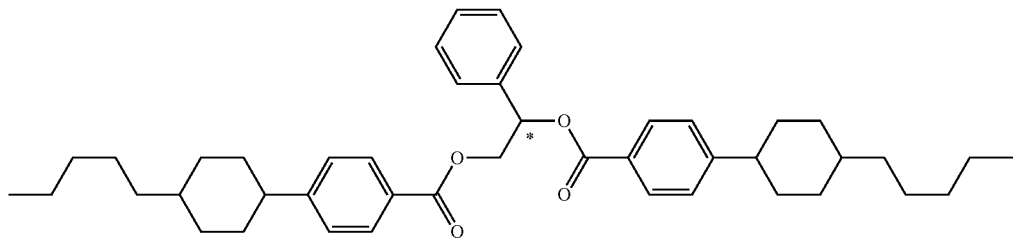

(Op-14)
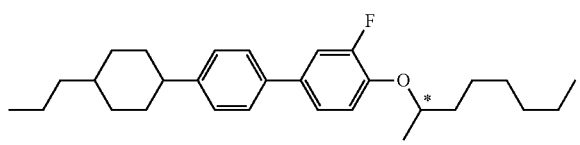

(Op-15)
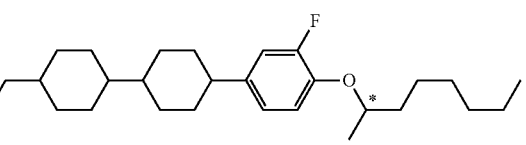

(Op-16)
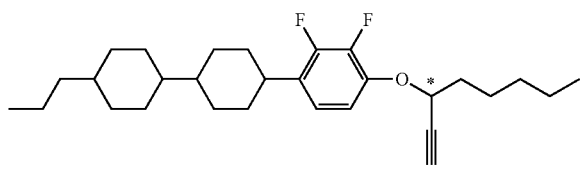

(Op-17)
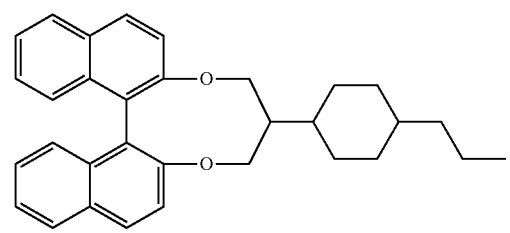

(Op-18)
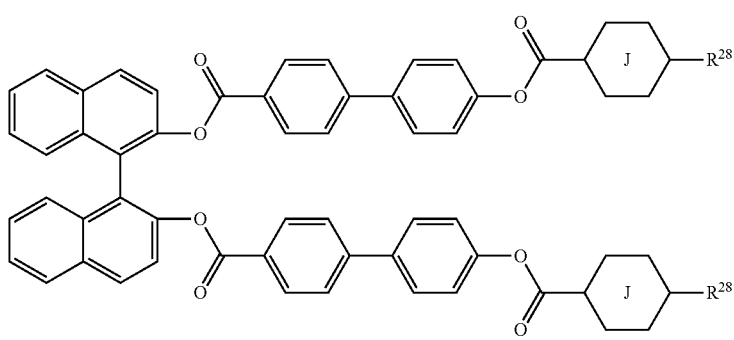

The antioxidant is effective for maintaining the large voltage holding ratio. Preferred examples of the antioxidant include compounds (AO-1) and (AO-2) described below; and IRGANOX 415, IRGANOX 565, IRGANOX 1010, IRGANOX 1035, IRGANOX 3114 and IRGANOX 1098 (trade names; BASF SE). The ultraviolet light absorber is effective for preventing a decrease of the maximum temperature. Preferred examples of the ultraviolet light absorber include a benzophenone derivative, a benzoate derivative and a triazole derivative. Specific examples thereof include compounds (AO-3) and (AO-4) described below; TINUVIN 329, TINUVIN P, TINUVIN 326, TINUVIN 234, TINUVIN 213, TINUVIN 400, TINUVIN 328 and TINUVIN 99-2 (trade names; BASF SE); and 1,4-diazabicyclo[2.2.2]octane (DABCO).

The light stabilizer such as an amine having steric hindrance is preferred for maintaining the large voltage holding ratio. Specific examples of a preferred light stabilizer include compounds (AO-5) and (AO-6) described below; and TINUVIN 144, TINUVIN 765 and TINUVIN 770DF (trade names: BASF SE). The heat stabilizer is also effective for maintaining the large voltage holding ratio, and specific preferred examples include IRGAFOS 168 (trade name; BASF SE). The antifoaming agent is effective for preventing foam formation. Preferred examples of the antifoaming agent include dimethyl silicone oil and methylphenyl silicone oil.

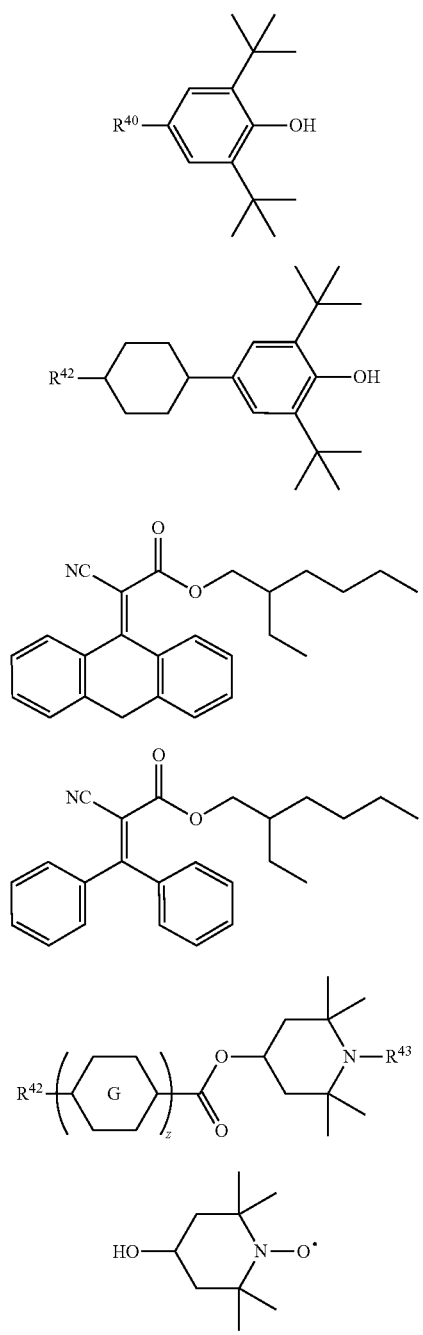

(AO-1)

(AO-2)

(AO-3)

(AO-4)

(AO-5)

(AO-6)

In compound (AO-1), $R^{40}$ is alkyl having 1 to 20 carbons, alkoxy having 1 to 20 carbons, —COOR$^{41}$ or —CH$_2$CH$_2$COOR$^{41}$, in which R$^{41}$ is alkyl having 1 to 20 carbons. In compounds (AO-2) and (AO-5), $R^{42}$ is alkyl having 1 to 20 carbons. In compound (AO-5), $R^{43}$ is hydrogen, methyl or O. (oxygen radical), ring G is 1,4-cyclohexylene or 1,4-phenylene, and z is 1, 2 or 3.

4. Liquid Crystal Display Device

The liquid crystal composition can be used in a liquid crystal display device having an operating mode such as the PC mode, the TN mode, the STN mode, the OCB mode and the PSA mode, and driven by an active matrix mode. The composition can also be used in a liquid crystal display device having the operating mode such as the PC mode, the TN mode, the STN mode, the OCB mode, the VA mode and the IPS mode, and driven by a passive matrix mode. The devices can be applied to any of a reflective type, a transmissive type and a transflective type.

The composition can also be used in a nematic curvilinear aligned phase (NCAP) device prepared by microencapsulating a nematic liquid crystal, and a polymer dispersed liquid crystal display device (PDLCD) and a polymer network liquid crystal display device (PNLCD), in which a three-dimensional network-polymer is formed in the liquid crystal. When an amount of addition of the polymerizable compound is about 10% by weight or less based on the weight of the liquid crystal composition, a liquid crystal display device having the PSA mode is prepared. A preferred proportion thereof is in the range of about 0.1% by weight to about 2% by weight. A further preferred proportion is in the range of about 0.2% by weight to about 1.0% by weight. The device having the PSA mode can be driven by the driving mode such as the active matrix mode and the passive matrix mode. Such a device can be applied to any of the reflective type, the transmissive type and the transflective type. A polymer dispersed mode device can also be prepared by increasing the amount of addition of the polymerizable compound.

In the polymer sustained alignment mode device, the polymer contained in the composition aligns the liquid crystal molecules. The polar compound assists alignment of the liquid crystal molecules. More specifically, the polar compound can be used in place of the alignment film. One example of a method for producing such a device is as described below.

A device having two substrates referred to as an array substrate and a color filter substrate is arranged. The substrate has no alignment film. At least one of the substrates has an electrode layer. The liquid crystal composition is prepared by mixing the liquid crystal compounds. The polymerizable compound and the polar compound are added to the composition. The additive may be further added thereto when necessary. The composition is injected into the device. The device is irradiated with light. Ultraviolet light is preferred. The polymerizable compound is polymerized by irradiation with light. The composition containing the polymer is formed by the polymerization to prepare a device having the PSA mode.

A method for producing the device will be described. First, the method includes a step of adding a polar compound to a liquid crystal composition, and then warming the resulting composition at a temperature higher than the maximum temperature thereof to dissolve the composition. Second, the method includes a step of injecting the composition into a liquid crystal display device. Third, the method includes a step of irradiating the composition with polarized ultraviolet light while warming the liquid crystal composition at a temperature higher than the maximum temperature thereof. The polar compound causes any one of the photo-Fries rearrangement, photo-dimerization or cis-trans isomerization of a double bond by linearly polarized light, and simultaneously polymerization thereof also progresses. A polymer formed of the polar compound is formed as the thin film on the substrate, and immobilized thereon. The compound is aligned in a fixed direction at a molecular level, and therefore the thin film has the function as the liquid crystal alignment film. A liquid crystal display device having no alignment film such as polyimide can be produced by the method described above.

In the procedure, the polar group interacts with the substrate surface, and therefore the polar compound is unevenly distributed on the substrate. The polar compound is unevenly distributed, and thus an amount of addition of the compound can be suppressed in comparison with the compound having no polar group. The polar compound aligns the liquid crystal molecules by irradiation with polarized ultraviolet light, and simultaneously the polymerizable compound is polymerized by ultraviolet light, and therefore a polymer maintaining the alignment is formed. The alignment of the liquid crystal molecules is additionally stabilized by an effect of the polymer, and therefore the response time in the device is shortened. The image persistence is caused due to poor operation of the liquid crystal molecules, and therefore the persistence is also simultaneously improved by the effect of the polymer. In particular, compound (1) of the invention is a polymerizable polar compound, and therefore aligns liquid crystal molecules, and also is copolymerized with any other polymerizable compound. Thus, the polar compound is no longer leaked into the liquid crystal composition, and therefore the liquid crystal display device having a large voltage holding ratio can be obtained.

EXAMPLES

Hereinafter, the invention will be described in greater detail by way of Examples (including Synthesis Examples and Use Examples of devices). However, the invention is not limited by the Examples. The invention includes a mixture of a composition in Use Example 1 and a composition in Use Example 2. The invention also includes a mixture prepared by mixing at least two compositions in each Use Example.

1. Example of Compound (1)

Compound (1) was prepared according to procedures shown in Example. Unless otherwise specified, a reaction was performed under a nitrogen atmosphere. Compound (1) was prepared according to procedures shown in Example 1 or the like. The thus prepared compound was identified by methods such as an NMR analysis. Characteristics of compound (1), the liquid crystal compound, the composition and the device were measured by methods described below.

NMR analysis: For measurement, DRX-500 made by Bruker BioSpin Corporation was used. In $^1$H-NMR measurement, a sample was dissolved in a deuterated solvent such as $CDCl_3$, and measurement was carried out under conditions of room temperature, 500 MHz and 16 times of accumulation. Tetramethylsilane was used as an internal standard. In $^{19}$F-NMR measurement, $CFCl_3$ was used as an internal standard, and measurement was carried out under conditions of 24 times of accumulation. In explaining nuclear magnetic resonance spectra obtained, s, d, t, q, quin, sex and m stand for a singlet, a doublet, a triplet, a quartet, a quintet, a sextet and a multiplet, and br being broad, respectively.

Gas chromatographic analysis: For measurement, GC-2010 Gas Chromatograph made by Shimadzu Corporation was used. As a column, a capillary column DB-1 (length 60 m, bore 0.25 mm, film thickness 0.25 μm) made by Agilent Technologies, Inc. was used. As a carrier gas, helium (1 mL/minute) was used. A temperature of a sample vaporizing chamber and a temperature of a detector (FID) part were set to 300° C. and 300° C., respectively. A sample was dissolved in acetone and prepared to be 1% by weight of a solution, and then 1 microliter of the solution obtained was injected into the sample vaporizing chamber. As a recorder, GC Solution System made by Shimadzu Corporation or the like was used.

HPLC analysis: For measurement, Prominence (LC-20AD; SPD-20A) made by Shimadzu Corporation was used. As a column, YMC-Pack ODS-A (length 150 mm, bore 4.6 mm, particle diameter 5 μm) made by YMC Co., Ltd. was used. As an eluate, acetonitrile and water were appropriately mixed and used. As a detector, a UV detector, an RI detector, a CORONA detector or the like was appropriately used. When the UV detector was used, a detection wavelength was set to 254 nanometers. A sample was dissolved in acetonitrile and prepared to be 0.1% by weight of a solution, and then 1 microliter of the solution was introduced into a sample chamber. As a recorder, C-R7Aplus made by Shimadzu Corporation was used.

Ultraviolet-visible spectrophotometry: For measurement, PharmaSpec UV-1700 made by Shimadzu Corporation was used. A detection wavelength was adjusted in the range of 190 nanometers to 700 nanometers. A sample was dissolved in acetonitrile and prepared to be a 0.01 mmol/L solution, and measurement was carried out by putting the solution in a quartz cell (optical path length: 1 cm).

Sample for measurement: Upon measuring phase structure and a transition temperature (a clearing point, a melting point, a polymerization starting temperature or the like), the compound itself was used as a sample.

Measuring method: Measurement of characteristics was carried out by the methods described below. Most of the measuring methods are applied as described in the Standard of the Japan Electronics and Information Technology Industries Association (JEITA) (JEITA ED-2521B) discussed and established by JEITA, or modified thereon. No thin film transistor (TFT) was attached to a TN device used for measurement.

(1) Phase Structure

A sample was placed on a hot plate in a melting point apparatus (FP-52 Hot Stage made by Mettler-Toledo International Inc.) equipped with a polarizing microscope. A state of phase and a change thereof were observed with the polarizing microscope while the sample was heated at a rate of 3° C. per minute, and a kind of the phase was specified.

(2) Transition Temperature (° C.)

For measurement, a differential scanning calorimeter, Diamond DSC System, made by PerkinElmer, Inc., or a high sensitivity differential scanning calorimeter, X-DSC7000, made by SSI NanoTechnology Inc. was used. A sample was heated and then cooled at a rate of 3° C. per minute, and a starting point of an endothermic peak or an exothermic peak caused by a phase change of the sample was determined by extrapolation, whereby a transition temperature was determined. A melting point and a polymerization starting temperature of a compound were also measured using the apparatus. Temperature at which a compound undergoes transition from a solid to a liquid crystal phase such as the smectic phase and the nematic phase may be occasionally abbreviated as "minimum temperature of the liquid crystal phase." Temperature at which the compound undergoes transition from the liquid crystal phase to liquid may be occasionally abbreviated as "clearing point."

A crystal was expressed as C. When kinds of the crystals were distinguishable, each of the crystals was expressed as $C_1$ or $C_2$. The smectic phase or the nematic phase was expressed as S or N. In the smectic phase, when smectic A phase, smectic B phase, smectic C phase or smectic F phase was distinguishable, the phases were expressed as $S_A$, $S_B$, $S_C$ or $S_F$, respectively. The liquid (isotropic) was expressed as I. A transition temperature was expressed as "C 50.0 N 100.0 I," for example. The expression indicates that a transition temperature from the crystals to the nematic phase is 50.0° C., and a transition temperature from the nematic phase to the liquid is 100.0° C.

(3) Maximum Temperature of Nematic Phase ($T_{NI}$ or NI; ° C.)

A sample was placed on a hot plate in a melting point apparatus equipped with a polarizing microscope, and heated at a rate of 1° C. per minute. Temperature when part of the sample began to change from a nematic phase to an isotropic liquid was measured. A maximum temperature of the nematic phase may be occasionally abbreviated as "maximum temperature." When the sample was a mixture of compound (1) and the base liquid crystal, the maximum temperature was expressed in terms of a symbol $T_{NI}$. When the sample was a mixture of compound (1) and a compound such as components B, C and D, the maximum temperature was expressed in terms of a symbol NI.

(4) Minimum Temperature of Nematic Phase ($T_C$; ° C.)

Samples each having a nematic phase were kept in freezers at temperatures of 0° C., −10° C., −20° C., −30° C. and −40° C. for 10 days, and then liquid crystal phases were observed. For example, when the sample maintained the nematic phase at −20° C. and changed to crystals or a smectic phase at −30° C., $T_C$ was expressed as $T_C \leq −20°$ C. A minimum temperature of the nematic phase may be occasionally abbreviated as "minimum temperature."

(5) Viscosity (Bulk Viscosity; r; Measured at 20° C.; mPa·s)

For measurement, a cone-plate (E type) rotational viscometer made by Tokyo Keiki Inc. was used.

(6) Optical Anisotropy (Refractive Index Anisotropy; Measured at 25° C.; Δn)

Measurement was carried out by an Abbe refractometer with a polarizing plate mounted on an ocular, using light at a wavelength of 589 nanometers. A surface of a main prism was rubbed in one direction, and then a sample was added dropwise onto the main prism. A refractive index (n∥) was measured when a direction of polarized light was parallel to a direction of rubbing. A refractive index (n⊥) was measured when the direction of polarized light was perpendicular to the direction of rubbing. A value of optical anisotropy (Δn) was calculated from an equation: Δn=n∥−n⊥.

(7) Specific Resistance (ρ; Measured at 25° C.; Ω cm)

Into a vessel equipped with electrodes, 1.0 milliliter of a sample was injected. A direct current voltage (10V) was applied to the vessel, and a direct current after 10 seconds was measured. Specific resistance was calculated from the following equation: (specific resistance)={(voltage)× (electric capacity of a vessel)}/{(direct current)× (dielectric constant of vacuum)}.

The measuring method of the characteristics may be different between a sample having positive dielectric anisotropy and a sample having negative dielectric anisotropy. When the dielectric anisotropy was positive, the measuring methods were described in sections (8a) to (12a). When the dielectric anisotropy was negative, the measuring methods were described in sections (8b) to (12b).

(8a) Viscosity (Rotational Viscosity; Yl; Measured at 25° C.; mPa·s)

Positive dielectric anisotropy: Measurement was carried out according to a method described in M. Imai et al., Molecular Crystals and Liquid Crystals, Vol. 259, p. 37 (1995). A sample was put in a TN device in which a twist angle was 0 degrees and a distance (cell gap) between two glass substrates was 5 micrometers. Voltage was applied stepwise to the device in the range of 16 V to 19.5 V at an increment of 0.5 V. After a period of 0.2 second with no voltage application, voltage was repeatedly applied under conditions of only one rectangular wave (rectangular pulse; 0.2 second) and no voltage application (2 seconds). A peak current and a peak time of transient current generated by the applied voltage were measured. A value of rotational viscosity was obtained from the measured values and calculation equation (8) described on page 40 of the paper presented by M. Imai et al. A value of dielectric anisotropy required for the calculation was determined using the device by which the rotational viscosity was measured and by a method described below.

(8b) Viscosity (Rotational Viscosity; Yl; Measured at 25° C.; mPa·s)

Negative dielectric anisotropy: Measurement was carried out according to a method described in M. Imai et al., Molecular Crystals and Liquid Crystals, Vol. 259, p. 37 (1995). A sample was put in a VA device in which a distance (cell gap) between two glass substrates was 20 micrometers. Voltage was applied stepwise to the device in the range of 39 V to 50 V at an increment of 1 V. After a period of 0.2 second with no voltage application, voltage was repeatedly applied under conditions of only one rectangular wave (rectangular pulse; 0.2 second) and no voltage application (2 seconds). A peak current and a peak time of transient current generated by the applied voltage were measured. A value of rotational viscosity was obtained from the measured values and calculation equation (8) described on page 40 of the paper presented by M. Imai et al. In dielectric anisotropy required for the calculation, a value measured according to sections of dielectric anisotropy described below was used.

(9a) Dielectric Anisotropy (as; Measured at 25° C.)

Positive dielectric anisotropy: A sample was put in a TN device in which a distance (cell gap) between two glass substrates was 9 micrometers and a twist angle was 80 degrees. Sine waves (10 V, 1 kHz) were applied to the device, and after 2 seconds, a dielectric constant (ε∥) of liquid crystal molecules in a major axis direction was measured. Sine waves (0.5 V, 1 kHz) were applied to the device, and after 2 seconds, a dielectric constant (ε⊥) of liquid crystal molecules in a minor axis direction was measured. A value of dielectric anisotropy was calculated from an equation: Δε=ε∥−ε⊥.

(9b) Dielectric Anisotropy (Δε; Measured at 25° C.)

Negative dielectric anisotropy: A value of dielectric anisotropy was calculated from an equation: Δε=ε∥−ε⊥. A dielectric constant (ε∥ and ε⊥) was measured as described below.

(1) Measurement of dielectric constant (ε∥): an ethanol (20 mL) solution of octadecyltriethoxysilane (0.16 mL) was applied to a well-cleaned glass substrate. After rotating the glass substrate with a spinner, the glass substrate was heated at 150° C. for 1 hour. A sample was put in a VA device in which a distance (cell gap) between two glass substrates was 4 micrometers, and the device was sealed with an ultraviolet-curable adhesive. Sine waves (0.5 V, 1 kHz) were applied to the device, and after 2 seconds, a dielectric constant (ε∥) of liquid crystal molecules in a major axis direction was measured.

(2) Measurement of dielectric constant (ε⊥): a polyimide solution was applied to a well-cleaned glass substrate. After calcining the glass substrate, rubbing treatment was applied to the alignment film obtained. A sample was put in a TN device in which a distance (cell gap) between two glass substrates was 9 micrometers and a twist angle was 80 degrees. Sine waves (0.5 V, 1 kHz) were applied to the device, and after 2 seconds, a dielectric constant (ε∥) of liquid crystal molecules in a minor axis direction was measured.

(10a) Elastic Constant (K; Measured at 25° C.; pN)

Positive dielectric anisotropy: For measurement, HP4284A LCR Meter made by Yokogawa-Hewlett-Packard Co. was used. A sample was put in a horizontal alignment device in which a distance (cell gap) between two glass substrates was 20 micrometers. An electric charge of 0 V to 20 V was applied to the device, and electrostatic capacity and applied voltage were measured. The measured values of electrostatic capacity (C) and applied voltage (V) were fitted to equation (2.98) and equation (2.101) on page 75 of "Liquid Crystal Device Handbook" (Ekisho Debaisu Handobukku in Japanese; Nikkan Kogyo Shimbun, Ltd.), and values of $K_{11}$ and $K_{33}$ were obtained from equation (2.99). Next, $K_{22}$ was calculated using the previously determined values of $K_{11}$ and $K_{33}$ in equation (3.18) on page 171. Elastic constant K was expressed in terms of a mean value of the thus determined $K_{11}$, $K_{22}$ and $K_{33}$.

(10b) Elastic Constant (Ku and $K_{33}$; Measured at 25° C.; pN)

Negative dielectric anisotropy: For measurement, Elastic Constant Measurement System Model EC-1 made by TOYO Corporation was used. A sample was put in a vertical alignment device in which a distance (cell gap) between two glass substrates was 20 micrometers. An electric charge of 20 V to 0 V was applied to the device, and electrostatic capacity and applied voltage were measured. Values of electrostatic capacity (C) and applied voltage (V) were fitted to equation (2.98) and equation (2.101) on page 75 of "Liquid Crystal Device Handbook" (Ekisho Debaisu Handobukku in Japanese; Nikkan Kogyo Shimbun, Ltd.), and a value of elastic constant was obtained from equation (2.100).

(11a) Threshold Voltage (Vth; Measured at 25° C.; V)

Positive dielectric anisotropy: For measurement, an LCD-5100 luminance meter made by Otsuka Electronics Co., Ltd. was used. A light source was a halogen lamp. A sample was put in a normally white mode TN device in which a distance (cell gap) between two glass substrates was 0.45/Δn (μm) and a twist angle was 80 degrees. A voltage (32 Hz, rectangular waves) to be applied to the device was stepwise increased from 0 V to 10 V at an increment of 0.02 V. On the occasion, the device was irradiated with light from a direction perpendicular to the device, and an amount of light transmitted through the device was measured. A voltage-transmittance curve was prepared, in which the maximum amount of light corresponds to 100% transmittance and the minimum amount of light corresponds to 0% transmittance. A threshold voltage is expressed in terms of voltage at 90% transmittance.

(11b) Threshold Voltage (Vth; Measured at 25° C.; V)

Negative dielectric anisotropy: For measurement, an LCD-5100 luminance meter made by Otsuka Electronics Co., Ltd. was used.

A light source was a halogen lamp. A sample was put in a normally black mode VA device in which a distance (cell gap) between two glass substrates was 4 micrometers and a rubbing direction was anti-parallel, and the device was sealed with an ultraviolet-curable adhesive. A voltage (60 Hz, rectangular waves) to be applied to the device was stepwise increased from 0 V to 20 V at an increment of 0.02 V. On the occasion, the device was irradiated with light from a direction perpendicular to the device, and an amount of light transmitted through the device was measured. A voltage-transmittance curve was prepared, in which the maximum amount of light corresponds to 100% transmittance and the minimum amount of light corresponds to 0% transmittance. A threshold voltage is expressed in terms of voltage at 10% transmittance.

(12a) Response Time (T; Measured at 25° C.; Ms)

Positive dielectric anisotropy: For measurement, an LCD-5100 luminance meter made by Otsuka Electronics Co., Ltd. was used. A light source was a halogen lamp. A low-pass filter was set to 5 kHz. A sample was put in a normally white mode TN device in which a distance (cell gap) between two glass substrates was 5.0 micrometers and a twist angle was 80 degrees. A voltage (rectangular waves; 60 Hz, 5 V, 0.5 second) was applied to the device. On the occasion, the device was irradiated with light from a direction perpendicular to the device, and an amount of light transmitted through the device was measured. The maximum amount of light corresponds to 100% transmittance, and the minimum amount of light corresponds to 0% transmittance. A rise time (τr; millisecond) was expressed in terms of time required for a change from 90% transmittance to 10% transmittance. A fall time (τf; millisecond) was expressed in terms of time required for a change from 10% transmittance to 90% transmittance. A response time was expressed by a sum of the rise time and the fall time thus determined.

(12b) Response Time (τ; Measured at 25° C.; Ms)

Negative dielectric anisotropy: For measurement, an LCD-5100 luminance meter made by Otsuka Electronics Co., Ltd. was used. A light source was a halogen lamp. A low-pass filter was set to 5 kHz. A sample was put in a normally black mode PVA device in which a distance (cell gap) between two glass substrates was 3.2 micrometers, and a rubbing direction was anti-parallel. The device was sealed with an ultraviolet-curable adhesive. A voltage of a little exceeding a threshold voltage was applied to the device for 1 minute, and then the device was irradiated with ultraviolet light of 23.5 mW/cm² for 8 minutes, while applying a voltage of 5.6 V. A voltage (rectangular waves; 60 Hz, 10 V, 0.5 second) was applied to the device. On the occasion, the device was irradiated with light from a direction perpendicular to the device, and an amount of light transmitted through the device was measured. The maximum amount of light corresponds to 100% transmittance, and the minimum amount of light corresponds to 0% transmittance. A response time was expressed in terms of time required for a change from 90% transmittance to 10% transmittance (fall time; millisecond).

Raw Material

Solmix (registered trademark) A-11 is a mixture of ethanol (85.5%), methanol (13.4%) and isopropanol (1.1%), and was purchased from Japan Alcohol Trading Co., Ltd.

Synthesis Example 1

Synthesis of Compound (No. 59)

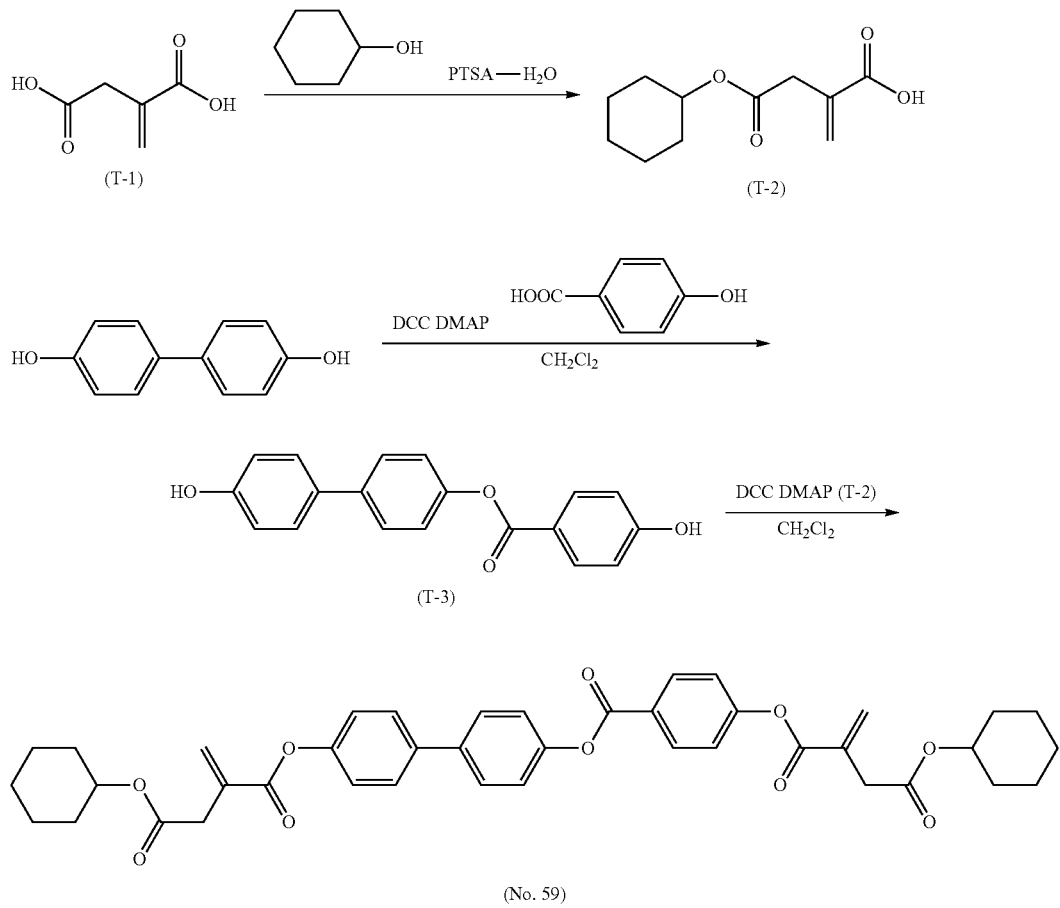

First Step

Compound (T-1) (20 g), cyclohexanol (200 mL) and p-toluene sulfonic acid monohydrate (PTSA-H$_2$O) (0.4 g) were put in a reaction vessel, and the resulting mixture was stirred at 60° C. for 48 hours. The resulting solution was concentrated under reduced pressure, and the residue was purified by silica gel chromatography (toluene: ethyl acetate=2:1 in a volume ratio) to obtain compound (T-2) (32 g; 98%).

Second Step

In a reaction vessel, 4,4'-biphenyldiol (10 g), 4-hydroxybenzoic acid (7.4 g), 4-dimethylaminopyridine (DMAP) (0.34 g), and dichloromethane (200 mL) were put, and the resulting mixture was cooled down to 0° C. Thereto, DCC (11 g) was added, and the resulting mixture was stirred for 12 hours while returning to room temperature. After an insoluble matter was filtered off, the reaction mixture was poured into water, and an aqueous layer was subjected to extraction with ethyl acetate. An organic layer was washed with water, and dried over anhydrous magnesium sulfate. The resulting solution was concentrated under reduced pressure, and the residue was purified by silica gel chromatography (ethyl acetate:toluene=1:1 in a volume ratio) to obtain compound (T-3) (3 g; 40%).

Third Step

Compound (T-3) (1.1 g), compound (T-2) (1.8 g), DMAP (0.26 g) and dichloromethane (100 mL) were put in a reaction vessel, and the resulting mixture was cooled down to 0° C. Thereto, DCC (1.8 g) was added, and the resulting mixture was stirred for 12 hours while returning to room temperature. After an insoluble matter was filtered off, the reaction mixture was poured into water, and an aqueous layer was subjected to extraction with dichloromethane. An organic layer was washed with water, and dried over anhydrous magnesium sulfate. The resulting solution was concentrated under reduced pressure, and the residue was purified by silica gel chromatography (ethyl acetate:toluene=1:5 in a volume ratio) to obtain compound (No. 59) (1.25 g; 50%).

An NMR analysis value of the resulting compound (No. 59) was as described below.

$^1$H-NMR: chemical shift δ (ppm; CDCl$_3$): 8.27 (d, 2H), 7.62 (d, 2H), 7.60 (d, 2H), 7.30 (d, 2H), 7.28 (d, 2H), 7.20 (d, 2H), 6.58 (d, 2H), 5.92 (d, 2H), 4.65-4.79 (m, 2H), 3.46 (s, 4H), 1.90-1.80 (m, 4H), 1.75-1.65 (m, 4H), 1.57-1.20 (m, 12H).

Physical properties of compound (No. 59) were as described below.

Transition temperature (° C.): C 137.0 I

Synthesis Example 2

Synthesis of Compound (No. 401)

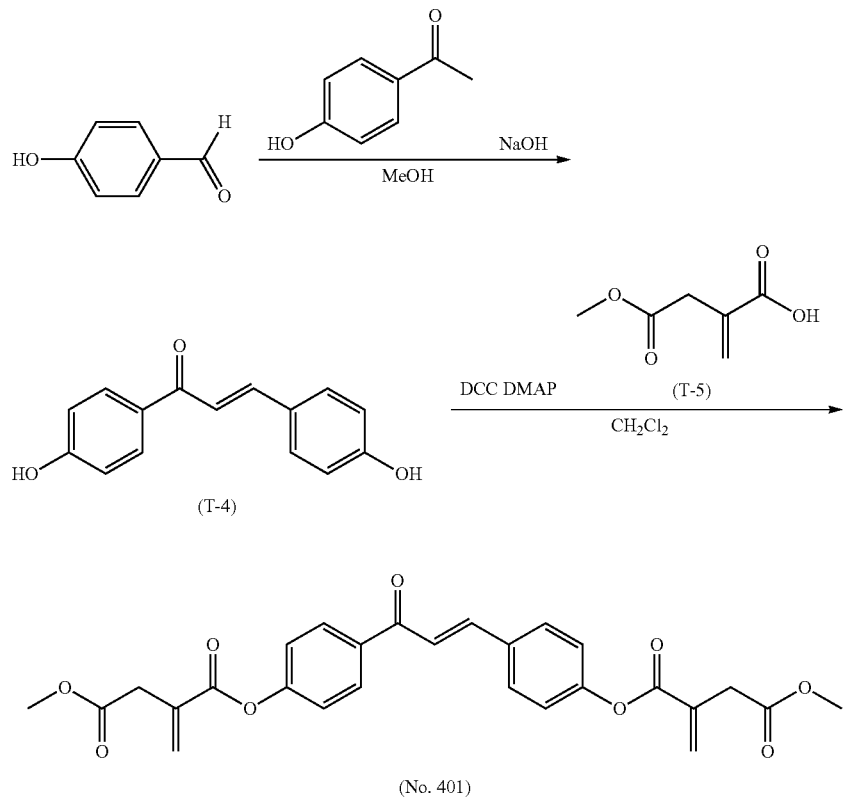

First Step

In a reaction vessel, 4-hydroxybenzaldehyde (10 g), 4-hydroxyacetophenone (11 g), sodium hydroxide (6.5 g), and methanol (200 mL) were put, and the resulting mixture was stirred at 40° C. for 12 hours. The reaction mixture was poured into water, neutralized with hydrochloric acid, and then subjected to extraction with ethyl acetate. An organic layer was washed with water, and dried over anhydrous magnesium sulfate. The solution was concentrated under reduced pressure, and the resulting residue was recrystallized in ethyl acetate to obtain compound (T-4) (5 g; 25%).

Second Step

Compound (T-4) (5 g), compound (T-5) (6 g), DMAP (0.25 g) and dichloromethane (200 mL) were put in a reaction vessel, and the resulting mixture was cooled down to 0° C. Thereto, DCC (8.6 g) was added, and the resulting mixture was stirred for 12 hours while returning to room temperature. After an insoluble matter was filtered off, the reaction mixture was poured into water, and an aqueous layer was subjected to extraction with dichloromethane. An organic layer was washed with water, and dried over anhydrous magnesium sulfate. The resulting solution was concentrated under reduced pressure, and the residue was purified by silica gel chromatography (ethyl acetate:toluene=1:5 in a volume ratio) to obtain compound (No. 401) (7 g; 68%).

An NMR analysis value of the resulting compound (No. 401) was as described below.

$^1$H-NMR: chemical shift δ (ppm; CDCl$_3$): 8.07 (d, 2H), 7.80 (d, 1H), 7.68 (d, 2H), 7.48 (d, 1H), 7.28 (d, 2H), 7.21 (d, 2H), 6.60 (d, 2H), 5.94 (d, 2H), 5.74 (s, 6H), 3.49 (s, 2H), 3.48 (s, 2H).

Physical properties of compound (No. 401) were as described below.

Transition temperature (° C.): C 97.8 I

Compounds (No. 1) to (No. 588) described below were prepared according to the synthesis methods described in Synthesis Examples.

| | No. |
|---|---|
| 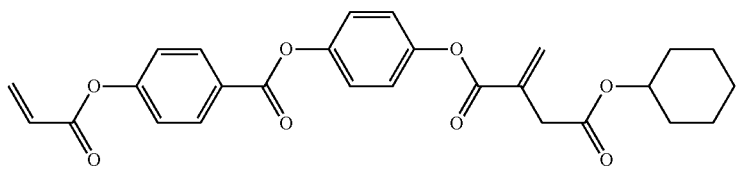 [SMILES: C=CC(=O)Oc1ccc(C(=O)Oc2ccc(OC(=O)C(=C)CC(=O)OC3CCCCC3)cc2)cc1] | 1 |

| No. |
|---|
| 2 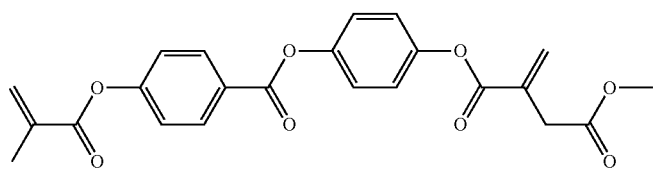 [SMILES: C=C(C)C(=O)Oc1ccc(C(=O)Oc2ccc(OC(=O)C(=C)CC(=O)OC)cc2)cc1] |
| 3 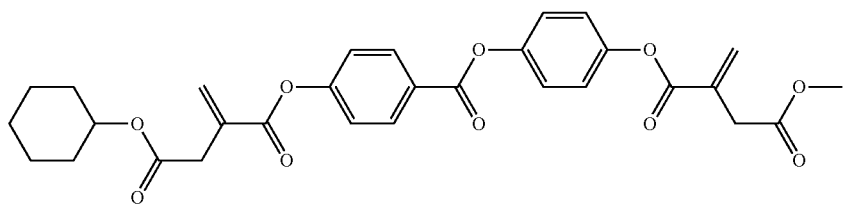 [SMILES: C=C(CC(=O)OC)C(=O)Oc1ccc(OC(=O)c2ccc(OC(=O)C(=C)CC(=O)OC3CCCCC3)cc2)cc1] |
| 4 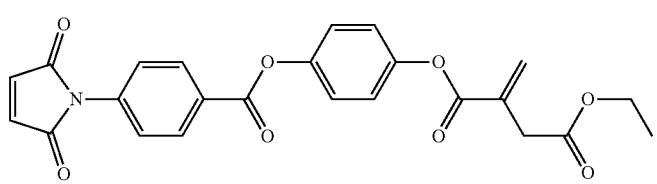 [SMILES: C=C(CC(=O)OCC)C(=O)Oc1ccc(OC(=O)c2ccc(N3C(=O)C=CC3=O)cc2)cc1] |
| 5 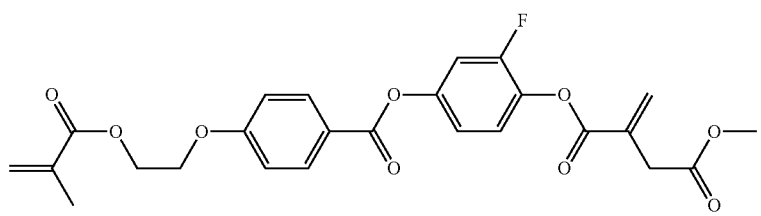 [SMILES: C=C(C)C(=O)OCCOc1ccc(C(=O)Oc2ccc(OC(=O)C(=C)CC(=O)OC)c(F)c2)cc1] |
| 6 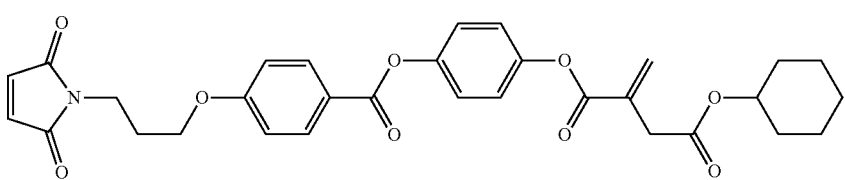 [SMILES: C=C(CC(=O)OC1CCCCC1)C(=O)Oc1ccc(OC(=O)c2ccc(OCCCN3C(=O)C=CC3=O)cc2)cc1] |
| 7 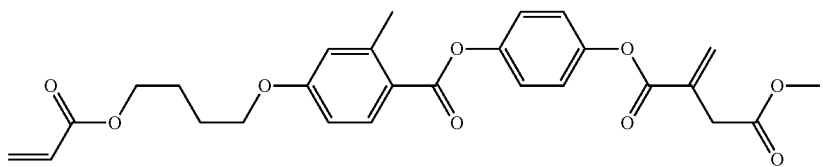 [SMILES: C=CC(=O)OCCCCOc1ccc(C(=O)Oc2ccc(OC(=O)C(=C)CC(=O)OC)cc2)c(C)c1] |
| 8 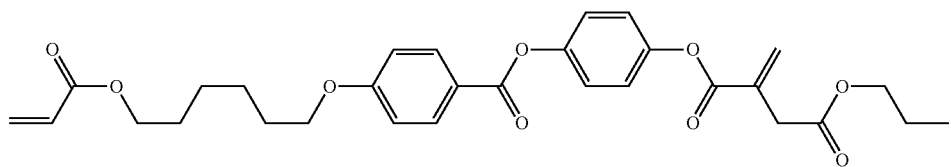 [SMILES: C=CC(=O)OCCCCCCOc1ccc(C(=O)Oc2ccc(OC(=O)C(=C)CC(=O)OCCC)cc2)cc1] |
| 9 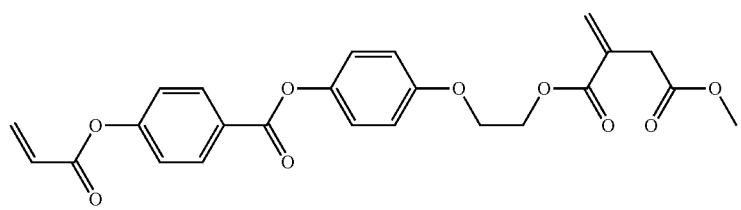 [SMILES: C=CC(=O)Oc1ccc(C(=O)Oc2ccc(OCCOC(=O)C(=C)CC(=O)OC)cc2)cc1] |

-continued
| No. |
|---|
| 10 |
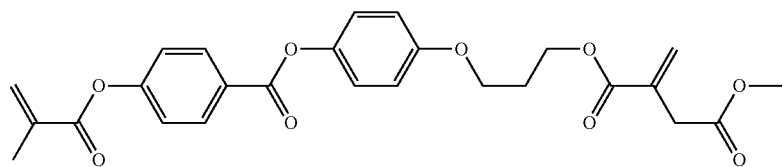 [SMILES: C=C(C)C(=O)Oc1ccc(C(=O)Oc2ccc(OCCCOC(=O)C(=C)CC(=O)OC)cc2)cc1]
| 11 |
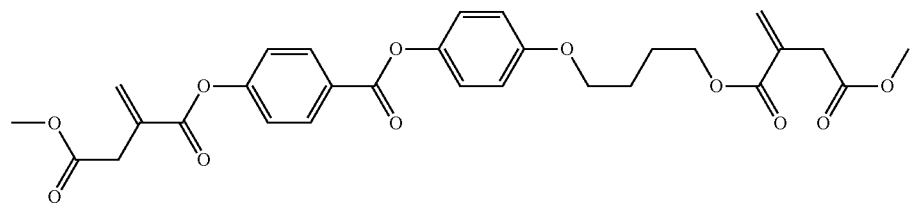
| 12 |
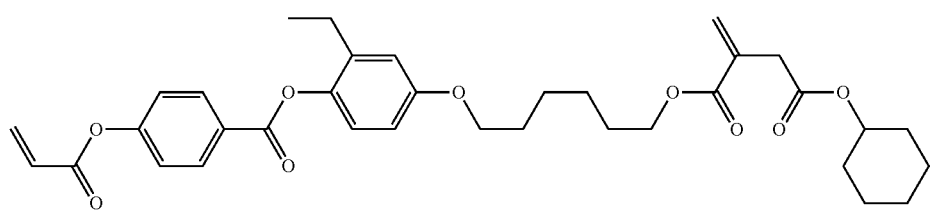 [SMILES: C=CC(=O)Oc1ccc(C(=O)Oc2ccc(OCCCCCCOC(=O)C(=C)CC(=O)OC3CCCCC3)cc2CC)cc1]
| 13 |
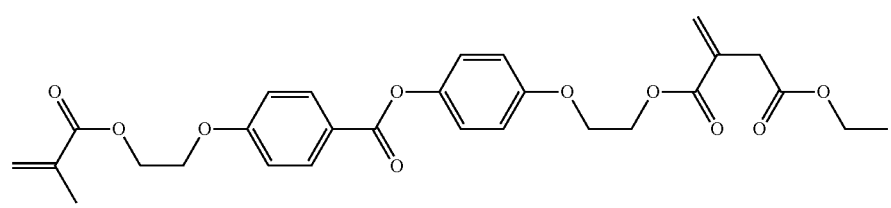 [SMILES: C=C(C)C(=O)OCCOc1ccc(C(=O)Oc2ccc(OCCOC(=O)C(=C)CC(=O)OCC)cc2)cc1]
| 14 |
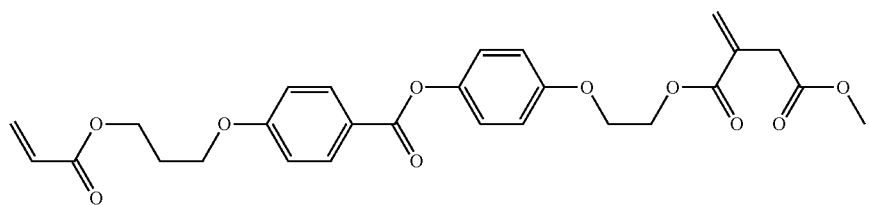 [SMILES: C=CC(=O)OCCCOc1ccc(C(=O)Oc2ccc(OCCOC(=O)C(=C)CC(=O)OC)cc2)cc1]
| 15 |
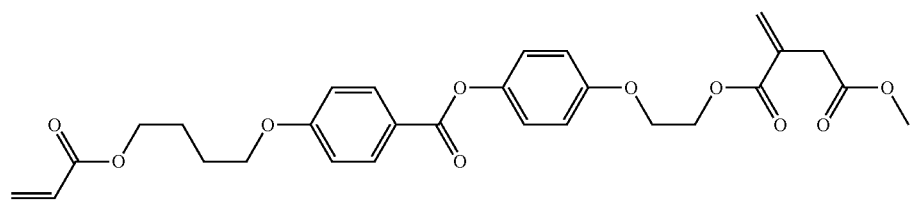 [SMILES: C=CC(=O)OCCCCOc1ccc(C(=O)Oc2ccc(OCCOC(=O)C(=C)CC(=O)OC)cc2)cc1]
| 16 |
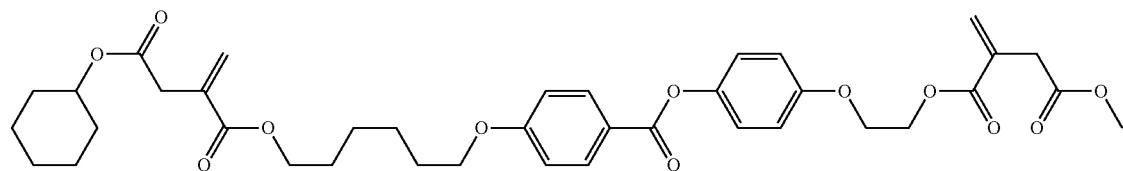 [SMILES: C=C(CC(=O)OC)C(=O)OCCOc1ccc(OC(=O)c2ccc(OCCCCCCOC(=O)C(=C)CC(=O)OC3CCCCC3)cc2)cc1]
| 17 |
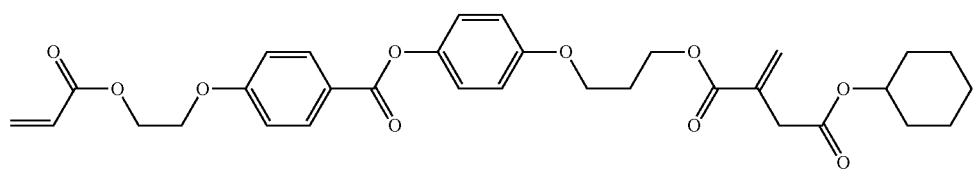 [SMILES: C=CC(=O)OCCOc1ccc(C(=O)Oc2ccc(OCCCOC(=O)C(=C)CC(=O)OC3CCCCC3)cc2)cc1]

-continued
| | No. |
|---|---|
| 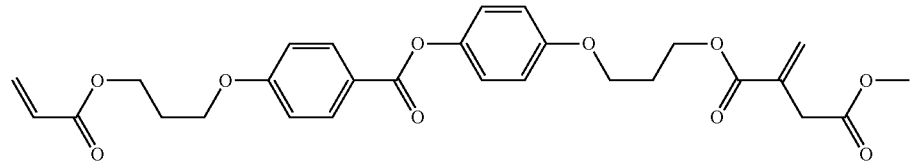 | 18 |
| 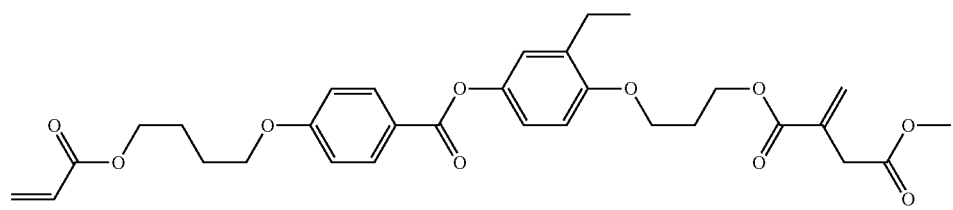 | 19 |
| 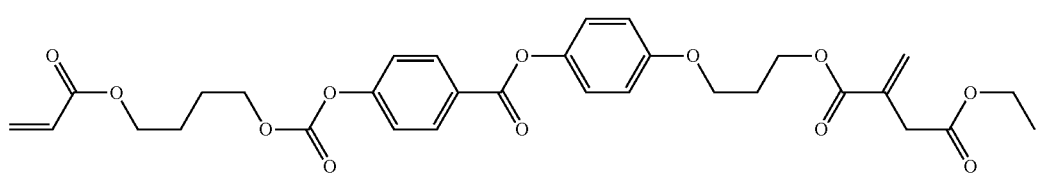 [SMILES: C=CC(=O)OCCCCOC(=O)Oc1ccc(C(=O)Oc2ccc(OCCCOC(=O)C(=C)CC(=O)OCC)cc2)cc1] | 20 |
| 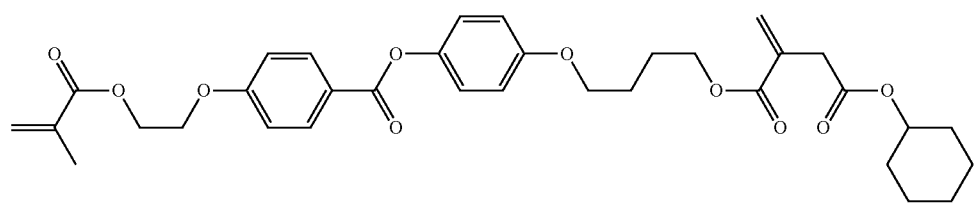 [SMILES: C=C(C)C(=O)OCCOc1ccc(C(=O)Oc2ccc(OCCCCOC(=O)C(=C)CC(=O)OC3CCCCC3)cc2)cc1] | 21 |
| 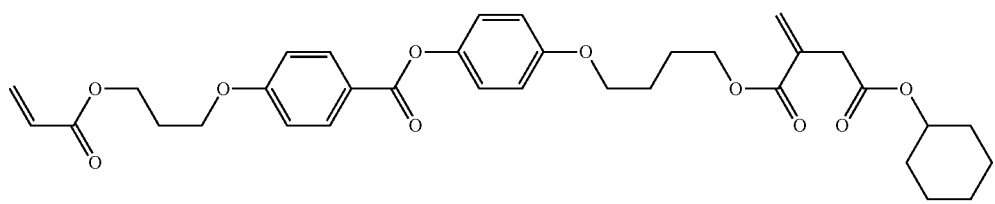 [SMILES: C=CC(=O)OCCCOc1ccc(C(=O)Oc2ccc(OCCCCOC(=O)C(=C)CC(=O)OC3CCCCC3)cc2)cc1] | 22 |
| 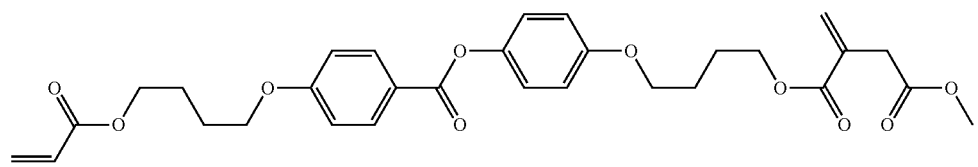 [SMILES: C=CC(=O)OCCCCOc1ccc(C(=O)Oc2ccc(OCCCCOC(=O)C(=C)CC(=O)OC)cc2)cc1] | 23 |
| 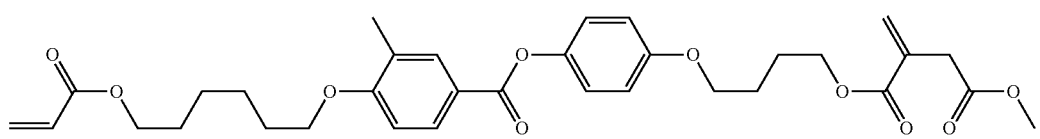 | 24 |
| 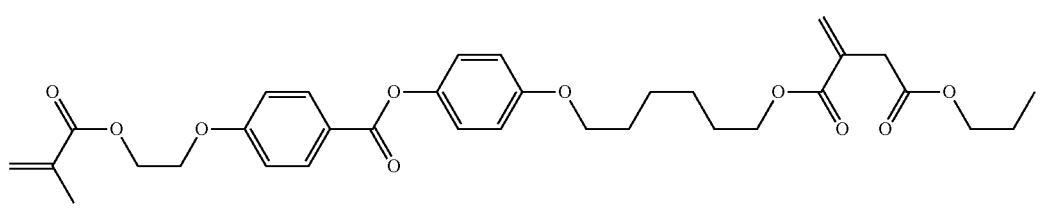 [SMILES: C=C(C)C(=O)OCCOc1ccc(C(=O)Oc2ccc(OCCCCCCOC(=O)C(=C)CC(=O)OCCC)cc2)cc1] | 25 |

-continued
| | No. |
|---|---|
| 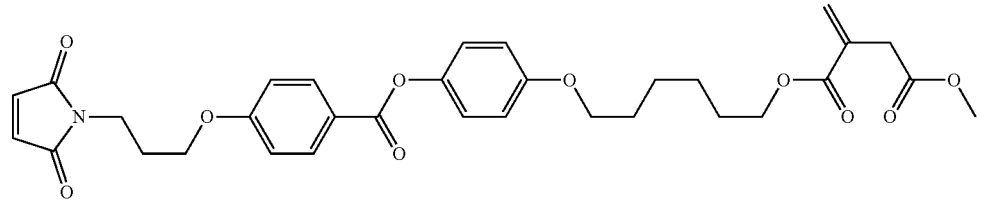 [SMILES: C=C(CC(=O)OC)C(=O)OCCCCCCOc1ccc(OC(=O)c2ccc(OCCCN3C(=O)C=CC3=O)cc2)cc1] | 26 |
| 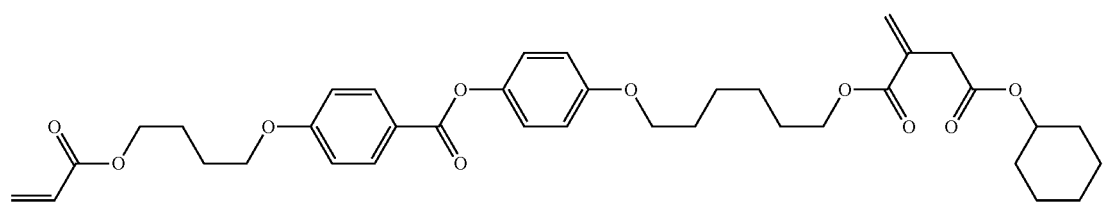 [SMILES: C=CC(=O)OCCCCOc1ccc(C(=O)Oc2ccc(OCCCCCCOC(=O)C(=C)CC(=O)OC3CCCCC3)cc2)cc1] | 27 |
| 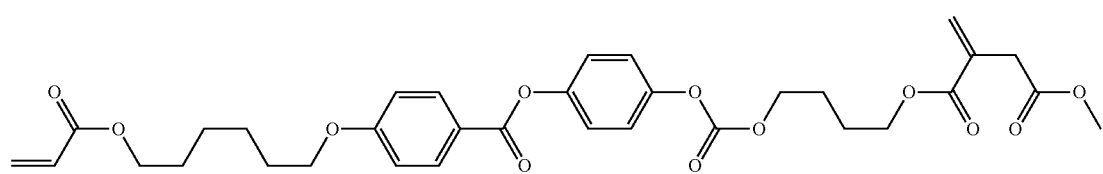 [SMILES: C=CC(=O)OCCCCCCOc1ccc(C(=O)Oc2ccc(OC(=O)OCCCCOC(=O)C(=C)CC(=O)OC)cc2)cc1] | 28 |
| 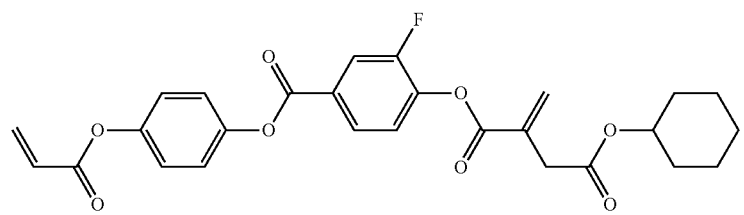 [SMILES: C=CC(=O)Oc1ccc(OC(=O)c2ccc(OC(=O)C(=C)CC(=O)OC3CCCCC3)c(F)c2)cc1] | 29 |
| 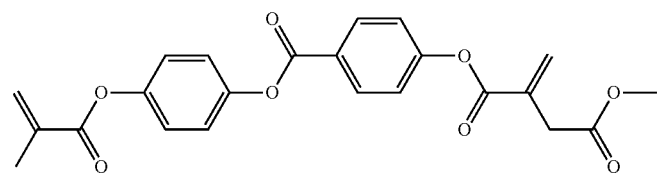 [SMILES: C=C(C)C(=O)Oc1ccc(OC(=O)c2ccc(OC(=O)C(=C)CC(=O)OC)cc2)cc1] | 30 |
| 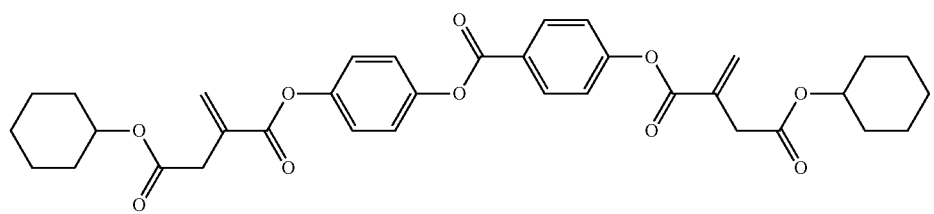 [SMILES: C=C(CC(=O)OC1CCCCC1)C(=O)Oc1ccc(OC(=O)c2ccc(OC(=O)C(=C)CC(=O)OC3CCCCC3)cc2)cc1] | 31 |
| 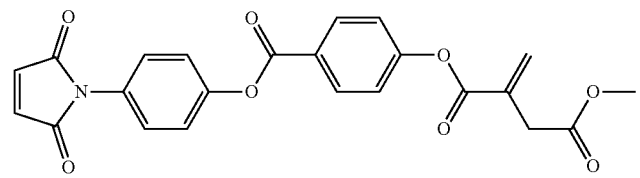 [SMILES: C=C(CC(=O)OC)C(=O)Oc1ccc(C(=O)Oc2ccc(N3C(=O)C=CC3=O)cc2)cc1] | 32 |

-continued
| | No. |
|---|---|
| 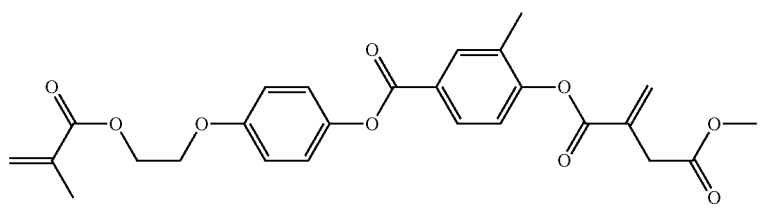 [SMILES: C=C(C)C(=O)OCCOc1ccc(OC(=O)c2ccc(OC(=O)C(=C)CC(=O)OC)c(C)c2)cc1] | 33 |
| 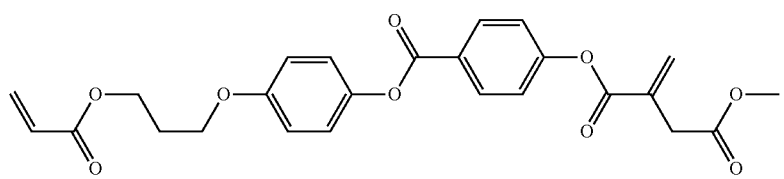 [SMILES: C=CC(=O)OCCCOc1ccc(OC(=O)c2ccc(OC(=O)C(=C)CC(=O)OC)cc2)cc1] | 34 |
| 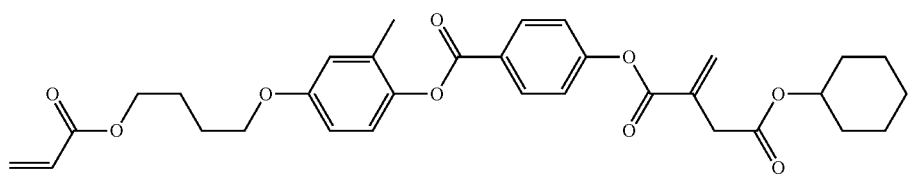 [SMILES: C=CC(=O)OCCCCOc1ccc(OC(=O)c2ccc(OC(=O)C(=C)CC(=O)OC3CCCCC3)cc2)c(C)c1] | 35 |
| 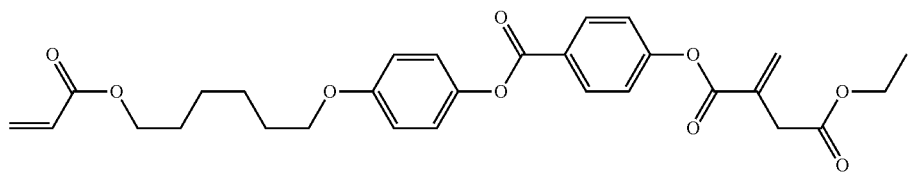 [SMILES: C=CC(=O)OCCCCCCOc1ccc(OC(=O)c2ccc(OC(=O)C(=C)CC(=O)OCC)cc2)cc1] | 36 |
| 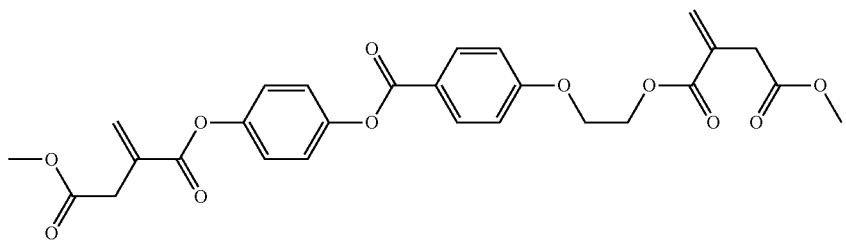 | 37 |
| 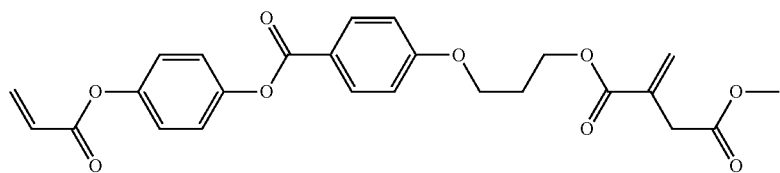 [SMILES: C=CC(=O)Oc1ccc(OC(=O)c2ccc(OCCCOC(=O)C(=C)CC(=O)OC)cc2)cc1] | 38 |
| 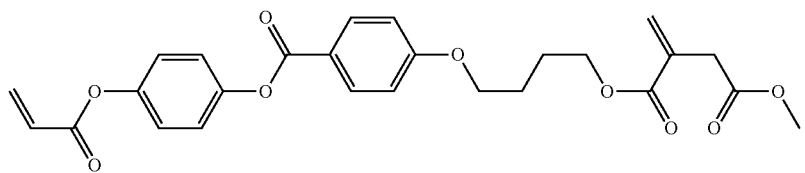 [SMILES: C=CC(=O)Oc1ccc(OC(=O)c2ccc(OCCCCOC(=O)C(=C)CC(=O)OC)cc2)cc1] | 39 |
| 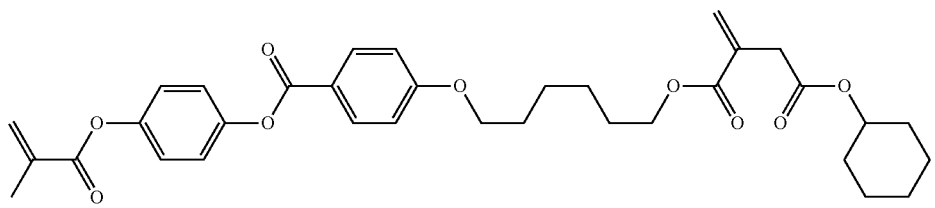 [SMILES: C=C(C)C(=O)Oc1ccc(OC(=O)c2ccc(OCCCCCCOC(=O)C(=C)CC(=O)OC3CCCCC3)cc2)cc1] | 40 |

-continued
| | No. |
|---|---|
| 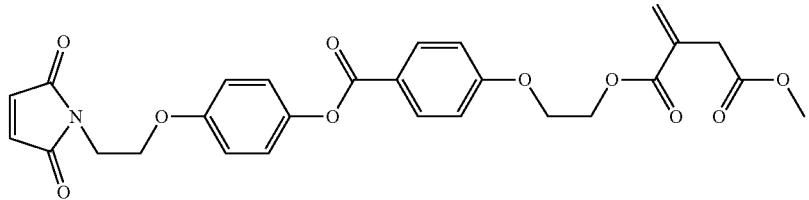 [SMILES: C=C(CC(=O)OC)C(=O)OCCOc1ccc(C(=O)Oc2ccc(OCCN3C(=O)C=CC3=O)cc2)cc1] | 41 |
| 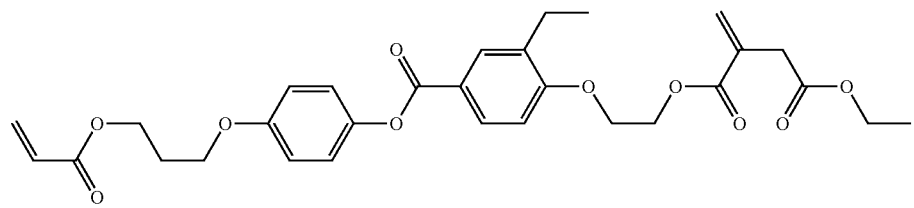 [SMILES: C=CC(=O)OCCCOc1ccc(OC(=O)c2ccc(OCCOC(=O)C(=C)CC(=O)OCC)c(CC)c2)cc1] | 42 |
| 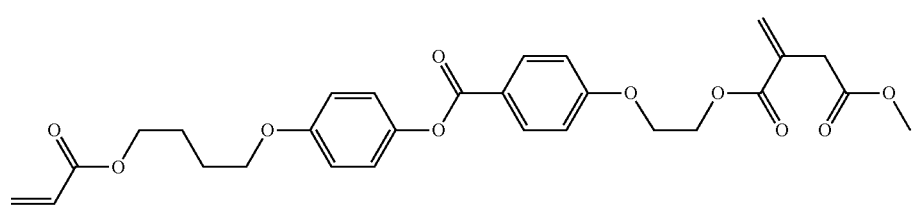 [SMILES: C=CC(=O)OCCCCOc1ccc(OC(=O)c2ccc(OCCOC(=O)C(=C)CC(=O)OC)cc2)cc1] | 43 |
| 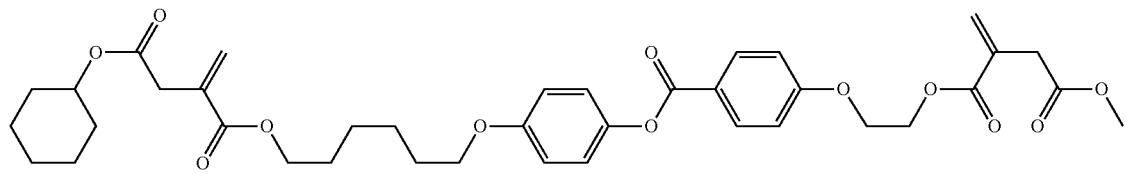 [SMILES: C=C(CC(=O)OC)C(=O)OCCOc1ccc(C(=O)Oc2ccc(OCCCCCCOC(=O)C(=C)CC(=O)OC3CCCCC3)cc2)cc1] | 44 |
| 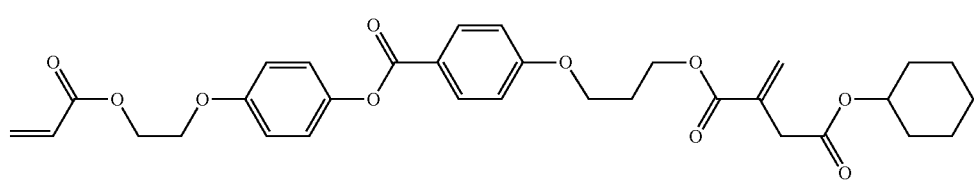 [SMILES: C=CC(=O)OCCOc1ccc(OC(=O)c2ccc(OCCCOC(=O)C(=C)CC(=O)OC3CCCCC3)cc2)cc1] | 45 |
| 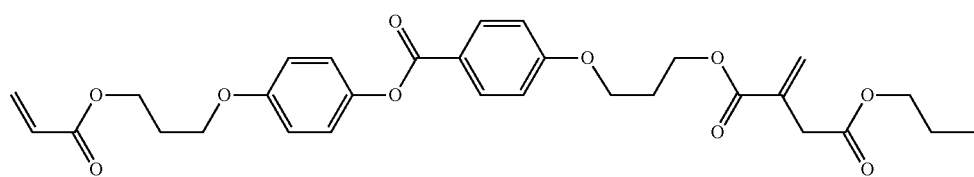 [SMILES: C=CC(=O)OCCCOc1ccc(OC(=O)c2ccc(OCCCOC(=O)C(=C)CC(=O)OCCC)cc2)cc1] | 46 |
| 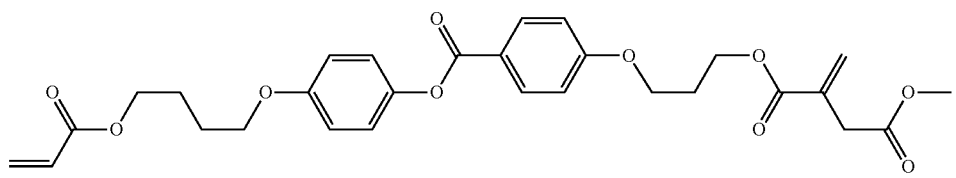 [SMILES: C=CC(=O)OCCCCOc1ccc(OC(=O)c2ccc(OCCCOC(=O)C(=C)CC(=O)OC)cc2)cc1] | 47 |
| 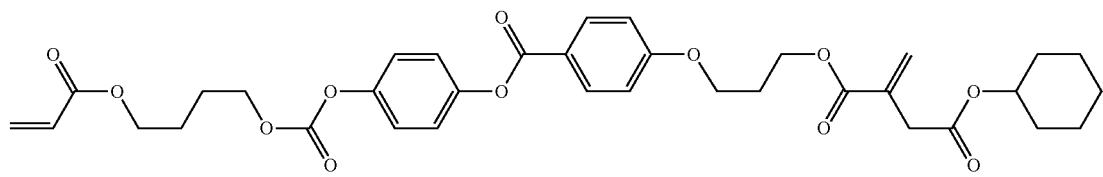 [SMILES: C=CC(=O)OCCCCOC(=O)Oc1ccc(OC(=O)c2ccc(OCCCOC(=O)C(=C)CC(=O)OC3CCCCC3)cc2)cc1] | 48 |

-continued
No.
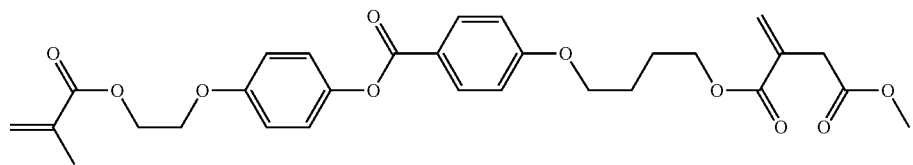 [SMILES: C=C(C)C(=O)OCCOc1ccc(OC(=O)c2ccc(OCCCCOC(=O)C(=C)CC(=O)OC)cc2)cc1]
49
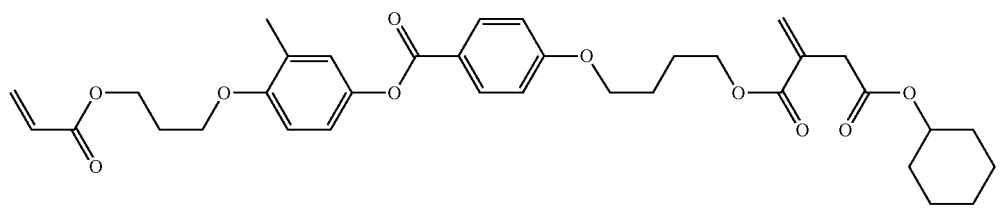 [SMILES: C=CC(=O)OCCCOc1ccc(OC(=O)c2ccc(OCCCCOC(=O)C(=C)CC(=O)OC3CCCCC3)cc2)cc1C]
50
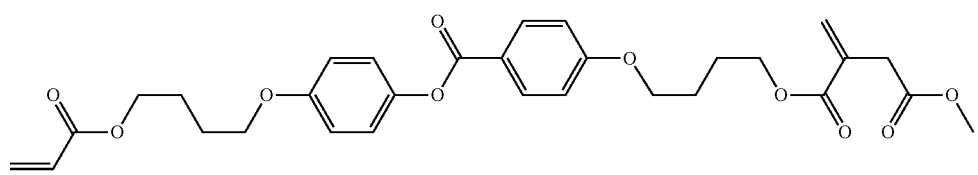 [SMILES: C=CC(=O)OCCCCOc1ccc(OC(=O)c2ccc(OCCCCOC(=O)C(=C)CC(=O)OC)cc2)cc1]
51
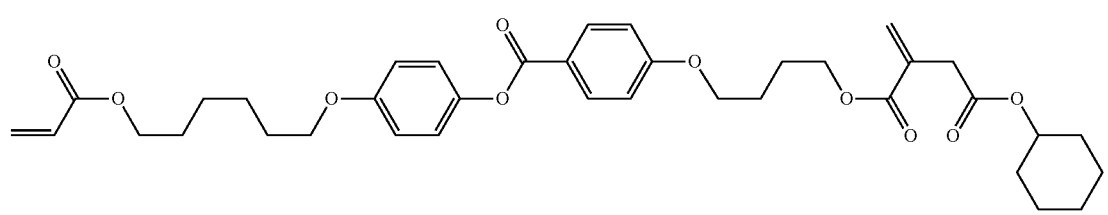 [SMILES: C=CC(=O)OCCCCCCOc1ccc(OC(=O)c2ccc(OCCCCOC(=O)C(=C)CC(=O)OC3CCCCC3)cc2)cc1]
52
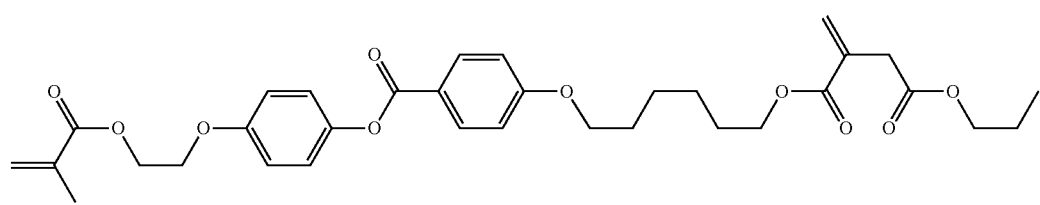
53
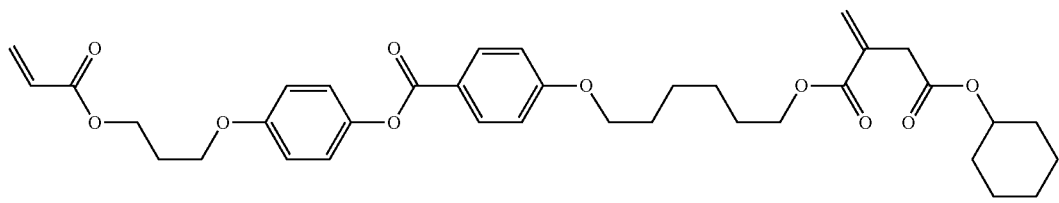 [SMILES: C=CC(=O)OCCCOc1ccc(OC(=O)c2ccc(OCCCCCCOC(=O)C(=C)CC(=O)OC3CCCCC3)cc2)cc1]
54
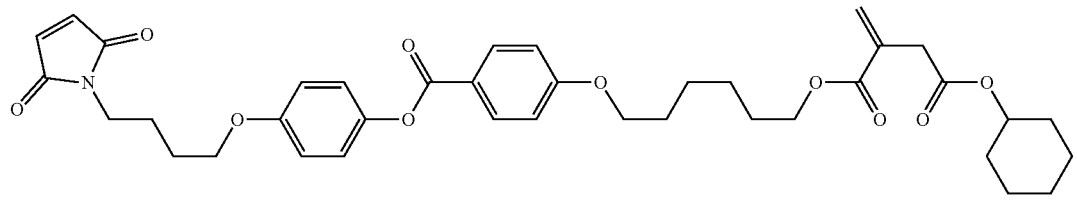 [SMILES: C=C(CC(=O)OC1CCCCC1)C(=O)OCCCCCCOc1ccc(C(=O)Oc2ccc(OCCCCN3C(=O)C=CC3=O)cc2)cc1]
55
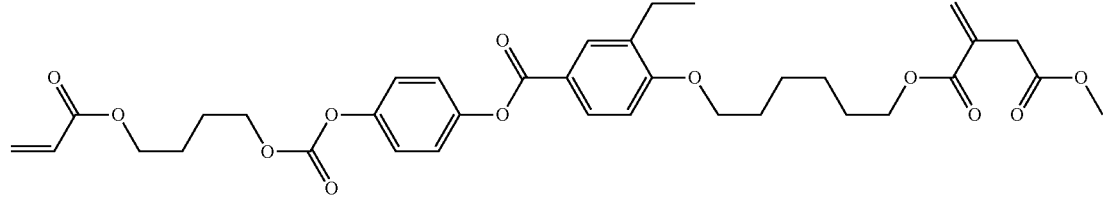 [SMILES: C=CC(=O)OCCCCOC(=O)Oc1ccc(OC(=O)c2ccc(OCCCCCCOC(=O)C(=C)CC(=O)OC)c(CC)c2)cc1]
56

-continued
| | No. |
|---|---|
| 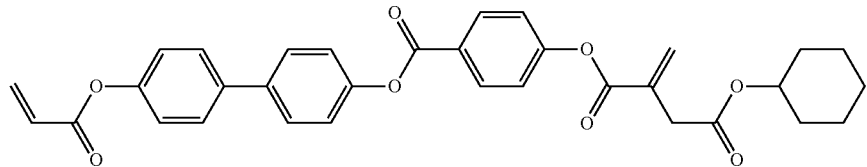 [SMILES: C=CC(=O)Oc1ccc(-c2ccc(OC(=O)c3ccc(OC(=O)C(=C)CC(=O)OC4CCCCC4)cc3)cc2)cc1] | 57 |
| 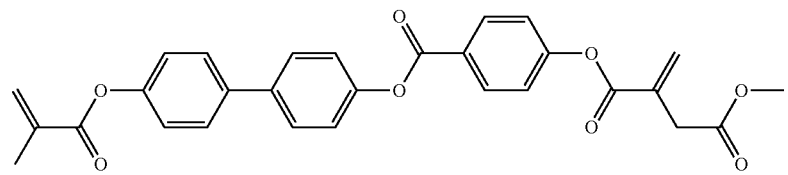 [SMILES: C=C(C)C(=O)Oc1ccc(-c2ccc(OC(=O)c3ccc(OC(=O)C(=C)CC(=O)OC)cc3)cc2)cc1] | 58 |
| 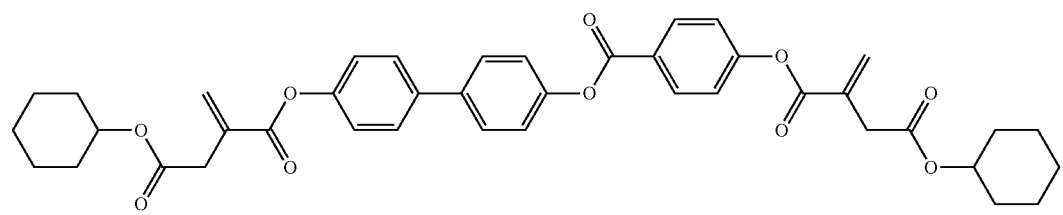 [SMILES: C=C(CC(=O)OC1CCCCC1)C(=O)Oc1ccc(C(=O)Oc2ccc(-c3ccc(OC(=O)C(=C)CC(=O)OC4CCCCC4)cc3)cc2)cc1] | 59 |
| 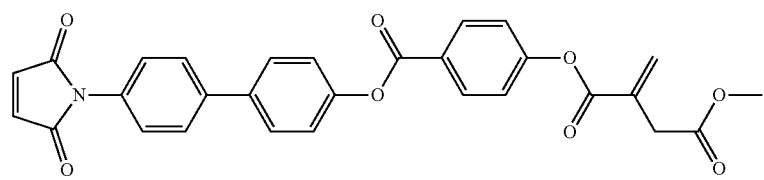 | 60 |
| 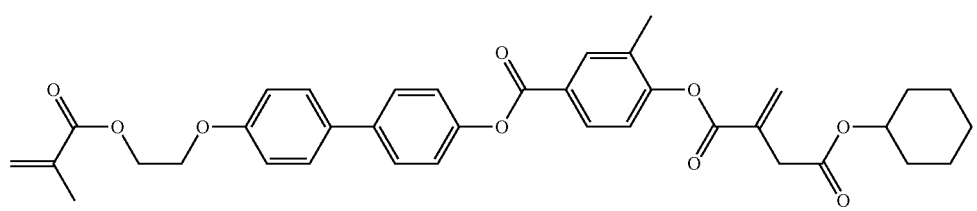 [SMILES: C=C(C)C(=O)OCCOc1ccc(-c2ccc(OC(=O)c3ccc(OC(=O)C(=C)CC(=O)OC4CCCCC4)c(C)c3)cc2)cc1] | 61 |
| 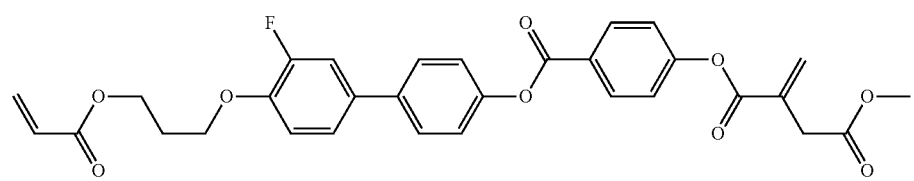 [SMILES: C=CC(=O)OCCCOc1ccc(-c2ccc(OC(=O)c3ccc(OC(=O)C(=C)CC(=O)OC)cc3)cc2)cc1F] | 62 |
| 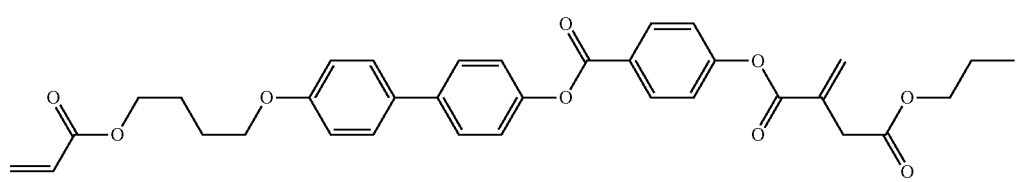 [SMILES: C=CC(=O)OCCCCOc1ccc(-c2ccc(OC(=O)c3ccc(OC(=O)C(=C)CC(=O)OCCC)cc3)cc2)cc1] | 63 |
| 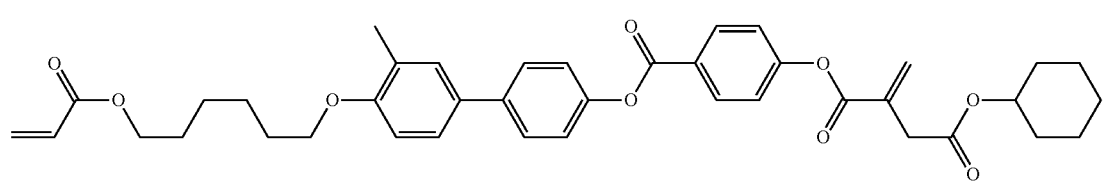 [SMILES: C=CC(=O)OCCCCCCOc1ccc(-c2ccc(OC(=O)c3ccc(OC(=O)C(=C)CC(=O)OC4CCCCC4)cc3)cc2)cc1C] | 64 |

-continued
| No. |
|---|
| 65 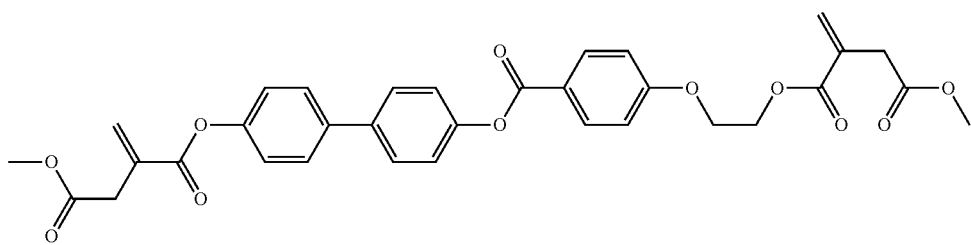 |
| 66 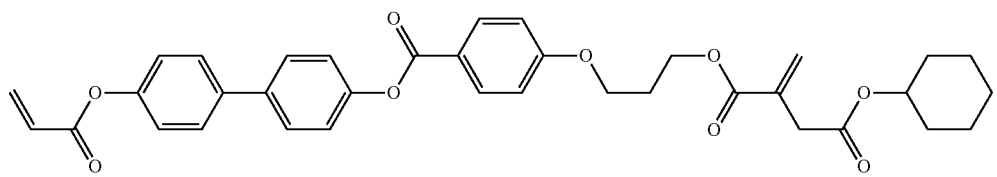 [SMILES: C=CC(=O)Oc1ccc(-c2ccc(OC(=O)c3ccc(OCCCOC(=O)C(=C)CC(=O)OC4CCCCC4)cc3)cc2)cc1] |
| 67 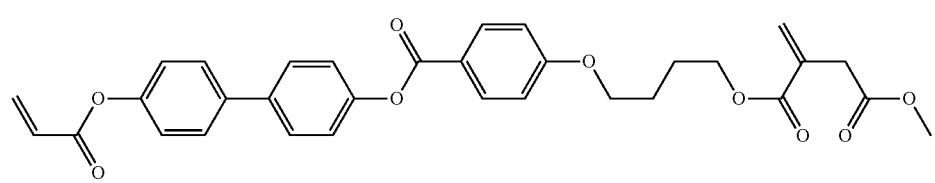 [SMILES: C=CC(=O)Oc1ccc(-c2ccc(OC(=O)c3ccc(OCCCCOC(=O)C(=C)CC(=O)OC)cc3)cc2)cc1] |
| 68 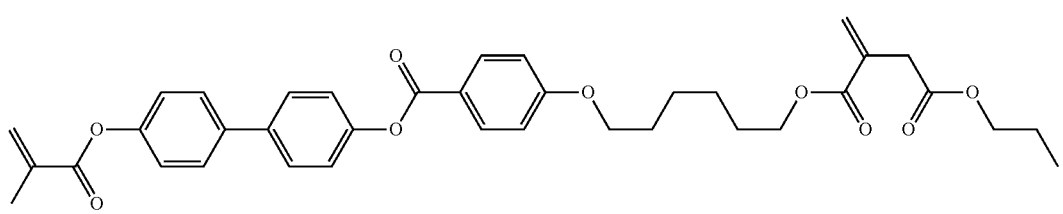 [SMILES: C=C(C)C(=O)Oc1ccc(-c2ccc(OC(=O)c3ccc(OCCCCCCOC(=O)C(=C)CC(=O)OCCC)cc3)cc2)cc1] |
| 69 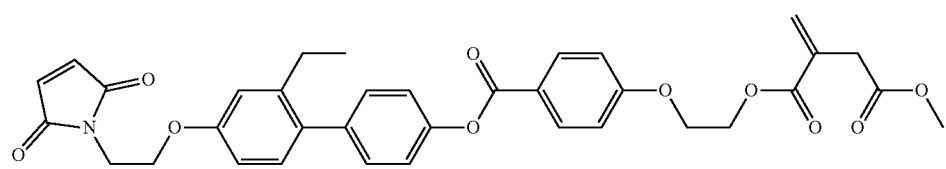 [SMILES: C=C(CC(=O)OC)C(=O)OCCOc1ccc(C(=O)Oc2ccc(-c3ccc(OCCN4C(=O)C=CC4=O)cc3CC)cc2)cc1] |
| 70 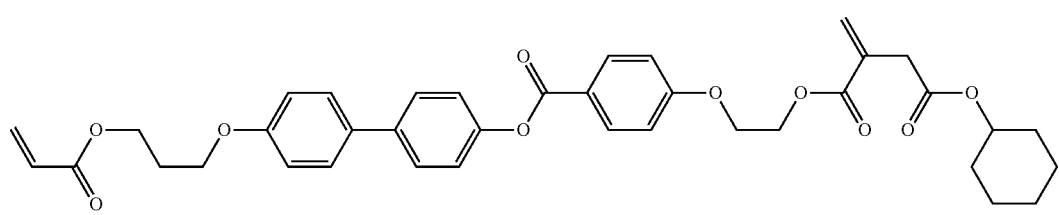 [SMILES: C=CC(=O)OCCCOc1ccc(-c2ccc(OC(=O)c3ccc(OCCOC(=O)C(=C)CC(=O)OC4CCCCC4)cc3)cc2)cc1] |
| 71 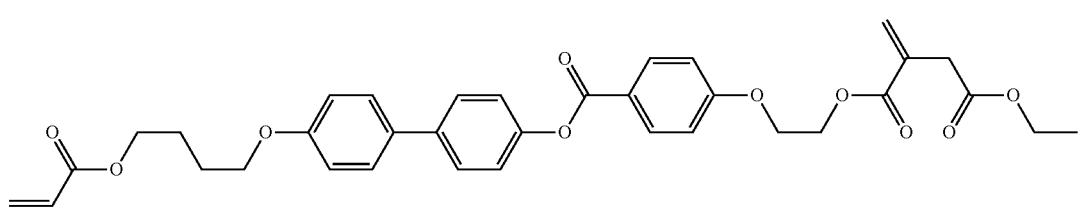 [SMILES: C=CC(=O)OCCCCOc1ccc(-c2ccc(OC(=O)c3ccc(OCCOC(=O)C(=C)CC(=O)OCC)cc3)cc2)cc1] |
| 72 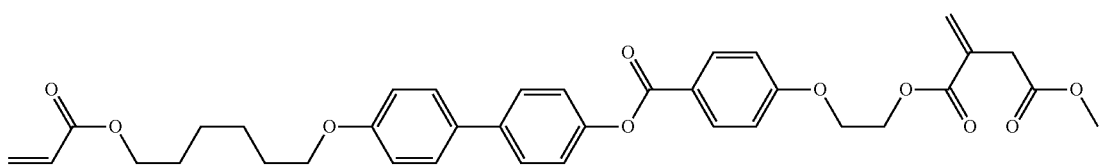 |

-continued
| | No. |
|---|---|
| 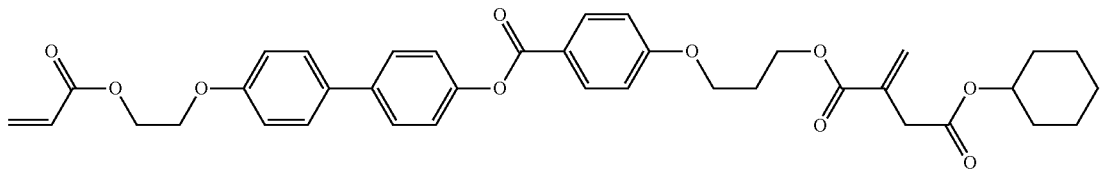 [SMILES: C=CC(=O)OCCOc1ccc(-c2ccc(OC(=O)c3ccc(OCCCOC(=O)C(=C)CC(=O)OC4CCCCC4)cc3)cc2)cc1] | 73 |
| 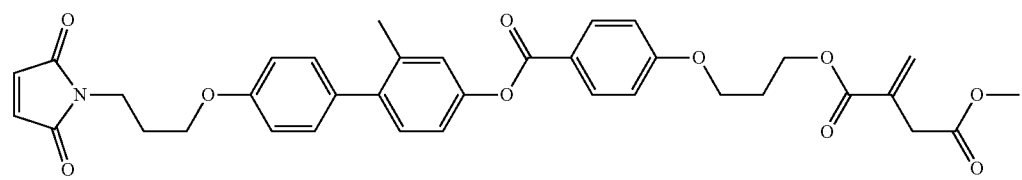 [SMILES: C=C(CC(=O)OC)C(=O)OCCCOc1ccc(C(=O)Oc2ccc(-c3ccc(OCCCN4C(=O)C=CC4=O)cc3)c(C)c2)cc1] | 74 |
| 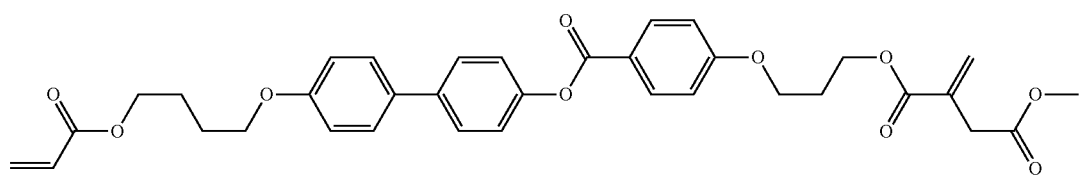 [SMILES: C=CC(=O)OCCCCOc1ccc(-c2ccc(OC(=O)c3ccc(OCCCOC(=O)C(=C)CC(=O)OC)cc3)cc2)cc1] | 75 |
| 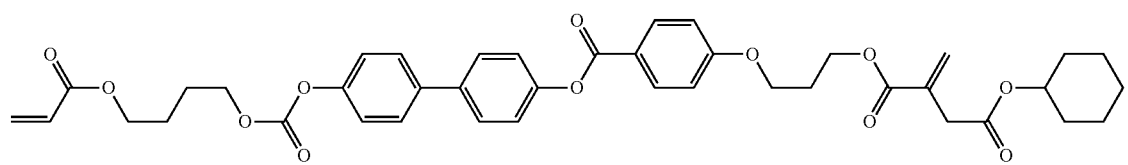 [SMILES: C=CC(=O)OCCCCOC(=O)Oc1ccc(-c2ccc(OC(=O)c3ccc(OCCCOC(=O)C(=C)CC(=O)OC4CCCCC4)cc3)cc2)cc1] | 76 |
| 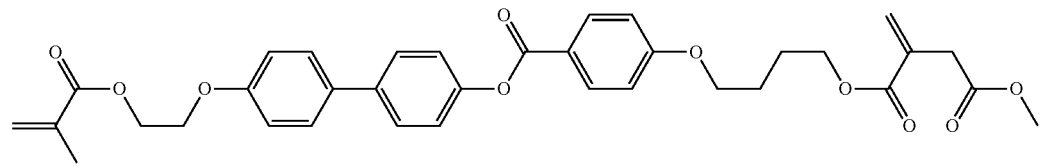 [SMILES: C=C(C)C(=O)OCCOc1ccc(-c2ccc(OC(=O)c3ccc(OCCCCOC(=O)C(=C)CC(=O)OC)cc3)cc2)cc1] | 77 |
| 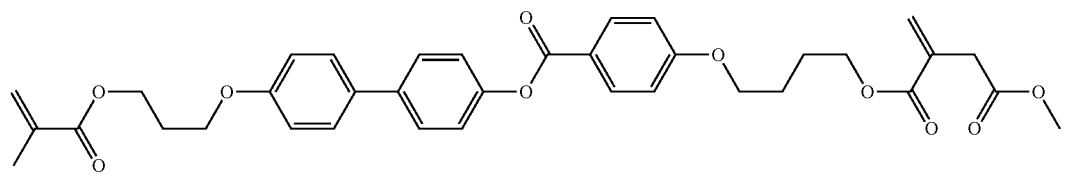 [SMILES: C=C(C)C(=O)OCCCOc1ccc(-c2ccc(OC(=O)c3ccc(OCCCCOC(=O)C(=C)CC(=O)OC)cc3)cc2)cc1] | 78 |
| 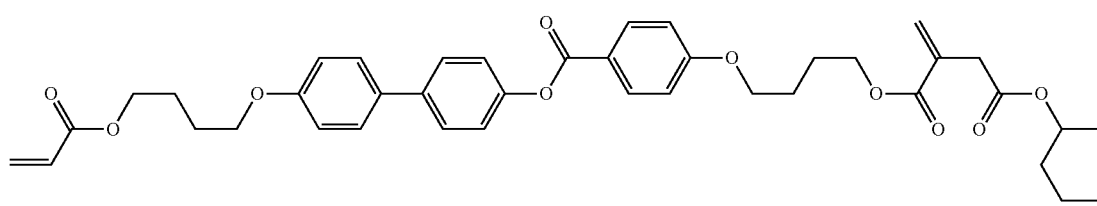 | 79 |
| 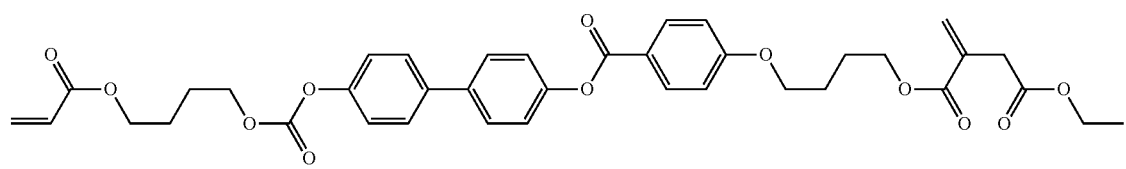 [SMILES: C=CC(=O)OCCCCOC(=O)Oc1ccc(-c2ccc(OC(=O)c3ccc(OCCCCOC(=O)C(=C)CC(=O)OCC)cc3)cc2)cc1] | 80 |

-continued
| No. |
|---|
| 81 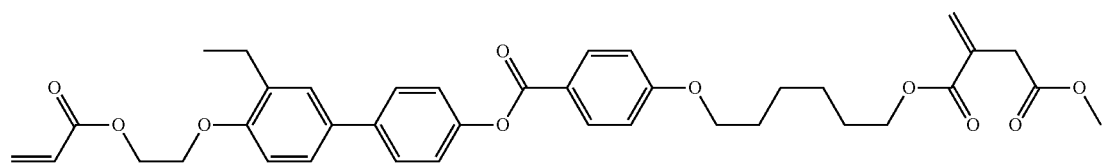 [SMILES: C=CC(=O)OCCOc1ccc(-c2ccc(OC(=O)c3ccc(OCCCCCCOC(=O)C(=C)CC(=O)OC)cc3)cc2)cc1CC] |
| 82 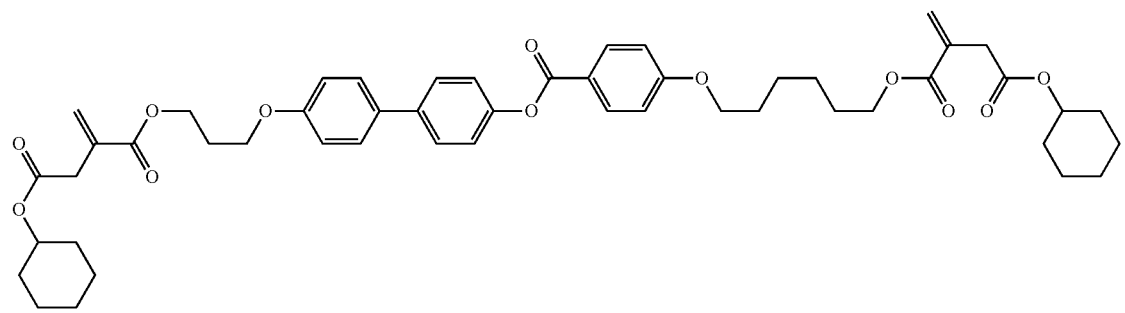 [SMILES: C=C(CC(=O)OC1CCCCC1)C(=O)OCCCCCCOc1ccc(C(=O)Oc2ccc(-c3ccc(OCCCOC(=O)C(=C)CC(=O)OC4CCCCC4)cc3)cc2)cc1] |
| 83 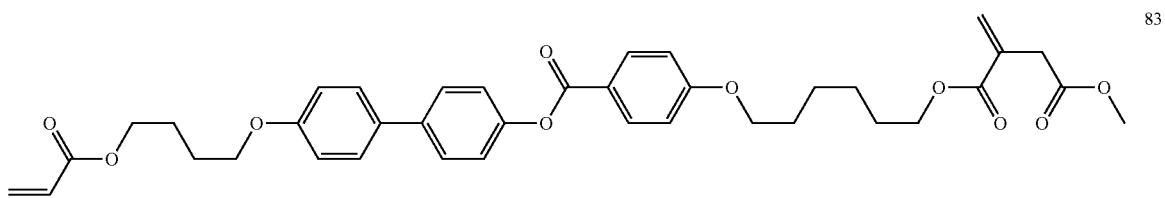 |
| 84 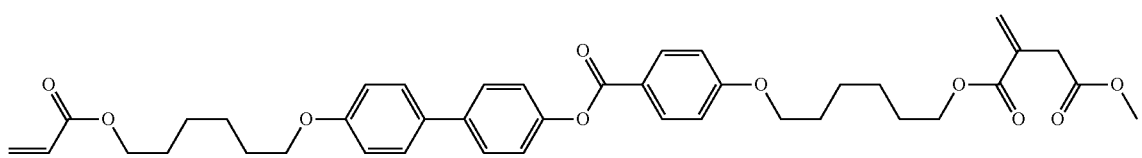 |
| 85 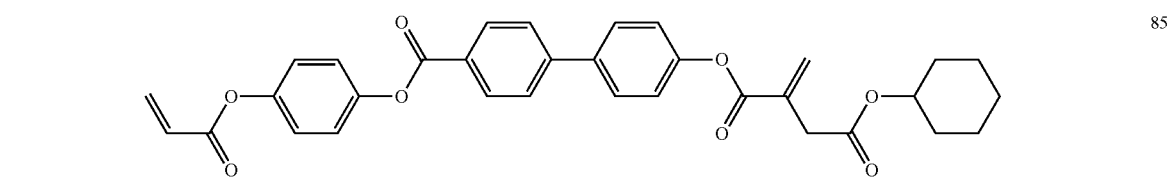 |
| 86 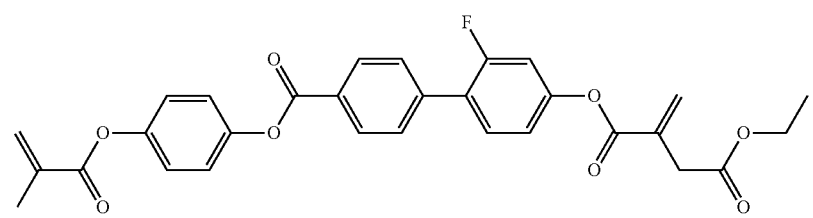 [SMILES: C=C(C)C(=O)Oc1ccc(OC(=O)c2ccc(-c3ccc(OC(=O)C(=C)CC(=O)OCC)cc3F)cc2)cc1] |
| 87 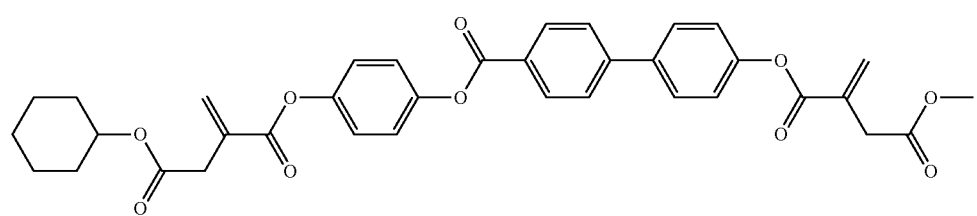 [SMILES: C=C(CC(=O)OC)C(=O)Oc1ccc(-c2ccc(C(=O)Oc3ccc(OC(=O)C(=C)CC(=O)OC4CCCCC4)cc3)cc2)cc1] |

-continued
| | No. |
|---|---|
| 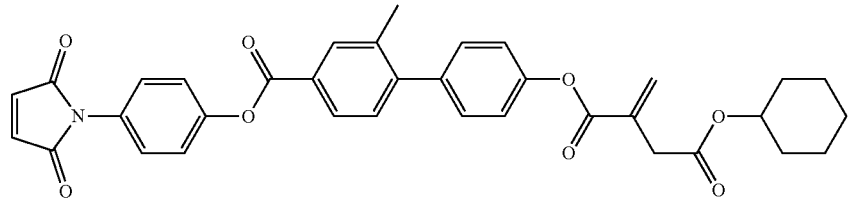 [SMILES: C=C(CC(=O)OC1CCCCC1)C(=O)Oc1ccc(-c2ccc(C(=O)Oc3ccc(N4C(=O)C=CC4=O)cc3)cc2C)cc1] | 88 |
| 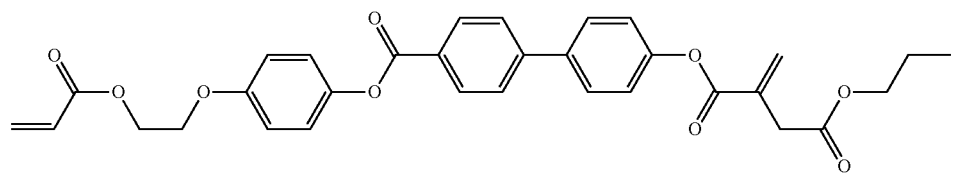 [SMILES: C=CC(=O)OCCOc1ccc(OC(=O)c2ccc(-c3ccc(OC(=O)C(=C)CC(=O)OCCC)cc3)cc2)cc1] | 89 |
| 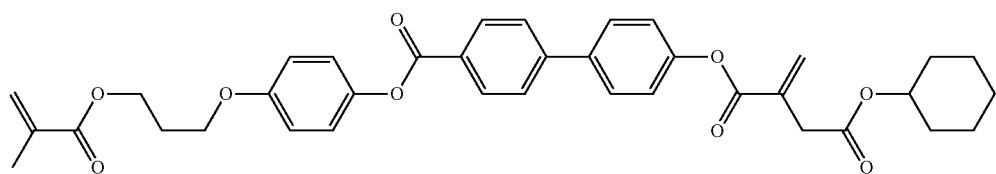 [SMILES: C=C(C)C(=O)OCCCOc1ccc(OC(=O)c2ccc(-c3ccc(OC(=O)C(=C)CC(=O)OC4CCCCC4)cc3)cc2)cc1] | 90 |
| 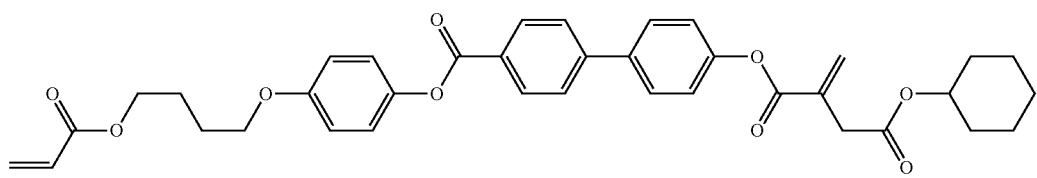 [SMILES: C=CC(=O)OCCCCOc1ccc(OC(=O)c2ccc(-c3ccc(OC(=O)C(=C)CC(=O)OC4CCCCC4)cc3)cc2)cc1] | 91 |
| 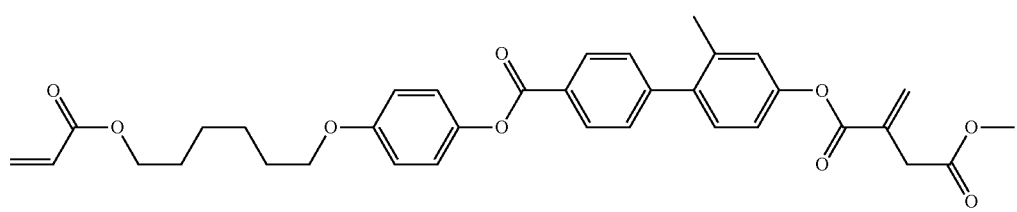 [SMILES: C=CC(=O)OCCCCCCOc1ccc(OC(=O)c2ccc(-c3ccc(OC(=O)C(=C)CC(=O)OC)cc3C)cc2)cc1] | 92 |
| 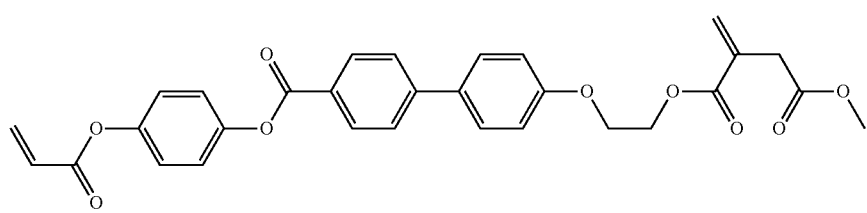 [SMILES: C=CC(=O)Oc1ccc(OC(=O)c2ccc(-c3ccc(OCCOC(=O)C(=C)CC(=O)OC)cc3)cc2)cc1] | 93 |
| 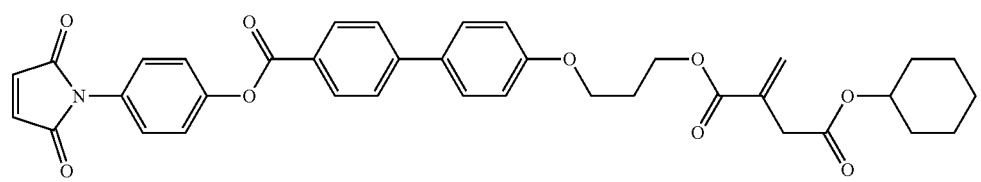 [SMILES: C=C(CC(=O)OC1CCCCC1)C(=O)OCCCOc1ccc(-c2ccc(C(=O)Oc3ccc(N4C(=O)C=CC4=O)cc3)cc2)cc1] | 94 |
| 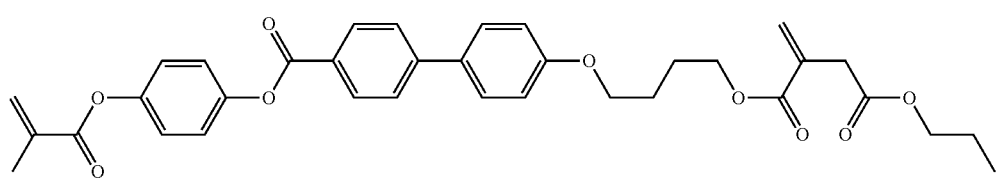 [SMILES: C=C(C)C(=O)Oc1ccc(OC(=O)c2ccc(-c3ccc(OCCCCOC(=O)C(=C)CC(=O)OCCC)cc3)cc2)cc1] | 95 |

-continued
| No. |
|---|
| 96 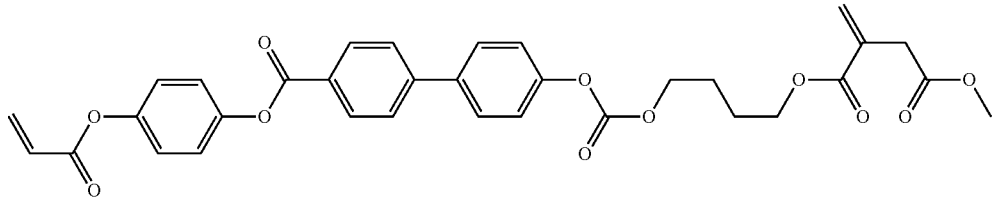 [SMILES: C=CC(=O)Oc1ccc(OC(=O)c2ccc(-c3ccc(OC(=O)OCCCCOC(=O)C(=C)CC(=O)OC)cc3)cc2)cc1] |
| 97 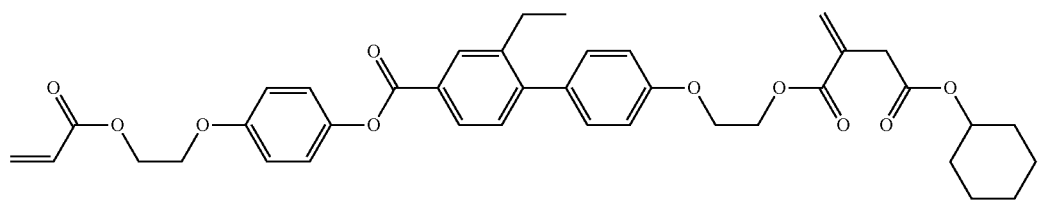 [SMILES: C=CC(=O)OCCOc1ccc(OC(=O)c2ccc(-c3ccc(OCCOC(=O)C(=C)CC(=O)OC4CCCCC4)cc3)c(CC)c2)cc1] |
| 98 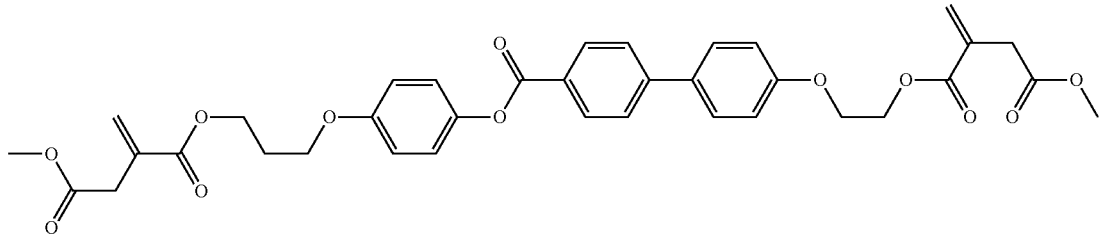 |
| 99 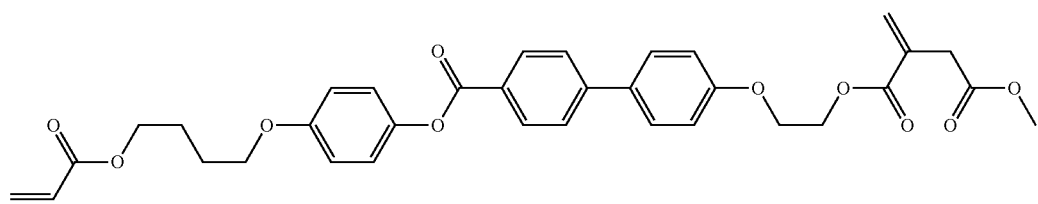 [SMILES: C=CC(=O)OCCCCOc1ccc(OC(=O)c2ccc(-c3ccc(OCCOC(=O)C(=C)CC(=O)OC)cc3)cc2)cc1] |
| 100 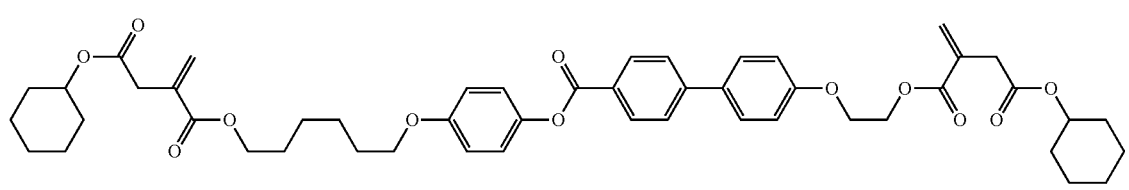 [SMILES: C=C(CC(=O)OC1CCCCC1)C(=O)OCCCCCCOc1ccc(OC(=O)c2ccc(-c3ccc(OCCOC(=O)C(=C)CC(=O)OC4CCCCC4)cc3)cc2)cc1] |
| 101 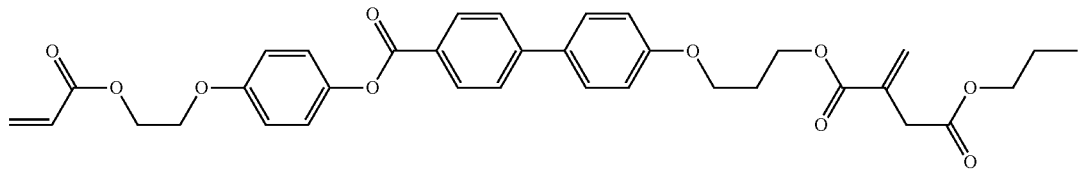 [SMILES: C=CC(=O)OCCOc1ccc(OC(=O)c2ccc(-c3ccc(OCCCOC(=O)C(=C)CC(=O)OCCC)cc3)cc2)cc1] |
| 102 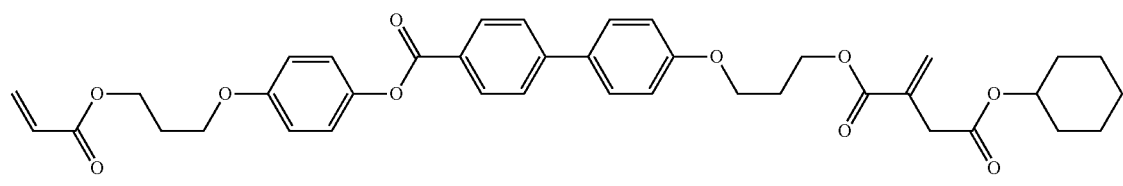 [SMILES: C=CC(=O)OCCCOc1ccc(OC(=O)c2ccc(-c3ccc(OCCCOC(=O)C(=C)CC(=O)OC4CCCCC4)cc3)cc2)cc1] |
| 103 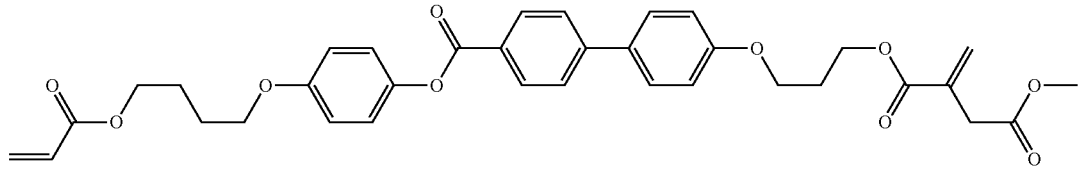 [SMILES: C=CC(=O)OCCCCOc1ccc(OC(=O)c2ccc(-c3ccc(OCCCOC(=O)C(=C)CC(=O)OC)cc3)cc2)cc1] |

| No. |
|---|
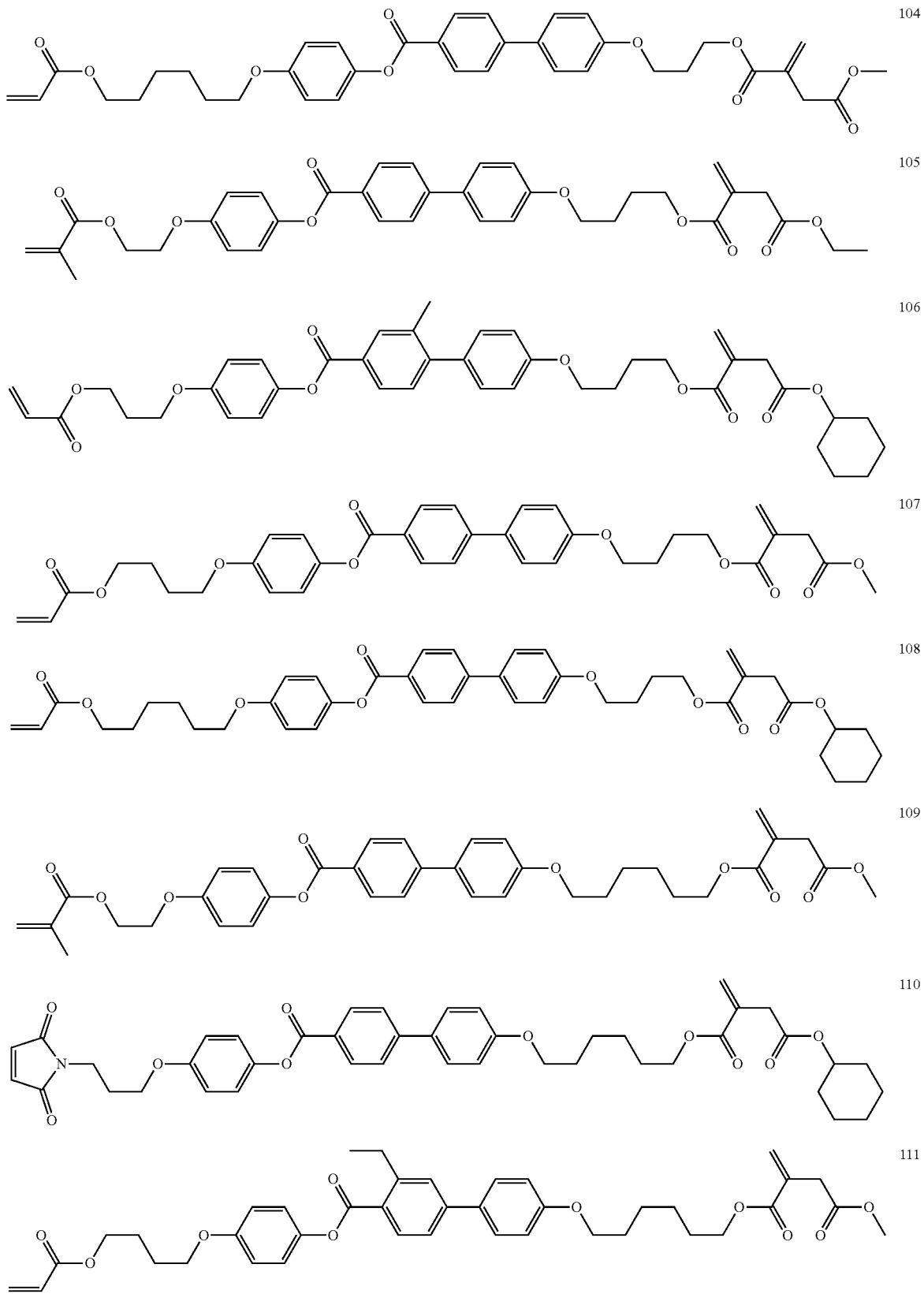
104
105
106
107
108
109
110
111

-continued
| No. |
|---|
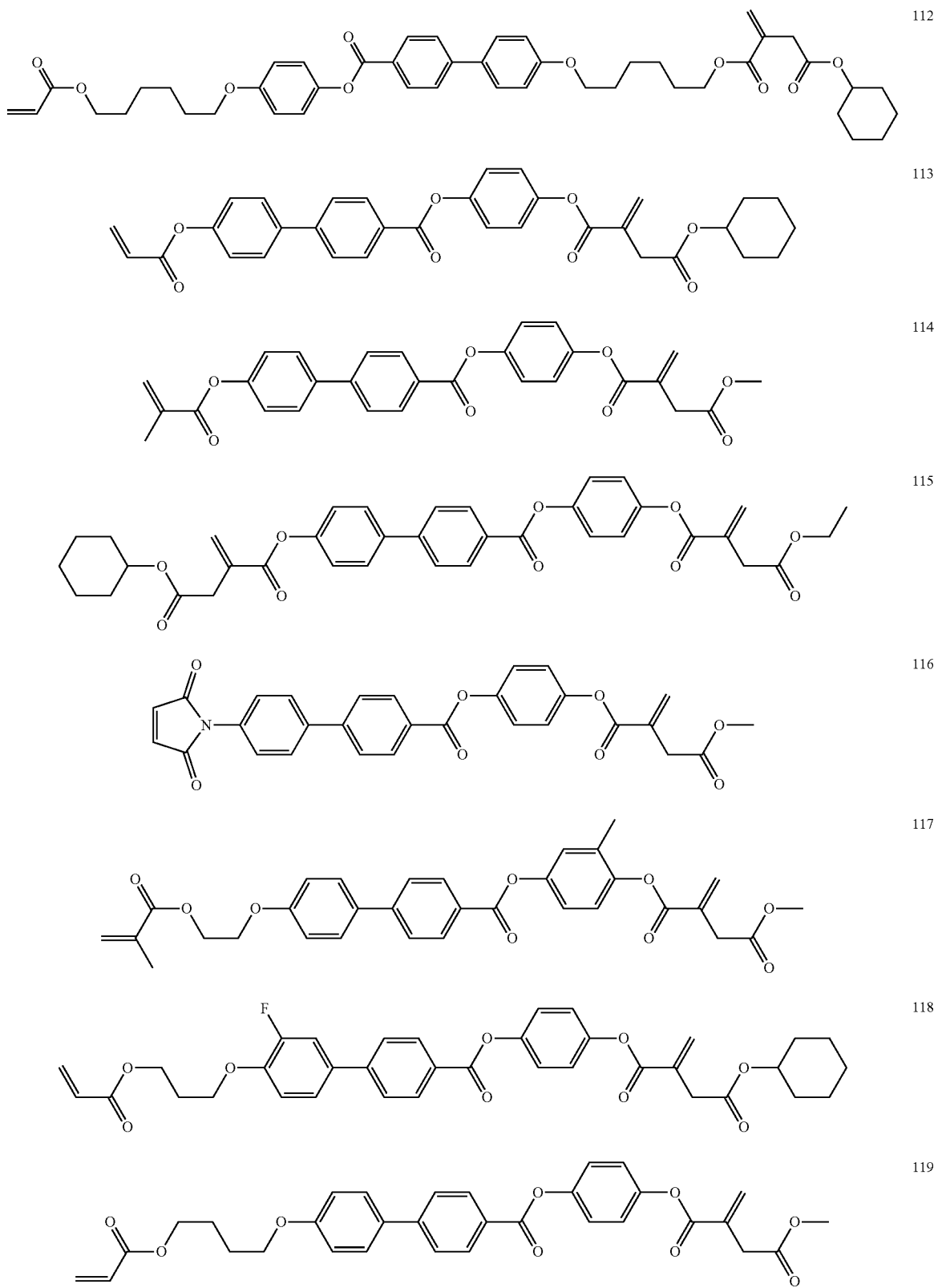

-continued
| No. |
|---|
| 120 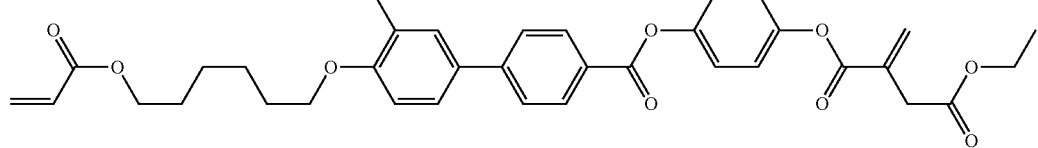 |
| 121 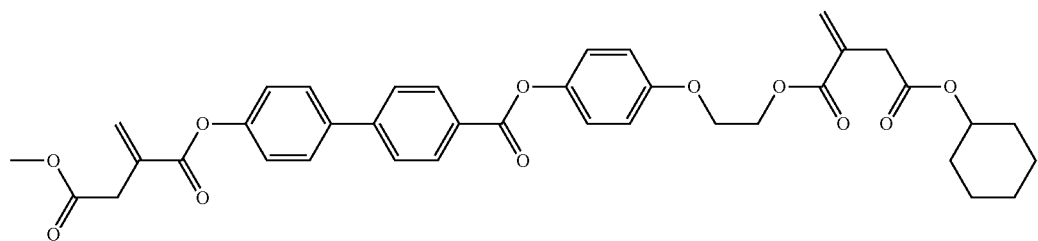 [SMILES: C=C(CC(=O)OC1CCCCC1)C(=O)OCCOc1ccc(OC(=O)c2ccc(-c3ccc(OC(=O)C(=C)CC(=O)OC)cc3)cc2)cc1] |
| 122 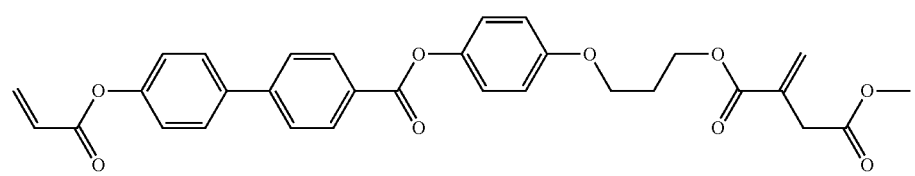 [SMILES: C=CC(=O)Oc1ccc(-c2ccc(C(=O)Oc3ccc(OCCCOC(=O)C(=C)CC(=O)OC)cc3)cc2)cc1] |
| 123 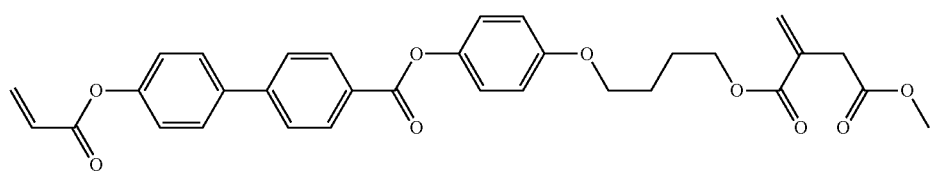 [SMILES: C=CC(=O)Oc1ccc(-c2ccc(C(=O)Oc3ccc(OCCCCOC(=O)C(=C)CC(=O)OC)cc3)cc2)cc1] |
| 124 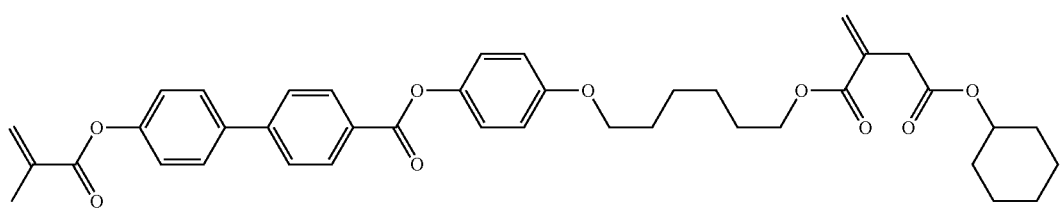 [SMILES: C=C(C)C(=O)Oc1ccc(-c2ccc(C(=O)Oc3ccc(OCCCCCCOC(=O)C(=C)CC(=O)OC4CCCCC4)cc3)cc2)cc1] |
| 125 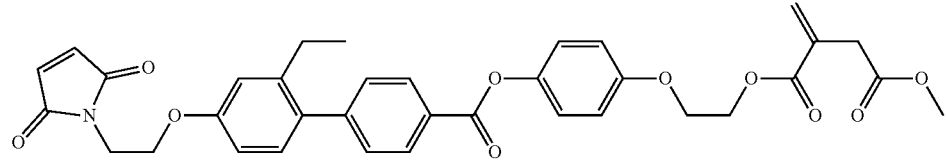 [SMILES: C=C(CC(=O)OC)C(=O)OCCOc1ccc(OC(=O)c2ccc(-c3ccc(OCCN4C(=O)C=CC4=O)cc3CC)cc2)cc1] |
| 126 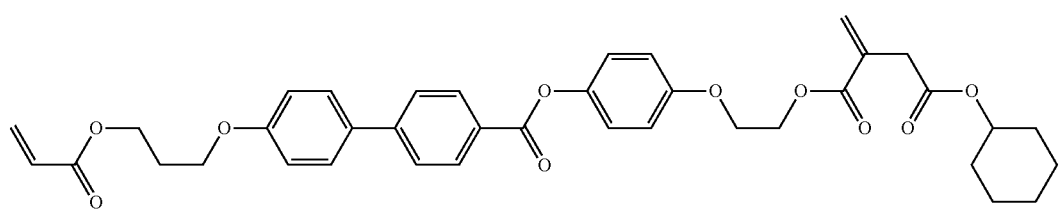 [SMILES: C=CC(=O)OCCCOc1ccc(-c2ccc(C(=O)Oc3ccc(OCCOC(=O)C(=C)CC(=O)OC4CCCCC4)cc3)cc2)cc1] |
| 127 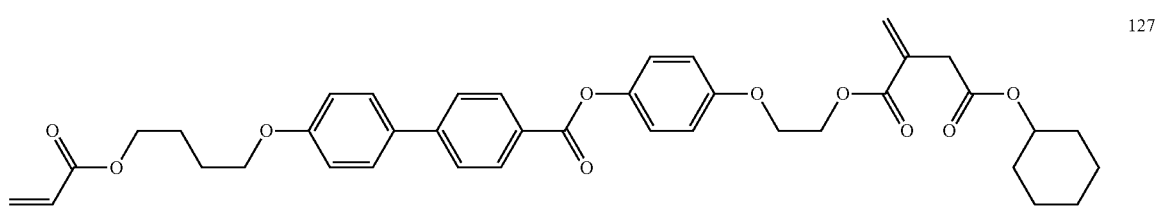 |

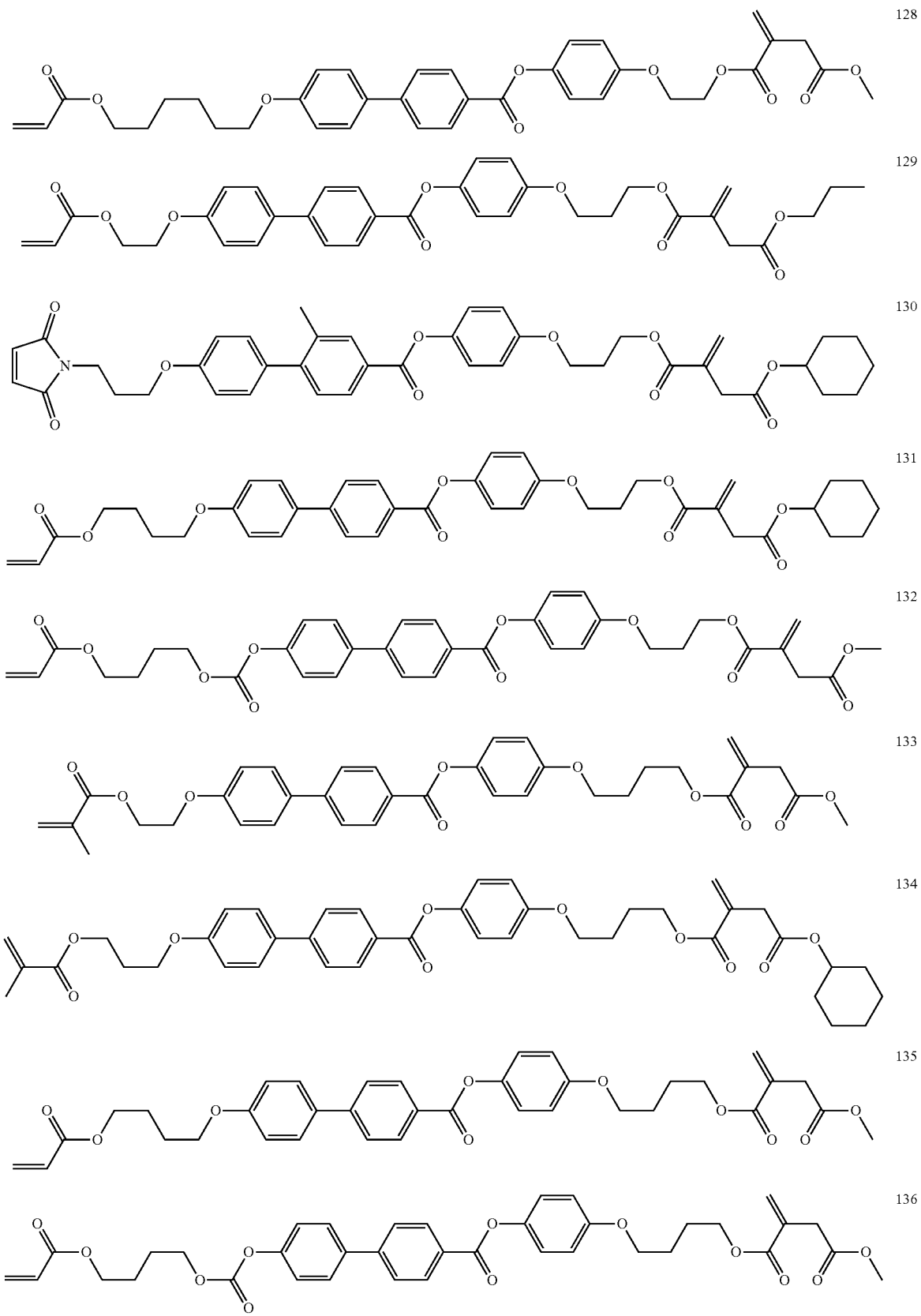

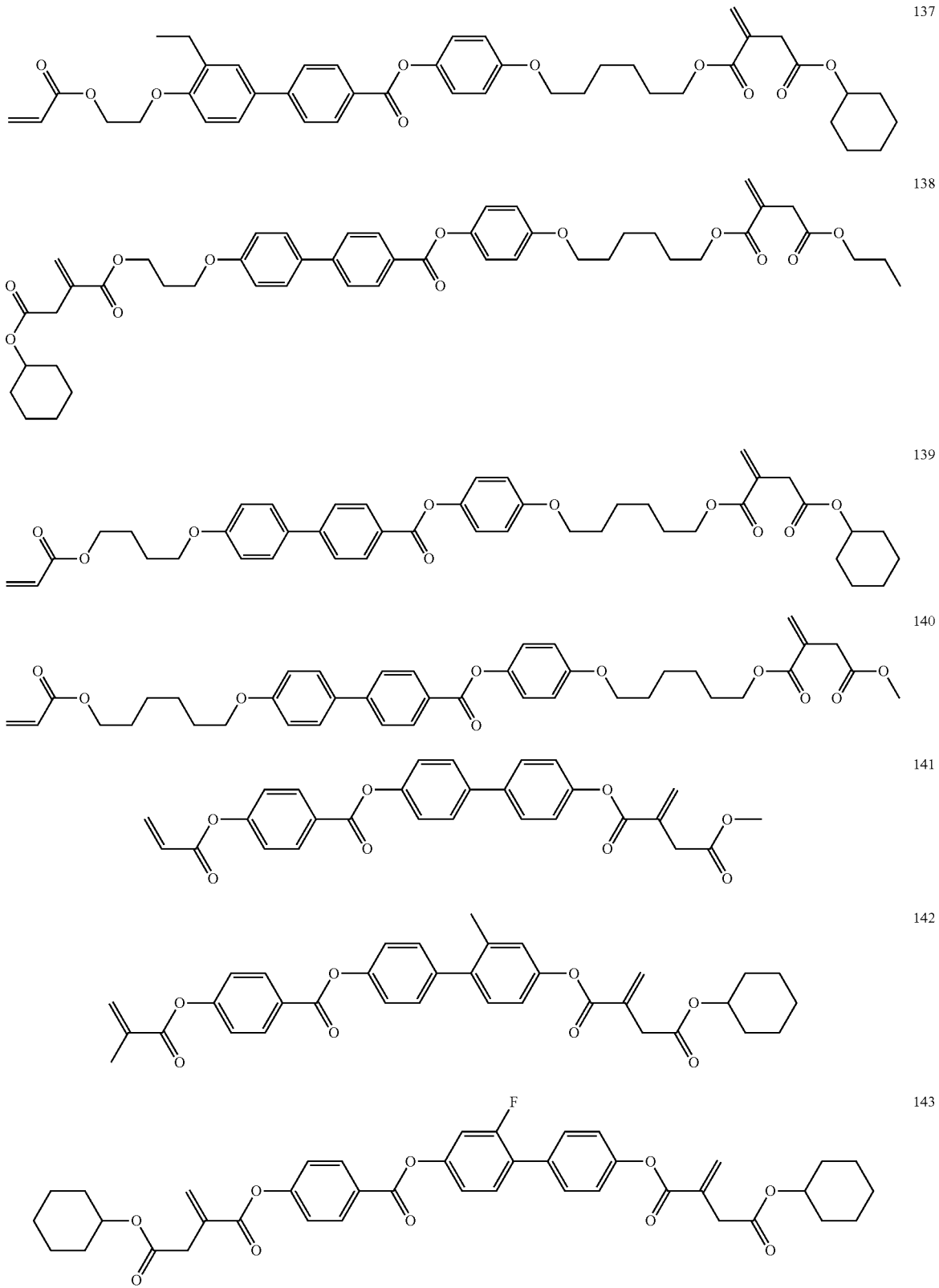

-continued
| | No. |
|---|---|
| 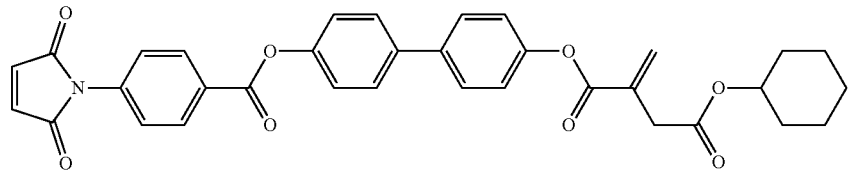 [SMILES: C=C(CC(=O)OC1CCCCC1)C(=O)Oc1ccc(-c2ccc(OC(=O)c3ccc(N4C(=O)C=CC4=O)cc3)cc2)cc1] | 144 |
| 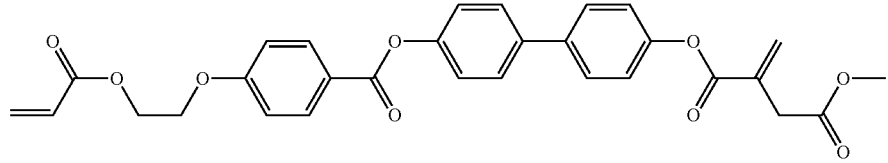 [SMILES: C=CC(=O)OCCOc1ccc(C(=O)Oc2ccc(-c3ccc(OC(=O)C(=C)CC(=O)OC)cc3)cc2)cc1] | 145 |
| 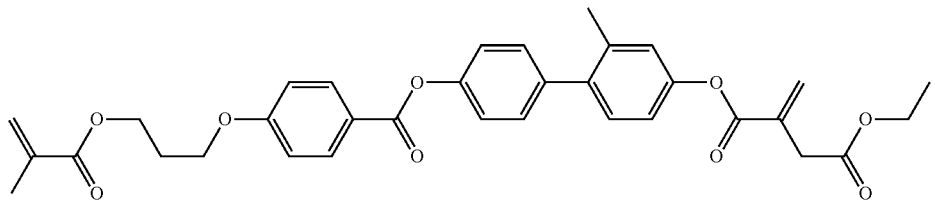 [SMILES: C=C(C)C(=O)OCCCOc1ccc(C(=O)Oc2ccc(-c3ccc(OC(=O)C(=C)CC(=O)OCC)cc3C)cc2)cc1] | 146 |
| 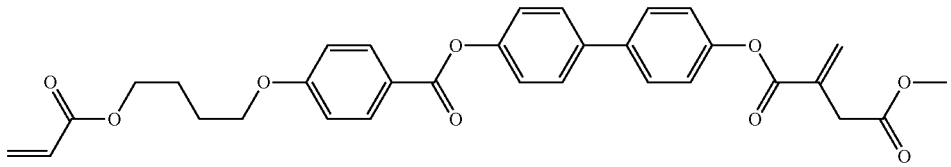 [SMILES: C=CC(=O)OCCCCOc1ccc(C(=O)Oc2ccc(-c3ccc(OC(=O)C(=C)CC(=O)OC)cc3)cc2)cc1] | 147 |
| 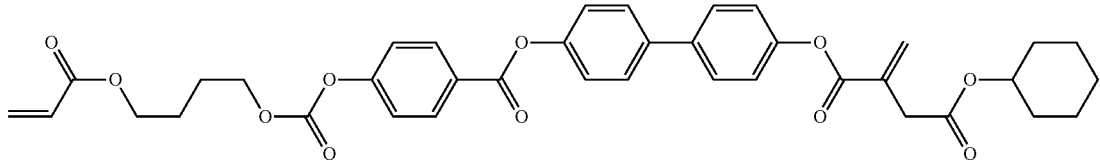 [SMILES: C=CC(=O)OCCCCOC(=O)Oc1ccc(C(=O)Oc2ccc(-c3ccc(OC(=O)C(=C)CC(=O)OC4CCCCC4)cc3)cc2)cc1] | 148 |
| 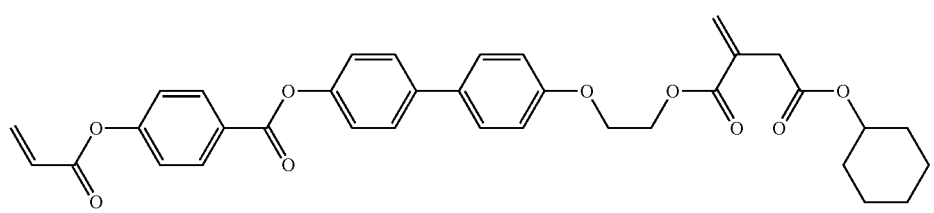 [SMILES: C=CC(=O)Oc1ccc(C(=O)Oc2ccc(-c3ccc(OCCOC(=O)C(=C)CC(=O)OC4CCCCC4)cc3)cc2)cc1] | 149 |
| 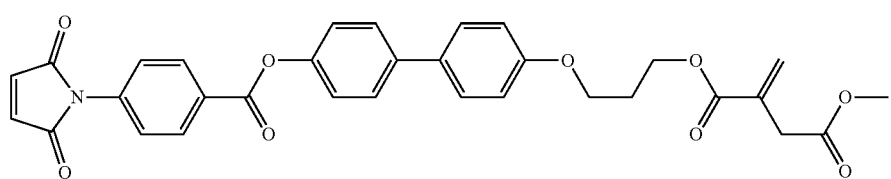 [SMILES: C=C(CC(=O)OC)C(=O)OCCCOc1ccc(-c2ccc(OC(=O)c3ccc(N4C(=O)C=CC4=O)cc3)cc2)cc1] | 150 |
| 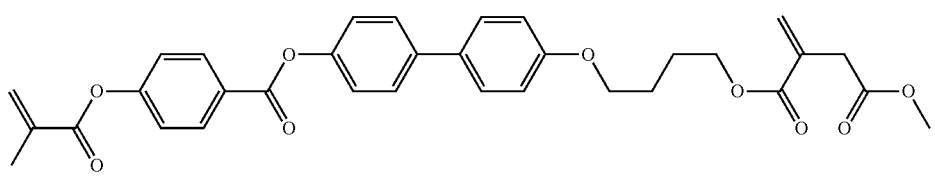 [SMILES: C=C(C)C(=O)Oc1ccc(C(=O)Oc2ccc(-c3ccc(OCCCCOC(=O)C(=C)CC(=O)OC)cc3)cc2)cc1] | 151 |

-continued
| No. |
|---|
| 152 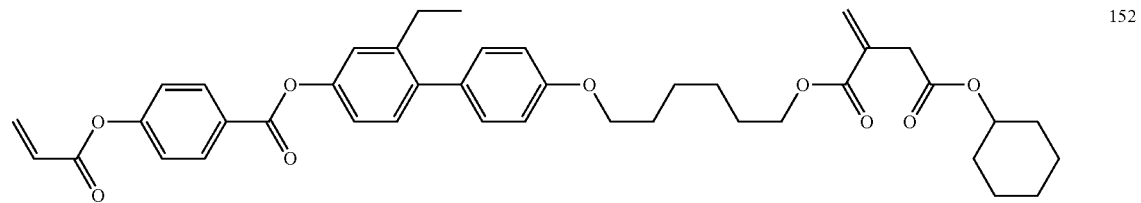 |
| 153 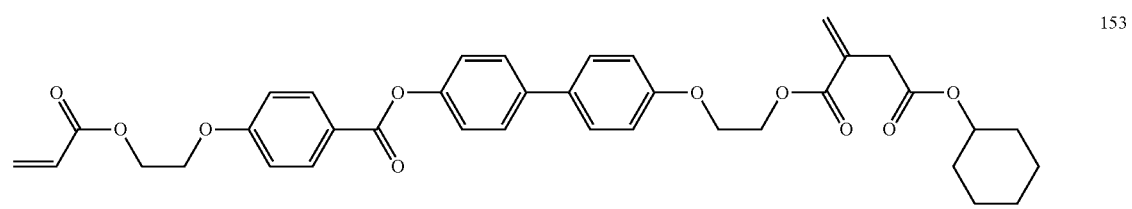 |
| 154 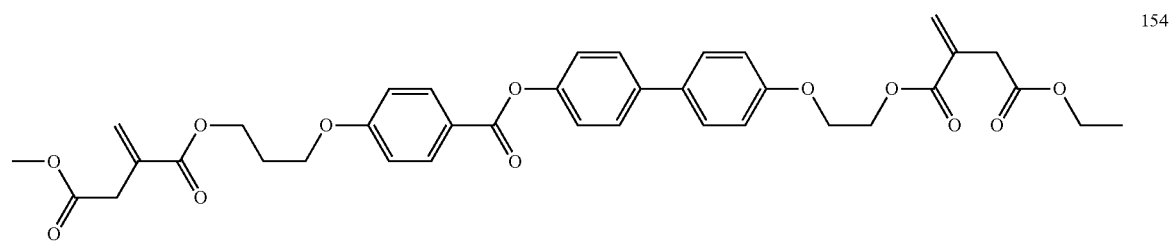 |
| 155 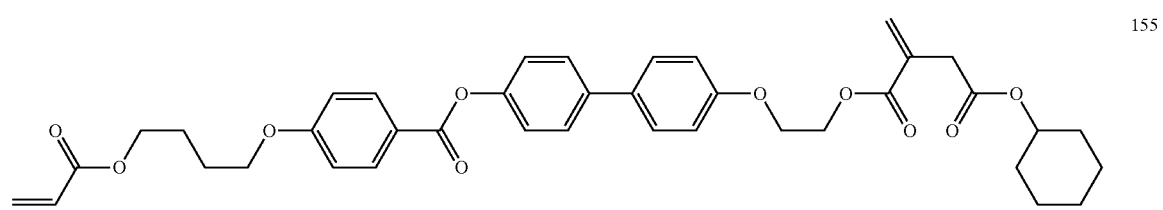 |
| 156 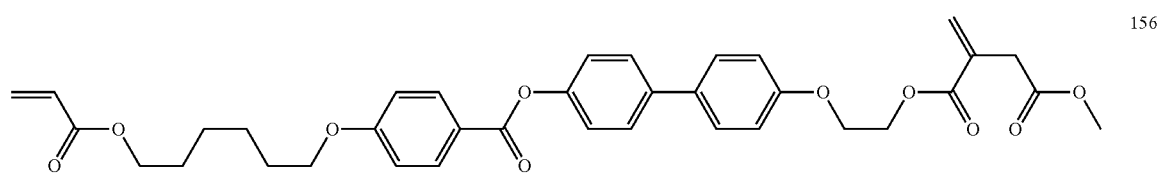 |
| 157 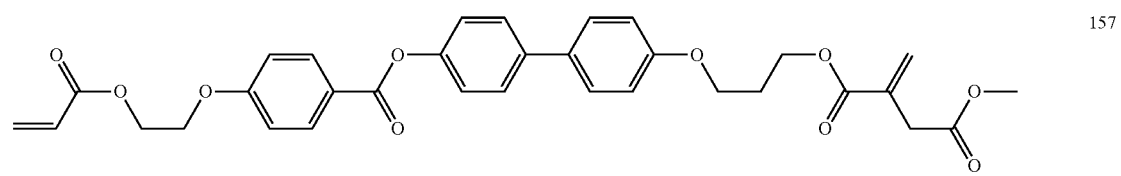 |
| 158 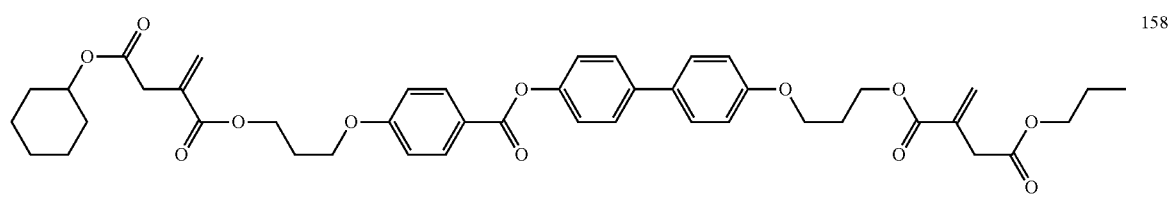 |

-continued
| No. |
|---|
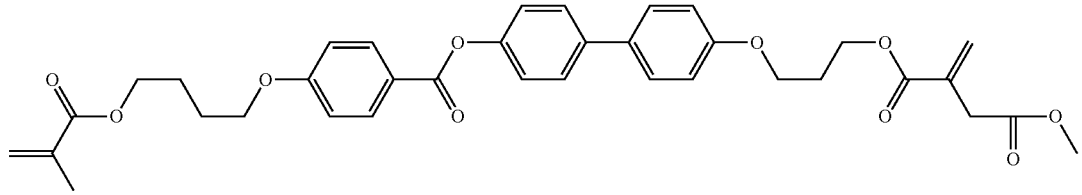 [SMILES: C=C(C)C(=O)OCCCCOc1ccc(C(=O)Oc2ccc(-c3ccc(OCCCOC(=O)C(=C)CC(=O)OC)cc3)cc2)cc1]
159
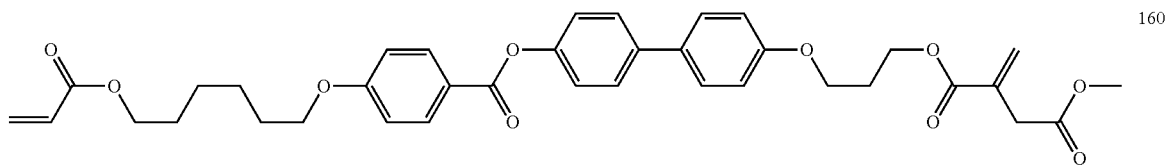
160
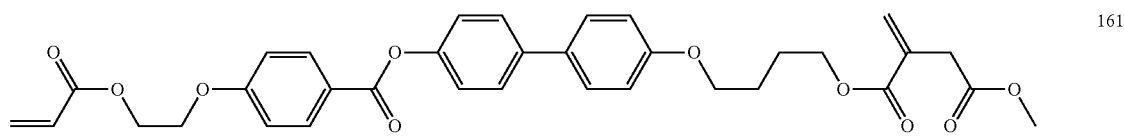
161
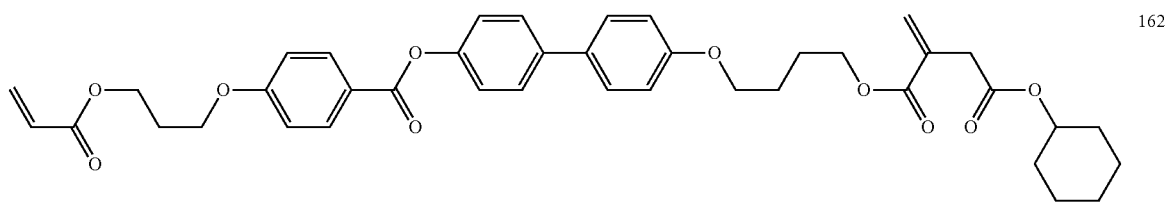
162
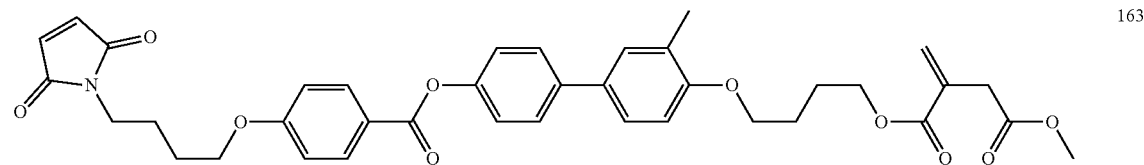
163
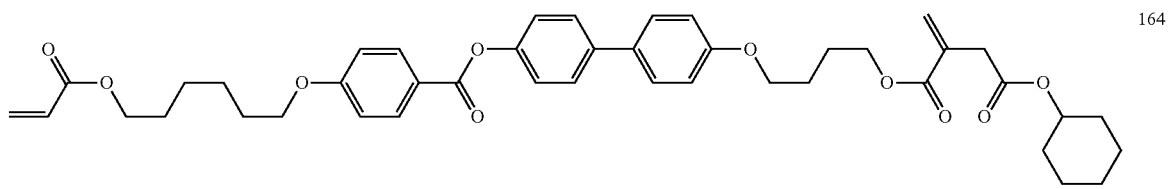
164
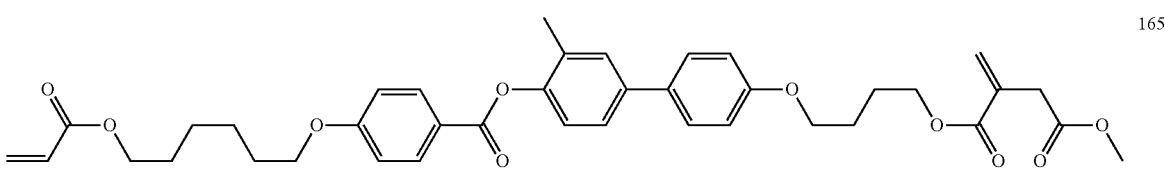
165
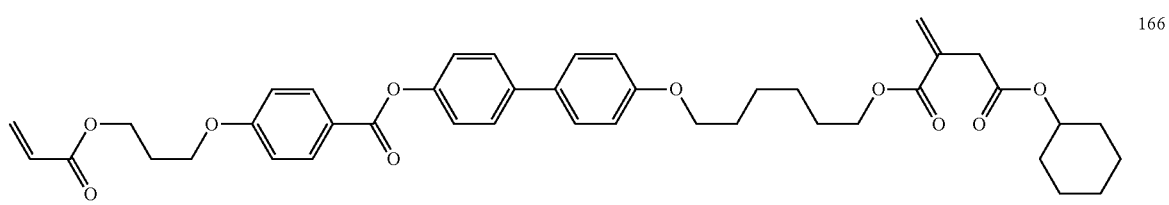
166

| No. |
|---|
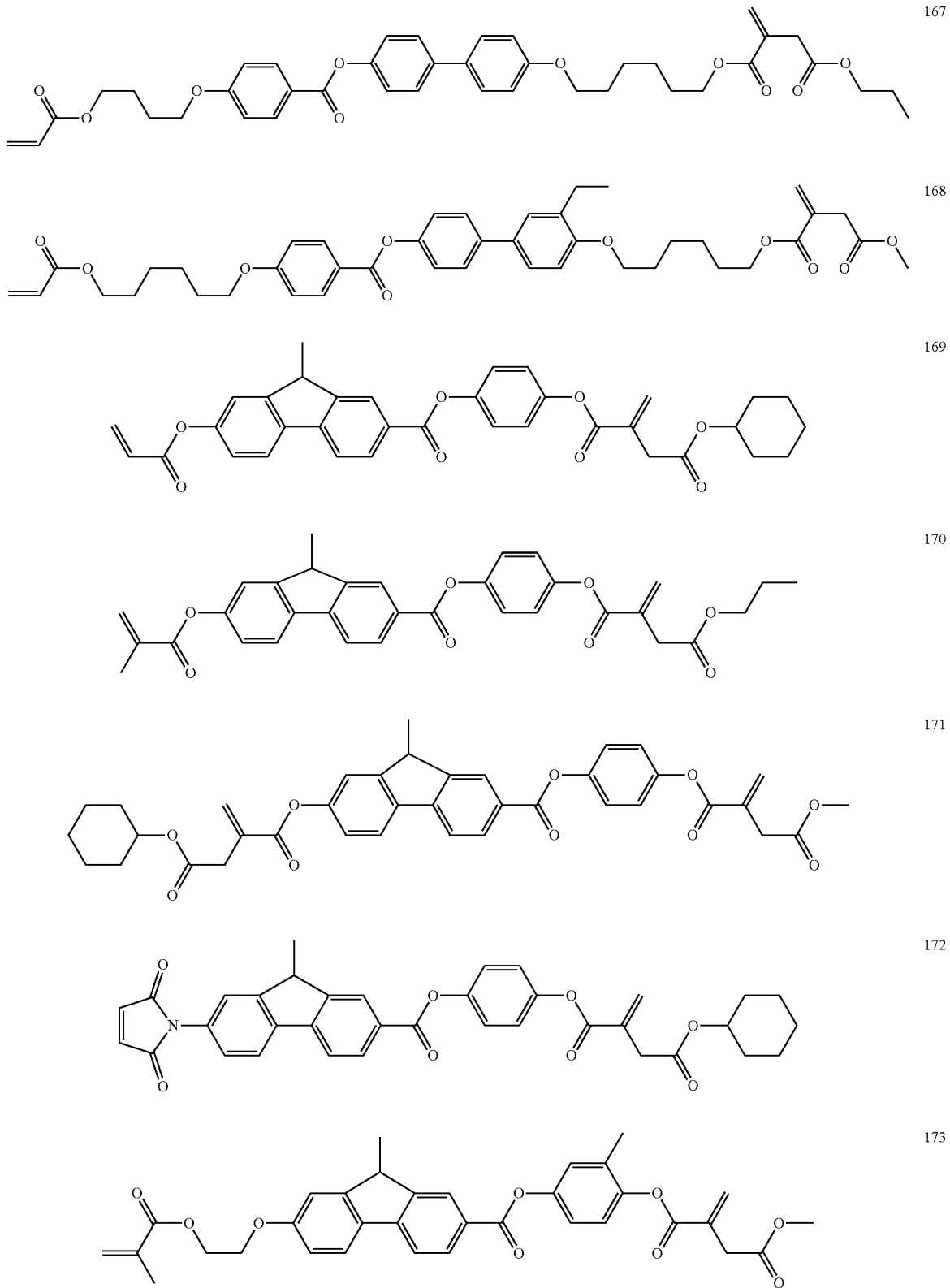

| No. |
|---|
| 174 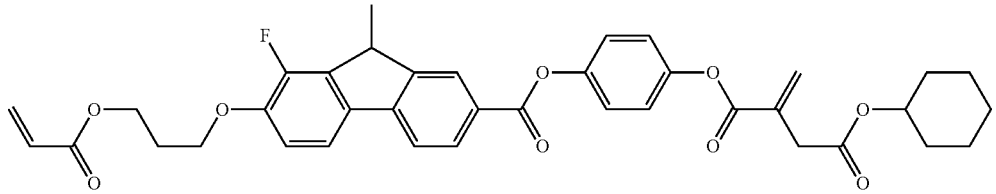 [SMILES: C=CC(=O)OCCCOc1ccc2c(c1F)C(C)c1cc(C(=O)Oc3ccc(OC(=O)C(=C)CC(=O)OC4CCCCC4)cc3)ccc1-2] |
| 175 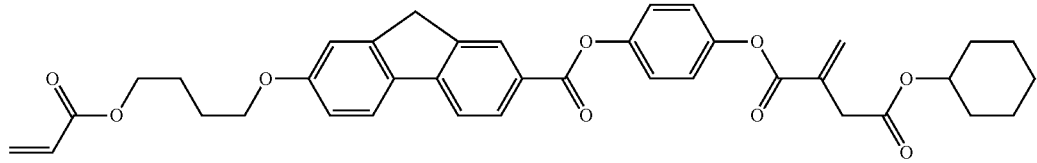 [SMILES: C=CC(=O)OCCCCOc1ccc2c(c1)Cc1cc(C(=O)Oc3ccc(OC(=O)C(=C)CC(=O)OC4CCCCC4)cc3)ccc1-2] |
| 176 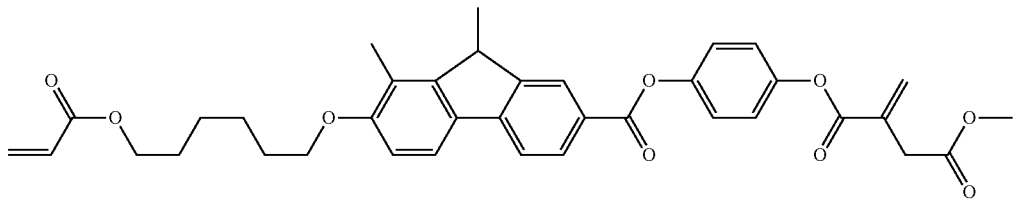 [SMILES: C=CC(=O)OCCCCCCOc1ccc2c(c1C)C(C)c1cc(C(=O)Oc3ccc(OC(=O)C(=C)CC(=O)OC)cc3)ccc1-2] |
| 177 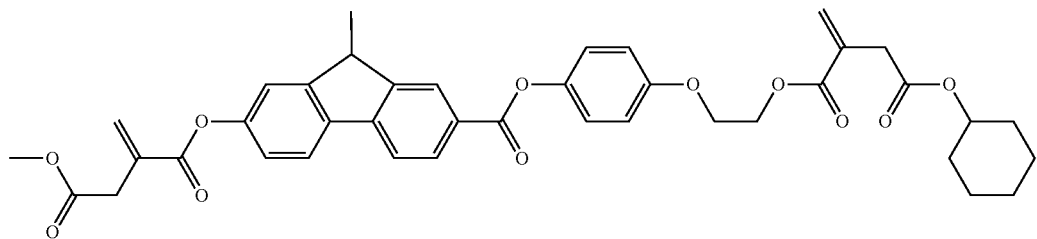 [SMILES: C=C(CC(=O)OC1CCCCC1)C(=O)OCCOc1ccc(OC(=O)c2ccc3c(c2)C(C)c2cc(OC(=O)C(=C)CC(=O)OC)ccc2-3)cc1] |
| 178 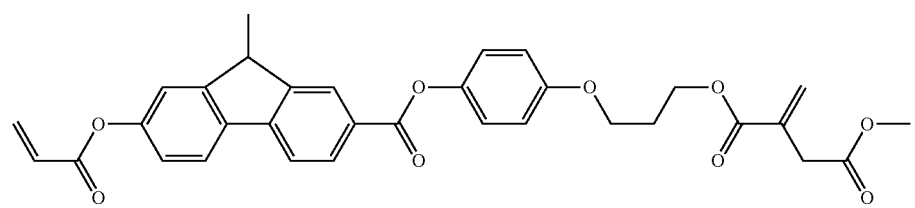 [SMILES: C=CC(=O)Oc1ccc2c(c1)C(C)c1cc(C(=O)Oc3ccc(OCCCOC(=O)C(=C)CC(=O)OC)cc3)ccc1-2] |
| 179 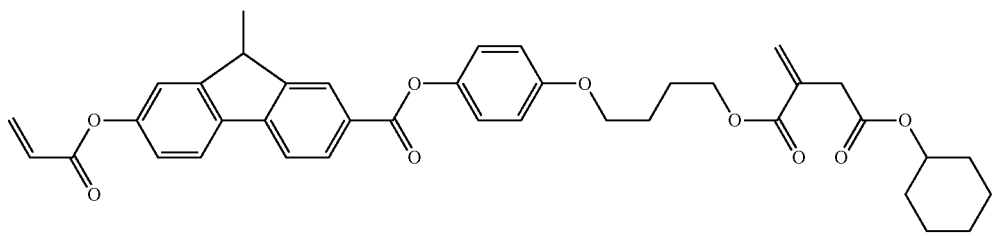 [SMILES: C=CC(=O)Oc1ccc2c(c1)C(C)c1cc(C(=O)Oc3ccc(OCCCCOC(=O)C(=C)CC(=O)OC4CCCCC4)cc3)ccc1-2] |
| 180 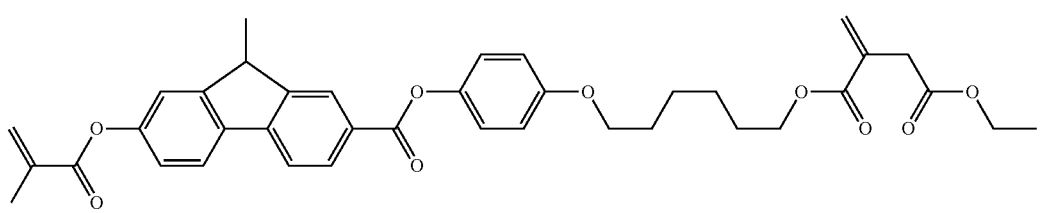 [SMILES: C=C(C)C(=O)Oc1ccc2c(c1)C(C)c1cc(C(=O)Oc3ccc(OCCCCCCOC(=O)C(=C)CC(=O)OCC)cc3)ccc1-2] |

-continued
| No. |
|---|
| 181 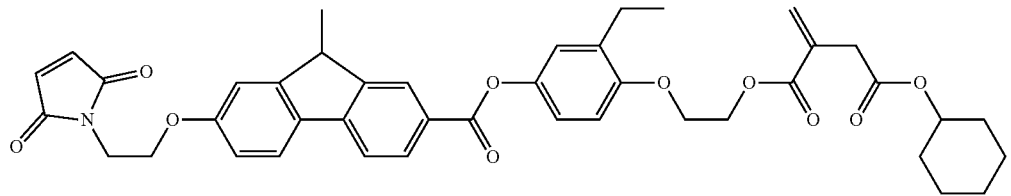 [SMILES: C=C(CC(=O)OC1CCCCC1)C(=O)OCCOc1ccc(OC(=O)c2ccc3c(c2)C(C)c2cc(OCCN4C(=O)C=CC4=O)ccc2-3)cc1CC] |
| 182 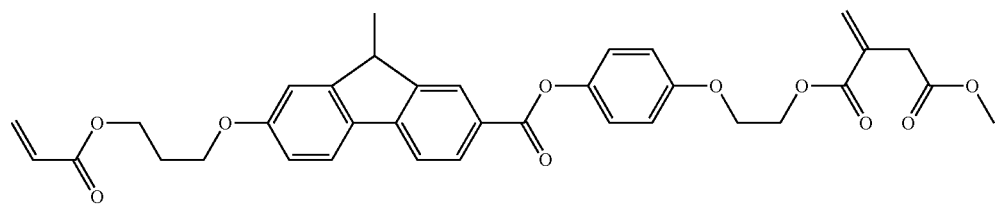 [SMILES: C=CC(=O)OCCCOc1ccc2c(c1)C(C)c1cc(C(=O)Oc3ccc(OCCOC(=O)C(=C)CC(=O)OC)cc3)ccc1-2] |
| 183 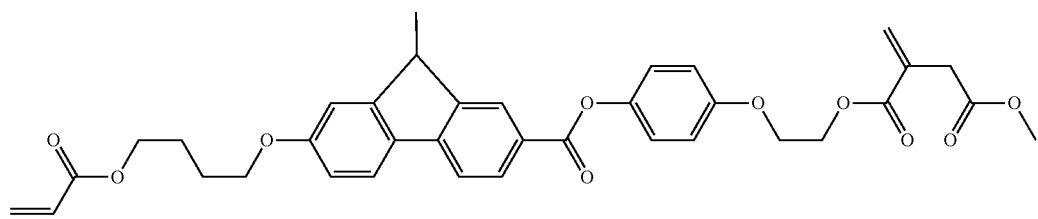 [SMILES: C=CC(=O)OCCCCOc1ccc2c(c1)C(C)c1cc(C(=O)Oc3ccc(OCCOC(=O)C(=C)CC(=O)OC)cc3)ccc1-2] |
| 184 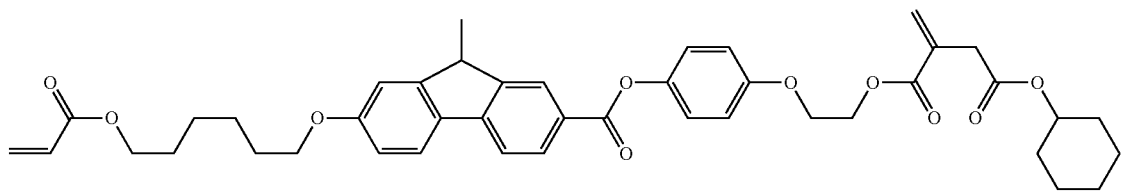 [SMILES: C=CC(=O)OCCCCCCOc1ccc2c(c1)C(C)c1cc(C(=O)Oc3ccc(OCCOC(=O)C(=C)CC(=O)OC4CCCCC4)cc3)ccc1-2] |
| 185 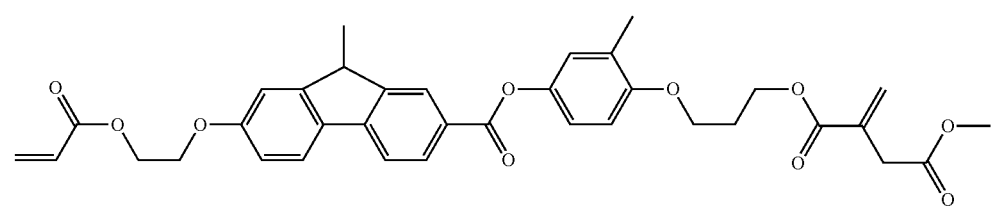 [SMILES: C=CC(=O)OCCOc1ccc2c(c1)C(C)c1cc(C(=O)Oc3ccc(OCCCOC(=O)C(=C)CC(=O)OC)c(C)c3)ccc1-2] |
| 186 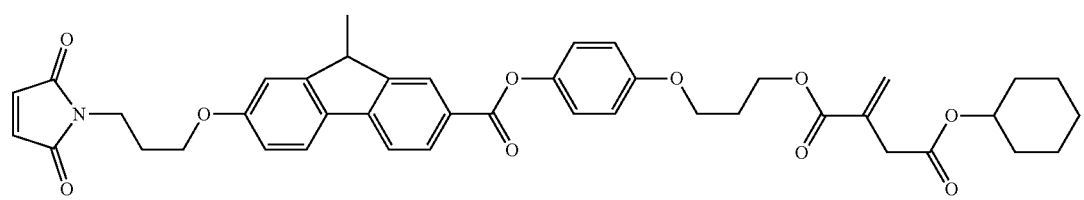 [SMILES: C=C(CC(=O)OC1CCCCC1)C(=O)OCCCOc1ccc(OC(=O)c2ccc3c(c2)C(C)c2cc(OCCCN4C(=O)C=CC4=O)ccc2-3)cc1] |
| 187 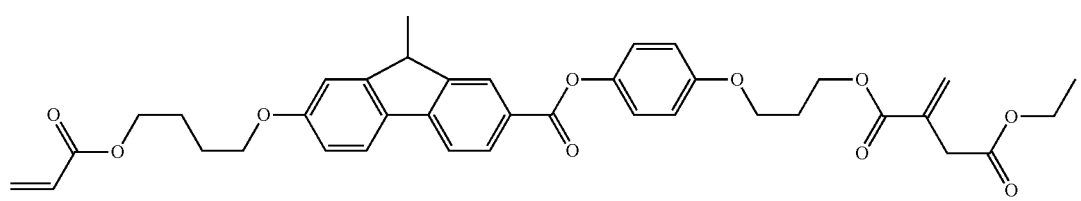 [SMILES: C=CC(=O)OCCCCOc1ccc2c(c1)C(C)c1cc(C(=O)Oc3ccc(OCCCOC(=O)C(=C)CC(=O)OCC)cc3)ccc1-2] |

-continued
| | No. |
|---|---|
| 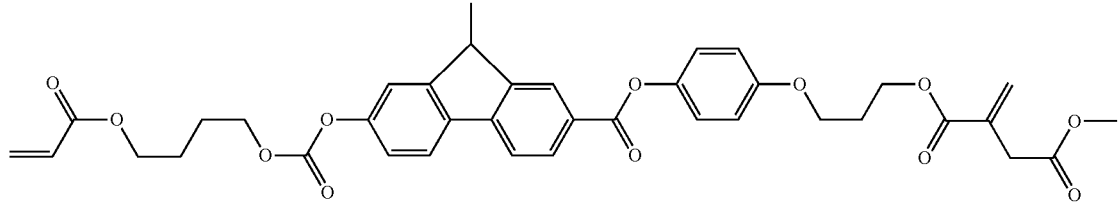 [SMILES: C=CC(=O)OCCCCOC(=O)Oc1ccc2c(c1)C(C)c1cc(C(=O)Oc3ccc(OCCCOC(=O)C(=C)CC(=O)OC)cc3)ccc1-2] | 188 |
| 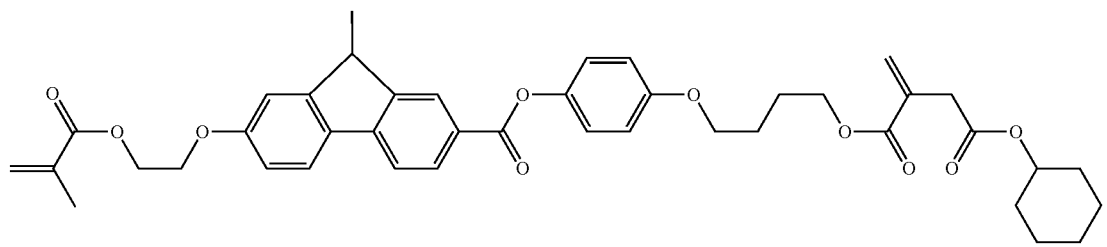 [SMILES: C=C(C)C(=O)OCCOc1ccc2c(c1)C(C)c1cc(C(=O)Oc3ccc(OCCCCOC(=O)C(=C)CC(=O)OC4CCCCC4)cc3)ccc1-2] | 189 |
| 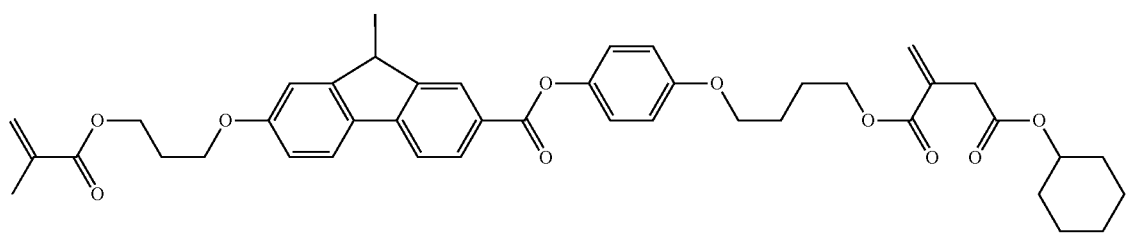 [SMILES: C=C(C)C(=O)OCCCOc1ccc2c(c1)C(C)c1cc(C(=O)Oc3ccc(OCCCCOC(=O)C(=C)CC(=O)OC4CCCCC4)cc3)ccc1-2] | 190 |
| 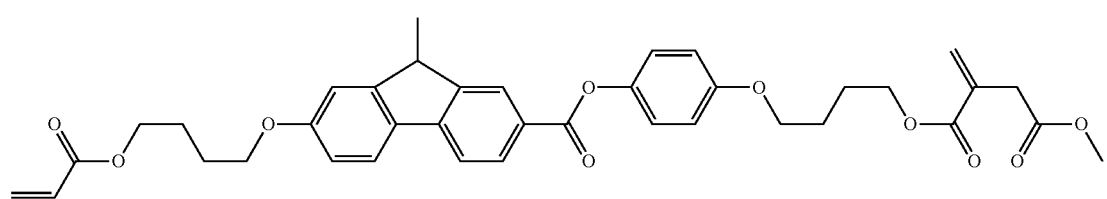 [SMILES: C=CC(=O)OCCCCOc1ccc2c(c1)C(C)c1cc(C(=O)Oc3ccc(OCCCCOC(=O)C(=C)CC(=O)OC)cc3)ccc1-2] | 191 |
| 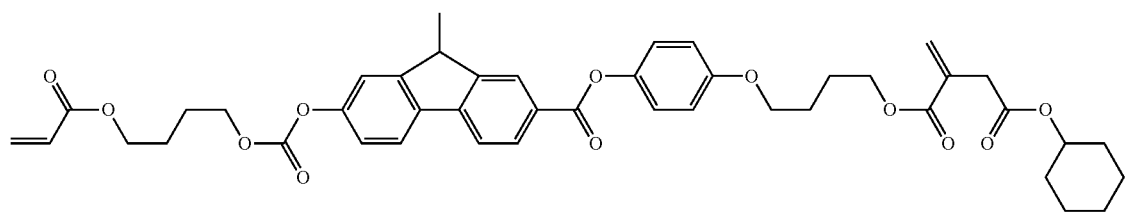 [SMILES: C=CC(=O)OCCCCOC(=O)Oc1ccc2c(c1)C(C)c1cc(C(=O)Oc3ccc(OCCCCOC(=O)C(=C)CC(=O)OC4CCCCC4)cc3)ccc1-2] | 192 |
| 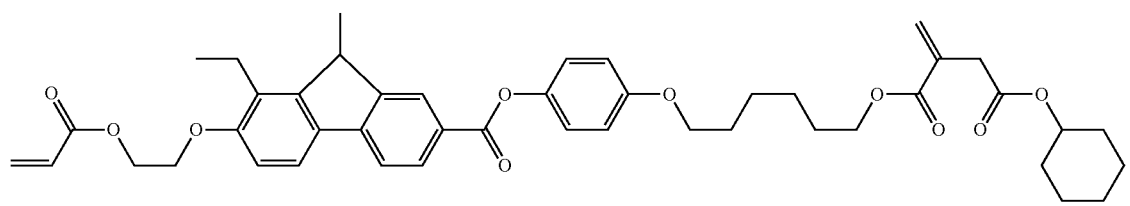 [SMILES: C=CC(=O)OCCOc1ccc2c(c1CC)C(C)c1cc(C(=O)Oc3ccc(OCCCCCCOC(=O)C(=C)CC(=O)OC4CCCCC4)cc3)ccc1-2] | 193 |

-continued
| No. |
|---|
| 194 |
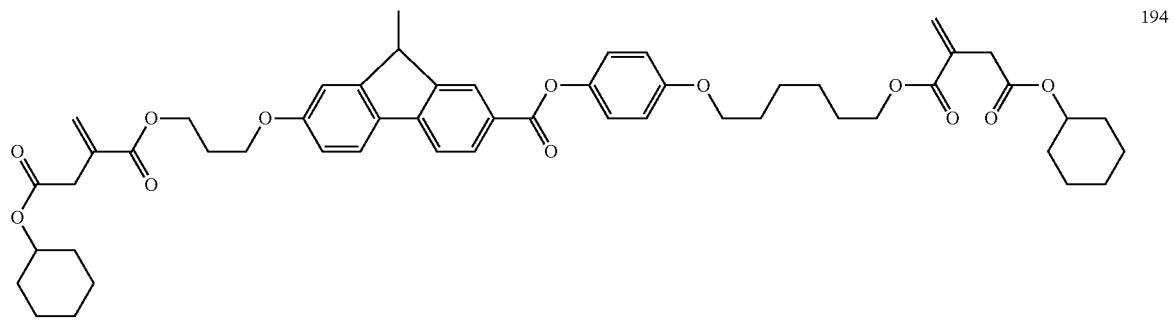
| 195 |
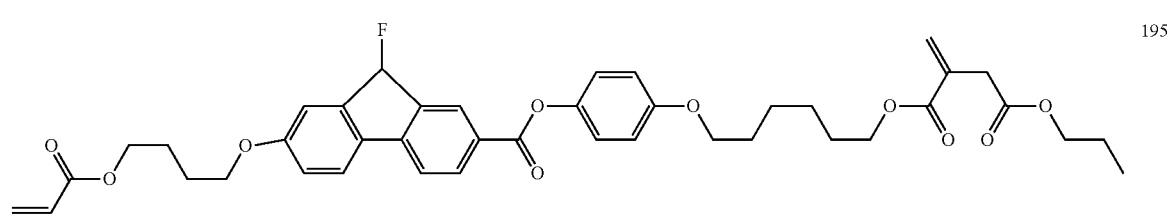
| 196 |
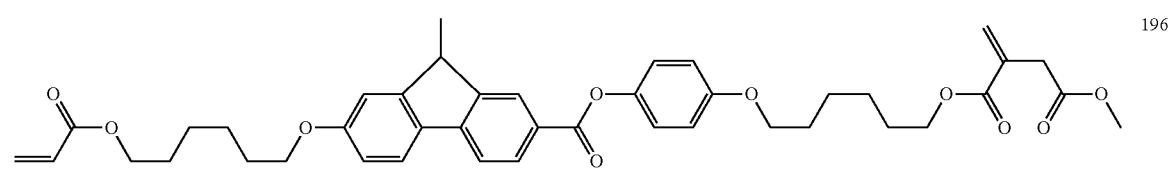
| 197 |
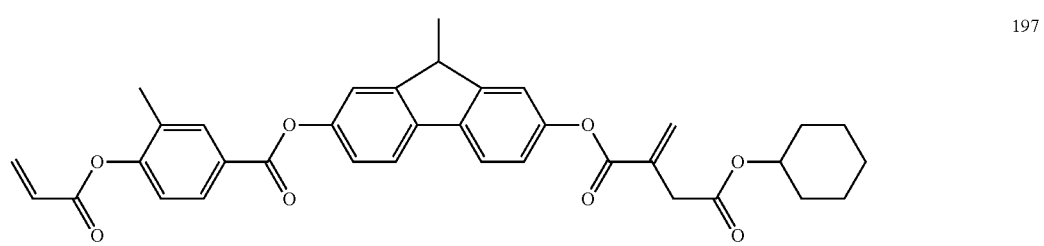
| 198 |
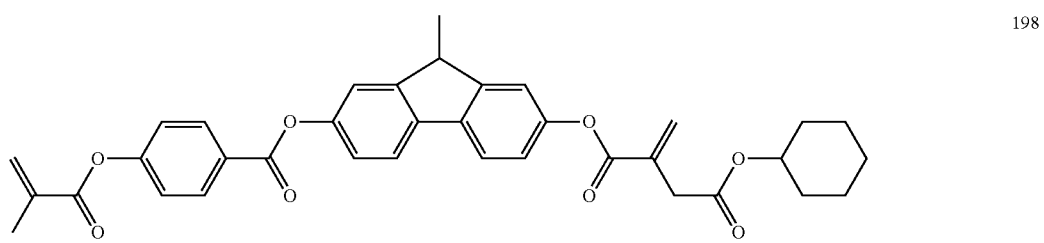
| 199 |
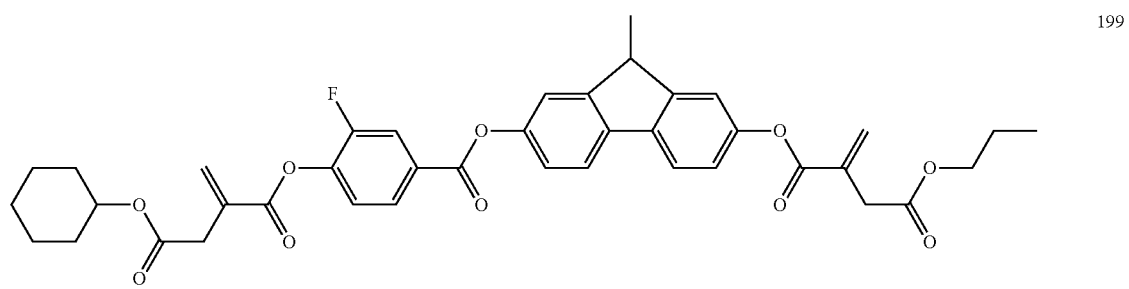

| No. |
|---|
| 200 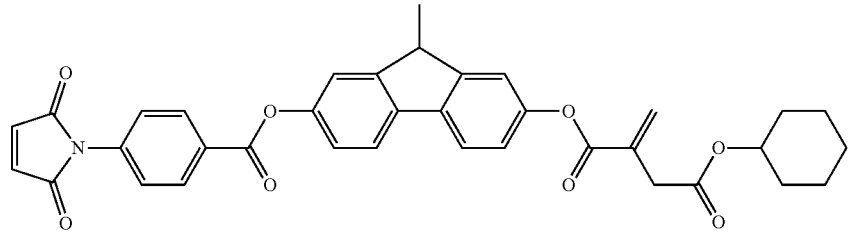 [SMILES: C=C(CC(=O)OC1CCCCC1)C(=O)Oc1ccc2c(c1)C(C)c1cc(OC(=O)c3ccc(N4C(=O)C=CC4=O)cc3)ccc1-2] |
| 201 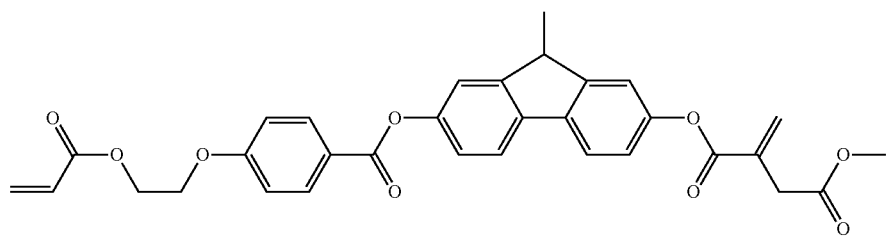 [SMILES: C=CC(=O)OCCOc1ccc(C(=O)Oc2ccc3c(c2)C(C)c2cc(OC(=O)C(=C)CC(=O)OC)ccc2-3)cc1] |
| 202 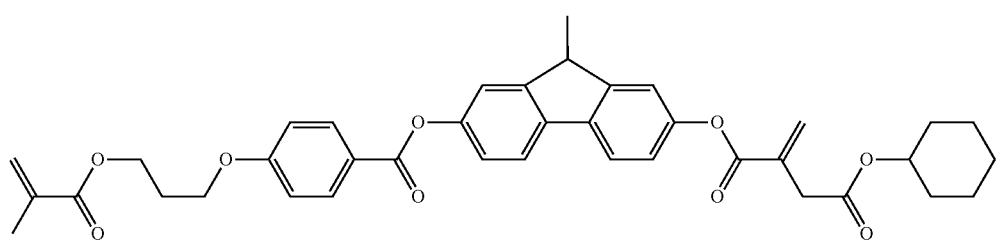 [SMILES: C=C(C)C(=O)OCCCOc1ccc(C(=O)Oc2ccc3c(c2)C(C)c2cc(OC(=O)C(=C)CC(=O)OC4CCCCC4)ccc2-3)cc1] |
| 203 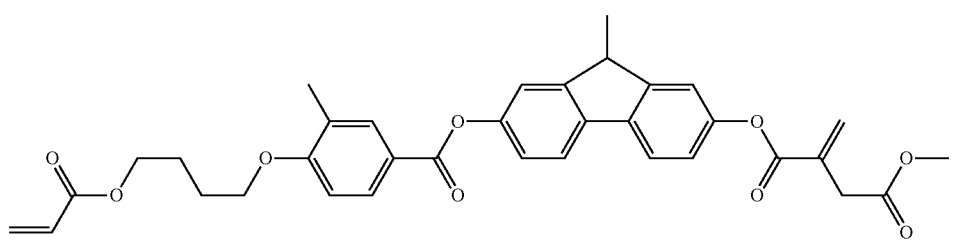 [SMILES: C=CC(=O)OCCCCOc1ccc(C(=O)Oc2ccc3c(c2)C(C)c2cc(OC(=O)C(=C)CC(=O)OC)ccc2-3)cc1C] |
| 204 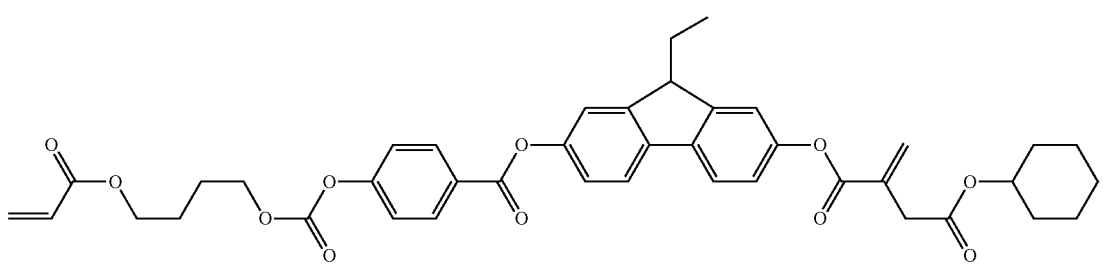 [SMILES: C=CC(=O)OCCCCOC(=O)Oc1ccc(C(=O)Oc2ccc3c(c2)C(CC)c2cc(OC(=O)C(=C)CC(=O)OC4CCCCC4)ccc2-3)cc1] |
| 205 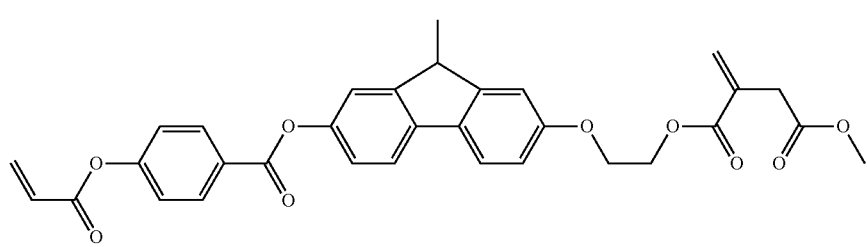 [SMILES: C=CC(=O)Oc1ccc(C(=O)Oc2ccc3c(c2)C(C)c2cc(OCCOC(=O)C(=C)CC(=O)OC)ccc2-3)cc1] |

-continued
| No. |
|---|
| 206 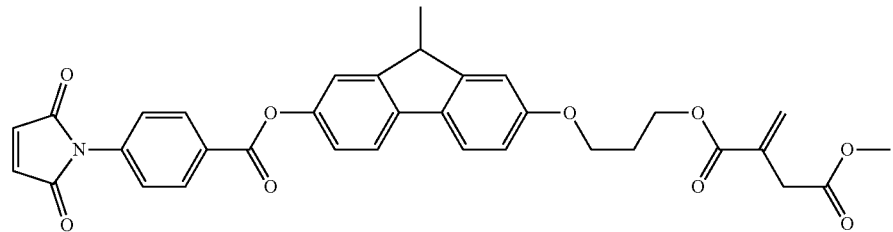 [SMILES: C=C(CC(=O)OC)C(=O)OCCCOc1ccc2c(c1)C(C)c1cc(OC(=O)c3ccc(N4C(=O)C=CC4=O)cc3)ccc1-2] |
| 207 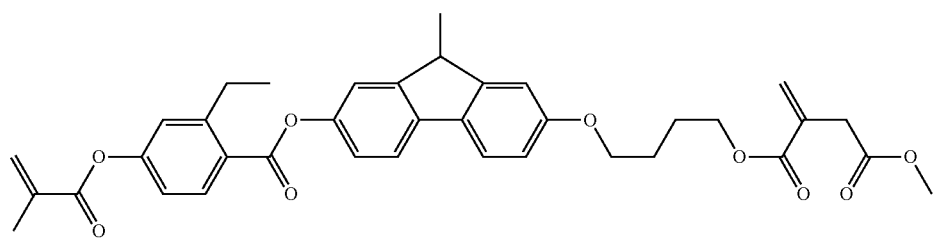 [SMILES: C=C(C)C(=O)Oc1ccc(C(=O)Oc2ccc3c(c2)C(C)c2cc(OCCCCOC(=O)C(=C)CC(=O)OC)ccc2-3)c(CC)c1] |
| 208 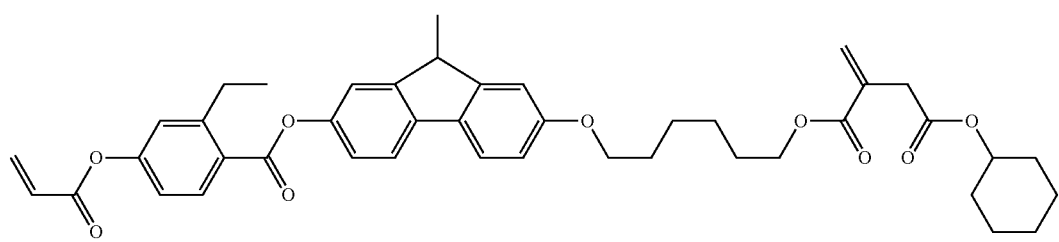 [SMILES: C=CC(=O)Oc1ccc(C(=O)Oc2ccc3c(c2)C(C)c2cc(OCCCCCCOC(=O)C(=C)CC(=O)OC4CCCCC4)ccc2-3)c(CC)c1] |
| 209 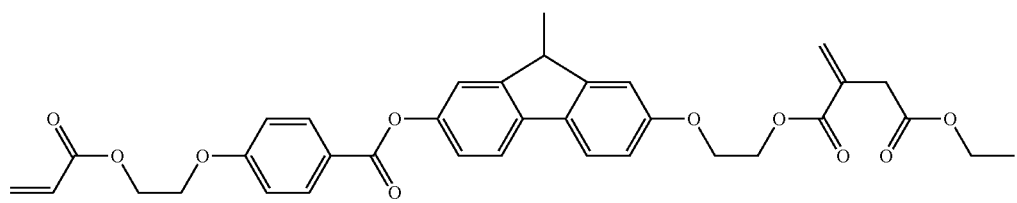 [SMILES: C=CC(=O)OCCOc1ccc(C(=O)Oc2ccc3c(c2)C(C)c2cc(OCCOC(=O)C(=C)CC(=O)OCC)ccc2-3)cc1] |
| 210 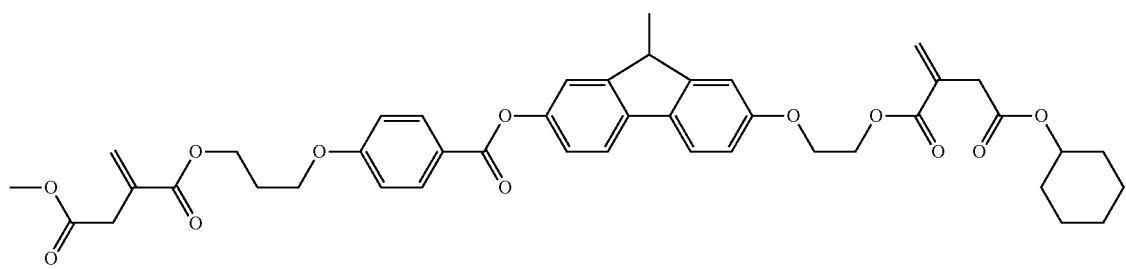 [SMILES: C=C(CC(=O)OC)C(=O)OCCCOc1ccc(C(=O)Oc2ccc3c(c2)C(C)c2cc(OCCOC(=O)C(=C)CC(=O)OC4CCCCC4)ccc2-3)cc1] |
| 211 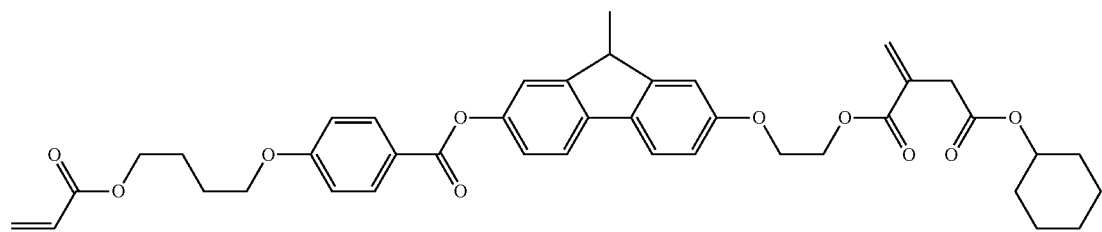 |

-continued
| | No. |
|---|---|
| 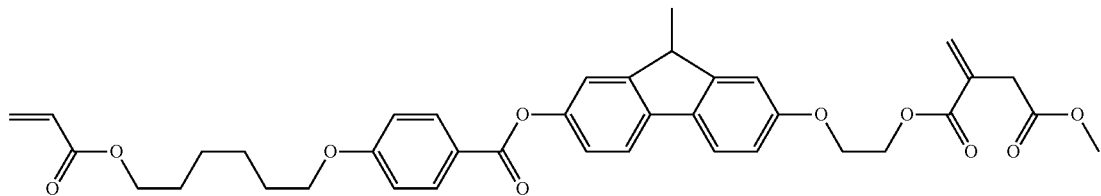 [SMILES: C=CC(=O)OCCCCCCOc1ccc(C(=O)Oc2ccc3c(c2)C(C)c2cc(OCCOC(=O)C(=C)CC(=O)OC)ccc2-3)cc1] | 212 |
| 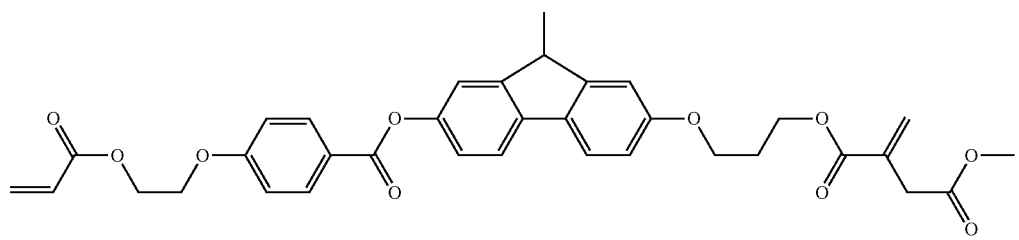 [SMILES: C=CC(=O)OCCOc1ccc(C(=O)Oc2ccc3c(c2)C(C)c2cc(OCCCOC(=O)C(=C)CC(=O)OC)ccc2-3)cc1] | 213 |
| 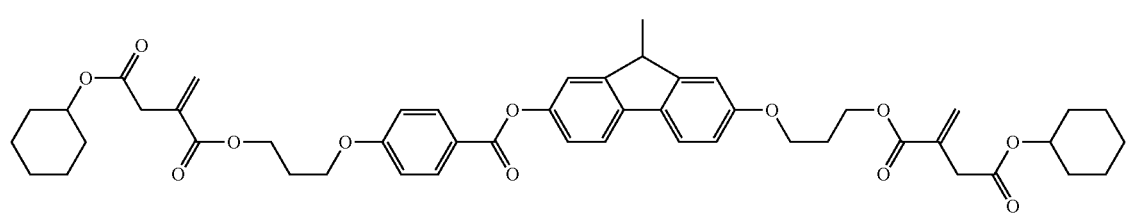 [SMILES: C=C(CC(=O)OC1CCCCC1)C(=O)OCCCOc1ccc(C(=O)Oc2ccc3c(c2)C(C)c2cc(OCCCOC(=O)C(=C)CC(=O)OC4CCCCC4)ccc2-3)cc1] | 214 |
| 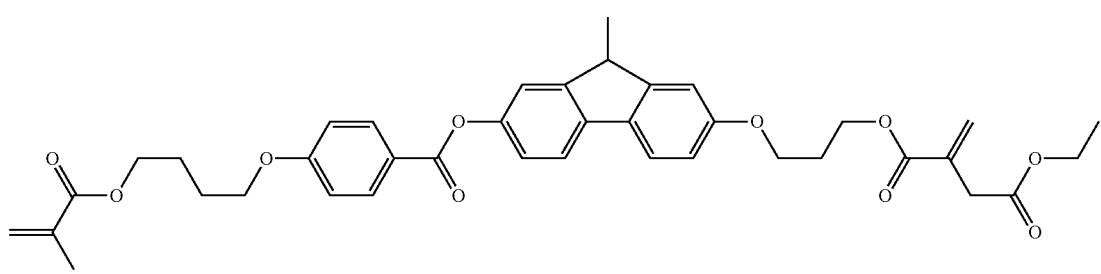 [SMILES: C=C(C)C(=O)OCCCCOc1ccc(C(=O)Oc2ccc3c(c2)C(C)c2cc(OCCCOC(=O)C(=C)CC(=O)OCC)ccc2-3)cc1] | 215 |
| 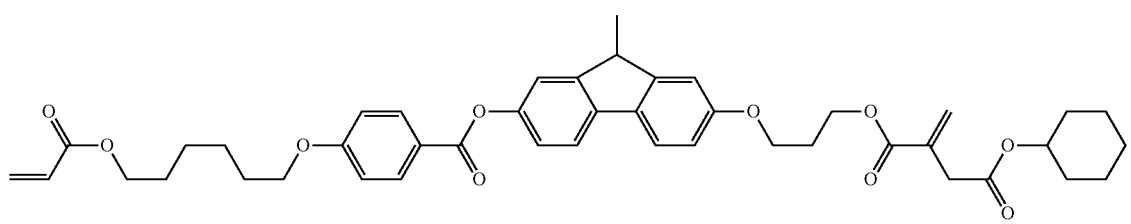 [SMILES: C=CC(=O)OCCCCCCOc1ccc(C(=O)Oc2ccc3c(c2)C(C)c2cc(OCCCOC(=O)C(=C)CC(=O)OC4CCCCC4)ccc2-3)cc1] | 216 |
| 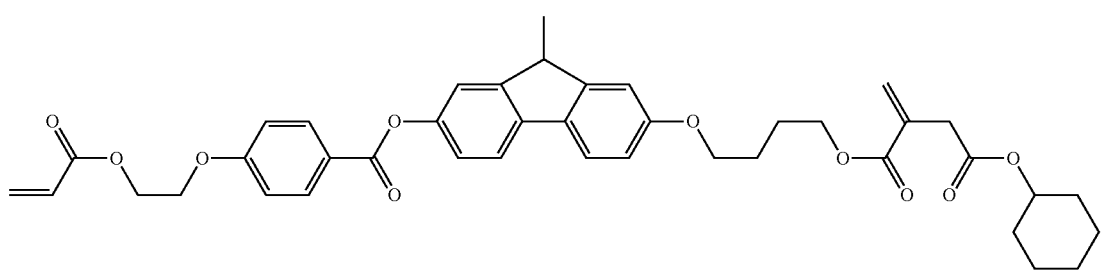 [SMILES: C=CC(=O)OCCOc1ccc(C(=O)Oc2ccc3c(c2)C(C)c2cc(OCCCCOC(=O)C(=C)CC(=O)OC4CCCCC4)ccc2-3)cc1] | 217 |

-continued
| No. |
|---|
| 218 |
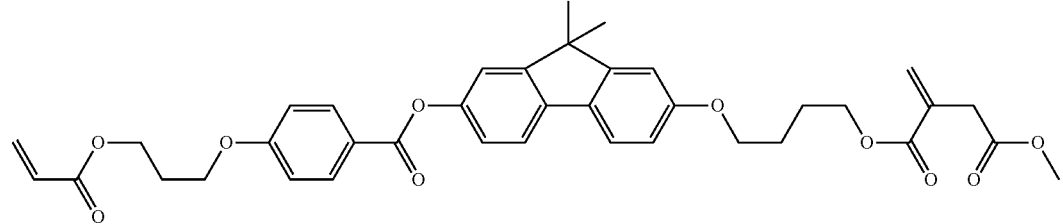 [SMILES: C=CC(=O)OCCCOc1ccc(C(=O)Oc2ccc3c(c2)C(C)(C)c2cc(OCCCCOC(=O)C(=C)CC(=O)OC)ccc2-3)cc1]
| 219 |
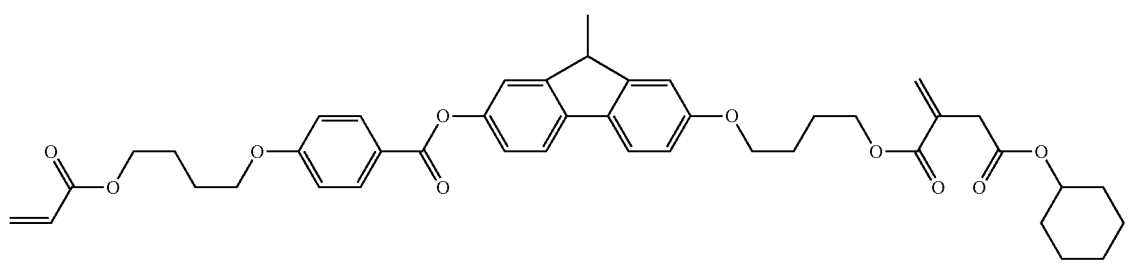 [SMILES: C=CC(=O)OCCCCOc1ccc(C(=O)Oc2ccc3c(c2)C(C)c2cc(OCCCCOC(=O)C(=C)CC(=O)OC4CCCCC4)ccc2-3)cc1]
| 220 |
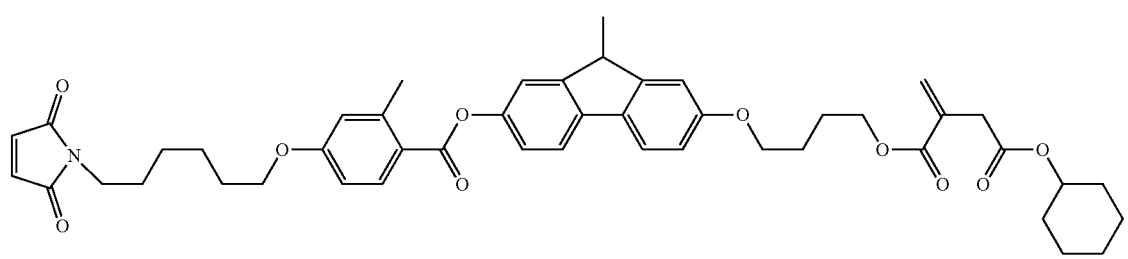 [SMILES: C=C(CC(=O)OC1CCCCC1)C(=O)OCCCCOc1ccc2c(c1)C(C)c1cc(OC(=O)c3ccc(OCCCCCCN4C(=O)C=CC4=O)cc3C)ccc1-2]
| 221 |
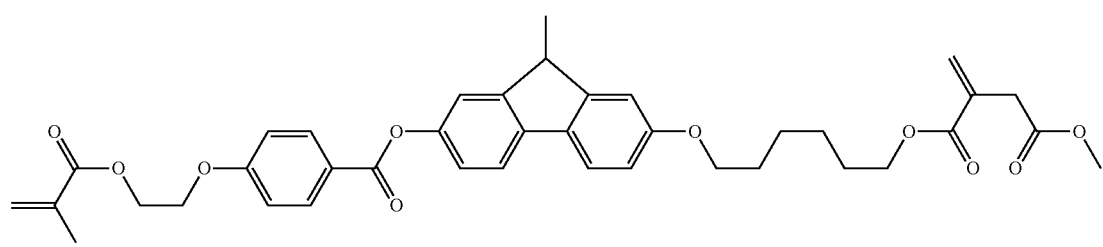 [SMILES: C=C(C)C(=O)OCCOc1ccc(C(=O)Oc2ccc3c(c2)C(C)c2cc(OCCCCCCOC(=O)C(=C)CC(=O)OC)ccc2-3)cc1]
| 222 |
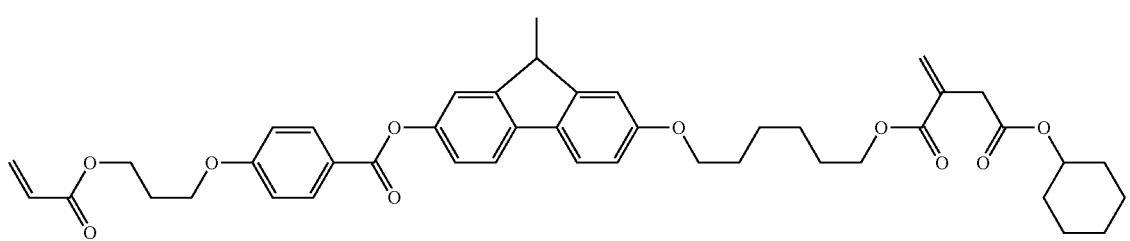 [SMILES: C=CC(=O)OCCCOc1ccc(C(=O)Oc2ccc3c(c2)C(C)c2cc(OCCCCCCOC(=O)C(=C)CC(=O)OC4CCCCC4)ccc2-3)cc1]
| 223 |
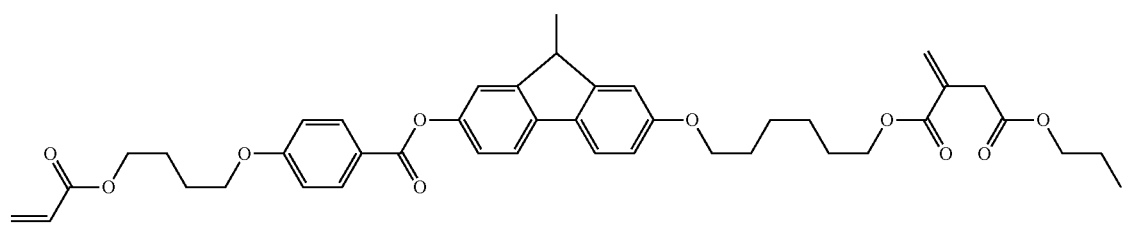 [SMILES: C=CC(=O)OCCCCOc1ccc(C(=O)Oc2ccc3c(c2)C(C)c2cc(OCCCCCCOC(=O)C(=C)CC(=O)OCCC)ccc2-3)cc1]

-continued
| No. |
|---|
| 224 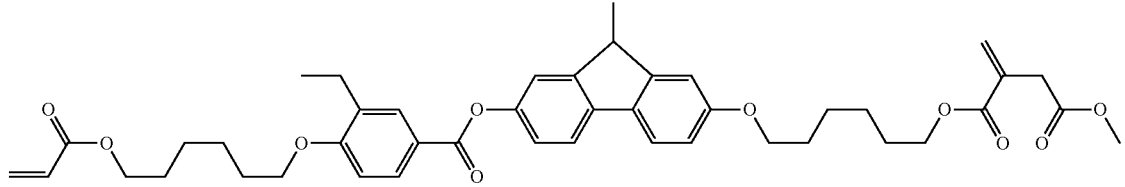 [SMILES: C=CC(=O)OCCCCCCOc1ccc(C(=O)Oc2ccc3c(c2)C(C)c2cc(OCCCCCCOC(=O)C(=C)CC(=O)OC)ccc2-3)cc1CC] |
| 225 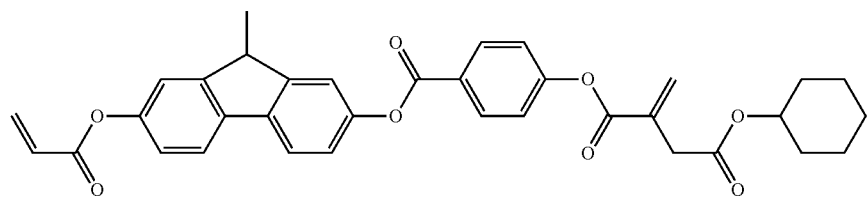 [SMILES: C=CC(=O)Oc1ccc2c(c1)C(C)c1cc(OC(=O)c3ccc(OC(=O)C(=C)CC(=O)OC4CCCCC4)cc3)ccc1-2] |
| 226 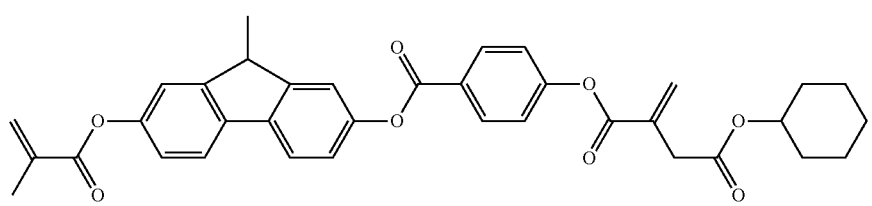 |
| 227 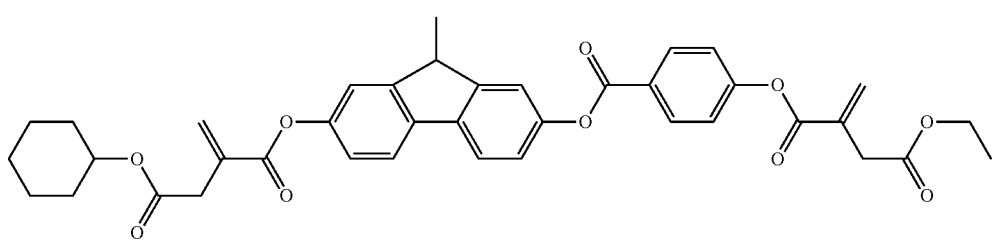 [SMILES: C=C(CC(=O)OCC)C(=O)Oc1ccc(C(=O)Oc2ccc3c(c2)C(C)c2cc(OC(=O)C(=C)CC(=O)OC4CCCCC4)ccc2-3)cc1] |
| 228 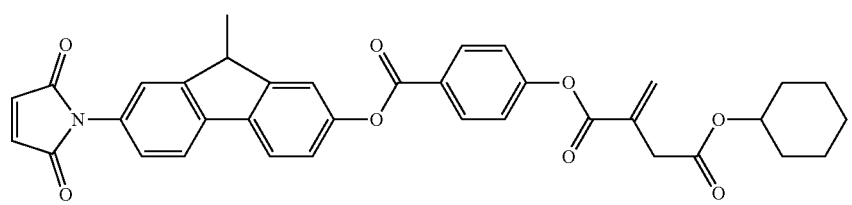 |
| 229 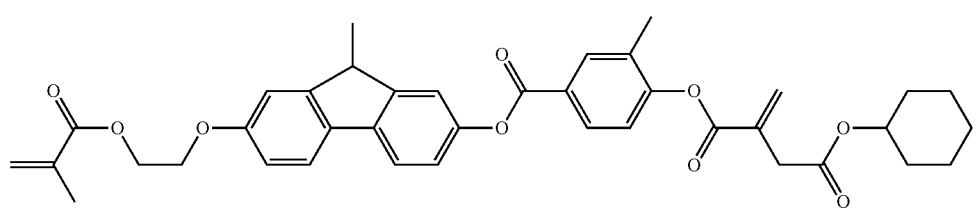 |
| 230 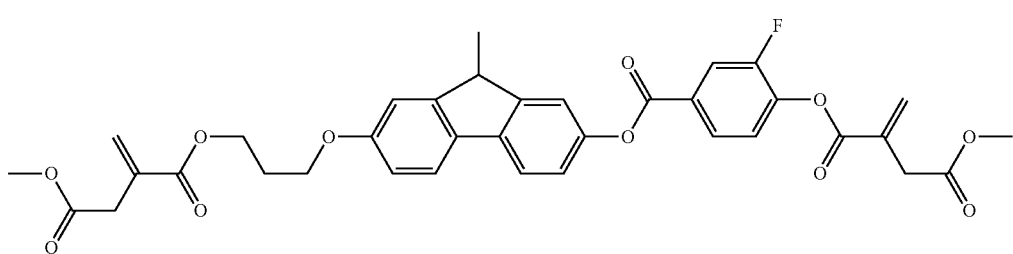 |

| No. |
|---|
| 231 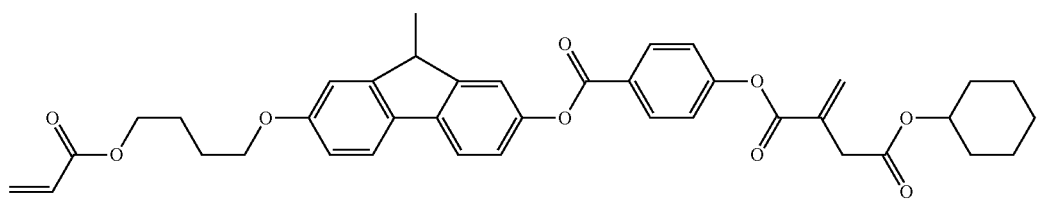 [SMILES: C=CC(=O)OCCCCOc1ccc2c(c1)C(C)c1cc(OC(=O)c3ccc(OC(=O)C(=C)CC(=O)OC4CCCCC4)cc3)ccc1-2] |
| 232 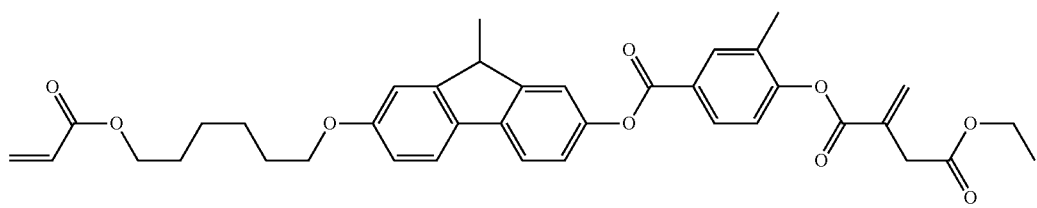 [SMILES: C=CC(=O)OCCCCCCOc1ccc2c(c1)C(C)c1cc(OC(=O)c3ccc(OC(=O)C(=C)CC(=O)OCC)c(C)c3)ccc1-2] |
| 233 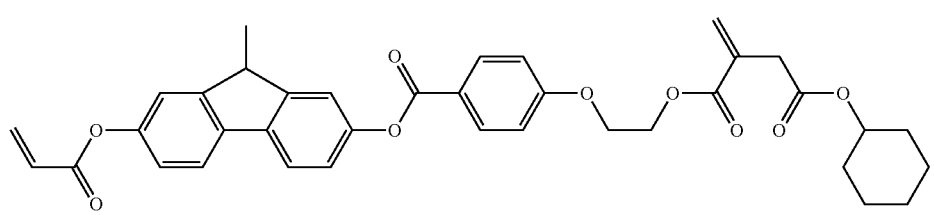 [SMILES: C=CC(=O)Oc1ccc2c(c1)C(C)c1cc(OC(=O)c3ccc(OCCOC(=O)C(=C)CC(=O)OC4CCCCC4)cc3)ccc1-2] |
| 234 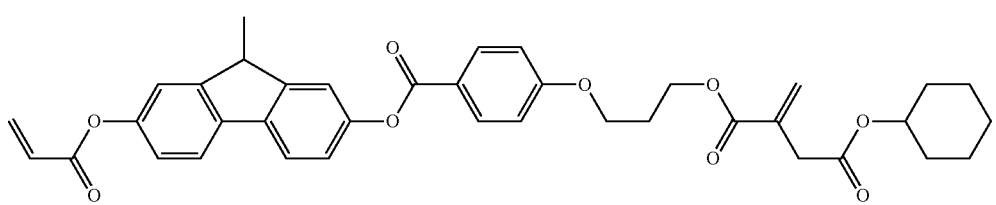 [SMILES: C=CC(=O)Oc1ccc2c(c1)C(C)c1cc(OC(=O)c3ccc(OCCCOC(=O)C(=C)CC(=O)OC4CCCCC4)cc3)ccc1-2] |
| 235 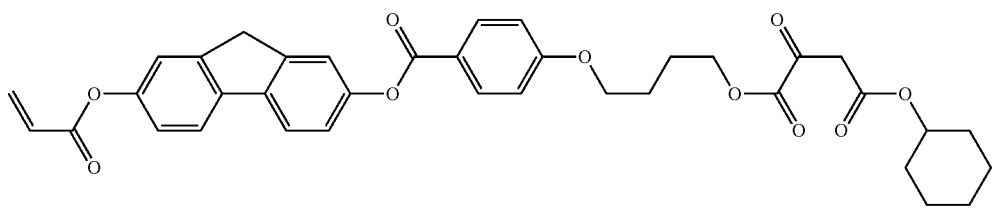 [SMILES: C=CC(=O)Oc1ccc2c(c1)Cc1cc(OC(=O)c3ccc(OCCCCOC(=O)C(=O)CC(=O)OC4CCCCC4)cc3)ccc1-2] |
| 236 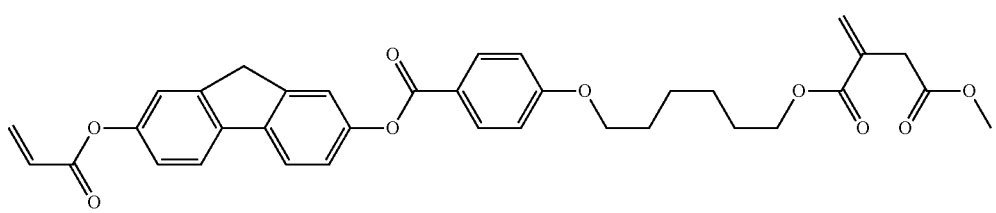 [SMILES: C=CC(=O)Oc1ccc2c(c1)Cc1cc(OC(=O)c3ccc(OCCCCCCOC(=O)C(=C)CC(=O)OC)cc3)ccc1-2] |
| 237 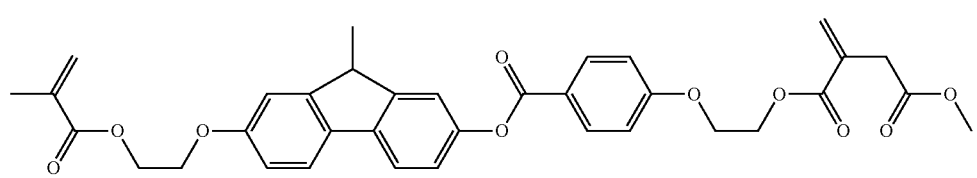 [SMILES: C=C(C)C(=O)OCCOc1ccc2c(c1)C(C)c1cc(OC(=O)c3ccc(OCCOC(=O)C(=C)CC(=O)OC)cc3)ccc1-2] |

| | No. |
|---|---|
| 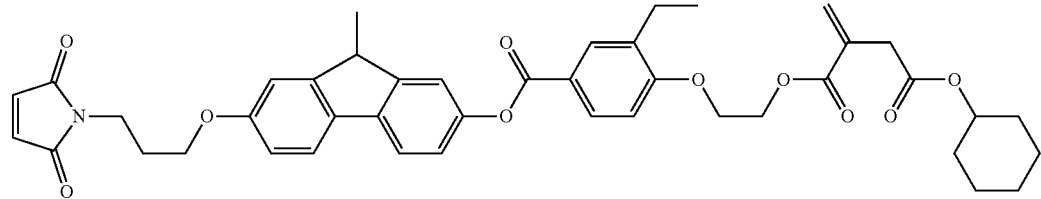 [SMILES: C=C(CC(=O)OC1CCCCC1)C(=O)OCCOc1ccc(C(=O)Oc2ccc3c(c2)C(C)c2cc(OCCCN4C(=O)C=CC4=O)ccc2-3)cc1CC] | 238 |
| 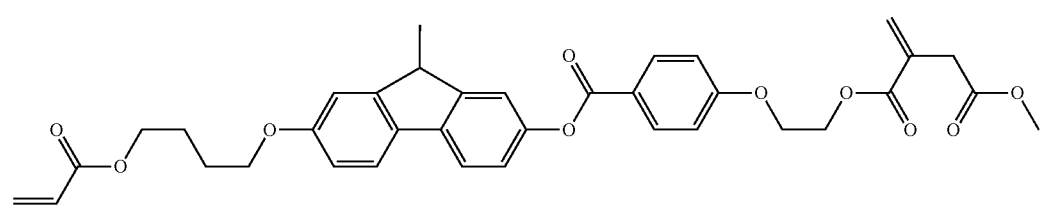 [SMILES: C=CC(=O)OCCCCOc1ccc2c(c1)C(C)c1cc(OC(=O)c3ccc(OCCOC(=O)C(=C)CC(=O)OC)cc3)ccc1-2] | 239 |
| 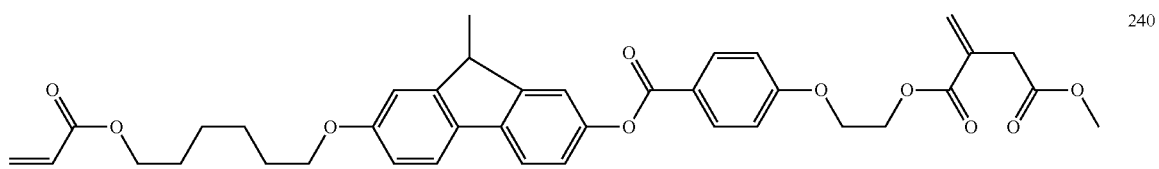 | 240 |
| 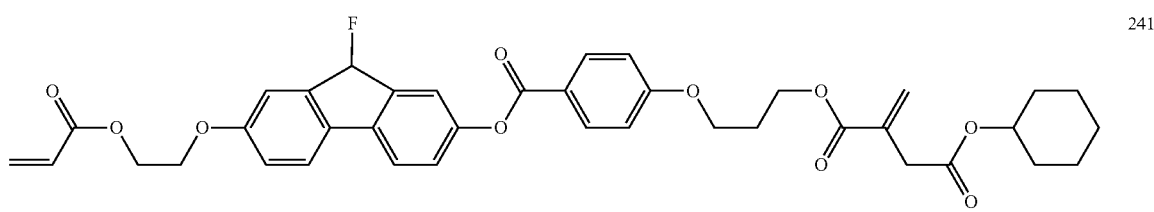 | 241 |
| 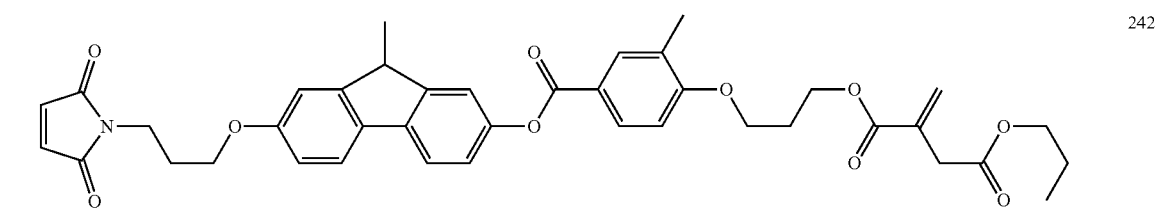 | 242 |
| 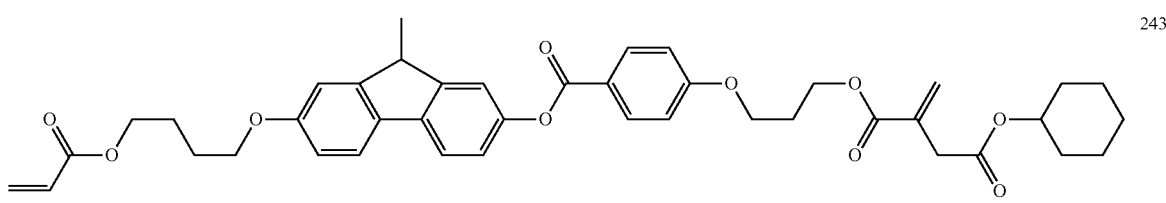 | 243 |
| 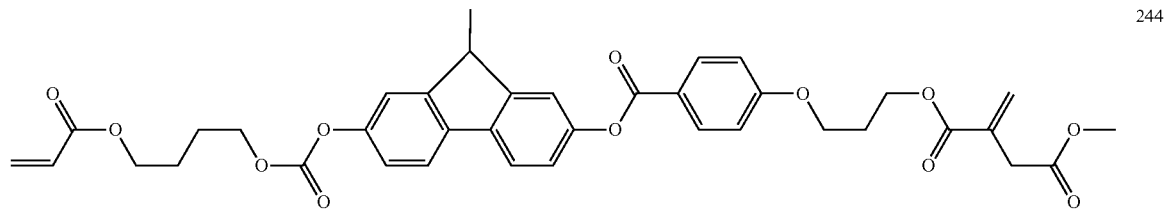 | 244 |

| No. |
|---|
| 245 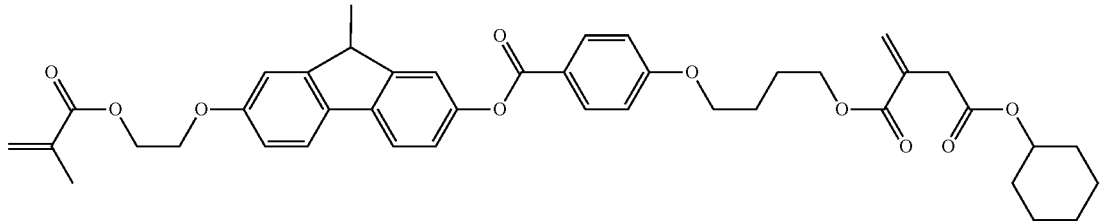 [SMILES: C=C(C)C(=O)OCCOc1ccc2c(c1)C(C)c1cc(OC(=O)c3ccc(OCCCCOC(=O)C(=C)CC(=O)OC4CCCCC4)cc3)ccc1-2] |
| 246 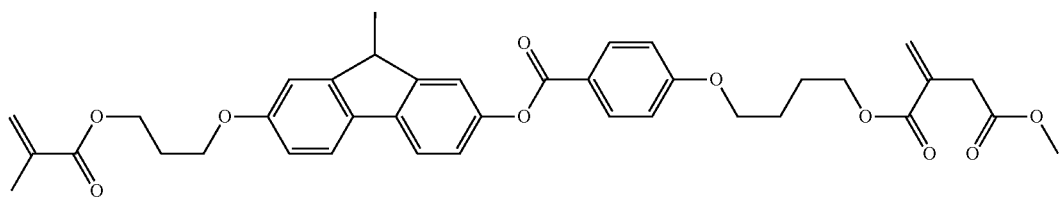 [SMILES: C=C(C)C(=O)OCCCOc1ccc2c(c1)C(C)c1cc(OC(=O)c3ccc(OCCCCOC(=O)C(=C)CC(=O)OC)cc3)ccc1-2] |
| 247 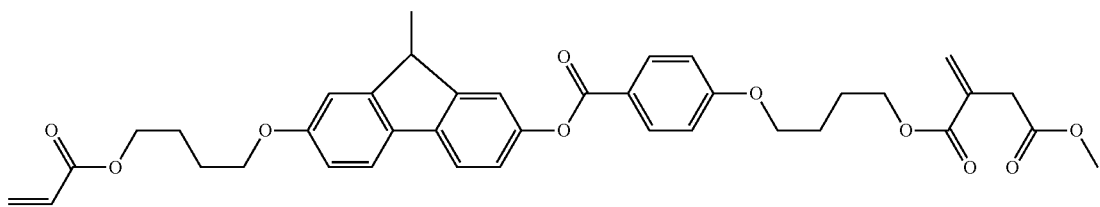 [SMILES: C=CC(=O)OCCCCOc1ccc2c(c1)C(C)c1cc(OC(=O)c3ccc(OCCCCOC(=O)C(=C)CC(=O)OC)cc3)ccc1-2] |
| 248 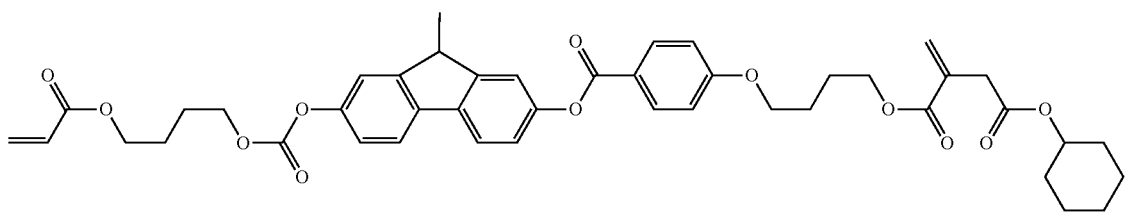 [SMILES: C=CC(=O)OCCCCOC(=O)Oc1ccc2c(c1)C(C)c1cc(OC(=O)c3ccc(OCCCCOC(=O)C(=C)CC(=O)OC4CCCCC4)cc3)ccc1-2] |
| 249 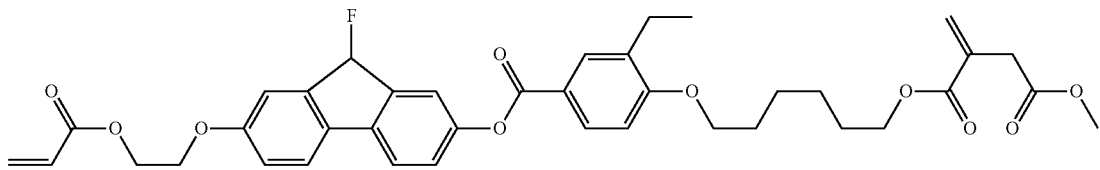 [SMILES: C=CC(=O)OCCOc1ccc2c(c1)C(F)c1cc(OC(=O)c3ccc(OCCCCCCOC(=O)C(=C)CC(=O)OC)c(CC)c3)ccc1-2] |
| 250 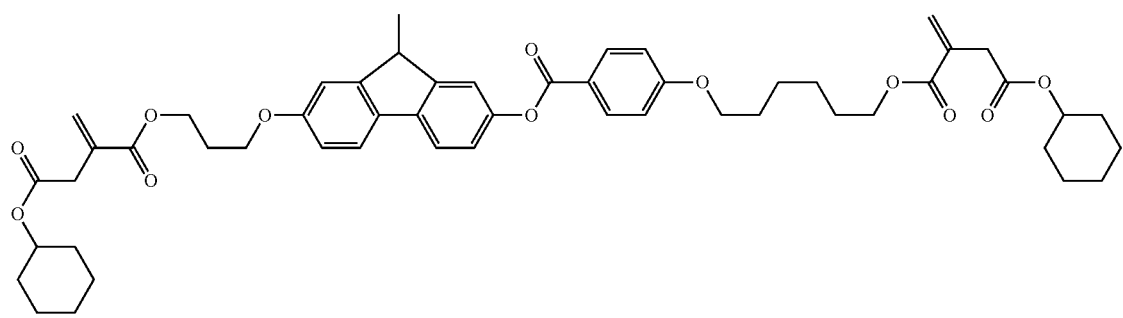 [SMILES: C=C(CC(=O)OC1CCCCC1)C(=O)OCCCCCCOc1ccc(C(=O)Oc2ccc3c(c2)C(C)c2cc(OCCCOC(=O)C(=C)CC(=O)OC4CCCCC4)ccc2-3)cc1] |
| 251 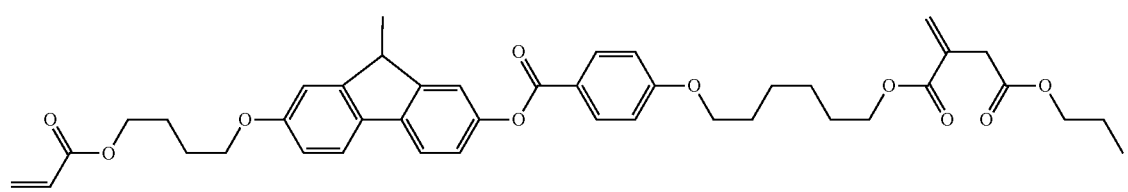 [SMILES: C=CC(=O)OCCCCOc1ccc2c(c1)C(C)c1cc(OC(=O)c3ccc(OCCCCCCOC(=O)C(=C)CC(=O)OCCC)cc3)ccc1-2] |

| No. |
|---|
| 252 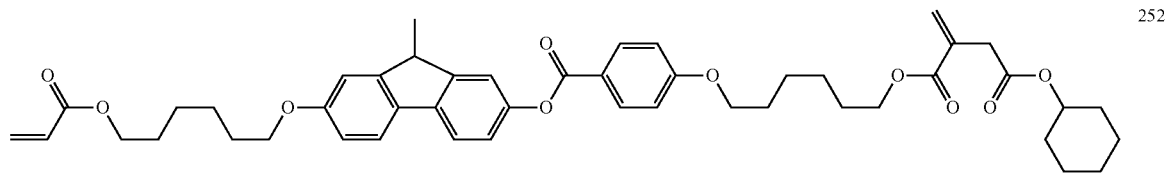 |
| 253 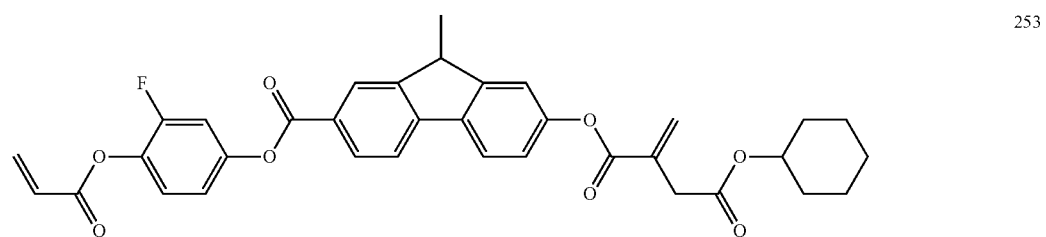 |
| 254 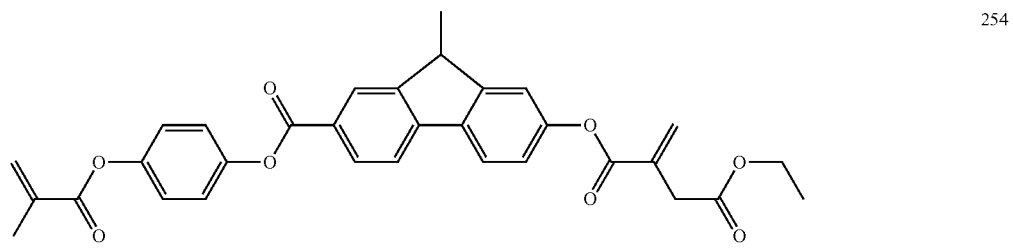 |
| 255 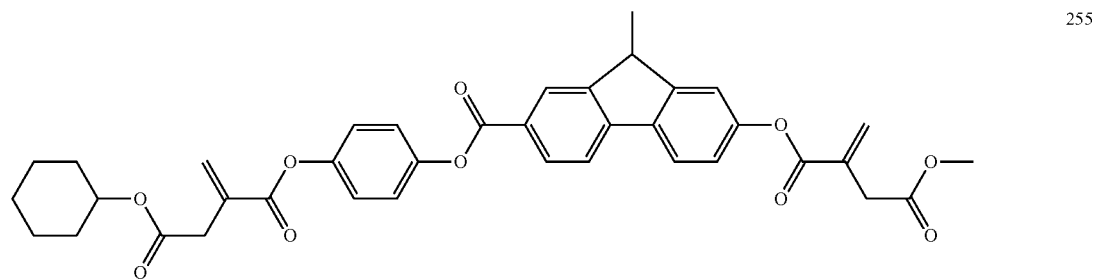 |
| 256 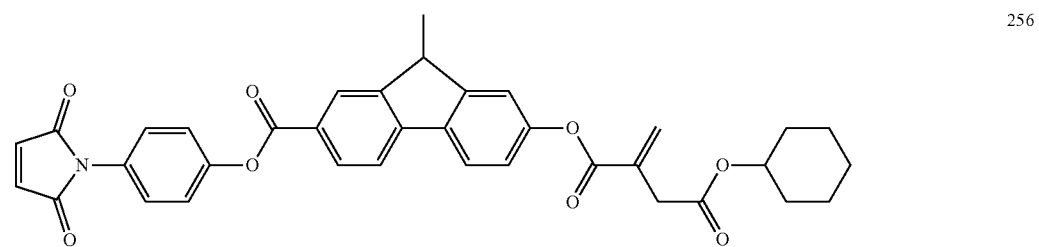 |
| 257 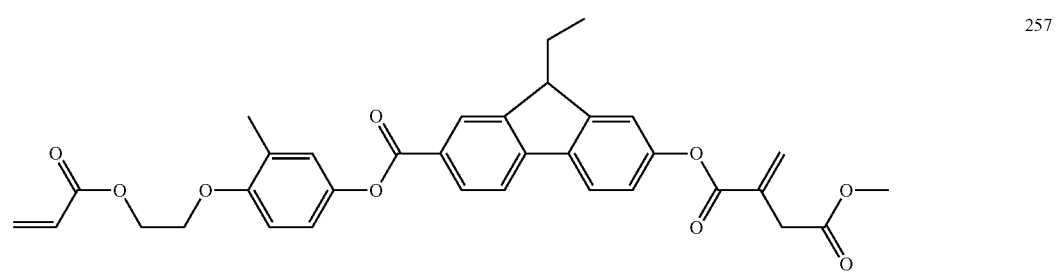 |

| No. |
|---|
| 258 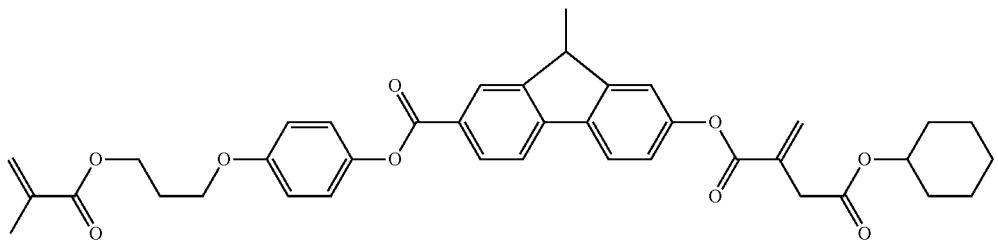 [SMILES: C=C(C)C(=O)OCCCOc1ccc(OC(=O)c2ccc3c(c2)C(C)c2cc(OC(=O)C(=C)CC(=O)OC4CCCCC4)ccc2-3)cc1] |
| 259 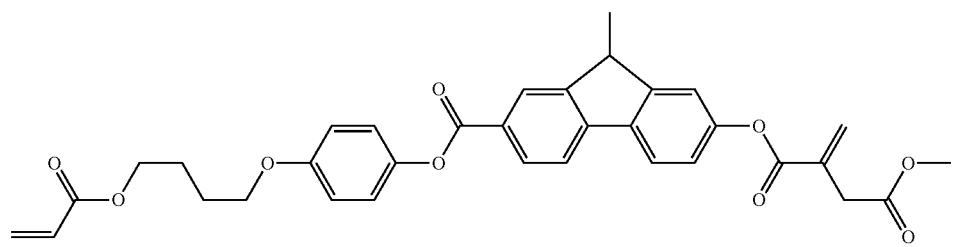 [SMILES: C=CC(=O)OCCCCOc1ccc(OC(=O)c2ccc3c(c2)C(C)c2cc(OC(=O)C(=C)CC(=O)OC)ccc2-3)cc1] |
| 260 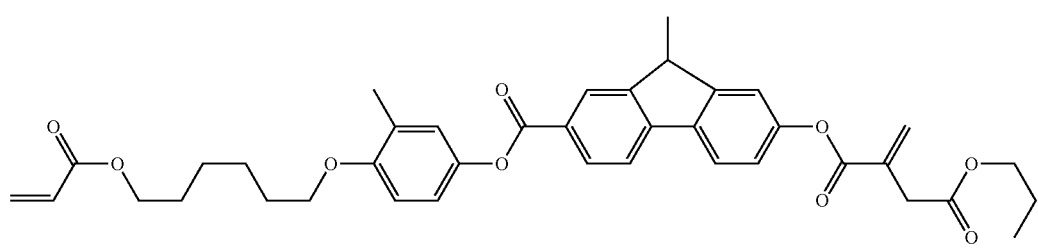 [SMILES: C=CC(=O)OCCCCCCOc1ccc(OC(=O)c2ccc3c(c2)C(C)c2cc(OC(=O)C(=C)CC(=O)OCCC)ccc2-3)cc1C] |
| 261 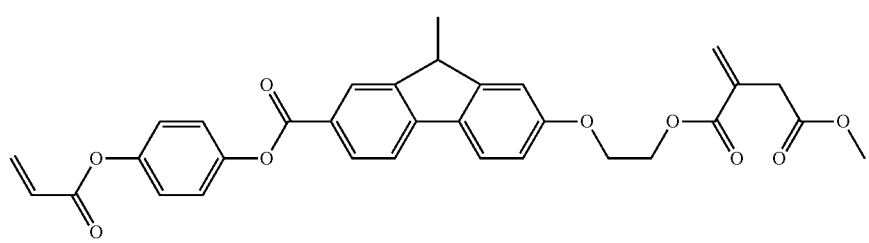 [SMILES: C=CC(=O)Oc1ccc(OC(=O)c2ccc3c(c2)C(C)c2cc(OCCOC(=O)C(=C)CC(=O)OC)ccc2-3)cc1] |
| 262 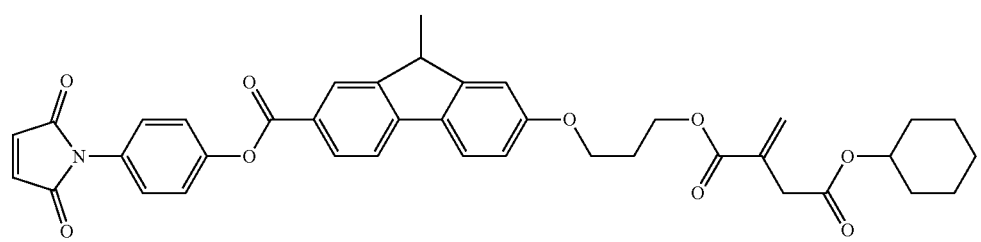 [SMILES: C=C(CC(=O)OC1CCCCC1)C(=O)OCCCOc1ccc2c(c1)C(C)c1cc(C(=O)Oc3ccc(N4C(=O)C=CC4=O)cc3)ccc1-2] |
| 263 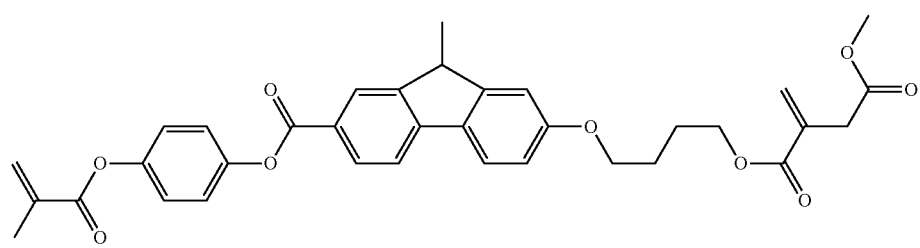 [SMILES: C=C(C)C(=O)Oc1ccc(OC(=O)c2ccc3c(c2)C(C)c2cc(OCCCCOC(=O)C(=C)CC(=O)OC)ccc2-3)cc1] |

| No. |
|---|
| 264 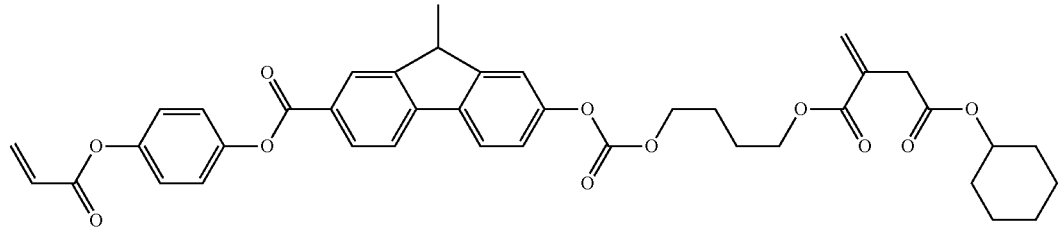 [SMILES: C=CC(=O)Oc1ccc(OC(=O)c2ccc3c(c2)C(C)c2cc(OC(=O)OCCCCOC(=O)C(=C)CC(=O)OC4CCCCC4)ccc2-3)cc1] |
| 265 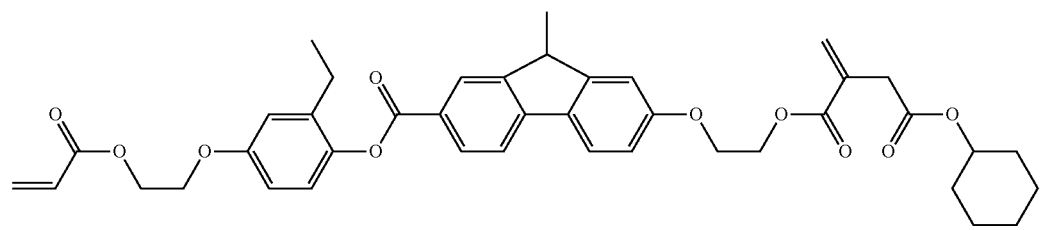 [SMILES: C=CC(=O)OCCOc1ccc(OC(=O)c2ccc3c(c2)C(C)c2cc(OCCOC(=O)C(=C)CC(=O)OC4CCCCC4)ccc2-3)c(CC)c1] |
| 266 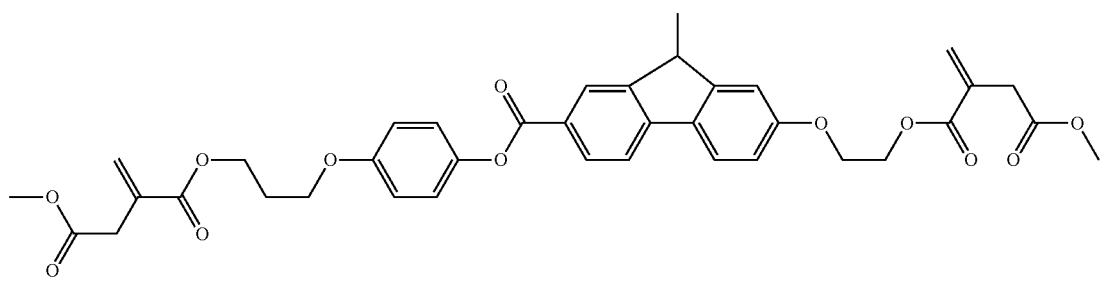 |
| 267 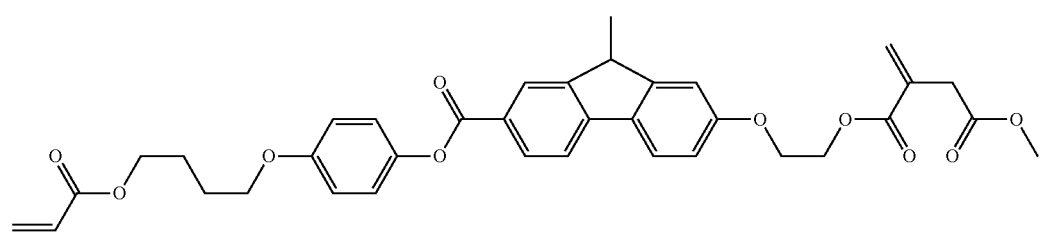 [SMILES: C=CC(=O)OCCCCOc1ccc(OC(=O)c2ccc3c(c2)C(C)c2cc(OCCOC(=O)C(=C)CC(=O)OC)ccc2-3)cc1] |
| 268 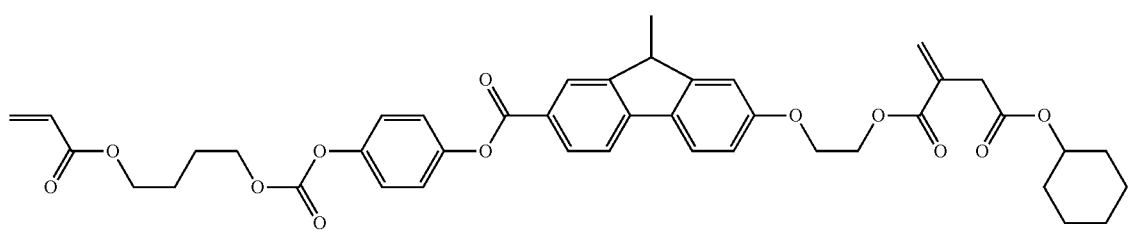 [SMILES: C=CC(=O)OCCCCOC(=O)Oc1ccc(OC(=O)c2ccc3c(c2)C(C)c2cc(OCCOC(=O)C(=C)CC(=O)OC4CCCCC4)ccc2-3)cc1] |
| 269 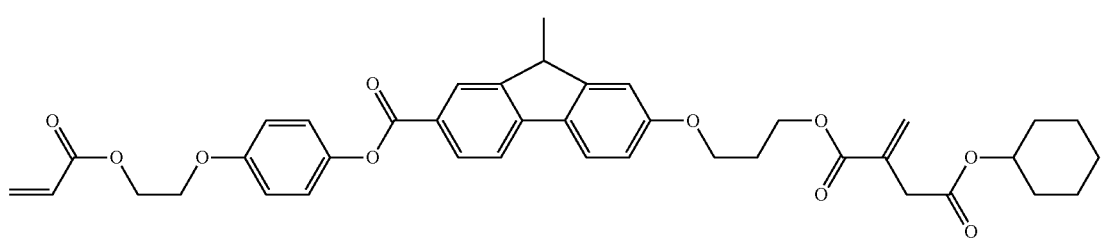 [SMILES: C=CC(=O)OCCOc1ccc(OC(=O)c2ccc3c(c2)C(C)c2cc(OCCCOC(=O)C(=C)CC(=O)OC4CCCCC4)ccc2-3)cc1] |

-continued
| No. |
|---|
| 270 |
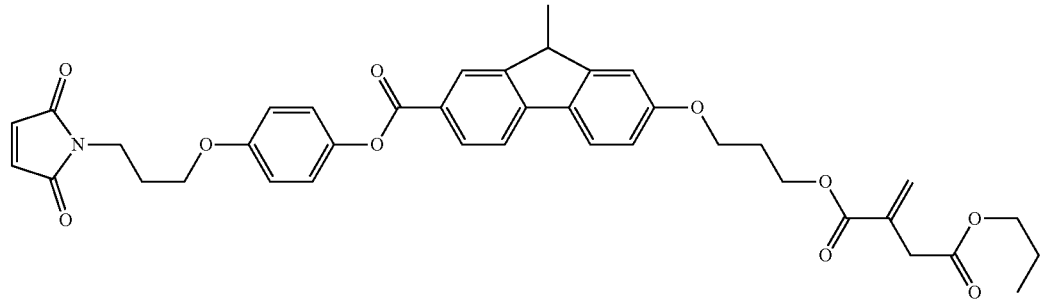 [SMILES: C=C(CC(=O)OCCC)C(=O)OCCCOc1ccc2c(c1)C(C)c1cc(C(=O)Oc3ccc(OCCCN4C(=O)C=CC4=O)cc3)ccc1-2]
271
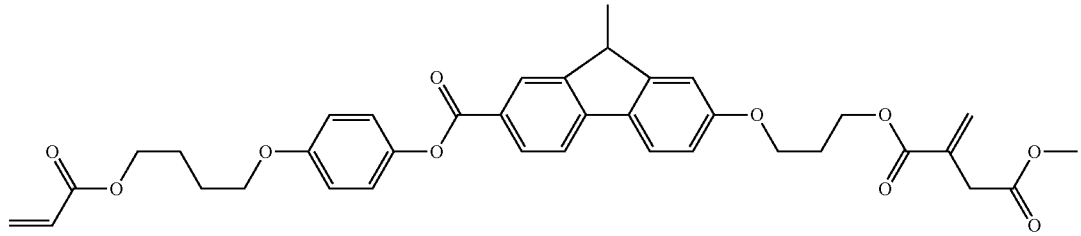 [SMILES: C=CC(=O)OCCCCOc1ccc(OC(=O)c2ccc3c(c2)C(C)c2cc(OCCCOC(=O)C(=C)CC(=O)OC)ccc2-3)cc1]
272
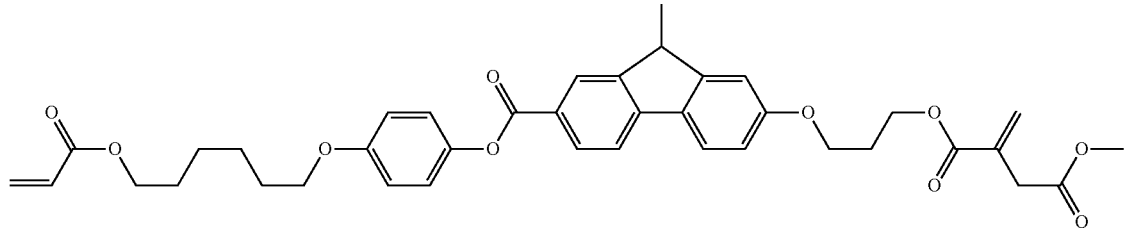 [SMILES: C=CC(=O)OCCCCCCOc1ccc(OC(=O)c2ccc3c(c2)C(C)c2cc(OCCCOC(=O)C(=C)CC(=O)OC)ccc2-3)cc1]
273
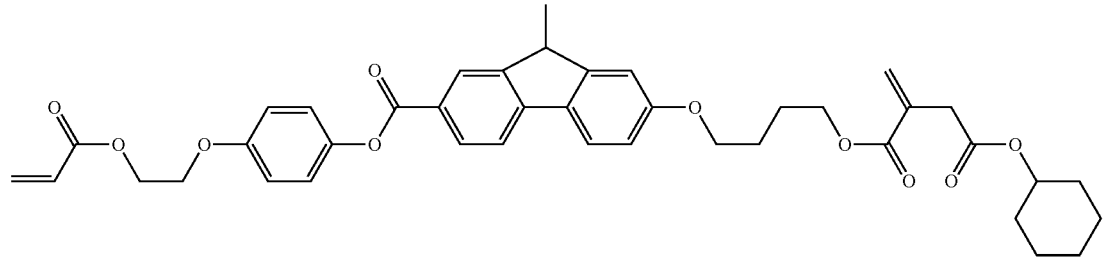 [SMILES: C=CC(=O)OCCOc1ccc(OC(=O)c2ccc3c(c2)C(C)c2cc(OCCCCOC(=O)C(=C)CC(=O)OC4CCCCC4)ccc2-3)cc1]
274
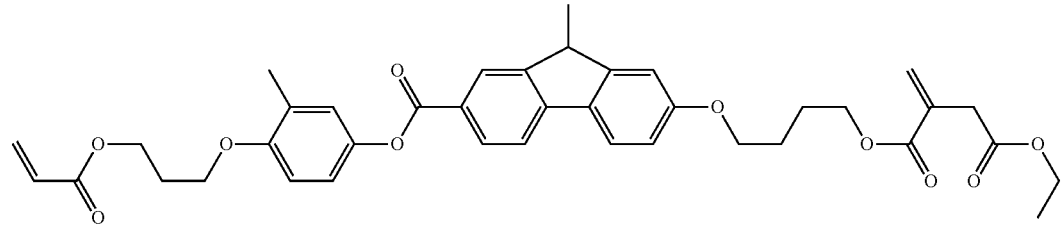 [SMILES: C=CC(=O)OCCCOc1ccc(OC(=O)c2ccc3c(c2)C(C)c2cc(OCCCCOC(=O)C(=C)CC(=O)OCC)ccc2-3)cc1C]
275
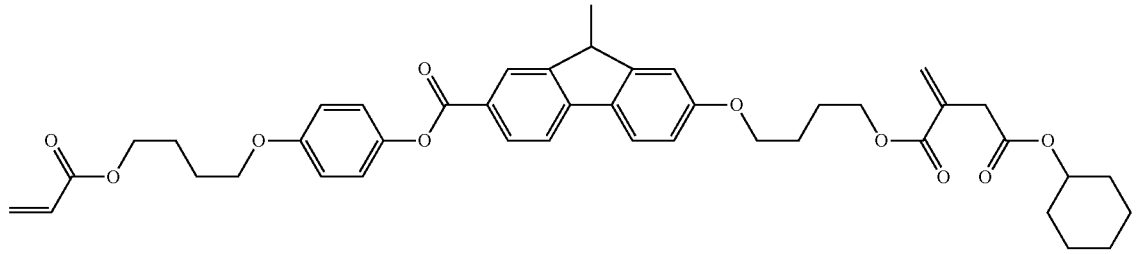 [SMILES: C=CC(=O)OCCCCOc1ccc(OC(=O)c2ccc3c(c2)C(C)c2cc(OCCCCOC(=O)C(=C)CC(=O)OC4CCCCC4)ccc2-3)cc1]

-continued
| | No. |
|---|---|
| 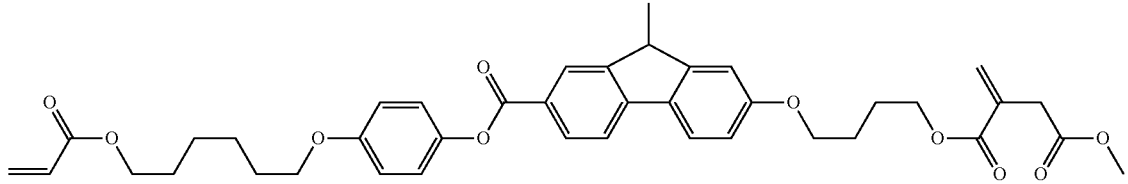 [SMILES: C=CC(=O)OCCCCCCOc1ccc(OC(=O)c2ccc3c(c2)C(C)c2cc(OCCCCOC(=O)C(=C)CC(=O)OC)ccc2-3)cc1] | 276 |
| 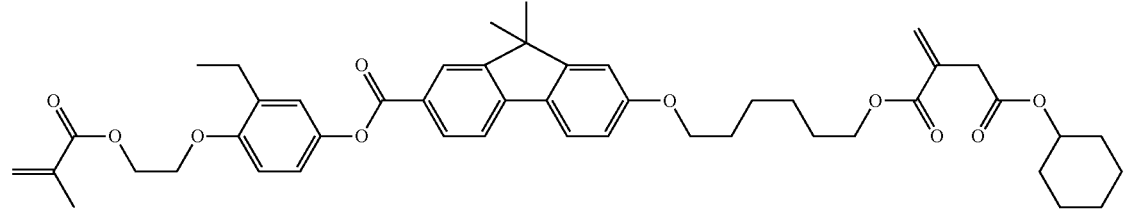 [SMILES: C=C(C)C(=O)OCCOc1ccc(OC(=O)c2ccc3c(c2)C(C)(C)c2cc(OCCCCCCOC(=O)C(=C)CC(=O)OC4CCCCC4)ccc2-3)cc1CC] | 277 |
| 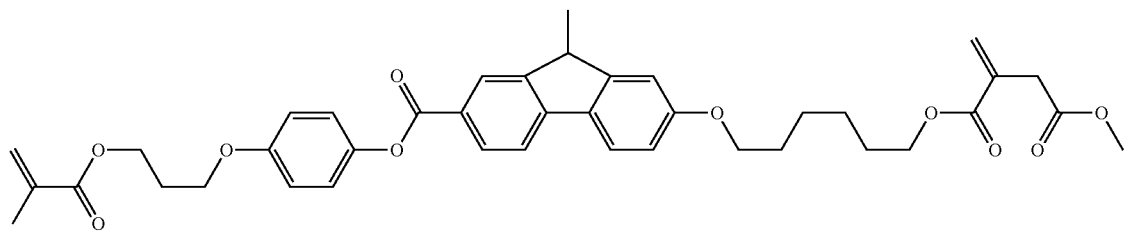 [SMILES: C=C(C)C(=O)OCCCOc1ccc(OC(=O)c2ccc3c(c2)C(C)c2cc(OCCCCCCOC(=O)C(=C)CC(=O)OC)ccc2-3)cc1] | 278 |
| 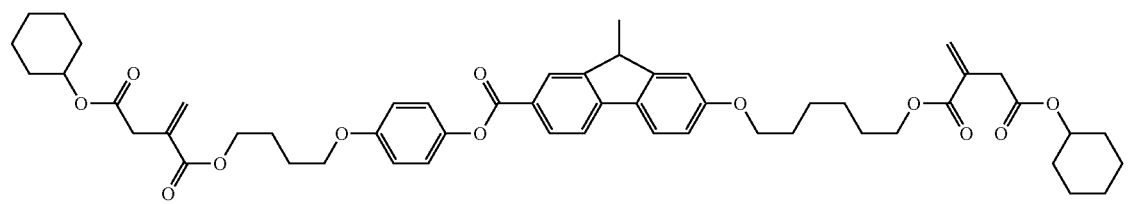 [SMILES: C=C(CC(=O)OC1CCCCC1)C(=O)OCCCCCCOc1ccc2c(c1)C(C)c1cc(C(=O)Oc3ccc(OCCCCOC(=O)C(=C)CC(=O)OC4CCCCC4)cc3)ccc1-2] | 279 |
| 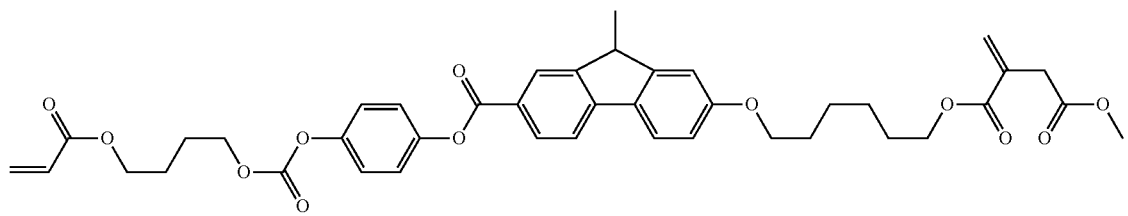 [SMILES: C=CC(=O)OCCCCOC(=O)Oc1ccc(OC(=O)c2ccc3c(c2)C(C)c2cc(OCCCCCCOC(=O)C(=C)CC(=O)OC)ccc2-3)cc1] | 280 |
| 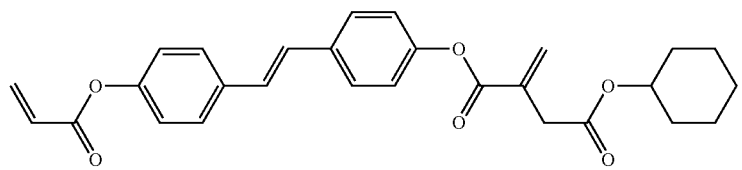 [SMILES: C=CC(=O)Oc1ccc(/C=C/c2ccc(OC(=O)C(=C)CC(=O)OC3CCCCC3)cc2)cc1] | 281 |
| 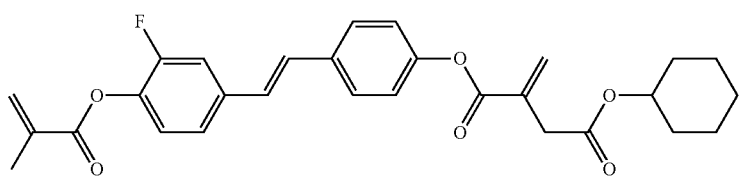 [SMILES: C=C(C)C(=O)Oc1ccc(/C=C/c2ccc(OC(=O)C(=C)CC(=O)OC3CCCCC3)cc2)cc1F] | 282 |

| No. |
|---|
| 283 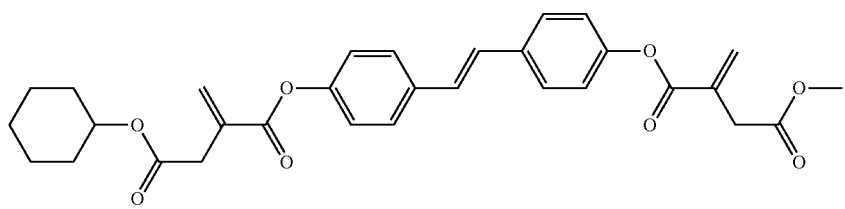 [SMILES: C=C(CC(=O)OC)C(=O)Oc1ccc(/C=C/c2ccc(OC(=O)C(=C)CC(=O)OC3CCCCC3)cc2)cc1] |
| 284 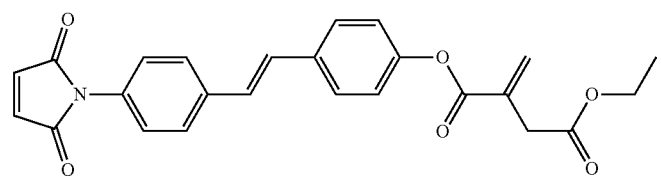 [SMILES: C=C(CC(=O)OCC)C(=O)Oc1ccc(/C=C/c2ccc(N3C(=O)C=CC3=O)cc2)cc1] |
| 285 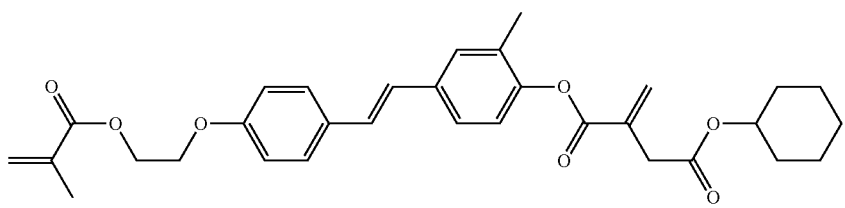 [SMILES: C=C(C)C(=O)OCCOc1ccc(/C=C/c2ccc(OC(=O)C(=C)CC(=O)OC3CCCCC3)c(C)c2)cc1] |
| 286 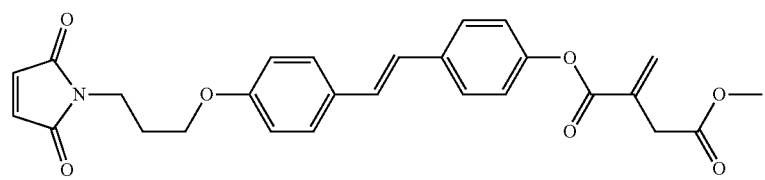 [SMILES: C=C(CC(=O)OC)C(=O)Oc1ccc(/C=C/c2ccc(OCCCN3C(=O)C=CC3=O)cc2)cc1] |
| 287 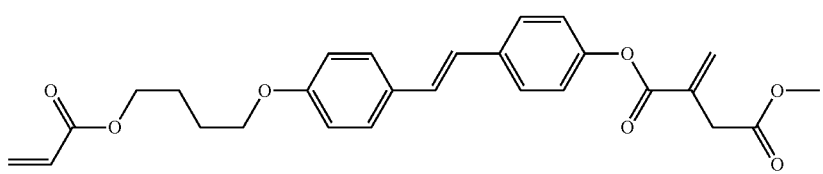 |
| 288 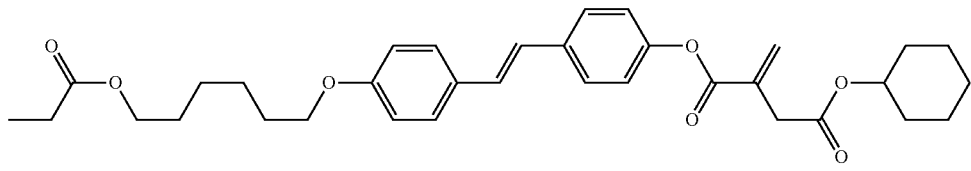 [SMILES: C=C(CC(=O)OC1CCCCC1)C(=O)Oc1ccc(/C=C/c2ccc(OCCCCCCOC(=O)CC)cc2)cc1] |
| 289 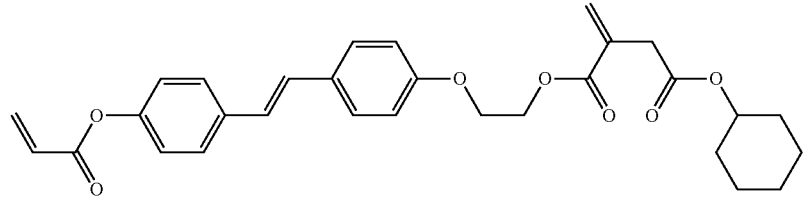 [SMILES: C=CC(=O)Oc1ccc(/C=C/c2ccc(OCCOC(=O)C(=C)CC(=O)OC3CCCCC3)cc2)cc1] |
| 290 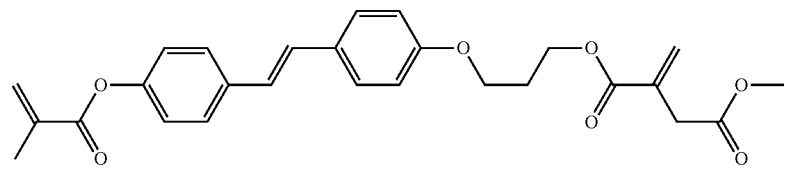 [SMILES: C=C(C)C(=O)Oc1ccc(/C=C/c2ccc(OCCCOC(=O)C(=C)CC(=O)OC)cc2)cc1] |

-continued
| No. |
|---|
| 291 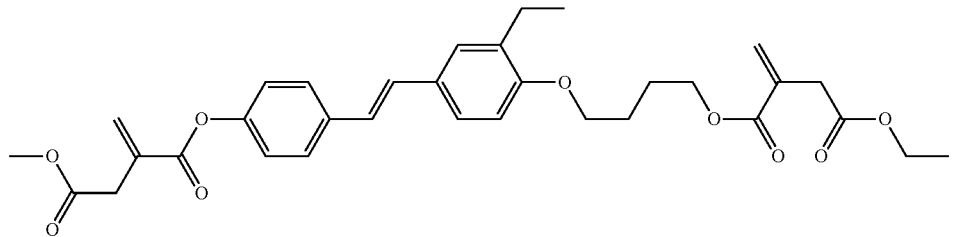 [SMILES: C=C(CC(=O)OCC)C(=O)OCCCCOc1ccc(/C=C/c2ccc(OC(=O)C(=C)CC(=O)OC)cc2)cc1CC] |
| 292 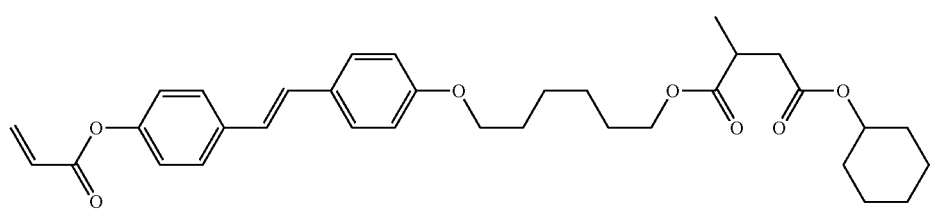 |
| 293 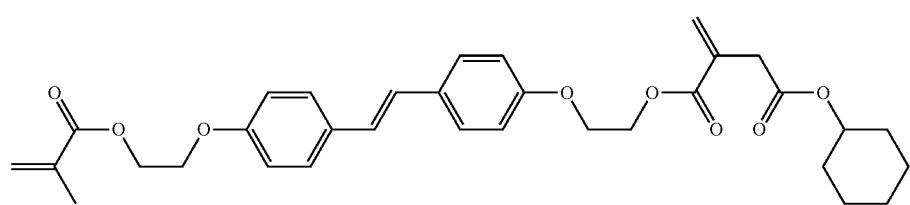 [SMILES: C=C(C)C(=O)OCCOc1ccc(/C=C/c2ccc(OCCOC(=O)C(=C)CC(=O)OC3CCCCC3)cc2)cc1] |
| 294 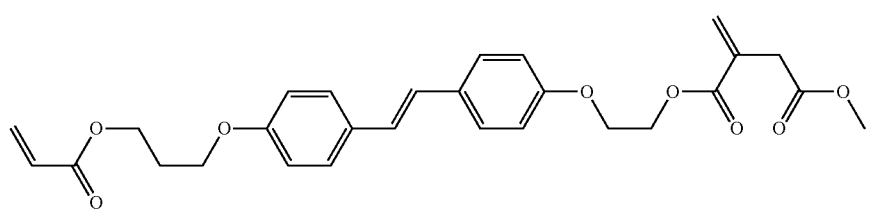 [SMILES: C=CC(=O)OCCCOc1ccc(/C=C/c2ccc(OCCOC(=O)C(=C)CC(=O)OC)cc2)cc1] |
| 295 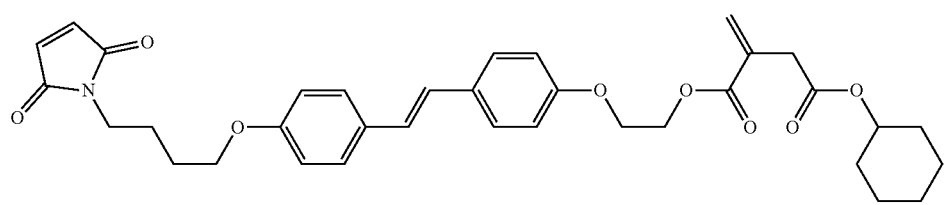 [SMILES: C=C(CC(=O)OC1CCCCC1)C(=O)OCCOc1ccc(/C=C/c2ccc(OCCCCN3C(=O)C=CC3=O)cc2)cc1] |
| 296 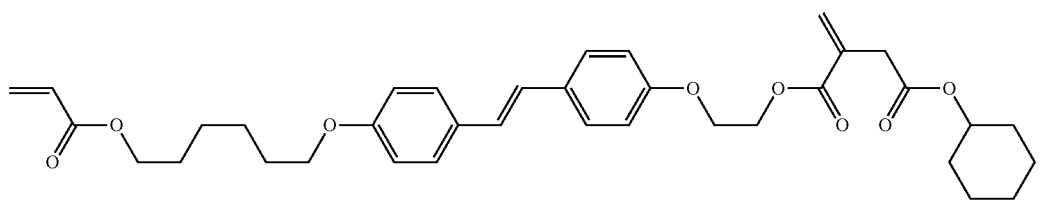 [SMILES: C=CC(=O)OCCCCCCOc1ccc(/C=C/c2ccc(OCCOC(=O)C(=C)CC(=O)OC3CCCCC3)cc2)cc1] |
| 297 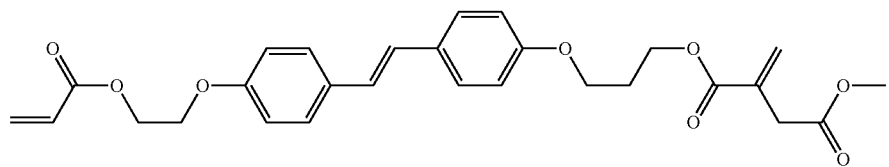 [SMILES: C=CC(=O)OCCOc1ccc(/C=C/c2ccc(OCCCOC(=O)C(=C)CC(=O)OC)cc2)cc1] |

-continued
| No. |
|---|
| 298 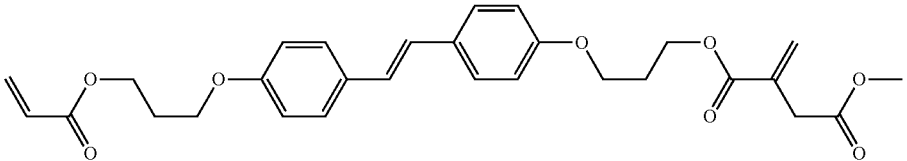 |
| 299 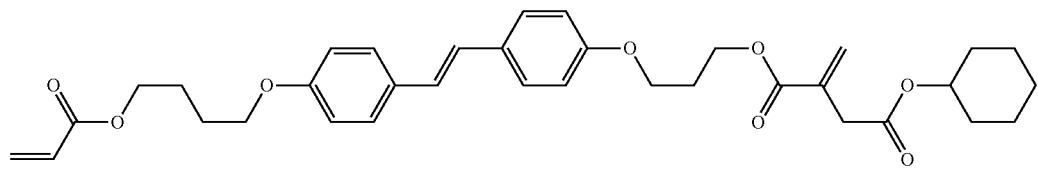 |
| 300 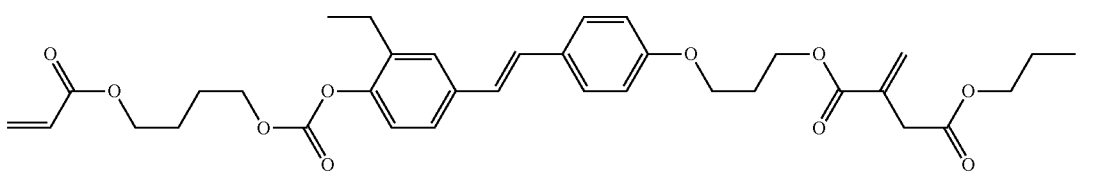 [SMILES: C=CC(=O)OCCCCOC(=O)Oc1ccc(/C=C/c2ccc(OCCCOC(=O)C(=C)CC(=O)OCCC)cc2)cc1CC] |
| 301 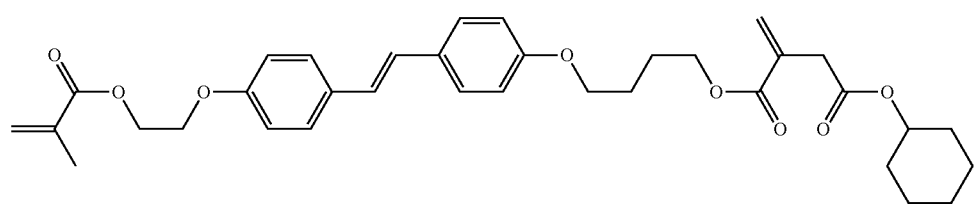 [SMILES: C=C(C)C(=O)OCCOc1ccc(/C=C/c2ccc(OCCCCOC(=O)C(=C)CC(=O)OC3CCCCC3)cc2)cc1] |
| 302 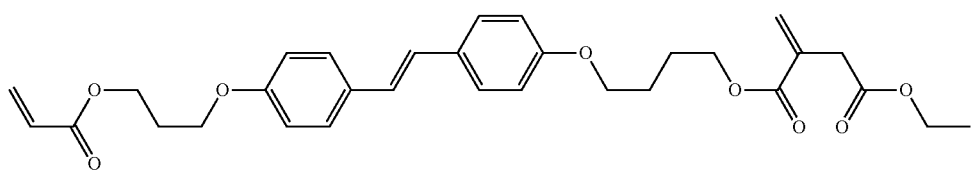 [SMILES: C=CC(=O)OCCCOc1ccc(/C=C/c2ccc(OCCCCOC(=O)C(=C)CC(=O)OCC)cc2)cc1] |
| 303 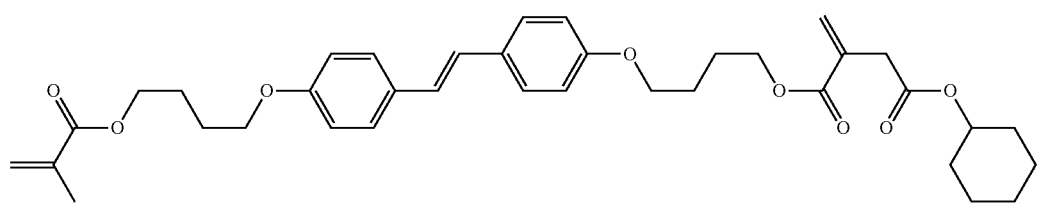 [SMILES: C=C(C)C(=O)OCCCCOc1ccc(/C=C/c2ccc(OCCCCOC(=O)C(=C)CC(=O)OC3CCCCC3)cc2)cc1] |
| 304 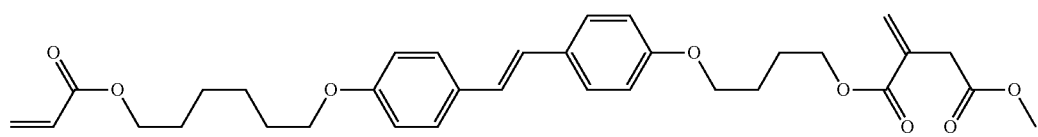 [SMILES: C=CC(=O)OCCCCCCOc1ccc(/C=C/c2ccc(OCCCCOC(=O)C(=C)CC(=O)OC)cc2)cc1] |
| 305 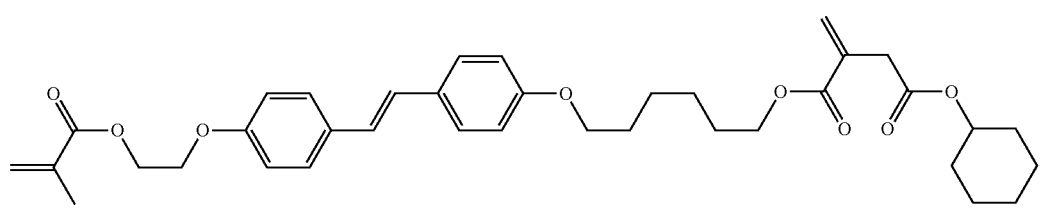 [SMILES: C=C(C)C(=O)OCCOc1ccc(/C=C/c2ccc(OCCCCCCOC(=O)C(=C)CC(=O)OC3CCCCC3)cc2)cc1] |

-continued
| | No. |
|---|---|
| 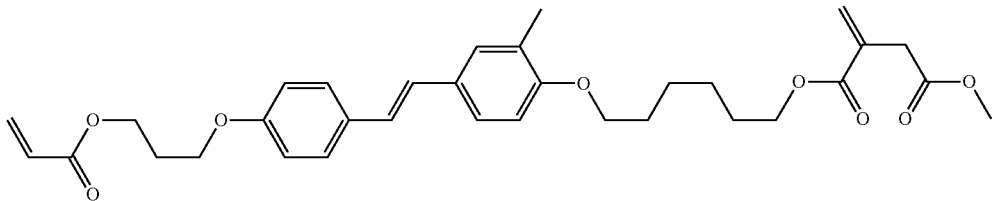 [SMILES: C=CC(=O)OCCCOc1ccc(/C=C/c2ccc(OCCCCCCOC(=O)C(=C)CC(=O)OC)c(C)c2)cc1] | 306 |
| 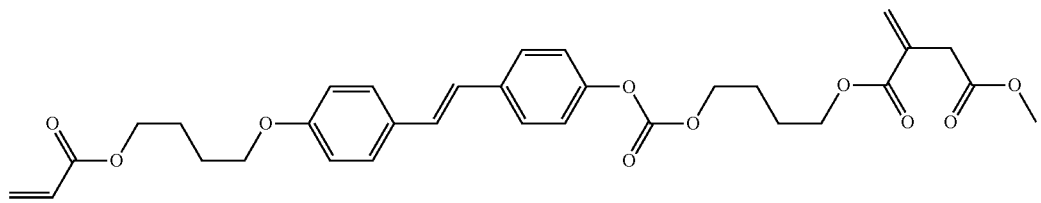 [SMILES: C=CC(=O)OCCCCOc1ccc(/C=C/c2ccc(OC(=O)OCCCCOC(=O)C(=C)CC(=O)OC)cc2)cc1] | 307 |
| 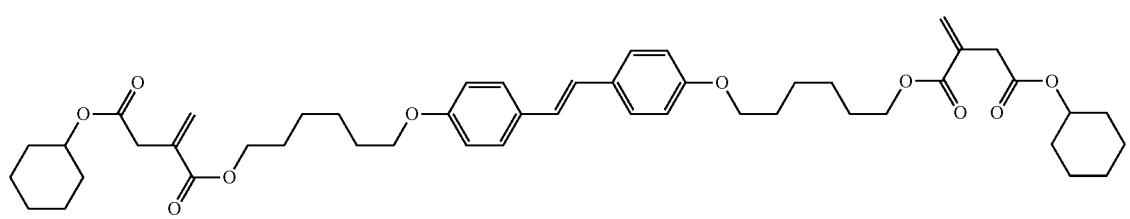 [SMILES: C=C(CC(=O)OC1CCCCC1)C(=O)OCCCCCCOc1ccc(/C=C/c2ccc(OCCCCCCOC(=O)C(=C)CC(=O)OC3CCCCC3)cc2)cc1] | 308 |
| 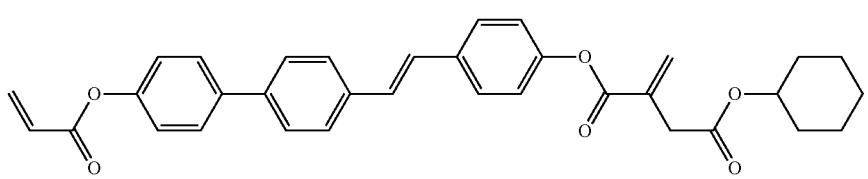 [SMILES: C=CC(=O)Oc1ccc(-c2ccc(/C=C/c3ccc(OC(=O)C(=C)CC(=O)OC4CCCCC4)cc3)cc2)cc1] | 309 |
| 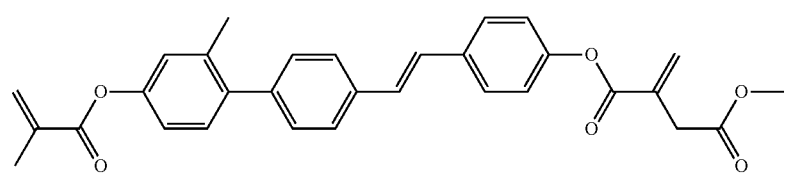 | 310 |
| 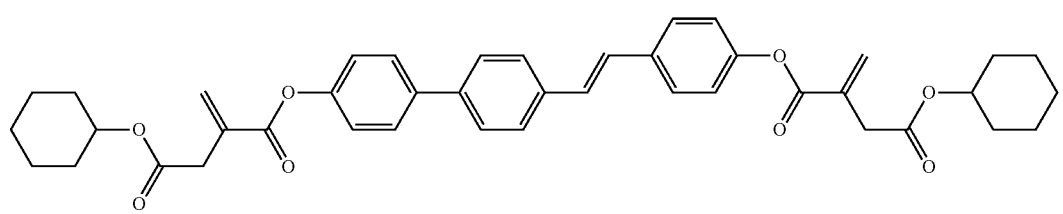 [SMILES: C=C(CC(=O)OC1CCCCC1)C(=O)Oc1ccc(/C=C/c2ccc(-c3ccc(OC(=O)C(=C)CC(=O)OC4CCCCC4)cc3)cc2)cc1] | 311 |
| 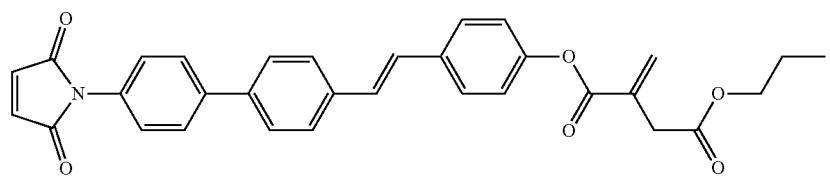 [SMILES: C=C(CC(=O)OCCC)C(=O)Oc1ccc(/C=C/c2ccc(-c3ccc(N4C(=O)C=CC4=O)cc3)cc2)cc1] | 312 |
| 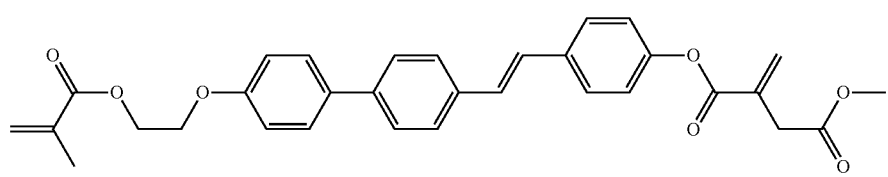 [SMILES: C=C(C)C(=O)OCCOc1ccc(-c2ccc(/C=C/c3ccc(OC(=O)C(=C)CC(=O)OC)cc3)cc2)cc1] | 313 |

-continued
| No. |
|---|
| 314 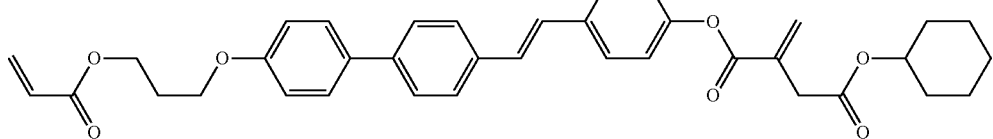 |
| 315 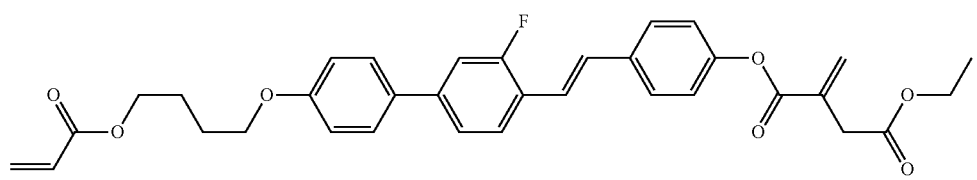 [SMILES: C=CC(=O)OCCCCOc1ccc(-c2ccc(/C=C/c3ccc(OC(=O)C(=C)CC(=O)OCC)cc3)c(F)c2)cc1] |
| 316 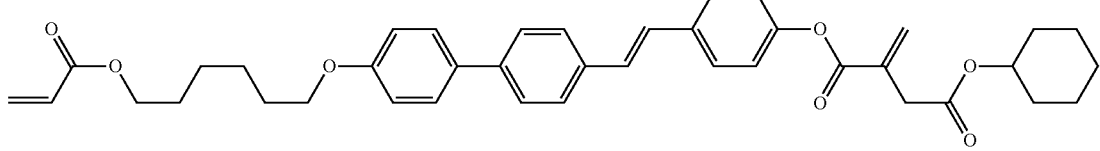 |
| 317 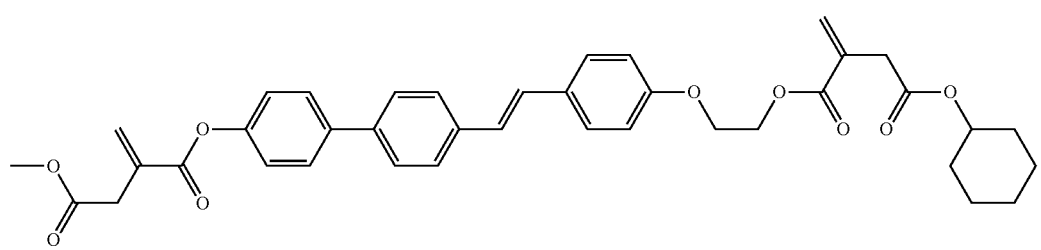 [SMILES: C=C(CC(=O)OC1CCCCC1)C(=O)OCCOc1ccc(/C=C/c2ccc(-c3ccc(OC(=O)C(=C)CC(=O)OC)cc3)cc2)cc1] |
| 318 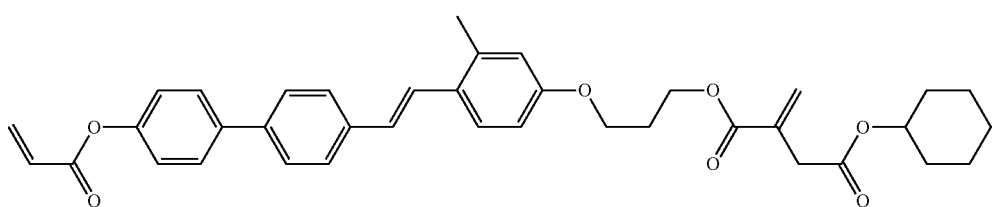 [SMILES: C=CC(=O)Oc1ccc(-c2ccc(/C=C/c3ccc(OCCCOC(=O)C(=C)CC(=O)OC4CCCCC4)cc3C)cc2)cc1] |
| 319 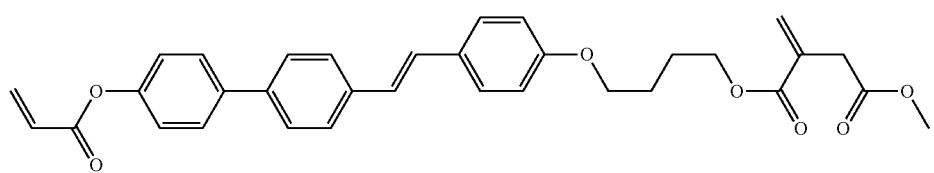 [SMILES: C=CC(=O)Oc1ccc(-c2ccc(/C=C/c3ccc(OCCCCOC(=O)C(=C)CC(=O)OC)cc3)cc2)cc1] |
| 320 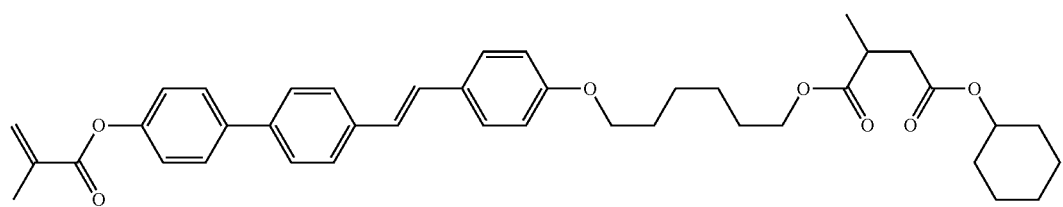 [SMILES: C=C(C)C(=O)Oc1ccc(-c2ccc(/C=C/c3ccc(OCCCCCCOC(=O)C(C)CC(=O)OC4CCCCC4)cc3)cc2)cc1] |
| 321 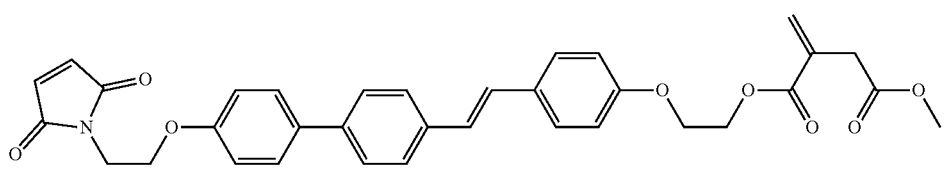 [SMILES: C=C(CC(=O)OC)C(=O)OCCOc1ccc(/C=C/c2ccc(-c3ccc(OCCN4C(=O)C=CC4=O)cc3)cc2)cc1] |

| No. |
|---|
| 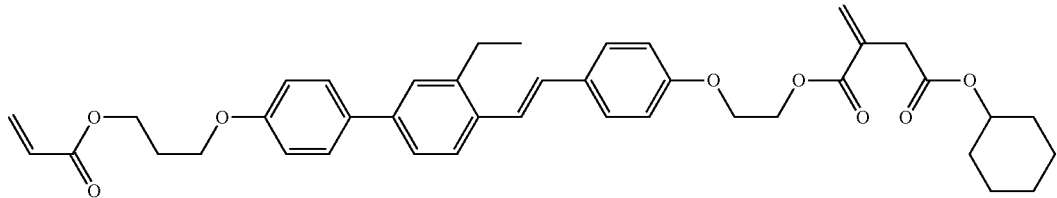 [SMILES: C=CC(=O)OCCCOc1ccc(-c2ccc(/C=C/c3ccc(OCCOC(=O)C(=C)CC(=O)OC4CCCCC4)cc3)c(CC)c2)cc1] 322 |
| 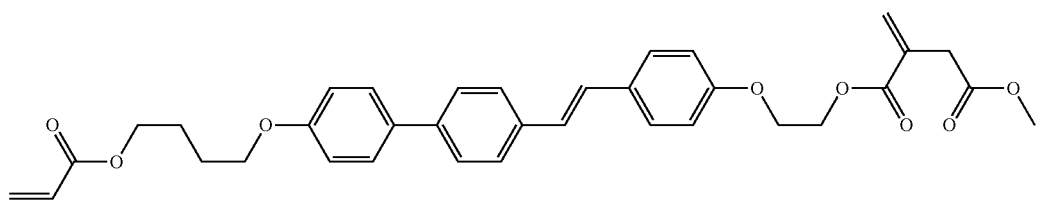 [SMILES: C=CC(=O)OCCCCOc1ccc(-c2ccc(/C=C/c3ccc(OCCOC(=O)C(=C)CC(=O)OC)cc3)cc2)cc1] 323 |
| 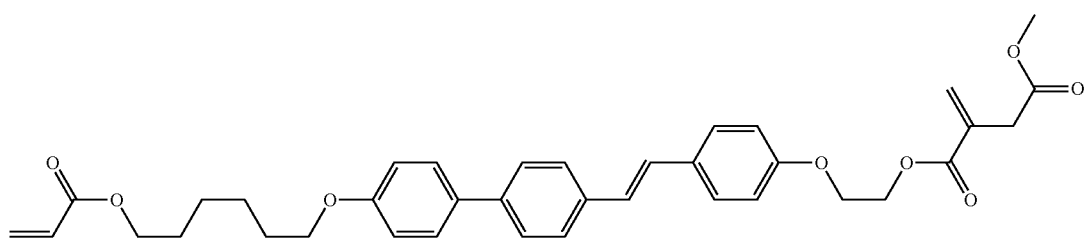 [SMILES: C=CC(=O)OCCCCCCOc1ccc(-c2ccc(/C=C/c3ccc(OCCOC(=O)C(=C)CC(=O)OC)cc3)cc2)cc1] 324 |
| 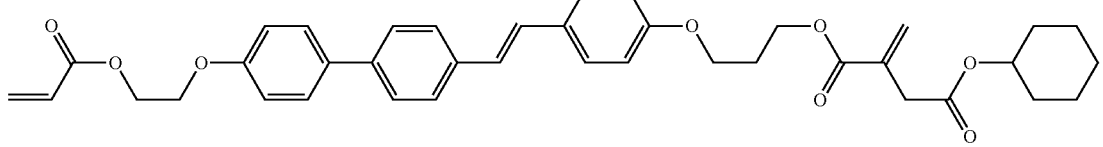 325 |
| 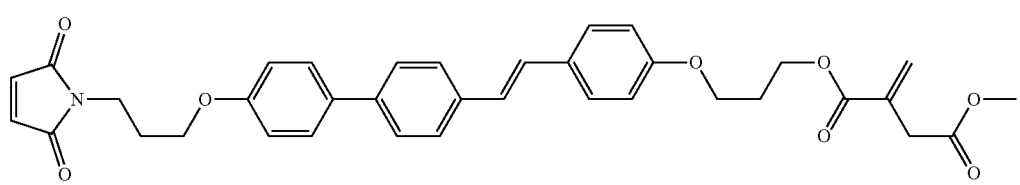 [SMILES: C=C(CC(=O)OC)C(=O)OCCCOc1ccc(/C=C/c2ccc(-c3ccc(OCCCN4C(=O)C=CC4=O)cc3)cc2)cc1] 326 |
| 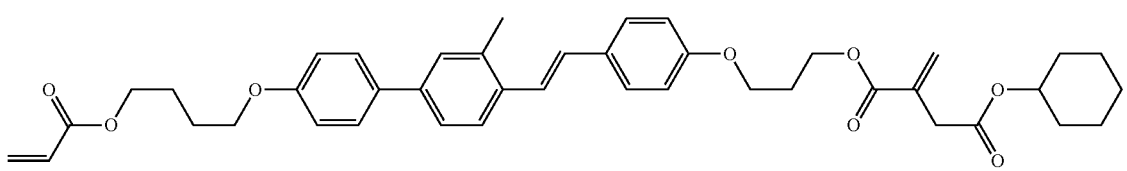 327 |
| 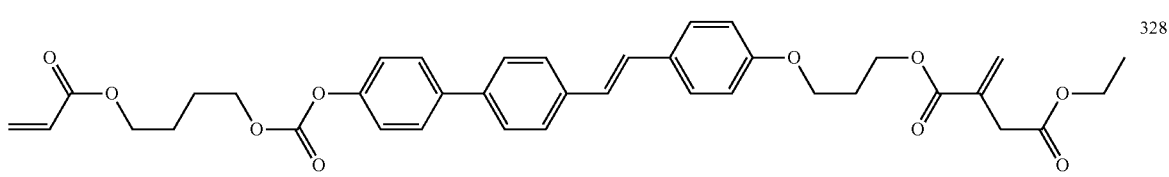 328 |
| 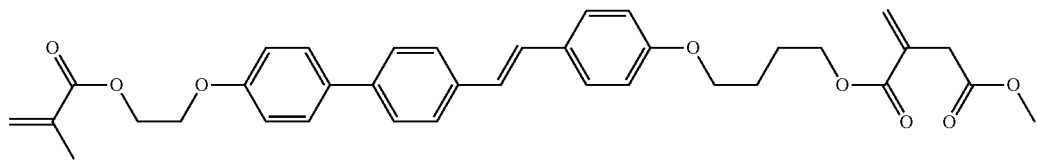 [SMILES: C=C(C)C(=O)OCCOc1ccc(-c2ccc(/C=C/c3ccc(OCCCCOC(=O)C(=C)CC(=O)OC)cc3)cc2)cc1] 329 |

| No. |
|---|
| 330 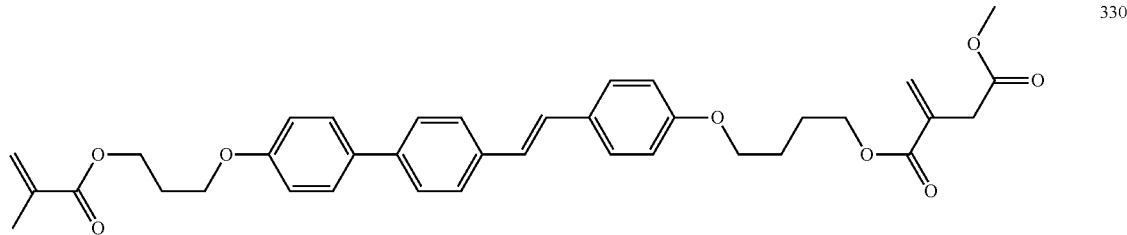 |
| 331 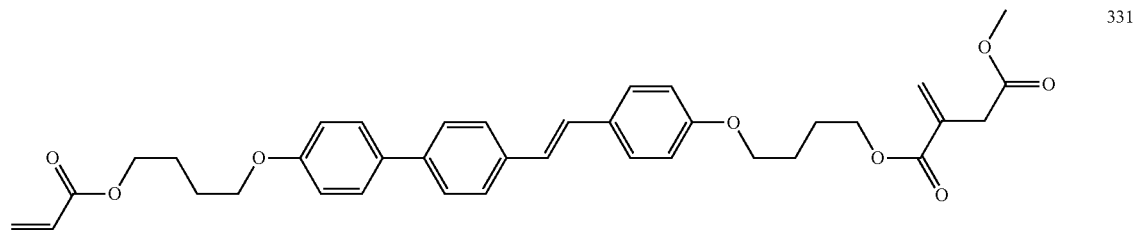 |
| 332 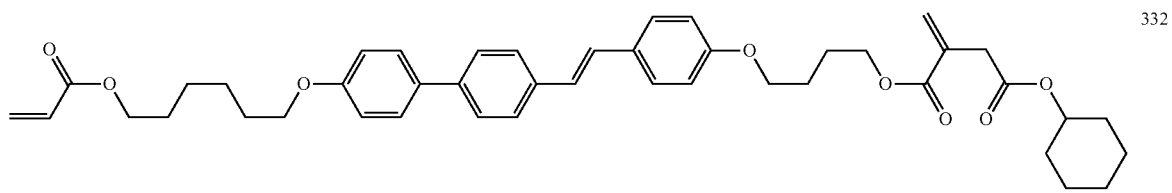 |
| 333 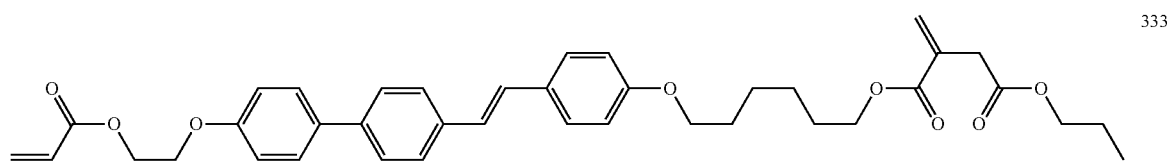 |
| 334 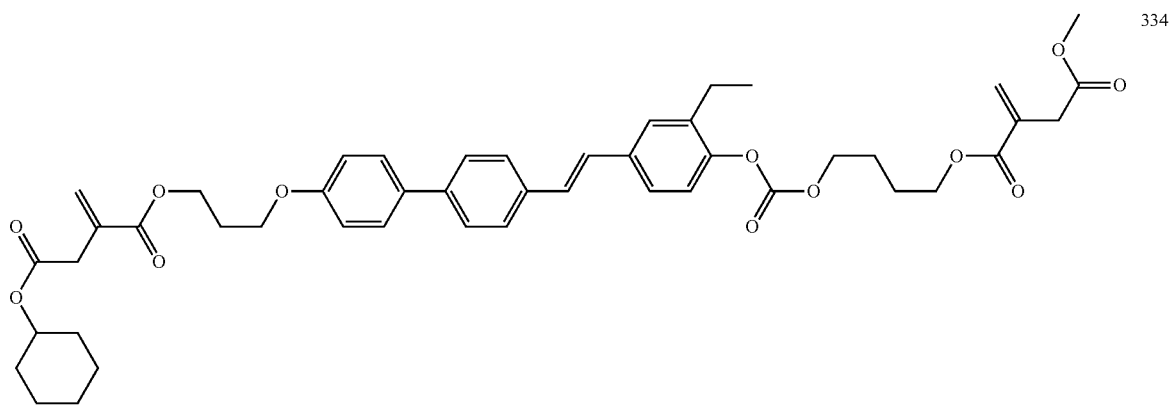 |
| 335 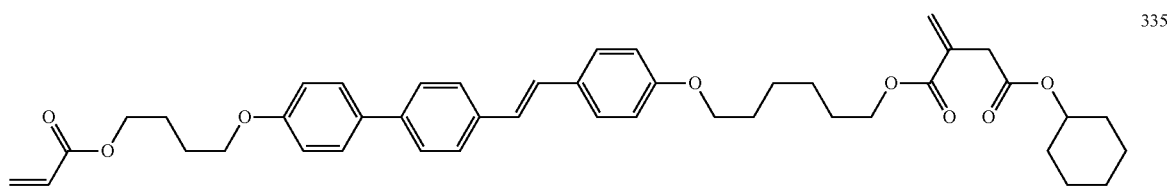 |
| 336 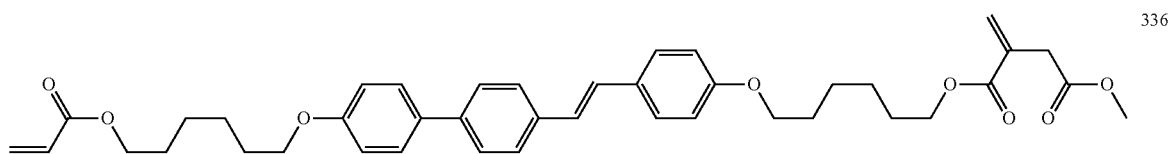 |

-continued
| No. |
|---|
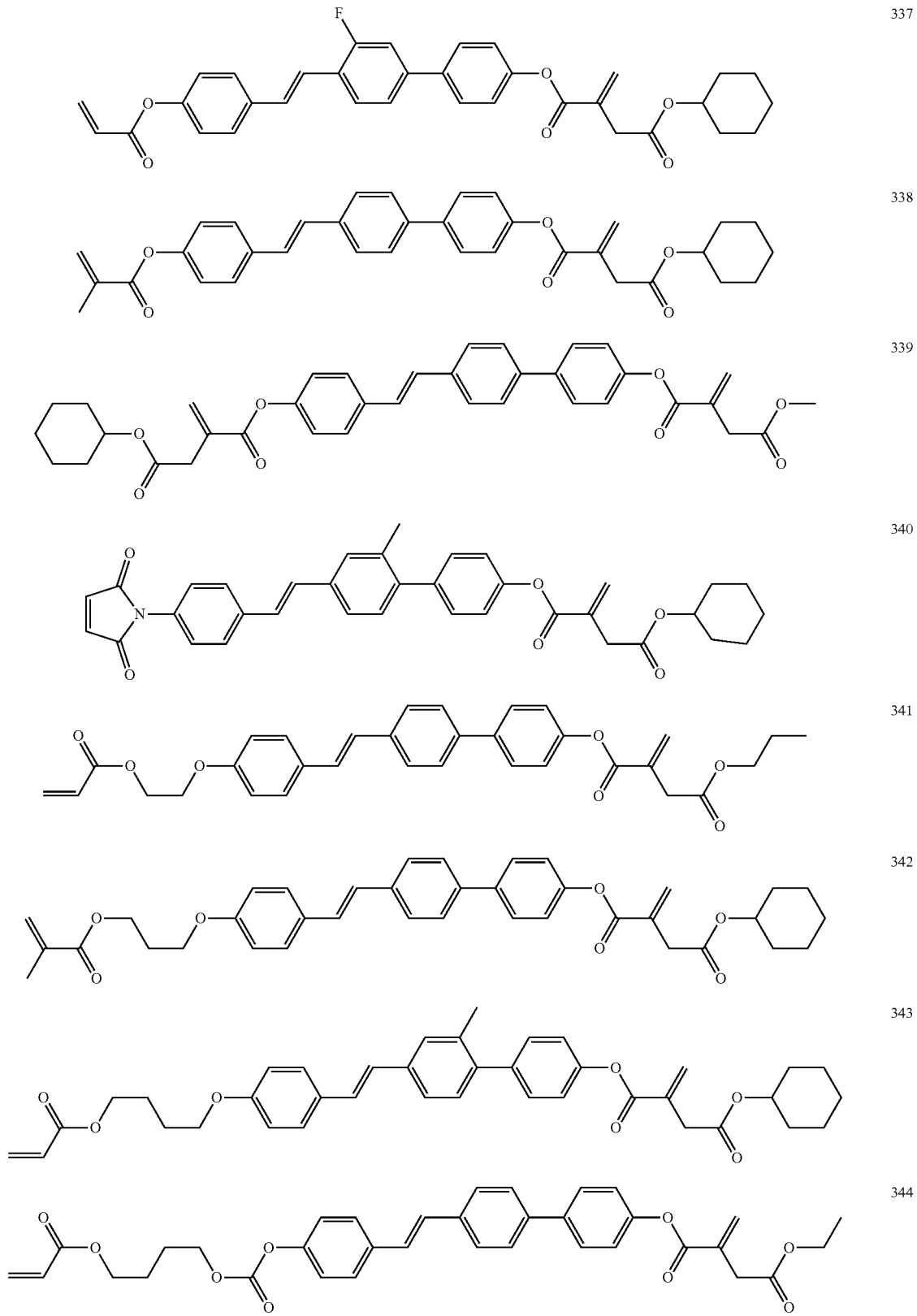

-continued
| | No. |
|---|---|
| 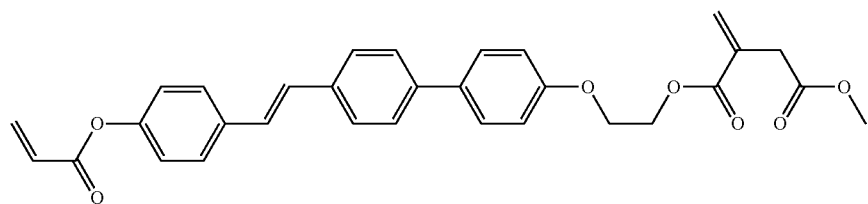 [SMILES: C=CC(=O)Oc1ccc(/C=C/c2ccc(-c3ccc(OCCOC(=O)C(=C)CC(=O)OC)cc3)cc2)cc1] | 345 |
| 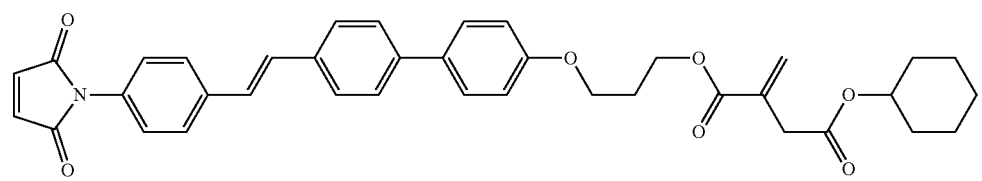 [SMILES: C=C(CC(=O)OC1CCCCC1)C(=O)OCCCOc1ccc(-c2ccc(/C=C/c3ccc(N4C(=O)C=CC4=O)cc3)cc2)cc1] | 346 |
| 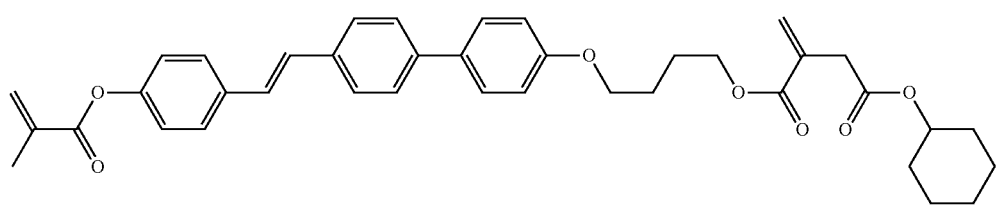 [SMILES: C=C(C)C(=O)Oc1ccc(/C=C/c2ccc(-c3ccc(OCCCCOC(=O)C(=C)CC(=O)OC4CCCCC4)cc3)cc2)cc1] | 347 |
| 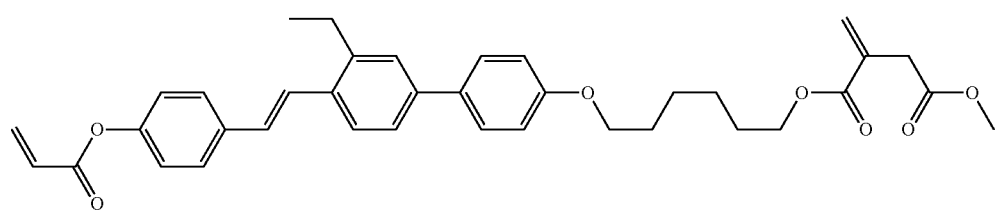 [SMILES: C=CC(=O)Oc1ccc(/C=C/c2ccc(-c3ccc(OCCCCCCOC(=O)C(=C)CC(=O)OC)cc3)cc2CC)cc1] | 348 |
| 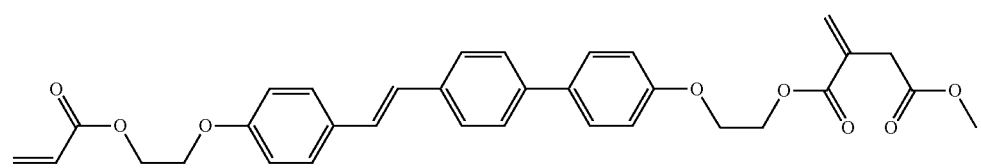 [SMILES: C=CC(=O)OCCOc1ccc(/C=C/c2ccc(-c3ccc(OCCOC(=O)C(=C)CC(=O)OC)cc3)cc2)cc1] | 349 |
| 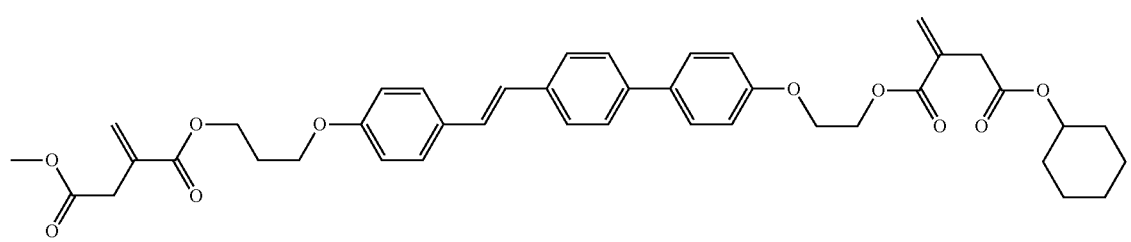 [SMILES: C=C(CC(=O)OC)C(=O)OCCCOc1ccc(/C=C/c2ccc(-c3ccc(OCCOC(=O)C(=C)CC(=O)OC4CCCCC4)cc3)cc2)cc1] | 350 |
| 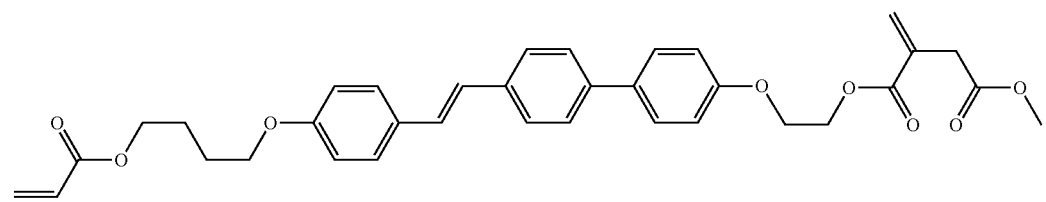 [SMILES: C=CC(=O)OCCCCOc1ccc(/C=C/c2ccc(-c3ccc(OCCOC(=O)C(=C)CC(=O)OC)cc3)cc2)cc1] | 351 |

-continued
| No. |
|---|
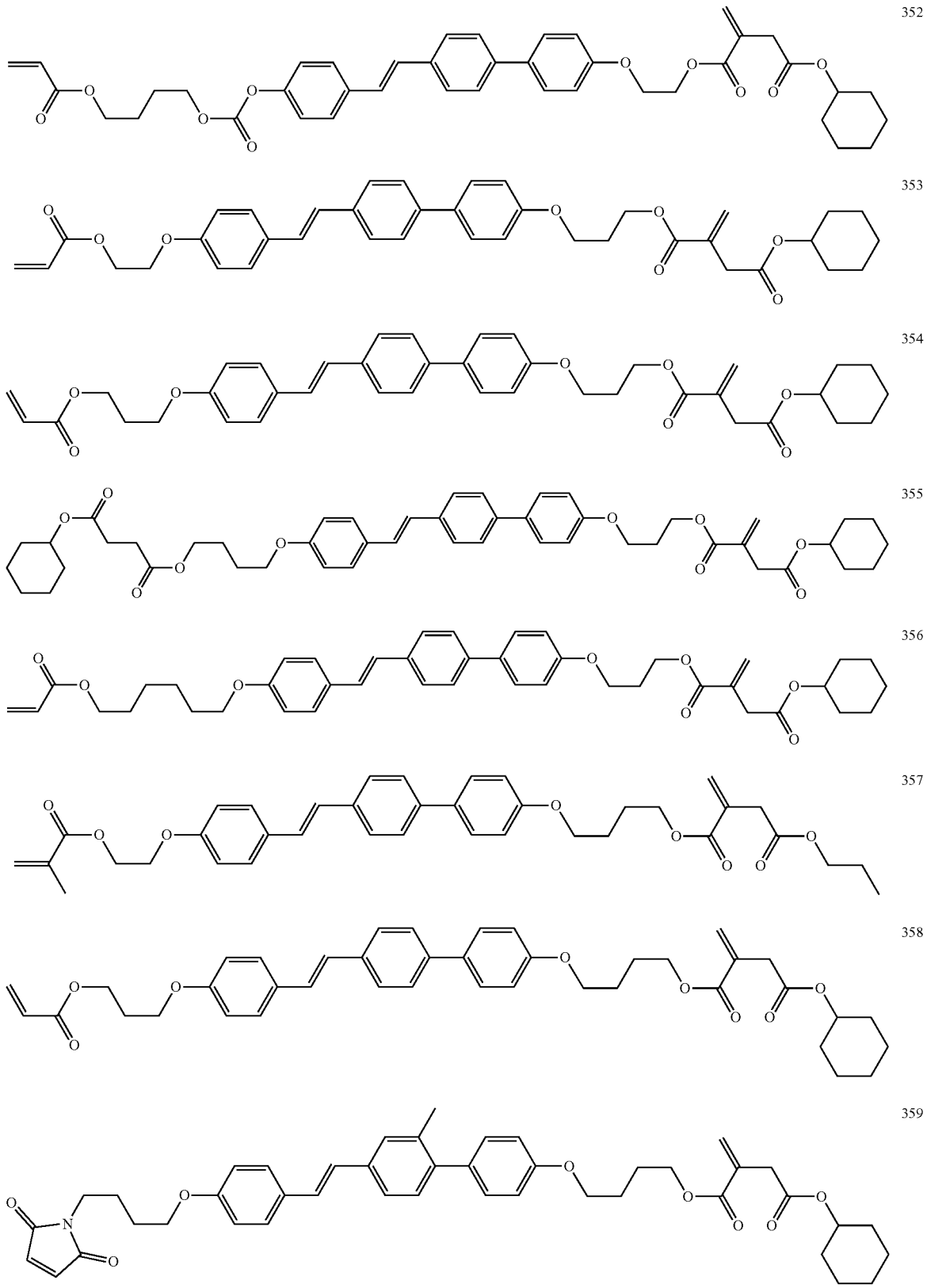

-continued
| | No. |
|---|---|
| 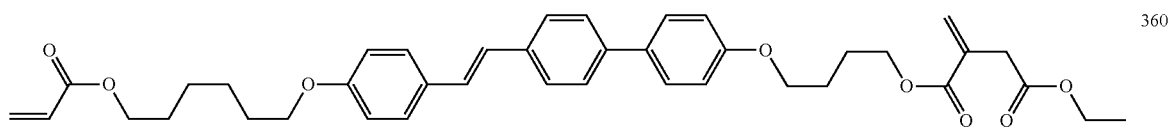 | 360 |
| 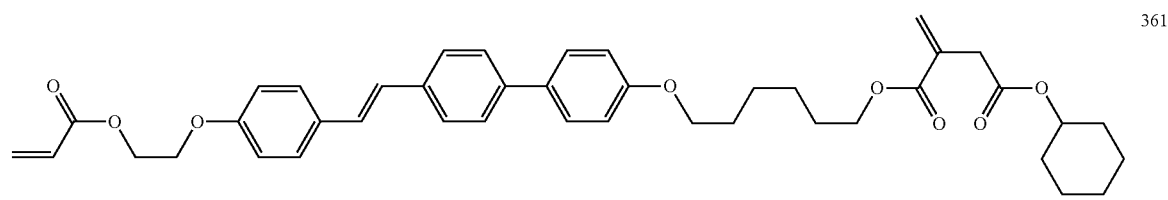 | 361 |
| 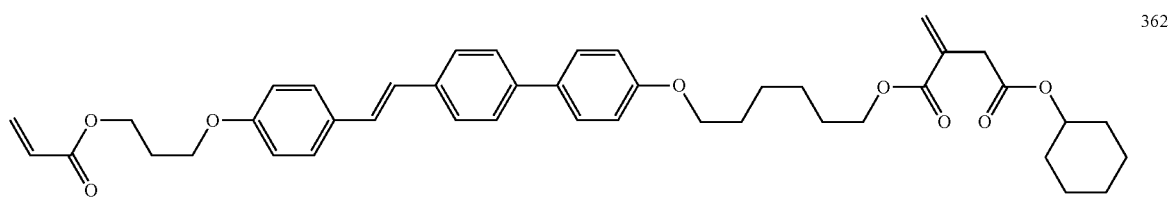 | 362 |
| 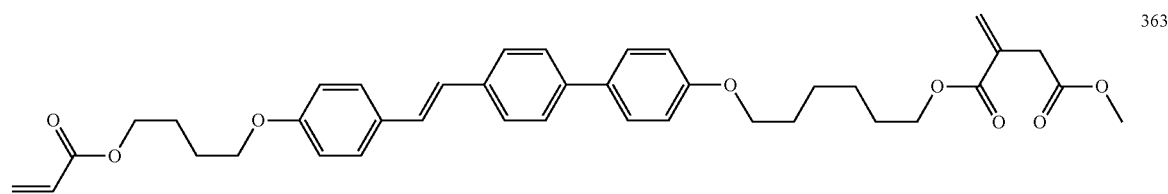 | 363 |
| 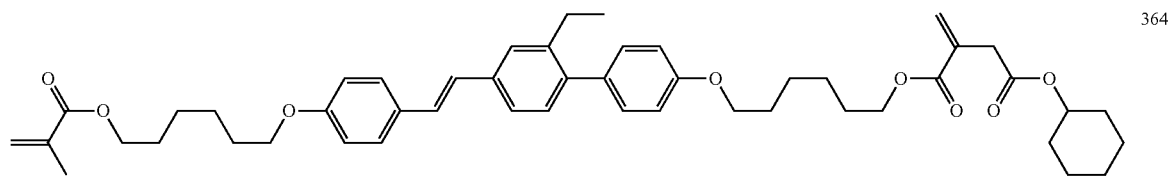 | 364 |
| 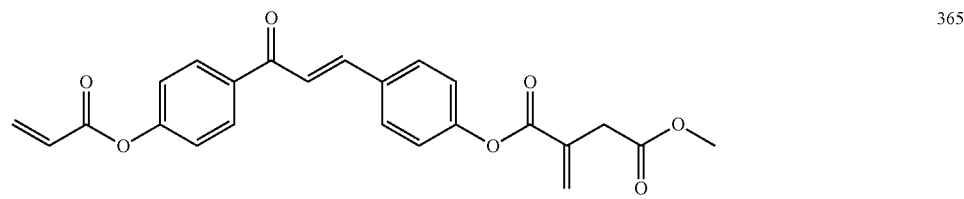 | 365 |
| 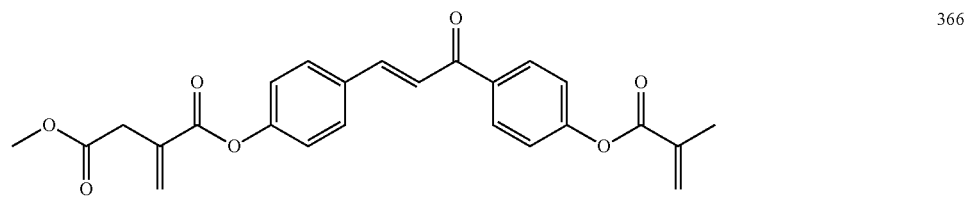 | 366 |
| 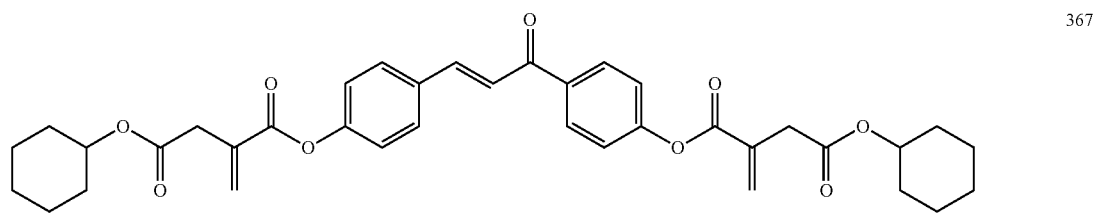 | 367 |

| No. |
|---|
| 368 |
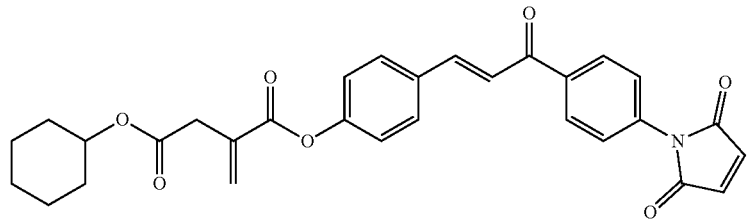 [SMILES: C=C(CC(=O)OC1CCCCC1)C(=O)Oc1ccc(/C=C/C(=O)c2ccc(N3C(=O)C=CC3=O)cc2)cc1]
| 369 |
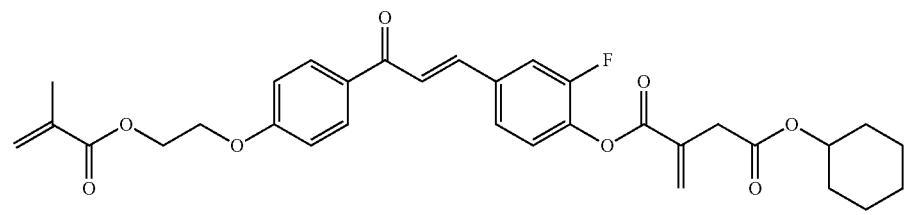 [SMILES: C=C(C)C(=O)OCCOc1ccc(C(=O)/C=C/c2ccc(OC(=O)C(=C)CC(=O)OC3CCCCC3)c(F)c2)cc1]
| 370 |
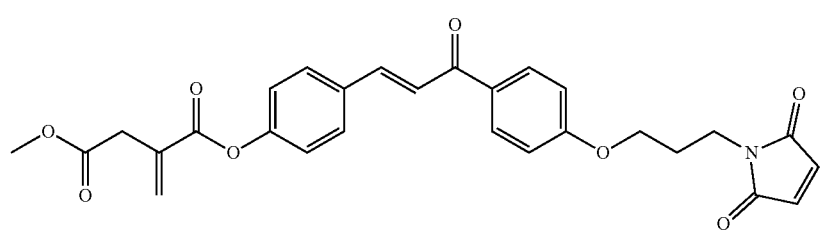 [SMILES: C=C(CC(=O)OC)C(=O)Oc1ccc(/C=C/C(=O)c2ccc(OCCCN3C(=O)C=CC3=O)cc2)cc1]
| 371 |
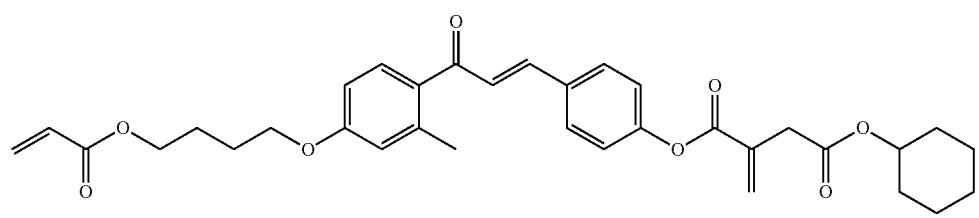 [SMILES: C=CC(=O)OCCCCOc1ccc(C(=O)/C=C/c2ccc(OC(=O)C(=C)CC(=O)OC3CCCCC3)cc2)c(C)c1]
| 372 |
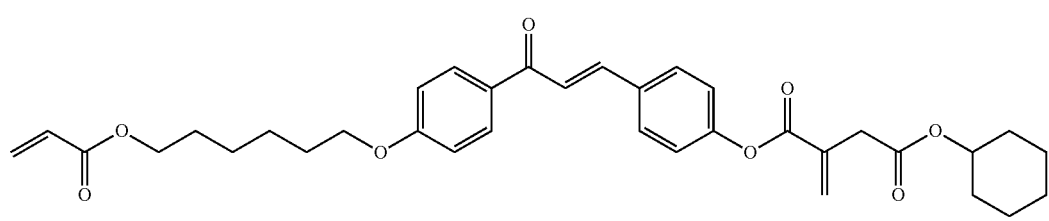 [SMILES: C=CC(=O)OCCCCCCOc1ccc(C(=O)/C=C/c2ccc(OC(=O)C(=C)CC(=O)OC3CCCCC3)cc2)cc1]
| 373 |
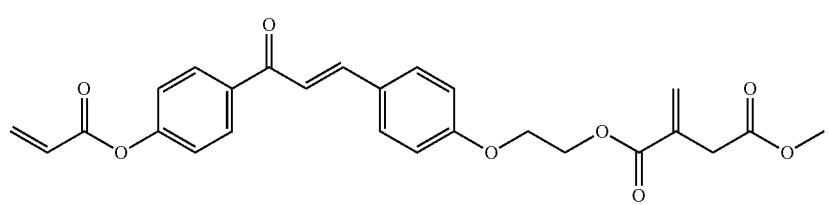 [SMILES: C=CC(=O)Oc1ccc(C(=O)/C=C/c2ccc(OCCOC(=O)C(=C)CC(=O)OC)cc2)cc1]
| 374 |
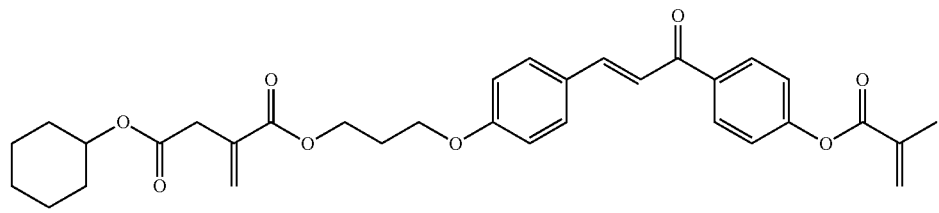 [SMILES: C=C(C)C(=O)Oc1ccc(C(=O)/C=C/c2ccc(OCCCOC(=O)C(=C)CC(=O)OC3CCCCC3)cc2)cc1]

-continued
| No. |
|---|
| 375 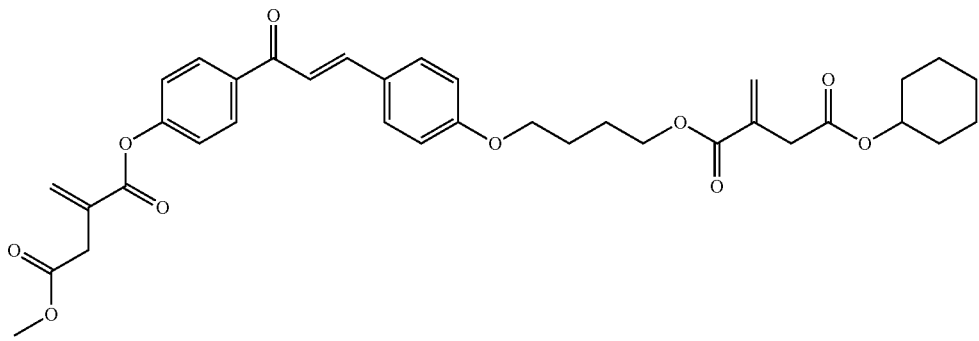 [SMILES: C=C(CC(=O)OC1CCCCC1)C(=O)OCCCCOc1ccc(/C=C/C(=O)c2ccc(OC(=O)C(=C)CC(=O)OC)cc2)cc1] |
| 376 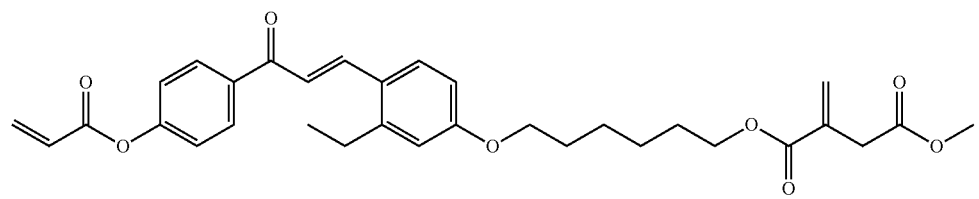 [SMILES: C=CC(=O)Oc1ccc(C(=O)/C=C/c2ccc(OCCCCCCOC(=O)C(=C)CC(=O)OC)cc2CC)cc1] |
| 377 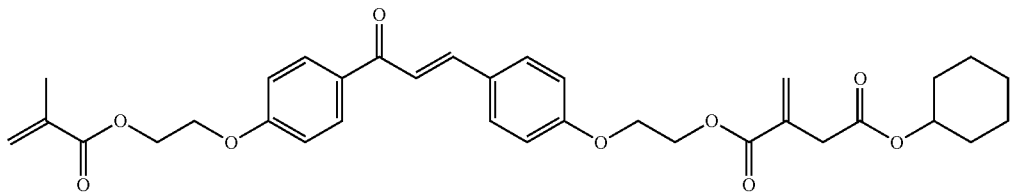 [SMILES: C=C(C)C(=O)OCCOc1ccc(C(=O)/C=C/c2ccc(OCCOC(=O)C(=C)CC(=O)OC3CCCCC3)cc2)cc1] |
| 378 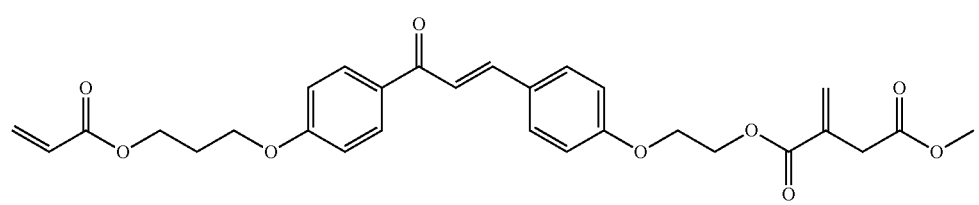 [SMILES: C=CC(=O)OCCCOc1ccc(C(=O)/C=C/c2ccc(OCCOC(=O)C(=C)CC(=O)OC)cc2)cc1] |
| 379 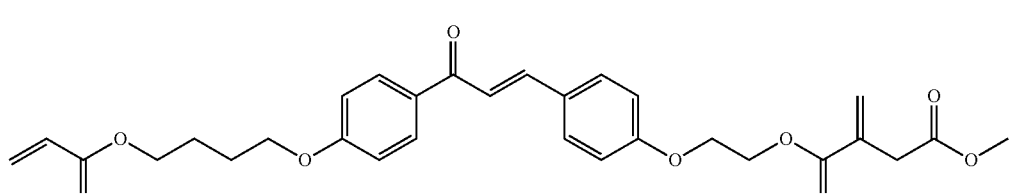 |
| 380 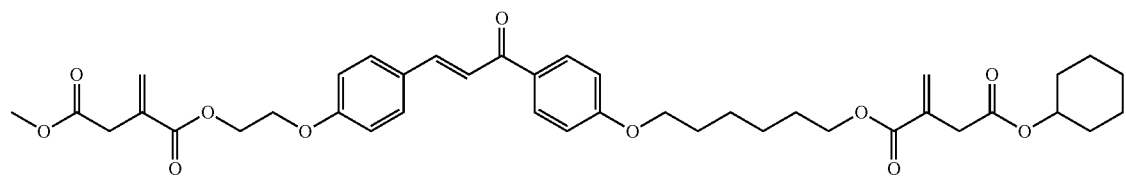 [SMILES: C=C(CC(=O)OC)C(=O)OCCOc1ccc(/C=C/C(=O)c2ccc(OCCCCCCOC(=O)C(=C)CC(=O)OC3CCCCC3)cc2)cc1] |
| 381 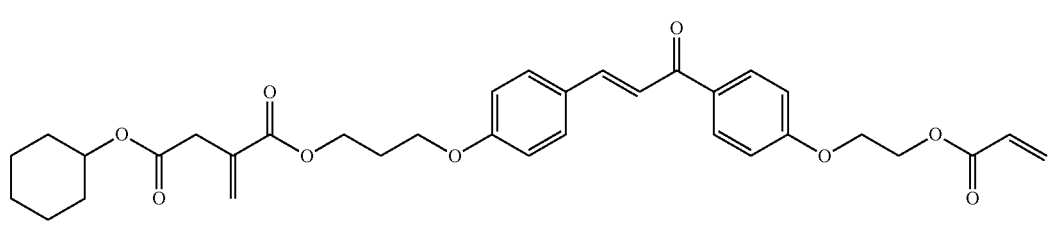 [SMILES: C=CC(=O)OCCOc1ccc(C(=O)/C=C/c2ccc(OCCCOC(=O)C(=C)CC(=O)OC3CCCCC3)cc2)cc1] |

| No. |
|---|
| 382 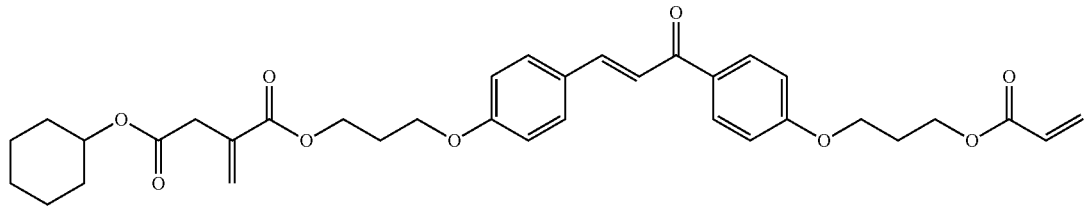 [SMILES: C=CC(=O)OCCCOc1ccc(C(=O)/C=C/c2ccc(OCCCOC(=O)C(=C)CC(=O)OC3CCCCC3)cc2)cc1] |
| 383 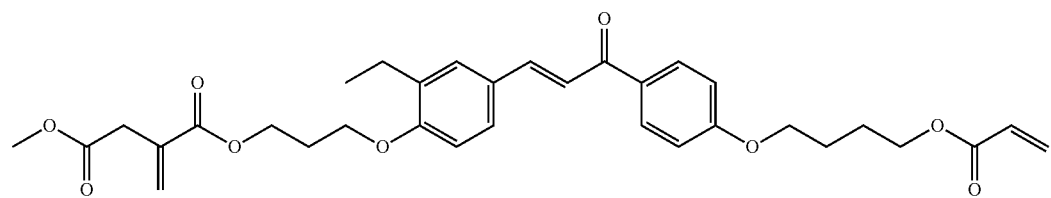 [SMILES: C=CC(=O)OCCCCOc1ccc(C(=O)/C=C/c2ccc(OCCCOC(=O)C(=C)CC(=O)OC)c(CC)c2)cc1] |
| 384 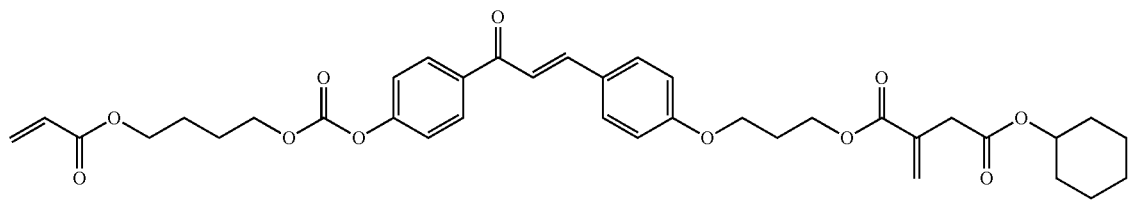 [SMILES: C=CC(=O)OCCCCOC(=O)Oc1ccc(C(=O)/C=C/c2ccc(OCCCOC(=O)C(=C)CC(=O)OC3CCCCC3)cc2)cc1] |
| 385 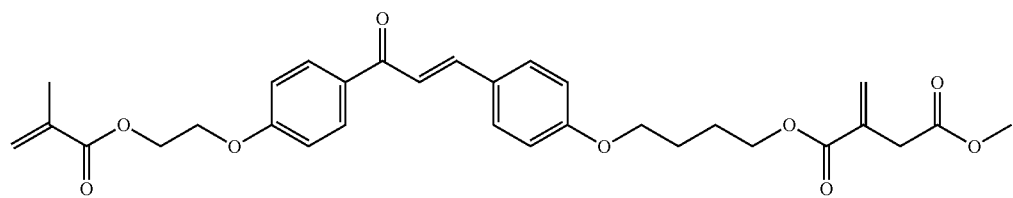 [SMILES: C=C(C)C(=O)OCCOc1ccc(C(=O)/C=C/c2ccc(OCCCCOC(=O)C(=C)CC(=O)OC)cc2)cc1] |
| 386 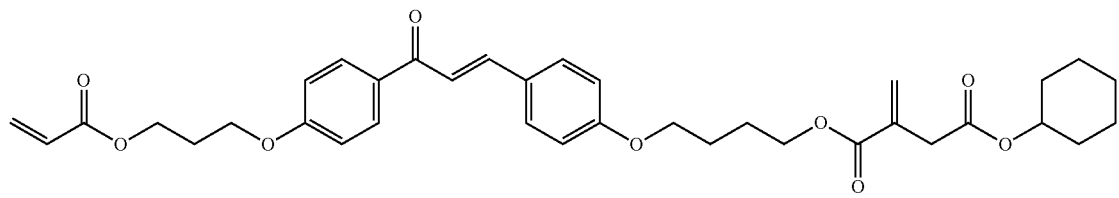 [SMILES: C=CC(=O)OCCCOc1ccc(C(=O)/C=C/c2ccc(OCCCCOC(=O)C(=C)CC(=O)OC3CCCCC3)cc2)cc1] |
| 387 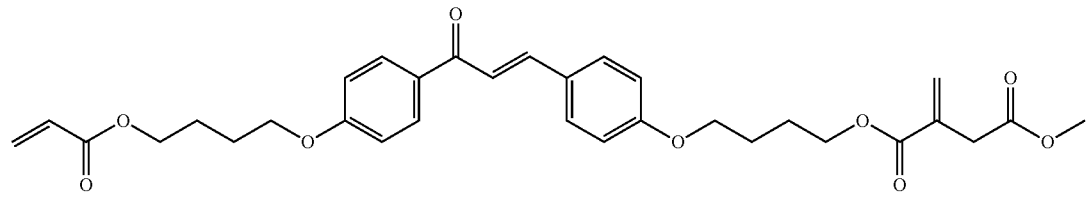 [SMILES: C=CC(=O)OCCCCOc1ccc(C(=O)/C=C/c2ccc(OCCCCOC(=O)C(=C)CC(=O)OC)cc2)cc1] |
| 388 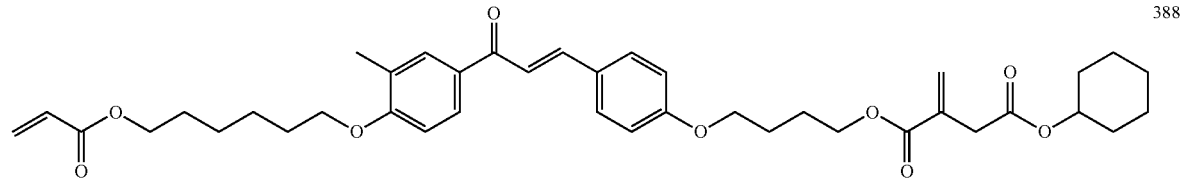 |

| No. |
|---|
| 389 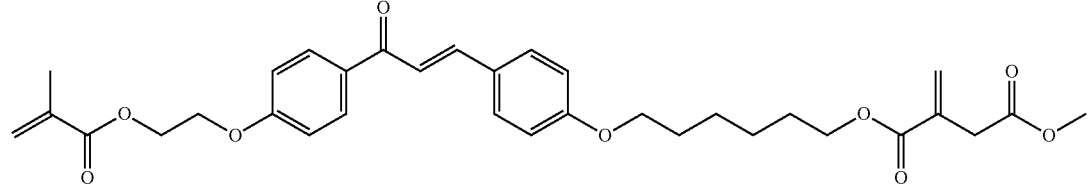 [SMILES: C=C(C)C(=O)OCCOc1ccc(C(=O)/C=C/c2ccc(OCCCCCCOC(=O)C(=C)CC(=O)OC)cc2)cc1] |
| 390 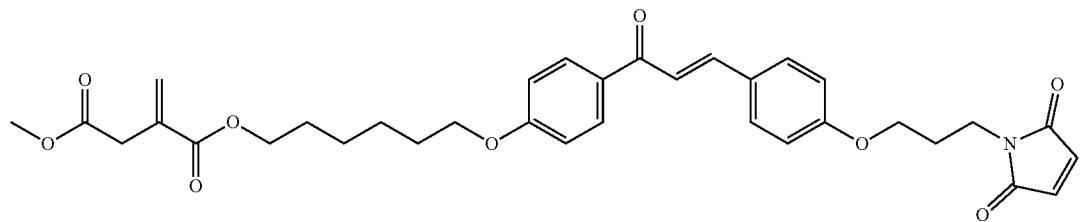 [SMILES: C=C(CC(=O)OC)C(=O)OCCCCCCOc1ccc(C(=O)/C=C/c2ccc(OCCCN3C(=O)C=CC3=O)cc2)cc1] |
| 391 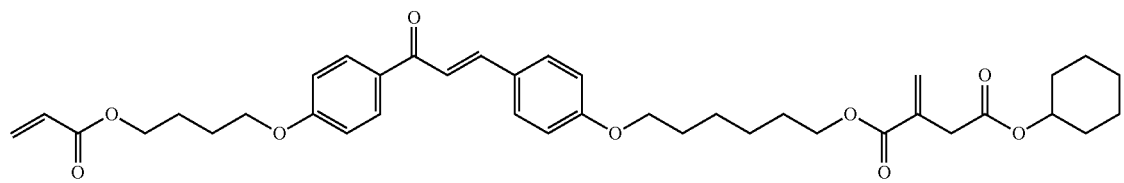 [SMILES: C=CC(=O)OCCCCOc1ccc(C(=O)/C=C/c2ccc(OCCCCCCOC(=O)C(=C)CC(=O)OC3CCCCC3)cc2)cc1] |
| 392 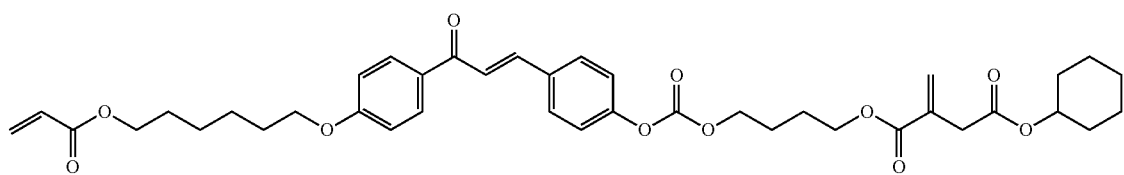 [SMILES: C=CC(=O)OCCCCCCOc1ccc(C(=O)/C=C/c2ccc(OC(=O)OCCCCOC(=O)C(=C)CC(=O)OC3CCCCC3)cc2)cc1] |
| 393 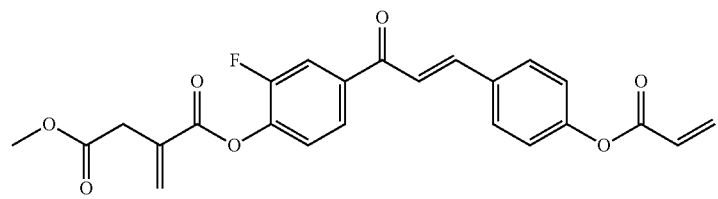 [SMILES: C=CC(=O)Oc1ccc(/C=C/C(=O)c2ccc(OC(=O)C(=C)CC(=O)OC)c(F)c2)cc1] |
| 394 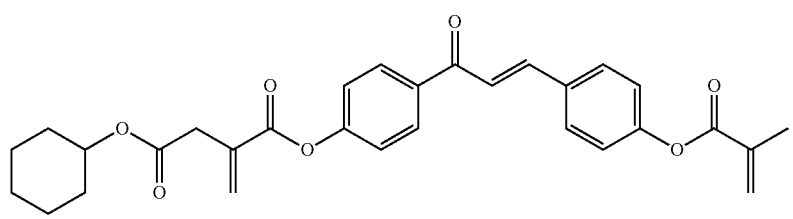 [SMILES: C=C(C)C(=O)Oc1ccc(/C=C/C(=O)c2ccc(OC(=O)C(=C)CC(=O)OC3CCCCC3)cc2)cc1] |
| 395 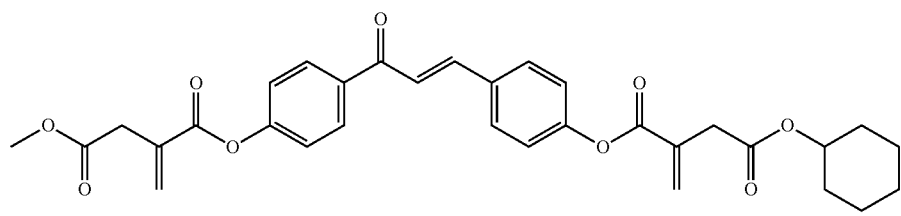 [SMILES: C=C(CC(=O)OC)C(=O)Oc1ccc(C(=O)/C=C/c2ccc(OC(=O)C(=C)CC(=O)OC3CCCCC3)cc2)cc1] |

-continued
| | No. |
|---|---|
| 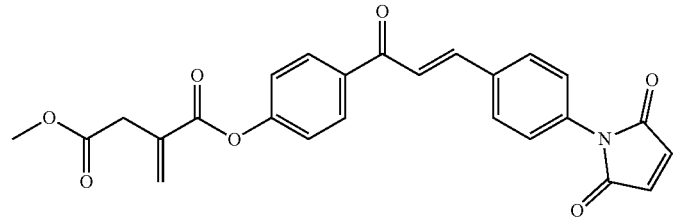 [SMILES: C=C(CC(=O)OC)C(=O)Oc1ccc(C(=O)/C=C/c2ccc(N3C(=O)C=CC3=O)cc2)cc1] | 396 |
| 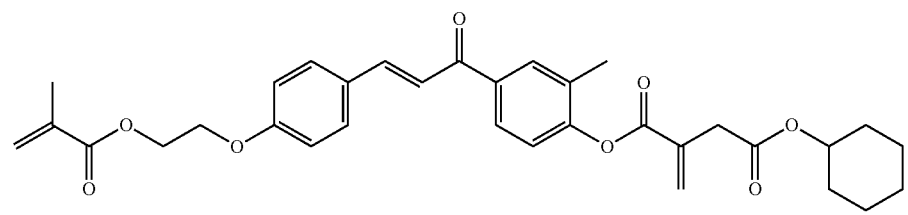 [SMILES: C=C(C)C(=O)OCCOc1ccc(/C=C/C(=O)c2ccc(OC(=O)C(=C)CC(=O)OC3CCCCC3)c(C)c2)cc1] | 397 |
| 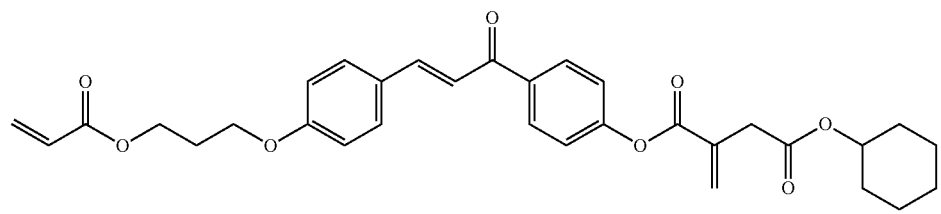 [SMILES: C=CC(=O)OCCCOc1ccc(/C=C/C(=O)c2ccc(OC(=O)C(=C)CC(=O)OC3CCCCC3)cc2)cc1] | 398 |
| 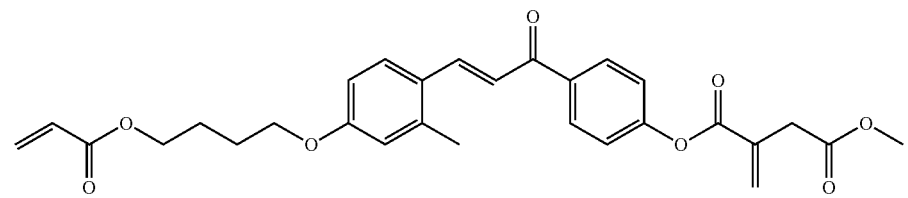 [SMILES: C=CC(=O)OCCCCOc1ccc(/C=C/C(=O)c2ccc(OC(=O)C(=C)CC(=O)OC)cc2)c(C)c1] | 399 |
| 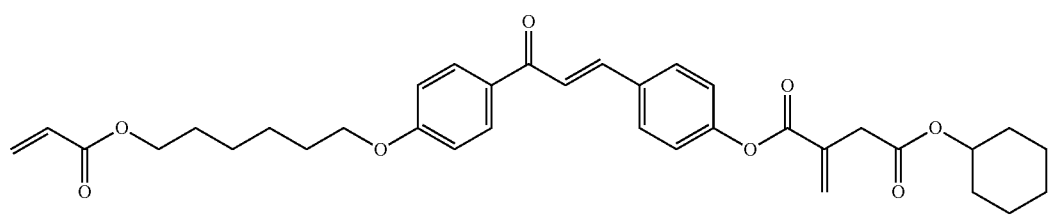 [SMILES: C=CC(=O)OCCCCCCOc1ccc(C(=O)/C=C/c2ccc(OC(=O)C(=C)CC(=O)OC3CCCCC3)cc2)cc1] | 400 |
| 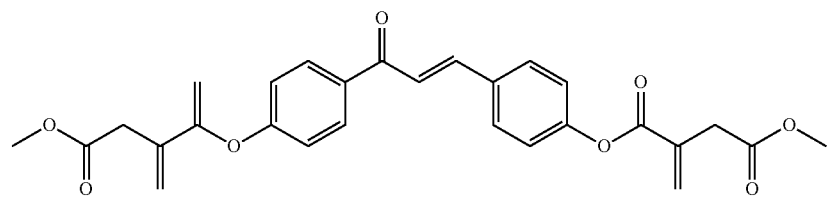 | 401 |
| 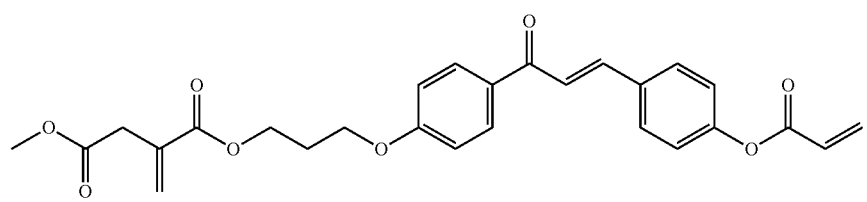 [SMILES: C=CC(=O)Oc1ccc(/C=C/C(=O)c2ccc(OCCCOC(=O)C(=C)CC(=O)OC)cc2)cc1] | 402 |

| No. |
|---|
| 403 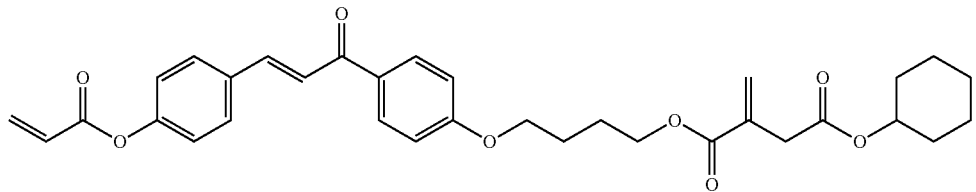 [SMILES: C=CC(=O)Oc1ccc(/C=C/C(=O)c2ccc(OCCCCOC(=O)C(=C)CC(=O)OC3CCCCC3)cc2)cc1] |
| 404 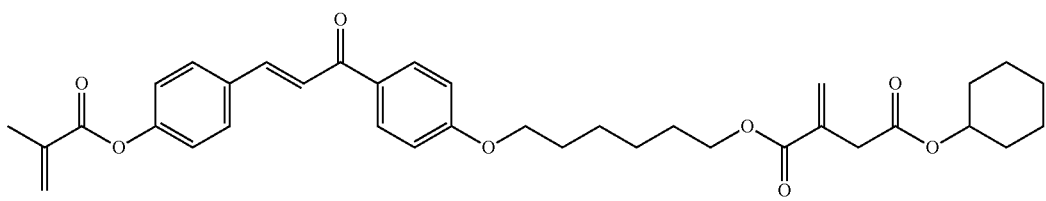 [SMILES: C=C(C)C(=O)Oc1ccc(/C=C/C(=O)c2ccc(OCCCCCCOC(=O)C(=C)CC(=O)OC3CCCCC3)cc2)cc1] |
| 405 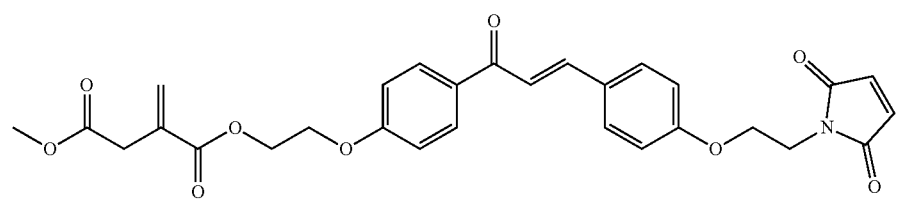 [SMILES: C=C(CC(=O)OC)C(=O)OCCOc1ccc(C(=O)/C=C/c2ccc(OCCN3C(=O)C=CC3=O)cc2)cc1] |
| 406 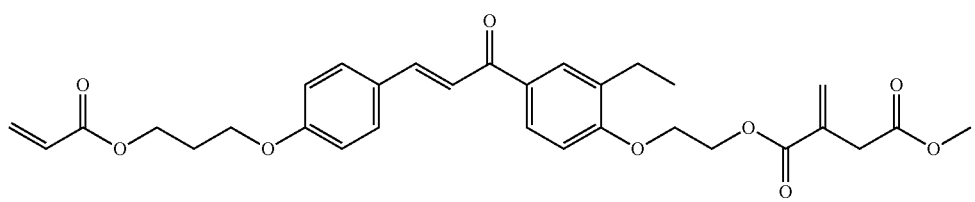 [SMILES: C=CC(=O)OCCCOc1ccc(/C=C/C(=O)c2ccc(OCCOC(=O)C(=C)CC(=O)OC)c(CC)c2)cc1] |
| 407 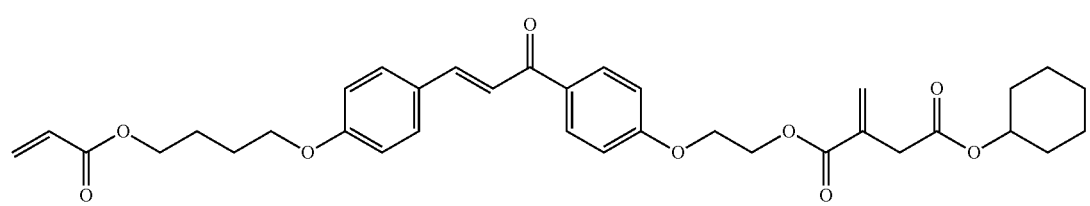 [SMILES: C=CC(=O)OCCCCOc1ccc(/C=C/C(=O)c2ccc(OCCOC(=O)C(=C)CC(=O)OC3CCCCC3)cc2)cc1] |
| 408 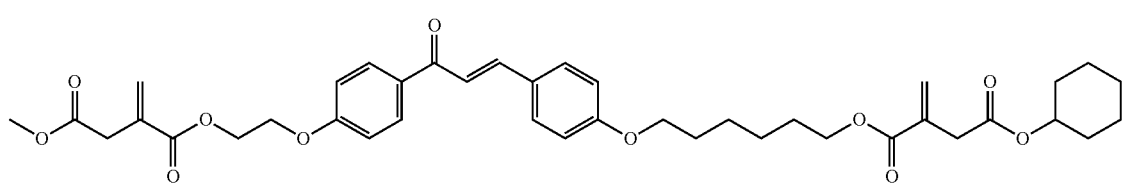 [SMILES: C=C(CC(=O)OC)C(=O)OCCOc1ccc(C(=O)/C=C/c2ccc(OCCCCCCOC(=O)C(=C)CC(=O)OC3CCCCC3)cc2)cc1] |
| 409 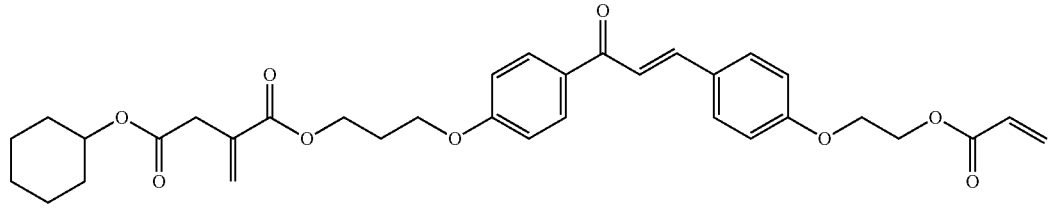 [SMILES: C=CC(=O)OCCOc1ccc(/C=C/C(=O)c2ccc(OCCCOC(=O)C(=C)CC(=O)OC3CCCCC3)cc2)cc1] |

-continued
| | No. |
|---|---|
| 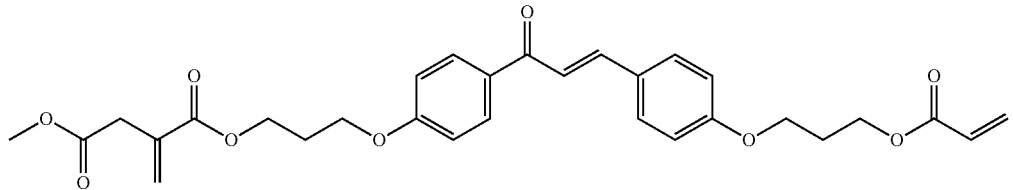 [SMILES: C=CC(=O)OCCCOc1ccc(/C=C/C(=O)c2ccc(OCCCOC(=O)C(=C)CC(=O)OC)cc2)cc1] | 410 |
| 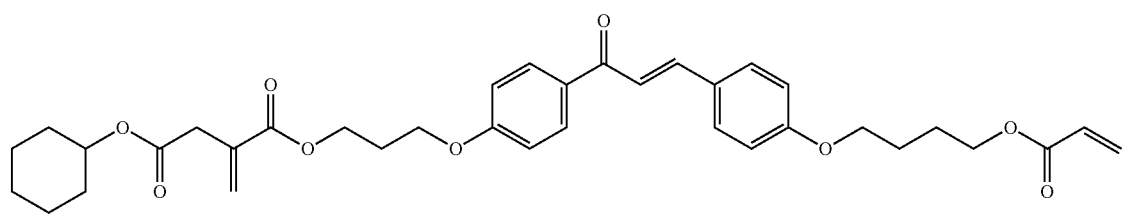 [SMILES: C=CC(=O)OCCCCOc1ccc(/C=C/C(=O)c2ccc(OCCCOC(=O)C(=C)CC(=O)OC3CCCCC3)cc2)cc1] | 411 |
| 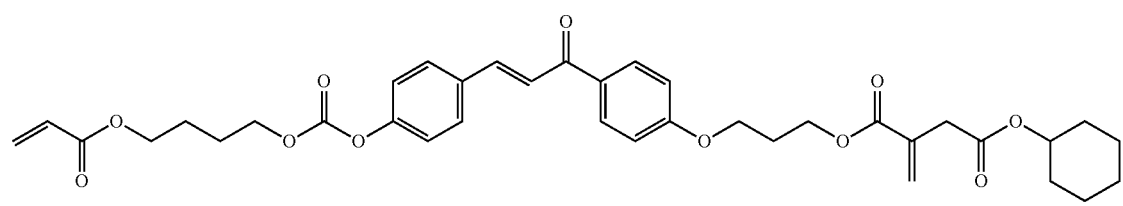 [SMILES: C=CC(=O)OCCCCOC(=O)Oc1ccc(/C=C/C(=O)c2ccc(OCCCOC(=O)C(=C)CC(=O)OC3CCCCC3)cc2)cc1] | 412 |
| 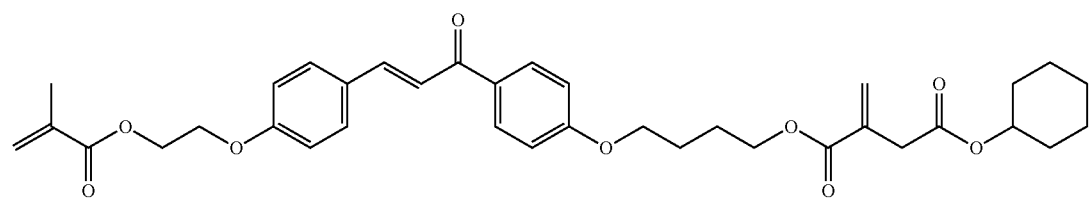 [SMILES: C=C(C)C(=O)OCCOc1ccc(/C=C/C(=O)c2ccc(OCCCCOC(=O)C(=C)CC(=O)OC3CCCCC3)cc2)cc1] | 413 |
| 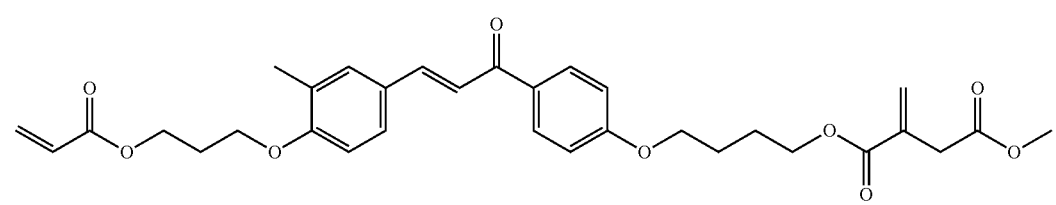 [SMILES: C=CC(=O)OCCCOc1ccc(/C=C/C(=O)c2ccc(OCCCCOC(=O)C(=C)CC(=O)OC)cc2)cc1C] | 414 |
| 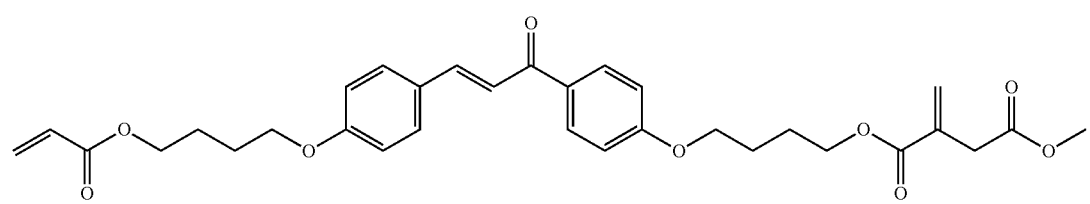 [SMILES: C=CC(=O)OCCCCOc1ccc(/C=C/C(=O)c2ccc(OCCCCOC(=O)C(=C)CC(=O)OC)cc2)cc1] | 415 |
| 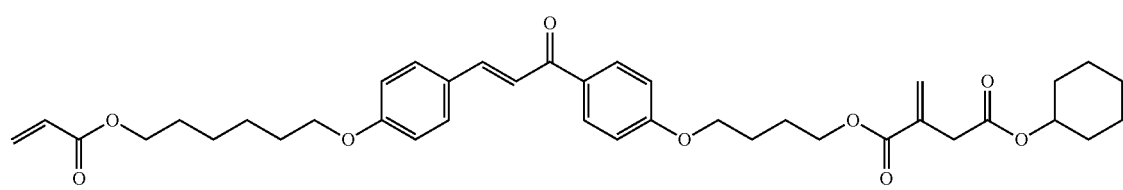 [SMILES: C=CC(=O)OCCCCCCOc1ccc(/C=C/C(=O)c2ccc(OCCCCOC(=O)C(=C)CC(=O)OC3CCCCC3)cc2)cc1] | 416 |

| No. |
|---|
| 417 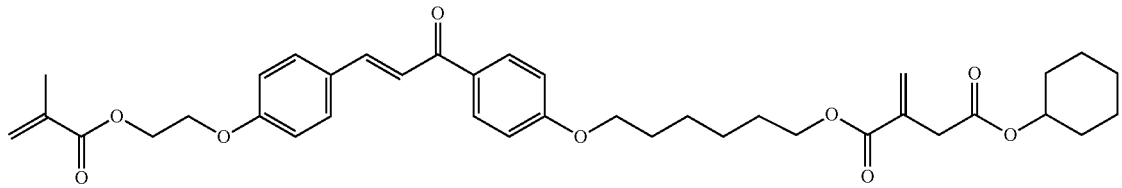 [SMILES: C=C(C)C(=O)OCCOc1ccc(/C=C/C(=O)c2ccc(OCCCCCCOC(=O)C(=C)CC(=O)OC3CCCCC3)cc2)cc1] |
| 418 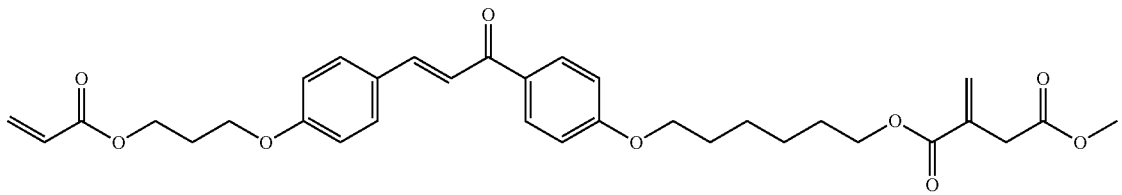 [SMILES: C=CC(=O)OCCCOc1ccc(/C=C/C(=O)c2ccc(OCCCCCCOC(=O)C(=C)CC(=O)OC)cc2)cc1] |
| 419 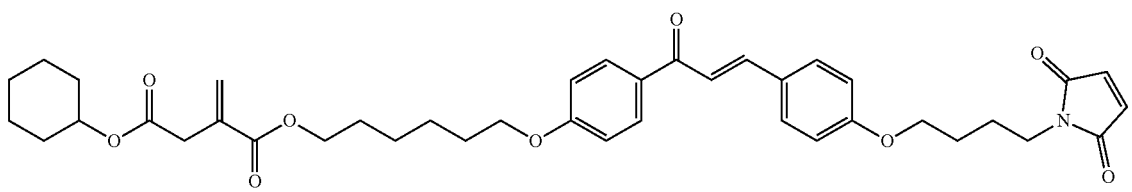 [SMILES: C=C(CC(=O)OC1CCCCC1)C(=O)OCCCCCCOc1ccc(C(=O)/C=C/c2ccc(OCCCCN3C(=O)C=CC3=O)cc2)cc1] |
| 420 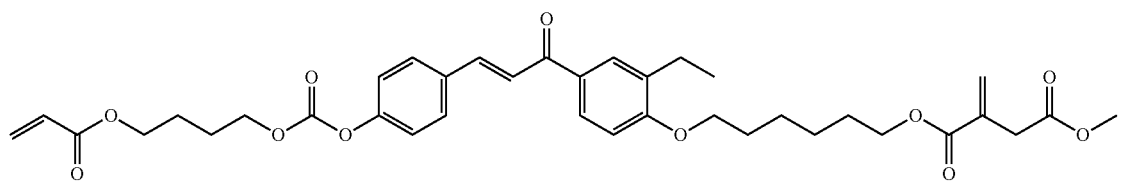 [SMILES: C=CC(=O)OCCCCOC(=O)Oc1ccc(/C=C/C(=O)c2ccc(OCCCCCCOC(=O)C(=C)CC(=O)OC)c(CC)c2)cc1] |
| 421 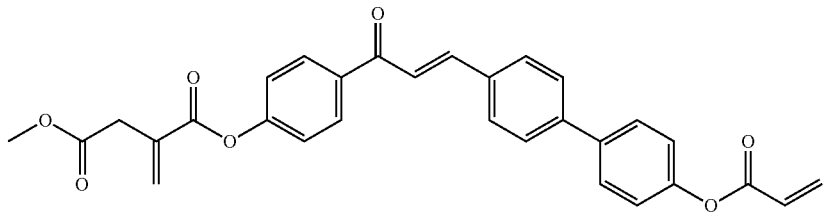 [SMILES: C=CC(=O)Oc1ccc(-c2ccc(/C=C/C(=O)c3ccc(OC(=O)C(=C)CC(=O)OC)cc3)cc2)cc1] |
| 422 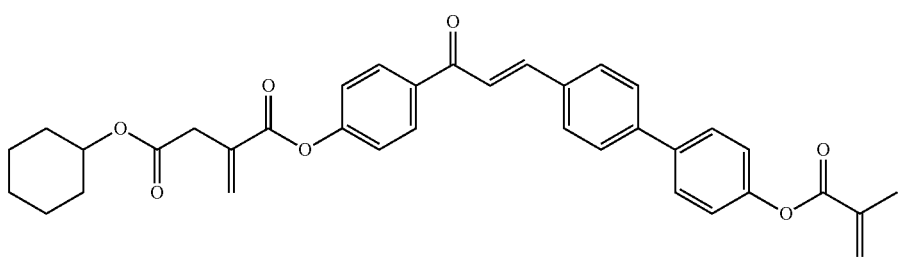 [SMILES: C=C(C)C(=O)Oc1ccc(-c2ccc(/C=C/C(=O)c3ccc(OC(=O)C(=C)CC(=O)OC4CCCCC4)cc3)cc2)cc1] |
| 423 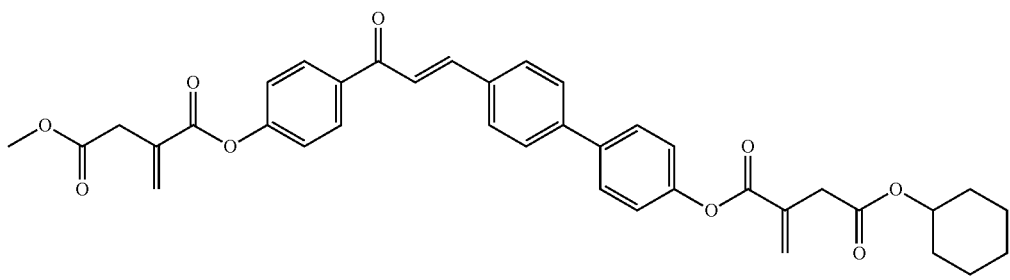 [SMILES: C=C(CC(=O)OC)C(=O)Oc1ccc(C(=O)/C=C/c2ccc(-c3ccc(OC(=O)C(=C)CC(=O)OC4CCCCC4)cc3)cc2)cc1] |

| No. |
|---|
| 424 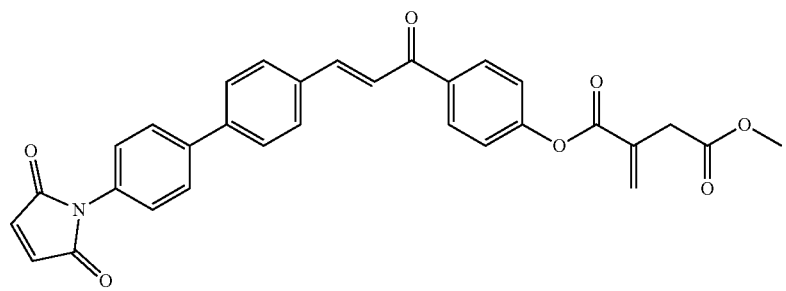 [SMILES: C=C(CC(=O)OC)C(=O)Oc1ccc(C(=O)/C=C/c2ccc(-c3ccc(N4C(=O)C=CC4=O)cc3)cc2)cc1] |
| 425 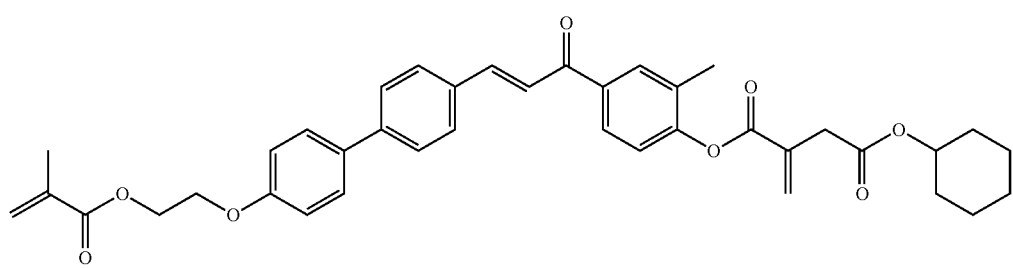 [SMILES: C=C(C)C(=O)OCCOc1ccc(-c2ccc(/C=C/C(=O)c3ccc(OC(=O)C(=C)CC(=O)OC4CCCCC4)c(C)c3)cc2)cc1] |
| 426 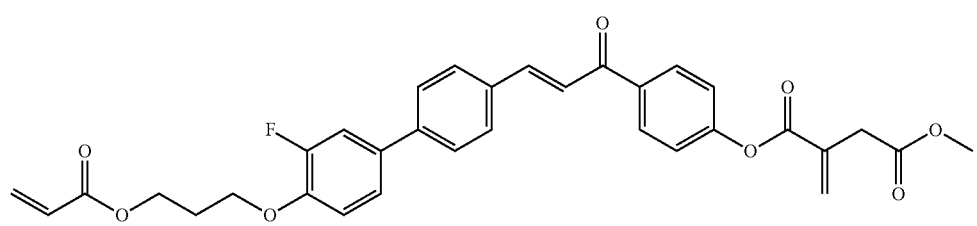 [SMILES: C=CC(=O)OCCCOc1ccc(-c2ccc(/C=C/C(=O)c3ccc(OC(=O)C(=C)CC(=O)OC)cc3)cc2)cc1F] |
| 427 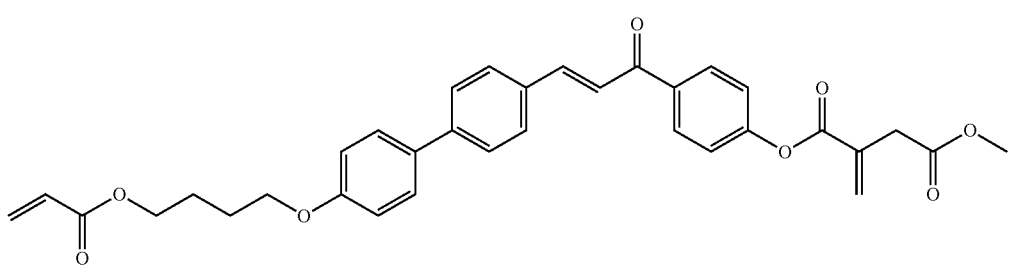 [SMILES: C=CC(=O)OCCCCOc1ccc(-c2ccc(/C=C/C(=O)c3ccc(OC(=O)C(=C)CC(=O)OC)cc3)cc2)cc1] |
| 428 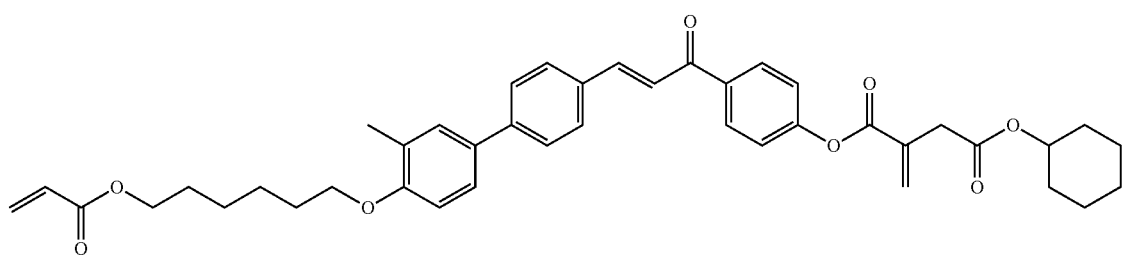 [SMILES: C=CC(=O)OCCCCCCOc1ccc(-c2ccc(/C=C/C(=O)c3ccc(OC(=O)C(=C)CC(=O)OC4CCCCC4)cc3)cc2)cc1C] |
| 429 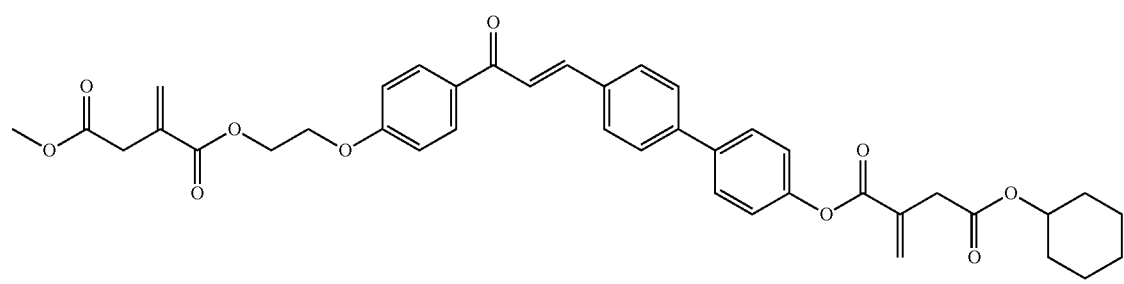 [SMILES: C=C(CC(=O)OC)C(=O)OCCOc1ccc(C(=O)/C=C/c2ccc(-c3ccc(OC(=O)C(=C)CC(=O)OC4CCCCC4)cc3)cc2)cc1] |

| No. |
|---|
| 430 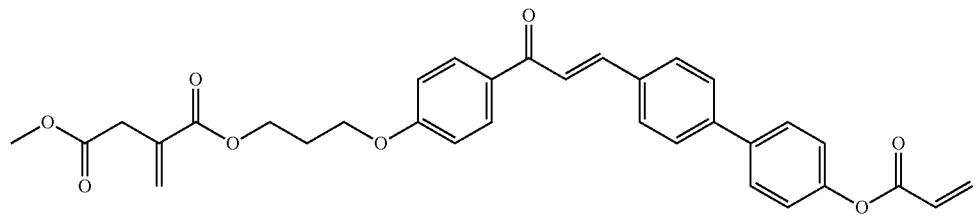 [SMILES: C=CC(=O)Oc1ccc(-c2ccc(/C=C/C(=O)c3ccc(OCCCOC(=O)C(=C)CC(=O)OC)cc3)cc2)cc1] |
| 431 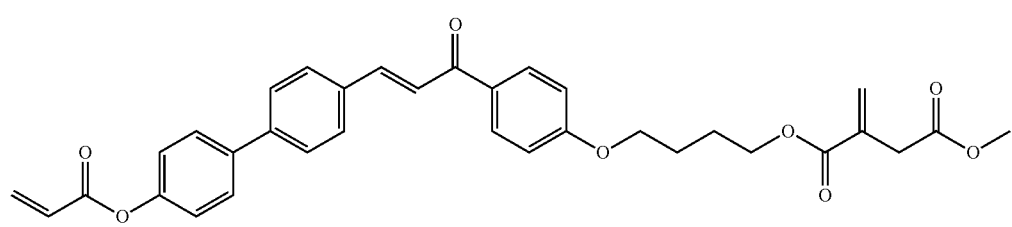 [SMILES: C=CC(=O)Oc1ccc(-c2ccc(/C=C/C(=O)c3ccc(OCCCCOC(=O)C(=C)CC(=O)OC)cc3)cc2)cc1] |
| 432 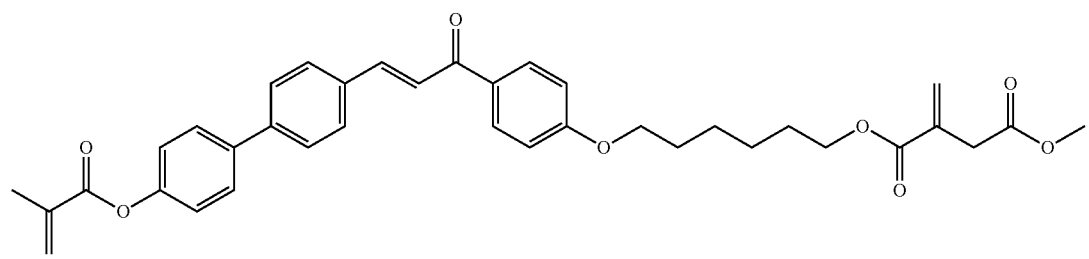 [SMILES: C=C(C)C(=O)Oc1ccc(-c2ccc(/C=C/C(=O)c3ccc(OCCCCCCOC(=O)C(=C)CC(=O)OC)cc3)cc2)cc1] |
| 433 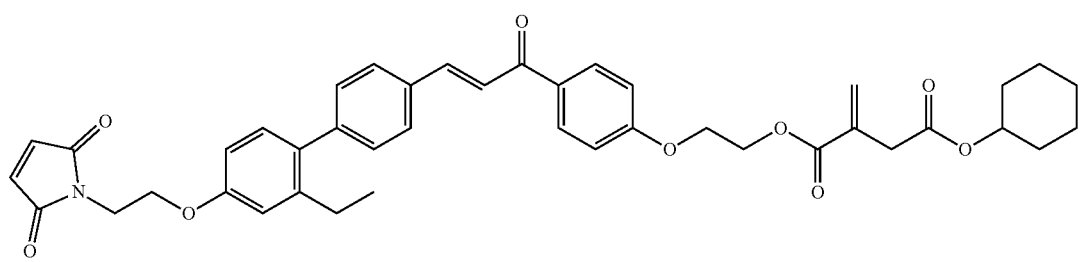 [SMILES: C=C(CC(=O)OC1CCCCC1)C(=O)OCCOc1ccc(C(=O)/C=C/c2ccc(-c3ccc(OCCN4C(=O)C=CC4=O)cc3CC)cc2)cc1] |
| 434 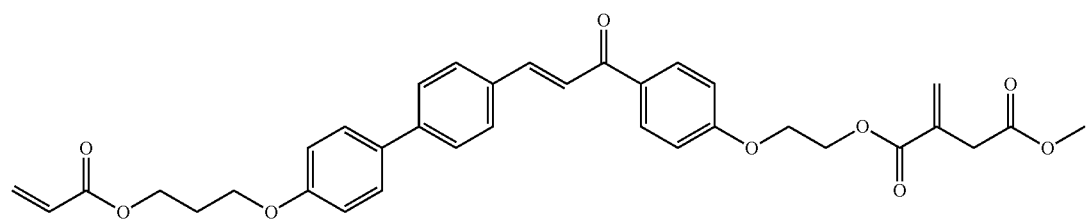 [SMILES: C=CC(=O)OCCCOc1ccc(-c2ccc(/C=C/C(=O)c3ccc(OCCOC(=O)C(=C)CC(=O)OC)cc3)cc2)cc1] |
| 435 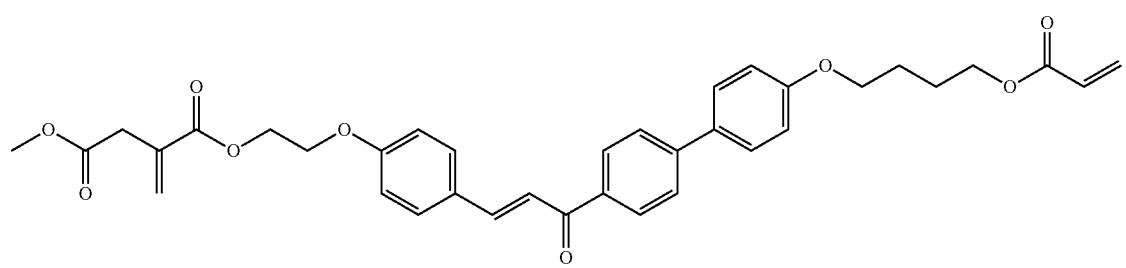 [SMILES: C=CC(=O)OCCCCOc1ccc(-c2ccc(C(=O)/C=C/c3ccc(OCCOC(=O)C(=C)CC(=O)OC)cc3)cc2)cc1] |

| No. |
|---|
| 436 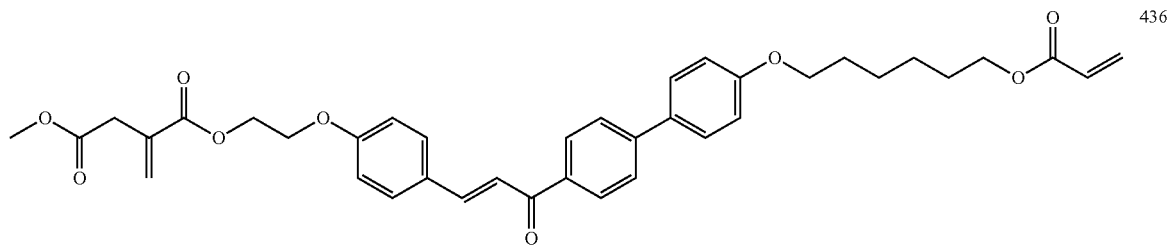 |
| 437 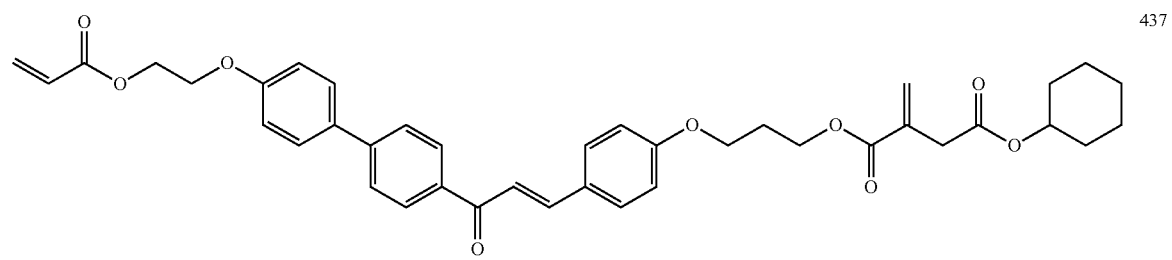 |
| 438 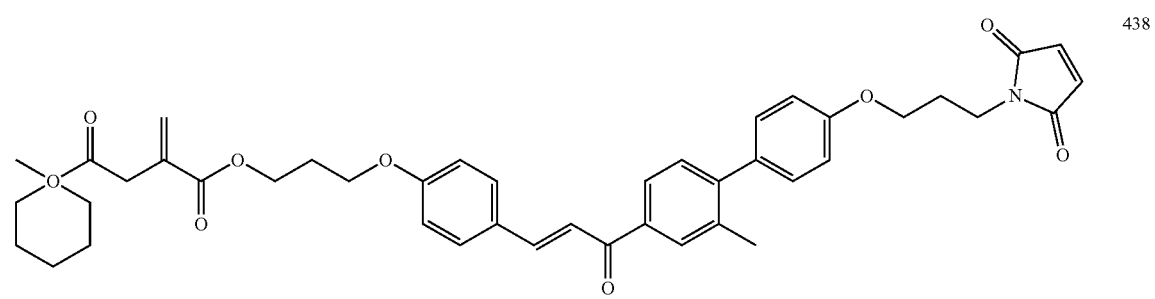 |
| 439 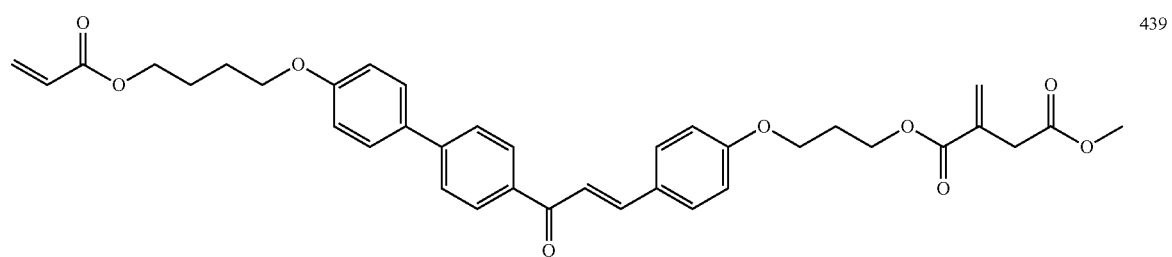 |
| 440 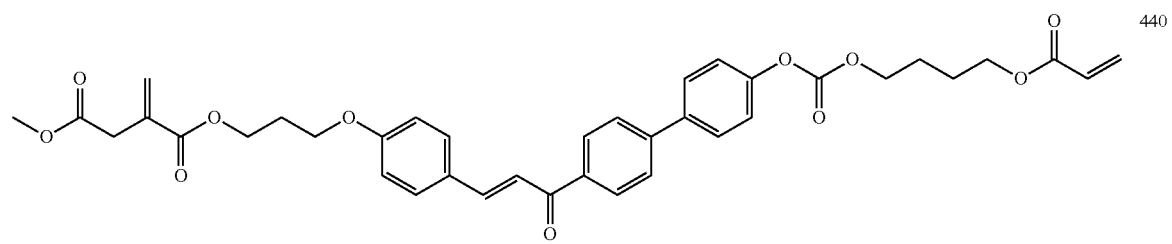 |
| 441 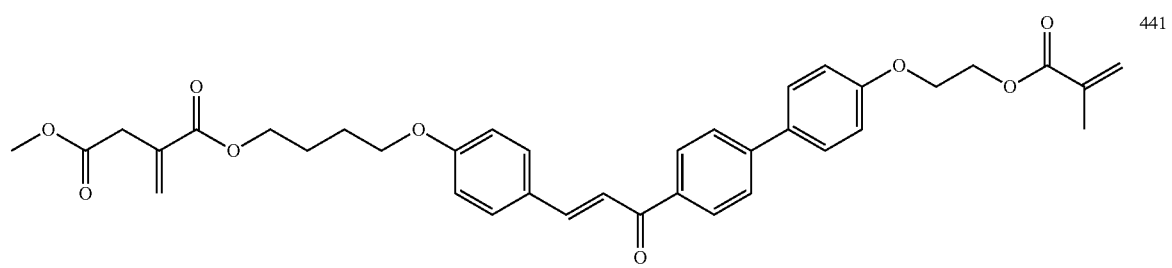 |

-continued
| | No. |
|---|---|
| 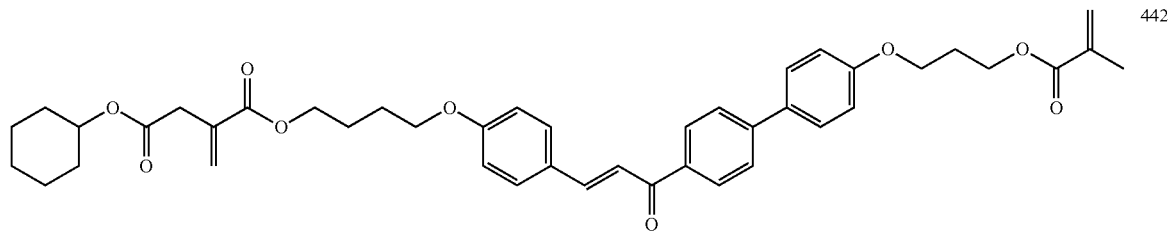 | 442 |
| 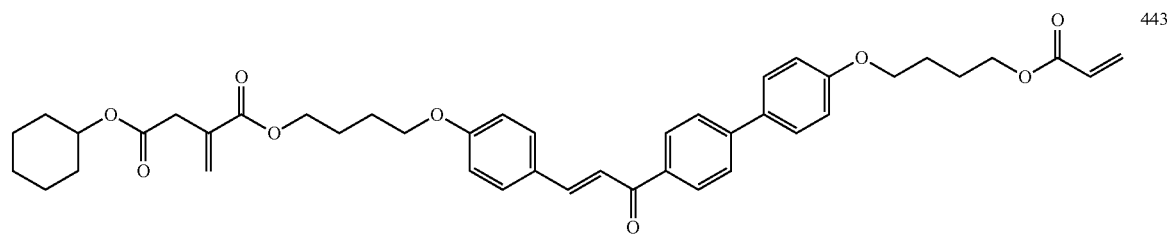 | 443 |
| 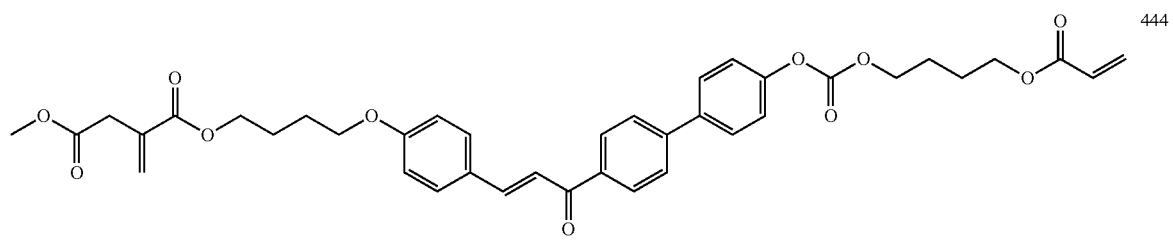 | 444 |
| 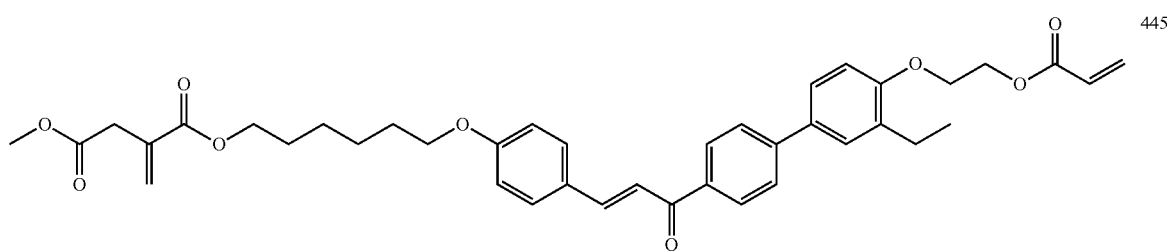 | 445 |
| 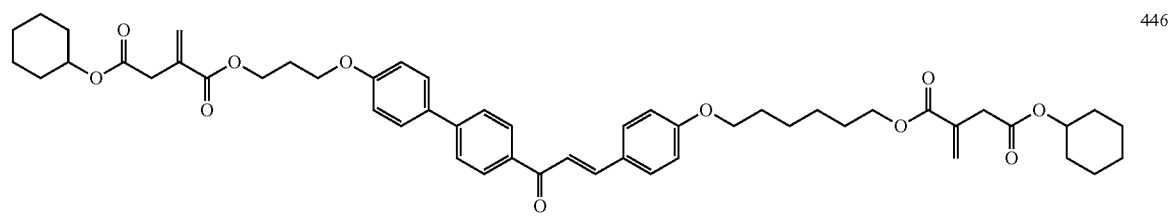 | 446 |
| 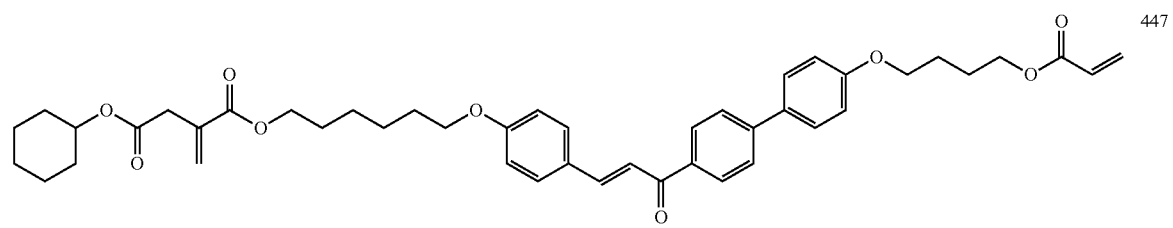 | 447 |

| No. |
|---|
| 448 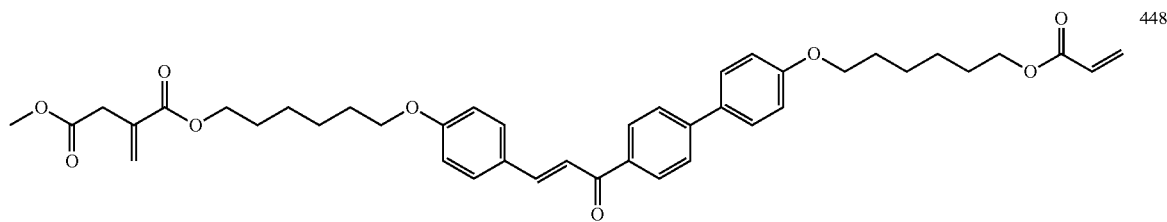 |
| 449 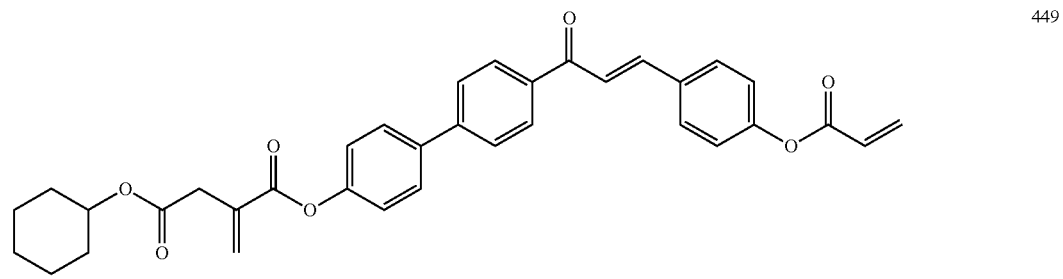 |
| 450 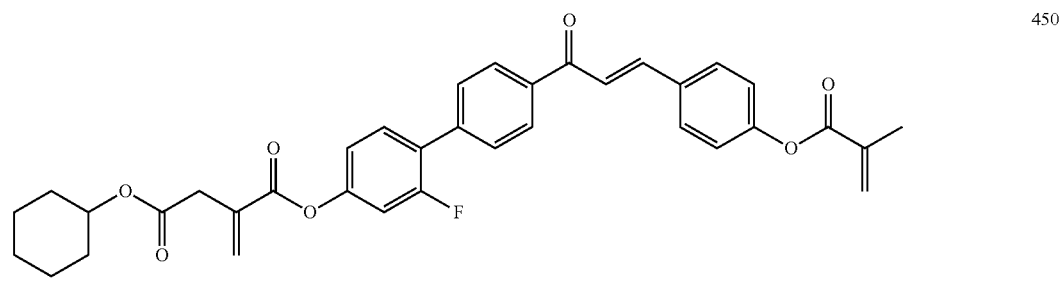 |
| 451 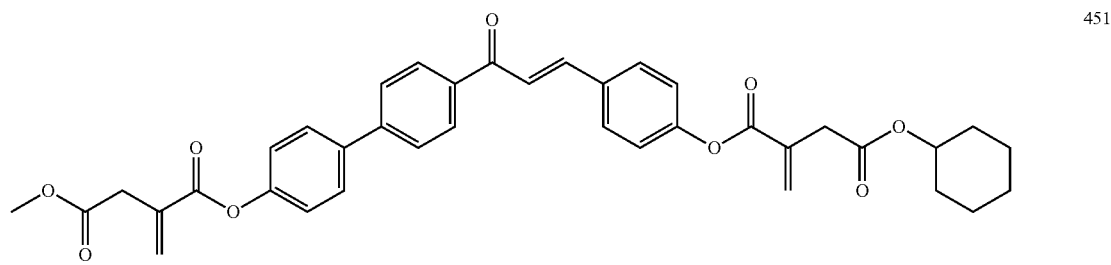 |
| 452 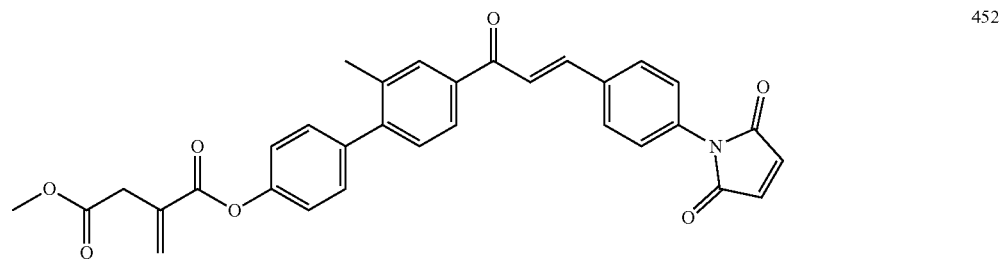 |
| 453 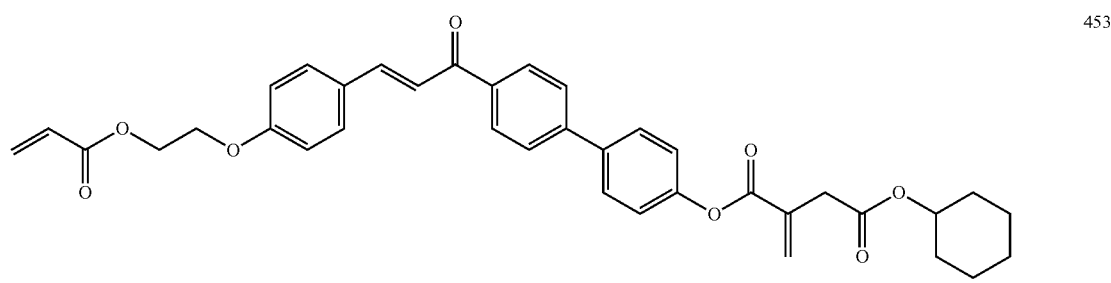 |

| No. |
|---|
| 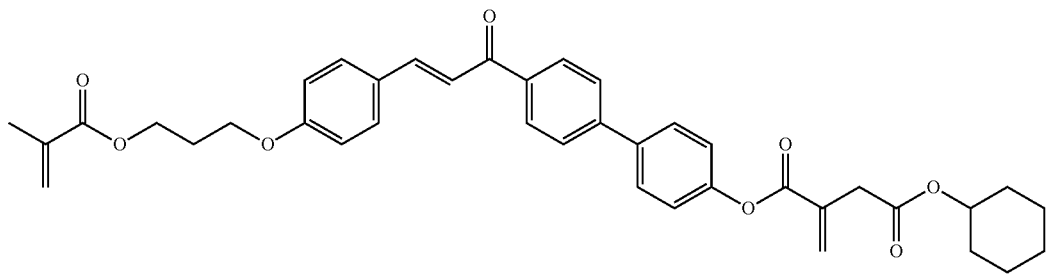 [SMILES: C=C(C)C(=O)OCCCOc1ccc(/C=C/C(=O)c2ccc(-c3ccc(OC(=O)C(=C)CC(=O)OC4CCCCC4)cc3)cc2)cc1] 454 |
| 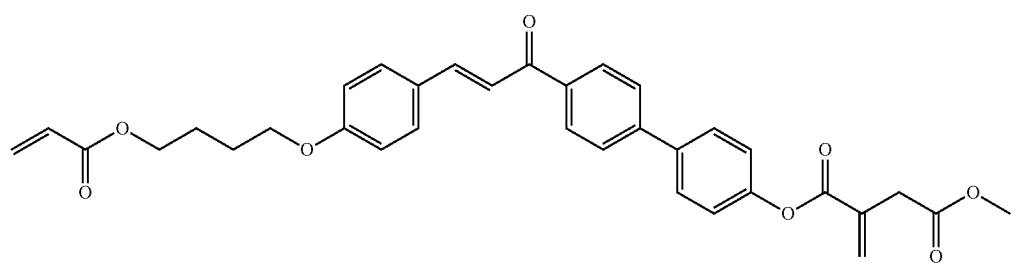 [SMILES: C=CC(=O)OCCCCOc1ccc(/C=C/C(=O)c2ccc(-c3ccc(OC(=O)C(=C)CC(=O)OC)cc3)cc2)cc1] 455 |
| 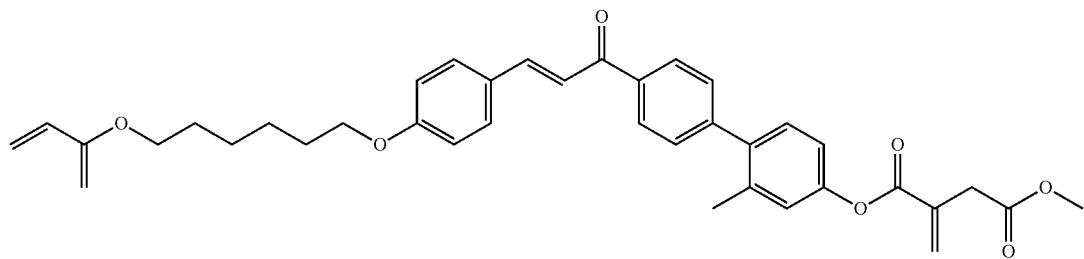 [SMILES: C=CC(=C)OCCCCCCOc1ccc(/C=C/C(=O)c2ccc(-c3ccc(OC(=O)C(=C)CC(=O)OC)cc3C)cc2)cc1] 456 |
| 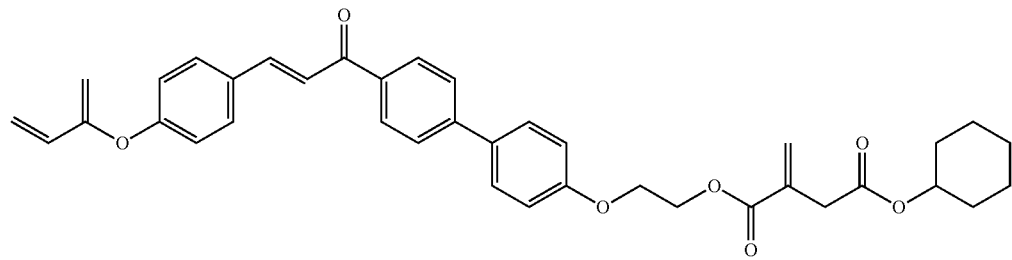 [SMILES: C=CC(=C)Oc1ccc(/C=C/C(=O)c2ccc(-c3ccc(OCCOC(=O)C(=C)CC(=O)OC4CCCCC4)cc3)cc2)cc1] 457 |
| 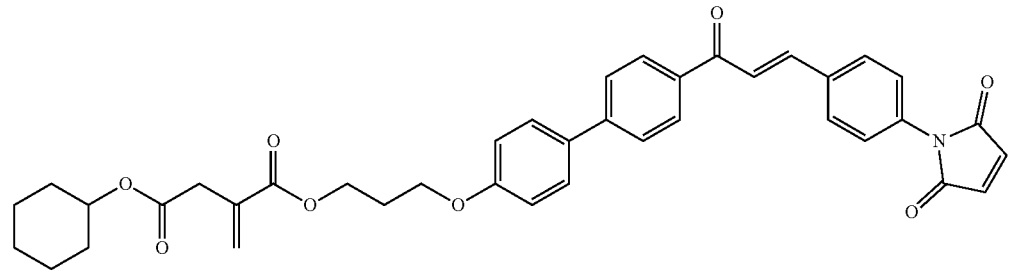 [SMILES: C=C(CC(=O)OC1CCCCC1)C(=O)OCCCOc1ccc(-c2ccc(C(=O)/C=C/c3ccc(N4C(=O)C=CC4=O)cc3)cc2)cc1] 458 |

| No. |
|---|
| 459 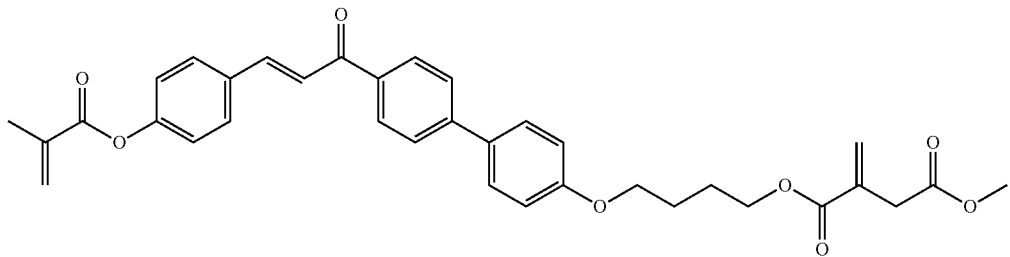 [SMILES: C=C(C)C(=O)Oc1ccc(/C=C/C(=O)c2ccc(-c3ccc(OCCCCOC(=O)C(=C)CC(=O)OC)cc3)cc2)cc1] |
| 460 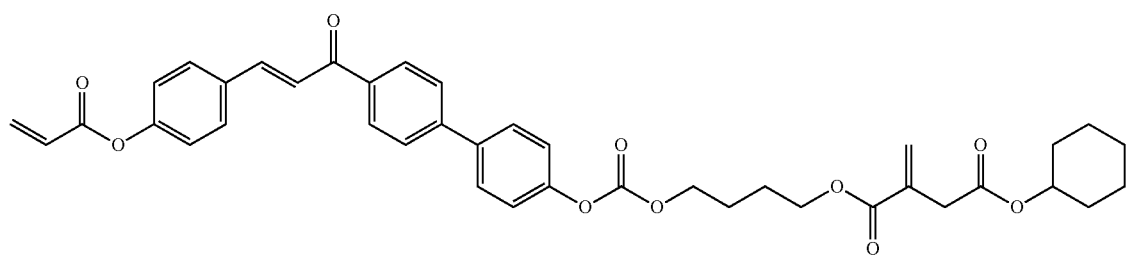 [SMILES: C=CC(=O)Oc1ccc(/C=C/C(=O)c2ccc(-c3ccc(OC(=O)OCCCCOC(=O)C(=C)CC(=O)OC4CCCCC4)cc3)cc2)cc1] |
| 461 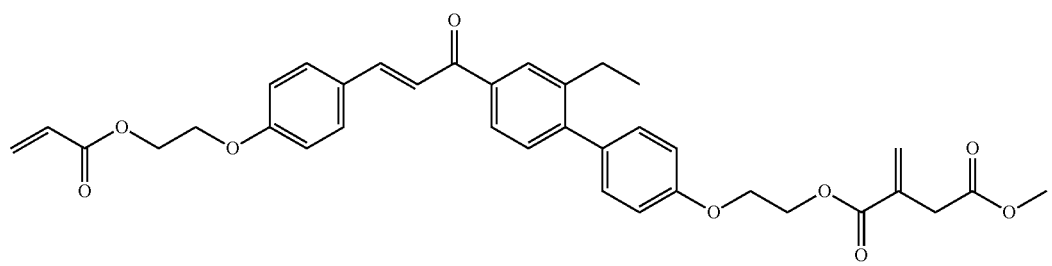 [SMILES: C=CC(=O)OCCOc1ccc(/C=C/C(=O)c2ccc(-c3ccc(OCCOC(=O)C(=C)CC(=O)OC)cc3)c(CC)c2)cc1] |
| 462 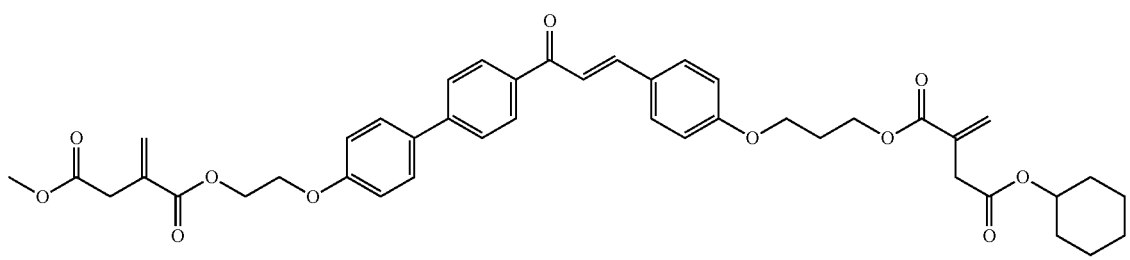 [SMILES: C=C(CC(=O)OC)C(=O)OCCOc1ccc(-c2ccc(C(=O)/C=C/c3ccc(OCCCOC(=O)C(=C)CC(=O)OC4CCCCC4)cc3)cc2)cc1] |
| 463 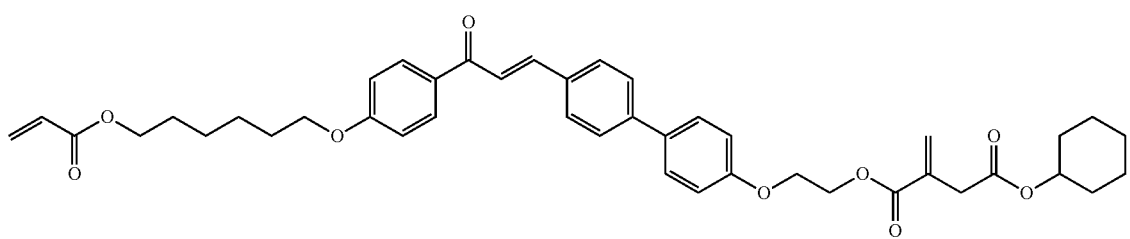 [SMILES: C=CC(=O)OCCCCCCOc1ccc(C(=O)/C=C/c2ccc(-c3ccc(OCCOC(=O)C(=C)CC(=O)OC4CCCCC4)cc3)cc2)cc1] |
| 464 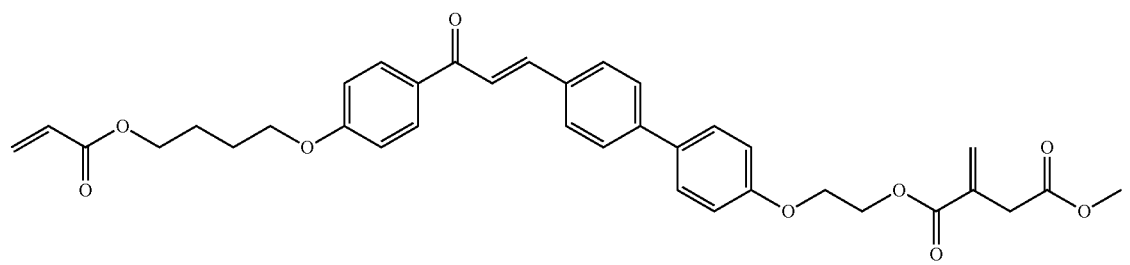 [SMILES: C=CC(=O)OCCCCOc1ccc(C(=O)/C=C/c2ccc(-c3ccc(OCCOC(=O)C(=C)CC(=O)OC)cc3)cc2)cc1] |

| | No. |
|---|---|
| 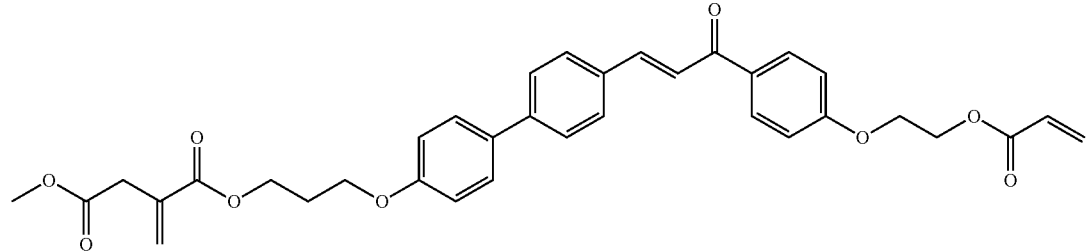 [SMILES: C=CC(=O)OCCOc1ccc(C(=O)/C=C/c2ccc(-c3ccc(OCCCOC(=O)C(=C)CC(=O)OC)cc3)cc2)cc1] | 465 |
| 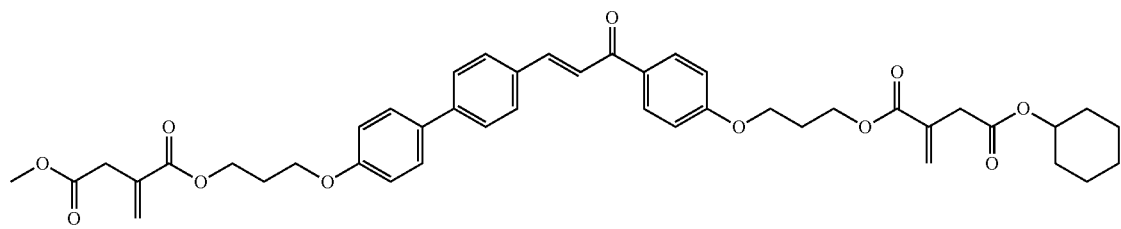 [SMILES: C=C(CC(=O)OC)C(=O)OCCCOc1ccc(-c2ccc(/C=C/C(=O)c3ccc(OCCCOC(=O)C(=C)CC(=O)OC4CCCCC4)cc3)cc2)cc1] | 466 |
| 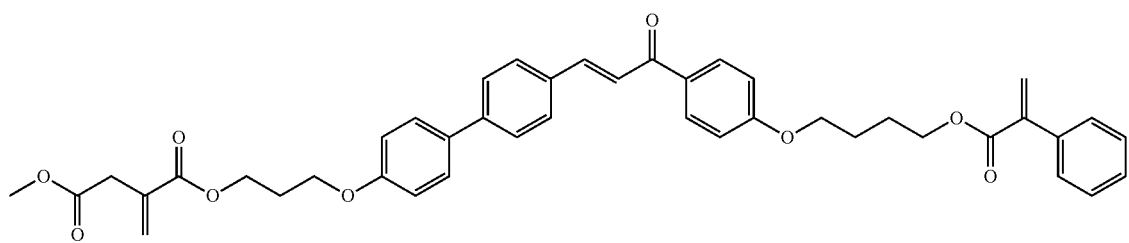 [SMILES: C=C(CC(=O)OC)C(=O)OCCCOc1ccc(-c2ccc(/C=C/C(=O)c3ccc(OCCCCOC(=O)C(=C)c4ccccc4)cc3)cc2)cc1] | 467 |
| 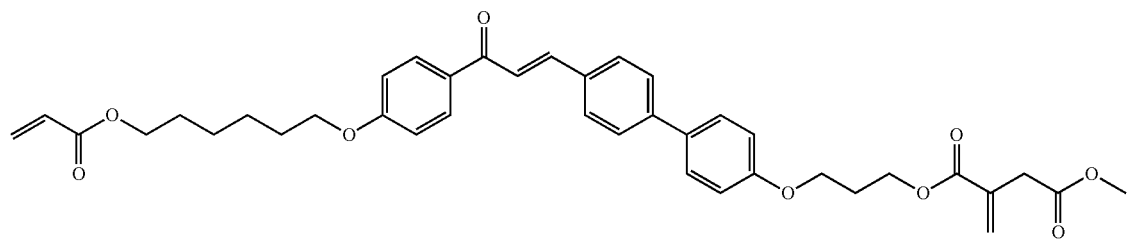 [SMILES: C=CC(=O)OCCCCCCOc1ccc(C(=O)/C=C/c2ccc(-c3ccc(OCCCOC(=O)C(=C)CC(=O)OC)cc3)cc2)cc1] | 468 |
| 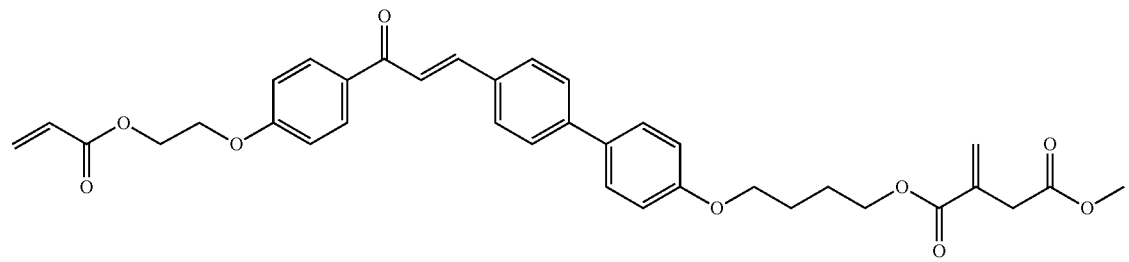 [SMILES: C=CC(=O)OCCOc1ccc(C(=O)/C=C/c2ccc(-c3ccc(OCCCCOC(=O)C(=C)CC(=O)OC)cc3)cc2)cc1] | 469 |
| 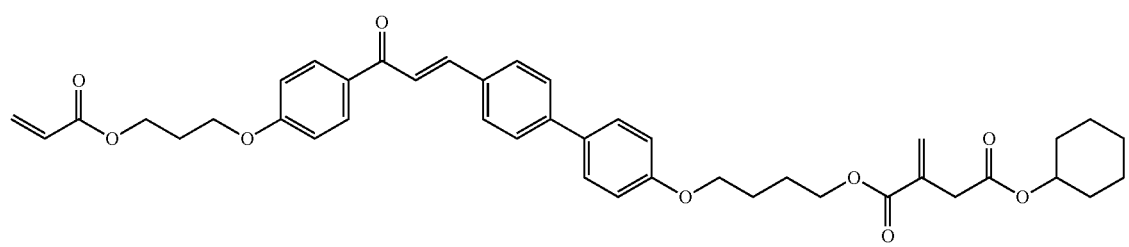 [SMILES: C=CC(=O)OCCCOc1ccc(C(=O)/C=C/c2ccc(-c3ccc(OCCCCOC(=O)C(=C)CC(=O)OC4CCCCC4)cc3)cc2)cc1] | 470 |

|No.|
|---|
|471 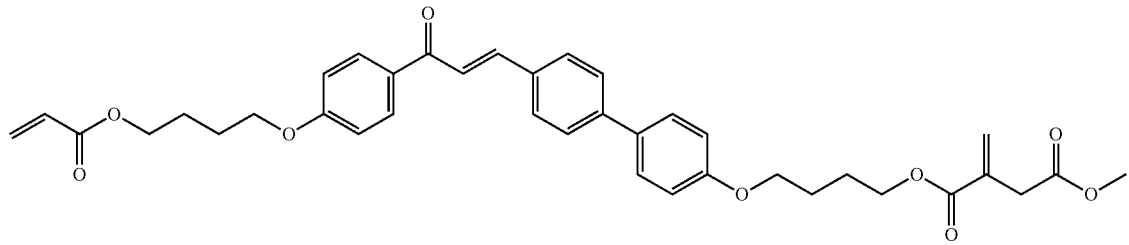 [SMILES: C=CC(=O)OCCCCOc1ccc(C(=O)/C=C/c2ccc(-c3ccc(OCCCCOC(=O)C(=C)CC(=O)OC)cc3)cc2)cc1]|
|472 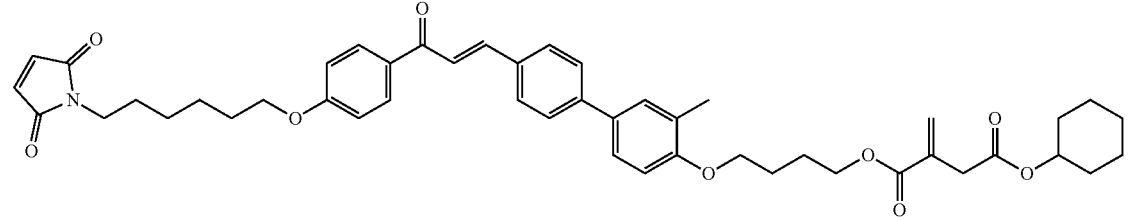 [SMILES: C=C(CC(=O)OC1CCCCC1)C(=O)OCCCCOc1ccc(-c2ccc(/C=C/C(=O)c3ccc(OCCCCCCN4C(=O)C=CC4=O)cc3)cc2)cc1C]|
|473 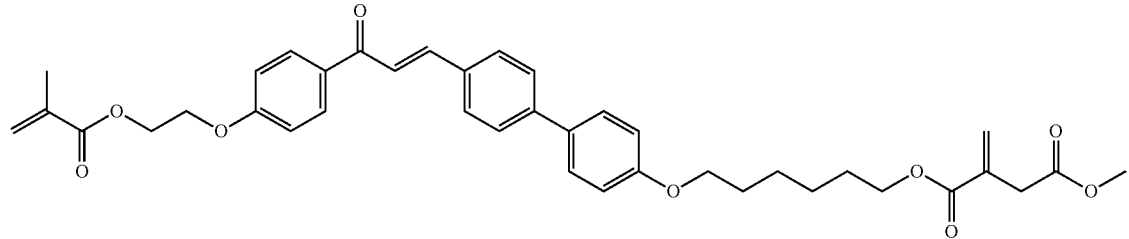 [SMILES: C=C(C)C(=O)OCCOc1ccc(C(=O)/C=C/c2ccc(-c3ccc(OCCCCCCOC(=O)C(=C)CC(=O)OC)cc3)cc2)cc1]|
|474 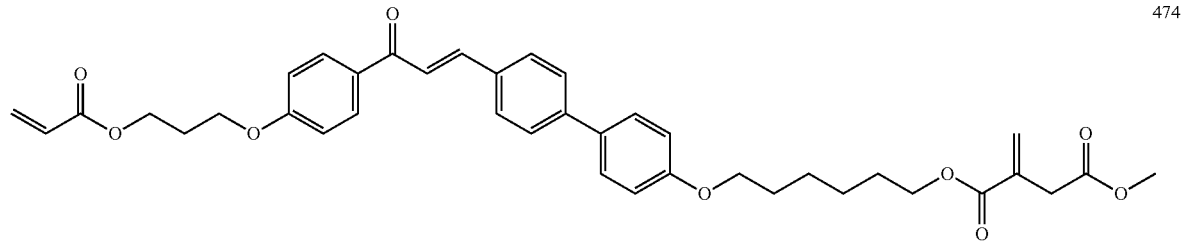|
|475 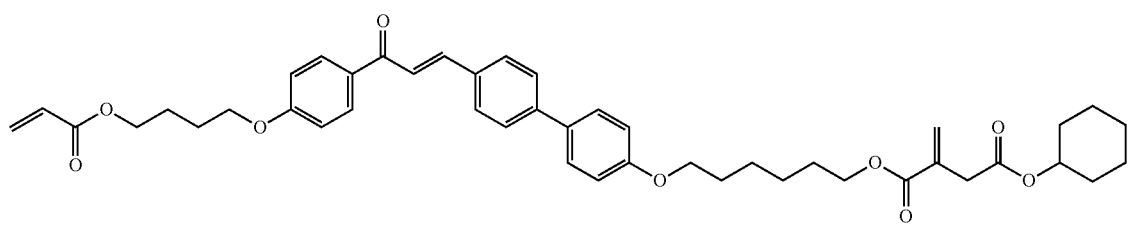 [SMILES: C=CC(=O)OCCCCOc1ccc(C(=O)/C=C/c2ccc(-c3ccc(OCCCCCCOC(=O)C(=C)CC(=O)OC4CCCCC4)cc3)cc2)cc1]|
|476 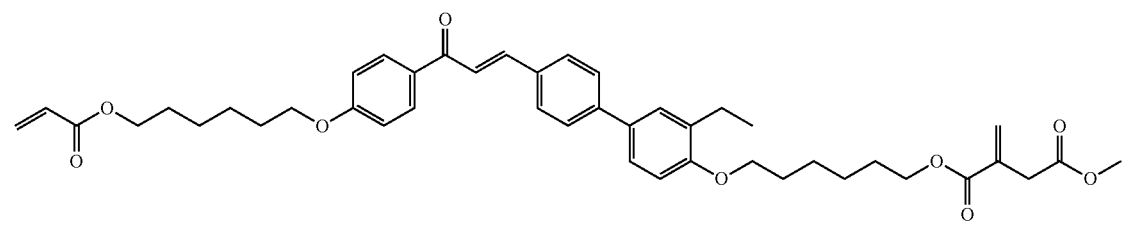 [SMILES: C=CC(=O)OCCCCCCOc1ccc(C(=O)/C=C/c2ccc(-c3ccc(OCCCCCCOC(=O)C(=C)CC(=O)OC)c(CC)c3)cc2)cc1]|

| | No. |
|---|---|
| 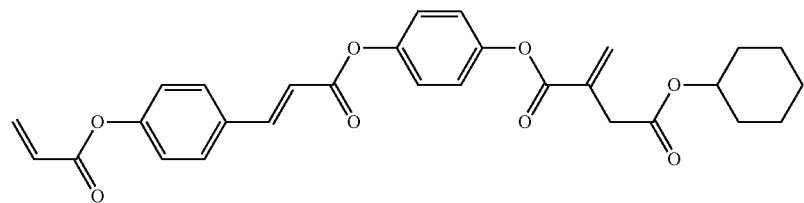 [SMILES: C=CC(=O)Oc1ccc(/C=C/C(=O)Oc2ccc(OC(=O)C(=C)CC(=O)OC3CCCCC3)cc2)cc1] | 477 |
| 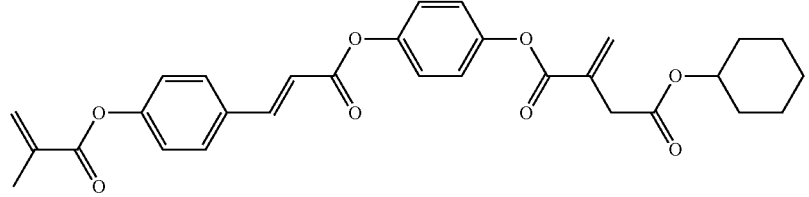 [SMILES: C=C(C)C(=O)Oc1ccc(/C=C/C(=O)Oc2ccc(OC(=O)C(=C)CC(=O)OC3CCCCC3)cc2)cc1] | 478 |
| 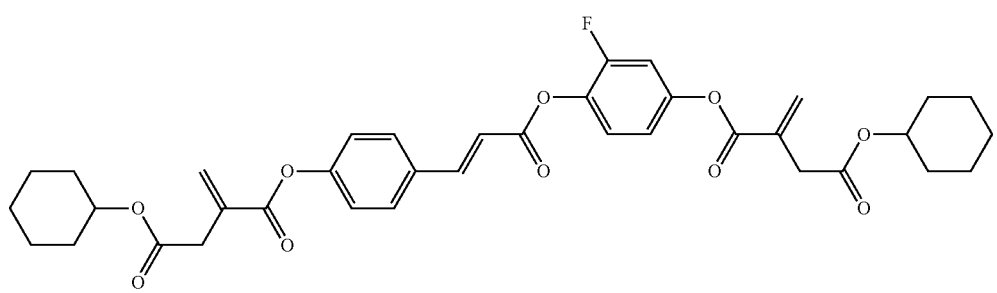 [SMILES: C=C(CC(=O)OC1CCCCC1)C(=O)Oc1ccc(/C=C/C(=O)Oc2ccc(OC(=O)C(=C)CC(=O)OC3CCCCC3)cc2F)cc1] | 479 |
| 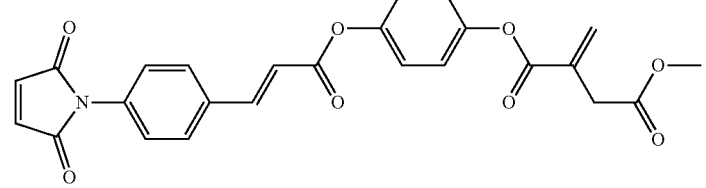 | 480 |
| 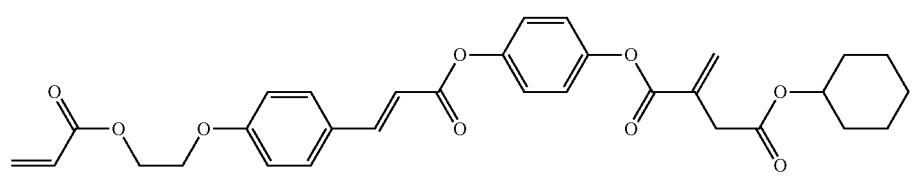 [SMILES: C=CC(=O)OCCOc1ccc(/C=C/C(=O)Oc2ccc(OC(=O)C(=C)CC(=O)OC3CCCCC3)cc2)cc1] | 481 |
| 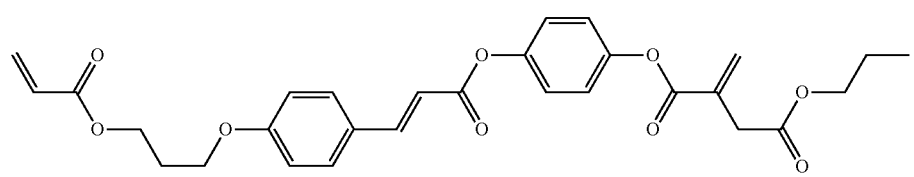 [SMILES: C=CC(=O)OCCCOc1ccc(/C=C/C(=O)Oc2ccc(OC(=O)C(=C)CC(=O)OCCC)cc2)cc1] | 482 |
| 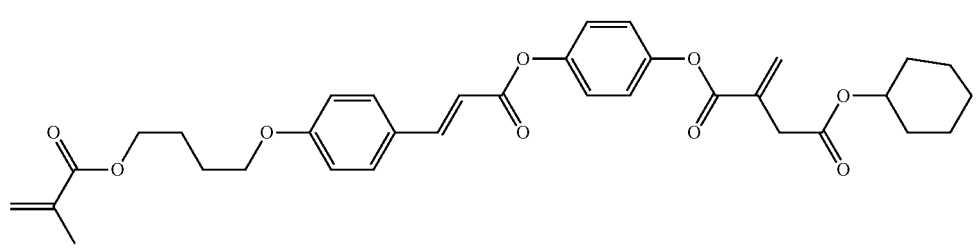 [SMILES: C=C(C)C(=O)OCCCCOc1ccc(/C=C/C(=O)Oc2ccc(OC(=O)C(=C)CC(=O)OC3CCCCC3)cc2)cc1] | 483 |

| No. |
|---|
| 484 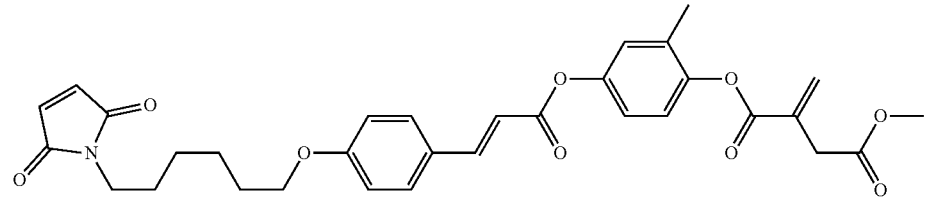 [SMILES: C=C(CC(=O)OC)C(=O)Oc1ccc(OC(=O)/C=C/c2ccc(OCCCCCCN3C(=O)C=CC3=O)cc2)cc1C] |
| 485 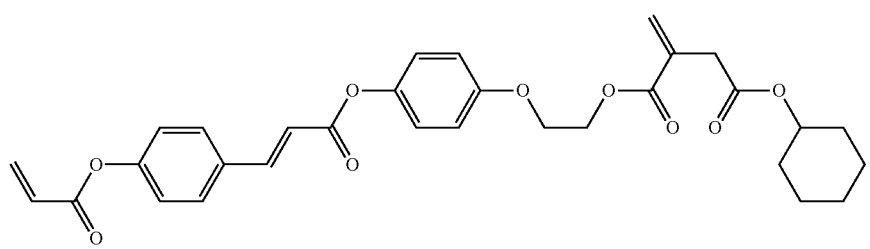 [SMILES: C=CC(=O)Oc1ccc(/C=C/C(=O)Oc2ccc(OCCOC(=O)C(=C)CC(=O)OC3CCCCC3)cc2)cc1] |
| 486 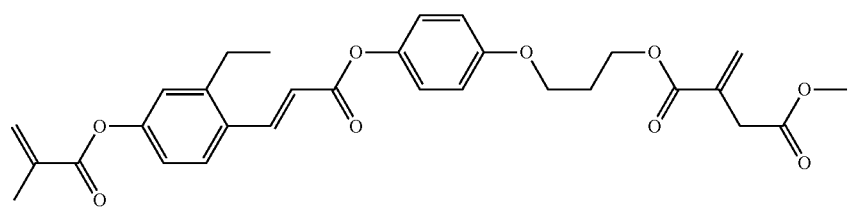 [SMILES: C=C(C)C(=O)Oc1ccc(/C=C/C(=O)Oc2ccc(OCCCOC(=O)C(=C)CC(=O)OC)cc2)c(CC)c1] |
| 487 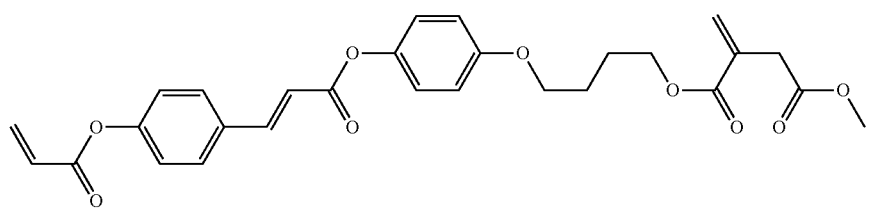 [SMILES: C=CC(=O)Oc1ccc(/C=C/C(=O)Oc2ccc(OCCCCOC(=O)C(=C)CC(=O)OC)cc2)cc1] |
| 488 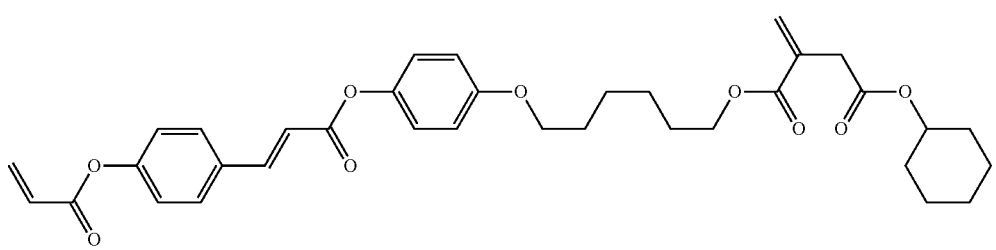 [SMILES: C=CC(=O)Oc1ccc(/C=C/C(=O)Oc2ccc(OCCCCCCOC(=O)C(=C)CC(=O)OC3CCCCC3)cc2)cc1] |
| 489 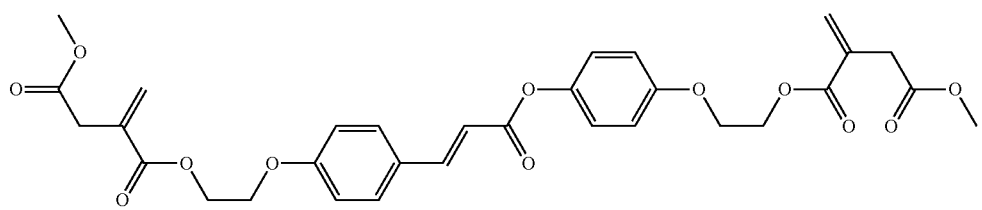 [SMILES: C=C(CC(=O)OC)C(=O)OCCOc1ccc(/C=C/C(=O)Oc2ccc(OCCOC(=O)C(=C)CC(=O)OC)cc2)cc1] |
| 490 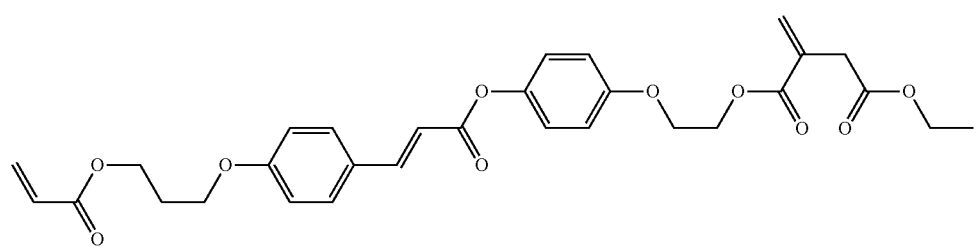 [SMILES: C=CC(=O)OCCCOc1ccc(/C=C/C(=O)Oc2ccc(OCCOC(=O)C(=C)CC(=O)OCC)cc2)cc1] |

| No. |
|---|
| 491 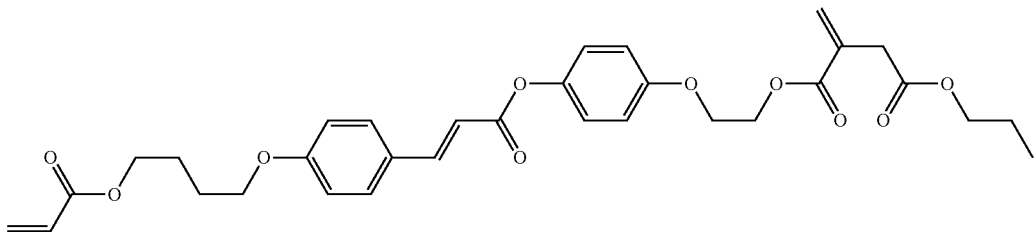 [SMILES: C=CC(=O)OCCCCOc1ccc(/C=C/C(=O)Oc2ccc(OCCOC(=O)C(=C)CC(=O)OCCC)cc2)cc1] |
| 492 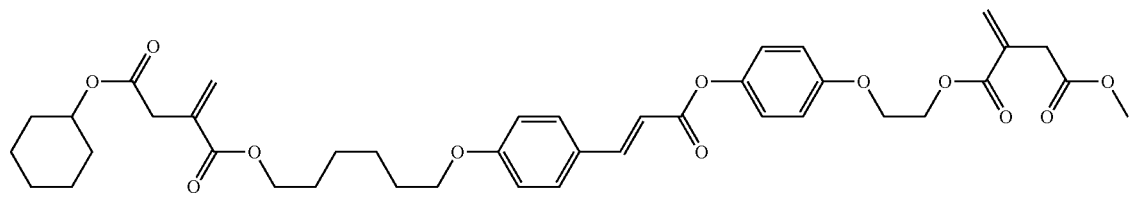 [SMILES: C=C(CC(=O)OC)C(=O)OCCOc1ccc(OC(=O)/C=C/c2ccc(OCCCCCCOC(=O)C(=C)CC(=O)OC3CCCCC3)cc2)cc1] |
| 493 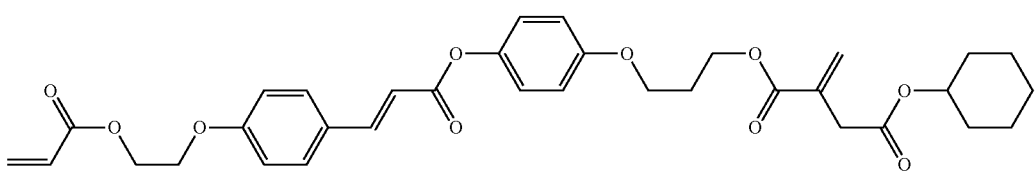 [SMILES: C=CC(=O)OCCOc1ccc(/C=C/C(=O)Oc2ccc(OCCCOC(=O)C(=C)CC(=O)OC3CCCCC3)cc2)cc1] |
| 494 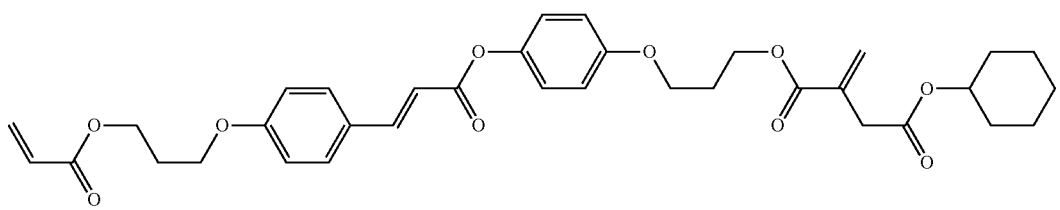 [SMILES: C=CC(=O)OCCCOc1ccc(/C=C/C(=O)Oc2ccc(OCCCOC(=O)C(=C)CC(=O)OC3CCCCC3)cc2)cc1] |
| 495 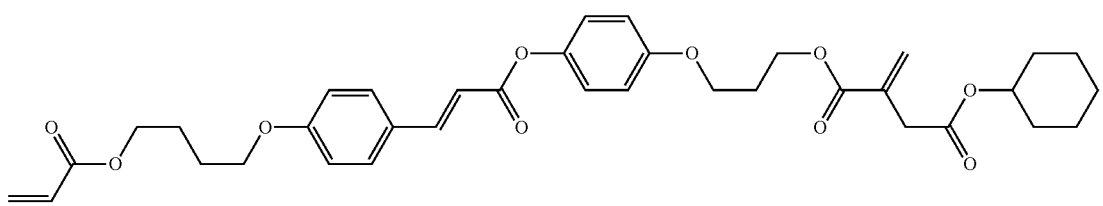 [SMILES: C=CC(=O)OCCCCOc1ccc(/C=C/C(=O)Oc2ccc(OCCCOC(=O)C(=C)CC(=O)OC3CCCCC3)cc2)cc1] |
| 496 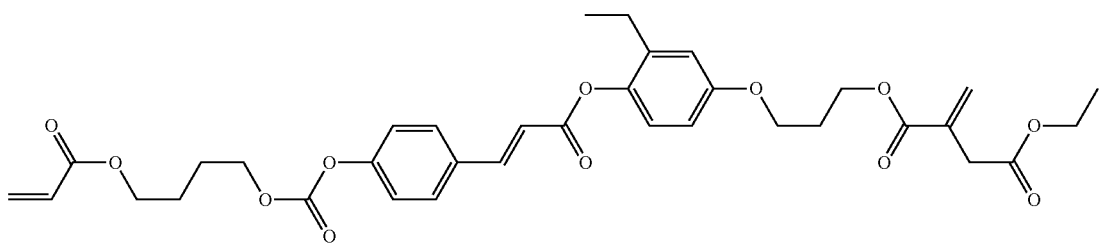 [SMILES: C=CC(=O)OCCCCOC(=O)Oc1ccc(/C=C/C(=O)Oc2ccc(OCCCOC(=O)C(=C)CC(=O)OCC)cc2CC)cc1] |
| 497 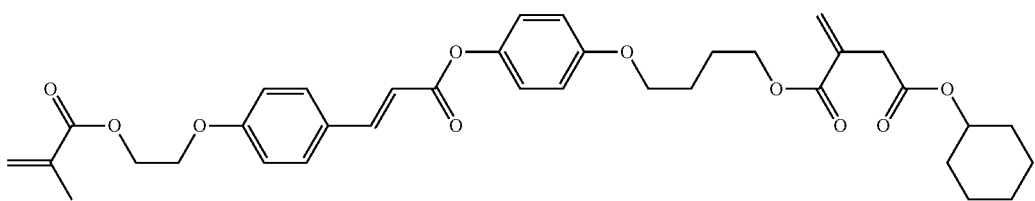 [SMILES: C=C(C)C(=O)OCCOc1ccc(/C=C/C(=O)Oc2ccc(OCCCCOC(=O)C(=C)CC(=O)OC3CCCCC3)cc2)cc1] |

| No. |
|---|
| 498 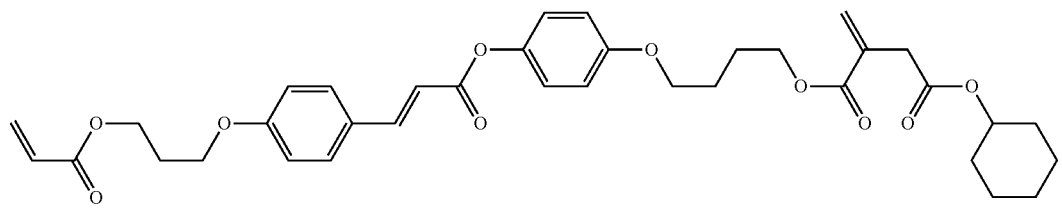 [SMILES: C=CC(=O)OCCCOc1ccc(/C=C/C(=O)Oc2ccc(OCCCCOC(=O)C(=C)CC(=O)OC3CCCCC3)cc2)cc1] |
| 499 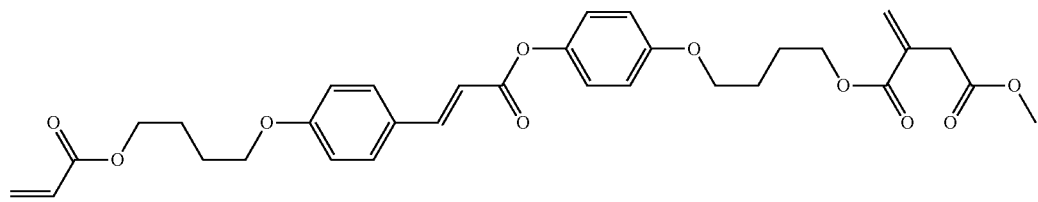 [SMILES: C=CC(=O)OCCCCOc1ccc(/C=C/C(=O)Oc2ccc(OCCCCOC(=O)C(=C)CC(=O)OC)cc2)cc1] |
| 500 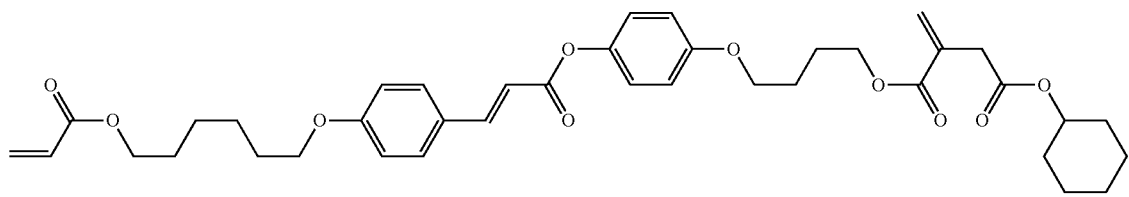 [SMILES: C=CC(=O)OCCCCCCOc1ccc(/C=C/C(=O)Oc2ccc(OCCCCOC(=O)C(=C)CC(=O)OC3CCCCC3)cc2)cc1] |
| 501 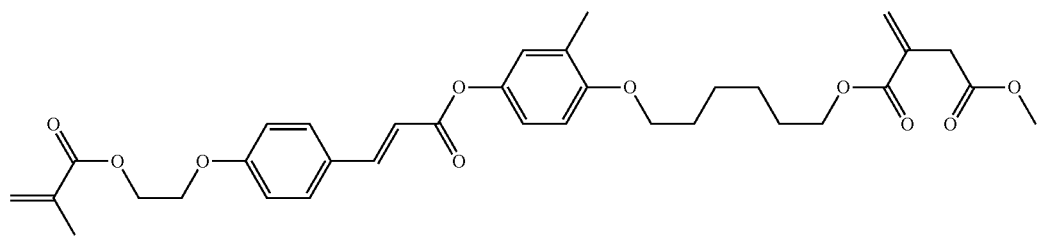 [SMILES: C=C(C)C(=O)OCCOc1ccc(/C=C/C(=O)Oc2ccc(OCCCCCCOC(=O)C(=C)CC(=O)OC)c(C)c2)cc1] |
| 502 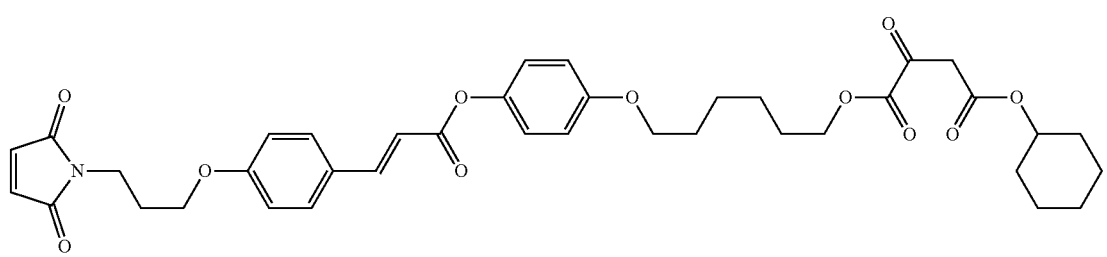 [SMILES: O=C(/C=C/c1ccc(OCCCN2C(=O)C=CC2=O)cc1)Oc1ccc(OCCCCCCOC(=O)C(=O)CC(=O)OC2CCCCC2)cc1] |
| 503 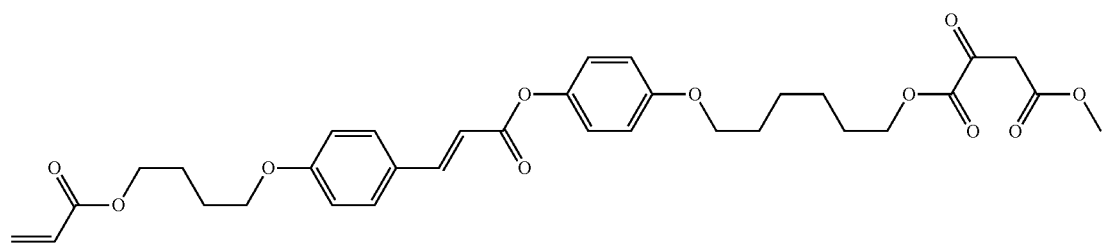 [SMILES: C=CC(=O)OCCCCOc1ccc(/C=C/C(=O)Oc2ccc(OCCCCCCOC(=O)C(=O)CC(=O)OC)cc2)cc1] |
| 504 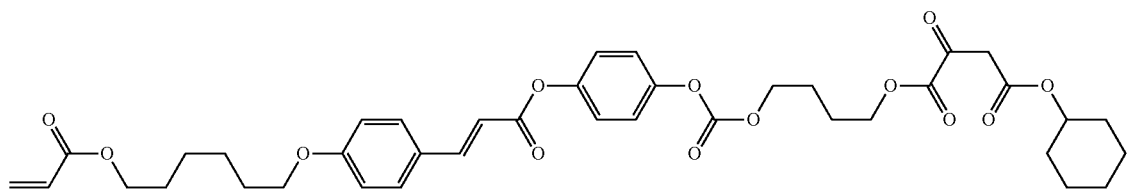 [SMILES: C=CC(=O)OCCCCCCOc1ccc(/C=C/C(=O)Oc2ccc(OC(=O)OCCCCOC(=O)C(=O)CC(=O)OC3CCCCC3)cc2)cc1] |

-continued
| No. |
|---|
| 505 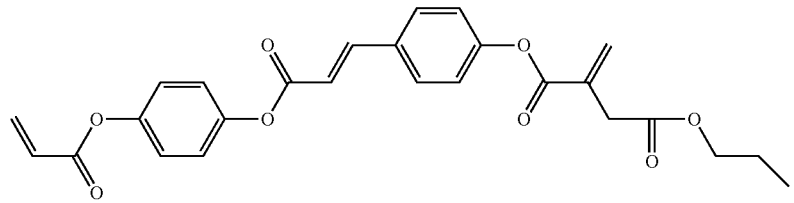 [SMILES: C=CC(=O)Oc1ccc(OC(=O)/C=C/c2ccc(OC(=O)C(=C)CC(=O)OCCC)cc2)cc1] |
| 506 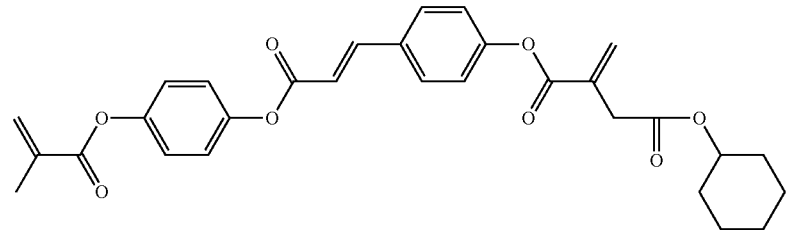 [SMILES: C=C(C)C(=O)Oc1ccc(OC(=O)/C=C/c2ccc(OC(=O)C(=C)CC(=O)OC3CCCCC3)cc2)cc1] |
| 507 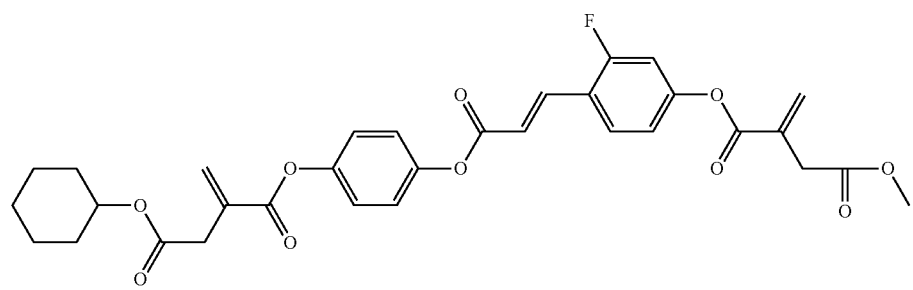 [SMILES: C=C(CC(=O)OC)C(=O)Oc1ccc(/C=C/C(=O)Oc2ccc(OC(=O)C(=C)CC(=O)OC3CCCCC3)cc2)c(F)c1] |
| 508 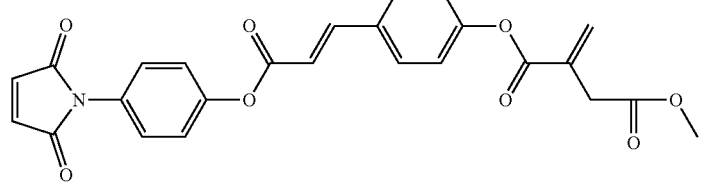 |
| 509 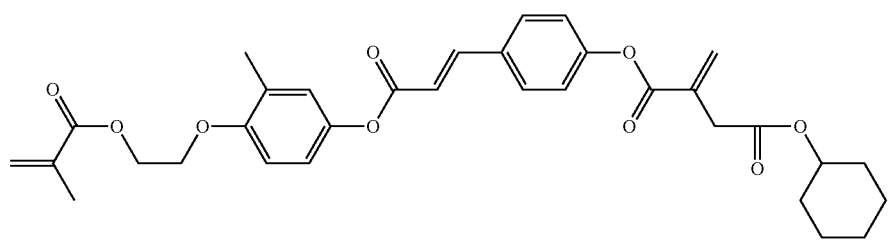 [SMILES: C=C(C)C(=O)OCCOc1ccc(OC(=O)/C=C/c2ccc(OC(=O)C(=C)CC(=O)OC3CCCCC3)cc2)cc1C] |
| 510 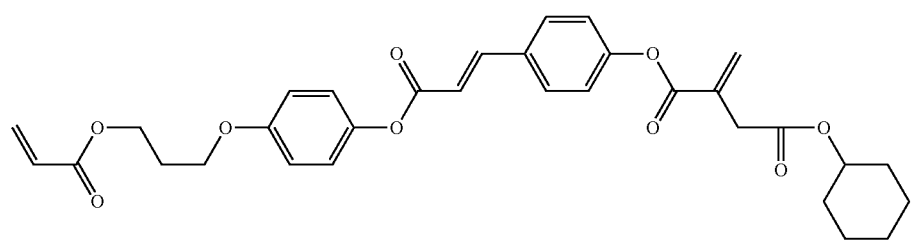 [SMILES: C=CC(=O)OCCCOc1ccc(OC(=O)/C=C/c2ccc(OC(=O)C(=C)CC(=O)OC3CCCCC3)cc2)cc1] |

-continued
| | No. |
|---|---|
| 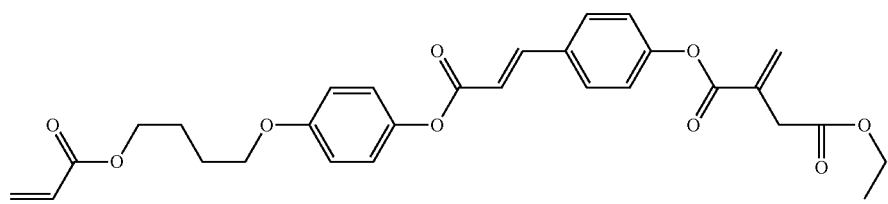 [SMILES: C=CC(=O)OCCCCOc1ccc(OC(=O)/C=C/c2ccc(OC(=O)C(=C)CC(=O)OCC)cc2)cc1] | 511 |
| 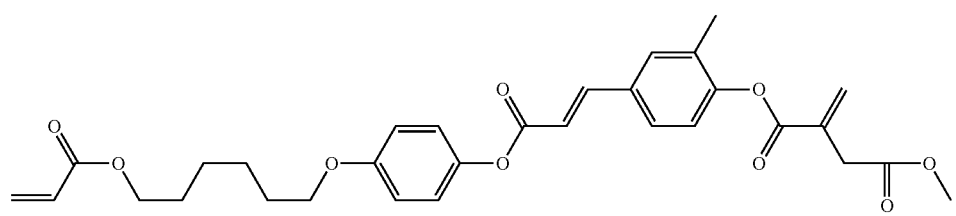 [SMILES: C=CC(=O)OCCCCCCOc1ccc(OC(=O)/C=C/c2ccc(OC(=O)C(=C)CC(=O)OC)c(C)c2)cc1] | 512 |
| 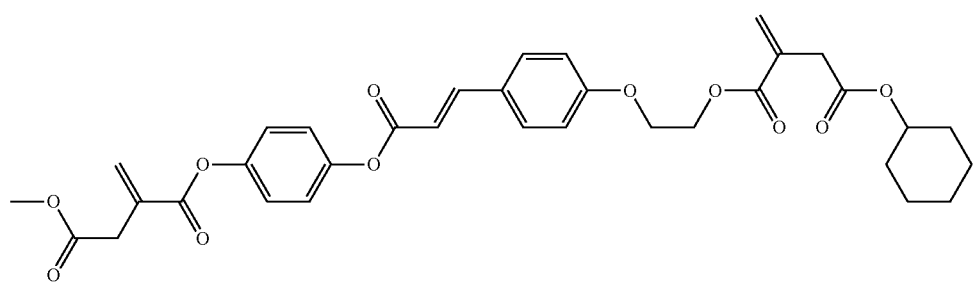 [SMILES: C=C(CC(=O)OC1CCCCC1)C(=O)OCCOc1ccc(/C=C/C(=O)Oc2ccc(OC(=O)C(=C)CC(=O)OC)cc2)cc1] | 513 |
| 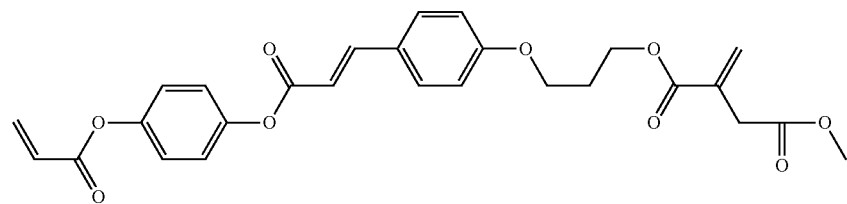 [SMILES: C=CC(=O)Oc1ccc(OC(=O)/C=C/c2ccc(OCCCOC(=O)C(=C)CC(=O)OC)cc2)cc1] | 514 |
| 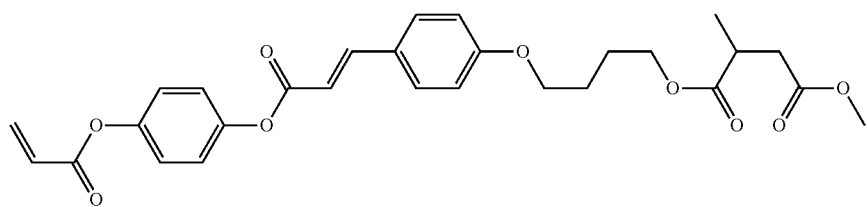 [SMILES: C=CC(=O)Oc1ccc(OC(=O)/C=C/c2ccc(OCCCCOC(=O)C(C)CC(=O)OC)cc2)cc1] | 515 |
| 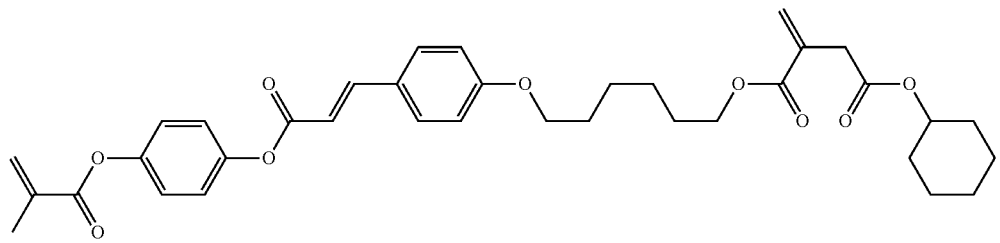 [SMILES: C=C(C)C(=O)Oc1ccc(OC(=O)/C=C/c2ccc(OCCCCCCOC(=O)C(=C)CC(=O)OC3CCCCC3)cc2)cc1] | 516 |

-continued
| No. |
|---|
| 517 |
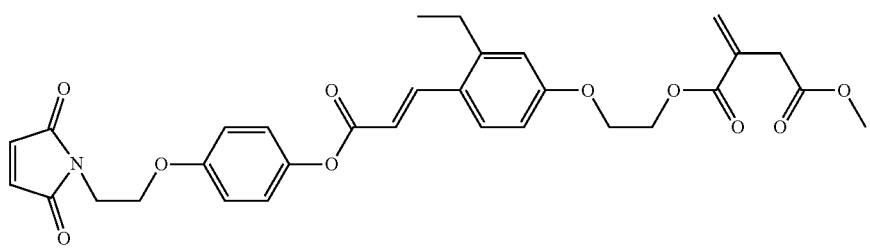 [SMILES: C=C(CC(=O)OC)C(=O)OCCOc1ccc(/C=C/C(=O)Oc2ccc(OCCN3C(=O)C=CC3=O)cc2)c(CC)c1]
| 518 |
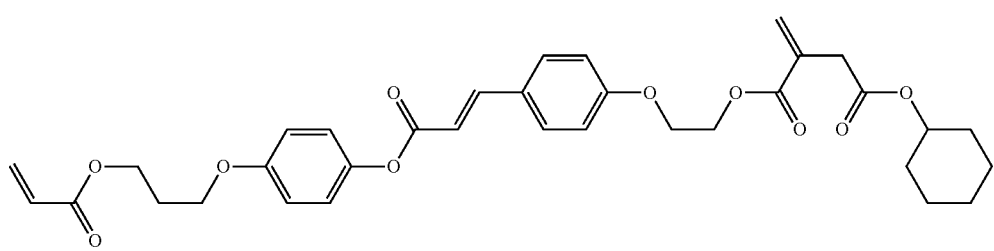 [SMILES: C=CC(=O)OCCCOc1ccc(OC(=O)/C=C/c2ccc(OCCOC(=O)C(=C)CC(=O)OC3CCCCC3)cc2)cc1]
| 519 |
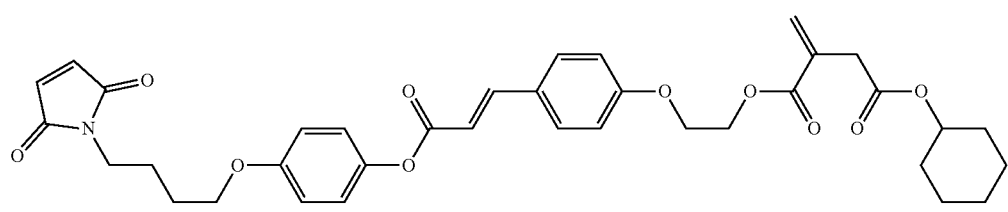 [SMILES: C=C(CC(=O)OC1CCCCC1)C(=O)OCCOc1ccc(/C=C/C(=O)Oc2ccc(OCCCCN3C(=O)C=CC3=O)cc2)cc1]
| 520 |
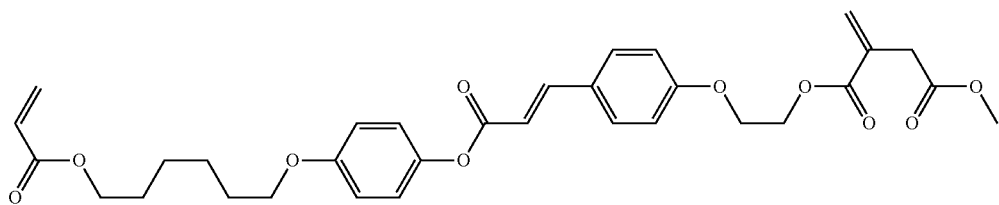 [SMILES: C=CC(=O)OCCCCCCOc1ccc(OC(=O)/C=C/c2ccc(OCCOC(=O)C(=C)CC(=O)OC)cc2)cc1]
| 521 |
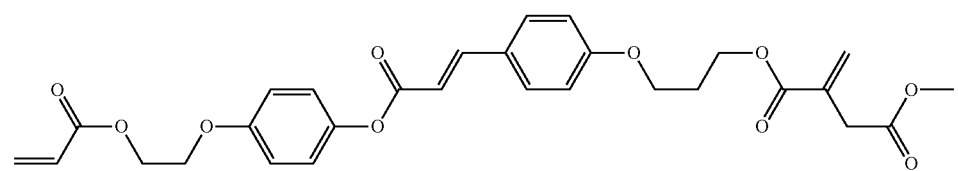
| 522 |
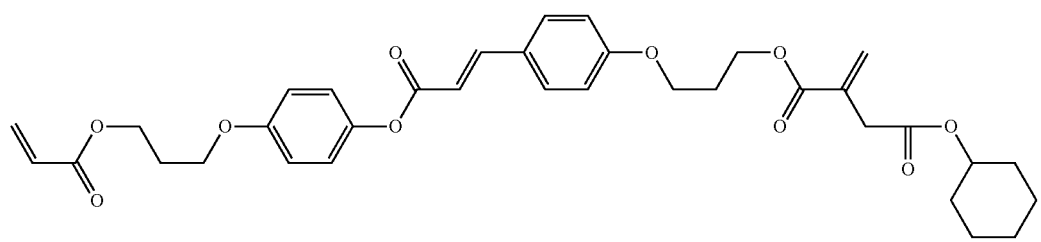 [SMILES: C=CC(=O)OCCCOc1ccc(OC(=O)/C=C/c2ccc(OCCCOC(=O)C(=C)CC(=O)OC3CCCCC3)cc2)cc1]
| 523 |
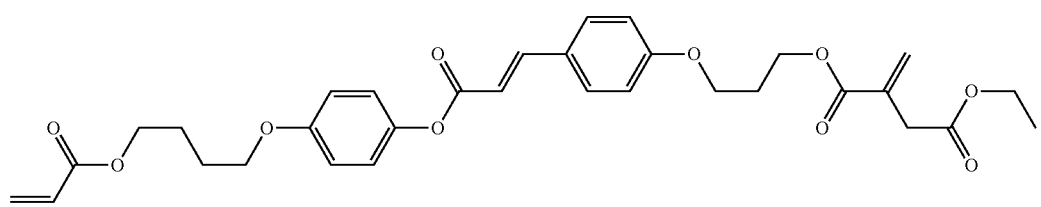 [SMILES: C=CC(=O)OCCCCOc1ccc(OC(=O)/C=C/c2ccc(OCCCOC(=O)C(=C)CC(=O)OCC)cc2)cc1]

| No. |
|---|
| 524 |
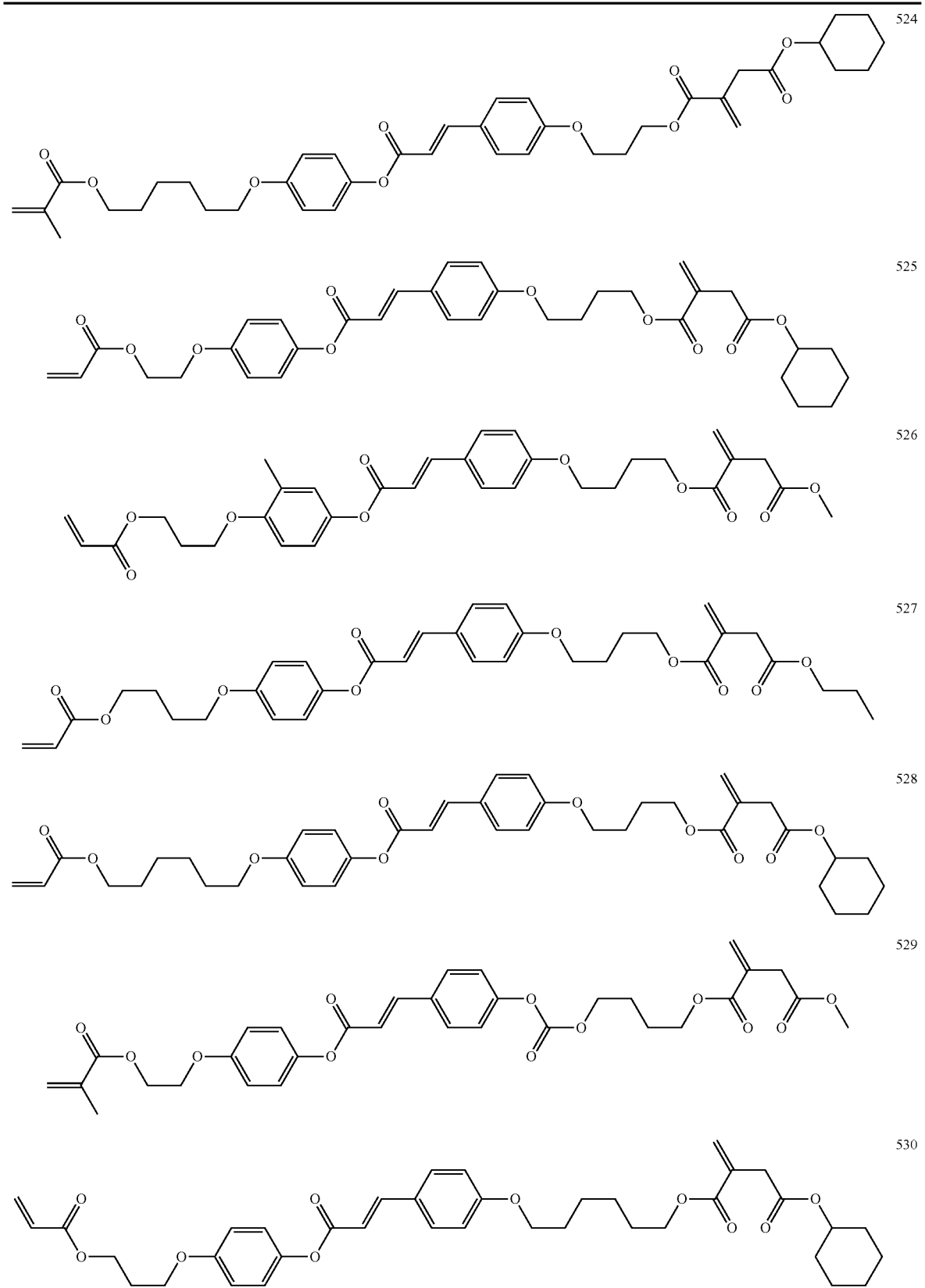

| No. |
|---|
| 531 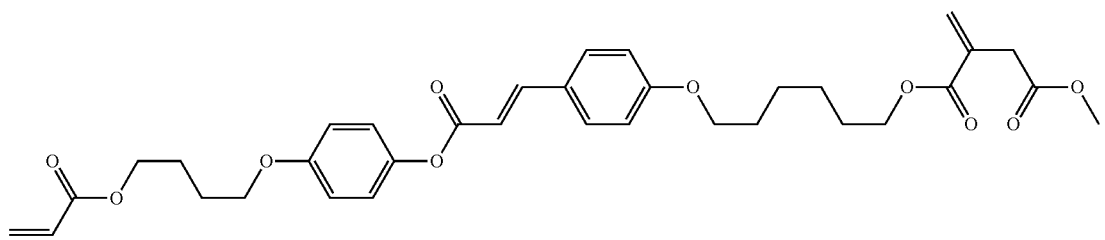 [SMILES: C=CC(=O)OCCCCOc1ccc(OC(=O)/C=C/c2ccc(OCCCCCCOC(=O)C(=C)CC(=O)OC)cc2)cc1] |
| 532 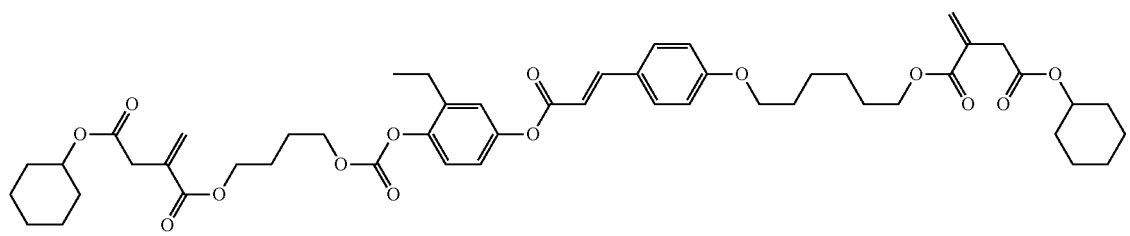 [SMILES: C=C(CC(=O)OC1CCCCC1)C(=O)OCCCCCCOc1ccc(/C=C/C(=O)Oc2ccc(OC(=O)OCCCCOC(=O)C(=C)CC(=O)OC3CCCCC3)c(CC)c2)cc1] |
| 533 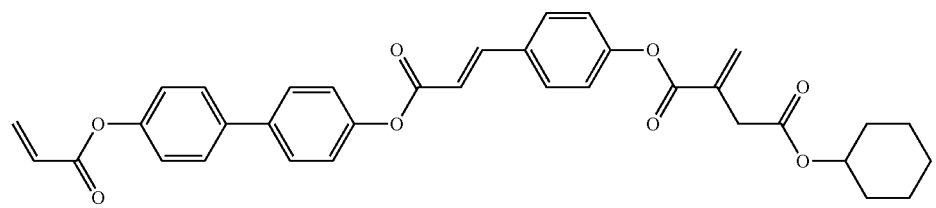 [SMILES: C=CC(=O)Oc1ccc(-c2ccc(OC(=O)/C=C/c3ccc(OC(=O)C(=C)CC(=O)OC4CCCCC4)cc3)cc2)cc1] |
| 534 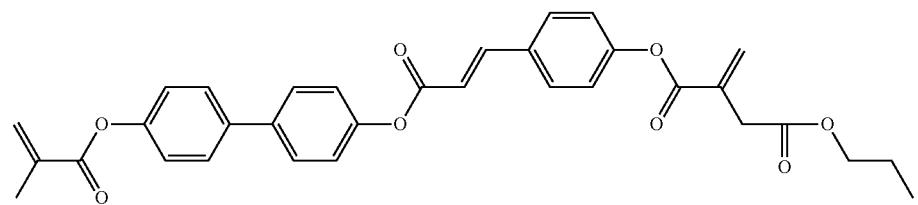 [SMILES: C=C(C)C(=O)Oc1ccc(-c2ccc(OC(=O)/C=C/c3ccc(OC(=O)C(=C)CC(=O)OCCC)cc3)cc2)cc1] |
| 535 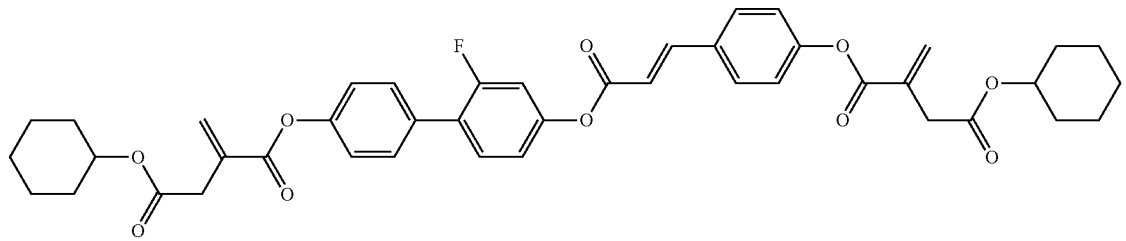 [SMILES: C=C(CC(=O)OC1CCCCC1)C(=O)Oc1ccc(/C=C/C(=O)Oc2ccc(-c3ccc(OC(=O)C(=C)CC(=O)OC4CCCCC4)cc3)c(F)c2)cc1] |
| 536 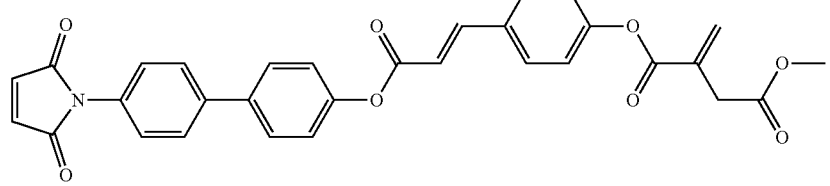 |
| 537 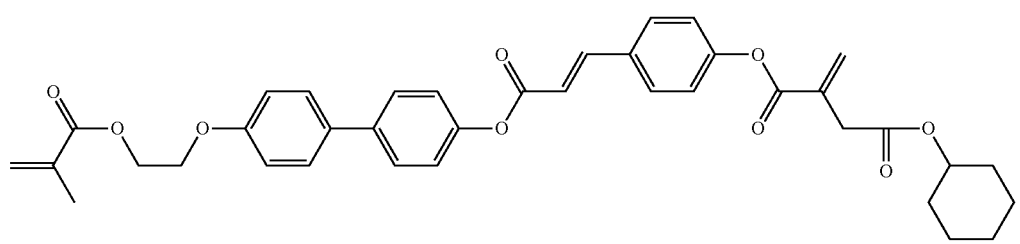 [SMILES: C=C(C)C(=O)OCCOc1ccc(-c2ccc(OC(=O)/C=C/c3ccc(OC(=O)C(=C)CC(=O)OC4CCCCC4)cc3)cc2)cc1] |

| No. |
|---|
| 538 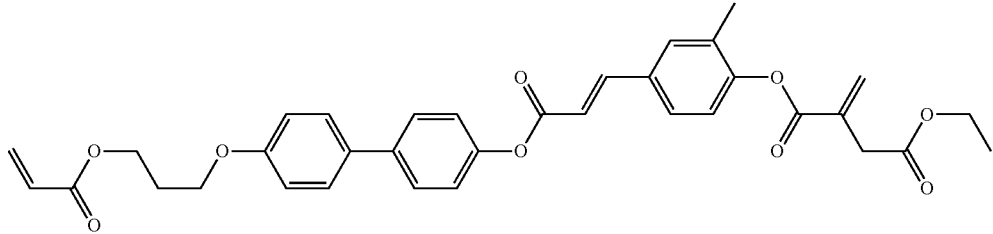 [SMILES: C=CC(=O)OCCCOc1ccc(-c2ccc(OC(=O)/C=C/c3ccc(OC(=O)C(=C)CC(=O)OCC)c(C)c3)cc2)cc1] |
| 539 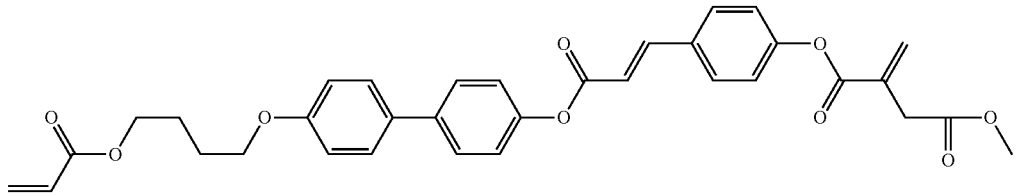 [SMILES: C=CC(=O)OCCCCOc1ccc(-c2ccc(OC(=O)/C=C/c3ccc(OC(=O)C(=C)CC(=O)OC)cc3)cc2)cc1] |
| 540 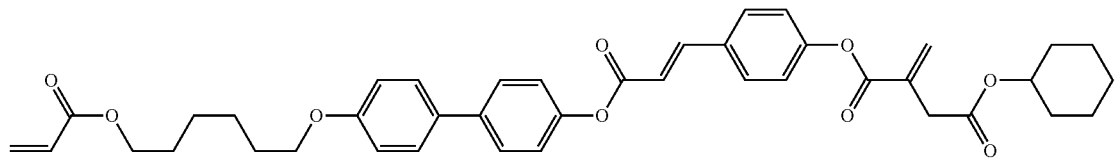 [SMILES: C=CC(=O)OCCCCCCOc1ccc(-c2ccc(OC(=O)/C=C/c3ccc(OC(=O)C(=C)CC(=O)OC4CCCCC4)cc3)cc2)cc1] |
| 541 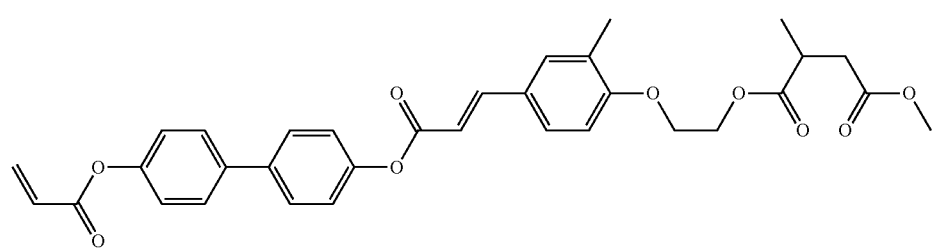 [SMILES: C=CC(=O)Oc1ccc(-c2ccc(OC(=O)/C=C/c3ccc(OCCOC(=O)C(C)CC(=O)OC)c(C)c3)cc2)cc1] |
| 542 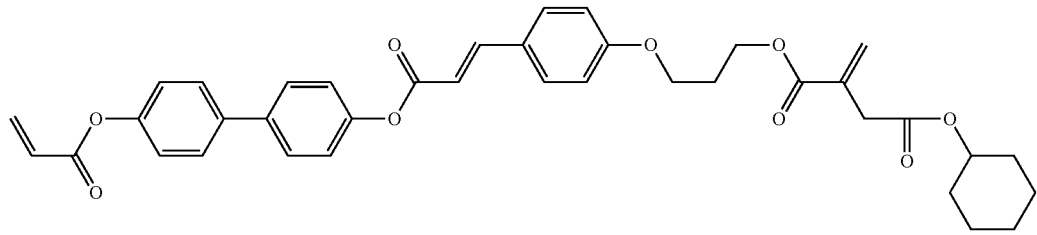 [SMILES: C=CC(=O)Oc1ccc(-c2ccc(OC(=O)/C=C/c3ccc(OCCCOC(=O)C(=C)CC(=O)OC4CCCCC4)cc3)cc2)cc1] |
| 543 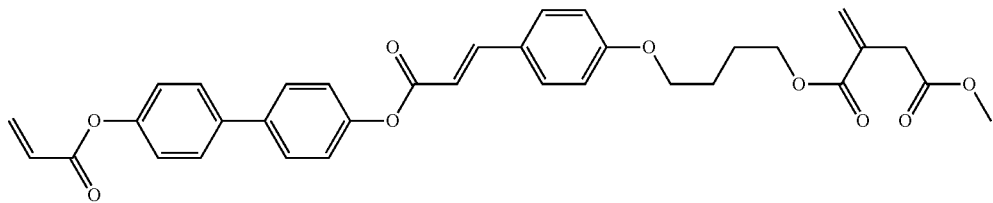 [SMILES: C=CC(=O)Oc1ccc(-c2ccc(OC(=O)/C=C/c3ccc(OCCCCOC(=O)C(=C)CC(=O)OC)cc3)cc2)cc1] |
| 544 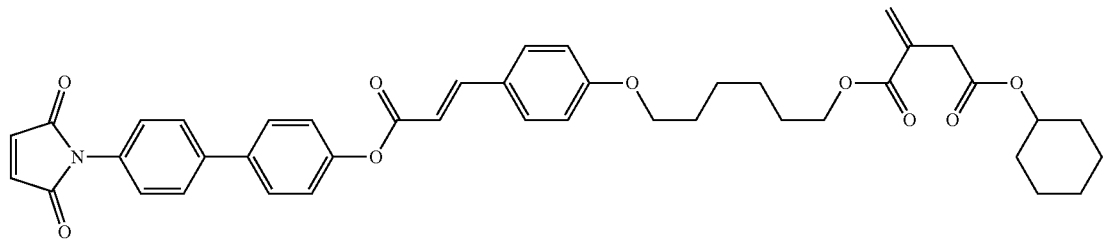 [SMILES: C=C(CC(=O)OC1CCCCC1)C(=O)OCCCCCCOc1ccc(/C=C/C(=O)Oc2ccc(-c3ccc(N4C(=O)C=CC4=O)cc3)cc2)cc1] |

| No. |
|---|
| 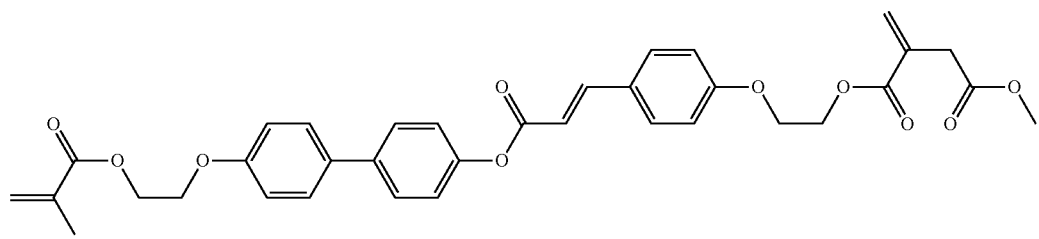 [SMILES: C=C(C)C(=O)OCCOc1ccc(-c2ccc(OC(=O)/C=C/c3ccc(OCCOC(=O)C(=C)CC(=O)OC)cc3)cc2)cc1] 545 |
| 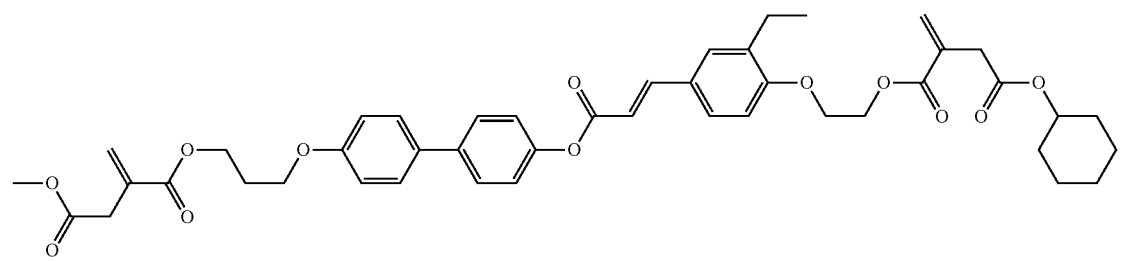 [SMILES: C=C(CC(=O)OC)C(=O)OCCCOc1ccc(-c2ccc(OC(=O)/C=C/c3ccc(OCCOC(=O)C(=C)CC(=O)OC4CCCCC4)c(CC)c3)cc2)cc1] 546 |
| 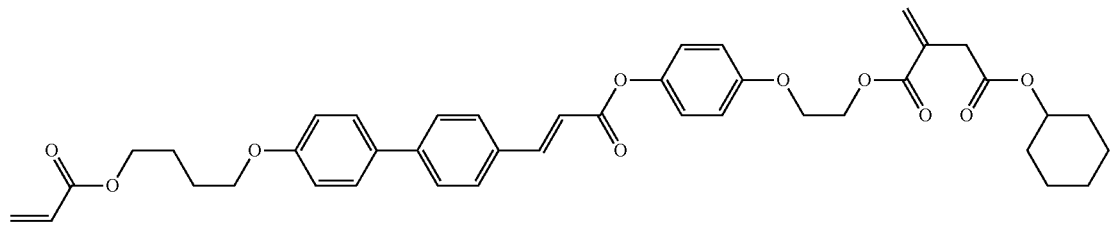 [SMILES: C=CC(=O)OCCCCOc1ccc(-c2ccc(/C=C/C(=O)Oc3ccc(OCCOC(=O)C(=C)CC(=O)OC4CCCCC4)cc3)cc2)cc1] 547 |
| 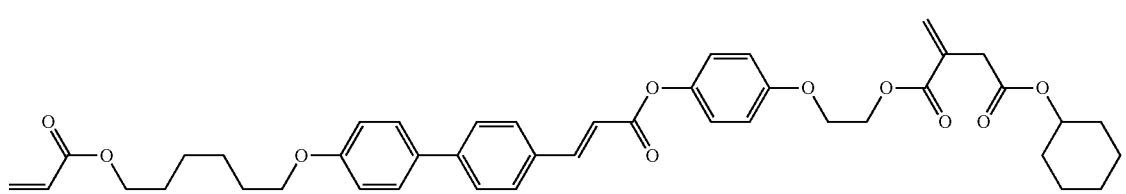 [SMILES: C=CC(=O)OCCCCCCOc1ccc(-c2ccc(/C=C/C(=O)Oc3ccc(OCCOC(=O)C(=C)CC(=O)OC4CCCCC4)cc3)cc2)cc1] 548 |
| 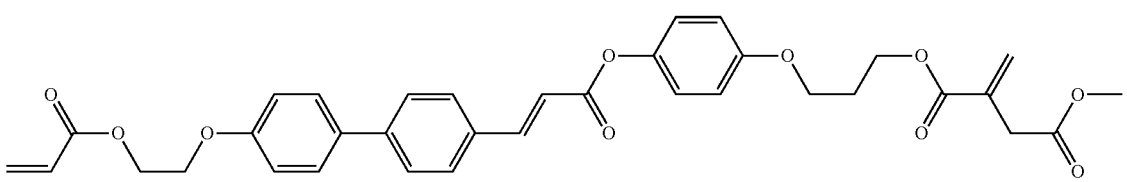 [SMILES: C=CC(=O)OCCOc1ccc(-c2ccc(/C=C/C(=O)Oc3ccc(OCCCOC(=O)C(=C)CC(=O)OC)cc3)cc2)cc1] 549 |
| 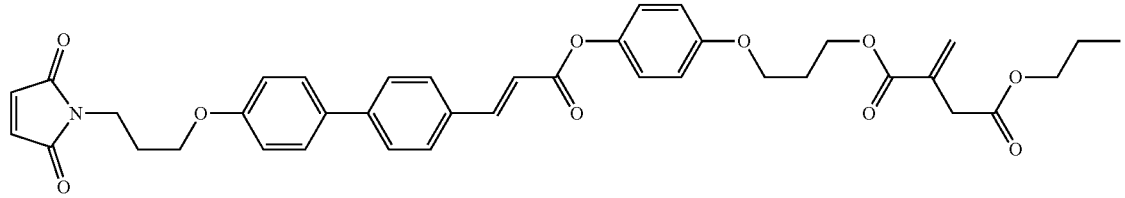 [SMILES: C=C(CC(=O)OCCC)C(=O)OCCCOc1ccc(OC(=O)/C=C/c2ccc(-c3ccc(OCCCN4C(=O)C=CC4=O)cc3)cc2)cc1] 550 |
| 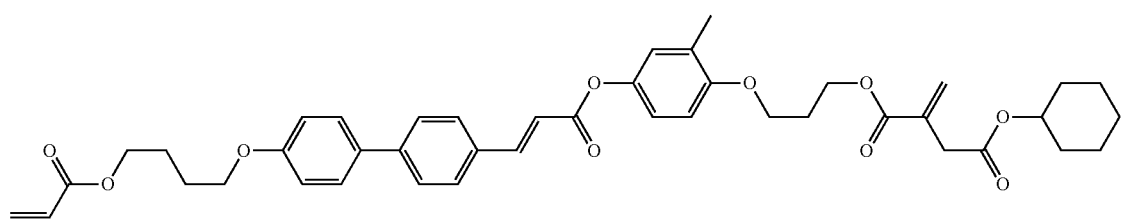 [SMILES: C=CC(=O)OCCCCOc1ccc(-c2ccc(/C=C/C(=O)Oc3ccc(OCCCOC(=O)C(=C)CC(=O)OC4CCCCC4)c(C)c3)cc2)cc1] 551 |

| No. |
|---|
| 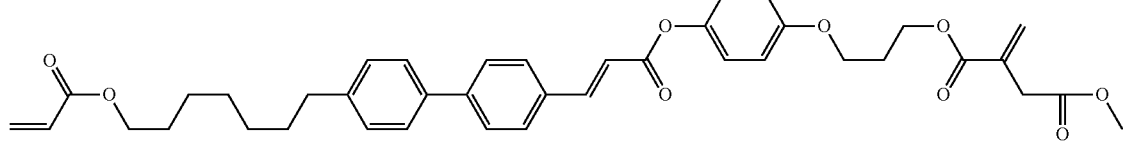 552 |
| 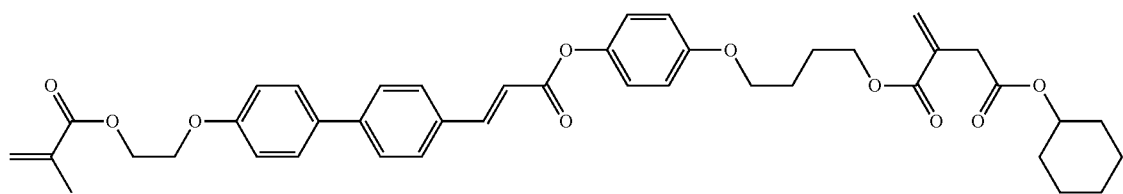 [SMILES: C=C(C)C(=O)OCCOc1ccc(-c2ccc(/C=C/C(=O)Oc3ccc(OCCCCOC(=O)C(=C)CC(=O)OC4CCCCC4)cc3)cc2)cc1] 553 |
| 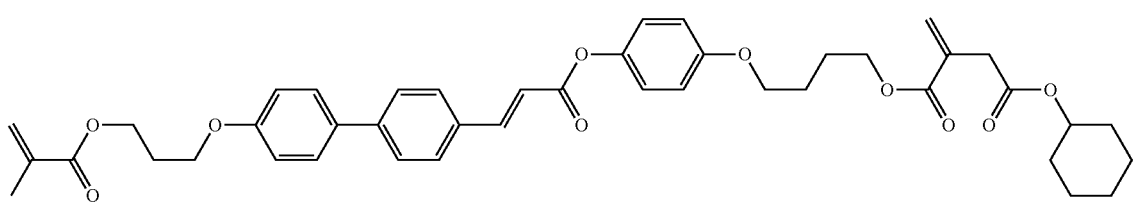 [SMILES: C=C(C)C(=O)OCCCOc1ccc(-c2ccc(/C=C/C(=O)Oc3ccc(OCCCCOC(=O)C(=C)CC(=O)OC4CCCCC4)cc3)cc2)cc1] 554 |
| 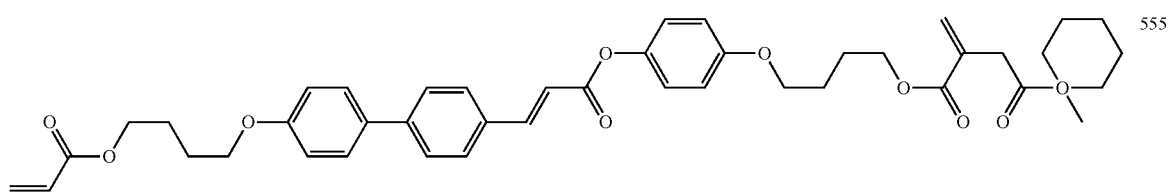 555 |
| 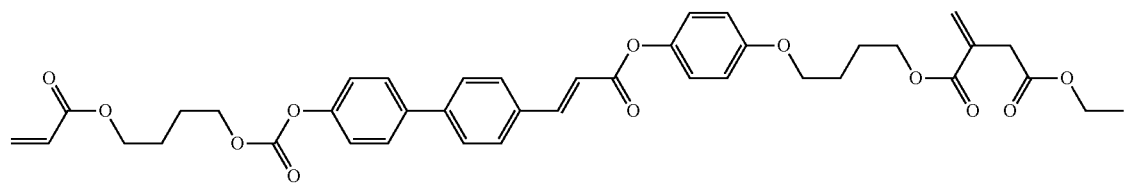 [SMILES: C=CC(=O)OCCCCOC(=O)Oc1ccc(-c2ccc(/C=C/C(=O)Oc3ccc(OCCCCOC(=O)C(=C)CC(=O)OCC)cc3)cc2)cc1] 556 |
| 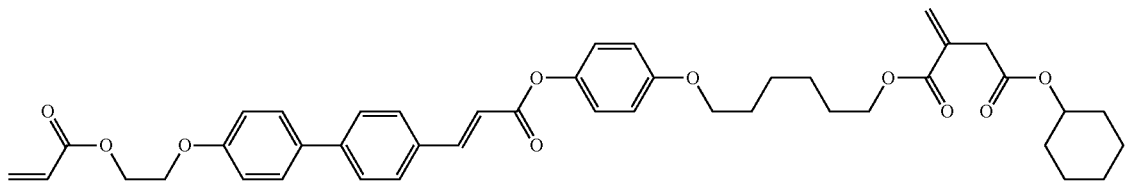 [SMILES: C=CC(=O)OCCOc1ccc(-c2ccc(/C=C/C(=O)Oc3ccc(OCCCCCCOC(=O)C(=C)CC(=O)OC4CCCCC4)cc3)cc2)cc1] 557 |
| 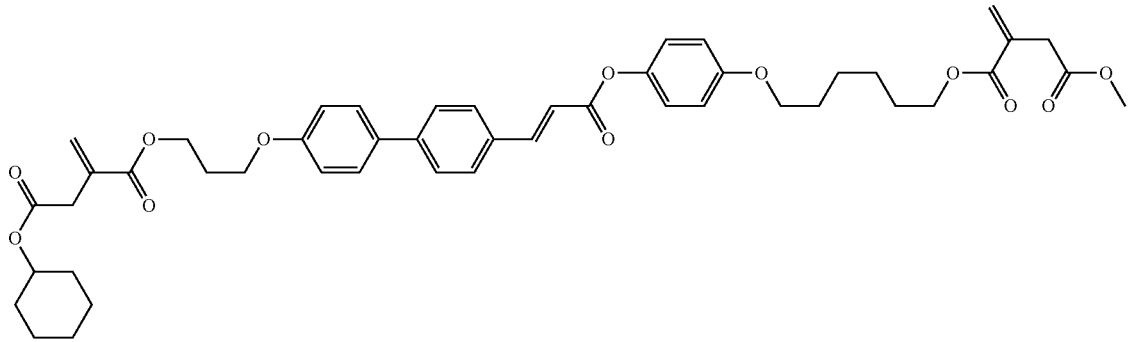 [SMILES: C=C(CC(=O)OC)C(=O)OCCCCCCOc1ccc(OC(=O)/C=C/c2ccc(-c3ccc(OCCCOC(=O)C(=C)CC(=O)OC4CCCCC4)cc3)cc2)cc1] 558 |

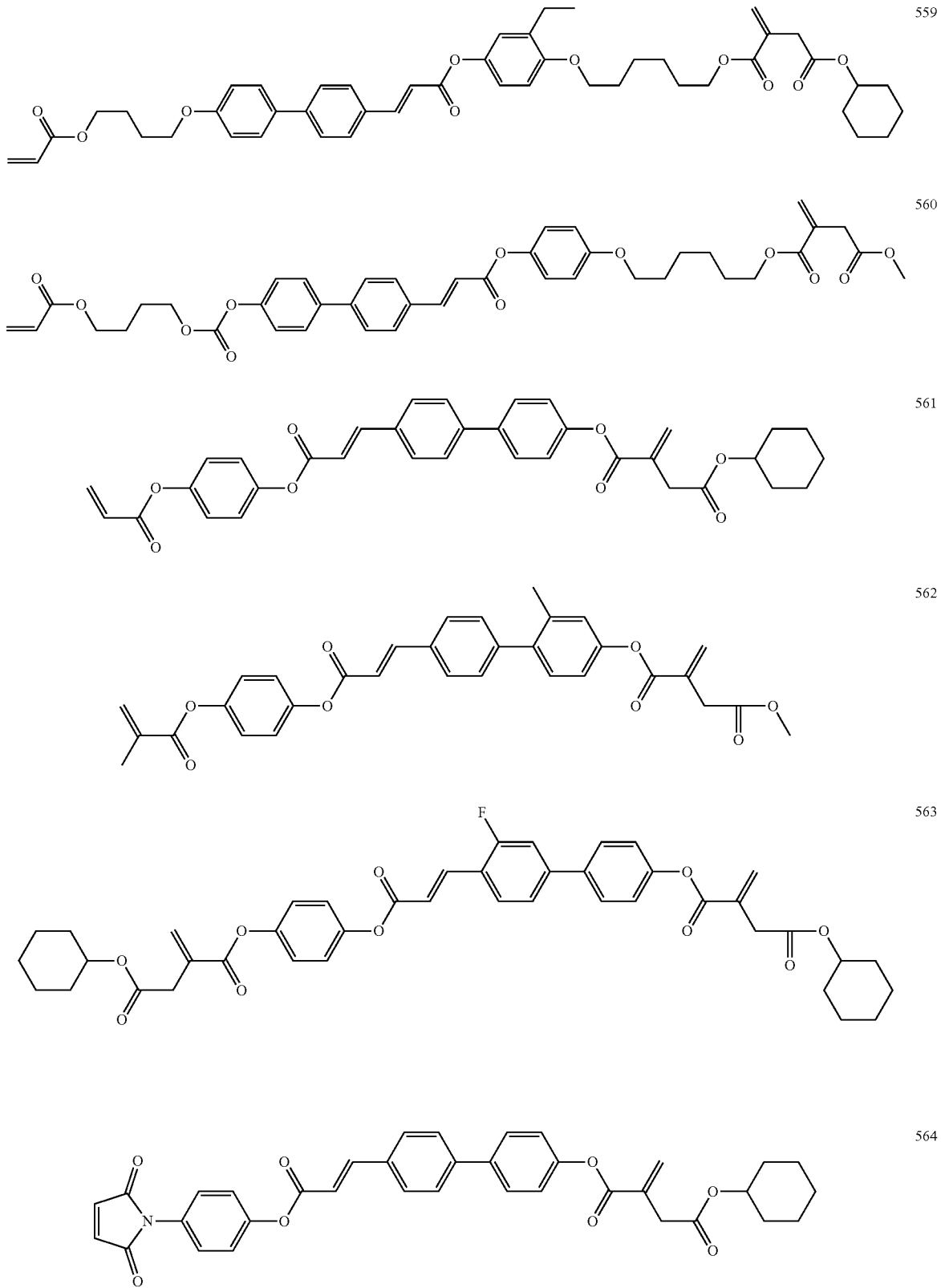

| No. |
|---|
| 565 |
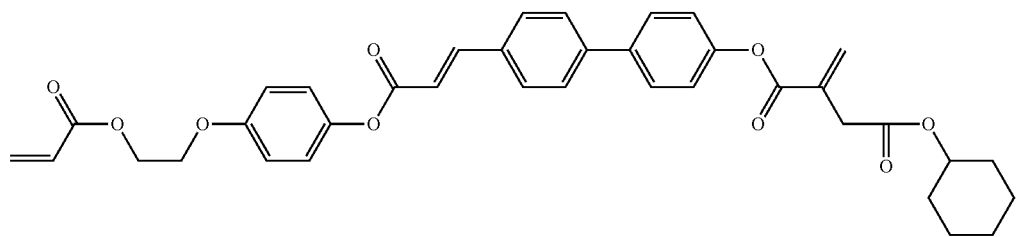 [SMILES: C=CC(=O)OCCOc1ccc(OC(=O)/C=C/c2ccc(-c3ccc(OC(=O)C(=C)CC(=O)OC4CCCCC4)cc3)cc2)cc1]
| 566 |
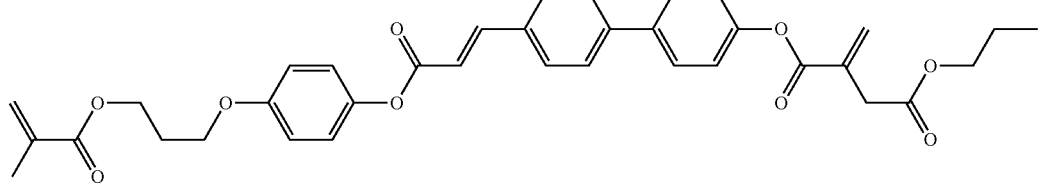
| 567 |
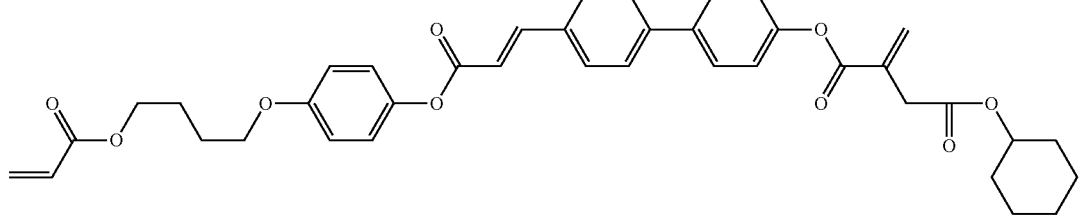
| 568 |
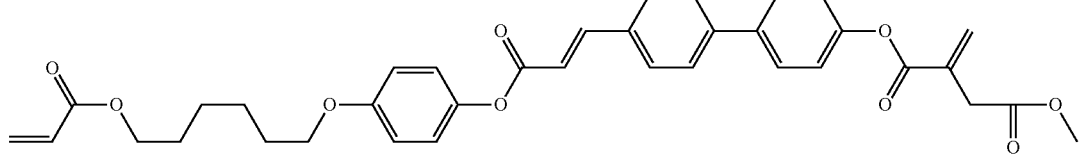
| 569 |
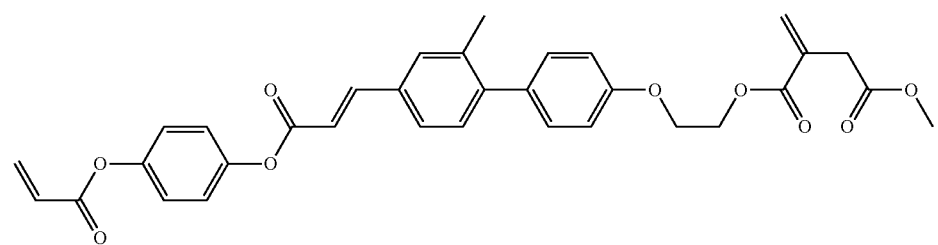 [SMILES: C=CC(=O)Oc1ccc(OC(=O)/C=C/c2ccc(-c3ccc(OCCOC(=O)C(=C)CC(=O)OC)cc3)c(C)c2)cc1]
| 570 |
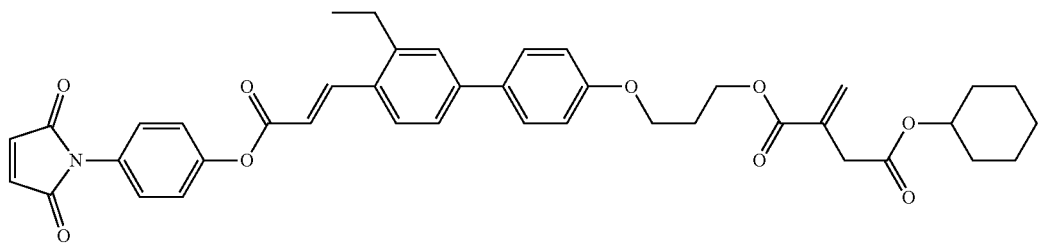 [SMILES: C=C(CC(=O)OC1CCCCC1)C(=O)OCCCOc1ccc(-c2ccc(/C=C/C(=O)Oc3ccc(N4C(=O)C=CC4=O)cc3)c(CC)c2)cc1]
| 571 |
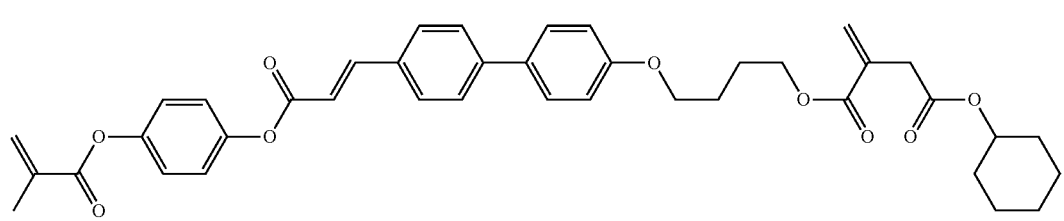 [SMILES: C=C(C)C(=O)Oc1ccc(OC(=O)/C=C/c2ccc(-c3ccc(OCCCCOC(=O)C(=C)CC(=O)OC4CCCCC4)cc3)cc2)cc1]

-continued
| No. |
|---|
| 572 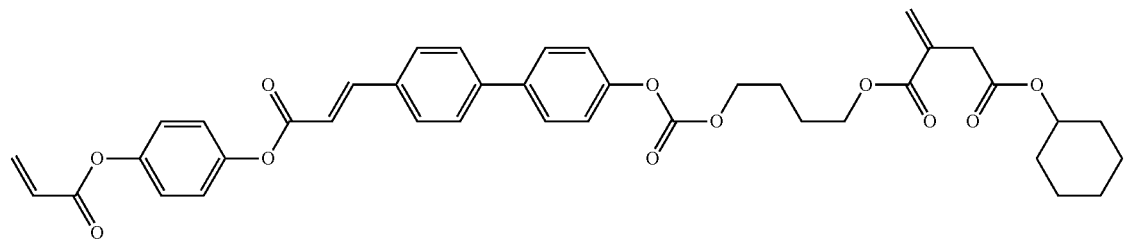 [SMILES: C=CC(=O)Oc1ccc(OC(=O)/C=C/c2ccc(-c3ccc(OC(=O)OCCCCOC(=O)C(=C)CC(=O)OC4CCCCC4)cc3)cc2)cc1] |
| 573 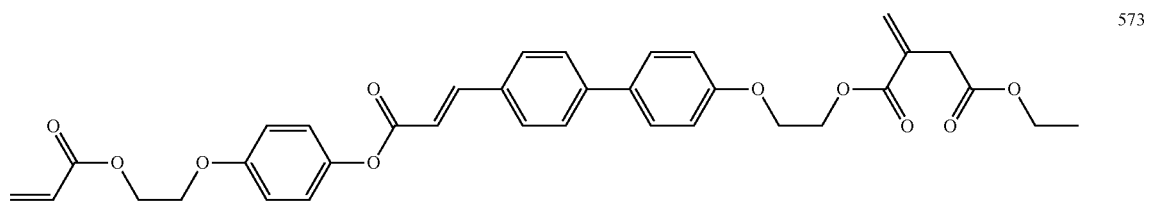 |
| 574 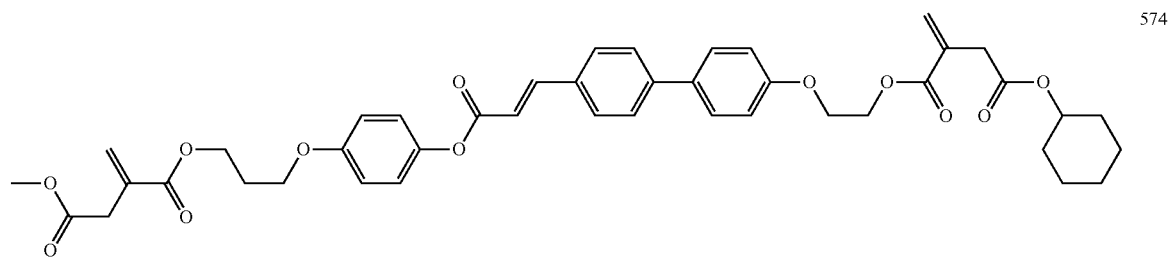 |
| 575 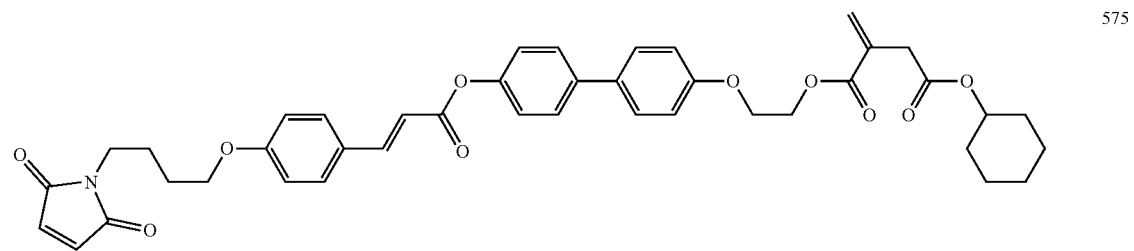 |
| 576 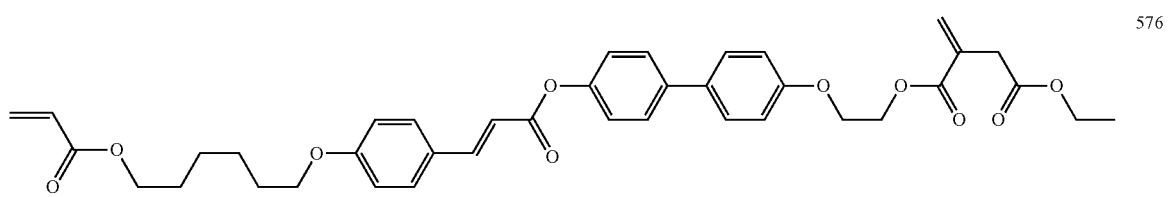 |
| 577 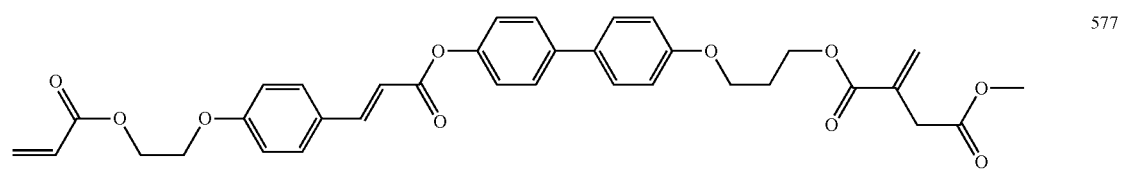 |
| 578 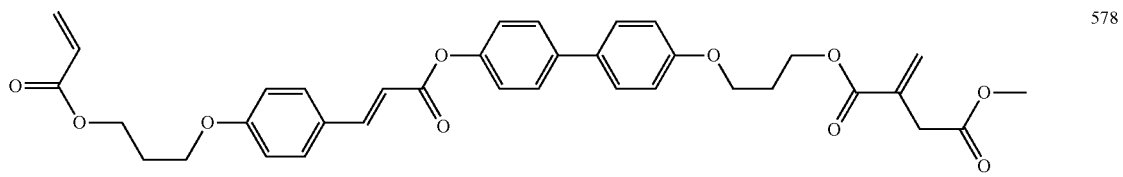 |

-continued
| No. |
|---|
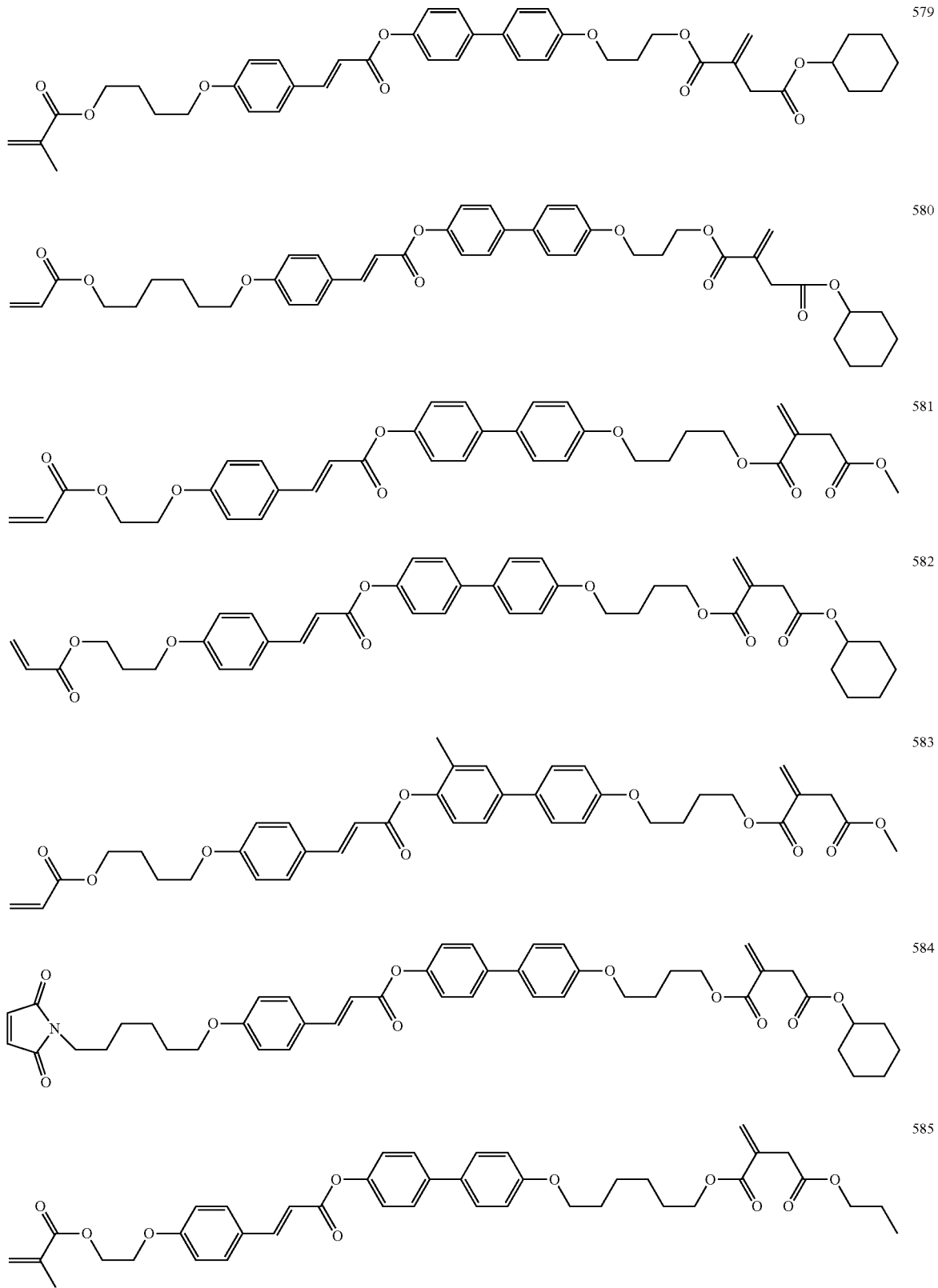

-continued

| No. |
|---|
| 586 |

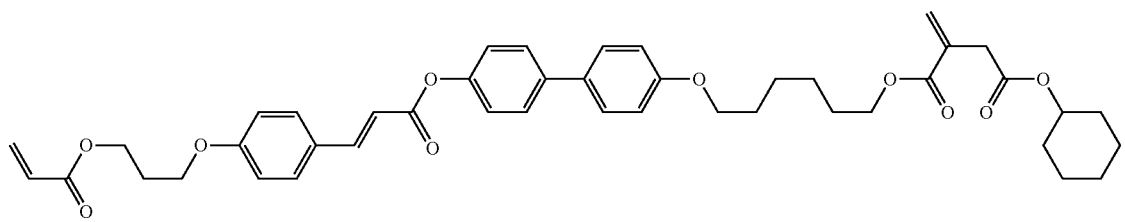 [SMILES: C=CC(=O)OCCCOc1ccc(/C=C/C(=O)Oc2ccc(-c3ccc(OCCCCCCOC(=O)C(=C)CC(=O)OC4CCCCC4)cc3)cc2)cc1]

| 587 |

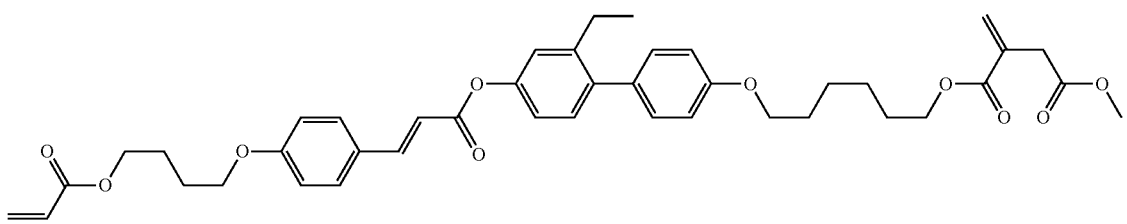 [SMILES: C=CC(=O)OCCCCOc1ccc(/C=C/C(=O)Oc2ccc(-c3ccc(OCCCCCCOC(=O)C(=C)CC(=O)OC)cc3)c(CC)c2)cc1]

| 588 |

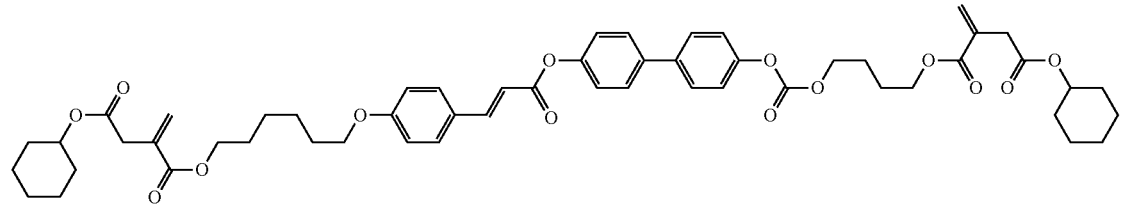 [SMILES: C=C(CC(=O)OC1CCCCC1)C(=O)OCCCCCCOc1ccc(/C=C/C(=O)Oc2ccc(-c3ccc(OC(=O)OCCCCOC(=O)C(=C)CC(=O)OC4CCCCC4)cc3)cc2)cc1]

2. Use Examples of Devices

The compounds in Use Examples were represented using symbols according to definitions in Table 3 below. In Table 3, a configuration of 1,4-cyclohexylene is trans. A parenthesized number next to a symbolized compound corresponds to the number of the compound. A symbol (-) means any other liquid crystal compound. A proportion (percentage) of the liquid crystal compound is expressed in terms of weight percent (% by weight) based on the weight of the liquid crystal composition. Values of the characteristics of the composition are summarized in a last part.

TABLE 3

Method for description of compounds using symbols
R—($A_1$)—$Z_1$—. . . —$Z_n$—($A_n$)—R'

| 1) Left-terminal group R— | Symbol |
|---|---|
| $FC_nH_{2n}$— | Fn— |
| $C_nH_{2n+1}$— | n— |
| $C_nH_{2n+1}O$— | nO— |
| $C_mH_{2m+1}OC_nH_{2n}$— | mOn— |
| $CH_2$=CH— | V— |
| $C_nH_{2n+1}$—CH=CH— | nV— |
| $CH_2$=CH—$C_nH_{2n}$— | Vn— |
| $C_mH_{2m+1}$—CH=CH—$C_nH_{2n}$— | mVn— |
| $CF_2$=CH— | VFF— |
| $CF_2$=CH—$C_nH_{2n}$— | VFFn— |
| $C_mH_{2m+1}CF_2C_nH_{2n}$— | m(CF2)n— |
| $CH_2$=CHCOO— | AC— |
| CH2=C(CH$_3$)COO— | MAC— |

| 2) Right-terminal group —R' | Symbol |
|---|---|
| —$C_nH_{2n+1}$ | —n |
| —$OC_nH_{2n+1}$ | —On |
| —COOCH$_3$ | —EMe |
| —CH=CH$_2$ | —V |
| —CH=CH—$C_nH_{2n+1}$ | —Vn |
| —$C_nH_{2n}$—CH=CH$_2$ | —nV |
| —$C_mH_{2m}$—CH=CH—$C_nH_{2n+1}$ | —mVn |
| —CH=CF$_2$ | —VFF |
| —F | —F |
| —Cl | —CL |
| —OCF$_3$ | —OCF3 |

TABLE 3-continued
| Method for description of compounds using symbols R—(A₁)—Z₁—...—Zₙ—(Aₙ)—R' | |
|---|---|
| —OCF₂H | —OCF2H |
| —CF₃ | —CF3 |
| —CF=CH—CF₃ | —FVCF3 |
| —OCH=CH—CF₃ | —OVCF3 |
| —C≡N | —C |
| —OCOCH=CH₂ | —AC |
| —OCOC(CH₃)=CH₂ | —MAC |
| 3) Bonding group —Zₙ— | Symbol |
|---|---|
| —CₙH₂ₙ— | n |
| —COO— | E |
| —CH=CH— | V |
| —CH₂O— | 1O |
| —CH=CHO— | VO |
| —OCH=CH— | OV |
| —CF=CF— | VFF |
| —CH=CF— | VF |
| —OCH₂— | O1 |
| —OCF₂— | x |
| —CF₂O— | X |
| —C≡C— | T |
| 4) Ring structure —Aₙ— | Symbol |
|---|---|
| 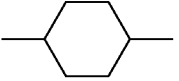 | H |
|  | B |
| 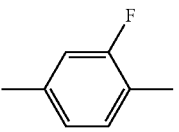 | B(F) |
| 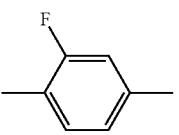 | B(2F) |
| 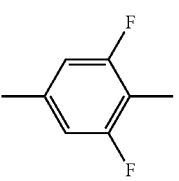 | B(F,F) |
| 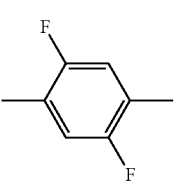 | B(2F,5F) |
| 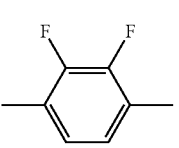 | B(2F,3F) |

TABLE 3-continued
Method for description of compounds using symbols
R—(A₁)—Z₁—. . .—Zₙ—(Aₙ)—R'
| | |
|---|---|
| 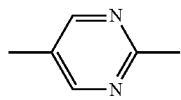 | Py |
| 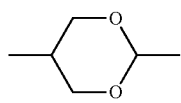 | G |
| 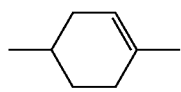 | ch |
| 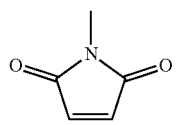 | Mi |
| 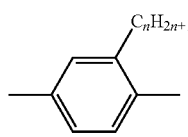 | Bm(n) |
| 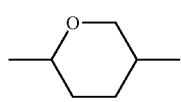 | Dh |
| 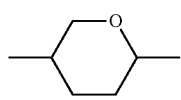 | dh |
| 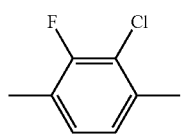 | B(2F,3Cl) |
| 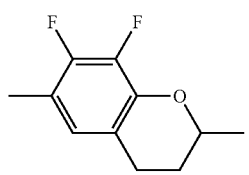 | Cro(7F,8F) |
5) Examples of description
Example 1 3-HBB(2F,3F)—O2
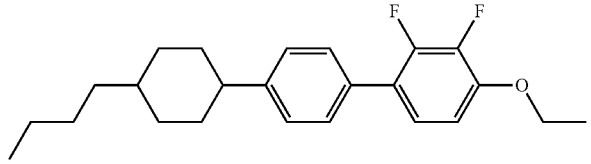 [SMILES: CCCCC1CCC(c2ccc(-c3ccc(OCC)c(F)c3F)cc2)CC1]

TABLE 3-continued

Method for description of compounds using symbols
R—(A$_1$)—Z$_1$—...—Z$_n$—(A$_n$)—R'

Example 2  5-HHBB(F,F)—F

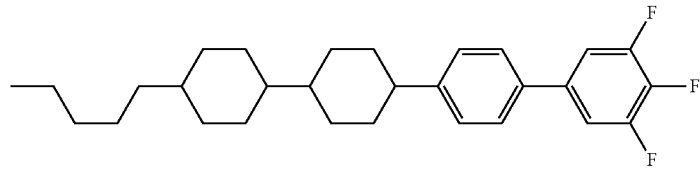 [SMILES: CCCCCC1CCC(C2CCC(c3ccc(-c4cc(F)c(F)c(F)c4)cc3)CC2)CC1]

Example 3  3-HB—O2

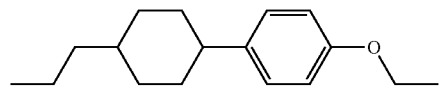 [SMILES: CCCC1CCC(c2ccc(OCC)cc2)CC1]

Example 4  3-HBB(F,F)—F

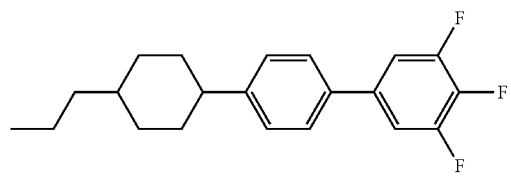 [SMILES: CCCC1CCC(c2ccc(-c3cc(F)c(F)c(F)c3)cc2)CC1]

1. Raw Material

A composition to which an alignment control monomer was added was injected into a device having no alignment film. After the device was irradiated with linearly polarized light, alignment of liquid crystal molecules in the device was confirmed. First, a raw material will be described. The raw material was appropriately selected from compositions such as compositions (M1) to (M41), and alignment controls monomer such as compounds (No. 1) to (No. 588). The composition is as described below.

| Compound | Code | % |
|---|---|---|
| 3-HB (2F, 3F)-O2 | (9-1) | 10% |
| 5-HB (2F, 3F)-O2 | (9-1) | 7% |
| 2-BB (2F, 3F)-O2 | (9-3) | 7% |
| 3-BB (2F, 3F)-O2 | (9-3) | 7% |
| 3-B (2F, 3F) B (2F, 3F)-O2 | (9-7) | 3% |
| 2-HHB (2F, 3F)-O2 | (10-1) | 5% |
| 3-HHB (2F, 3F)-O2 | (10-1) | 10% |
| 2-HBB (2F, 3F)-O2 | (10-7) | 8% |
| 3-HBB (2F, 3F)-O2 | (10-7) | 10% |
| 2-HH-3 | (2-1) | 14% |
| 3-HB-O1 | (2-5) | 5% |
| 3-HHB-1 | (3-1) | 3% |
| 3-HHB-O1 | (3-1) | 3% |
| 3-HHB-3 | (3-1) | 4% |
| 2-BB (F) B-3 | (3-6) | 4% |

NI=73.2° C.; Tc<−20° C.; Δn=0.113; Δε=−4.0; Vth=2.18 V; η=22.6 mPa·s.
Composition (M2)

| Compound | Code | % |
|---|---|---|
| 3-HB (2F, 3F)-O4 | (9-1) | 6% |
| 3-H2B (2F, 3F)-O2 | (9-4) | 8% |
| 3-H1OB (2F, 3F)-O2 | (9-5) | 4% |
| 3-BB (2F, 3F)-O2 | (9-3) | 7% |
| 2-HHB (2F, 3F)-O2 | (10-1) | 7% |
| 3-HHB (2F, 3F)-O2 | (10-1) | 7% |
| 3-HH2B (2F, 3F)-O2 | (10-4) | 7% |
| 5-HH2B (2F, 3F)-O2 | (10-4) | 4% |
| 2-HBB (2F, 3F)-O2 | (10-7) | 5% |
| 3-HBB (2F, 3F)-O2 | (10-7) | 5% |
| 4-HBB (2F, 3F)-O2 | (10-7) | 6% |
| 2-HH-3 | (2-1) | 12% |
| 1-BB-5 | (2-8) | 12% |
| 3-HHB-1 | (3-1) | 4% |
| 3-HHB-O1 | (3-1) | 3% |
| 3-HBB-2 | (3-4) | 3% |

NI=82.8° C.; Tc<−30° C.; Δn=0.118; Δε=−4.4; Vth=2.13 V; η=22.5 mPa·s.
Composition (M3)

| Compound | Code | % |
|---|---|---|
| 3-HB (2F, 3F)-O2 | (9-1) | 7% |
| 5-HB (2F, 3F)-O2 | (9-1) | 7% |
| 3-BB (2F, 3F)-O2 | (9-3) | 8% |
| 3-HHB (2F, 3F)-O2 | (10-1) | 5% |
| 5-HHB (2F, 3F)-O2 | (10-1) | 4% |
| 3-HH1OB (2F, 3F)-O2 | (10-5) | 4% |
| 2-BB (2F, 3F) B-3 | (11-1) | 5% |
| 2-HBB (2F, 3F)-O2 | (10-7) | 3% |
| 3-HBB (2F, 3F)-O2 | (10-7) | 8% |
| 4-HBB (2F, 3F)-O2 | (10-7) | 5% |
| 5-HBB (2F, 3F)-O2 | (10-7) | 8% |
| 3-HH-V | (2-1) | 27% |
| 3-HH-V1 | (2-1) | 6% |
| V-HHB-1 | (3-1) | 3% |

NI=78.1° C.; Tc<−30° C.; Δn=0.107; Δε=−3.2; Vth=2.02 V; η=15.9 mPa·s.
Composition (M4)

| Compound | Code | % |
|---|---|---|
| 3-HB (2F, 3F)-O2 | (9-1) | 10% |
| 5-HB (2F, 3F)-O2 | (9-1) | 10% |
| 3-H2B (2F, 3F)-O2 | (9-4) | 8% |
| 5-H2B (2F, 3F)-O2 | (9-4) | 8% |
| 2-HBB (2F, 3F)-O2 | (10-7) | 6% |

-continued

| | | |
|---|---|---|
| 3-HBB (2F, 3F)-O2 | (10-7) | 8% |
| 4-HBB (2F, 3F)-O2 | (10-7) | 7% |
| 5-HBB (2F, 3F)-O2 | (10-7) | 7% |
| 3-HDhB (2F, 3F)-O2 | (10-3) | 5% |
| 3-HH-4 | (2-1) | 14% |
| V-HHB-1 | (3-1) | 10% |
| 3-HBB-2 | (3-4) | 7% |

NI=88.5° C.; Tc<−30° C.; $\Delta n$=0.108; $\Delta\varepsilon$=−3.8; Vth=2.25 V; $\eta$=24.6 mPa·s; VHR-1=99.1%; VHR-2=98.2%: VHR-3=97.8%.

Composition (M5)

| | | |
|---|---|---|
| 3-HB (2F, 3F)-O2 | (9-1) | 7% |
| 3-HB (2F, 3F)-O4 | (9-1) | 8% |
| 3-H2B (2F, 3F)-O2 | (9-4) | 8% |
| 3-BB (2F, 3F)-O2 | (9-3) | 10% |
| 2-HHB (2F, 3F)-O2 | (10-1) | 4% |
| 3-HHB (2F, 3F)-O2 | (10-1) | 7% |
| 3-HHB (2F, 3F)-1 | (10-1) | 6% |
| 2-HBB (2F, 3F)-O2 | (10-7) | 6% |
| 3-HBB (2F, 3F)-O2 | (10-7) | 6% |
| 4-HBB (2F, 3F)-O2 | (10-7) | 5% |
| 5-HBB (2F, 3F)-O2 | (10-7) | 4% |
| 3-HEB (2F, 3F) B (2F, 3F)-O2 | (16-1) | 3% |
| 3-H1OCro (7F, 8F)-5 | (13-2) | 3% |
| 3-HDhB (2F, 3F)-O2 | (10-3) | 5% |
| 3-HH-O1 | (2-1) | 5% |
| 1-BB-5 | (2-8) | 4% |
| V-HHB-1 | (3-1) | 4% |
| 5-HB (F) BH-3 | (4-2) | 5% |

NI=81.1° C.; Tc<−30° C.; $\Delta n$=0.119; $\Delta\varepsilon$=−4.5; Vth=1.69 V; $\eta$=31.4 mPa·s.

Composition (M6)

| | | |
|---|---|---|
| 3-HB (2F, 3F)-O4 | (9-1) | 15% |
| 3-HBB (2F, 3F)-O2 | (10-7) | 8% |
| 4-HBB (2F, 3F)-O2 | (10-7) | 5% |
| 5-HBB (2F, 3F)-O2 | (10-7) | 7% |
| 3-dhBB (2F, 3F)-O2 | (10-9) | 5% |
| 3-chB (2F, 3F)-O2 | (16-2) | 7% |
| 2-HchB (2F, 3F)-O2 | (16-3) | 8% |
| 5-HH-V | (2-1) | 18% |
| 7-HB-1 | (2-5) | 5% |
| V-HHB-1 | (3-1) | 7% |
| V2-HHB-1 | (3-1) | 7% |
| 3-HBB (F) B-3 | (4-5) | 8% |

NI=98.8° C.; Tc<−30° C.; $\Delta n$=0.111; $\Delta\varepsilon$=−3.2; Vth=2.47 V; $\eta$=23.9 mPa·s.

Composition (M7)

| | | |
|---|---|---|
| 3-H2B (2F, 3F)-O2 | (9-4) | 18% |
| 5-H2B (2F, 3F)-O2 | (9-4) | 17% |
| 3-HHB (2F, 3Cl)-O2 | (10-12) | 5% |
| 3-HBB (2F, 3Cl)-O2 | (10-13) | 8% |
| 5-HBB (2F, 3Cl)-O2 | (10-13) | 7% |
| 3-HDhB (2F, 3F)-O2 | (10-3) | 5% |
| 3-HH-V | (2-1) | 11% |
| 3-HH-VFF | (2-1) | 7% |
| F3-HH-V | (2-1) | 10% |
| 3-HHEH-3 | (3-13) | 4% |
| 3-HB (F) HH-2 | (4-7) | 4% |
| 3-HHEBH-3 | (4-6) | 4% |

NI=77.5° C.; Tc<−30° C.; $\Delta n$=0.084; $\Delta\varepsilon$=−2.6; Vth=2.43 V; $\eta$=22.8 mPa·s.

Composition (M8)

| | | |
|---|---|---|
| 3-HB (2F, 3F)-O2 | (9-1) | 8% |
| 3-H2B (2F, 3F)-O2 | (9-4) | 10% |
| 3-BB (2F, 3F)-O2 | (9-3) | 10% |
| 2O-BB (2F, 3F)-O2 | (9-3) | 3% |
| 2-HHB (2F, 3F)-O2 | (10-1) | 4% |
| 3-HHB (2F, 3F)-O2 | (10-1) | 7% |
| 2-HHB (2F, 3F)-1 | (10-1) | 5% |
| 2-BB (2F, 3F) B-3 | (11-1) | 6% |
| 2-BB (2F, 3F) B-4 | (11-1) | 6% |
| 2-HBB (2F, 3F)-O2 | (10-7) | 4% |
| 3-HBB (2F, 3F)-O2 | (10-7) | 7% |
| 3-HH1OCro (7F, 8F)-5 | (13-6) | 4% |
| 3-HDhB (2F, 3F)-O2 | (10-3) | 6% |
| 3-dhBB (2F, 3F)-O2 | (10-9) | 4% |
| 3-HH-V | (2-1) | 11% |
| 1-BB-5 | (2-8) | 5% |

NI=70.6° C.; Tc<−20° C.; $\Delta n$=0.129; $\Delta\varepsilon$=−4.3; Vth=1.69 V; $\eta$=27.0 mPa·s.

Composition (M9)

| | | |
|---|---|---|
| 3-HB (2F, 3F)-O4 | (9-1) | 14% |
| 3-H1OB (2F, 3F)-O2 | (9-5) | 3% |
| 3-BB (2F, 3F)-O2 | (9-3) | 10% |
| 2-HHB (2F, 3F)-O2 | (10-1) | 7% |
| 3-HHB (2F, 3F)-O2 | (10-1) | 7% |
| 3-HH1OB (2F, 3F)-O2 | (10-5) | 6% |
| 2-HBB (2F, 3F)-O2 | (10-7) | 4% |
| 3-HBB (2F, 3F)-O2 | (10-7) | 6% |
| 4-HBB (2F, 3F)-O2 | (10-7) | 4% |
| 3-HH-V | (2-1) | 14% |
| 1-BB-3 | (2-8) | 3% |
| 3-HHB-1 | (3-1) | 4% |
| 3-HHB-O1 | (3-1) | 4% |
| V-HBB-2 | (3-4) | 4% |
| 1-BB (F) B-2V | (3-6) | 6% |
| 5-HBBH-1O1 | (4-1) | 4% |

NI=93.0° C.; Tc<−30° C.; $\Delta n$=0.123; $\Delta\varepsilon$=−4.0; Vth=2.27 V; $\eta$=29.6 mPa·s.

Composition (M10)

| | | |
|---|---|---|
| 3-HB (2F, 3F)-O4 | (9-1) | 6% |
| 3-H2B (2F, 3F)-O2 | (9-4) | 8% |
| 3-H1OB (2F, 3F)-O2 | (9-5) | 5% |
| 3-BB (2F, 3F)-O2 | (9-3) | 10% |
| 2-HHB (2F, 3F)-O2 | (10-1) | 7% |
| 3-HHB (2F, 3F)-O2 | (10-1) | 7% |
| 5-HHB (2F, 3F)-O2 | (10-1) | 7% |
| 2-HBB (2F, 3F)-O2 | (10-7) | 4% |
| 3-HBB (2F, 3F)-O2 | (10-7) | 7% |
| 5-HBB (2F, 3F)-O2 | (10-7) | 6% |
| 3-HH-V | (2-1) | 11% |
| 1-BB-3 | (2-8) | 6% |
| 3-HHB-1 | (3-1) | 4% |
| 3-HHB-O1 | (3-1) | 4% |
| V-HBB-2 | (3-4) | 4% |
| 3-B (F) BB-2 | (3-8) | 4% |

NI=87.6° C.; Tc<−30° C.; $\Delta n$=0.126; $\Delta\varepsilon$=−4.5; Vth=2.21 V; $\eta$=25.3 mPa·s.

Composition (M11)

| | | |
|---|---|---|
| 3-HB (2F, 3F)-O4 | (9-1) | 6% |
| 3-H2B (2F, 3F)-O2 | (9-4) | 8% |
| 3-H1OB (2F, 3F)-O2 | (9-5) | 4% |
| 3-BB (2F, 3F)-O2 | (9-3) | 7% |

-continued

| | | |
|---|---|---|
| 2-HHB (2F, 3F)-O2 | (10-1) | 6% |
| 3-HHB (2F, 3F)-O2 | (10-1) | 10% |
| 5-HHB (2F, 3F)-O2 | (10-1) | 8% |
| 2-HBB (2F, 3F)-O2 | (10-7) | 5% |
| 3-HBB (2F, 3F)-O2 | (10-7) | 7% |
| 5-HBB (2F, 3F)-O2 | (10-7) | 5% |
| 2-HH-3 | (2-1) | 12% |
| 1-BB-3 | (2-8) | 6% |
| 3-HHB-1 | (3-1) | 3% |
| 3-HHB-O1 | (3-1) | 4% |
| 3-HBB-2 | (3-4) | 6% |
| 3-B (F) BB-2 | (3-8) | 3% |

NI=93.0° C.; Tc<−20° C.; Δn=0.124; Δε=−4.5; Vth=2.22 V; η=25.0 mPa·s.

Composition (M12)

| | | |
|---|---|---|
| 3-HB (2F, 3F)-O2 | (9-1) | 7% |
| 5-HB (2F, 3F)-O2 | (9-1) | 7% |
| 3-BB (2F, 3F)-O2 | (9-3) | 8% |
| 3-HHB (2F, 3F)-O2 | (10-1) | 4% |
| 5-HHB (2F, 3F)-O2 | (10-1) | 5% |
| 3-HH1OB (2F, 3F)-O2 | (10-5) | 5% |
| 2-BB (2F, 3F) B-3 | (11-1) | 4% |
| 2-HBB (2F, 3F)-O2 | (10-7) | 3% |
| 3-HBB (2F, 3F)-O2 | (10-7) | 8% |
| 4-HBB (2F, 3F)-O2 | (10-7) | 5% |
| 5-HBB (2F, 3F)-O2 | (10-7) | 8% |
| 3-HH-V | (2-1) | 33% |
| V-HHB-1 | (3-1) | 3% |

NI=76.4° C.; Tc<−30° C.; Δn=0.104; Δε=−3.2; Vth=2.06 V; η=15.6 mPa·s.

Composition (M13)

| | | |
|---|---|---|
| 2-H1OB (2F, 3F)-O2 | (9-5) | 6% |
| 3-H1OB (2F, 3F)-O2 | (9-5) | 4% |
| 3-BB (2F, 3F)-O2 | (9-3) | 3% |
| 2-HH1OB (2F, 3F)-O2 | (10-5) | 14% |
| 2-HBB (2F, 3F)-O2 | (10-7) | 7% |
| 3-HBB (2F, 3F)-O2 | (10-7) | 11% |
| 5-HBB (2F, 3F)-O2 | (10-7) | 9% |
| 2-HH-3 | (2-1) | 5% |
| 3-HH-VFF | (2-1) | 30% |
| 1-BB-3 | (2-8) | 5% |
| 3-HHB-1 | (3-1) | 3% |
| 3-HBB-2 | (3-4) | 3% |

NI=78.3° C.; Tc<−20° C.; Δn=0.103; Δε=−3.2; Vth=2.17 V; η=17.7 mPa·s.

Composition (M14)

| | | |
|---|---|---|
| 3-HB(2F, 3F)—O2 | (9-1) | 5% |
| 5-HB(2F, 3F)—O2 | (9-1) | 7% |
| 3-BB(2F, 3F)—O2 | (9-3) | 8% |
| 3-HHB(2F, 3F)—O2 | (10-1) | 5% |
| 5-HHB(2F, 3F)—O2 | (10-1) | 4% |
| 3-HH1OB(2F, 3F)—O2 | (10-5) | 5% |
| 2-BB(2F, 3F)B-3 | (11-1) | 4% |
| 2-HBB(2F, 3F)—O2 | (10-7) | 3% |
| 3-HBB(2F, 3F)—O2 | (10-7) | 9% |
| 4-HBB(2F, 3F)—O2 | (10-7) | 4% |
| 5-HBB(2F, 3F)—O2 | (10-7) | 8% |
| 3-HH—V | (2-1) | 27% |
| 3-HH—V1 | (2-1) | 6% |
| V—HHB-1 | (3-1) | 5% |

NI=81.2° C.; Tc<−20° C.; Δn=0.107; Δε=−3.2; Vth=2.11 V; η=15.5 mPa·s.

Composition (M15)

| | | |
|---|---|---|
| 3-H2B(2F, 3F)—O2 | (9-4) | 7% |
| 3-HHB(2F, 3F)—O2 | (10-1) | 8% |
| 3-HH1OB(2F, 3F)—O2 | (10-5) | 5% |
| 2-BB(2F, 3F)B-3 | (11-1) | 7% |
| 2-BB(2F, 3F)B-4 | (11-1) | 7% |
| 3-HDhB(2F, 3F)—O2 | (10-3) | 3% |
| 5-HDhB(2F, 3F)—O2 | (10-3) | 4% |
| 2-HchB(2F, 3F)—O2 | (16-3) | 8% |
| 4-HH—V | (2-1) | 15% |
| 3-HH—V1 | (2-1) | 6% |
| 1-HH—2V1 | (2-1) | 6% |
| 3-HH—2V1 | (2-1) | 4% |
| V2—BB-1 | (2-8) | 5% |
| 1V2—BB-1 | (2-8) | 5% |
| 3-HHB-1 | (3-1) | 6% |
| 3-HB(F)BH-3 | (4-2) | 4% |

NI=88.7° C.; Tc<−30° C.; Δn=0.115; Δε=−1.9; Vth=2.82 V; η=17.3 mPa·s.

Composition (M16)

| | | |
|---|---|---|
| V2—H2B(2F, 3F)—O2 | (9-4) | 8% |
| V2—H1OB(2F, 3F)—O4 | (9-5) | 4% |
| 3-BB(2F, 3F)—O2 | (9-3) | 7% |
| 2-HHB(2F, 3F)—O2 | (10-1) | 7% |
| 3-HHB(2F, 3F)—O2 | (10-1) | 7% |
| 3-HH2B(2F, 3F)—O2 | (10-4) | 7% |
| 5-HH2B(2F, 3F)—O2 | (10-4) | 4% |
| V—HH2B(2F, 3F)—O2 | (10-4) | 6% |
| V2—HBB(2F, 3F)—O2 | (10-7) | 5% |
| V—HBB(2F, 3F)—O2 | (10-7) | 5% |
| V—HBB(2F, 3F)—O4 | (10-7) | 6% |
| 2-HH-3 | (2-1) | 12% |
| 1-BB-5 | (2-8) | 12% |
| 3-HHB-1 | (3-1) | 4% |
| 3-HHB—O1 | (3-1) | 3% |
| 3-HBB-2 | (3-4) | 3% |

NI=89.9° C.; Tc<−20° C.; Δn=0.122; Δε=−4.2; Vth=2.16 V; η=23.4 mPa·s.

Composition (M17)

| | | |
|---|---|---|
| 3-HB(2F, 3F)—O2 | (9-1) | 3% |
| V—HB(2F, 3F)—O2 | (9-1) | 3% |
| V2—HB(2F, 3F)—O2 | (9-1) | 5% |
| 5-H2B(2F, 3F)—O2 | (9-4) | 5% |
| V2—BB(2F, 3F)—O2 | (9-3) | 3% |
| 1V2—BB(2F, 3F)—O2 | (9-3) | 3% |
| 3-HHB(2F, 3F)—O2 | (10-1) | 6% |
| V—HHB(2F, 3F)—O2 | (10-1) | 6% |
| V—HB(2F, 3F)—O4 | (10-1) | 5% |
| V2—HHB(2F, 3F)—O2 | (10-1) | 4% |
| V2—BB(2F, 3F)B-1 | (11-1) | 4% |
| V2—HBB(2F, 3F)—O2 | (10-7) | 5% |
| V—HBB(2F, 3F)—O2 | (10-7) | 4% |
| V—HBB(2F, 3F)—O4 | (10-7) | 5% |
| V—HHB(2F, 3Cl)—O2 | (10-12) | 3% |
| 3-HH—V | (2-1) | 27% |
| 3-HH—V1 | (2-1) | 6% |
| V—HHB-1 | (3-1) | 3% |

NI=77.1° C.; Tc<−20° C.; Δn=0.101; Δε=−3.0; Vth=2.04 V; η=13.9 mPa·s.

Composition (M18)

| | | |
|---|---|---|
| V—HB(2F, 3F)—O2 | (9-1) | 10% |
| V2—HB(2F, 3F)—O2 | (9-1) | 10% |

-continued

| | | |
|---|---|---|
| 2-H1OB(2F, 3F)—O2 | (9-5) | 3% |
| 3-H1OB(2F, 3F)—O2 | (9-5) | 3% |
| 2O—BB(2F, 3F)—O2 | (9-3) | 3% |
| V2—BB(2F, 3F)—O2 | (9-3) | 8% |
| V2—HHB(2F, 3F)—O2 | (10-1) | 5% |
| 2-HBB(2F, 3F)—O2 | (10-7) | 3% |
| 3-HBB(2F, 3F)—O2 | (10-7) | 3% |
| V—HBB(2F, 3F)—O2 | (10-7) | 6% |
| V—HBB(2F, 3F)—O4 | (10-7) | 8% |
| V—HHB(2F, 3Cl)—O2 | (10-12) | 7% |
| 3-HH-4 | (2-1) | 14% |
| V—HHB-1 | (3-1) | 10% |
| 3-HBB-2 | (3-4) | 7% |

NI=75.9° C.; Tc<−20° C.; Δn=0.114; Δε=−3.9; Vth=2.20 V; η=24.7 mPa·s.

Composition (M19)

| | | |
|---|---|---|
| 2-H1OB(2F, 3F)—O2 | (9-5) | 7% |
| 3-H1OB(2F, 3F)—O2 | (9-5) | 11% |
| 3-HH1OB(2F, 3F)—O2 | (10-5) | 8% |
| 2-HBB(2F, 3F)—O2 | (10-7) | 3% |
| 3-HBB(2F, 3F)—O2 | (10-7) | 9% |
| 5-HBB(2F, 3F)—O2 | (10-7) | 7% |
| V—HBB(2F, 3F)—O2 | (10-7) | 8% |
| 3-HDhB(2F, 3F)—O2 | (10-3) | 3.5% |
| 2-HH-3 | (2-1) | 21% |
| 3-HH-4 | (2-1) | 5% |
| 3-HB—O2 | (2-5) | 2.5% |
| 1-BB-3 | (2-8) | 4% |
| 3-HHB-1 | (3-1) | 1.5% |
| 3-HBB-2 | (3-4) | 9.5% |

NI=80.8° C.; Tc<−20° C.; Δn=0.108; Δε=−3.8; Vth=2.02 V; η=19.8 mPa·s.

Composition (M20)

| | | |
|---|---|---|
| 2-H1OB(2F, 3F)—O2 | (9-5) | 5.5% |
| 2-BB(2F, 3F)—O2 | (9-3) | 11% |
| 2-HH1OB(2F, 3F)—O2 | (10-5) | 13% |
| 3-HH1OB(2F, 3F)—O2 | (10-5) | 15.5% |
| 3-HBB(2F, 3F)—O2 | (10-7) | 9% |
| 2-HH-3 | (2-1) | 25% |
| 3-HH-4 | (2-1) | 3% |
| 3-HBB-2 | (3-4) | 14% |
| 5-B(F)BB-2 | (3-8) | 4% |

NI=85.3° C.; Tc<−20° C.; Δn=0.109; Δε=−3.6; Vth=2.06 V; η=20.9 mPa·s.

Composition (M21)

| | | |
|---|---|---|
| V—HB(2F, 3F)—O2 | (9-1) | 7% |
| V—2BB(2F, 3F)—O2 | (9-3) | 10% |
| V—HHB(2F, 3F)—O1 | (10-1) | 7% |
| V—HHB(2F, 3F)—O2 | (10-1) | 9% |
| V—2HHB(2F, 3F)—O2 | (10-1) | 8% |
| 3-HH2B(2F, 3F)—O2 | (10-4) | 9% |
| V—HBB(2F, 3F)—O2 | (10-7) | 7% |
| V—HBB(2F, 3F)—O4 | (10-7) | 7% |
| 2-HH-3 | (2-1) | 9% |
| 3-HH-4 | (2-1) | 3% |
| 3-HH—V | (2-1) | 15% |
| 3-HH—V1 | (2-1) | 6% |
| 1V2—HH-3 | (2-1) | 3% |

NI=87.5° C.; Tc<−20° C.; Δn=0.100; Δε=−3.4; Vth=2.25 V; η=16.6 mPa·s.

Composition (M22)

| | | |
|---|---|---|
| 3-HHXB(F, F)—F | (6-100) | 6% |
| 3-BB(F, F)XB(F, F)—F | (6-97) | 13% |
| 3-HHBB(F, F)—F | (7-6) | 4% |
| 4-HHBB(F, F)—F | (7-6) | 5% |
| 3-HBBXB(F, F)—F | (7-32) | 3% |
| 3-BB(F)B(F, F)XB(F)—F | (7-46) | 2% |
| 4-BB(F)B(F, F)XB(F, F)—F | (7-47) | 8% |
| 5-BB(F)B(F, F)XB(F, F)—F | (7-47) | 7% |
| 3-HH—V | (2-1) | 44% |
| V—HHB-1 | (3-1) | 6% |
| 2-BB(F)B-3 | (3-6) | 2% |

NI=79.8° C.; Tc<−30° C.; Δn=0.106; Δε=8.5; Vth=1.45 V; η=11.6 mPa·s; γ1=60.0 mPa·s.

Composition (M23)

| | | |
|---|---|---|
| 5-HXB(F, F)—F | (5-13) | 3% |
| 3-HHXB(F, F)—F | (6-100) | 3% |
| 3-HHXB(F, F)—CF3 | (6-100) | 3% |
| 3-HGB(F, F)—F | (6-103) | 3% |
| 3-HB(F)B(F, F)—F | (6-50) | 5% |
| 3-BB(F, F)XB(F, F)—F | (6-97) | 6% |
| 3-HHBB(F, F)—F | (7-6) | 6% |
| 5-BB(F)B(F, F)XB(F)B(F, F)—F | (-) | 2% |
| 3-BB(2F, 3F)XB(F, F)—F | (6-114) | 4% |
| 3-B(2F, 3F)BXB(F, F)—F | (6-115) | 5% |
| 3-HHB(F, F)XB(F, F)—F | (7-29) | 4% |
| 3-HB—CL | (5-2) | 3% |
| 3-HHB—OCF3 | (6-1) | 3% |
| 3-HH—V | (2-1) | 22% |
| 3-HH—V1 | (2-1) | 10% |
| 5-HB—O2 | (2-5) | 5% |
| 3-HHEH-3 | (3-13) | 3% |
| 3-HBB-2 | (3-4) | 7% |
| 5-B(F)BB-3 | (3-8) | 3% |

NI=71.2° C.; Tc<−20° C.; Δn=0.099; Δε=6.1; Vth=1.74 V; η=13.2 mPa·s; γ1=59.3 mPa·s.

Composition (M24)

| | | |
|---|---|---|
| 5-HXB(F, F)—F | (5-13) | 6% |
| 3-HHXB(F, F)—F | (6-100) | 6% |
| V—HB(F)B(F, F)—F | (6-50) | 5% |
| 3-HHB(F)B(F, F)—F | (7-9) | 7% |
| 2-BB(F)B(F, F)XB(F)—F | (7-47) | 3% |
| 3-BB(F)B(F, F)XB(F)—F | (7-47) | 3% |
| 4-BB(F)B(F, F)XB(F)—F | (7-47) | 4% |
| 5-HB—CL | (5-2) | 5% |
| 2-HH-5 | (2-1) | 8% |
| 3-HH—V | (2-1) | 10% |
| 3-HH—V1 | (2-1) | 7% |
| 4-HH—V | (2-1) | 10% |
| 4-HH—V1 | (2-1) | 8% |
| 5-HB—O2 | (2-5) | 7% |
| 4-HHEH-3 | (3-13) | 3% |
| 1-BB(F)B—2V | (3-6) | 3% |
| 1O1—HBBH-3 | (4-1) | 5% |

NI=78.5° C.; Tc<−20° C.; Δn=0.095; Δε=3.4; Vth=1.50 V; η=8.4 mPa·s; γ1=54.2 mPa·s.

Composition (M25)

| | | |
|---|---|---|
| 3-HHEB(F, F)—F | (6-12) | 5% |
| 3-HHXB(F, F)—F | (6-100) | 7% |
| 5-HBEB(F, F)—F | (6-39) | 5% |
| 3-BB(F, F)XB(F, F)—F | (6-97) | 10% |
| 2-HHB(F)B(F, F)—F | (7-9) | 3% |

-continued

| | | |
|---|---|---|
| 3-HB(2F, 3F)BXB(F, F)—F | (7-58) | 3% |
| 3-BB(2F, 3F)BXB(F, F)—F | (7-59) | 2% |
| 5-HHB(F, F)XB(F, F)—F | (7-28) | 6% |
| 2-HH-3 | (2-1) | 8% |
| 3-HH—V | (2-1) | 20% |
| 3-HH—V1 | (2-1) | 7% |
| 4-HH—V | (2-1) | 6% |
| 5-HB—O2 | (2-5) | 5% |
| V2—B2BB-1 | (3) | 3% |
| 3-HHEBH-3 | (4-6) | 5% |
| 3-HHEBH-5 | (4-6) | 5% |

NI=90.3° C.; Tc<−20° C.; Δn=0.089; Δε=5.5; Vth=1.65 V; η=13.6 mPa·s; γ1=60.1 mPa·s.
Composition (M26)

| | | |
|---|---|---|
| 3-BB(F, F)XB(F, F)—F | (6-97) | 12% |
| 3-HHBB(F, F)—F | (7-6) | 5% |
| 4-HHBB(F, F)—F | (7-6) | 4% |
| 3-HBBXB(F, F)—F | (7-32) | 3% |
| 3-BB(F)B(F, F)XB(F)—F | (7-46) | 3% |
| 3-BB(F)B(F, F)XB(F, F)—F | (7-47) | 3% |
| 4-BB(F)B(F, F)XB(F, F)—F | (7-47) | 5% |
| 5-BB(F)B(F, F)XB(F, F)—F | (7-47) | 4% |
| 2-HH-3 | (2-1) | 6% |
| 3-HH-5 | (2-1) | 6% |
| 3-HH—V | (2-1) | 25% |
| 3-HH—VFF | (2-1) | 6% |
| 5-HB—O2 | (2-5) | 7% |
| V—HHB-1 | (3-1) | 6% |
| V—HBB-2 | (3-4) | 5% |

NI=78.3° C.; Tc<−20° C.; Δn=0.107; Δε=7.0; Vth=1.55 V; η=11.6 mPa·s; γ1=55.6 mPa·s.
Composition (M27)

| | | |
|---|---|---|
| 3-HHXB(F, F)—F | (6-100) | 3% |
| 3-BBXB(F, F)—F | (6-91) | 3% |
| 3-BB(F, F)XB(F, F)—F | (6-97) | 8% |
| 3-HHBB(F, F)—F | (7-6) | 5% |
| 4-HHBB(F, F)—F | (7-6) | 4% |
| 3-BB(F)B(F, F)XB(F, F)—F | (7-47) | 3% |
| 4-BB(F)B(F, F)XB(F, F)—F | (7-47) | 6% |
| 5-BB(F)B(F, F)XB(F, F)—F | (7-47) | 5% |
| 3-HH—V | (2-1) | 30% |
| 3-HH—V1 | (2-1) | 5% |
| 3-HHB—O1 | (3-1) | 2% |
| V—HHB-1 | (3-1) | 5% |
| 2-BB(F)B-3 | (3-6) | 6% |
| F3-HH—V | (2-1) | 15% |

NI=80.4° C.; Tc<−20° C.; Δn=0.106; Δε=5.8; Vth=1.40 V; η=11.6 mPa·s; γ1=61.0 mPa·s.
Composition (M28)

| | | |
|---|---|---|
| 3-HGB(F, F)—F | (6-103) | 3% |
| 5-GHB(F, F)—F | (6-109) | 4% |
| 3-GB(F, F)XB(F, F)—F | (6-113) | 5% |
| 3-BB(F)B(F, F)—CF3 | (6-69) | 2% |
| 3-HHBB(F, F)—F | (7-6) | 4% |
| 3-GBB(F)B(F, F)—F | (7-55) | 2% |
| 2-dhBB(F, F)XB(F, F)—F | (7-50) | 4% |
| 3-GB(F)B(F, F)XB(F, F)—F | (7-57) | 3% |
| 3-HGB(F, F)XB(F, F)—F | (—) | 5% |
| 7-HB(F, F)—F | (5-4) | 3% |
| 2-HH-3 | (2-1) | 14% |
| 2-HH-5 | (2-1) | 4% |
| 3-HH—V | (2-1) | 26% |
| 1V2-HH-3 | (2-1) | 5% |
| 1V2-BB-1 | (2-8) | 3% |
| 2-BB(F)B-3 | (3-6) | 3% |
| 3-HB(F)HH-2 | (4-7) | 4% |
| 5-HBB(F)B-2 | (4-5) | 6% |

NI=78.4° C.; Tc<−20° C.; Δn=0.094; Δε=5.6; Vth=1.45 V; η=11.5 mPa·s; γ1=61.7 mPa·s.
Composition (M29)

| | | |
|---|---|---|
| 3-HBB(F, F)-F | (6-24) | 5% |
| 5-HBB(F, F)-F | (6-24) | 4% |
| 3-BB(F)B(F, F)-F | (6-69) | 3% |
| 3-BB(F)B(F, F)XB(F, F)-F | (7-47) | 3% |
| 4-BB(F)B(F, F)XB(F, F)-F | (7-47) | 5% |
| 3-BB(F, F)XB(F)B(F, F)-F | (7-60) | 3% |
| 5-BB(F)B(F, F)XB(F)B(F, F)-F | (—) | 4% |
| 3-HH2BB(F, F)-F | (7-15) | 3% |
| 4-HH2BB(F, F)-F | (7-15) | 3% |
| 2-HH-5 | (2-1) | 8% |
| 3-HH-V | (2-1) | 25% |
| 3-HH-V1 | (2-1) | 7% |
| 4-HH-V1 | (2-1) | 6% |
| 5-HB-O2 | (2-5) | 5% |
| 7-HB-1 | (2-5) | 5% |
| VFF-HHB-O1 | (3-1) | 8% |
| VFF-HHB-1 | (3-1) | 3% |

NI=80.0° C.; Tc<−20° C.; Δn=0.101; Δε=4.6; Vth=1.71 V; η=11.0 mPa·s; γ1=47.2 mPa·s.
Composition (M30)

| | | |
|---|---|---|
| 3-HHB(F, F)-F | (6-3) | 8% |
| 3-GB(F)B(F)-F | (6-116) | 2% |
| 3-GB(F)B(F, F)-F | (6-117) | 3% |
| 3-BB(F, F)XB(F, F)-F | (6-97) | 8% |
| 3-GB(F)B(F, F)XB(F, F)-F | (7-57) | 6% |
| 5-GB(F)B(F, F)XB(F, F)-F | (7-57) | 5% |
| 3-HH-V | (2-1) | 30% |
| 3-HH-V1 | (2-1) | 10% |
| 1V2-HH-3 | (2-1) | 8% |
| 3-HH-VFF | (2-1) | 8% |
| V2-BB-1 | (2-8) | 2% |
| 5-HB(F)BH-3 | (4-2) | 5% |
| 5-HBBH-3 | (4-1) | 5% |

NI=78.6° C.; Tc<−20° C.; Δn=0.088; Δε=5.6; Vth=1.85 V; η=13.9 mPa·s; γ1=66.9 mPa·s.
Composition (M31)

| | | |
|---|---|---|
| 3-HHEB(F, F)-F | (6-12) | 4% |
| 5-HHEB(F, F)-F | (6-12) | 3% |
| 3-HBEB(F, F)-F | (6-39) | 3% |
| 5-HBEB(F, F)-F | (6-39) | 3% |
| 3-BB(F)B(F, F)-F | (6-69) | 3% |
| 3-GB(F)B(F, F)XB(F, F)-F | (7-57) | 5% |
| 4-GB(F)B(F, F)XB(F, F)-F | (7-57) | 5% |
| 5-HB-CL | (2-5) | 5% |
| 3-HHB-OCF3 | (3-1) | 4% |
| 3-HHB(F, F)XB(F, F)-F | (7-29) | 5% |
| 5-HHB(F, F)XB(F, F)-F | (7-29) | 3% |
| 3-HGB(F, F)XB(F, F)-F | (—) | 5% |
| 2-HH-5 | (2-1) | 3% |
| 3-HH-5 | (2-1) | 5% |
| 3-HH-V | (2-1) | 24% |
| 4-HH-V | (2-1) | 5% |
| 1V2-HH-3 | (2-1) | 5% |
| 3-HHEH-3 | (3-13) | 5% |
| 5-B(F)BB-2 | (3-8) | 3% |
| 5-B(F)BB-3 | (3-8) | 2% |

NI=82.9° C.; Tc<−20° C.; Δn=0.093; Δε=6.9; Vth=1.50 V; η=16.3 mPa·s; γ1=65.2 mPa·s.
Composition (M32)

| 3-HHXB(F, F)-F | (6-100) | 9% |
| 3-HBB(F, F)-F | (6-24) | 3% |
| 3-BB(F)B(F, F)-F | (6-69) | 4% |
| 3-BB(F)B(F, F)-CF3 | (6-69) | 4% |
| 3-BB(F, F)XB(F, F)-F | (6-97) | 5% |
| 3-GBB(F)B(F, F)-F | (7-55) | 3% |
| 4-GBB(F)B(F, F)-F | (7-55) | 4% |
| 3-HH-V | (2-1) | 25% |
| 3-HH-V1 | (2-1) | 10% |
| 5-HB-O2 | (2-5) | 10% |
| 7-HB-1 | (2-5) | 5% |
| V2-BB-1 | (2-8) | 3% |
| 3-HHB-1 | (3-1) | 4% |
| 1V-HBB-2 | (3-4) | 5% |
| 5-HBB(F)B-2 | (4-5) | 6% |

NI=79.6° C.; Tc<−20° C.; Δn=0.111; Δε=4.7; Vth=1.86 V; η=9.7 mPa·s; γ1=49.9 mPa·s.
Composition (M33)

| 3-BB(F, F)XB(F, F)-F | (6-97) | 14% |
| 5-BB(F)B(F, F)XB(F, F)-F | (7-47) | 7% |
| 7-HB(F, F)-F | (5-4) | 6% |
| 2-HH-5 | (2-1) | 5% |
| 3-HH-V | (2-1) | 30% |
| 3-HH-V1 | (2-1) | 3% |
| 3-HH-VFF | (2-1) | 10% |
| 3-HHB-1 | (3-1) | 4% |
| 3-HHB-3 | (3-1) | 5% |
| 3-HHB-O1 | (3-1) | 3% |
| 1-BB(F)B-2V | (3-6) | 3% |
| 3-HHEBH-3 | (4-6) | 3% |
| 3-HHEBH-4 | (4-6) | 4% |
| 3-HHEBH-5 | (4-6) | 3% |

NI=83.0° C.; Tc<−20° C.; Δn=0.086; Δε=3.8; Vth=1.94 V; η=7.5 mPa·s; γ1=51.5 mPa·s.
Composition (M34)

| 3-HBB(F, F)-F | (6-24) | 5% |
| 5-HBB(F, F)-F | (6-24) | 4% |
| 3-BB(F)B(F, F)-F | (6-69) | 3% |
| 3-BB(F)B(F, F)XB(F, F)-F | (7-47) | 3% |
| 4-BB(F)B(F, F)XB(F, F)-F | (7-47) | 5% |
| 3-BB(F)XB(F)B(F, F)-F | (7-60) | 3% |
| 5-BB(F)B(F, F)XB(F)B(F, F)-F | (—) | 4% |
| 3-HH2BB(F, F)-F | (7-15) | 3% |
| 4-HH2BB(F, F)-F | (7-15) | 3% |
| 2-HH-5 | (2-1) | 8% |
| 3-HH-V | (2-1) | 28% |
| 4-HH-V1 | (2-1) | 7% |
| 5-HB-O2 | (2-5) | 2% |
| 7-HB-1 | (2-5) | 5% |
| VFF-HHB-O1 | (3-1) | 8% |
| VFF-HHB-1 | (3-1) | 3% |
| 2-BB(2F, 3F)B-3 | (11-1) | 4% |
| 3-HBB(2F, 3F)-O2 | (10-7) | 2% |

NI=81.9° C.; Tc<−20° C.; Δn=0.109; Δε=4.8; Vth=1.75 V; η=13.3 mPa·s; γ1=57.4 mPa·s.
Composition (M35)

| 3-HHEB(F, F)-F | (6-12) | 4% |
| 3-HBEB(F, F)-F | (6-39) | 3% |
| 5-HBEB(F, F)-F | (6-39) | 3% |
| 3-BB(F)B(F, F)-F | (6-69) | 3% |
| 3-HBBXB(F, F)-F | (7-32) | 6% |
| 4-GBB(F, F)XB(F, F)-F | (7-62) | 2% |
| 5-GBB(F, F)XB(F, F)-F | (7-62) | 2% |
| 3-GB(F)B(F, F)XB(F, F)-F | (7-57) | 5% |
| 4-GB(F)B(F, F)XB(F, F)-F | (7-57) | 5% |
| 5-HHB(F, F)XB(F, F)-F | (7-29) | 3% |
| 5-HEB(F, F)-F | (5-10) | 3% |
| 5-HB-CL | (5-2) | 2% |
| 3-HHB-OCF3 | (6-1) | 4% |
| 3-HH-5 | (2-1) | 4% |
| 3-HH-V | (2-1) | 21% |
| 3-HH-V1 | (2-1) | 3% |
| 4-HH-V | (2-1) | 4% |
| 1V2-HH-3 | (2-1) | 6% |
| 5-B(F)BB-2 | (3-8) | 3% |
| 5-B(F)BB-3 | (3-8) | 2% |
| 3-HB(2F, 3F)-O2 | (10-7) | 3% |
| 3-BB(2F, 3F)-O2 | (9-3) | 2% |
| 3-HHB(2F, 3F)-O2 | (10-1) | 4% |
| F3-HH-V | (2-1) | 3% |

NI=78.2° C.; Tc<−20° C.; Δn=0.101; Δε=6.7; Vth=1.45 V; η=17.8 mPa·s; γ1=67.8 mPa·s.
Composition (M36)

| 3-HHB(F, F)-F | (6-3) | 10% |
| 3-HHXB(F, F)-F | (6-100) | 2% |
| 3-GHB(F, F)-F | (6-109) | 5% |
| 3-BB(F)B(F, F)-F | (6-69) | 6% |
| 3-BB(F, F)XB(F, F)-F | (6-97) | 14% |
| 4-BB(F)B(F, F)XB(F, F)-F | (7-47) | 10% |
| 5-BB(F)B(F, F)XB(F, F)-F | (7-47) | 6% |
| 2-HH-3 | (2-1) | 5% |
| 3-HH-4 | (2-1) | 11% |
| 3-HH-O1 | (2-1) | 5% |
| 5-HB-O2 | (2-5) | 8% |
| 3-HHB-1 | (3-1) | 6% |
| 3-HHB-3 | (3-1) | 6% |
| 3-HHB-O1 | (3-1) | 6% |

NI=77.6° C.; Tc<−20° C.; Δn=0.109; Δε=10.6; Vth=1.34 V; η=22.6 mPa·s; γ1=92.4 mPa·s.
Composition (M37)

| 3-HBB-F | (6-22) | 3% |
| 3-BB(F, F)XB(F)-OCF3 | (6-96) | 3% |
| 3-HHB(F)-F | (6-2) | 3% |
| 3-HGB(F, F)-F | (6-103) | 3% |
| 5-GHB(F, F)-F | (6-109) | 3% |
| 3-HBB(F, F)-F | (6-24) | 4% |
| 3-BB(F, F)XB(F, F)-F | (6-97) | 5% |
| 3-HHBB(F, F)-F | (7-6) | 5% |
| 3-HBBXB(F, F)-F | (7-32) | 5% |
| 3-BBVFFXB(F, F)-F | (6-119) | 8% |
| 3-HH-V | (2-1) | 39% |
| 1-HH-V1 | (2-1) | 3% |
| 1-HH-2V1 | (2-1) | 4% |
| 3-HHEH-5 | (3-13) | 3% |
| 1-BB(F)B-2V | (3-6) | 3% |
| 3-HHEBH-3 | (4-6) | 3% |
| 5-HBB(F)B-2 | (4-5) | 3% |

NI=85.2° C.; Tc<−20° C.; Δn=0.102; Δε=4.1; γ1=43.0 mPa·s.
Composition (M38)

| 3-HHBB(F)-F | (7-5) | 3% |
| 2-HHEB(F, F)-F | (6-12) | 3% |
| 5-BB(F)B(F, F)-F | (6-69) | 7% |
| 3-HHB(F)B(F, F)-F | (7-9) | 3% |
| 3-GB(F)B(F, F)XB(F, F)-F | (7-57) | 3% |
| 3-BB(F, F)XB(F)B(F, F)-F | (7-60) | 3% |

-continued

| | | |
|---|---|---|
| 3-HHVFFXB(F, F)-F | (6-120) | 5% |
| 3-BBVFFXB(F, F)-F | (6-119) | 5% |
| 3-HBBVFFXB(F, F)-F | (7-61) | 3% |
| 2-HH-5 | (2-1) | 5% |
| 3-HH-V | (2-1) | 20% |
| 5-HH-V | (2-1) | 12% |
| 3-HH-V1 | (2-1) | 4% |
| 4-HH-V1 | (2-1) | 5% |
| 2-HH-2V1 | (2-1) | 3% |
| 1-BB-3 | (2-8) | 3% |
| V2-BB(F)B-1 | (3-6) | 5% |
| V2-B(F)BB-1 | (3-8) | 5% |
| 3-HB(F)HH-5 | (4-7) | 3% |

NI=85.8° C.; Tc<−20° C.; Δn=0.115; Δε=4.2; γ1=41.4 mPa·s.

Composition (M39)

| | | |
|---|---|---|
| 3-BB(F)XB(F)B(F, F)-F | (7-60) | 5% |
| 3-HGB(F, F)-F | (6-103) | 3% |
| 5-GHB(F, F)-F | (6-109) | 4% |
| 3-GB(F, F)XB(F, F)-F | (6-113) | 5% |
| 3-HHBB(F, F)-F | (7-6) | 4% |
| 2-dhBB(F, F)XB(F, F)-F | (7-50) | 4% |
| 3-GB(F)B(F, F)XB(F, F)-F | (7-57) | 3% |
| 3-HGB(F, F)XB(F, F)-F | (7) | 5% |
| 7-HB(F, F)-F | (5-4) | 3% |
| 2-HH-3 | (2-1) | 14% |
| 2-HH-5 | (2-1) | 4% |
| 3-HH-V | (2-1) | 26% |
| 1V2-HH-3 | (2-1) | 5% |
| 1V2-BB-1 | (2-8) | 3% |
| 2-BB(F)B-3 | (3-6) | 3% |
| 3-HB(F)HH-2 | (4-7) | 4% |
| 5-HBB(F)B-2 | (4-5) | 5% |

NI=78.4° C.; Tc<−20° C.; Δn=0.094; Δε=5.6; Vth=1.45 V; η=11.5 mPa·s; γ1=61.7 mPa·s.

Composition (M40)

| | | |
|---|---|---|
| 3-HBB(F, F)-F | (6-24) | 5% |
| 5-HBB(F, F)-F | (6-24) | 4% |
| 3-BB(F)B(F, F)XB(F, F)-F | (7-47) | 3% |
| 4-BB(F)B(F, F)XB(F, F)-F | (7-47) | 5% |
| 3-BB(F, F)XB(F)B(F, F)-F | (7-60) | 10% |
| 3-HH2BB(F, F)-F | (7-15) | 3% |
| 4-HH2BB(F, F)-F | (7-15) | 3% |
| 2-HH-5 | (2-1) | 4% |
| 3-HH-V | (2-1) | 25% |
| 3-HH-V1 | (2-1) | 10% |
| 4-HH-V1 | (2-1) | 7% |
| 5-HB-O2 | (2-5) | 5% |
| 7-HB-1 | (2-5) | 5% |
| VFF-HHB-O1 | (3-1) | 8% |
| VFF-HHB-1 | (3-1) | 3% |

NI=79.3° C.; Tc<−20° C.; Δn=0.099; Δε=5.0; Vth=1.64 V; η=10.4 mPa·s; γ1=44.7 mPa·s.

Composition (M41)

| | | |
|---|---|---|
| 3-GBXB(F)B(F, F)-F | (7) | 5% |
| 3-HHB(F, F)-F | (6-3) | 7% |
| 3-GB(F)B(F)-F | (6-116) | 2% |
| 3-GB(F)B(F, F)-F | (6-117) | 3% |
| 3-BB(F, F)XB(F, F)-F | (6-97) | 7% |
| 3-GB(F)B(F, F)XB(F, F)-F | (7-57) | 4% |
| 5-GB(F)B(F, F)XB(F, F)-F | (7-57) | 5% |
| 3-HH-V | (2-1) | 30% |
| 3-HH-V1 | (2-1) | 10% |
| 1V2-HH-3 | (2-1) | 8% |
| 3-HH-VFF | (2-1) | 8% |
| V2-BB-1 | (2-8) | 2% |
| 5-HB(F)BH-3 | (4-2) | 4% |
| 5-HBBH-3 | (4-1) | 5% |

NI=79.7° C.; Tc<−20° C.; Δn=0.091; Δε=5.7; Vth=1.83 V; η=14.9 mPa·s; γ1=69.3 mPa·s.

2. Alignment of Liquid Crystal Molecules

Use Example 1

To composition (M1), compound (No. 59) was added at a proportion of 0.1% by weight as a first additive, and compound (AO-1) in which $R^{40}$ is n-heptyl was added at a proportion of 150 ppm as an antioxidant. The resulting mixture was injected into an IPS device having no alignment film at 90° C. (equal to or higher than a maximum temperature of a nematic phase). The IPS device was irradiated with linearly polarized ultraviolet light (313 nm, 2.0 J/cm$^2$) from a direction normal to the device while heating the device at 90° C. to obtain a device subjected to alignment treatment. The resulting device was set on a polarizing microscope in which a polarizer and an analyzer were arranged perpendicularly to each other to be parallel to a polarization axis of linearly polarized light in the device. The device was irradiated with light from below, and presence or absence of light leakage was observed. A case where no light passed through the device was judged to be "Good" in alignment. A case where light passing through the device was observed was expressed by "Poor." No light leakage was observed in the present Example 1, and therefore alignment was good.

Use Examples 2 to 589

As shown in Tables 4 to 27 below, compositions (M1) to (M41) were used, compound (AO-1) in which $R^{40}$ is n-heptyl was added at a proportion of 150 ppm as an antioxidant, and a first additive was mixed thereto at a proportion of 0.1% by weight as described in the following tables. Operation was performed in the same manner as in Use Example 1 except for the operation described above. When presence or absence of light leakage was observed in the same manner as in Use Example 1, no light leakage was observed, and therefore alignment was good.

TABLE 4

| Use Example | Liquid crystal composition | First additive | Alignment |
|---|---|---|---|
| 2 | M2 | No. 1 | Good |
| 3 | M3 | No. 2 | Good |
| 4 | M4 | No. 3 | Good |
| 5 | M5 | No. 4 | Good |
| 6 | M6 | No. 5 | Good |
| 7 | M7 | No. 6 | Good |
| 8 | M8 | No. 7 | Good |
| 9 | M9 | No. 8 | Good |
| 10 | M10 | No. 9 | Good |
| 11 | M11 | No. 10 | Good |
| 12 | M12 | No. 11 | Good |

TABLE 5

| | | | |
|---|---|---|---|
| 13 | M13 | No. 12 | Good |
| 14 | M14 | No. 13 | Good |

TABLE 5-continued

| | | | |
|---|---|---|---|
| 15 | M15 | No. 14 | Good |
| 16 | M16 | No. 15 | Good |
| 17 | M17 | No. 16 | Good |
| 18 | M18 | No. 17 | Good |
| 19 | M19 | No. 18 | Good |
| 20 | M20 | No. 19 | Good |
| 21 | M21 | No. 20 | Good |
| 22 | M22 | No. 21 | Good |
| 23 | M23 | No. 22 | Good |
| 24 | M24 | No. 23 | Good |
| 25 | M25 | No. 24 | Good |
| 26 | M26 | No. 25 | Good |
| 27 | M27 | No. 26 | Good |
| 28 | M28 | No. 27 | Good |
| 29 | M29 | No. 28 | Good |
| 30 | M30 | No. 29 | Good |
| 31 | M31 | No. 30 | Good |
| 32 | M32 | No. 31 | Good |
| 33 | M33 | No. 32 | Good |
| 34 | M34 | No. 33 | Good |
| 35 | M35 | No. 34 | Good |
| 36 | M36 | No. 35 | Good |
| 37 | M37 | No. 36 | Good |

TABLE 6

| | | | |
|---|---|---|---|
| 38 | M38 | No. 37 | Good |
| 39 | M39 | No. 38 | Good |
| 40 | M40 | No. 39 | Good |
| 41 | M41 | No. 40 | Good |
| 42 | M1 | No. 41 | Good |
| 43 | M2 | No. 42 | Good |
| 44 | M3 | No. 43 | Good |
| 45 | M4 | No. 44 | Good |
| 46 | M5 | No. 45 | Good |
| 47 | M6 | No. 46 | Good |
| 48 | M7 | No. 47 | Good |
| 49 | M8 | No. 48 | Good |
| 50 | M9 | No. 49 | Good |
| 51 | M10 | No. 50 | Good |
| 52 | M11 | No. 51 | Good |
| 53 | M12 | No. 52 | Good |
| 54 | M13 | No. 53 | Good |
| 55 | M14 | No. 54 | Good |
| 56 | M15 | No. 55 | Good |
| 57 | M16 | No. 56 | Good |
| 58 | M17 | No. 57 | Good |
| 59 | M18 | No. 58 | Good |
| 60 | M19 | No. 59 | Good |
| 61 | M20 | No. 60 | Good |

TABLE 7

| | | | |
|---|---|---|---|
| 62 | M21 | No. 61 | Good |
| 63 | M22 | No. 62 | Good |
| 64 | M23 | No. 63 | Good |
| 65 | M24 | No. 64 | Good |
| 66 | M25 | No. 65 | Good |
| 67 | M26 | No. 66 | Good |
| 68 | M27 | No. 67 | Good |
| 69 | M28 | No. 68 | Good |
| 70 | M29 | No. 69 | Good |
| 71 | M30 | No. 70 | Good |
| 72 | M31 | No. 71 | Good |
| 73 | M32 | No. 72 | Good |
| 74 | M33 | No. 73 | Good |
| 75 | M34 | No. 74 | Good |
| 76 | M35 | No. 75 | Good |
| 77 | M36 | No. 76 | Good |
| 78 | M37 | No. 77 | Good |
| 79 | M38 | No. 78 | Good |

TABLE 7-continued

| | | | |
|---|---|---|---|
| 80 | M39 | No. 79 | Good |
| 81 | M40 | No. 80 | Good |
| 82 | M41 | No. 81 | Good |
| 83 | M1 | No. 82 | Good |

TABLE 8

| | | | |
|---|---|---|---|
| 84 | M2 | No. 83 | Good |
| 85 | M3 | No. 84 | Good |
| 86 | M4 | No. 85 | Good |
| 87 | M5 | No. 86 | Good |
| 88 | M6 | No. 87 | Good |
| 89 | M7 | No. 88 | Good |
| 90 | M8 | No. 89 | Good |
| 91 | M9 | No. 90 | Good |
| 92 | M10 | No. 91 | Good |
| 93 | M11 | No. 92 | Good |
| 94 | M12 | No. 93 | Good |
| 95 | M13 | No. 94 | Good |
| 96 | M14 | No. 95 | Good |
| 97 | M15 | No. 96 | Good |
| 98 | M16 | No. 97 | Good |
| 99 | M17 | No. 98 | Good |
| 100 | M18 | No. 99 | Good |
| 101 | M19 | No. 100 | Good |
| 102 | M20 | No. 101 | Good |
| 103 | M21 | No. 102 | Good |
| 104 | M22 | No. 103 | Good |
| 105 | M23 | No. 104 | Good |
| 106 | M24 | No. 105 | Good |
| 107 | M25 | No. 106 | Good |
| 108 | M26 | No. 107 | Good |
| 109 | M27 | No. 108 | Good |
| 110 | M28 | No. 109 | Good |

TABLE 9

| | | | |
|---|---|---|---|
| 111 | M29 | No. 110 | Good |
| 112 | M30 | No. 111 | Good |
| 113 | M31 | No. 112 | Good |
| 114 | M32 | No. 113 | Good |
| 115 | M33 | No. 114 | Good |
| 116 | M34 | No. 115 | Good |
| 117 | M35 | No. 116 | Good |
| 118 | M36 | No. 117 | Good |
| 119 | M37 | No. 118 | Good |
| 120 | M38 | No. 119 | Good |
| 121 | M39 | No. 120 | Good |
| 122 | M40 | No. 121 | Good |
| 123 | M41 | No. 122 | Good |
| 124 | M1 | No. 123 | Good |
| 125 | M2 | No. 124 | Good |
| 126 | M3 | No. 125 | Good |
| 127 | M4 | No. 126 | Good |
| 128 | M5 | No. 127 | Good |
| 129 | M6 | No. 128 | Good |
| 130 | M7 | No. 129 | Good |
| 131 | M8 | No. 130 | Good |
| 132 | M9 | No. 131 | Good |
| 133 | M10 | No. 132 | Good |
| 134 | M11 | No. 133 | Good |

TABLE 10

| | | | |
|---|---|---|---|
| 135 | M12 | No. 134 | Good |
| 136 | M13 | No. 135 | Good |
| 137 | M14 | No. 136 | Good |
| 138 | M15 | No. 137 | Good |
| 139 | M16 | No. 138 | Good |
| 140 | M17 | No. 139 | Good |
| 141 | M18 | No. 140 | Good |
| 142 | M19 | No. 141 | Good |
| 143 | M20 | No. 142 | Good |

TABLE 10-continued

| | | | |
|---|---|---|---|
| 144 | M21 | No. 143 | Good |
| 145 | M22 | No. 144 | Good |
| 146 | M23 | No. 145 | Good |
| 147 | M24 | No. 146 | Good |
| 148 | M25 | No. 147 | Good |
| 149 | M26 | No. 148 | Good |
| 150 | M27 | No. 149 | Good |
| 151 | M28 | No. 150 | Good |
| 152 | M29 | No. 151 | Good |
| 153 | M30 | No. 152 | Good |
| 154 | M31 | No. 153 | Good |
| 155 | M32 | No. 154 | Good |
| 156 | M33 | No. 155 | Good |
| 157 | M34 | No. 156 | Good |
| 158 | M35 | No. 157 | Good |
| 159 | M36 | No. 158 | Good |

TABLE 11

| | | | |
|---|---|---|---|
| 160 | M37 | No. 159 | Good |
| 161 | M38 | No. 160 | Good |
| 162 | M39 | No. 161 | Good |
| 163 | M40 | No. 162 | Good |
| 164 | M41 | No. 163 | Good |
| 165 | M1 | No. 164 | Good |
| 166 | M2 | No. 165 | Good |
| 167 | M3 | No. 166 | Good |
| 168 | M4 | No. 167 | Good |
| 169 | M5 | No. 168 | Good |
| 170 | M6 | No. 169 | Good |
| 171 | M7 | No. 170 | Good |
| 172 | M8 | No. 171 | Good |
| 173 | M9 | No. 172 | Good |
| 174 | M10 | No. 173 | Good |
| 175 | M11 | No. 174 | Good |
| 176 | M12 | No. 175 | Good |
| 177 | M13 | No. 176 | Good |
| 178 | M14 | No. 177 | Good |
| 179 | M15 | No. 178 | Good |
| 180 | M16 | No. 179 | Good |
| 181 | M17 | No. 180 | Good |
| 182 | M18 | No. 181 | Good |
| 183 | M19 | No. 182 | Good |
| 184 | M20 | No. 183 | Good |

TABLE 12

| | | | |
|---|---|---|---|
| 185 | M21 | No. 184 | Good |
| 186 | M22 | No. 185 | Good |
| 187 | M23 | No. 186 | Good |
| 188 | M24 | No. 187 | Good |
| 189 | M25 | No. 188 | Good |
| 190 | M26 | No. 189 | Good |
| 191 | M27 | No. 190 | Good |
| 192 | M28 | No. 191 | Good |
| 193 | M29 | No. 192 | Good |
| 194 | M30 | No. 193 | Good |
| 195 | M31 | No. 194 | Good |
| 196 | M32 | No. 195 | Good |
| 197 | M33 | No. 196 | Good |
| 198 | M34 | No. 197 | Good |
| 199 | M35 | No. 198 | Good |
| 200 | M36 | No. 199 | Good |
| 201 | M37 | No. 200 | Good |
| 202 | M38 | No. 201 | Good |
| 203 | M39 | No. 202 | Good |
| 204 | M40 | No. 203 | Good |
| 205 | M41 | No. 204 | Good |
| 206 | M1 | No. 205 | Good |
| 207 | M2 | No. 206 | Good |
| 208 | M3 | No. 207 | Good |

TABLE 13

| | | | |
|---|---|---|---|
| 209 | M4 | No. 208 | Good |
| 210 | M5 | No. 209 | Good |
| 211 | M6 | No. 210 | Good |
| 212 | M7 | No. 211 | Good |
| 213 | M8 | No. 212 | Good |
| 214 | M9 | No. 213 | Good |
| 215 | M10 | No. 214 | Good |
| 216 | M11 | No. 215 | Good |
| 217 | M12 | No. 216 | Good |
| 218 | M13 | No. 217 | Good |
| 219 | M14 | No. 218 | Good |
| 220 | M15 | No. 219 | Good |
| 221 | M16 | No. 220 | Good |
| 222 | M17 | No. 221 | Good |
| 223 | M18 | No. 222 | Good |
| 224 | M19 | No. 223 | Good |
| 225 | M20 | No. 224 | Good |
| 226 | M21 | No. 225 | Good |
| 227 | M22 | No. 226 | Good |
| 228 | M23 | No. 227 | Good |
| 229 | M24 | No. 228 | Good |
| 230 | M25 | No. 229 | Good |

TABLE 14

| | | | |
|---|---|---|---|
| 231 | M26 | No. 230 | Good |
| 232 | M27 | No. 231 | Good |
| 233 | M28 | No. 232 | Good |
| 234 | M29 | No. 233 | Good |
| 235 | M30 | No. 234 | Good |
| 236 | M31 | No. 235 | Good |
| 237 | M32 | No. 236 | Good |
| 238 | M33 | No. 237 | Good |
| 239 | M34 | No. 238 | Good |
| 240 | M35 | No. 239 | Good |
| 241 | M36 | No. 240 | Good |
| 242 | M37 | No. 241 | Good |
| 243 | M38 | No. 242 | Good |
| 244 | M39 | No. 243 | Good |
| 245 | M40 | No. 244 | Good |
| 246 | M41 | No. 245 | Good |
| 247 | M1 | No. 246 | Good |
| 248 | M2 | No. 247 | Good |
| 249 | M3 | No. 248 | Good |
| 250 | M4 | No. 249 | Good |
| 251 | M5 | No. 250 | Good |
| 252 | M6 | No. 251 | Good |
| 253 | M7 | No. 252 | Good |
| 254 | M8 | No. 253 | Good |
| 255 | M9 | No. 254 | Good |
| 256 | M10 | No. 255 | Good |
| 257 | M11 | No. 256 | Good |

TABLE 15

| | | | |
|---|---|---|---|
| 258 | M12 | No. 257 | Good |
| 259 | M13 | No. 258 | Good |
| 260 | M14 | No. 259 | Good |
| 261 | M15 | No. 260 | Good |
| 262 | M16 | No. 261 | Good |
| 263 | M17 | No. 262 | Good |
| 264 | M18 | No. 263 | Good |
| 265 | M19 | No. 264 | Good |
| 266 | M20 | No. 265 | Good |
| 267 | M21 | No. 266 | Good |
| 268 | M22 | No. 267 | Good |
| 269 | M23 | No. 268 | Good |
| 270 | M24 | No. 269 | Good |
| 271 | M25 | No. 270 | Good |
| 272 | M26 | No. 271 | Good |
| 273 | M27 | No. 272 | Good |
| 274 | M28 | No. 273 | Good |
| 275 | M29 | No. 274 | Good |
| 276 | M30 | No. 275 | Good |
| 277 | M31 | No. 276 | Good |

TABLE 15-continued

| 278 | M32 | No. 277 | Good |
| 279 | M33 | No. 278 | Good |
| 280 | M34 | No. 279 | Good |
| 281 | M35 | No. 280 | Good |
| 282 | M36 | No. 281 | Good |

TABLE 16

| 283 | M37 | No. 282 | Good |
| 284 | M38 | No. 283 | Good |
| 285 | M39 | No. 284 | Good |
| 286 | M40 | No. 285 | Good |
| 287 | M41 | No. 286 | Good |
| 288 | M1 | No. 287 | Good |
| 289 | M2 | No. 288 | Good |
| 290 | M3 | No. 289 | Good |
| 291 | M4 | No. 290 | Good |
| 292 | M5 | No. 291 | Good |
| 293 | M6 | No. 292 | Good |
| 294 | M7 | No. 293 | Good |
| 295 | M8 | No. 294 | Good |
| 296 | M9 | No. 295 | Good |
| 297 | M10 | No. 296 | Good |
| 298 | M11 | No. 297 | Good |
| 299 | M12 | No. 298 | Good |
| 300 | M13 | No. 299 | Good |
| 301 | M14 | No. 300 | Good |
| 302 | M15 | No. 301 | Good |
| 303 | M16 | No. 302 | Good |
| 304 | M17 | No. 303 | Good |
| 305 | M18 | No. 304 | Good |
| 306 | M19 | No. 305 | Good |

TABLE 17

| 307 | M20 | No. 306 | Good |
| 308 | M21 | No. 307 | Good |
| 309 | M22 | No. 308 | Good |
| 310 | M23 | No. 309 | Good |
| 311 | M24 | No. 310 | Good |
| 312 | M25 | No. 311 | Good |
| 313 | M26 | No. 312 | Good |
| 314 | M27 | No. 313 | Good |
| 315 | M28 | No. 314 | Good |
| 316 | M29 | No. 315 | Good |
| 317 | M30 | No. 316 | Good |
| 318 | M31 | No. 317 | Good |
| 319 | M32 | No. 318 | Good |
| 320 | M33 | No. 319 | Good |
| 321 | M34 | No. 320 | Good |
| 322 | M35 | No. 321 | Good |
| 323 | M36 | No. 322 | Good |
| 324 | M37 | No. 323 | Good |
| 325 | M38 | No. 324 | Good |
| 326 | M39 | No. 325 | Good |
| 327 | M40 | No. 326 | Good |
| 328 | M41 | No. 327 | Good |
| 329 | M1 | No. 328 | Good |

TABLE 18

| 330 | M2 | No. 329 | Good |
| 331 | M3 | No. 330 | Good |
| 332 | M4 | No. 331 | Good |
| 333 | M5 | No. 332 | Good |
| 334 | M6 | No. 333 | Good |
| 335 | M7 | No. 334 | Good |
| 336 | M8 | No. 335 | Good |
| 337 | M9 | No. 336 | Good |
| 338 | M10 | No. 337 | Good |
| 339 | M11 | No. 338 | Good |
| 340 | M12 | No. 339 | Good |
| 341 | M13 | No. 340 | Good |

TABLE 18-continued

| 342 | M14 | No. 341 | Good |
| 343 | M15 | No. 342 | Good |
| 344 | M16 | No. 343 | Good |
| 345 | M17 | No. 344 | Good |
| 346 | M18 | No. 345 | Good |
| 347 | M19 | No. 346 | Good |
| 348 | M20 | No. 347 | Good |
| 349 | M21 | No. 348 | Good |
| 350 | M22 | No. 349 | Good |
| 351 | M23 | No. 350 | Good |
| 352 | M24 | No. 351 | Good |
| 353 | M25 | No. 352 | Good |
| 354 | M26 | No. 353 | Good |
| 355 | M27 | No. 354 | Good |

TABLE 19

| 356 | M28 | No. 355 | Good |
| 357 | M29 | No. 356 | Good |
| 358 | M30 | No. 357 | Good |
| 359 | M31 | No. 358 | Good |
| 360 | M32 | No. 359 | Good |
| 361 | M33 | No. 360 | Good |
| 362 | M34 | No. 361 | Good |
| 363 | M35 | No. 362 | Good |
| 364 | M36 | No. 363 | Good |
| 365 | M37 | No. 364 | Good |
| 366 | M38 | No. 365 | Good |
| 367 | M39 | No. 366 | Good |
| 368 | M40 | No. 367 | Good |
| 369 | M41 | No. 368 | Good |
| 370 | M1 | No. 369 | Good |
| 371 | M2 | No. 370 | Good |
| 372 | M3 | No. 371 | Good |
| 373 | M4 | No. 372 | Good |
| 374 | M5 | No. 373 | Good |
| 375 | M6 | No. 374 | Good |
| 376 | M7 | No. 375 | Good |
| 377 | M8 | No. 376 | Good |
| 378 | M9 | No. 377 | Good |
| 379 | M10 | No. 378 | Good |
| 380 | M11 | No. 379 | Good |
| 381 | M12 | No. 380 | Good |
| 382 | M13 | No. 381 | Good |

TABLE 20

| 383 | M14 | No. 382 | Good |
| 384 | M15 | No. 383 | Good |
| 385 | M16 | No. 384 | Good |
| 386 | M17 | No. 385 | Good |
| 387 | M18 | No. 386 | Good |
| 388 | M19 | No. 387 | Good |
| 389 | M20 | No. 388 | Good |
| 390 | M21 | No. 389 | Good |
| 391 | M22 | No. 390 | Good |
| 392 | M23 | No. 391 | Good |
| 393 | M24 | No. 392 | Good |
| 394 | M25 | No. 393 | Good |
| 395 | M26 | No. 394 | Good |
| 396 | M27 | No. 395 | Good |
| 397 | M28 | No. 396 | Good |
| 398 | M29 | No. 397 | Good |
| 399 | M30 | No. 398 | Good |
| 400 | M31 | No. 399 | Good |
| 401 | M32 | No. 400 | Good |
| 402 | M33 | No. 401 | Good |
| 403 | M34 | No. 402 | Good |
| 404 | M35 | No. 403 | Good |

TABLE 21

| | | | |
|---|---|---|---|
| 405 | M36 | No. 404 | Good |
| 406 | M37 | No. 405 | Good |
| 407 | M38 | No. 406 | Good |
| 408 | M39 | No. 407 | Good |
| 409 | M40 | No. 408 | Good |
| 410 | M41 | No. 409 | Good |
| 411 | M1 | No. 410 | Good |
| 412 | M2 | No. 411 | Good |
| 413 | M3 | No. 412 | Good |
| 414 | M4 | No. 413 | Good |
| 415 | M5 | No. 414 | Good |
| 416 | M6 | No. 415 | Good |
| 417 | M7 | No. 416 | Good |
| 418 | M8 | No. 417 | Good |
| 419 | M9 | No. 418 | Good |
| 420 | M10 | No. 419 | Good |
| 421 | M11 | No. 420 | Good |
| 422 | M12 | No. 421 | Good |
| 423 | M13 | No. 422 | Good |
| 424 | M14 | No. 423 | Good |
| 425 | M15 | No. 424 | Good |

TABLE 22

| | | | |
|---|---|---|---|
| 426 | M16 | No. 425 | Good |
| 427 | M17 | No. 426 | Good |
| 428 | M18 | No. 427 | Good |
| 429 | M19 | No. 428 | Good |
| 430 | M20 | No. 429 | Good |
| 431 | M21 | No. 430 | Good |
| 432 | M22 | No. 431 | Good |
| 433 | M23 | No. 432 | Good |
| 434 | M24 | No. 433 | Good |
| 435 | M25 | No. 434 | Good |
| 436 | M26 | No. 435 | Good |
| 437 | M27 | No. 436 | Good |
| 438 | M28 | No. 437 | Good |
| 439 | M29 | No. 438 | Good |
| 440 | M30 | No. 439 | Good |
| 441 | M31 | No. 440 | Good |
| 442 | M32 | No. 441 | Good |
| 443 | M33 | No. 442 | Good |
| 444 | M34 | No. 443 | Good |
| 445 | M35 | No. 444 | Good |
| 446 | M36 | No. 445 | Good |
| 447 | M37 | No. 446 | Good |
| 448 | M38 | No. 447 | Good |
| 449 | M39 | No. 448 | Good |
| 450 | M40 | No. 449 | Good |
| 451 | M41 | No. 450 | Good |
| 452 | M1 | No. 451 | Good |
| 453 | M2 | No. 452 | Good |

TABLE 23

| | | | |
|---|---|---|---|
| 454 | M3 | No. 453 | Good |
| 455 | M4 | No. 454 | Good |
| 456 | M5 | No. 455 | Good |
| 457 | M6 | No. 456 | Good |
| 458 | M7 | No. 457 | Good |
| 459 | M8 | No. 458 | Good |
| 460 | M9 | No. 459 | Good |
| 461 | M10 | No. 460 | Good |
| 462 | M11 | No. 461 | Good |
| 463 | M12 | No. 462 | Good |
| 464 | M13 | No. 463 | Good |
| 465 | M14 | No. 464 | Good |
| 466 | M15 | No. 465 | Good |
| 467 | M16 | No. 466 | Good |
| 468 | M17 | No. 467 | Good |
| 469 | M18 | No. 468 | Good |
| 470 | M19 | No. 469 | Good |
| 471 | M20 | No. 470 | Good |
| 472 | M21 | No. 471 | Good |
| 473 | M22 | No. 472 | Good |

TABLE 23-continued

| | | | |
|---|---|---|---|
| 474 | M23 | No. 473 | Good |
| 475 | M24 | No. 474 | Good |
| 476 | M25 | No. 475 | Good |
| 477 | M26 | No. 476 | Good |

TABLE 24

| | | | |
|---|---|---|---|
| 478 | M27 | No. 477 | Good |
| 479 | M28 | No. 478 | Good |
| 480 | M29 | No. 479 | Good |
| 481 | M30 | No. 480 | Good |
| 482 | M31 | No. 481 | Good |
| 483 | M32 | No. 482 | Good |
| 484 | M33 | No. 483 | Good |
| 485 | M34 | No. 484 | Good |
| 486 | M35 | No. 485 | Good |
| 487 | M36 | No. 486 | Good |
| 488 | M37 | No. 487 | Good |
| 489 | M38 | No. 488 | Good |
| 490 | M39 | No. 489 | Good |
| 491 | M40 | No. 490 | Good |
| 492 | M41 | No. 491 | Good |
| 493 | M1 | No. 492 | Good |
| 494 | M2 | No. 493 | Good |
| 495 | M3 | No. 494 | Good |
| 496 | M4 | No. 495 | Good |
| 497 | M5 | No. 496 | Good |
| 498 | M6 | No. 497 | Good |
| 499 | M7 | No. 498 | Good |
| 500 | M8 | No. 499 | Good |
| 501 | M9 | No. 500 | Good |
| 502 | M10 | No. 501 | Good |

TABLE 25

| | | | |
|---|---|---|---|
| 503 | M11 | No. 502 | Good |
| 504 | M12 | No. 503 | Good |
| 505 | M13 | No. 504 | Good |
| 506 | M14 | No. 505 | Good |
| 507 | M15 | No. 506 | Good |
| 508 | M16 | No. 507 | Good |
| 509 | M17 | No. 508 | Good |
| 510 | M18 | No. 509 | Good |
| 511 | M19 | No. 510 | Good |
| 512 | M20 | No. 511 | Good |
| 513 | M21 | No. 512 | Good |
| 514 | M22 | No. 513 | Good |
| 515 | M23 | No. 514 | Good |
| 516 | M24 | No. 515 | Good |
| 517 | M25 | No. 516 | Good |
| 518 | M26 | No. 517 | Good |
| 519 | M27 | No. 518 | Good |
| 520 | M28 | No. 519 | Good |
| 521 | M29 | No. 520 | Good |
| 522 | M30 | No. 521 | Good |
| 523 | M31 | No. 522 | Good |
| 524 | M32 | No. 523 | Good |
| 525 | M33 | No. 524 | Good |
| 526 | M34 | No. 525 | Good |

TABLE 26

| | | | |
|---|---|---|---|
| 527 | M35 | No. 526 | Good |
| 528 | M36 | No. 527 | Good |
| 529 | M37 | No. 528 | Good |
| 530 | M38 | No. 529 | Good |
| 531 | M39 | No. 530 | Good |
| 532 | M40 | No. 531 | Good |
| 533 | M41 | No. 532 | Good |
| 534 | M1 | No. 533 | Good |
| 535 | M2 | No. 534 | Good |
| 536 | M3 | No. 535 | Good |
| 537 | M4 | No. 536 | Good |

TABLE 26-continued

| | | | |
|---|---|---|---|
| 538 | M5 | No. 537 | Good |
| 539 | M6 | No. 538 | Good |
| 540 | M7 | No. 539 | Good |
| 541 | M8 | No. 540 | Good |
| 542 | M9 | No. 541 | Good |
| 543 | M10 | No. 542 | Good |
| 544 | M11 | No. 543 | Good |
| 545 | M12 | No. 544 | Good |
| 546 | M13 | No. 545 | Good |
| 547 | M14 | No. 546 | Good |
| 548 | M15 | No. 547 | Good |
| 549 | M16 | No. 548 | Good |
| 550 | M17 | No. 549 | Good |
| 551 | M18 | No. 550 | Good |

TABLE 27

| | | | |
|---|---|---|---|
| 552 | M19 | No. 551 | Good |
| 553 | M20 | No. 552 | Good |
| 554 | M21 | No. 553 | Good |
| 555 | M22 | No. 554 | Good |
| 556 | M23 | No. 555 | Good |
| 557 | M24 | No. 556 | Good |
| 558 | M25 | No. 557 | Good |
| 559 | M26 | No. 558 | Good |
| 560 | M27 | No. 559 | Good |
| 561 | M28 | No. 560 | Good |
| 562 | M29 | No. 561 | Good |
| 563 | M30 | No. 562 | Good |
| 564 | M31 | No. 563 | Good |
| 565 | M32 | No. 564 | Good |
| 566 | M33 | No. 565 | Good |
| 567 | M34 | No. 566 | Good |
| 568 | M35 | No. 567 | Good |
| 569 | M36 | No. 568 | Good |
| 570 | M37 | No. 569 | Good |

TABLE 27-continued

| | | | |
|---|---|---|---|
| 571 | M38 | No. 570 | Good |
| 572 | M39 | No. 571 | Good |
| 573 | M40 | No. 572 | Good |
| 574 | M41 | No. 573 | Good |
| 575 | M1 | No. 574 | Good |
| 576 | M2 | No. 575 | Good |
| 577 | M3 | No. 576 | Good |
| 578 | M4 | No. 577 | Good |
| 579 | M5 | No. 578 | Good |
| 580 | M6 | No. 579 | Good |
| 581 | M7 | No. 580 | Good |
| 582 | M8 | No. 581 | Good |
| 583 | M9 | No. 582 | Good |
| 584 | M10 | No. 583 | Good |
| 585 | M11 | No. 584 | Good |
| 586 | M12 | No. 585 | Good |
| 587 | M13 | No. 586 | Good |
| 588 | M14 | No. 587 | Good |
| 589 | M15 | No. 588 | Good |

Comparative Examples 1 to 123

As shown in Tables 28 to 33 below, (A-1-1-1) or (A-1-3-1) in which a polymerizable group is an acrylate group for both, and Formula 2 in which a polymerizable group is a methacrylate group for all as described in the Patent literature were added to each of compositions (M1) to (M41) at a proportion of 0.1% by weight. The resulting mixture was injected into an IPS device having no alignment film. When operation was performed in the same manner as in Use Example 1 except for injecting the mixture, and presence or absence of light leakage was observed in the same manner as in Use Example 1, light leakage was observed in all cases, and therefore alignment was poor.

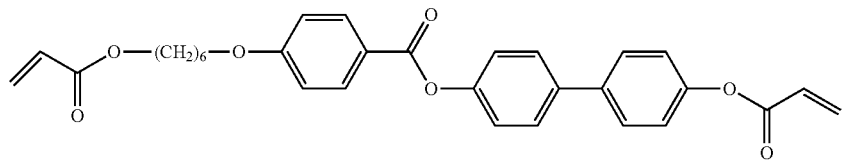

(A-1-1-1)

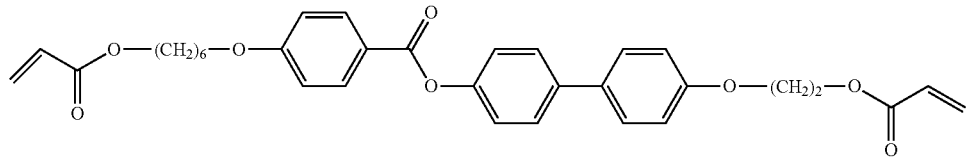

(A-1-3-1)

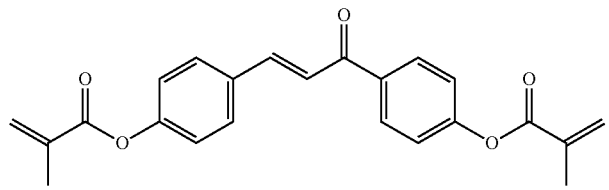

Formula 2

TABLE 28

| Comparative Example | Liquid crystal composition | First additive | Alignment |
|---|---|---|---|
| 1 | M1 | A-1-1-1 | Poor |
| 2 | M2 | A-1-1-1 | Poor |
| 3 | M3 | A-1-1-1 | Poor |
| 4 | M4 | A-1-1-1 | Poor |
| 5 | M5 | A-1-1-1 | Poor |
| 6 | M6 | A-1-1-1 | Poor |
| 7 | M7 | A-1-1-1 | Poor |
| 8 | M8 | A-1-1-1 | Poor |
| 9 | M9 | A-1-1-1 | Poor |
| 10 | M10 | A-1-1-1 | Poor |
| 11 | M11 | A-1-1-1 | Poor |
| 12 | M12 | A-1-1-1 | Poor |
| 13 | M13 | A-1-1-1 | Poor |

TABLE 29

| | | | |
|---|---|---|---|
| 14 | M14 | A-1-1-1 | Poor |
| 15 | M15 | A-1-1-1 | Poor |
| 16 | M16 | A-1-1-1 | Poor |
| 17 | M17 | A-1-1-1 | Poor |
| 18 | M18 | A-1-1-1 | Poor |
| 19 | M19 | A-1-1-1 | Poor |
| 20 | M20 | A-1-1-1 | Poor |
| 21 | M21 | A-1-1-1 | Poor |
| 22 | M22 | A-1-1-1 | Poor |
| 23 | M23 | A-1-1-1 | Poor |
| 24 | M24 | A-1-1-1 | Poor |
| 25 | M25 | A-1-1-1 | Poor |
| 26 | M26 | A-1-1-1 | Poor |
| 27 | M27 | A-1-1-1 | Poor |

TABLE 30

| | | | |
|---|---|---|---|
| 28 | M28 | A-1-1-1 | Poor |
| 29 | M29 | A-1-1-1 | Poor |
| 30 | M30 | A-1-1-1 | Poor |
| 31 | M31 | A-1-1-1 | Poor |
| 32 | M32 | A-1-1-1 | Poor |
| 33 | M33 | A-1-1-1 | Poor |
| 34 | M34 | A-1-1-1 | Poor |
| 35 | M35 | A-1-1-1 | Poor |
| 36 | M36 | A-1-1-1 | Poor |
| 37 | M37 | A-1-1-1 | Poor |
| 38 | M38 | A-1-1-1 | Poor |
| 39 | M39 | A-1-1-1 | Poor |
| 40 | M40 | A-1-1-1 | Poor |
| 41 | M41 | A-1-1-1 | Poor |
| 42 | M1 | A-1-3-1 | Poor |
| 43 | M2 | A-1-3-1 | Poor |
| 44 | M3 | A-1-3-1 | Poor |
| 45 | M4 | A-1-3-1 | Poor |
| 46 | M5 | A-1-3-1 | Poor |
| 47 | M6 | A-1-3-1 | Poor |
| 48 | M7 | A-1-3-1 | Poor |
| 49 | M8 | A-1-3-1 | Poor |
| 50 | M9 | A-1-3-1 | Poor |
| 51 | M10 | A-1-3-1 | Poor |

TABLE 31

| | | | |
|---|---|---|---|
| 52 | M11 | A-1-3-1 | Poor |
| 53 | M12 | A-1-3-1 | Poor |
| 54 | M13 | A-1-3-1 | Poor |
| 55 | M14 | A-1-3-1 | Poor |
| 56 | M15 | A-1-3-1 | Poor |
| 57 | M16 | A-1-3-1 | Poor |
| 58 | M17 | A-1-3-1 | Poor |
| 59 | M18 | A-1-3-1 | Poor |
| 60 | M19 | A-1-3-1 | Poor |
| 61 | M20 | A-1-3-1 | Poor |

TABLE 31-continued

| | | | |
|---|---|---|---|
| 62 | M21 | A-1-3-1 | Poor |
| 63 | M22 | A-1-3-1 | Poor |
| 64 | M23 | A-1-3-1 | Poor |
| 65 | M24 | A-1-3-1 | Poor |
| 66 | M25 | A-1-3-1 | Poor |
| 67 | M26 | A-1-3-1 | Poor |
| 68 | M27 | A-1-3-1 | Poor |
| 69 | M28 | A-1-3-1 | Poor |
| 70 | M29 | A-1-3-1 | Poor |
| 71 | M30 | A-1-3-1 | Poor |
| 72 | M31 | A-1-3-1 | Poor |
| 73 | M32 | A-1-3-1 | Poor |
| 74 | M33 | A-1-3-1 | Poor |
| 75 | M34 | A-1-3-1 | Poor |
| 76 | M35 | A-1-3-1 | Poor |

TABLE 32

| | | | |
|---|---|---|---|
| 77 | M36 | A-1-3-1 | Poor |
| 78 | M37 | A-1-3-1 | Poor |
| 79 | M38 | A-1-3-1 | Poor |
| 80 | M39 | A-1-3-1 | Poor |
| 81 | M40 | A-1-3-1 | Poor |
| 82 | M41 | A-1-3-1 | Poor |
| 83 | M1 | Formula 2 | Poor |
| 84 | M2 | Formula 2 | Poor |
| 85 | M3 | Formula 2 | Poor |
| 86 | M4 | Formula 2 | Poor |
| 87 | M5 | Formula 2 | Poor |
| 88 | M6 | Formula 2 | Poor |
| 89 | M7 | Formula 2 | Poor |
| 90 | M8 | Formula 2 | Poor |
| 91 | M9 | Formula 2 | Poor |
| 92 | M10 | Formula 2 | Poor |
| 93 | M11 | Formula 2 | Poor |
| 94 | M12 | Formula 2 | Poor |
| 95 | M13 | Formula 2 | Poor |
| 96 | M14 | Formula 2 | Poor |
| 97 | M15 | Formula 2 | Poor |
| 98 | M16 | Formula 2 | Poor |

TABLE 33

| | | | |
|---|---|---|---|
| 99 | M17 | Formula 2 | Poor |
| 100 | M18 | Formula 2 | Poor |
| 101 | M19 | Formula 2 | Poor |
| 102 | M20 | Formula 2 | Poor |
| 103 | M21 | Formula 2 | Poor |
| 104 | M22 | Formula 2 | Poor |
| 105 | M23 | Formula 2 | Poor |
| 106 | M24 | Formula 2 | Poor |
| 107 | M25 | Formula 2 | Poor |
| 108 | M26 | Formula 2 | Poor |
| 109 | M27 | Formula 2 | Poor |
| 110 | M28 | Formula 2 | Poor |
| 111 | M29 | Formula 2 | Poor |
| 112 | M30 | Formula 2 | Poor |
| 113 | M31 | Formula 2 | Poor |
| 114 | M32 | Formula 2 | Poor |
| 115 | M33 | Formula 2 | Poor |
| 116 | M34 | Formula 2 | Poor |
| 117 | M35 | Formula 2 | Poor |
| 118 | M36 | Formula 2 | Poor |
| 119 | M37 | Formula 2 | Poor |
| 120 | M38 | Formula 2 | Poor |
| 121 | M39 | Formula 2 | Poor |
| 122 | M40 | Formula 2 | Poor |
| 123 | M41 | Formula 2 | Poor |

In Use Examples 1 to 589, a kind and an amount of compositions or alignment control monomers, and a heating temperature during polarization exposure were changed, and no light leakage was observed. The results indicate that alignment is good even without any alignment film such as polyimide, and all liquid crystal molecules are arranged in a fixed direction. On the other hand, in Comparative Examples 1 to 123, light leakage was observed, indicating that the liquid crystal compounds were not aligned. From the results described above, the compounds of the present application are known to be able to form a thin film for aligning the liquid crystal composition by addition with a concentration lower than a level of the comparative compound. Accordingly, if the liquid crystal composition of the invention is used, a liquid crystal display device having characteristics such as a wide temperature range in which the device can be used, a short response time, a high voltage holding ratio, low threshold voltage, a large contrast ratio and a long service life can be obtained. Further, a liquid crystal display device having a liquid crystal composition satisfying at least one of characteristics such as high maximum temperature of a nematic phase, low minimum temperature of the nematic phase, small viscosity, suitable optical anisotropy, large negative dielectric anisotropy, large specific resistance, high stability to ultraviolet light and high stability to heat can be obtained.

INDUSTRIAL APPLICABILITY

A liquid crystal composition of the invention can be used in a liquid crystal monitor, a liquid crystal television and so forth.

What is claimed is:
1. A compound, represented by formula (1):

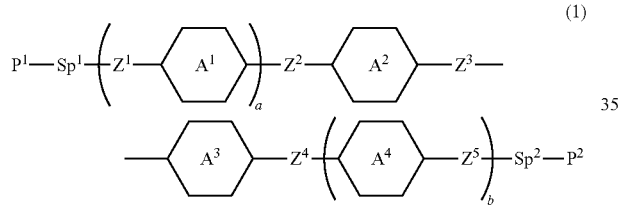

wherein, in formula (1),
a and b are independently 0, 1 or 2, wherein $0 \leq a+b \leq 3$,
ring $A^1$, ring $A^2$, ring $A^3$ and ring $A^4$ are independently 1,4-cyclohexylene, 1,4-cyclohexenylene, 1,4-phenylene, naphthalene-2,6-diyl, decahydronaphthalene-2,6-diyl, 1,2,3,4-tetrahydronaphthalene-2,6-diyl, tetrahydropyran-2,5-diyl, 1,3-dioxane-2,5-diyl, pyrimidine-2,5-diyl, pyridine-2,5-diyl, fluorene-2,7-diyl, phenanthrene-2,7-diyl, anthracene-2,6-diyl, perhydrocyclopenta[a]phenanthrene-3,17-diyl or 2,3,4,7,8,9,10,11,12,13,14,15,16,17-tetradecahydrocyclopenta[a]phenanthrene-3,17-diyl, and in the rings, at least one hydrogen may be replaced by fluorine, chlorine, alkyl having 1 to 12 carbons, alkenyl having 2 to 12 carbons, alkoxy having 1 to 11 carbons or alkenyloxy having 2 to 11 carbons, and in the groups, at least one hydrogen may be replaced by fluorine or chlorine, and when a is 2, two of ring $A^1$ may be different, and when b is 2, two of ring $A^4$ may be different;
$Z^1$, $Z^2$, $Z^3$, $Z^4$ and $Z^5$ are independently a single bond or alkylene having 1 to 10 carbons, and in the alkylene, at least one —CH$_2$— may be replaced by —O—, —CO—, —COO—, —OCO— or —OCOO—, and at least one —(CH$_2$)$_2$— may be replaced by —CH=CH— or —C≡C—, and in the groups, at least one hydrogen may be replaced by halogen, in which at least one in $Z^2$, $Z^3$ or $Z^4$ is —COO—, —OCO—, —CH=CHCOO—, —OCOCH=CH—, —CH=CH—, —CH=CHCO— or —COCH=CH—, and when a is 2, two Z*s may be different, and two $Z^5$s may be different;

Sp$^1$ and Sp$^2$ are independently a single bond or alkylene having 1 to 10 carbons, and in the alkylene, at least one —CH$_2$— may be replaced by —O—, —CO—, —COO—, —OCO— or —OCOO—, and at least one —(CH$_2$)$_2$— may be replaced by —CH=CH— or —C≡C—, and in the groups, at least one hydrogen may be replaced by halogen;

P$^1$ is a group represented by any one of formulas (1b) to (1i); and

P$^2$ is a group represented by formula (1d);

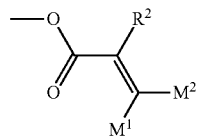

(1b)

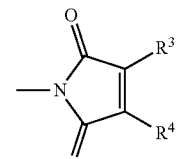

(1c)

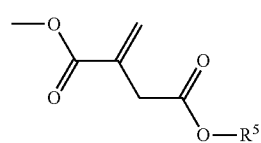

(1d)

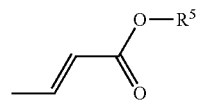

(1e)

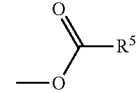

(1f)

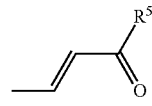

(1g)

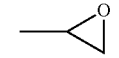

(1h)

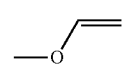

(1i)

wherein, in formulas (1b) to (1i),
M$^1$ and M$^2$ are independently hydrogen, halogen, alkyl having 1 to 5 carbons, or alkyl having 1 to 5 carbons in which at least one hydrogen is replaced by halogen;

$R^2$ is hydrogen, halogen or alkyl having 1 to 5 carbons, and in the alkyl, at least one hydrogen may be replaced by halogen, and at least one —$CH_2$— may be replaced by —O—; and $R^3$, $R^4$ and $R^5$ are independently hydrogen or alkyl having 1 to 15 carbons, and in the alkyl, at least one —$CH_2$— may be replaced by —O— or —S—, and at least one —$(CH_2)_2$— may be replaced by —CH=CH— or —C≡C—, and in the groups, at least one hydrogen may be replaced by halogen.

2. The compound according to claim 1, represented by formula (1):

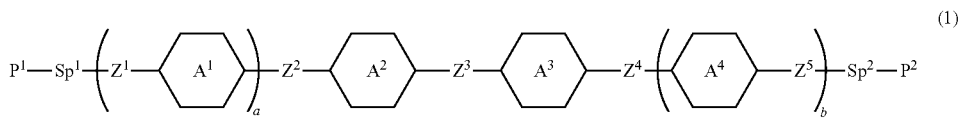

wherein, in formula (1), a and b are independently 0, 1 or 2, wherein 0≤a+b≤2;

ring $A^1$, ring $A^2$, ring $A^3$ and ring $A^4$ are independently 1,4-cyclohexylene, 1,4-cyclohexenylene, 1,4-phenylene, naphthalene-2,6-diyl, decahydronaphthalene-2,6-diyl, 1,2,3,4-tetrahydronaphthalene-2,6-diyl, tetrahydropyran-2,5-diyl, 1,3-dioxane-2,5-diyl, pyrimidine-2,5-diyl, pyridine-2,5-diyl, fluorene-2,7-diyl, phenanthrene-2,7-diyl, anthracene-2,6-diyl, perhydrocyclopenta[a]phenanthrene-3,17-diyl or 2,3,4,7,8,9,10,11,12,13,14,15,16,17-tetradecahydrocyclopenta[a]phenanthrene-3,17-diyl, and in the rings, at least one hydrogen may be replaced by fluorine, chlorine, alkyl having 1 to 12 carbons, alkenyl having 2 to 12 carbons, alkoxy having 1 to 11 carbons or alkenyloxy having 2 to 11 carbons, and in the groups, at least one hydrogen may be replaced by fluorine or chlorine, and when a is 2, two of ring $A^1$ may be different, and when b is 2, two of ring $A^4$ may be different;

$Z^1$, $Z^2$, $Z^3$, $Z^4$ and $Z^5$ are independently a single bond, —$(CH_2)_2$—, —C≡C—, —COO—, —OCO—, —$CF_2O$—, —$OCF_2$—, —$CH_2O$—, —$OCH_2$—, —CF=CF—, —CH=CHCOO—, —OCOCH=CH—, —CH=CH—, —CH=CHCO— or —COCH=CH—, in which at least one in $Z^2$, $Z^3$ or $Z^4$ is —COO—, —OCO—, —CH=CHCOO—, —OCOCH=CH—, —CH=CH—, —CH=CHCO— or —COCH=CH—, and when a is 2, two Z's may be different, and two $Z^5$s may be different;

$Sp^1$ and $Sp^2$ are independently a single bond or alkylene having 1 to 10 carbons, and in the alkylene, at least one —$CH_2$— may be replaced by —O—, —COO— or —OCO—, and at least one —$(CH_2)_2$— may be replaced by —CH=CH—, and in the groups, at least one hydrogen may be replaced by fluorine or chlorine; and $P^1$ is a group represented by any one of formulas (1b) to (1i), and $P^2$ is a group represented by formula (1d);

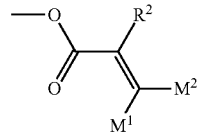

-continued

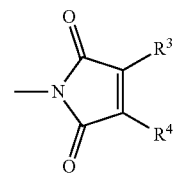

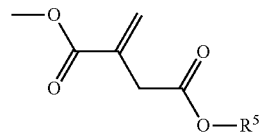

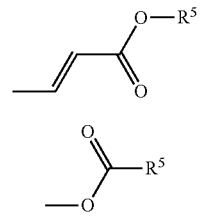

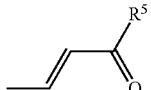

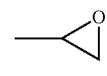

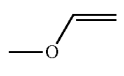

wherein, in formulas (1b) to (1i), $M^1$ and $M^2$ are independently hydrogen, halogen, alkyl having 1 to 5 carbons, or alkyl having 1 to 5 carbons in which at least one hydrogen is replaced by halogen;

$R^2$ is hydrogen, halogen or alkyl having 1 to 5 carbons, and in the alkyl, at least one hydrogen may be replaced by halogen, and at least one —$CH_2$— may be replaced by —O—; and $R^3$, $R^4$ and $R^5$ are independently hydrogen or alkyl having 1 to 15 carbons, and in the alkyl, at least one —$CH_2$— may be replaced by —O— or —S—, and at least one —(CH$_2$)$_2$— may be replaced by —CH=CH— or —C≡C—, and in the groups, at least one hydrogen may be replaced by halogen.

3. The compound according to claim 1, represented by any one of formulas (1-1) to (1-3):

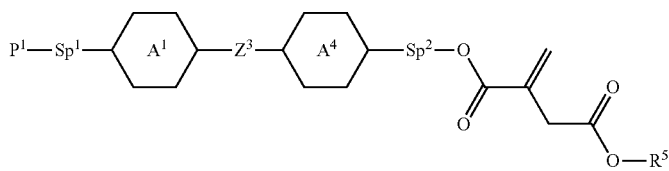
(1-1)

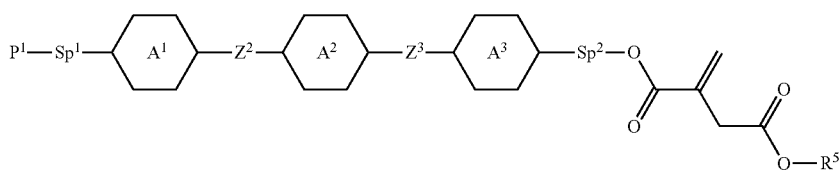
(1-2)

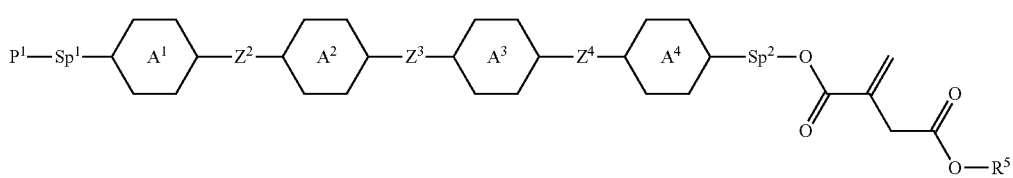
(1-3)

wherein, in formulas (1-1) to (1-3),
R$^5$ is hydrogen or alkyl having 1 to 15 carbons, and in the alkyl, at least one —CH$_2$— may be replaced by —O— or —S—, and at least one —(CH$_2$)$_2$— may be replaced by —CH=CH— or —C≡C—, and in the groups, at least one hydrogen may be replaced by halogen;
ring A$^1$, ring A$^2$, ring A$^3$ and ring A$^4$ are independently 1,4-cyclohexylene, 1,4-phenylene, naphthalene-2,6-diyl, pyrimidine-2,5-diyl, pyridine-2,5-diyl, fluorene-2,7-diyl, phenanthrene-2,7-diyl or anthracene-2,6-diyl, and in the rings, at least one hydrogen may be replaced by fluorine, chlorine, alkyl having 1 to 12 carbons, alkenyl having 2 to 12 carbons, alkoxy having 1 to 11 carbons or alkenyloxy having 2 to 11 carbons, and in the groups, at least one hydrogen may be replaced by fluorine or chlorine;
Z$^2$, Z$^3$ and Z$^4$ are independently a single bond, —(CH$_2$)$_2$—, —C≡C—, —COO—, —OCO—, —CF$_2$O—, —OCF$_2$—, —CH$_2$O—, —OCH$_2$—, —CF=CF—, —CH=CHCOO—, —OCOCH=CH—, —CH=CH—, —CH=CHCO— or —COCH=CH—, in which at least one in Z$^2$, Z$^3$ and Z$^4$ is —COO—, —OCO—, —CH=CHCOO—, —OCOCH=CH—, —CH=CH—, —CH=CHCO— or —COCHCH—;
Sp$^1$ and Sp$^2$ are independently a single bond or alkylene having 1 to 10 carbons, and in the alkylene, at least one —CH$_2$— may be replaced by —O—, —COO—, —OCOO— or —OCO—, and at least one —(CH$_2$)$_2$— may be replaced by —CH=CH—, and in the groups, at least one hydrogen may be replaced by fluorine or chlorine; and P$^1$ is a group represented by any one of formulas (1b) to (1i);

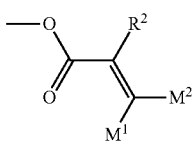
(1b)

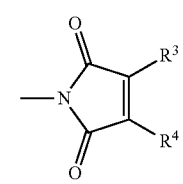
(1c)

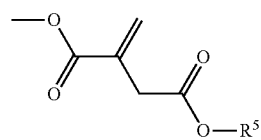
(1d)

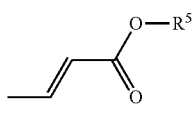
(1e)

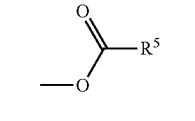
(1f)

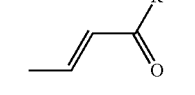
(1g)

-continued

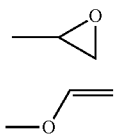
(1h)

(1i)

wherein
M1 and M2 are independently hydrogen, halogen, alkyl having 1 to 5 carbons, or alkyl having 1 to 5 carbons in which at least one hydrogen is replaced by halogen;

$R^2$ is hydrogen, halogen or alkyl having 1 to 5 carbons, and in the alkyl, at least one hydrogen may be replaced by halogen, and at least one —$CH_2$— may be replaced by —O—; and $R^3$, $R^4$ and $R^5$ are independently hydrogen or straight-chain, branched-chain or cyclic alkyl having 1 to 15 carbons, and in the alkyl, at least one —$CH_2$— may be replaced by —O— or —S—, and at least one —$(CH_2)_2$— may be replaced by —CH=CH— or —C≡C—, and in the groups, at least one hydrogen may be replaced by halogen.

4. The compound according to claim 1, represented by any one of formulas (1-1-1), (1-2-1) and (1-3-1):

carbons, alkenyl having 2 to 12 carbons, alkoxy having 1 to 11 carbons or alkenyloxy having 2 to 11 carbons;

$Z^2$, $Z^3$ and $Z^4$ are independently a single bond, —COO—, —OCO—, —CH=CHCOO—, —OCOCH=CH—, —CH=CH—, —CH=CHCO— or —COCH=CH—, in which at least one in $Z^2$, $Z^3$ and $Z^4$ is —COO—, —OCO—, —CH=CHCOO—, —OCOCH=CH—, —CH=CH—, —CH=CHCO— or —COCH=CH—;

$Sp^1$ and $Sp^2$ are independently a single bond or alkylene having 1 to 10 carbons, and in the alkylene, at least one —$CH_2$— may be replaced by —O—, —COO—, —OCOO— or —OCO—, and at least one —$(CH_2)_2$— may be replaced by —CH=CH—; and $P^1$ is a group represented by any one of formula (1b), (1c) or (1d);

(1b)

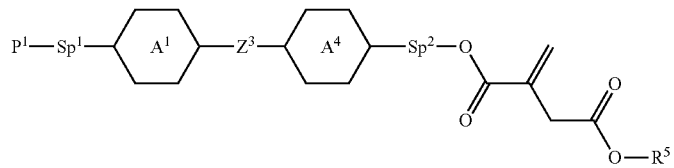
(1-1-1)

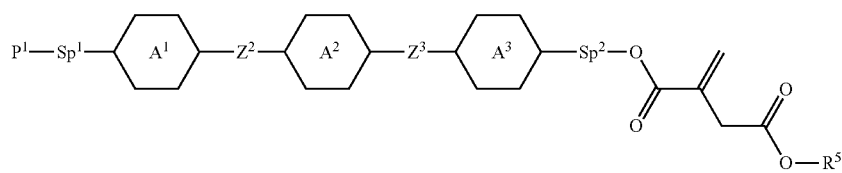
(1-2-1)

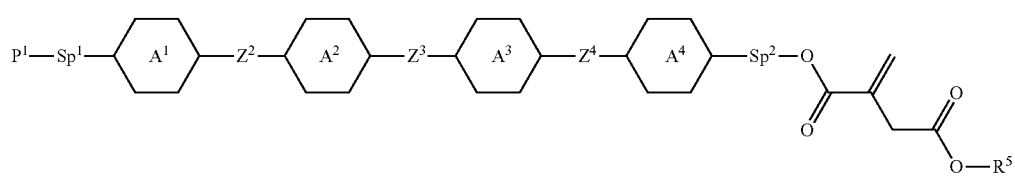
(1-3-1)

wherein, in formulas (1-1-1), (1-2-1) and (1-3-1),
$R^5$ is hydrogen or alkyl having 1 to 15 carbons, and in the alkyl, at least one —$CH_2$— may be replaced by —O— or —S—, and at least one —$(CH_2)_2$— may be replaced by —CH=CH— or —C≡C—, and in the groups, at least one hydrogen may be replaced by halogen;

ring $A^1$, ring $A^2$, ring $A^3$ and ring $A^4$ are independently 1,4-cyclohexylene, 1,4-phenylene or fluorene-2,7-diyl, and in the rings, at least one hydrogen may be replaced by fluorine, chlorine, alkyl having 1 to 12

-continued

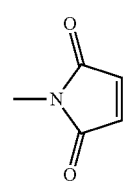
(1c)

-continued

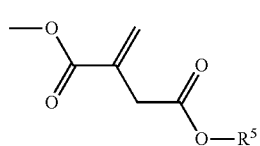
(1d)

wherein, in formulas (1b) to (1d),
- $R^2$ is hydrogen, halogen or alkyl having 1 to 5 carbons, and in the alkyl, at least one hydrogen may be replaced by halogen, and at least one —CH$_2$— may be replaced by —O—; and
- $R^5$ is hydrogen or alkyl having 1 to 15 carbons, and in the alkyl, at least one —CH$_2$— may be replaced by —O— or —S—, and at least one —(CH$_2$)$_2$— may be replaced by —CH=CH— or —C≡C—, and in the groups, at least one hydrogen may be replaced by halogen.

5. The compound according to claim 4, represented by any one of formula (1-1-1), (1-2-1) or (1-3-1), wherein any one of $Z^2$, $Z^3$ or $Z^4$ is —COO— or —OCO—.

6. The compound according to claim 4, represented by any one of formula (1-1-1), (1-2-1) or (1-3-1), wherein any one of $Z^2$, $Z^3$ or $Z^4$ is —CH=CHCOO—, —OCOCH=CH—, —CH=CH—, —CH=CHCO— or —COCH=CH—.

7. The compound according to claim 1, represented by formula (1-A):

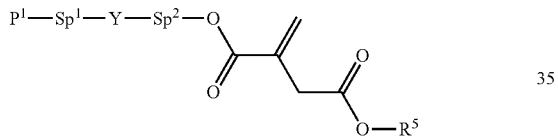
(1-A)

wherein
- $P^1$ is a group represented by formula (1b), (1c) or (1d);
- $Sp^1$ and $Sp^2$ are independently a single bond or alkylene having 1 to 10 carbons, and in the alkylene, at least one —CH$_2$— may be replaced by —O—, —COO—, —OCOO— or —OCO—, and at least one —(CH$_2$)$_2$— may be replaced by —CH=CH—; and
- $R^5$ is hydrogen or alkyl having 1 to 15 carbons, and in the alkyl, at least one —CH$_2$— may be replaced by —O— or —S—, and at least one —(CH$_2$)$_2$— may be replaced by —CH=CH— or —C≡C—, and in the groups, at least one hydrogen may be replaced by halogen;

(1b)

(1c)

-continued

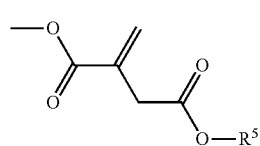
(1d)

wherein, in formula (1b), $R^2$ is hydrogen, halogen or alkyl having 1 to 5 carbons, and in the alkyl, at least one hydrogen may be replaced by halogen, and at least one —CH$_2$— may be replaced by —O—;

in formula (1d), $R^5$ is hydrogen or alkyl having 1 to 15 carbons, and in the alkyl, at least one —CH$_2$— may be replaced by —O— or —S—, and at least one —(CH$_2$)$_2$— may be replaced by —CH=CH— or —C≡C—, and in the groups, at least one hydrogen may be replaced by halogen; and Y is a group represented by any one of formulas (MES-1-01) to (MES-1-10);

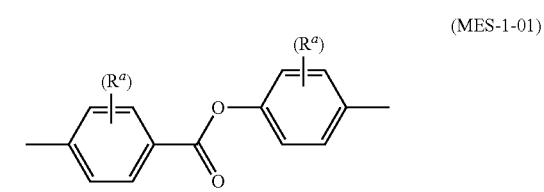
(MES-1-01)

(MES-1-02)

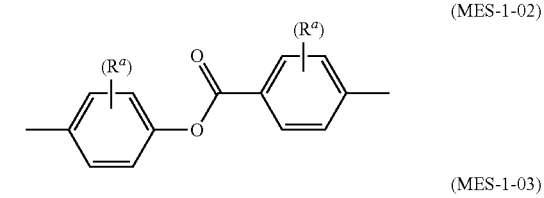
(MES-1-03)

(MES-1-04)

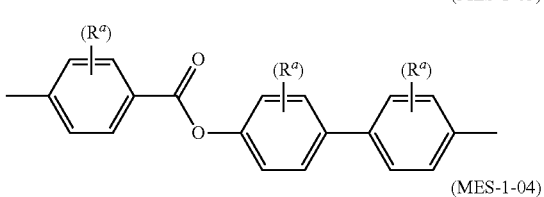
(MES-1-05)

(MES-1-06)

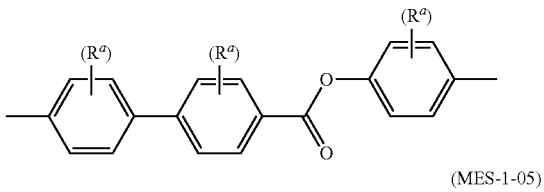

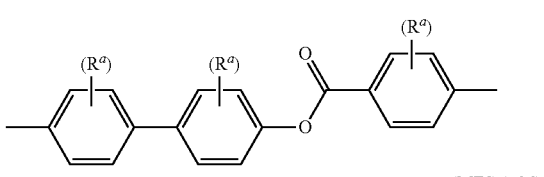

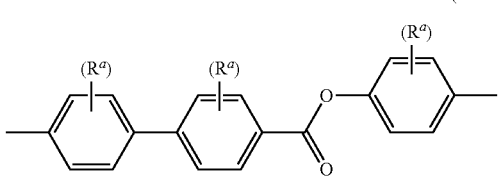

-continued (MES-1-07)

(MES-1-08)

(MES1-09)

(MES-1-10)

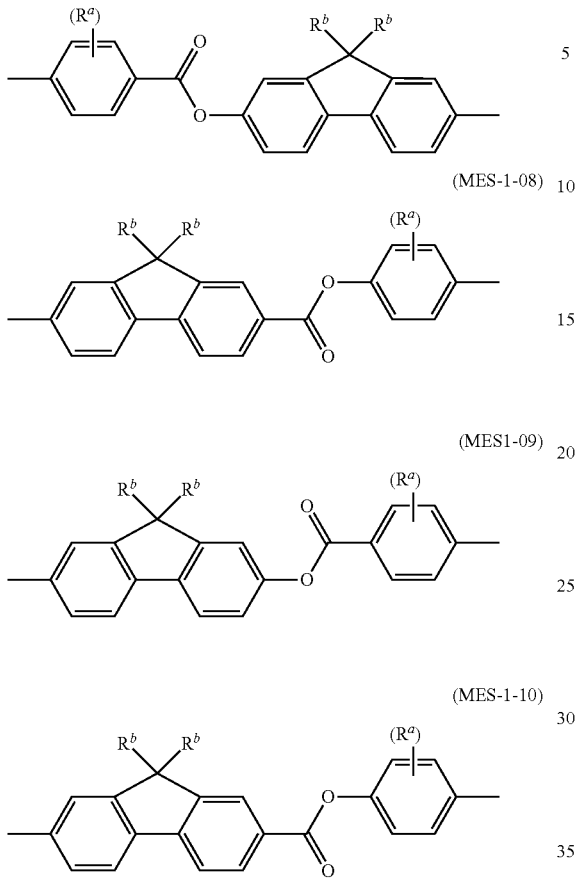

wherein
- $R^a$ is independently fluorine, chlorine, methyl or ethyl;
- $R^b$ is independently hydrogen, fluorine, methyl or ethyl; and
- a representation of connecting 1,4-phenylene with ($R^a$) by a straight line as shown below in the formulas indicates 1,4-phenylene in which one or two hydrogens may be replaced by $R^a$:

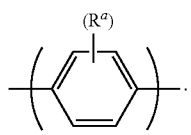

8. The compound according to claim 1, represented by formula (1-A):

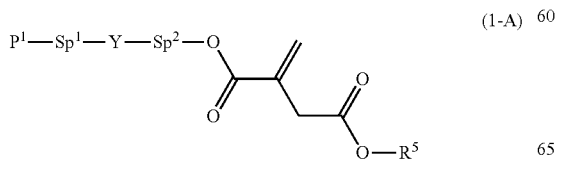

(1-A)

wherein
P$^1$ is a group represented by formula (1b), (1c) or (1d);

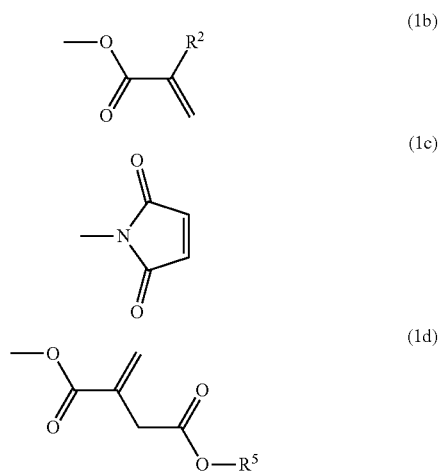

(1b)

(1c)

(1d)

wherein
- Sp$^1$ and Sp$^2$ are independently a single bond or alkylene having 1 to 10 carbons, and in the alkylene, at least one —CH$_2$— may be replaced by —O—, —COO—, —OCOO— or —OCO—, and at least one —(CH$_2$)$_2$— may be replaced by —CH=CH—;
- R$^2$ is hydrogen, halogen or alkyl having 1 to 5 carbons, and in the alkyl, at least one hydrogen may be replaced by halogen, and at least one —CH$_2$— may be replaced by —O—;
- R$^5$ is independently hydrogen or alkyl having 1 to 15 carbons, and in the alkyl, at least one —CH$_2$— may be replaced by —O— or —S—, and at least one —(CH$_2$)$_2$— may be replaced by —CH=CH— or —C≡C—, and in the groups, at least one hydrogen may be replaced by halogen; and
- Y is a group represented by any one of (MES-2-01) to (MES-2-16);

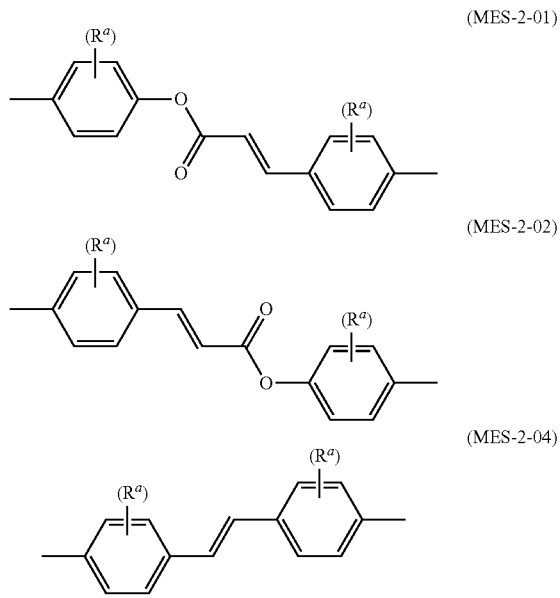

(MES-2-01)

(MES-2-02)

(MES-2-04)

(MES-2-05)
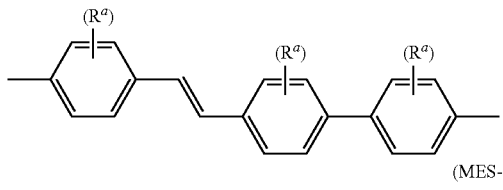

(MES-2-06)
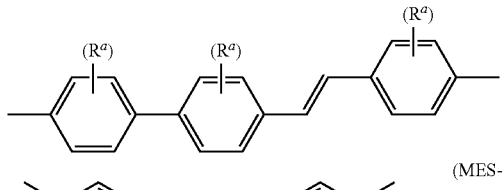

(MES-2-07)
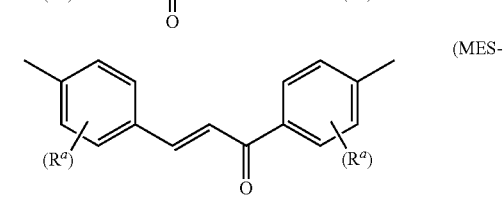

(MES-2-08)

(MES-2-09)
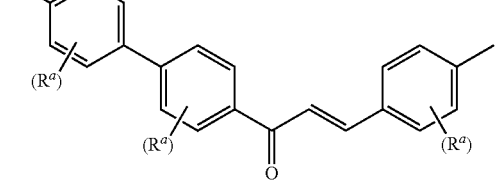

(MES-2-10)
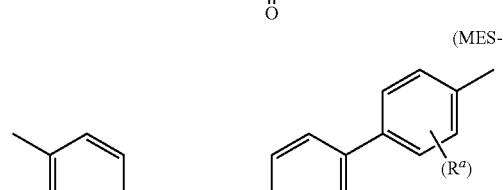

(MES-2-11)
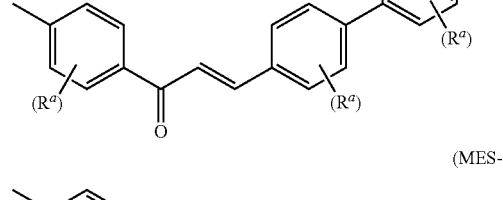

(MES-2-12)
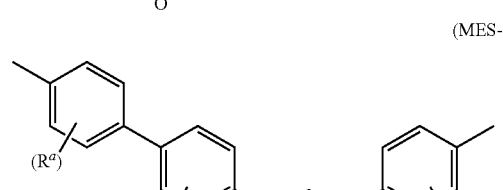

(MES-2-13)
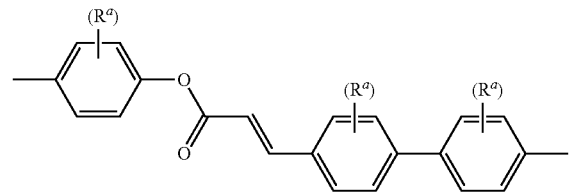

(MES-2-14)

(MES-2-15)

(MES-2-16)
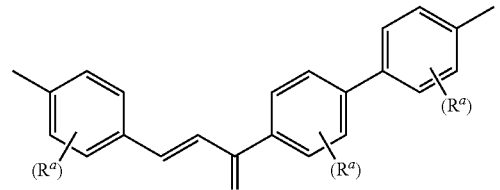

wherein $R^a$ is independently fluorine, chlorine, methyl or ethyl; and a representation of connecting 1,4-phenylene with ($R^a$) by a straight line as shown below in the formulas indicates 1,4-phenylene in which one or two hydrogens may be replaced by $R^a$:

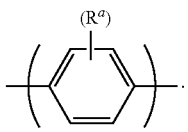

9. A liquid crystal composition, containing at least one compound according to claim 1.

10. The liquid crystal composition according to claim 9, further containing at least one compound selected from the group of compounds represented by formulas (2) to (4):

(2)
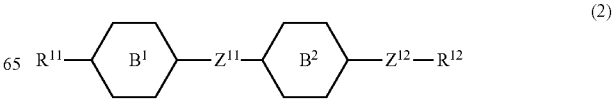

-continued (3)

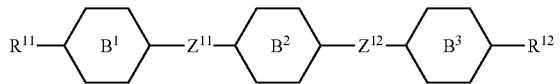

(4)

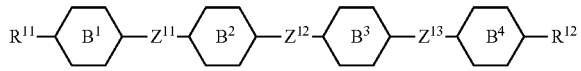

wherein, in formulas (2) to (4),
  $R^1$ and $R^2$ are independently alkyl having 1 to 10 carbons or alkenyl having 2 to 10 carbons, and in the alkyl and the alkenyl, at least one —$CH_2$— may be replaced by —O—, and at least one hydrogen may be replaced by fluorine;
  ring $B^1$, ring $B^2$, ring $B^3$ and ring $B^4$ are independently 1,4-cyclohexylene, 1,4-phenylene, 2-fluoro-1,4-phenylene, 2,5-difluoro-1,4-phenylene or pyrimidine-2,5-diyl; and
  $Z^{11}$, $Z^{12}$ and $Z^{13}$ are independently a single bond, —$CH_2CH_2$—, —CH=CH—, —C≡C— or —COO—.

11. The liquid crystal composition according to claim 9, further containing at least one compound selected from the group of compounds represented by formulas (5) to (7):

(5)

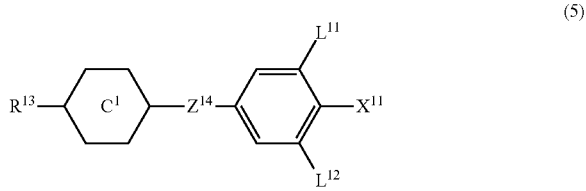

(6)

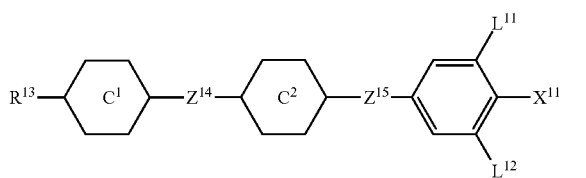

(7)

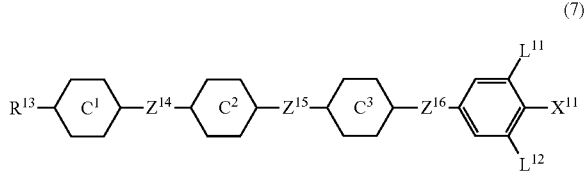

wherein, in formulas (5) to (7),
  $R^{13}$ is alkyl having 1 to 10 carbons or alkenyl having 2 to 10 carbons, and in the alkyl and the alkenyl, at least one —$CH_2$— may be replaced by —O—, and at least one hydrogen may be replaced by fluorine;
  $X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;
  ring $C^1$, ring $C^2$ and ring $C^3$ are independently 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;
  $Z^{14}$, $Z^{15}$ and $Z^{16}$ are independently a single bond, —$CH_2CH_2$—, —CH=CH—, —C≡C—, —COO—, —$CF_2O$—, —$OCF_2$—, —$CH_2O$—, —CF=CF—, —CH=CF— or —$(CH_2)_4$—; and
  $L^{11}$ and $L^{12}$ are independently hydrogen or fluorine.

12. The liquid crystal composition according to claim 9, further containing at least one compound represented by formula (8):

(8)

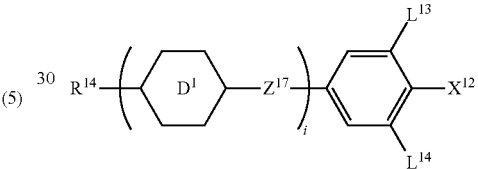

wherein, in formula (8),
  $R^{14}$ is alkyl having 1 to 10 carbons or alkenyl having 2 to 10 carbons, and in the alkyl and the alkenyl, at least one —$CH_2$— may be replaced by —O—, and at least one hydrogen may be replaced by fluorine;
  $X^{12}$ is —C≡N or —C≡C—C≡N;
  ring $D^1$ is 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;
  $Z^{17}$ is a single bond, —$CH_2CH_2$—, —C≡C—, —COO—, —$CF_2O$—, —$OCF_2$— or —$CH_2O$—;
  $L^{13}$ and $L^{14}$ are independently hydrogen or fluorine; and
  i is 1, 2, 3 or 4.

13. The liquid crystal composition according to claim 9, further containing at least one compound selected from the group of compounds represented by formulas (9) to (15):

(9)

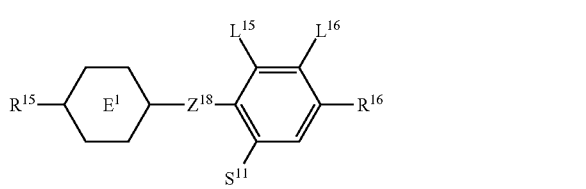

(10)

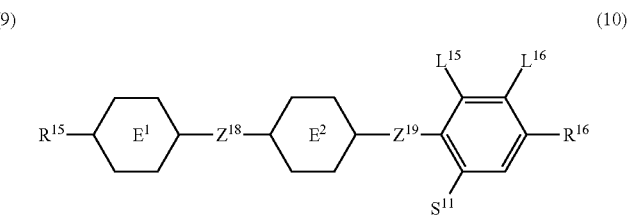

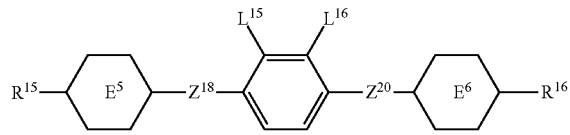
(11)

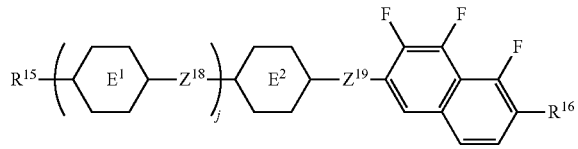
(12)

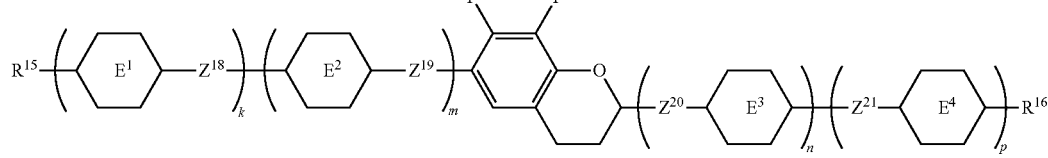
(13)

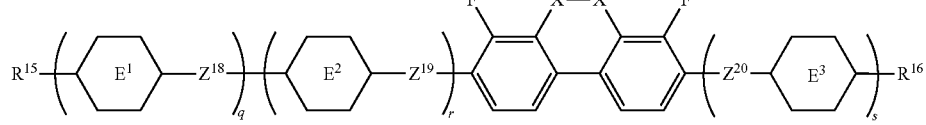
(14)

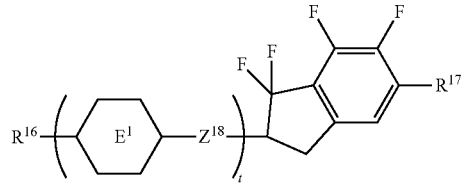
(15)

wherein, in formulas (9) to (15), $R^{15}$ and $R^{16}$ are independently alkyl having 1 to 10 carbons or alkenyl having 2 to 10 carbons, and in the alkyl and the alkenyl, at least one —CH$_2$— may be replaced by —O—, and at least one hydrogen may be replaced by fluorine;

$R^{17}$ is hydrogen, fluorine, alkyl having 1 to 10 carbons or alkenyl having 2 to 10 carbons, and in the alkyl and the alkenyl, at least one —CH$_2$— may be replaced by —O—, and at least one hydrogen may be replaced by fluorine;

ring $E^1$, ring $E^2$, ring $E^3$ and ring $E^4$ are independently 1,4-cyclohexylene, 1,4-cyclohexenylene, 1,4-phenylene in which at least one hydrogen may be replaced by fluorine, tetrahydropyran-2,5-diyl or decahydronaphthalene-2,6-diyl;

ring $E^5$ and ring $E^6$ are independently 1,4-cyclohexylene, 1,4-cyclohexenylene, 1,4-phenylene, tetrahydropyran-2,5-diyl or decahydronaphthalene-2,6-diyl;

$Z^{18}$, $Z^{19}$, $Z^{20}$ and $Z^{21}$ are independently a single bond, —CH$_2$CH$_2$—, —COO—, —CH$_2$O—, —OCF$_2$— or —OCF$_2$CH$_2$CH$_2$—;

$L^{15}$ and $L^{16}$ are independently fluorine or chlorine;

$S^{11}$ is hydrogen or methyl;

X is —CHF— or —CF$_2$—; and j, k, m, n, p, q, r and s are independently 0 or 1, a sum of k, m, n and p is 1 or 2, a sum of q, r and s is 0, 1, 2 or 3, and t is 1, 2 or 3.

14. The liquid crystal composition according to claim 9, further containing at least one polymerizable compound represented by formula (16):

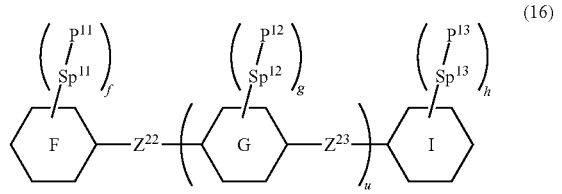
(16)

wherein, in formula (16), ring F and ring I are independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in the rings, at least one hydrogen may be replaced by halogen, alkyl having 1 to 12 carbons, or alkyl having 1 to 12 carbons in which at least one hydrogen is replaced by halogen;

ring G is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one hydrogen may be replaced by halogen, alkyl having 1 to 12 carbons, alkoxy having 1 to 12 carbons, or alkyl having 1 to 12 carbons in which at least one hydrogen is replaced by halogen;

$Z^{22}$ and $Z^{23}$ are independently a single bond or alkylene having 1 to 10 carbons, and in the alkylene, at least one —CH$_2$— may be replaced by —O—, —CO—, —COO— or —OCO—, and at least one —CH$_2$CH$_2$— may be replaced by —CH═CH—, —C(CH$_3$)═CH—, —CH═C(CH$_3$)— or —C(CH$_3$)

=C(CH₃)—, and in the groups, at least one hydrogen may be replaced by fluorine or chlorine; and
P¹¹, P¹² and P¹³ are independently a polymerizable group selected from the group of groups represented by formulas (P-1) to (P-5);

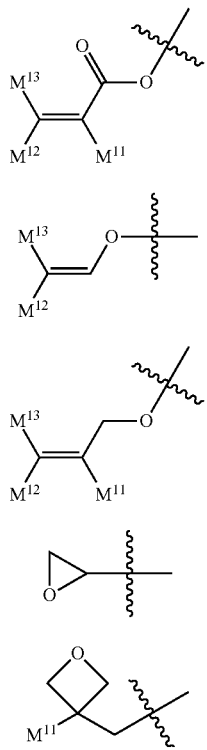

(P-1)

(P-2)

(P-3)

(P-4)

(P-5)

wherein
M¹¹, M¹² and M¹³ are independently hydrogen, fluorine, alkyl having 1 to 5 carbons, or alkyl having 1 to 5 carbons in which at least one hydrogen is replaced by fluorine or chlorine;
Sp¹¹, Sp¹² and Sp¹³ are independently a single bond or alkylene having 1 to 10 carbons, and in the alkylene, at least one —CH₂— may be replaced by —O—, —COO—, —OCO— or —OCOO—, and at least one —CH₂CH₂— may be replaced by —CH=CH— or —C≡C—, and in the groups, at least one hydrogen may be replaced by fluorine or chlorine;
u is 0, 1 or 2; and
f, g and h are independently 0, 1, 2, 3 or 4, and a sum of f, g and h is 2 or more.

15. The liquid crystal composition according to claim 9, further containing at least one polymerizable compound selected from the group of compounds represented by formulas (16-1) to (16-27):

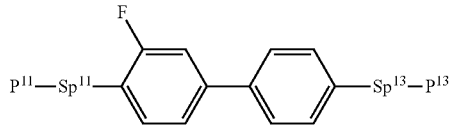

(16-1)

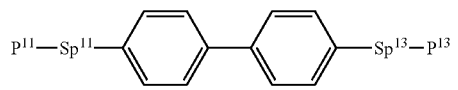

(16-2)

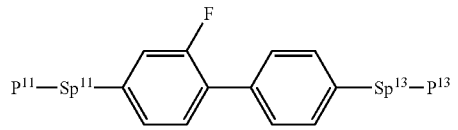

(16-3)

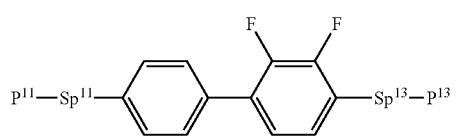

(16-4)

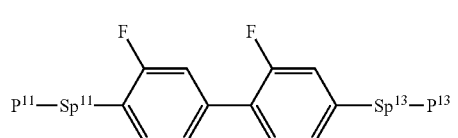

(16-5)

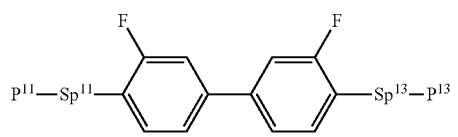

(16-6)

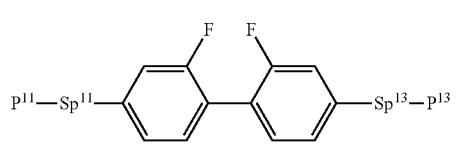

(16-7)

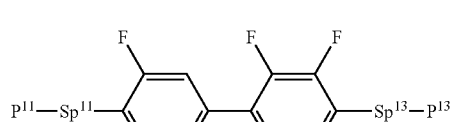

(16-8)

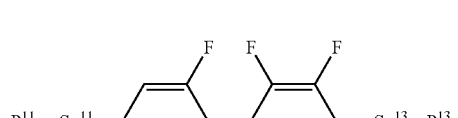

(16-9)

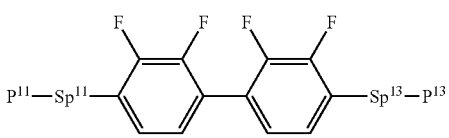

(16-10)

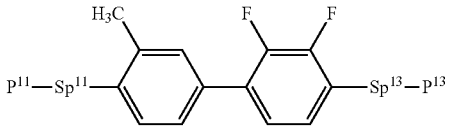

(16-11)

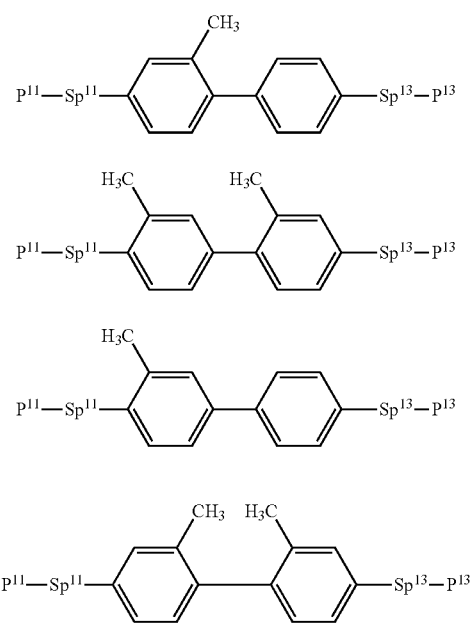
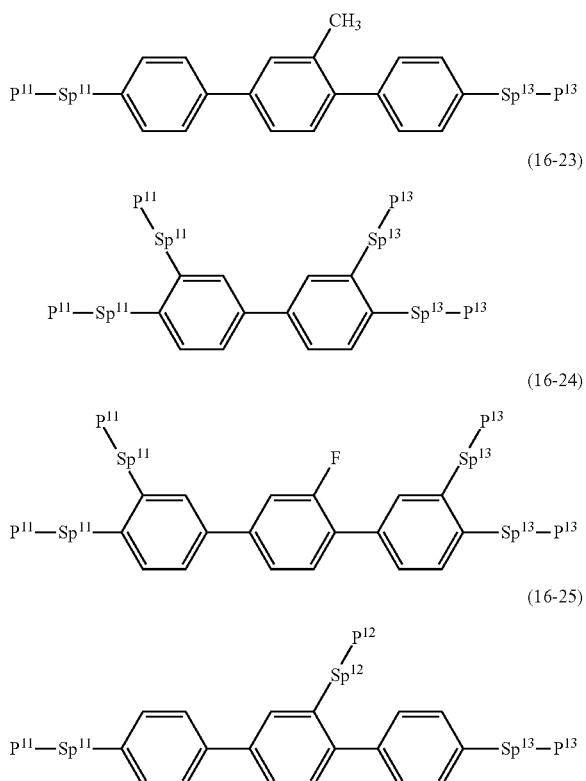
wherein, in formulas (16-1) to (16-27),
P$^{11}$, P$^{12}$ and P$^{13}$ are independently a polymerizable group selected from the group of groups represented by formulas (P-1) to (P-3), in which M$^{11}$, M$^{12}$ and M$^{13}$ are independently hydrogen, fluorine, alkyl having 1 to 5 carbons, or alkyl having 1 to 5 carbons in which at least one hydrogen is replaced by halogen;

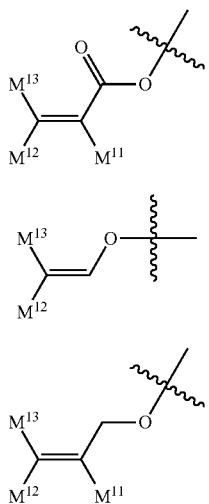

(P-1)
(P-2)
(P-3)

wherein
Sp$^{11}$, Sp$^{12}$ and Sp$^{13}$ are independently a single bond or alkylene having 1 to 10 carbons, and in the alkylene, at least one —CH$_2$— may be replaced by —O—, —COO—, —OCO— or —OCOO—, and at least one —CH$_2$CH$_2$— may be replaced by —CH=CH— or —C≡C—, and in the groups, at least one hydrogen may be replaced by fluorine or chlorine.

16. The liquid crystal composition according to claim 9, further containing at least one of a polymerizable compound other than formulas (1) and (16), a polymerization initiator, a polymerization inhibitor, an optically active compound, an antioxidant, an ultraviolet light absorber, a light stabilizer, a heat stabilizer and an antifoaming agent.

17. A liquid crystal display device, including at least one liquid crystal composition according to claim 9.

\* \* \* \* \*